(12) United States Patent
Schann et al.

(10) Patent No.: US 11,008,323 B2
(45) Date of Patent: May 18, 2021

(54) SUBSTITUTED TRICYCLIC 1,4-BENZODIAZEPINONE DERIVATIVES AS ALLOSTERIC MODULATORS OF GROUP II METABOTROPIC GLUTAMATE RECEPTORS

(71) Applicant: Domain Therapeutics, Illkirch Graffenstaden (FR)

(72) Inventors: Stephan Schann, Illkirch (FR); Stanislas Mayer, Eschau (FR); Baptiste Manteau, Lingolsheim (FR)

(73) Assignee: Domain Therapeutics, Illkirch Graffenstaden (FR)

( * ) Notice: Subject to any disclaimer, the term of this patent is extended or adjusted under 35 U.S.C. 154(b) by 0 days.

(21) Appl. No.: 15/775,725

(22) PCT Filed: Nov. 11, 2016

(86) PCT No.: PCT/GB2016/053550
§ 371 (c)(1),
(2) Date: May 11, 2018

(87) PCT Pub. No.: WO2017/081483
PCT Pub. Date: May 18, 2017

(65) Prior Publication Data
US 2018/0346468 A1 Dec. 6, 2018

(30) Foreign Application Priority Data

Nov. 13, 2015 (EP) .................................. 15194611

(51) Int. Cl.
*C07D 487/04* (2006.01)
*C07D 243/14* (2006.01)
*C07D 519/00* (2006.01)
*A61P 25/16* (2006.01)

(52) U.S. Cl.
CPC ............ *C07D 487/04* (2013.01); *A61P 25/16* (2018.01); *C07D 519/00* (2013.01)

(58) Field of Classification Search
CPC ............................ C07D 487/04; C07D 243/14
See application file for complete search history.

(56) References Cited

U.S. PATENT DOCUMENTS

| 4,153,799 A | 5/1979 | Gilman et al. |
| 4,863,920 A | 9/1989 | Hunkeler et al. |

FOREIGN PATENT DOCUMENTS

WO    WO 2014/117919    8/2014

OTHER PUBLICATIONS

Wang et al. (Tetrahedron Letters; vol. 52, Issue 4, Jan. 26, 2011, pp. 541-543). (Year: 2011).*
Wang et al. (Tetrahedron Letters; vol. 56, Issue 8, Feb. 18, 2015, pp. 1030-1033). (Year: 2015).*
Patani (Chemical Reviews, 1996, vol. 96, No. 8). (Year: 1996).*
Dick RM (2011). "Chapter 2. Pharmacodynamics: The Study of Drug Action". In Ouellette R, Joyce JA. Pharmacology for Nurse Anesthesiology. Jones & Bartlett Learning:pp. 17-26. (Year: 2011).*
J. G. Cannon Chapter Nineteen in Burger's Medicinal Chemistry and Drug Discovery, FifthEdition, vol. I: Principles and Practice, Wiley-Interscience 1995, pp. 783-802, 784. (Year: 1995).*
Anzini et al., "5,6-Dihydro-5-{4-[4-(2-methoxyphenyl)-1-piperazinyl]butyl}-4H-pyrrolo[1,2-a] {1,4} benzodiazepine-4,6-dione and related compounds as new 5-HT1A receptor ligands", *Medicinal Chemistry Research, Birkhaeuser*, Boston, US, XP009188082, vol. 3(4) pp. 249-256 (Jan. 1, 1993).
Bertelli et al., "1,2,3-Triazolo[1,5-a][1,4]- and 1,2,3-triazolo[1,5-a][1,5] benzodiazepine derivatives: Synthesis and benzodiazepine receptor binding", *IL Farmaco*, XP055242581, vol. 53(4), pp. 305-311 (Apr. 1, 1998).
PCT International Search Report and Written Opinion issued in International Application No. PCT/GB2016/053550, dated Jan. 19, 2017.

(Continued)

*Primary Examiner* — Jeffrey S Lundgren
*Assistant Examiner* — Chris E Simmons
(74) *Attorney, Agent, or Firm* — Parker Highlander PLLC

(57) ABSTRACT

The present invention provides novel tricyclic 1,4-benzodiazepinone derivatives of the general formula (I) and pharmaceutical compositions containing them. Moreover, the compounds of formula (I) and the pharmaceutical compositions containing them are provided for use in the treatment and/or prophylaxis of conditions associated with altered glutamatergic signalling and/or functions, and/or conditions which can be affected by alteration of glutamate level or signalling in mammals. The tricyclic 1,4-benzodiazepinone derivatives of formula (I) can act as modulators of nervous system receptors sensitive to glutamate, in particular as modulators of metabotropic glutamate receptors (mGluRs), which makes them particularly suitable for the treatment and/or prophylaxis of acute and chronic neurological and/or psychiatric disorders. The present invention further provides tricyclic 1,4-benzodiazepinone derivatives of formula (I) that are modulators of metabotropic glutamate receptors (mGluRs), particularly positive allosteric modulators of mGluRs, and more specifically positive allosteric modulators of mGluR3.

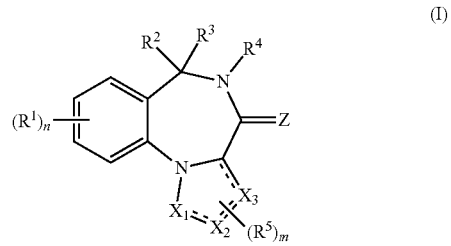

13 Claims, 2 Drawing Sheets

(56) References Cited

OTHER PUBLICATIONS

Figure 1:
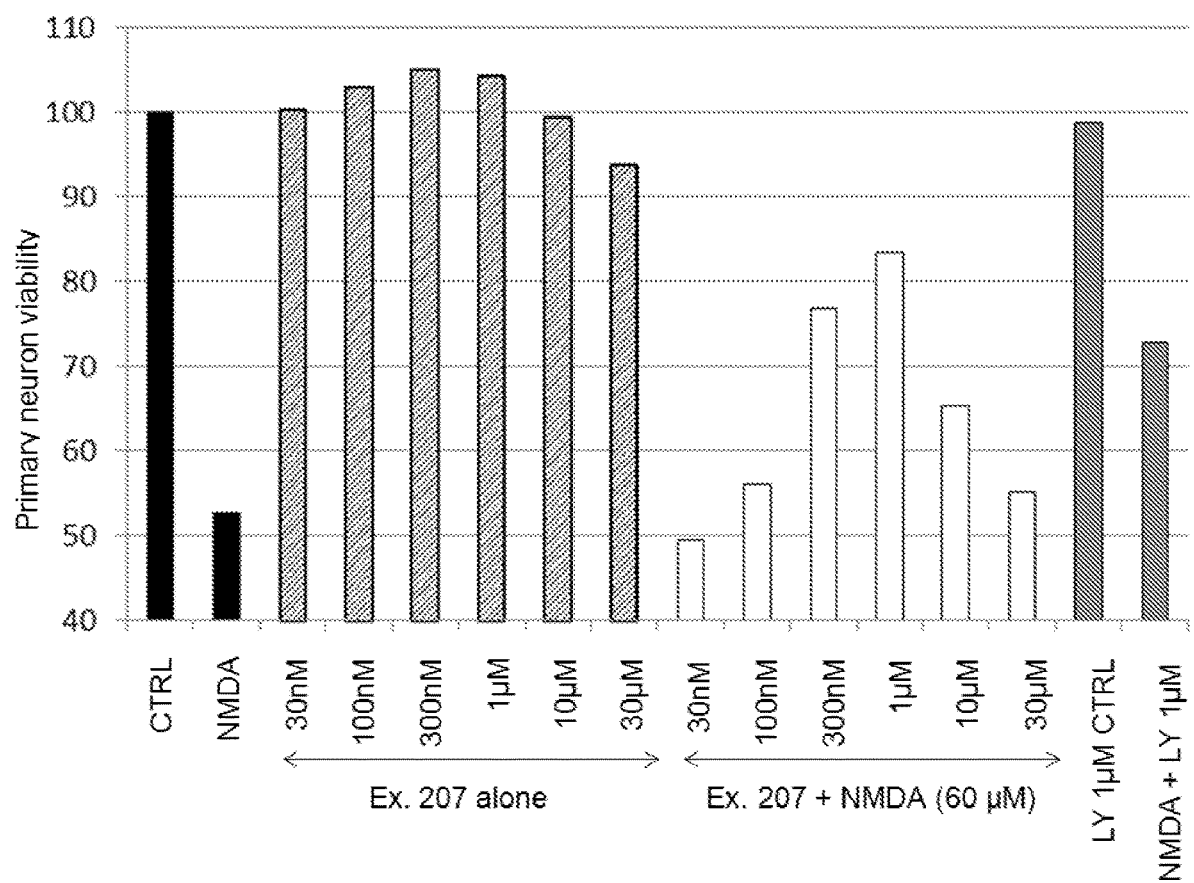

Wang et al., "Facile synthesis of 1,4-benzodiazepin-3-ones from o-bromobenzylamines and amino acids via a cascade coupling/condensation process", *Tetrahedron*, Elsevier Science Publishers, Amsterdam, NL, XP026652574, vol. 65(44), pp. 8956-8960 (Oct. 31, 2009).

Wang et al., "Facile synthesis of 6,12b-diaza-dibenzo[a,h]azulen-7-ones and benzo[f]pyrrolo[1,2-a][1,4]diazepin-4-ones via CuI/1-proline catalyzed intramolecular N-arylation," *Tetrahedron Letters*, 52:541-543, 2011.

Wang et al., "Synthesis of benzo [6,7] [1,4] diazepino [1,2-b] indazol-7(6H)-ones and benzo [f] pyrazolo [1,5-a] [1,4] diazepin-4-one s via CuI/1-proline catalyzed intramolecular N2-arylation", *Tetrahedron Letters*, XP055242623, vol. 56(8), pp. 1030-1033, (Feb. 1, 2015).

\* cited by examiner

SUBSTITUTED TRICYCLIC 1,4-BENZODIAZEPINONE DERIVATIVES AS ALLOSTERIC MODULATORS OF GROUP II METABOTROPIC GLUTAMATE RECEPTORS

This application is a national phase application under 35 U.S.C. § 371 of International Application No. PCT/GB2016/053550, filed Nov. 11, 2016, which claims benefit of European Application No. 15194611.8, filed Nov. 13, 2015, the entire contents of each of which are hereby incorporated by reference.

The present invention provides novel tricyclic 1,4-benzodiazepinone derivatives of the general formula (I) and pharmaceutical compositions containing them. Moreover, the compounds of formula (I) and the pharmaceutical compositions containing them are provided for use in the treatment and/or prophylaxis of conditions associated with altered glutamatergic signalling and/or functions, and/or conditions which can be affected by alteration of glutamate level or signalling in mammals. The tricyclic 1,4-benzodiazepinone derivatives of formula (I) can act as modulators of nervous system receptors sensitive to glutamate, in particular as modulators of metabotropic glutamate receptors (mGluRs), which makes them particularly suitable for the treatment and/or prophylaxis of acute and chronic neurological and/or psychiatric disorders. The present invention further provides tricyclic 1,4-benzodiazepinone derivatives of formula (I) that are modulators of metabotropic glutamate receptors (mGluRs), particularly positive allosteric modulators of mGluRs, and more specifically positive allosteric modulators of mGluR3.

Glutamatergic pathways have been shown to be involved in the physiopathology of a number of neuronal damages and injuries. Many nervous system disorders including epilepsy and chronic or acute degenerative processes such as for example Alzheimer's disease, Huntington's disease, Parkinson's disease and amyotrophic lateral sclerosis (Mattson M P., *Neuromolecular Med.*, 3(2), 65-94, 2003), but also AIDS-induced dementia, multiple sclerosis, spinal muscular atrophy, retinopathy, stroke, ischemia, hypoxia, hypoglycaemia and various traumatic brain injuries, involve neuronal cell death caused by imbalanced levels of glutamate. It has also been shown that drug-induced neurotoxicity, for example neurotoxic effects of methamphetamine (METH) on striatal dopaminergic neurons, could be mediated by over-stimulation of the glutamate receptors (Stephans S E and Yamamoto B K, *Synapse* 17(3), 203-9, 1994). Antidepressant and anxiolytic-like effects of compounds acting on glutamate have also been observed in mice, suggesting that glutamatergic transmission is implicated in the pathophysiology of affective disorders such as major depression, schizophrenia and anxiety (Palucha A et al., *Pharmacol. Ther.* 115(1), 116-47, 2007; Cryan J F et al., *Eur. J. Neurosc.* 17(11), 2409-17, 2003; Conn P J et al., Trends Pharmacol. Sci. 30(1), 25-31, 2009). Consequently, any compound able to modulate glutamatergic signalling or function could constitute a promising therapeutic agent for many disorders of the nervous system.

Moreover, compounds modulating glutamate level or signalling may be of great therapeutic value for diseases and/or disorders not directly mediated by glutamate levels and/or glutamate receptors malfunctioning, but which could be affected by alteration of glutamate levels or signalling.

In the central nervous system (CNS), L-glutamate (Glu) is the main excitatory neurotransmitter and is referred to as an excitatory amino-acid (EAA), and gamma-aminobutyric acid (GABA) is the main inhibitory neurotransmitter. The balance between excitation and inhibition is of utmost importance to CNS functions, and dysfunctions of either of the two can be related to various neurodegenerative or neurological disorders.

Glutamate is ubiquitously distributed in the nervous system in high concentrations, especially in the brain and spinal cord of mammals, where it is working at a variety of excitatory synapses and is thus involved in virtually all physiological functions such as motor control, vision, central control of heart, and processes of learning and memory. However, a large number of studies have established that cellular communication involving glutamate can also lead to a mechanism of cell destruction. This combination of neuroexcitatory activities and neurotoxic properties is called excitotoxicity.

Glutamate operates through two classes of receptors (Bräuner-Osborne H et al., *J. Med. Chem.* 43(14), 2609-45, 2000). The first class is directly coupled to the opening of cation channels in the cellular membrane of the neurons, namely the ionotropic glutamate receptors (iGluRs). The iGluRs are divided in three subtypes, which are named according to the depolarizing action of their selective agonists: N-methyl-D-aspartate (NMDA), α-amino-3-hydroxy-5-methylisoxazole-4-propionic acid (AMPA), and kainic acid (KA). The second class consists of G-protein coupled receptors (GPCRs) called metabotropic glutamate receptors (mGluRs). These mGluRs are localized both pre- and post-synaptically. They are coupled to multiple second messenger systems and their roles is to regulate the activity of ionic channels or enzymes producing second messengers via G-proteins binding the GTP (Nicoletti F et al.; *Neuropharmacol.*, 60(7-8), 1017-41, 2011). Although they are generally not directly involved in rapid synaptic transmission, the mGluRs modulate the efficacy of the synapses by regulating either the post-synaptic channels and their receptors, or the pre-synaptic release or recapture of glutamate. Therefore, mGluRs play an important role in a variety of physiological processes such as long-term potentiation and long-term depression of synaptic transmission, regulation of baroreceptive reflexes, spatial learning, motor learning, and postural and kinetic integration.

To date, eight mGluRs have been cloned and classified in three groups according to their sequence homologies, pharmacological properties and signal transduction mechanisms. Group I is constituted of mGluR1 and mGluR5, group II of mGluR2 and mGluR3 and group III of mGluR4, mGluR6, mGluR7 and mGluR8 (Schoepp D D et al., *Neuropharmacology*, 38(10), 1431-76, 1999).

mGluR modulators can be classified in two families depending on their site of interaction with the receptor (see Bräuner-Osborne H et al., *J. Med. Chem.* 43(14), 2609-45, 2000 for review). The first family consists of orthosteric modulators (or competitive modulators) able to interact with the glutamate binding-site of the mGluRs, which is localized in the large extra-cellular N-terminal part of the receptor (about 560 amino acids). Therefore, they are glutamate analogs and constitute a highly polar family of ligand. Examples of orthosteric modulators are S-DHPG or LY-367385 for group I mGluRs, LY-354740 or LY-379268 for group II mGluRs and ACPT-I or L-AP4 for group III mGluRs. The second family of mGluRs modulators consists of allosteric modulators that interact with a topologically different site from the orthosteric site of the receptor (see Bridges T M et al., *ACS Chem Biol*, 3(9), 530-41, 2008 for review). Their action results in a modulation of the effects induced by the endogenous ligand glutamate. Examples of such allosteric modulators are Ro-674853, MPEP or JNJ 16259685 for group I mGluRs and CBiPES, BINA or LY487379 for group II mGluRs and PHCCC, VUC$_{155041}$ or VU0359516 for group III mGluRs.

By interacting with allosteric binding sites, mGluR allosteric modulators stabilize a receptor conformation and equilibrium shift that increases or decreases the affinity and/or efficacy of an orthosteric agonist of the receptor, without activating the receptor on its own (Bridges T M et al., *ACS Chem Biol*, 3(9), 530-41, 2008). Such modulators are respectively termed positive allosteric modulators (PAMs) and negative allosteric modulators (NAMs).

Group II mGluR activation or potentiation has been shown to be associated with positive effects in animal models of anxiety (Swanson C J., *Nat Rev Drug Discov*, 4, 131-44, 2005), schizophrenia (Conn P J et al., *Trends in Pharmacol Sci*, 30, 25-31, 2009), memory-deficit of schizophrenia (Pitsikas N and Markou A, *Neuropharmacology*, 2014, 85, 27-35), drug-addiction (Adewale A S et al.; *J Pharmacol Exp Ther*, 318, 922-31, 2006—Justinova Z et al., *Biol. Psychiatry*, 2015), chronic pain (Jones C K et al.; *Neuropharmacology*, 49 (Suppl 1), 206-18, 2005), epilepsy (Caulder E H et al., *Epilepsy Res.*, 2014, 108(2), 171-81), Huntington's disease (Reiner A et al, *Brain Research*, 2012, 161-72—Reiner A et al, *Neurobiology of disease*, 2012, 47, 75-91), Parkinson's disease (Battaglia G et al, *PLoS ONE*, 2009, 4(8), e6591—Battaglia G et al., *Neuropharmacology*, 2003, 45, 155-66) or ALS (Battaglia G et al., *Neurobiology of disease*, 2015, 74, 126-36).

Neuroprotective role of mGluR3 was recently described by the teams of Ferdinando Nicoletti in Italy (Corti C, et al., *J. Neurosci*, 2007, 27(31), 8297-308. Battaglia G, et al., *PLoS ONE*, 2009, 4(8), e6591). They showed that activation of mGluR3, but not mGluR2 that seems to be neurotoxic (Caraci F. et al., *Mol. Pharmacol.*, 2011, 79(3), 618-26.), can 1) induce production of growth factors such as transforming growth factor β (TGF-β) and glial cell line-derived neurotrophic factor (GDNF), 2) exert neuroprotection in vitro in models of excitotoxicity and 3) protect nigro-striatal neurons in the experimental animal model of parkinsonism induced by 1-methyl-4-phenyl-1,2,3-6-tetrahydropyiridine (MPTP). Great potential of GDNF for both symptomatic and neuroprotective treatments of Parkinson's disease (PD) has already been demonstrated (Vastag, B., *Nature*, 2010, 466 (7309), 916-8). For example, it was shown that GDNF together with TGF-β exert neuroprotection in the MPTP mice model (Schober A., et al. *Neurobiol Dis*, 2006, 25(2), 378-91) or that intraputaminal infusion of GDNF attenuates parkinsonian symptoms in two clinical trials (Gill S S., *Nat Med*, 2003, 9(5), 589-95 and Slevin J T. *J. Neurosurg.* 2005, 102, 216-222). Moreover, GDNF was also shown to exert positive effects in other neurodegenerative disorders such as Alzheimer's disease (Revilla S et al., *CNS Neurosci. Ther.*, 2014, 20(11), 961-72—Pertusa M et al., *Neurobiology Aging*, 2008, 29(9), 1366-79) or Huntington's disease (Ebert A B et al., *Exp. Neurol.*, 2010, 224(1), 155-62).

Several examples of group II mGluR PAMs have already been described in research articles and patent literature (see Trabanco A A, et al., *Curr Med Chem*, 2011, 18(1), 47-68 for review). These molecules exhibit either dual mGluR2/mGluR3 PAM activity, or selective mGluR2 PAM activity. However, there is still an urgent need for novel mGluR3 PAMs, particularly PAMs that are selective for mGluR3 over mGluR2.

Syntheses of various specific pyrrolo-1,4-benzodiazepinone, imidazolo-1,4-benzodiazepinone, pyrrolidino-1,4-benzodiazepinone and pyrazolo-1,4-benzodiazepinone compounds are described in five articles dealing with organic chemistry only: Wang H et al., *Tetrahedron*, 2009, 65, 8956-8960; Wang H J et al., *Tet. Lett.*, 2011, 52, 541-543; Norris D et al., *Tet. Lett.*, 2001, 42, 4297-4299; Faigl F et al., *Chirality*, 2012, 24, 532-542 and Hong-Jun Wang et al., *Tetrahedron Letters*, 56(8), 2015, 1030-1033. Further compounds are described in Anzini Maurizio, *Medicinal Chemistry Research*, 3(4), 1993, 249-256. The relevant compounds described in these publications are not disclosed to exhibit any biological activity.

Bertelli et al., in *Il Farmaco*, 53(4), 1998, 305-311 discloses the synthesis of 1,2,3-triazolo[1,5-a][1,4]benzodiazepine derivatives. Compound 3a in this reference was tested for its affinity towards benzodiazepine receptors. However, only weak binding affinity was shown and this was not shown to have any therapeutic effect. The reference furthermore teaches that the N-methylation of the diazepine ring lowers the receptor binding, thus teaching away from this invention.

Certain pyrrolo-1,4-benzodiazepinone compounds and analogues are described in US 2008/161292 and in Miyashiro J et al., *Bioorg. Med. Chem. Lett.* 2009, 19, 4050-4054. A series of pyrazolo-1,4-benzodiazepines is furthermore described in U.S. Pat. Nos. 4,130,716 and 4,153,799. Certain imidazodiazepine derivatives are disclosed in U.S. Pat. No. 4,863,920.

WO 2014/117919 discloses substituted pyridine derivatives as positive allosteric modulators for modulating metabotropic glutamate receptor subtype 3 (mGluR3). The disclosed compounds are structurally remote from those of this invention.

The present invention provides novel compounds that exhibit highly potent positive allosteric modulator activity on mGluR3 as well as advantageous pharmacokinetic properties, which renders them particularly suitable as therapeutic agents. The invention further provides compounds that are mGluR3 PAMs showing an advantageous selectivity for mGluR3 over mGluR2. The present invention thus solves the problem of providing improved means and methods for the medical intervention in diseases, disorders and conditions associated with altered glutamatergic signalling and/or functions as well as conditions which can be affected by alteration of glutamate level or signalling, including in particular the treatment and/or prophylaxis of acute and chronic neurological and/or psychiatric disorders.

Accordingly, in a first aspect, the present invention provides a compound of the general formula (I):

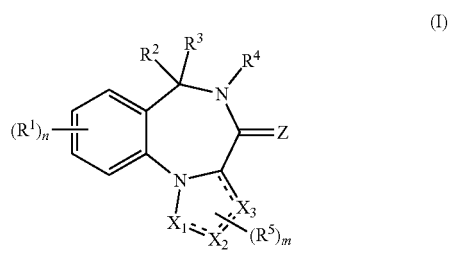

or a pharmaceutically acceptable salt, solvate or prodrug thereof, for use as a medicament.

In formula (I), the ring atoms $X_1$, $X_2$ and $X_3$ are each independently C or N.

Each ===== is independently a single bond or a double bond, wherein at least one of any two adjacent bonds ===== is a single bond.

Z is O, S or N(—$R^Z$).

$R^Z$ is selected from hydrogen, $C_1$-$C_{10}$ alkyl, $C_2$-$C_{10}$ alkenyl, $C_2$-$C_{10}$ alkynyl, aryl, heteroaryl, cycloalkyl, and heterocycloalkyl, wherein said aryl, said heteroaryl, said cycloalkyl, and said heterocycloalkyl are each optionally substituted with one or more groups independently selected from $C_1$-$C_{10}$ alkyl, $C_2$-$C_{10}$ alkenyl, $C_2$-$C_{10}$ alkynyl, halogen, $C_1$-$C_{10}$ haloalkyl, —CN, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), cycloalkyl, and heterocycloalkyl, and further wherein, if $R^Z$ is $C_1$-$C_{10}$ alkyl, $C_2$-$C_{10}$ alkenyl or $C_2$-$C_{10}$ alkynyl, then said alkyl, said alkenyl or said alkynyl is optionally substituted with one or more groups independently selected from halogen, $C_1$-$C_{10}$ haloalkyl, —CN, —OH, —O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), cycloalkyl, and heterocycloalkyl.

Each $R^1$ is independently a group -$L^1$-$R^{11}$.

Each $L^1$ is independently selected from a bond, $C_1$-$C_{10}$ alkylene, $C_2$-$C_{10}$ alkenylene, and $C_2$-$C_{10}$ alkynylene, wherein said alkylene, said alkenylene and said alkynylene are each optionally substituted with one or more groups independently selected from halogen, $C_1$-$C_{10}$ haloalkyl, —CN, —$OR^{12}$, —$NR^{12}R^{12}$, —$COR^{12}$, —$COOR^{12}$, —$OCOR^{12}$, —$CONR^{12}R^{12}$, —$NR^{12}COR^{12}$, —$SR^{12}$, —$SOR^{12}$, —$SO_2R^{12}$, —$SO_2NR^{12}R^{12}$, and —$NR^{12}SO_2R^{12}$, and further wherein one or more —$CH_2$— units comprised in said alkylene, said alkenylene or said alkynylene are each optionally replaced by a group independently selected from —O—, —$NR^{12}$—, —CO—, —S—, —SO—, and —$SO_2$—.

Each $R^{11}$ is independently selected from aryl, heteroaryl, cycloalkyl, heterocycloalkyl, cycloalkenyl, heterocycloalkenyl, halogen, $C_1$-$C_{10}$ haloalkyl, —CN, $C_1$-$C_{10}$ alkyl, $C_2$-$C_{10}$ alkenyl, $C_2$-$C_{10}$ alkynyl, —$NR^{12}R^{12}$, —$OR^{12}$, —$SR^{12}$, —$SOR^{12}$, —$SO_2R^{12}$, —$COR^{12}$, —$COOR^{12}$, —$OCOR^{12}$, —$CONR^{12}R^{12}$, —$NR^{12}COR^{12}$, —$SO_2NR^{12}R^{12}$, —$NR^{12}SO_2R^{12}$, and —$SO_3R^{12}$, wherein said aryl, said heteroaryl, said cycloalkyl, said heterocycloalkyl, said cycloalkenyl and said heterocycloalkenyl are each optionally substituted with one or more groups independently selected from halogen, $C_1$-$C_{10}$ haloalkyl, —CN, $C_1$-$C_{10}$ alkyl, $C_2$-$C_{10}$ alkenyl, $C_2$-$C_{10}$ alkynyl, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), —CHO, —CO($C_1$-$C_{10}$ alkyl), —COOH, tetrazolyl, —COO($C_1$-$C_{10}$ alkyl), —OCO($C_1$-$C_{10}$ alkyl), —CO—$NH_2$, —CO—NH($C_1$-$C_{10}$ alkyl), —CO—N($C_1$-$C_{10}$ alkyl)($C_1$-$C_{10}$ alkyl), —NH—CO—($C_1$-$C_{10}$ alkyl), —N($C_1$-$C_{10}$ alkyl)-CO—($C_1$-$C_{10}$ alkyl), —$SO_2$—$NH_2$, —$SO_2$—NH($C_1$-$C_{10}$ alkyl), —$SO_2$—N($C_1$-$C_{10}$ alkyl)($C_1$-$C_{10}$ alkyl), —NH—$SO_2$—($C_1$-$C_{10}$ alkyl), —N($C_1$-$C_{10}$ alkyl)-$SO_2$—($C_1$-$C_{10}$ alkyl), cycloalkyl, heterocycloalkyl, aryl, heteroaryl, and -$L^{11}$-$R^{13}$, and further wherein, if $R^{11}$ is $C_1$-$C_{10}$ alkyl, $C_2$-$C_{10}$ alkenyl or $C_2$-$C_{10}$ alkynyl, then said alkyl, said alkenyl or said alkynyl is optionally substituted with one or more groups independently selected from halogen, $C_1$-$C_{10}$ haloalkyl, —CN, —OH, —O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), —CHO, —CO($C_1$-$C_{10}$ alkyl), —COOH, tetrazolyl, —COO($C_1$-$C_{10}$ alkyl), —OCO($C_1$-$C_{10}$ alkyl), —CO—$NH_2$, —CO—NH($C_1$-$C_{10}$ alkyl), —CO—N($C_1$-$C_{10}$ alkyl)($C_1$-$C_{10}$ alkyl), —NH—CO—($C_1$-$C_{10}$ alkyl), —N($C_1$-$C_{10}$ alkyl)-CO—($C_1$-$C_{10}$ alkyl), —$SO_2$—$NH_2$, —$SO_2$—NH($C_1$-$C_{10}$ alkyl), —$SO_2$—N($C_1$-$C_{10}$ alkyl)($C_1$-$C_{10}$ alkyl), —NH—$SO_2$—($C_1$-$C_{10}$ alkyl), —N($C_1$-$C_{10}$ alkyl)-$SO_2$—($C_1$-$C_{10}$ alkyl), cycloalkyl, heterocycloalkyl, aryl, heteroaryl, and -$L^{11}$-$R^{13}$.

Each $R^{12}$ is independently selected from hydrogen, $C_1$-$C_{10}$ alkyl, $C_2$-$C_{10}$ alkenyl, $C_2$-$C_{10}$ alkynyl, aryl, heteroaryl, cycloalkyl, and heterocycloalkyl, wherein said aryl, said heteroaryl, said cycloalkyl, and said heterocycloalkyl are each optionally substituted with one or more groups independently selected from $C_1$-$C_{10}$ alkyl, $C_2$-$C_{10}$ alkenyl, $C_2$-$C_{10}$ alkynyl, halogen, $C_1$-$C_{10}$ haloalkyl, —CN, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), cycloalkyl, and heterocycloalkyl, wherein if $R^{12}$ is $C_1$-$C_{10}$ alkyl, $C_2$-$C_{10}$ alkenyl or $C_2$-$C_{10}$ alkynyl, then said alkyl, said alkenyl or said alkynyl is optionally substituted with one or more groups independently selected from halogen, $C_1$-$C_{10}$ haloalkyl, —CN, —OH, —O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), cycloalkyl, and heterocycloalkyl, and further if two groups $R^{12}$ are attached to the same nitrogen atom, then these two groups $R^{12}$ may also together form a $C_2$-$C_8$ alkylene (so that the resulting group is a 3- to 9-membered nitrogen-containing heterocycloalkyl ring which is formed from the two groups $R^{12}$ and the nitrogen atom that they are attached to).

Each $L^{11}$ is independently selected from a bond, $C_1$-$C_{10}$ alkylene, $C_2$-$C_{10}$ alkenylene, and $C_2$-$C_{10}$ alkynylene, wherein one or more —$CH_2$— units comprised in said alkylene, said alkenylene or said alkynylene are each optionally replaced by a group independently selected from —O—, —NH—, —N($C_1$-$C_{10}$ alkyl)-, —CO—, —S—, —SO—, and —$SO_2$—.

Each $R^{13}$ is independently selected from aryl, heteroaryl, cycloalkyl, heterocycloalkyl, cycloalkenyl, heterocycloalkenyl, halogen, $C_1$-$C_{10}$ haloalkyl, —CN, $C_1$-$C_{10}$ alkyl, $C_2$-$C_{10}$ alkenyl, $C_2$-$C_{10}$ alkynyl, —$NH_2$, —NH($C_1$-$C_{10}$ alkyl), —N($C_1$-$C_{10}$ alkyl)($C_1$-$C_{10}$ alkyl), —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —SH, and —S($C_1$-$C_{10}$ alkyl), wherein said aryl, said heteroaryl, said cycloalkyl, said heterocycloalkyl, said cycloalkenyl and said heterocycloalkenyl are each optionally substituted with one or more groups independently selected from halogen, $C_1$-$C_{10}$ haloalkyl, —CN, $C_1$-$C_{10}$ alkyl, $C_2$-$C_{10}$ alkenyl, $C_2$-$C_{10}$ alkynyl, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), cycloalkyl, and heterocycloalkyl.

n is an integer of 0 to 4.

$R^2$ and $R^3$ are mutually linked to form, together with the carbon atom that they are attached to, a cycloalkyl or a heterocycloalkyl; or $R^2$ and $R^3$ are each independently selected from hydrogen, halogen, $C_1$-$C_{10}$ haloalkyl, $C_1$-$C_{10}$ alkyl, $C_2$-$C_{10}$ alkenyl, $C_2$-$C_{10}$ alkynyl, —OH, —O($C_1$-$C_{10}$ alkyl), —SH, —S($C_1$-$C_{10}$ alkyl), —SO—($C_1$-$C_{10}$ alkyl), —$SO_2$—($C_1$-$C_{10}$ alkyl), —CN, aryl, heteroaryl, cycloalkyl, and heterocycloalkyl, wherein said aryl, said heteroaryl, said cycloalkyl, and said heterocycloalkyl are each optionally substituted with one or more groups independently selected from $C_1$-$C_{10}$ alkyl, $C_2$-$C_{10}$ alkenyl, $C_2$-$C_{10}$ alkynyl, halogen, $C_1$-$C_{10}$ haloalkyl, —CN, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —NH$_2$, —NH(C$_1$-C$_{10}$ alkyl), —N(C$_1$-C$_{10}$ alkyl)(C$_1$-C$_{10}$ alkyl), cycloalkyl, and heterocycloalkyl, and further wherein, if one or both of R$^2$ and R$^3$ is/are C$_1$-C$_{10}$ alkyl, C$_2$-C$_{10}$ alkenyl or C$_2$-C$_{10}$ alkynyl, then said alkyl, said alkenyl or said alkynyl is optionally substituted with one or more groups independently selected from halogen, C$_1$-C$_{10}$ haloalkyl, —CN, —OH, —O(C$_1$-C$_{10}$ alkyl), —NH$_2$, —NH(C$_1$-C$_{10}$ alkyl), —N(C$_1$-C$_{10}$ alkyl)(C$_1$-C$_{10}$ alkyl), cycloalkyl, and heterocycloalkyl; or R$^2$ and R$^3$ together form a divalent group selected from =O, =S, =NH and =N(C$_1$-C$_{10}$ alkyl).

R$^4$ is selected from C$_1$-C$_{10}$ alkyl, C$_2$-C$_{10}$ alkenyl, C$_2$-C$_{10}$ alkynyl, cycloalkyl, and heterocycloalkyl, wherein said alkyl, said alkenyl and said alkynyl are each optionally substituted with one or more groups independently selected from halogen, C$_1$-C$_{10}$ haloalkyl, —O—(C$_1$-C$_{10}$ haloalkyl), —CN, —OH, —O(C$_1$-C$_{10}$ alkyl), and cycloalkyl, and further wherein, if R$^4$ is cycloalkyl or heterocycloalkyl, then said cycloalkyl or said heterocycloalkyl is optionally substituted with one or more groups independently selected from C$_1$-C$_{10}$ alkyl, C$_2$-C$_{10}$ alkenyl, C$_2$-C$_{10}$ alkynyl, halogen, C$_1$-C$_{10}$ haloalkyl, —CN, —OH, —O(C$_1$-C$_{10}$ alkyl), and cycloalkyl.

Each R$^5$ is independently a group -L$^5$-R$^{51}$.

Each L$^5$ is independently selected from a bond, C$_1$-C$_{10}$ alkylene, C$_2$-C$_{10}$ alkenylene, and C$_2$-C$_{10}$ alkynylene, wherein said alkylene, said alkenylene and said alkynylene are each optionally substituted with one or more groups independently selected from halogen, C$_1$-C$_{10}$ haloalkyl, —CN, —OR$^{52}$, —NR$^{52}$R$^{52}$, —COR$^{52}$, —COOR$^{52}$, —OCOR$^{52}$, —CONR$^{52}$R$^{52}$, —NR$^{52}$COR$^{52}$, —SR$^{52}$, —SOR$^{52}$, —SO$_2$R$^{52}$, —SO$_2$NR$^{52}$R$^{52}$, and —NR$^{52}$SO$_2$R$^{52}$, and further wherein one or more —CH$_2$— units comprised in said alkylene, said alkenylene or said alkynylene are each optionally replaced by a group independently selected from —O—, —NR$^{52}$—, —CO—, —S—, —SO—, and —SO$_2$—.

Each R$^{51}$ is independently selected from aryl, heteroaryl, cycloalkyl, heterocycloalkyl, cycloalkenyl, heterocycloalkenyl, halogen, C$_1$-C$_{10}$ haloalkyl, —CN, C$_1$-C$_{10}$ alkyl, C$_2$-C$_{10}$ alkenyl, C$_2$-C$_{10}$ alkynyl, —NR$^{52}$R$^{52}$, —OR$^{52}$, —SR$^{52}$, —SOR$^{52}$, —SO$_2$R$^{52}$, —COR$^{52}$, —COOR$^{52}$, —OCOR$^{52}$, —CONR$^{52}$R$^{52}$, —NR$^{52}$COR$^{52}$, —SO$_2$NR$^{52}$R$^{52}$, —NR$^{52}$SO$_2$R$^{52}$, and —SO$_3$R$^{52}$, wherein said aryl, said heteroaryl, said cycloalkyl, said heterocycloalkyl, said cycloalkenyl and said heterocycloalkenyl are each optionally substituted with one or more groups independently selected from halogen, C$_1$-C$_{10}$ haloalkyl, —CN, C$_1$-C$_{10}$ alkyl, C$_2$-C$_{10}$ alkenyl, C$_2$-C$_{10}$ alkynyl, —OH, —O(C$_1$-C$_{10}$ alkyl), —(C$_1$-C$_{10}$ alkylene)-OH, —(C$_1$-C$_{10}$ alkylene)-O(C$_1$-C$_{10}$ alkyl), —NH$_2$, —NH(C$_1$-C$_{10}$ alkyl), —N(C$_1$-C$_{10}$ alkyl)(C$_1$-C$_{10}$ alkyl), —CHO, —CO(C$_1$-C$_{10}$ alkyl), —COOH, tetrazolyl, —COO(C$_1$-C$_{10}$ alkyl), —OCO(C$_1$-C$_{10}$ alkyl), —CO—NH$_2$, —CO—NH(C$_1$-C$_{10}$ alkyl), —CO—N(C$_1$-C$_{10}$ alkyl)(C$_1$-C$_{10}$ alkyl), —NH—CO—(C$_1$-C$_{10}$ alkyl), —N(C$_1$-C$_{10}$ alkyl)-CO—(C$_1$-C$_{10}$ alkyl), —SO$_2$—NH$_2$, —SO$_2$—NH(C$_1$-C$_{10}$ alkyl), —SO$_2$—N(C$_1$-C$_{10}$ alkyl)(C$_1$-C$_{10}$ alkyl), —NH—SO$_2$—(C$_1$-C$_{10}$ alkyl), —N(C$_1$-C$_{10}$ alkyl)-SO$_2$—(C$_1$-C$_{10}$ alkyl), cycloalkyl, heterocycloalkyl, aryl, heteroaryl, and -L$^{51}$-R$^{53}$, and further wherein, if R$^{51}$ is C$_1$-C$_{10}$ alkyl, C$_2$-C$_{10}$ alkenyl or C$_2$-C$_{10}$ alkynyl, then said alkyl, said alkenyl or said alkynyl is optionally substituted with one or more groups independently selected from halogen, C$_1$-C$_{10}$ haloalkyl, —CN, —OH, —O(C$_1$-C$_{10}$ alkyl), —NH$_2$, —NH(C$_1$-C$_{10}$ alkyl), —N(C$_1$-C$_{10}$ alkyl)(C$_1$-C$_{10}$ alkyl), —CHO, —CO(C$_1$-C$_{10}$ alkyl), —COOH, tetrazolyl, —COO(C$_1$-C$_{10}$ alkyl), —OCO(C$_1$-C$_{10}$ alkyl), —CO—NH$_2$, —CO—NH(C$_1$-C$_{10}$ alkyl), —CO—N(C$_1$-C$_{10}$ alkyl)(C$_1$-C$_{10}$ alkyl), —NH—CO—(C$_1$-C$_{10}$ alkyl), —N(C$_1$-C$_{10}$ alkyl)-CO—(C$_1$-C$_{10}$ alkyl), —SO$_2$—NH$_2$, —SO$_2$—NH(C$_1$-C$_{10}$ alkyl), —SO$_2$—N(C$_1$-C$_{10}$ alkyl)(C$_1$-C$_{10}$ alkyl), —NH—SO$_2$—(C$_1$-C$_{10}$ alkyl), —N(C$_1$-C$_{10}$ alkyl)-SO$_2$—(C$_1$-C$_{10}$ alkyl), cycloalkyl, heterocycloalkyl, aryl, heteroaryl, and -L$^{51}$-R$^{53}$.

Each R$^{52}$ is independently selected from hydrogen, C$_1$-C$_{10}$ alkyl, C$_2$-C$_{10}$ alkenyl, C$_2$-C$_{10}$ alkynyl, aryl, heteroaryl, cycloalkyl, and heterocycloalkyl, wherein said aryl, said heteroaryl, said cycloalkyl, and said heterocycloalkyl are each optionally substituted with one or more groups independently selected from C$_1$-C$_{10}$ alkyl, C$_2$-C$_{10}$ alkenyl, C$_2$-C$_{10}$ alkynyl, halogen, C$_1$-C$_{10}$ haloalkyl, —CN, —OH, —O(C$_1$-C$_{10}$ alkyl), —(C$_1$-C$_{10}$ alkylene)-OH, —(C$_1$-C$_{10}$ alkylene)-O(C$_1$-C$_{10}$ alkyl), —NH$_2$, —NH(C$_1$-C$_{10}$ alkyl), —N(C$_1$-C$_{10}$ alkyl)(C$_1$-C$_{10}$ alkyl), cycloalkyl, and heterocycloalkyl, wherein if R$^{52}$ is C$_1$-C$_{10}$ alkyl, C$_2$-C$_{10}$ alkenyl or C$_2$-C$_{10}$ alkynyl, then said alkyl, said alkenyl or said alkynyl is optionally substituted with one or more groups independently selected from halogen, C$_1$-C$_{10}$ haloalkyl, —CN, —OH, —O(C$_1$-C$_{10}$ alkyl), —NH$_2$, —NH(C$_1$-C$_{10}$ alkyl), —N(C$_1$-C$_{10}$ alkyl)(C$_1$-C$_{10}$ alkyl), cycloalkyl, and heterocycloalkyl, and further if two groups R$^{52}$ are attached to the same nitrogen atom, then these two groups R$^{52}$ may also together form a C$_2$-C$_8$ alkylene (so that the resulting group is a 3- to 9-membered nitrogen-containing heterocycloalkyl ring which is formed from the two groups R$^{52}$ and the nitrogen atom that they are attached to).

Each L$^{51}$ is independently selected from a bond, C$_1$-C$_{10}$ alkylene, C$_2$-C$_{10}$ alkenylene, and C$_2$-C$_{10}$ alkynylene, wherein one or more —CH$_2$— units comprised in said alkylene, said alkenylene or said alkynylene are each optionally replaced by a group independently selected from —O—, —NH—, —N(C$_1$-C$_{10}$ alkyl)-, —CO—, —S—, —SO—, and —SO$_2$—.

Each R$^{53}$ is independently selected from aryl, heteroaryl, cycloalkyl, heterocycloalkyl, cycloalkenyl, heterocycloalkenyl, halogen, C$_1$-C$_{10}$ haloalkyl, —CN, C$_1$-C$_{10}$ alkyl, C$_2$-C$_{10}$ alkenyl, C$_2$-C$_{10}$ alkynyl, —NH$_2$, —NH(C$_1$-C$_{10}$ alkyl), —N(C$_1$-C$_{10}$ alkyl)(C$_1$-C$_{10}$ alkyl), —OH, —O(C$_1$-C$_{10}$ alkyl), —(C$_1$-C$_{10}$ alkylene)-OH, —(C$_1$-C$_{10}$ alkylene)-O(C$_1$-C$_{10}$ alkyl), —SH, and —S(C$_1$-C$_{10}$ alkyl), wherein said aryl, said heteroaryl, said cycloalkyl, said heterocycloalkyl, said cycloalkenyl and said heterocycloalkenyl are each optionally substituted with one or more groups independently selected from halogen, C$_1$-C$_{10}$ haloalkyl, —CN, C$_1$-C$_{10}$ alkyl, C$_2$-C$_{10}$ alkenyl, C$_2$-C$_{10}$ alkynyl, —OH, —O(C$_1$-C$_{10}$ alkyl), —(C$_1$-C$_{10}$ alkylene)-OH, —(C$_1$-C$_{10}$ alkylene)-O(C$_1$-C$_{10}$ alkyl), —NH$_2$, —NH(C$_1$-C$_{10}$ alkyl), —N(C$_1$-C$_{10}$ alkyl)(C$_1$-C$_{10}$ alkyl), cycloalkyl, and heterocycloalkyl.

m is an integer of 0 to 3.

The present invention further provides novel compounds. In particular, in a second aspect, the invention relates to a compound of formula (I) or a pharmaceutically acceptable salt, solvate or prodrug thereof, as described and defined in the first aspect of the invention, with the proviso that the following compounds are excluded from formula (I):

5-allyl-3,3a,5,6-tetrahydro-1H-benzo[f]pyrrolo-[1,2-a][1,4]diazepin-4(2H)-one;

5-butyl-3,3a,5,6-tetrahydro-1H-benzo[f]pyrrolo-[1,2-a][1,4]diazepin-4(2H)-one;

5-methyl-5,6-dihydro-benzo[f]pyrrolo[1,2-a][1,4]diazepin-4-one; and 5-methyl-5,6-dihydro-3,5,10b-triaza-benzo[e]azulen-4-one.

It is preferred that the following compounds are also excluded from the second aspect of this invention:

5-methyl-4-oxo-5,6-dihydro-4H-1,2,5,10b-tetraaza-benzo[e]azulene-3-carboxylic acid ethyl ester;
5-methyl-5,6-dihydro-1,5,10b-triaza-benzo[e]azulen-4-one;
9-fluoro-5-methyl-5,6-dihydro-1,5,10b-triaza-benzo[e]azulen-4-one;
8-methoxy-5-methyl-5,6-dihydro-1,5,10b-triaza-benzo[e]azulen-4-one;
3-bromo-5-methyl-5,6-dihydro-1,5,10b-triaza-benzo[e]azulen-4-one;
5-(4-chloro-butyl)-5,6-dihydro-benzo[f]pyrrolo[1,2-a][1,4]diazepin-4-one; and
5-(4-chloro-butyl)-benzo[f]pyrrolo[1,2-a][1,4]diazepine-4,6-dione.

Even more preferably, 5-methyl-4-oxo-5,6-dihydro-4H-1,2,5,10b-tetraaza-benzo[e]azulene-3-carboxylic acid methyl ester is also excluded from the second aspect of the invention.

It is preferred that these compounds are also excluded from formula I:

5-methyl-4-oxo-5,6-dihydro-4H-1,2,5,10b-tetraaza-benzo[e]azulene-3-carboxylic acid ethyl ester;
5-methyl-5,6-dihydro-1,5,10b-triaza-benzo[e]azulen-4-one;
9-fluoro-5-methyl-5,6-dihydro-1,5,10b-triaza-benzo[e]azulen-4-one;
8-methoxy-5-methyl-5,6-dihydro-1,5,10b-triaza-benzo[e]azulen-4-one;
3-bromo-5-methyl-5,6-dihydro-1,5,10b-triaza-benzo[e]azulen-4-one;
5-(4-chloro-butyl)-5,6-dihydro-benzo[f]pyrrolo[1,2-a][1,4]diazepin-4-one; and
5-(4-chloro-butyl)-benzo[f]pyrrolo[1,2-a][1,4]diazepine-4,6-dione.

Even more preferably, 5-methyl-4-oxo-5,6-dihydro-4H-1,2,5,10b-tetraaza-benzo[e]azulene-3-carboxylic acid methyl ester is also excluded from formula I.

Moreover, the invention provides a pharmaceutical composition comprising a compound of formula (I), as defined in the first or second aspect of the invention, or a pharmaceutically acceptable salt, solvate or prodrug thereof, and optionally a pharmaceutically acceptable excipient.

The present invention furthermore relates to the compounds of formula (I) as well as their pharmaceutically acceptable salts, solvates and prodrugs, as defined in the first or second aspect of the invention, for use in the treatment and/or prophylaxis of conditions associated with altered glutamatergic signalling and/or functions, and/or conditions which can be affected by alteration of glutamate level or signalling. The invention likewise relates to a pharmaceutical composition comprising a compound of formula (I), as defined in the first or the second aspect of the invention, or a pharmaceutically acceptable salt, solvate or prodrug thereof, and optionally a pharmaceutically acceptable excipient, for use in the treatment and/or prophylaxis of conditions associated with altered glutamatergic signalling and/or functions, and/or conditions which can be affected by alteration of glutamate level or signalling.

The present invention also relates to the use of a compound of formula (I), as defined in the first or second aspect of the invention, or a pharmaceutically acceptable salt, solvate or prodrug thereof, for the preparation of a medicament for the treatment and/or prophylaxis of conditions associated with altered glutamatergic signalling and/or functions, and/or conditions which can be affected by alteration of glutamate level or signalling.

The invention further provides a method of treating and/or preventing conditions associated with altered glutamatergic signalling and/or functions, and/or conditions which can be affected by alteration of glutamate level or signalling in a mammal. Accordingly, the invention relates to a method of treating and/or preventing a disease or disorder, in particular a condition associated with altered glutamatergic signalling and/or functions, and/or a condition which can be affected by alteration of glutamate level or signalling, the method comprising the administration of a compound of formula (I), as defined in the first or second aspect of the invention, or a pharmaceutically acceptable salt, solvate or prodrug thereof, or a pharmaceutical composition comprising any of the aforementioned entities and optionally a pharmaceutically acceptable excipient, to a subject (preferably a mammal, more preferably a human) in need of such treatment or prevention.

The compounds of formula (I) as defined in the first or second aspect of the invention can be used as modulators of mGluRs of the nervous system, preferably as allosteric modulators of the mGluRs, and most preferably as positive allosteric modulators (PAMs) of mGluR3.

As noted above, the invention relates to the compounds of formula (I) as defined in the first or second aspect, their pharmaceutically acceptable salts, solvates and prodrugs, as well as pharmaceutical compositions comprising any of the aforementioned entities and optionally a pharmaceutically acceptable excipient, for use in the treatment and/or prophylaxis of conditions associated with altered glutamatergic signalling and/or functions, and/or conditions which can be affected by alteration of glutamate level or signalling.

The conditions associated with altered glutamatergic signalling and/or functions, and/or conditions which can be affected by alteration of glutamate level or signalling, that can be treated and/or prevented with the compounds or the pharmaceutical compositions according to the invention, include in particular: epilepsy, including newborn, infantile, childhood and adult syndromes, partial (localization-related) and generalized epilepsies, with partial and generalized, convulsive and non-convulsive seizures, with and without impairment of consciousness, and status epilepticus; Dementias and related diseases, including dementias of the Alzheimer's type (DAT), Alzheimer's disease, Pick's disease, vascular dementias, Lewy-body disease, dementias due to metabolic, toxic and deficiency diseases (including alcoholism, hypothyroidism, and vitamin B12 deficiency), AIDS-dementia complex, Creutzfeld-Jacob disease and atypical subacute spongiform encephalopathy; Parkinsonism and movement disorders, including Parkinson's disease, multiple system atrophy, progressive supranuclear palsy, corticobasal degeneration, hepatolenticular degeneration, chorea (including Huntington's disease and hemiballismus), athetosis, dystonias (including spasmodic torticollis, occupational movement disorder, Gilles de la Tourette syndrome), tardive or drug induced dyskinesias, tremor and myoclonus; Motor neuron disease or amyotrophic lateral sclerosis (ALS); Other neurodegenerative and/or hereditary disorders of the nervous system, including spinocerebrellar degenerations such as Friedrich's ataxia and other hereditary cerebellar ataxias, predominantly spinal muscular atrophies, hereditary neuropathies, and phakomatoses; Disorders of the peripheral nervous system, including trigeminal neuralgia, facial nerve disorders, disorders of the other cranial nerves, nerve root and plexus disorders, mononeuritis such as carpal tunnel syndrome and sciatica, hereditary and idiopathic peripheral neuropathies, inflammatory and toxic neuropathies; Multiple sclerosis and other demyelinating diseases of the nervous system; Infantile cerebral palsy (spastic), monoplegic, paraplegic or tetraplegic; Hemiplegia and hemiparesis, flaccid or spastic, and other paralytic syndromes; Cerebrovascular disorders, including subarachnoid hemorrhage, intracerebral hemorrhage, occlusion and stenosis of precerebral arteries, occlusion of cerebral arteries including thrombosis and embolism, brain ischemia, stroke, transient ischemic attacks, atherosclerosis, cerebrovascular dementias, aneurysms, cerebral deficits due to cardiac bypass surgery and grafting; Migraine, including classical migraine and variants such as cluster headache; Headache; Myoneural disorders including myasthenia gravis, acute muscle spasms, myopathies including muscular dystrophies, mytotonias and familial periodic paralysis; Disorders of the eye and visual pathways, including retinal disorders, and visual disturbances; Intracranial trauma/injury and their sequels; Trauma/injury to nerves and spinal cord and their sequels; Poisoning and toxic effects of nonmedicinal substances; Accidental poisoning by drugs, medicinal substances and biologicals acting on the central, peripheral and autonomic system; Neurological and psychiatric adverse effects of drugs, medicinal and biological substances; Disturbance of sphincter control and sexual function; Mental disorders usually diagnosed in infancy, childhood or adolescence, including: mental retardation, learning disorders, motor skill disorders, communication disorders, pervasive developmental disorders, attention deficit and disruptive behaviour disorders, feeding and eating disorders, TIC disorders, elimination disorders; Delirium and other cognitive disorders; Substance related disorders including: alcohol-related disorders, nicotine-related disorders, disorders related to cocaine, opioids, cannabis, hallucinogens and other drugs; Schizophrenia and other psychotic disorders; Mood disorders, including depressive disorders and bipolar disorders; Anxiety disorders, including panic disorders, phobias, obsessive-compulsive disorders, stress disorders, generalized anxiety disorders; Eating disorders, including anorexia and bulimia; Sleep disorders, including dyssomnias (insomnia, hypersomnia, narcolepsy, breathing related sleep disorder) and parasomnias; Medication-induced movement disorders (including neuroleptic-induced parkinsonism and tardive dyskinesia); Endocrine and metabolic diseases including diabetes, disorders of the endocrine glands, hypoglycaemia; Acute and chronic pain; Nausea and vomiting; Irritable bowel syndrome; or cancers.

In particular, the conditions associated with altered glutamatergic signalling and/or functions, and/or conditions which can be affected by alteration of glutamate level or signalling to be treated and/or prevented by the compounds or the pharmaceutical compositions according to the invention, include: Dementias and related diseases, including dementias of the Alzheimer's type (DAT), Alzheimer's disease, Pick's disease, vascular dementias, Lewy-body disease, dementias due to metabolic, toxic and deficiency diseases (including alcoholism, hypothyroidism, and vitamin B12 deficiency), AIDS-dementia complex, Creutzfeld-Jacob disease and atypical subacute spongiform encephalopathy; Parkinsonism and movement disorders, including Parkinson's disease, multiple system atrophy, progressive supranuclear palsy, corticobasal degeneration, hepatolenticular degeneration, chorea (including Huntington's disease and hemiballismus), athetosis, dystonias (including spasmodic torticollis, occupational movement disorder, Gilles de la Tourette syndrome), tardive or drug induced dyskinesias, tremor and myoclonus; Acute and chronic pain; Anxiety disorders, including panic disorders, phobias, obsessive-compulsive disorders, stress disorders and generalized anxiety disorders; Schizophrenia and other psychotic disorders; Mood disorders, including depressive disorders and bipolar disorders; Endocrine and metabolic diseases including diabetes, disorders of the endocrine glands and hypoglycaemia; or cancers.

The present invention particularly relates to a compound of formula (I) as defined in the first or second aspect, or a pharmaceutically acceptable salt, solvate or prodrug thereof, or a pharmaceutical composition comprising any of the aforementioned entities and optionally a pharmaceutically acceptable excipient, for use in the treatment or prevention/prophylaxis of Parkinson's disease.

The present invention furthermore provides a method for identifying an agent that binds to metabotropic glutamate receptor 3 (mGluR3), or in other words for determining the capability of one or more test agent(s) to bind to mGluR3, the method comprising the following steps: (a) contacting mGluR3 with a compound of formula (I) as defined in the first or second aspect of the invention, or a pharmaceutically acceptable salt, solvate or prodrug thereof, wherein the compound is labeled, preferably radio-labeled or fluorescence-labeled, under conditions that permit binding of the compound to mGluR3, thereby generating a bound, labeled compound; (b) detecting a signal that corresponds to the amount of the bound, labeled compound in the absence of test agent; (c) contacting the bound, labeled compound with a test agent; (d) detecting a signal that corresponds to the amount of the bound labeled compound in the presence of test agent; and (e) comparing the signal detected in step (d) to the signal detected in step (b) to determine whether the test agent binds to mGluR3. As will be understood, a substantially unchanged signal detected in step (d) in comparison with the signal detected in step (b) indicates that the test agent does not bind to the receptor, or binds to the receptor less strongly than the compound of formula (I). A decreased or increased signal detected in step (d) in comparison with the signal detected in step (b) indicates that the test agent binds to the receptor. Thus, agents that bind to mGluR3 can be identified among the test agents employed in this method. It will further be understood that it is preferred to remove unbound labeled compounds, e.g. in a washing step, before carrying out steps (b) and (d).

The mGluR3 that is used in the above method may be a human form, e.g., a protein of the accession number NP_000831.2, or a protein having at least 80% (preferably at least 90%, more preferably at least 95%, even more preferably at least 99%) amino acid identity to said protein of the accession number NP_000831.2, or a non-human form, including e.g. a mouse form or a homolog thereof found in a different species (e.g. in a different mammalian species), or a mutein of any of the aforementioned entities wherein the mutein retains the mGluR3 activity. Said mutein can preferably be obtained by substitution, insertion, addition and/or deletion of one or more (such as, e.g., 1 to 20, including 1 to 10 or 1 to 3) amino acid residues of said aforementioned entities. The mGluR3 to be used in the above method may also be a functional fragment of any of the aforementioned entities (including said muteins), i.e. a fragment which retains the mGluR3 activity of the respective aforementioned entity or, in other words, a fragment having essentially the same biological activity (i.e., at least about 60% activity, preferably at least about 70% activity, more preferably at least about 80% activity, even more preferably at least about 90% activity) as the respective aforementioned entity. A skilled person is readily in a position to determine whether mGluR3 activity is retained using techniques known in the art, e.g., knock-out and rescue experiments. Preferably, the mGluR3 to be used in the above method is human mGluR3.

The present invention also relates to the use of a compound of formula (I), as defined in the first or second aspect, or a pharmaceutically acceptable salt, solvate or prodrug thereof as a positive allosteric modulator of metabotropic glutamate receptor 3 (i.e., as an mGluR3 PAM) in research, particularly as a research tool compound. Accordingly, the invention refers to the in vitro use of a compound of formula (I) as defined in the first or second aspect, or a pharmaceutically acceptable salt, solvate or prodrug thereof as an mGluR3 PAM and, in particular, to the in vitro use of a compound of formula (I) or a pharmaceutically acceptable salt, solvate or prodrug thereof as a research tool compound acting as an mGluR3 PAM. The mGluR3 is preferably human mGluR3 (e.g., a protein of the accession number NP_000831.2), i.e., the present invention preferably relates to the in vitro use of a compound of formula (I) or a pharmaceutically acceptable salt, solvate or prodrug thereof as a positive allosteric modulator of human mGluR3 and, in particular, as a research tool compound acting as a positive allosteric modulator of human mGluR3. It is to be understood that the term "in vitro" is used in this specific context in the sense of "outside a living human or animal body", which includes, in particular, experiments performed with cells, cellular or subcellular extracts, and/or biological molecules in an artificial environment such as an aqueous solution or a culture medium which may be provided, e.g., in a flask, a test tube, a Petri dish, a microtiter plate, etc.

The compounds of the general formula (I) according to the first and the second aspect of the invention will be described in more detail in the following:

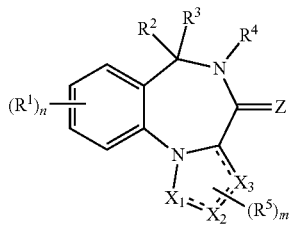

(I)

$X_1$, $X_2$ and $X_3$ are each independently C or N.

Accordingly, $X_1$, $X_2$ and $X_3$ are each independently a carbon ring atom or a nitrogen ring atom. It will be understood that the presence and the number of hydrogen atoms attached to each one of these carbon or nitrogen ring atoms depends on whether the respective ring atom is bound to its adjacent ring atoms via single or double bonds and whether it carries any substituent(s) $R^5$.

Preferably, at least one of $X_1$, $X_2$ and $X_3$ is C, and the other ones of $X_1$, $X_2$ and $X_3$ are each independently C or N. More preferably, at least two of $X_1$, $X_2$ and $X_3$ are each C, and the other one of $X_1$, $X_2$ and $X_3$ is C or N. Even more preferably, $X_1$ is C or N, and $X_2$ and $X_3$ are each C. Most preferably, $X_1$, $X_2$ and $X_3$ are each C.

Each ===== is independently a single bond or a double bond, wherein at least one of any two adjacent bonds ===== is a single bond.

Preferably, the bond ===== connecting $X_2$ and $X_3$ is a single bond, and the remaining bonds ===== (i.e., the bond connecting $X_1$ with $X_2$ and the bond connecting $X_3$ with its adjacent carbon ring atom which is depicted in formula (I)) are each independently a single bond or a double bond. More preferably, the bond ===== connecting $X_2$ and $X_3$ is a single bond, and the remaining bonds ===== are either both single bonds or they are both double bonds. Even more preferably, the bond ===== connecting $X_2$ and $X_3$ is a single bond, and each of the remaining two bonds ===== is a double bond.

Accordingly, it is particularly preferred that the fused 5-membered ring moiety containing $X_1$, $X_2$ and $X_3$ is selected from:

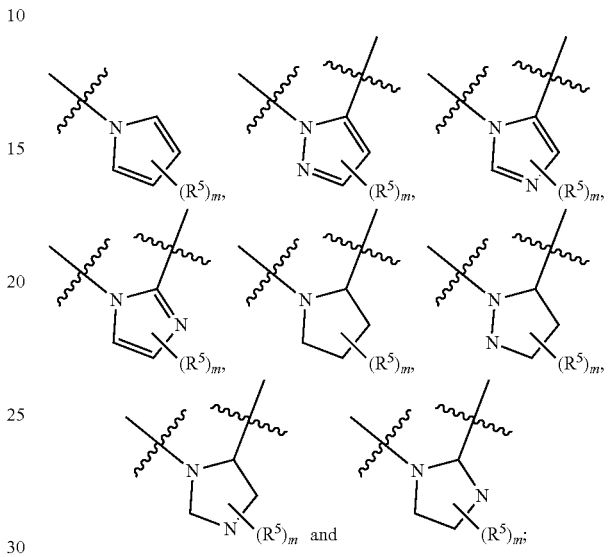

more preferably said fused 5-membered ring moiety is selected from:

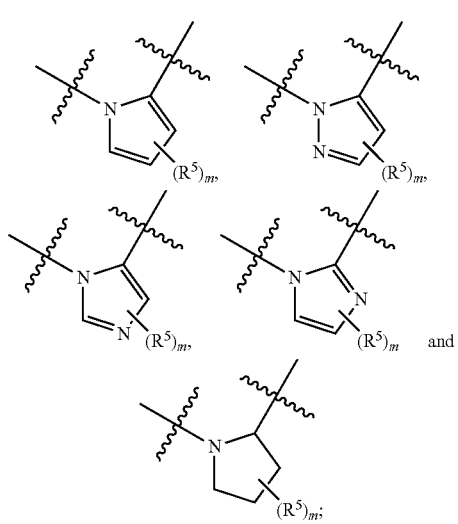

even more preferably said fused 5-membered ring moiety is selected from:

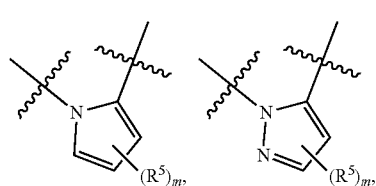

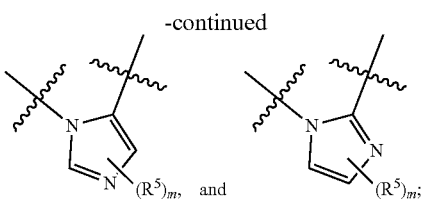

yet even more preferably said fused 5-membered ring moiety is:

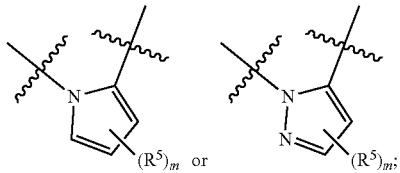

and most preferably said fused 5-membered ring moiety is:

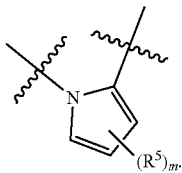

Z is O, S or N(—$R^Z$). Preferably, Z is O or S. More preferably, Z is O.

$R^Z$ is selected from hydrogen, $C_1$-$C_{10}$ alkyl, $C_2$-$C_{10}$ alkenyl, $C_2$-$C_{10}$ alkynyl, aryl, heteroaryl, cycloalkyl, and heterocycloalkyl, wherein said aryl, said heteroaryl, said cycloalkyl, and said heterocycloalkyl are each optionally substituted with one or more groups (e.g., one, two, or three groups) independently selected from $C_1$-$C_{10}$ alkyl, $C_2$-$C_{10}$ alkenyl, $C_2$-$C_{10}$ alkynyl, halogen, $C_1$-$C_{10}$ haloalkyl, —CN, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —NH$_2$, —NH($C_1$-$C_{10}$ alkyl), —N($C_1$-$C_{10}$ alkyl)($C_1$-$C_{10}$ alkyl), cycloalkyl, and heterocycloalkyl, and further wherein, if $R^Z$ is $C_1$-$C_{10}$ alkyl, $C_2$-$C_{10}$ alkenyl or $C_2$-$C_{10}$ alkynyl, then said alkyl, said alkenyl or said alkynyl is optionally substituted with one or more groups (e.g., one, two, or three groups) independently selected from halogen, $C_1$-$C_{10}$ haloalkyl, —CN, —OH, —O($C_1$-$C_{10}$ alkyl), —NH$_2$, —NH($C_1$-$C_{10}$ alkyl), —N($C_1$-$C_{10}$ alkyl)($C_1$-$C_{10}$ alkyl), cycloalkyl, and heterocycloalkyl.

Preferably, $R^Z$ is selected from hydrogen, $C_1$-$C_{10}$ alkyl, aryl, heteroaryl, cycloalkyl, and heterocycloalkyl, wherein said aryl, said heteroaryl, said cycloalkyl, and said heterocycloalkyl are each optionally substituted with one or more groups (e.g., one, two, or three groups) independently selected from $C_1$-$C_4$ alkyl, halogen, $C_1$-$C_4$ haloalkyl, —CN, —OH, —O($C_1$-$C_4$ alkyl), —($C_1$-$C_4$ alkylene)-OH, —($C_1$-$C_4$ alkylene)-O($C_1$-$C_4$ alkyl), —NH$_2$, —NH($C_1$-$C_4$ alkyl), —N($C_1$-$C_4$ alkyl)($C_1$-$C_4$ alkyl), cycloalkyl, and heterocycloalkyl, and further wherein said $C_1$-$C_{10}$ alkyl is optionally substituted with one or more groups (e.g., one, two, or three groups) independently selected from halogen, $C_1$-$C_4$ haloalkyl, —CN, —OH, —O($C_1$-$C_4$ alkyl), —NH$_2$, —NH($C_1$-$C_4$ alkyl), —N($C_1$-$C_4$ alkyl)($C_1$-$C_4$ alkyl), cycloalkyl, and heterocycloalkyl.

More preferably, $R^Z$ is selected from hydrogen and $C_1$-$C_{10}$ alkyl, wherein said alkyl is optionally substituted with one or more groups (e.g., one, two, or three groups) independently selected from halogen, $C_1$-$C_4$ haloalkyl, —CN, —OH, —O($C_1$-$C_4$ alkyl), —NH$_2$, —NH($C_1$-$C_4$ alkyl), —N($C_1$-$C_4$ alkyl)($C_1$-$C_4$ alkyl), cycloalkyl, and heterocycloalkyl.

Even more preferably, $R^Z$ is hydrogen or $C_1$-$C_{10}$ alkyl.

Yet even more preferably, $R^Z$ is hydrogen or $C_1$-$C_4$ alkyl (e.g., methyl or ethyl).

Each $R^1$ is independently a group -$L^1$-$R^{11}$.

Each $L^1$ is independently selected from a bond, $C_1$-$C_{10}$ alkylene, $C_2$-$C_{10}$ alkenylene, and $C_2$-$C_{10}$ alkynylene, wherein said alkylene, said alkenylene and said alkynylene are each optionally substituted with one or more groups (e.g., one, two, or three groups) independently selected from halogen, $C_1$-$C_{10}$ haloalkyl, —CN, —$OR^{12}$, —$NR^{12}R^{12}$, —$COR^{12}$, —$COOR^{12}$, —$OCOR^{12}$, —$CONR^{12}R^{12}$, —$NR^{12}COR^{12}$, —$SR^{12}$, —$SOR^{12}$, —$SO_2R^{12}$, —$SO_2NR^{12}R^{12}$, and —$NR^{12}SO_2R^{12}$, and further wherein one or more —CH$_2$— units (e.g., one, two, or three —CH$_2$— units) comprised in said alkylene, said alkenylene or said alkynylene are each optionally replaced by a group independently selected from —O—, —$NR^{12}$—, —CO—, —S—, —SO—, and —SO$_2$—.

Preferably, each $L^1$ is independently selected from a bond, $C_1$-$C_{10}$ alkylene, and $C_2$-$C_{10}$ alkenylene, wherein said alkylene and said alkenylene are each optionally substituted with one or more groups (e.g., one, two, or three groups) independently selected from halogen, $C_1$-$C_4$ haloalkyl, —CN, —$OR^{12}$, —$NR^{12}R^{12}$, —$COR^{12}$, —$COOR^{12}$, —$OCOR^{12}$, —$CONR^{12}R^{12}$, —$NR^{12}COR^{12}$, —$SR^{12}$, —$SOR^{12}$, —$SO_2R^{12}$, —$SO_2NR^{12}R^{12}$, and —$NR^{12}SO_2R^{12}$, and further wherein one or more —CH$_2$— units (e.g., one, two, or three —CH$_2$— units) comprised in said alkylene or said alkenylene are each optionally replaced by a group independently selected from —O—, —$NR^{12}$—, —CO—, —S—, —SO—, and —SO$_2$—.

More preferably, each $L^1$ is independently selected from a bond and $C_1$-$C_{10}$ alkylene, wherein said alkylene is optionally substituted with one or more groups (e.g., one, two, or three groups) independently selected from halogen, $C_1$-$C_4$ haloalkyl, —CN, —$OR^{12}$, —$NR^{12}R^{12}$, and —$SR^{12}$, and further wherein one or more —CH$_2$— units (e.g., one, two, or three —CH$_2$— units) comprised in said alkylene are each optionally replaced by a group independently selected from —O—, —$NR^{12}$—, —CO—, —S—, —SO—, and —SO$_2$—.

Even more preferably, each $L^1$ is independently selected from a bond and $C_1$-$C_{10}$ alkylene, wherein said alkylene is optionally substituted with one or more groups (e.g., one, two, or three groups) independently selected from halogen, $C_1$-$C_4$ haloalkyl, —CN, —OH, —O($C_1$-$C_4$ alkyl), —NH$_2$, —NH($C_1$-$C_4$ alkyl), —N($C_1$-$C_4$ alkyl)($C_1$-$C_4$ alkyl), —SH, and —S($C_1$-$C_4$ alkyl), and further wherein one or two —CH$_2$— units comprised in said alkylene is/are each optionally replaced by a group independently selected from —O—, —NH—, —N($C_1$-$C_4$ alkyl)-, —CO—, and —SO$_2$—.

Yet even more preferably, each $L^1$ is independently selected from a bond and $C_1$-$C_6$ alkylene, wherein said alkylene is optionally substituted with one or more groups (e.g., one or two groups) independently selected from halogen, $C_1$-$C_4$ haloalkyl, —CN, —OH, —O($C_1$-$C_4$ alkyl), —NH$_2$, —NH($C_1$-$C_4$ alkyl), and —N($C_1$-$C_4$ alkyl)($C_1$-$C_4$ alkyl), and further wherein one or two —CH$_2$— units comprised in said alkylene is/are each optionally replaced by a group independently selected from —O—, —NH—, —N($C_1$-$C_4$ alkyl)-, —CO—, and —SO$_2$—.

Still more preferably, each $L^1$ is independently selected from a bond and $C_1$-$C_4$ alkylene (e.g., methylene or ethylene).

Most preferably, $L^1$ is a bond.

Each $R^{11}$ is independently selected from aryl, heteroaryl, cycloalkyl, heterocycloalkyl, cycloalkenyl, heterocycloalkenyl, halogen, $C_1$-$C_{10}$ haloalkyl, —CN, $C_1$-$C_{10}$ alkyl, $C_2$-$C_{10}$ alkenyl, $C_2$-$C_{10}$ alkynyl, —NR$^{12}$R$^{12}$, —OR$^{12}$, —SR$^{12}$, —SOR$^{12}$, —SO$_2$R$^{12}$, —COR$^{12}$, —COOR$^{12}$, —OCOR$^{12}$, —CONR$^{12}$R$^{12}$, —NR$^{12}$COR$^{12}$, —SO$_2$NR$^{12}$R$^{12}$, —NR$^{12}$SO$_2$R$^{12}$, and —SO$_3$R$^{12}$, wherein said aryl, said heteroaryl, said cycloalkyl, said heterocycloalkyl, said cycloalkenyl and said heterocycloalkenyl are each optionally substituted with one or more groups (e.g., one, two or three groups) independently selected from halogen, $C_1$-$C_{10}$ haloalkyl, —CN, $C_1$-$C_{10}$ alkyl, $C_2$-$C_{10}$ alkenyl, $C_2$-$C_{10}$ alkynyl, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —NH$_2$, —NH($C_1$-$C_{10}$ alkyl), —N($C_1$-$C_{10}$ alkyl)($C_1$-$C_{10}$ alkyl), —CHO, —CO($C_1$-$C_{10}$ alkyl), —COOH, tetrazolyl, —COO($C_1$-$C_{10}$ alkyl), —OCO($C_1$-$C_{10}$ alkyl), —CO—NH$_2$, —CO—NH($C_1$-$C_{10}$ alkyl), —CO—N($C_1$-$C_{10}$ alkyl)($C_1$-$C_{10}$ alkyl), —NH—CO—($C_1$-$C_{10}$ alkyl), —N($C_1$-$C_{10}$ alkyl)-CO—($C_1$-$C_{10}$ alkyl), —SO$_2$—NH$_2$, —SO$_2$—NH($C_1$-$C_{10}$ alkyl), —SO$_2$—N($C_1$-$C_{10}$ alkyl)($C_1$-$C_{10}$ alkyl), —NH—SO$_2$—($C_1$-$C_{10}$ alkyl), —N($C_1$-$C_{10}$ alkyl)-SO$_2$—($C_1$-$C_{10}$ alkyl), cycloalkyl, heterocycloalkyl, aryl, heteroaryl, and -L$^{11}$-R$^{13}$, and further wherein, if $R^{11}$ is $C_1$-$C_{10}$ alkyl, $C_2$-$C_{10}$ alkenyl or $C_2$-$C_{10}$ alkynyl, then said alkyl, said alkenyl or said alkynyl is optionally substituted with one or more groups (e.g., one, two or three groups) independently selected from halogen, $C_1$-$C_{10}$ haloalkyl, —CN, —OH, —O($C_1$-$C_{10}$ alkyl), —NH$_2$, —NH($C_1$-$C_{10}$ alkyl), —N($C_1$-$C_{10}$ alkyl)($C_1$-$C_{10}$ alkyl), —CHO, —CO($C_1$-$C_{10}$ alkyl), —COOH, tetrazolyl, —COO($C_1$-$C_{10}$ alkyl), —OCO($C_1$-$C_{10}$ alkyl), —CO—NH$_2$, —CO—NH($C_1$-$C_{10}$ alkyl), —CO—N($C_1$-$C_{10}$ alkyl)($C_1$-$C_{10}$ alkyl), —NH—CO—($C_1$-$C_{10}$ alkyl), —N($C_1$-$C_{10}$ alkyl)-CO—($C_1$-$C_{10}$ alkyl), —SO$_2$—NH$_2$, —SO$_2$—NH($C_1$-$C_{10}$ alkyl), —SO$_2$—N($C_1$-$C_{10}$ alkyl)($C_1$-$C_{10}$ alkyl), —NH—SO$_2$—($C_1$-$C_{10}$ alkyl), —N($C_1$-$C_{10}$ alkyl)-SO$_2$—($C_1$-$C_{10}$ alkyl), cycloalkyl, heterocycloalkyl, aryl, heteroaryl, and -L$^{11}$-R$^{13}$.

Preferably, each $R^{11}$ is independently selected from aryl, heteroaryl, cycloalkyl, heterocycloalkyl, cycloalkenyl, heterocycloalkenyl, halogen, $C_1$-$C_{10}$ haloalkyl, —CN, $C_1$-$C_{10}$ alkyl, —NR$^{12}$R$^{12}$, —OR$^{12}$, —SR$^{12}$, —SO$_2$R$^{12}$, —COR$^{12}$, —COOR$^{12}$, —OCOR$^{12}$, —CONR$^{12}$R$^{12}$, —NR$^{12}$COR$^{12}$, —SO$_2$NR$^{12}$R$^{12}$, and —NR$^{12}$SO$_2$R$^{12}$, wherein said aryl, said heteroaryl, said cycloalkyl, said heterocycloalkyl, said cycloalkenyl and said heterocycloalkenyl are each optionally substituted with one or more groups (e.g., one, two or three groups) independently selected from halogen, $C_1$-$C_{10}$ haloalkyl, —CN, $C_1$-$C_{10}$ alkyl, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —NH$_2$, —NH($C_1$-$C_{10}$ alkyl), —N($C_1$-$C_{10}$ alkyl)($C_1$-$C_{10}$ alkyl), —CHO, —CO($C_1$-$C_{10}$ alkyl), —COOH, tetrazolyl, —COO($C_1$-$C_{10}$ alkyl), —OCO($C_1$-$C_{10}$ alkyl), —CO—NH$_2$, —CO—NH($C_1$-$C_{10}$ alkyl), —CO—N($C_1$-$C_{10}$ alkyl)($C_1$-$C_{10}$ alkyl), —NH—CO—($C_1$-$C_{10}$ alkyl), —N($C_1$-$C_{10}$ alkyl)-CO—($C_1$-$C_{10}$ alkyl), —SO$_2$—NH$_2$, —SO$_2$—NH($C_1$-$C_{10}$ alkyl), —SO$_2$—N($C_1$-$C_{10}$ alkyl)($C_1$-$C_{10}$ alkyl), —NH—SO$_2$—($C_1$-$C_{10}$ alkyl), —N($C_1$-$C_{10}$ alkyl)-SO$_2$—($C_1$-$C_{10}$ alkyl), cycloalkyl, heterocycloalkyl, aryl, heteroaryl, and -L$^{11}$-R$^{13}$, and further wherein, if $R^{11}$ is $C_1$-$C_{10}$ alkyl, then said alkyl is optionally substituted with one or more groups (e.g., one, two or three groups) independently selected from halogen, $C_1$-$C_{10}$ haloalkyl, —CN, —OH, —O($C_1$-$C_{10}$ alkyl), —NH$_2$, —NH($C_1$-$C_{10}$ alkyl), —N($C_1$-$C_{10}$ alkyl)($C_1$-$C_{10}$ alkyl), —CHO, —CO($C_1$-$C_{10}$ alkyl), —COOH, tetrazolyl, —COO($C_1$-$C_{10}$ alkyl), —OCO($C_1$-$C_{10}$ alkyl), —CO—NH$_2$, —CO—NH($C_1$-$C_{10}$ alkyl), —CO—N($C_1$-$C_{10}$ alkyl)($C_1$-$C_{10}$ alkyl), —NH—CO—($C_1$-$C_{10}$ alkyl), —N($C_1$-$C_{10}$ alkyl)-CO—($C_1$-$C_{10}$ alkyl), —SO$_2$—NH$_2$, —SO$_2$—NH($C_1$-$C_{10}$ alkyl), —SO$_2$—N($C_1$-$C_{10}$ alkyl)($C_1$-$C_{10}$ alkyl), —NH—SO$_2$—($C_1$-$C_{10}$ alkyl), —N($C_1$-$C_{10}$ alkyl)-SO$_2$—($C_1$-$C_{10}$ alkyl), cycloalkyl, heterocycloalkyl, aryl, heteroaryl, and -L$^{11}$-R$^{13}$.

More preferably, each $R^{11}$ is independently selected from aryl, heteroaryl, cycloalkyl, heterocycloalkyl, cycloalkenyl, heterocycloalkenyl, halogen, $C_1$-$C_4$ haloalkyl, —CN, $C_1$-$C_4$ alkyl, —NH$_2$, —NH($C_1$-$C_4$ alkyl), —N($C_1$-$C_4$ alkyl)($C_1$-$C_4$ alkyl), —OH, and —O($C_1$-$C_4$ alkyl), wherein said aryl, said heteroaryl, said cycloalkyl, said heterocycloalkyl, said cycloalkenyl and said heterocycloalkenyl are each optionally substituted with one or more groups (e.g., one, two or three groups) independently selected from halogen, $C_1$-$C_4$ haloalkyl, —CN, $C_1$-$C_4$ alkyl, —OH, —O($C_1$-$C_4$ alkyl), —($C_1$-$C_4$ alkylene)-OH, —($C_1$-$C_4$ alkylene)-O($C_1$-$C_4$ alkyl), —NH$_2$, —NH($C_1$-$C_4$ alkyl), —N($C_1$-$C_4$ alkyl)($C_1$-$C_4$ alkyl), —CHO, —CO($C_1$-$C_4$ alkyl), —COOH, tetrazolyl, —COO($C_1$-$C_4$ alkyl), —OCO($C_1$-$C_4$ alkyl), —CO—NH$_2$, —CO—NH($C_1$-$C_4$ alkyl), —CO—N($C_1$-$C_4$ alkyl)($C_1$-$C_4$ alkyl), —NH—CO—($C_1$-$C_4$ alkyl), —N($C_1$-$C_4$ alkyl)-CO—($C_1$-$C_4$ alkyl), —SO$_2$—NH($C_1$-$C_4$ alkyl), —SO$_2$—N($C_1$-$C_4$ alkyl)($C_1$-$C_4$ alkyl), —NH—SO$_2$—($C_1$-$C_4$ alkyl), —N($C_1$-$C_4$ alkyl)-SO$_2$—($C_1$-$C_4$ alkyl), cycloalkyl, heterocycloalkyl, aryl, and heteroaryl, and further wherein, if $R^{11}$ is $C_1$-$C_4$ alkyl, then said alkyl is optionally substituted with one or more groups (e.g., one, two or three groups) independently selected from halogen, $C_1$-$C_4$ haloalkyl, —CN, —OH, —O($C_1$-$C_4$ alkyl), —NH$_2$, —NH($C_1$-$C_4$ alkyl), —N($C_1$-$C_4$ alkyl)($C_1$-$C_4$ alkyl), —CHO, —CO($C_1$-$C_4$ alkyl), —COOH, tetrazolyl, —COO($C_1$-$C_4$ alkyl), —OCO ($C_1$-$C_4$ alkyl), —CO—NH$_2$, —CO—NH($C_1$-$C_4$ alkyl), —CO—N($C_1$-$C_4$ alkyl)($C_1$-$C_4$ alkyl), —NH—CO—($C_1$-$C_4$ alkyl), —N($C_1$-$C_4$ alkyl)-CO—($C_1$-$C_4$ alkyl), —SO$_2$—NH$_2$, —SO$_2$—NH($C_1$-$C_4$ alkyl), —SO$_2$—N($C_1$-$C_4$ alkyl)($C_1$-$C_4$ alkyl), —NH—SO$_2$—($C_1$-$C_4$ alkyl), —N($C_1$-$C_4$ alkyl)-SO$_2$—($C_1$-$C_4$ alkyl), cycloalkyl, heterocycloalkyl, aryl, and heteroaryl.

Even more preferably, each $R^{11}$ is independently selected from: phenyl; heteroaryl having 5 to 10 ring members, wherein 1, 2 or 3 ring members are heteroatoms selected independently from O, S and N, and the remaining ring members are carbon atoms (such as, e.g., pyridinyl (e.g., pyridin-2-yl, pyridin-3-yl, or pyridin-4-yl), pyrazolyl (e.g., pyrazol-4-yl or pyrazol-5-yl), oxazolyl (e.g., oxazol-5-yl), thiazolyl (e.g., thiazol-5-yl), pyrimidinyl (e.g., pyrimidin-5-yl), pyridazinyl (e.g., pyridazin-3-yl), pyrazinyl (e.g., pyrazin-2-yl), or imidazo[1,2-a]pyridinyl (e.g., imidazo[1,2-a]pyridin-6-yl)); $C_3$-$C_7$ cycloalkyl; heterocycloalkyl having 5, 6 or 7 ring members, wherein 1, 2 or 3 ring members are heteroatoms selected independently from O, S and N, and the remaining ring members are carbon atoms (such as, e.g., pyrrolidinyl (e.g., pyrrolidin-1-yl) or morpholinyl (e.g., morpholin-4-yl)); $C_5$-$C_7$ cycloalkenyl; and heterocycloalkenyl having 5, 6 or 7 ring members, wherein 1, 2 or 3 ring members are heteroatoms selected independently from O, S and N, and the remaining ring members are carbon atoms (such as, e.g., 1,2,3,6-tetrahydropyridinyl (e.g., 1,2,3,6-tetrahydropyridin-4-yl)); wherein said phenyl, said heteroaryl, said cycloalkyl, said heterocycloalkyl, said cycloalkenyl and said heterocycloalkenyl are each optionally substituted with one or more groups (e.g., one, two or three groups) independently selected from halogen (e.g., —F, —Cl, or —Br), $C_1$-$C_4$ haloalkyl (e.g., —$CF_3$), —CN, $C_1$-$C_4$ alkyl (e.g., methyl, ethyl, or n-propyl), —OH, —O($C_1$-$C_4$ alkyl) (e.g., —$OCH_3$), —($C_1$-$C_4$ alkylene)-OH, —($C_1$-$C_4$ alkylene)-O($C_1$-$C_4$ alkyl), —$NH_2$, —NH($C_1$-$C_4$ alkyl) (e.g., —$NHCH_3$), —N($C_1$-$C_4$ alkyl)($C_1$-$C_4$ alkyl) (e.g., —N($CH_3$)$_2$), —CHO, —CO($C_1$-$C_4$ alkyl) (e.g., —$COCH_3$), —COOH, tetrazolyl (e.g., 1H-tetrazol-5-yl or 2H-tetrazol-5-yl), —COO($C_1$-$C_4$ alkyl) (e.g., —$COOCH_3$), —$SO_2$—NH($C_1$-$C_4$ alkyl) (e.g., —$SO_2$—$NHCH_3$), —$SO_2$—N($C_1$-$C_4$ alkyl)($C_1$-$C_4$ alkyl) (e.g., —$SO_2$—N($CH_3$)$_2$), cycloalkyl (e.g., cyclopropyl), heterocycloalkyl (e.g., piperidinyl or morpholinyl), aryl (e.g., phenyl), and heteroaryl (e.g., pyrimidinyl).

Yet even more preferably, each $R^{11}$ is independently selected from phenyl, pyridinyl, and imidazo[1,2-a]pyridinyl, wherein said phenyl, said pyridinyl and said imidazo[1,2-a]pyridinyl are each optionally substituted with one or more groups (e.g., one or two groups) independently selected from halogen, $C_1$-$C_4$ haloalkyl, —CN, $C_1$-$C_4$ alkyl, —OH, —O($C_1$-$C_4$ alkyl), —$NH_2$, —NH($C_1$-$C_4$ alkyl), —N($C_1$-$C_4$ alkyl)($C_1$-$C_4$ alkyl), and —COOH.

Still more preferably, each $R^{11}$ is independently pyridinyl (e.g., pyridin-2-yl, pyridin-3-yl, or pyridin-4-yl), wherein said pyridinyl is optionally substituted with one or two groups independently selected from halogen, $C_1$-$C_4$ haloalkyl, —CN, $C_1$-$C_4$ alkyl, —OH, —O($C_1$-$C_4$ alkyl), —$NH_2$, —NH($C_1$-$C_4$ alkyl), —N($C_1$-$C_4$ alkyl)($C_1$-$C_4$ alkyl), and —COOH.

Most preferably, each $R^{11}$ is independently pyridinyl (e.g., pyridin-2-yl, pyridin-3-yl, or pyridin-4-yl; particularly pyridin-2-yl or pyridin-3-yl) which is substituted with one methyl or fluoro group (such as, e.g., 2-methylpyridin-3-yl, 6-fluoropyridin-3-yl, or 5-fluoropyridin-2-yl; particularly 2-methylpyridin-3-yl or 6-fluoropyridin-3-yl).

Each $R^{12}$ is independently selected from hydrogen, $C_1$-$C_{10}$ alkyl, $C_2$-$C_{10}$ alkenyl, $C_2$-$C_{10}$ alkynyl, aryl, heteroaryl, cycloalkyl, and heterocycloalkyl, wherein said aryl, said heteroaryl, said cycloalkyl, and said heterocycloalkyl are each optionally substituted with one or more groups (e.g., one, two, or three groups) independently selected from $C_1$-$C_{10}$ alkyl, $C_2$-$C_{10}$ alkenyl, $C_2$-$C_{10}$ alkynyl, halogen, $C_1$-$C_{10}$ haloalkyl, —CN, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), cycloalkyl, and heterocycloalkyl, wherein if $R^{12}$ is $C_1$-$C_{10}$ alkyl, $C_2$-$C_{10}$ alkenyl or $C_2$-$C_{10}$ alkynyl, then said alkyl, said alkenyl or said alkynyl is optionally substituted with one or more groups (e.g., one, two, or three groups) independently selected from halogen, $C_1$-$C_{10}$ haloalkyl, —CN, —OH, —O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), cycloalkyl, and heterocycloalkyl, and further if two groups $R^{12}$ are attached to the same nitrogen atom, then these two groups $R^{12}$ may also together form a $C_2$-$C_8$ alkylene (so that the resulting group is a 3- to 9-membered nitrogen-containing heterocycloalkyl ring which is formed from the two groups $R^{12}$ and the nitrogen atom that they are attached to).

Preferably, each $R^{12}$ is independently selected from hydrogen, $C_1$-$C_{10}$ alkyl, aryl, heteroaryl, cycloalkyl, and heterocycloalkyl, wherein said aryl, said heteroaryl, said cycloalkyl, and said heterocycloalkyl are each optionally substituted with one or more groups (e.g., one, two, or three groups) independently selected from $C_1$-$C_4$ alkyl, halogen, $C_1$-$C_4$ haloalkyl, —CN, —OH, —O($C_1$-$C_4$ alkyl), —($C_1$-$C_4$ alkylene)-OH, —($C_1$-$C_4$ alkylene)-O($C_1$-$C_4$ alkyl), —$NH_2$, —NH($C_1$-$C_4$ alkyl), —N($C_1$-$C_4$ alkyl)($C_1$-$C_4$ alkyl), cycloalkyl, and heterocycloalkyl, wherein said $C_1$-$C_{10}$ alkyl is optionally substituted with one or more groups (e.g., one, two, or three groups) independently selected from halogen, $C_1$-$C_4$ haloalkyl, —CN, —OH, —O($C_1$-$C_4$ alkyl), —$NH_2$, —NH($C_1$-$C_4$ alkyl), —N($C_1$-$C_4$ alkyl)($C_1$-$C_4$ alkyl), cycloalkyl, and heterocycloalkyl, and further if two groups $R^{12}$ are attached to the same nitrogen atom, then these two groups $R^{12}$ may also together form a $C_2$-$C_8$ alkylene (so that the resulting group is a 3- to 9-membered nitrogen-containing heterocycloalkyl ring which is formed from the two groups $R^{12}$ and the nitrogen atom that they are attached to).

More preferably, each $R^{12}$ is independently selected from hydrogen and $C_1$-$C_{10}$ alkyl, wherein said alkyl is optionally substituted with one or more groups (e.g., one, two, or three groups) independently selected from halogen, $C_1$-$C_4$ haloalkyl, —CN, —OH, —O($C_1$-$C_4$ alkyl), —$NH_2$, —NH($C_1$-$C_4$ alkyl), —N($C_1$-$C_4$ alkyl)($C_1$-$C_4$ alkyl), cycloalkyl, and heterocycloalkyl, and further if two groups $R^{12}$ are attached to the same nitrogen atom, then these two groups $R^{12}$ may also together form a $C_2$-$C_8$ alkylene (so that the resulting group is a 3- to 9-membered nitrogen-containing heterocycloalkyl ring which is formed from the two groups $R^{12}$ and the nitrogen atom that they are attached to).

Even more preferably, each $R^{12}$ is independently selected from hydrogen and $C_1$-$C_4$ alkyl, wherein said alkyl is optionally substituted with one or more groups (e.g., one, two, or three groups) independently selected from halogen, $C_1$-$C_4$ haloalkyl, —CN, —OH, —O($C_1$-$C_4$ alkyl), —$NH_2$, —NH($C_1$-$C_4$ alkyl), and —N($C_1$-$C_4$ alkyl)($C_1$-$C_4$ alkyl), and further if two groups $R^{12}$ are attached to the same nitrogen atom, then these two groups $R^{12}$ may also together form a $C_4$-$C_6$ alkylene.

Yet even more preferably, each $R^{12}$ is independently selected from hydrogen and $C_1$-$C_4$ alkyl, and if two groups $R^{12}$ are attached to the same nitrogen atom, then these two groups $R^{12}$ may also together form a $C_4$-$C_6$ alkylene.

Most preferably, each $R^{12}$ is independently selected from hydrogen and $C_1$-$C_4$ alkyl (e.g., methyl or ethyl).

Each $L^{11}$ is independently selected from a bond, $C_1$-$C_{10}$ alkylene, $C_2$-$C_{10}$ alkenylene, and $C_2$-$C_{10}$ alkynylene, wherein one or more —$CH_2$— units (e.g., one, two or three —$CH_2$— units) comprised in said alkylene, said alkenylene or said alkynylene are each optionally replaced by a group independently selected from —O—, —NH—, —N($C_1$-$C_{10}$ alkyl)-, —CO—, —S—, —SO—, and —$SO_2$—.

Preferably, each $L^{11}$ is independently selected from a bond and $C_1$-$C_{10}$ alkylene, wherein one or more —$CH_2$— units (e.g., one or two —$CH_2$— units) comprised in said alkylene are each optionally replaced by a group independently selected from —O—, —NH—, —N($C_1$-$C_4$ alkyl)-, —CO—, —S—, —SO—, and —$SO_2$—.

Each $R^{13}$ is independently selected from aryl, heteroaryl, cycloalkyl, heterocycloalkyl, cycloalkenyl, heterocycloalkenyl, halogen, $C_1$-$C_{10}$ haloalkyl, —CN, $C_1$-$C_{10}$ alkyl, $C_2$-$C_{10}$ alkenyl, $C_2$-$C_{10}$ alkynyl, —$NH_2$, —NH($C_1$-$C_{10}$ alkyl), —N($C_1$-$C_{10}$ alkyl)($C_1$-$C_{10}$ alkyl), —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —SH, and —S($C_1$-$C_{10}$ alkyl), wherein said aryl, said heteroaryl, said cycloalkyl, said heterocycloalkyl, said cycloalkenyl and said heterocycloalkenyl are each optionally substituted with one or more groups (e.g., one, two or three groups) independently selected from halogen, $C_1$-$C_{10}$ haloalkyl, —CN, $C_1$-$C_{10}$ alkyl, $C_2$-$C_{10}$ alkenyl, $C_2$-$C_{10}$ alkynyl, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), cycloalkyl, and heterocycloalkyl.

Preferably, each $R^{13}$ is independently selected from aryl, heteroaryl, cycloalkyl, heterocycloalkyl, cycloalkenyl, heterocycloalkenyl, halogen, $C_1$-$C_4$ haloalkyl, —CN, $C_1$-$C_4$ alkyl, —$NH_2$, —NH($C_1$-$C_4$ alkyl), —N($C_1$-$C_4$ alkyl)($C_1$-$C_4$ alkyl), —OH, —O($C_1$-$C_4$ alkyl), —($C_1$-$C_4$ alkylene)-OH, —($C_1$-$C_4$ alkylene)-O($C_1$-$C_4$ alkyl), —SH, and —S($C_1$-$C_4$ alkyl), wherein said aryl, said heteroaryl, said cycloalkyl, said heterocycloalkyl, said cycloalkenyl and said heterocycloalkenyl are each optionally substituted with one or more groups (e.g., one, two or three groups) independently selected from halogen, $C_1$-$C_4$ haloalkyl, —CN, $C_1$-$C_4$ alkyl, —OH, —O($C_1$-$C_4$ alkyl), —($C_1$-$C_4$ alkylene)-OH, —($C_1$-$C_4$ alkylene)-O($C_1$-$C_4$ alkyl), —$NH_2$, —NH($C_1$-$C_4$ alkyl), —N($C_1$-$C_4$ alkyl)($C_1$-$C_4$ alkyl), cycloalkyl, and heterocycloalkyl.

n is an integer of 0 to 4 (such as, for instance, an integer in the range of 1 to 4). Preferably, n is 0, 1, 2 or 3 (e.g., 1, 2 or 3). More preferably, n is 0, 1 or 2. Even more preferably, n is 1 or 2. Most preferably, n is 1

It is to be understood that n indicates the number of substituents $R^1$ that are bound to the phenyl moiety comprised in the tricyclic ring system of the compound of formula (I). If n is 0, then this phenyl moiety is not substituted with any group $R^1$, i.e. is substituted with hydrogen instead of $R^1$.

Preferred points of attachment of the group(s) $R^1$, if present, on the phenyl ring comprised in the tricyclic moiety of the compound of formula (I) are the positions 8 and 9 (particularly position 9) of said tricyclic moiety, as indicated in the following:

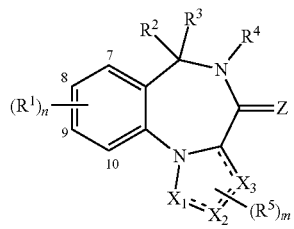

Accordingly, if n is 1, it is preferred that the corresponding group $R^1$ is attached to the above-depicted tricyclic moiety at position 8 or 9, most preferably at position 9. Moreover, if n is 2, it is preferred that the two groups $R^1$ are attached to the above-depicted tricyclic moiety at positions 8 and 9, respectively.

In accordance with the above definitions of n, $L^1$ and $R^{11}$, it is particularly preferred that the compound of formula (I) comprises one group $R^1$ (i.e., n is 1), which is attached to position 9 of the tricyclic moiety shown in formula (I) (as described and depicted above), and wherein said group $R^1$ is selected from: phenyl; heteroaryl having 5 to 10 ring members, wherein 1, 2 or 3 ring members are heteroatoms selected independently from O, S and N, and the remaining ring members are carbon atoms (such as, e.g., pyridinyl (e.g., pyridin-2-yl, pyridin-3-yl, or pyridin-4-yl), pyrazolyl (e.g., pyrazol-4-yl or pyrazol-5-yl), oxazolyl (e.g., oxazol-5-yl), thiazolyl (e.g., thiazol-5-yl), pyrimidinyl (e.g., pyrimidin-5-yl), pyridazinyl (e.g., pyridazin-3-yl), pyrazinyl (e.g., pyrazin-2-yl), or imidazo[1,2-a]pyridinyl (e.g., imidazo[1,2-a]pyridin-6-yl)); $C_3$-$C_7$ cycloalkyl; heterocycloalkyl having 5, 6 or 7 ring members, wherein 1, 2 or 3 ring members are heteroatoms selected independently from O, S and N, and the remaining ring members are carbon atoms (such as, e.g., pyrrolidinyl (e.g., pyrrolidin-1-yl) or morpholinyl (e.g., morpholin-4-yl)); $C_5$-$C_7$ cycloalkenyl; and heterocycloalkenyl having 5, 6 or 7 ring members, wherein 1, 2 or 3 ring members are heteroatoms selected independently from O, S and N, and the remaining ring members are carbon atoms (such as, e.g., 1,2,3,6-tetrahydropyridinyl (e.g., 1,2,3,6-tetrahydropyridin-4-yl)); wherein said phenyl, said heteroaryl, said cycloalkyl, said heterocycloalkyl, said cycloalkenyl and said heterocycloalkenyl are each optionally substituted with one or more groups (e.g., one, two or three groups) independently selected from halogen (e.g., —F, —Cl, or —Br), $C_1$-$C_4$ haloalkyl (e.g., —$CF_3$), —CN, $C_1$-$C_4$ alkyl (e.g., methyl, ethyl, or n-propyl), —OH, —O($C_1$-$C_4$ alkyl) (e.g., —$OCH_3$), —($C_1$-$C_4$ alkylene)-OH, —($C_1$-$C_4$ alkylene)-O($C_1$-$C_4$ alkyl), —$NH_2$, —NH($C_1$-$C_4$ alkyl) (e.g., —$NHCH_3$), —N($C_1$-$C_4$ alkyl)($C_1$-$C_4$ alkyl) (e.g., —N($CH_3$)$_2$), —CHO, —CO($C_1$-$C_4$ alkyl) (e.g., —$COCH_3$), —COOH, tetrazolyl (e.g., 1H-tetrazol-5-yl or 2H-tetrazol-5-yl), —COO($C_1$-$C_4$ alkyl) (e.g., —$COOCH_3$), —$SO_2$—NH($C_1$-$C_4$ alkyl) (e.g., —$SO_2$—$NHCH_3$), —$SO_2$—N($C_1$-$C_4$ alkyl)($C_1$-$C_4$ alkyl) (e.g., —$SO_2$—N($CH_3$)$_2$), cycloalkyl (e.g., cyclopropyl), heterocycloalkyl (e.g., piperidinyl or morpholinyl), aryl (e.g., phenyl), and heteroaryl (e.g., pyrimidinyl).

Even more preferably, n is 1, the group $R^1$ is attached to position 9 of the tricyclic moiety shown in formula (I), and said group $R^1$ is selected from phenyl, pyridinyl, and imidazo[1,2-a]pyridinyl, wherein said phenyl, said pyridinyl and said imidazo[1,2-a]pyridinyl are each optionally substituted with one or more groups (e.g., one or two groups) independently selected from halogen, $C_1$-$C_4$ haloalkyl, —CN, $C_1$-$C_4$ alkyl, —OH, —O($C_1$-$C_4$ alkyl), —$NH_2$, —NH($C_1$-$C_4$ alkyl), —N($C_1$-$C_4$ alkyl)($C_1$-$C_4$ alkyl), and —COOH.

Yet even more preferably, n is 1, the group $R^1$ is attached to position 9 of the tricyclic moiety shown in formula (I), and said group $R^1$ is pyridinyl (e.g., pyridin-2-yl, pyridin-3-yl, or pyridin-4-yl), wherein said pyridinyl is optionally substituted with one or two groups independently selected from halogen, $C_1$-$C_4$ haloalkyl, —CN, $C_1$-$C_4$ alkyl, —OH, —O($C_1$-$C_4$ alkyl), —$NH_2$, —NH($C_1$-$C_4$ alkyl), —N($C_1$-$C_4$ alkyl)($C_1$-$C_4$ alkyl), and —COOH.

Still more preferably, n is 1, the group $R^1$ is attached to position 9 of the tricyclic moiety shown in formula (I), and said group $R^1$ is pyridinyl (e.g., pyridin-2-yl, pyridin-3-yl, or pyridin-4-yl; particularly pyridin-2-yl or pyridin-3-yl) which is substituted with one methyl or fluoro group; corresponding particularly preferred examples of $R^1$ include 2-methylpyridin-3-yl, 6-fluoropyridin-3-yl, and 5-fluoropyridin-2-yl.

Most preferably, n is 1, the group $R^1$ is attached to position 9 of the tricyclic moiety shown in formula (I), and said group $R^1$ is 2-methylpyridin-3-yl or 6-fluoropyridin-3-yl.

$R^2$ and $R^3$ are mutually linked to form, together with the carbon atom that they are attached to, a cycloalkyl or a heterocycloalkyl; or $R^2$ and $R^3$ are each independently selected from hydrogen, halogen, $C_1$-$C_{10}$ haloalkyl, $C_1$-$C_{10}$ alkyl, $C_2$-$C_{10}$ alkenyl, $C_2$-$C_{10}$ alkynyl, —OH, —O($C_1$-$C_{10}$ alkyl), —SH, —S($C_1$-$C_{10}$ alkyl), —SO—($C_1$-$C_{10}$ alkyl), —$SO_2$—($C_1$-$C_{10}$ alkyl), —CN, aryl, heteroaryl, cycloalkyl, and heterocycloalkyl, wherein said aryl, said heteroaryl, said cycloalkyl, and said heterocycloalkyl are each optionally substituted with one or more groups (e.g., one, two or three groups) independently selected from $C_1$-$C_{10}$ alkyl, $C_2$-$C_{10}$ alkenyl, $C_2$-$C_{10}$ alkynyl, halogen, $C_1$-$C_{10}$ haloalkyl, —CN, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), cycloalkyl, and heterocycloalkyl, and further wherein, if one or both of $R^2$ and $R^3$ is/are $C_1$-$C_{10}$ alkyl, $C_2$-$C_{10}$ alkenyl or $C_2$-$C_{10}$ alkynyl, then said alkyl, said alkenyl or said alkynyl is optionally substituted with one or more groups (e.g., one, two or three groups) independently selected from halogen, $C_1$-$C_{10}$ haloalkyl, —CN, —OH, —O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), cycloalkyl, and heterocycloalkyl; or $R^2$ and $R^3$ together form a divalent group selected from =O, =S, =NH and =N($C_1$-$C_{10}$ alkyl).

If $R^2$ and $R^3$ are mutually linked, it is preferred that they form, together with the carbon atom that they are attached to, a $C_3$-$C_7$ cycloalkyl or a 3- to 7-membered heterocycloalkyl containing 1, 2 or 3 ring heteroatoms independently selected from O, S and N, more preferably a $C_3$-$C_7$ cycloalkyl, even more preferably a $C_3$-$C_5$ cycloalkyl (e.g., cyclopropyl, cyclobutyl, or cyclopentyl), and most preferably a cyclopropyl. It will be understood that any such cycloalkyl or heterocycloalkyl group, which is formed from $R^2$, $R^3$ and the carbon atom that they are attached to, is a spiro group since said carbon atom is also a ring member of the 7-membered ring comprised in the central ring system of the compound of formula (I).

If $R^2$ and $R^3$ are each independently selected from the above-defined groups, it is preferred that they are each independently selected from hydrogen, halogen, $C_1$-$C_4$ haloalkyl, $C_1$-$C_4$ alkyl, —OH, —O($C_1$-$C_4$ alkyl), —SH, —S($C_1$-$C_4$ alkyl), —SO—($C_1$-$C_4$ alkyl), —$SO_2$—($C_1$-$C_4$ alkyl), —CN, aryl, heteroaryl, cycloalkyl, and heterocycloalkyl, wherein said aryl, said heteroaryl, said cycloalkyl, and said heterocycloalkyl are each optionally substituted with one or more groups (e.g., one, two or three groups) independently selected from $C_1$-$C_4$ alkyl, halogen, $C_1$-$C_4$ haloalkyl, —CN, —OH, —O($C_1$-$C_4$ alkyl), —($C_1$-$C_4$ alkylene)-OH, —($C_1$-$C_4$ alkylene)-O($C_1$-$C_4$ alkyl), —$NH_2$, —NH($C_1$-$C_4$ alkyl), —N($C_1$-$C_4$ alkyl)($C_1$-$C_4$ alkyl), cycloalkyl, and heterocycloalkyl, and further wherein, if one or both of $R^2$ and $R^3$ is/are $C_1$-$C_4$ alkyl, then said alkyl is optionally substituted with one or more groups (e.g., one, two or three groups) independently selected from halogen, $C_1$-$C_4$ haloalkyl, —CN, —OH, —O($C_1$-$C_4$ alkyl), —$NH_2$, —NH($C_1$-$C_4$ alkyl), —N($C_1$-$C_4$ alkyl)($C_1$-$C_4$ alkyl), cycloalkyl, and heterocycloalkyl; more preferably, $R^2$ and $R^3$ are each independently selected from hydrogen, halogen, $C_1$-$C_4$ haloalkyl, $C_1$-$C_4$ alkyl, —OH, —O($C_1$-$C_4$ alkyl), —SH, —S($C_1$-$C_4$ alkyl), —SO—($C_1$-$C_4$ alkyl), —$SO_2$—($C_1$-$C_4$ alkyl), —CN, wherein said $C_1$-$C_4$ alkyl is optionally substituted with one or more groups (e.g., one, two or three groups) independently selected from halogen, $C_1$-$C_4$ haloalkyl, —CN, —OH, —O($C_1$-$C_4$ alkyl), —$NH_2$, —NH($C_1$-$C_4$ alkyl), and —N($C_1$-$C_4$ alkyl)($C_1$-$C_4$ alkyl); even more preferably, $R^2$ and $R^3$ are each independently selected from hydrogen, halogen, $C_1$-$C_4$ haloalkyl, $C_1$-$C_4$ alkyl, —OH, —O($C_1$-$C_4$ alkyl), and —CN; yet even more preferably, $R^2$ and $R^3$ are each independently selected from hydrogen, halogen, $C_1$-$C_4$ alkyl, —OH, and —O($C_1$-$C_4$ alkyl); still more preferably, $R^2$ and $R^3$ are each independently from hydrogen and $C_1$-$C_4$ alkyl (e.g., methyl or ethyl). For example, $R^2$ and $R^3$ may both be hydrogen, or may both independently be $C_1$-$C_4$ alkyl (e.g., they may both be methyl), or may be hydrogen and $C_1$-$C_4$ alkyl (e.g., $R^2$ may be hydrogen, and $R^3$ may be methyl or ethyl).

If $R^2$ and $R^3$ together form a divalent group, it is preferred that they form a group =O.

Thus, it is particularly preferred that $R^2$ and $R^3$ are mutually linked to form, together with the carbon atom that they are attached to, a $C_3$-$C_5$ cycloalkyl (e.g., a cyclopropyl, a cyclobutyl, or a cyclopentyl), or that $R^2$ and $R^3$ are each independently selected from hydrogen, halogen, $C_1$-$C_4$ alkyl, —OH, and —O($C_1$-$C_4$ alkyl). Even more preferably, $R^2$ and $R^3$ are mutually linked to form, together with the carbon atom that they are attached to, a $C_3$-$C_5$ cycloalkyl (e.g., cyclopropyl), or $R^2$ and $R^3$ are each independently selected from hydrogen and $C_1$-$C_4$ alkyl (e.g., methyl or ethyl). Yet even more preferably, $R^2$ and $R^3$ are mutually linked to form, together with the carbon atom that they are attached to, a $C_3$-$C_5$ cycloalkyl. Most preferably, $R^2$ and $R^3$ are mutually linked to form, together with the carbon atom that they are attached to, a cyclopropyl.

In a preferred embodiment of the invention, $R^2$ and $R^3$ are not both hydrogen.

$R^4$ is selected from $C_1$-$C_{10}$ alkyl, $C_2$-$C_{10}$ alkenyl, $C_2$-$C_{10}$ alkynyl, cycloalkyl, and heterocycloalkyl, wherein said alkyl, said alkenyl and said alkynyl are each optionally substituted with one or more groups (e.g., one, two, or three groups) independently selected from halogen, $C_1$-$C_{10}$ haloalkyl, —O—($C_1$-$C_{10}$ haloalkyl), —CN, —OH, —O($C_1$-$C_{10}$ alkyl), and cycloalkyl, and further wherein, if $R^4$ is cycloalkyl or heterocycloalkyl, then said cycloalkyl or said heterocycloalkyl is optionally substituted with one or more groups (e.g., one, two, or three groups) independently selected from $C_1$-$C_{10}$ alkyl, $C_2$-$C_{10}$ alkenyl, $C_2$-$C_{10}$ alkynyl, halogen, $C_1$-$C_{10}$ haloalkyl, —CN, —OH, —O($C_1$-$C_{10}$ alkyl), and cycloalkyl.

It will be noted that the $R^4$ group cannot be hydrogen. The inventors found that it is important to have a substituent in this $R^4$ position to allow positive allosteric modulator activity on mGluR3.

Preferably, $R^4$ is $C_1$-$C_{10}$ alkyl, wherein said alkyl is optionally substituted with one or more groups (e.g., one, two, or three groups) independently selected from halogen, $C_1$-$C_{10}$ haloalkyl, —O—($C_1$-$C_{10}$ haloalkyl), —CN, —OH, —O($C_1$-$C_{10}$ alkyl), and cycloalkyl.

More preferably, $R^4$ is $C_1$-$C_4$ alkyl, wherein said alkyl is optionally substituted with one or more groups (e.g., one, two, or three groups) independently selected from halogen, $C_1$-$C_4$ haloalkyl, —O—($C_1$-$C_4$ haloalkyl), —CN, —OH and —O($C_1$-$C_4$ alkyl).

Even more preferably, $R^4$ is $C_1$-$C_4$ alkyl, wherein said alkyl is optionally substituted with one or more groups (e.g., one or two groups) independently selected from —OH and —O($C_1$-$C_4$ alkyl) (e.g., —$OCH_3$); for example, $R^4$ may be methyl which is optionally substituted with one or two groups independently selected from —OH and —$OCH_3$, particularly with one group —$OCH_3$.

Yet even more preferably, $R^4$ is $C_1$-$C_4$ alkyl.

Most preferably, $R^4$ is methyl (e.g., —$C(^1H)_3$ or —$C(^2H)_3$).

In a preferred embodiment, $R^4$ is methyl (e.g., —$C(^1H)_3$ or —$C(^2H)_3$) or methyl substituted with one group —$OCH_3$.

Each $R^5$ is independently a group -$L^5$-$R^{51}$.

Each $L^5$ is independently selected from a bond, $C_1$-$C_{10}$ alkylene, $C_2$-$C_{10}$ alkenylene, and $C_2$-$C_{10}$ alkynylene, wherein said alkylene, said alkenylene and said alkynylene are each optionally substituted with one or more groups (e.g., one, two, or three groups) independently selected from halogen, $C_1$-$C_{10}$ haloalkyl, —CN, —OR$^{52}$, —NR$^{52}$R$^{52}$, —COR$^{52}$, —COOR$^{52}$, —OCOR$^{52}$, —CONR$^{52}$R$^{52}$, —NR$^{52}$COR$^{52}$, —SR$^{52}$, —SOR$^{52}$, —SO$_2$R$^{52}$, —SO$_2$NR$^{52}$R$^{52}$, and —NR$^{52}$SO$_2$R$^{52}$, and further wherein one or more —CH$_2$— units (e.g., one, two, or three —CH$_2$— units) comprised in said alkylene, said alkenylene or said alkynylene are each optionally replaced by a group independently selected from —O—, —NR$^{52}$—, —CO—, —S—, —SO—, and —SO$_2$—.

Preferably, each L$^5$ is independently selected from a bond and C$_1$-C$_{10}$ alkylene, wherein said alkylene is optionally substituted with one or more groups (e.g., one, two, or three groups) independently selected from halogen, C$_1$-C$_4$ haloalkyl, —CN, —OR$^{52}$, —NR$^{52}$R$^{52}$, —COR$^{52}$, —COOR$^{52}$, —OCOR$^{52}$, —CONR$^{52}$R$^{52}$, —NR$^{52}$COR$^{52}$, —SR$^{52}$, —SOR$^{52}$, —SO$_2$R$^{52}$, —SO$_2$NR$^{52}$R$^{52}$, and —NR$^{52}$SO$_2$R$^{52}$, and further wherein one or more —CH$_2$— units (e.g., one, two, or three —CH$_2$— units) comprised in said alkylene are each optionally replaced by a group independently selected from —O—, —NR$^{52}$—, —CO—, —S—, —SO—, and —SO$_2$—.

More preferably, each L$^5$ is independently selected from a bond and C$_1$-C$_{10}$ alkylene, wherein said alkylene is optionally substituted with one or more groups (e.g., one, two, or three groups) independently selected from halogen, C$_1$-C$_4$ haloalkyl, —CN, —OR$^{52}$, —NR$^{52}$R$^{52}$, and —SR$^{52}$, and further wherein one or more —CH$_2$— units (e.g., one, two, or three —CH$_2$— units) comprised in said alkylene are each optionally replaced by a group independently selected from —O—, —NR$^{52}$—, —CO—, —S—, —SO—, and —SO$_2$—.

Even more preferably, each L$^5$ is independently selected from a bond and C$_1$-C$_{10}$ alkylene, wherein said alkylene is optionally substituted with one or more groups (e.g., one, two, or three groups) independently selected from halogen, C$_1$-C$_4$ haloalkyl, —CN, —OH, —O(C$_1$-C$_4$ alkyl), —NH$_2$, —NH(C$_1$-C$_4$ alkyl), —N(C$_1$-C$_4$ alkyl)(C$_1$-C$_4$ alkyl), —SH, and —S(C$_1$-C$_4$ alkyl), and further wherein one or two —CH$_2$— units comprised in said alkylene is/are each optionally replaced by a group independently selected from —O—, —NH—, —N(C$_1$-C$_4$ alkyl)-, —CO—, and —SO$_2$—.

Even more preferably, each L$^5$ is independently selected from a bond and C$_1$-C$_6$ alkylene, wherein said alkylene is optionally substituted with one or more groups (e.g., one or two groups) independently selected from halogen, C$_1$-C$_4$ haloalkyl, —CN, —OH, —O(C$_1$-C$_4$ alkyl), —NH$_2$, —NH(C$_1$-C$_4$ alkyl), and —N(C$_1$-C$_4$ alkyl)(C$_1$-C$_4$ alkyl), and further wherein one or two —CH$_2$— units comprised in said alkylene is/are each optionally replaced by a group independently selected from —O—, —NH—, —N(C$_1$-C$_4$ alkyl)-, —CO—, and —SO$_2$—.

Yet even more preferably, each L$^5$ is independently selected from a bond and C$_1$-C$_4$ alkylene. Still more preferably, each L$^5$ is independently selected from a bond and methylene.

Most preferably, L$^5$ is a bond.

Each R$^{51}$ is independently selected from aryl, heteroaryl, cycloalkyl, heterocycloalkyl, cycloalkenyl, heterocycloalkenyl, halogen, C$_1$-C$_{10}$ haloalkyl, —CN, C$_1$-C$_{10}$ alkyl, C$_2$-C$_{10}$ alkenyl, C$_2$-C$_{10}$ alkynyl, —NR$^{52}$R$^{52}$, —OR$^{52}$, —SR$^{52}$, —SOR$^{52}$, —SO$_2$R$^{52}$, —COR$^{52}$, —COOR$^{52}$, —OCOR$^{52}$, —CONR$^{52}$R$^{52}$, —NR$^{52}$COR$^{52}$, —SO$_2$NR$^{52}$R$^{52}$, —NR$^{52}$SO$_2$R$^{52}$, and —SO$_3$R$^{52}$, wherein said aryl, said heteroaryl, said cycloalkyl, said heterocycloalkyl, said cycloalkenyl and said heterocycloalkenyl are each optionally substituted with one or more groups (e.g., one, two or three groups) independently selected from halogen, C$_1$-C$_{10}$ haloalkyl, —CN, C$_1$-C$_{10}$ alkyl, C$_2$-C$_{10}$ alkenyl, C$_2$-C$_{10}$ alkynyl, —OH, —O(C$_1$-C$_{10}$ alkyl), —(C$_1$-C$_{10}$ alkylene)-OH, —(C$_1$-C$_{10}$ alkylene)-O(C$_1$-C$_{10}$ alkyl), —NH$_2$, —NH(C$_1$-C$_{10}$ alkyl), —N(C$_1$-C$_{10}$ alkyl)(C$_1$-C$_{10}$ alkyl), —CHO, —CO(C$_1$-C$_{10}$ alkyl), —COOH, tetrazolyl, —COO(C$_1$-C$_{10}$ alkyl), —OCO(C$_1$-C$_{10}$ alkyl), —CO—NH$_2$, —CO—NH(C$_1$-C$_{10}$ alkyl), —CO—N(C$_1$-C$_{10}$ alkyl)(C$_1$-C$_{10}$ alkyl), —NH—CO—(C$_1$-C$_{10}$ alkyl), —N(C$_1$-C$_{10}$ alkyl)-CO—(C$_1$-C$_{10}$ alkyl), —SO$_2$—NH$_2$, —SO$_2$—NH(C$_1$-C$_{10}$ alkyl), —SO$_2$—N(C$_1$-C$_{10}$ alkyl)(C$_1$-C$_{10}$ alkyl), —NH—SO$_2$—(C$_1$-C$_{10}$ alkyl), —N(C$_1$-C$_{10}$ alkyl)-SO$_2$—(C$_1$-C$_{10}$ alkyl), cycloalkyl, heterocycloalkyl, aryl, heteroaryl, and -L$^{51}$-R$^{53}$, and further wherein, if R$^{51}$ is C$_1$-C$_{10}$ alkyl, C$_2$-C$_{10}$ alkenyl or C$_2$-C$_{10}$ alkynyl, then said alkyl, said alkenyl or said alkynyl is optionally substituted with one or more groups (e.g., one, two or three groups) independently selected from halogen, C$_1$-C$_{10}$ haloalkyl, —CN, —OH, —O(C$_1$-C$_{10}$ alkyl), —NH$_2$, —NH(C$_1$-C$_{10}$ alkyl), —N(C$_1$-C$_{10}$ alkyl)(C$_1$-C$_{10}$ alkyl), —CHO, —CO(C$_1$-C$_{10}$ alkyl), —COOH, tetrazolyl, —COO(C$_1$-C$_{10}$ alkyl), —OCO(C$_1$-C$_{10}$ alkyl), —CO—NH$_2$, —CO—NH(C$_1$-C$_{10}$ alkyl), —CO—N(C$_1$-C$_{10}$ alkyl)(C$_1$-C$_{10}$ alkyl), —NH—CO—(C$_1$-C$_{10}$ alkyl), —N(C$_1$-C$_{10}$ alkyl)-CO—(C$_1$-C$_{10}$ alkyl), —SO$_2$—NH$_2$, —SO$_2$—NH(C$_1$-C$_{10}$ alkyl), —SO$_2$—N(C$_1$-C$_{10}$ alkyl)(C$_1$-C$_{10}$ alkyl), —NH—SO$_2$—(C$_1$-C$_{10}$ alkyl), —N(C$_1$-C$_{10}$ alkyl)-SO$_2$—(C$_1$-C$_{10}$ alkyl), cycloalkyl, heterocycloalkyl, aryl, heteroaryl, and -L$^{51}$-R$^{53}$.

Preferably, each R$^{51}$ is independently selected from aryl, heteroaryl, cycloalkyl, heterocycloalkyl, cycloalkenyl, heterocycloalkenyl, halogen, C$_1$-C$_{10}$ haloalkyl, —CN, C$_1$-C$_{10}$ alkyl, —NR$^{52}$R$^{52}$, —OR$^{52}$, —SR$^{52}$, —SO$_2$R$^{52}$, —COR$^{52}$, —COOR$^{52}$, —OCOR$^{52}$, —CONR$^{52}$R$^{52}$, —NR$^{52}$COR$^{52}$, —SO$_2$NR$^{52}$R$^{52}$, and —NR$^{52}$SO$_2$R$^{52}$, wherein said aryl, said heteroaryl, said cycloalkyl, said heterocycloalkyl, said cycloalkenyl and said heterocycloalkenyl are each optionally substituted with one or more groups (e.g., one, two or three groups) independently selected from halogen, C$_1$-C$_{10}$ haloalkyl, —CN, C$_1$-C$_{10}$ alkyl, —OH, —O(C$_1$-C$_{10}$ alkyl), —(C$_1$-C$_{10}$ alkylene)-OH, —(C$_1$-C$_{10}$ alkylene)-O(C$_1$-C$_{10}$ alkyl), —NH$_2$, —NH(C$_1$-C$_{10}$ alkyl), —N(C$_1$-C$_{10}$ alkyl)(C$_1$-C$_{10}$ alkyl), —CHO, —CO(C$_1$-C$_{10}$ alkyl), —COOH, tetrazolyl, —COO(C$_1$-C$_{10}$ alkyl), —OCO(C$_1$-C$_{10}$ alkyl), —CO—NH$_2$, —CO—NH(C$_1$-C$_{10}$ alkyl), —CO—N(C$_1$-C$_{10}$ alkyl)(C$_1$-C$_{10}$ alkyl), —NH—CO—(C$_1$-C$_{10}$ alkyl), —N(C$_1$-C$_{10}$ alkyl)-CO—(C$_1$-C$_{10}$ alkyl), —SO$_2$—NH$_2$, —SO$_2$—NH(C$_1$-C$_{10}$ alkyl), —SO$_2$—N(C$_1$-C$_{10}$ alkyl)(C$_1$-C$_{10}$ alkyl), —NH—SO$_2$—(C$_1$-C$_{10}$ alkyl), —N(C$_1$-C$_{10}$ alkyl)-SO$_2$—(C$_1$-C$_{10}$ alkyl), cycloalkyl, heterocycloalkyl, aryl, heteroaryl, and -L$^{51}$-R$^{53}$, and further wherein, if R$^{51}$ is C$_1$-C$_{10}$ alkyl, then said alkyl is optionally substituted with one or more groups (e.g., one, two or three groups) independently selected from halogen, C$_1$-C$_{10}$ haloalkyl, —CN, —OH, —O(C$_1$-C$_{10}$ alkyl), —NH$_2$, —NH(C$_1$-C$_{10}$ alkyl), —N(C$_1$-C$_{10}$ alkyl)(C$_1$-C$_{10}$ alkyl), —CHO, —CO(C$_1$-C$_{10}$ alkyl), —COOH, tetrazolyl, —COO(C$_1$-C$_{10}$ alkyl), —OCO(C$_1$-C$_{10}$ alkyl), —CO—NH$_2$, —CO—NH(C$_1$-C$_{10}$ alkyl), —CO—N(C$_1$-C$_{10}$ alkyl)(C$_1$-C$_{10}$ alkyl), —NH—CO—(C$_1$-C$_{10}$ alkyl), —N(C$_1$-C$_{10}$ alkyl)-CO—(C$_1$-C$_{10}$ alkyl), —SO$_2$—NH$_2$, —SO$_2$—NH(C$_1$-C$_{10}$ alkyl), —SO$_2$—N(C$_1$-C$_{10}$ alkyl)(C$_1$-C$_{10}$ alkyl), —NH—SO$_2$—(C$_1$-C$_{10}$ alkyl), —N(C$_1$-C$_{10}$ alkyl)-SO$_2$—(C$_1$-C$_{10}$ alkyl), cycloalkyl, heterocycloalkyl, aryl, heteroaryl, and -L$^{51}$-R$^{53}$.

More preferably, each R$^{51}$ is independently selected from aryl, heteroaryl, cycloalkyl, heterocycloalkyl, cycloalkenyl, heterocycloalkenyl, halogen, C$_1$-C$_4$ haloalkyl, —CN, C$_1$-C$_4$ alkyl, —NH$_2$, —NH(C$_1$-C$_4$ alkyl), —N(C$_1$-C$_4$ alkyl)(C$_1$-C$_4$ alkyl), —OH, and —O($C_1$-$C_4$ alkyl), wherein said aryl, said heteroaryl, said cycloalkyl, said heterocycloalkyl, said cycloalkenyl and said heterocycloalkenyl are each optionally substituted with one or more groups (e.g., one, two or three groups) independently selected from halogen, $C_1$-$C_4$ haloalkyl, —CN, $C_1$-$C_4$ alkyl, —OH, —O($C_1$-$C_4$ alkyl), —($C_1$-$C_4$ alkylene)-OH, —($C_1$-$C_4$ alkylene)-O($C_1$-$C_4$ alkyl), —$NH_2$, —NH($C_1$-$C_4$ alkyl), —N($C_1$-$C_4$ alkyl)($C_1$-$C_4$ alkyl), —CHO, —CO($C_1$-$C_4$ alkyl), —COOH, tetrazolyl, —COO($C_1$-$C_4$ alkyl), —OCO($C_1$-$C_4$ alkyl), —CO—$NH_2$, —CO—NH($C_1$-$C_4$ alkyl), —CO—N($C_1$-$C_4$ alkyl)($C_1$-$C_4$ alkyl), —NH—CO—($C_1$-$C_4$ alkyl), —N($C_1$-$C_4$ alkyl)-CO—($C_1$-$C_4$ alkyl), —$SO_2$—$NH_2$, —$SO_2$—NH($C_1$-$C_4$ alkyl), —$SO_2$—N($C_1$-$C_4$ alkyl)($C_1$-$C_4$ alkyl), —NH—$SO_2$—($C_1$-$C_4$ alkyl), —N($C_1$-$C_4$ alkyl)-$SO_2$—($C_1$-$C_4$ alkyl), cycloalkyl, heterocycloalkyl, aryl, and heteroaryl, and further wherein, if $R^{51}$ is $C_1$-$C_4$ alkyl, then said alkyl is optionally substituted with one or more groups (e.g., one, two or three groups) independently selected from halogen, $C_1$-$C_4$ haloalkyl, —CN, —OH, —O($C_1$-$C_4$ alkyl), —$NH_2$, —NH($C_1$-$C_4$ alkyl), —N($C_1$-$C_4$ alkyl)($C_1$-$C_4$ alkyl), —CHO, —CO($C_1$-$C_4$ alkyl), —COOH, tetrazolyl, —COO($C_1$-$C_4$ alkyl), —OCO($C_1$-$C_4$ alkyl), —CO—$NH_2$, —CO—NH($C_1$-$C_4$ alkyl), —CO—N($C_1$-$C_4$ alkyl)($C_1$-$C_4$ alkyl), —NH—CO—($C_1$-$C_4$ alkyl), —N($C_1$-$C_4$ alkyl)-CO—($C_1$-$C_4$ alkyl), —$SO_2$—$NH_2$, —$SO_2$—NH($C_1$-$C_4$ alkyl), —$SO_2$—N($C_1$-$C_4$ alkyl)($C_1$-$C_4$ alkyl), —NH—$SO_2$—($C_1$-$C_4$ alkyl), —N($C_1$-$C_4$ alkyl)-$SO_2$—($C_1$-$C_4$ alkyl), cycloalkyl, heterocycloalkyl, aryl, and heteroaryl.

Even more preferably, each $R^{51}$ is independently selected from: phenyl; heteroaryl having 5 or 6 ring members, wherein 1, 2 or 3 ring members are heteroatoms selected independently from O, S and N, and the remaining ring members are carbon atoms; $C_3$-$C_7$ cycloalkyl; heterocycloalkyl having 5, 6 or 7 ring members, wherein 1, 2 or 3 ring members are heteroatoms selected independently from O, S and N, and the remaining ring members are carbon atoms; $C_5$-$C_7$ cycloalkenyl; heterocycloalkenyl having 5, 6 or 7 ring members, wherein 1, 2 or 3 ring members are heteroatoms selected independently from O, S and N, and the remaining ring members are carbon atoms; halogen; $C_1$-$C_4$ haloalkyl; —CN; $C_1$-$C_4$ alkyl; —$NH_2$; —NH($C_1$-$C_4$ alkyl); —N($C_1$-$C_4$ alkyl)($C_1$-$C_4$ alkyl); —OH; and —O($C_1$-$C_4$ alkyl); wherein said phenyl, said heteroaryl, said cycloalkyl, said heterocycloalkyl, said cycloalkenyl and said heterocycloalkenyl are each optionally substituted with one or more groups (e.g., one, two or three groups) independently selected from halogen (e.g., —F, —Cl, or —Br), $C_1$-$C_4$ haloalkyl (e.g., —$CF_3$), —CN, $C_1$-$C_4$ alkyl (e.g., methyl, ethyl, or n-propyl), —OH, —O($C_1$-$C_4$ alkyl) (e.g., —$OCH_3$), —($C_1$-$C_4$ alkylene)-OH, —($C_1$-$C_4$ alkylene)-O($C_1$-$C_4$ alkyl), —$NH_2$, —NH($C_1$-$C_4$ alkyl) (e.g., —$NHCH_3$), —N($C_1$-$C_4$ alkyl)($C_1$-$C_4$ alkyl) (e.g., —N($CH_3$)$_2$), —CHO, —CO($C_1$-$C_4$ alkyl) (e.g., —$COCH_3$), —COOH, tetrazolyl (e.g., 1H-tetrazol-5-yl or 2H-tetrazol-5-yl), —COO($C_1$-$C_4$ alkyl) (e.g., —$COOCH_3$), —$SO_2$—$NH_2$, —$SO_2$—NH($C_1$-$C_4$ alkyl) (e.g., —$SO_2$—$NHCH_3$), —$SO_2$—N($C_1$-$C_4$ alkyl)($C_1$-$C_4$ alkyl) (e.g., —$SO_2$—N($CH_3$)$_2$), cycloalkyl (e.g., cyclopropyl), heterocycloalkyl (e.g., piperidinyl or morpholinyl), aryl (e.g., phenyl), and heteroaryl (e.g., pyrimidinyl); and further wherein, if $R^{51}$ is $C_1$-$C_4$ alkyl, then said alkyl is optionally substituted with one or more groups (e.g., one, two or three groups) independently selected from halogen, $C_1$-$C_4$ haloalkyl, —CN, —OH, —O($C_1$-$C_4$ alkyl), —$NH_2$, —NH($C_1$-$C_4$ alkyl), —N($C_1$-$C_4$ alkyl)($C_1$-$C_4$ alkyl), —CHO, —CO($C_1$-$C_4$ alkyl), —COOH, tetrazolyl, —COO($C_1$-$C_4$ alkyl), —$SO_2$—$NH_2$, —$SO_2$—NH($C_1$-$C_4$ alkyl), —$SO_2$—N($C_1$-$C_4$ alkyl)($C_1$-$C_4$ alkyl), —NH—$SO_2$—($C_1$-$C_4$ alkyl), cycloalkyl, heterocycloalkyl, aryl, and heteroaryl.

Even more preferably, each $R^{51}$ is independently selected from: phenyl; heteroaryl having 5 or 6 ring members, wherein 1, 2 or 3 ring members are heteroatoms selected independently from O, S and N, and the remaining ring members are carbon atoms (such as, e.g., pyridinyl (e.g., pyridin-3-yl or pyridin-4-yl), thiazolyl (e.g., thiazol-2-yl), imidazolyl (e.g., 1H-imidazol-2-yl or 3H-imidazol-4-yl), pyrazolyl (e.g., 1H-pyrazol-3-yl or 2H-pyrazol-3-yl), oxazolyl (e.g., oxazol-5-yl), or oxadiazolyl (e.g., [1,3,4]oxadiazol-2-yl)); $C_1$-$C_4$ haloalkyl (e.g., —$CF_3$ or —$CHF_2$); $C_1$-$C_4$ alkyl (e.g., methyl or ethyl); —$NH_2$; —NH($C_1$-$C_4$ alkyl) (e.g., —$NHCH_3$); —N($C_1$-$C_4$ alkyl)($C_1$-$C_4$ alkyl) (e.g., —N($CH_3$)$_2$); —OH; and —O($C_1$-$C_4$ alkyl); wherein said phenyl and said heteroaryl are each optionally substituted with one or more groups (e.g., one or two groups) independently selected from halogen, $C_1$-$C_4$ haloalkyl, —CN, $C_1$-$C_4$ alkyl, —OH, —O($C_1$-$C_4$ alkyl) (e.g., methoxy), —$NH_2$, —NH($C_1$-$C_4$ alkyl), and —N($C_1$-$C_4$ alkyl)($C_1$-$C_4$ alkyl); and further wherein, if $R^{51}$ is $C_1$-$C_4$ alkyl, then said alkyl is optionally substituted with one or more groups (e.g., one or two groups) independently selected from halogen, $C_1$-$C_4$ haloalkyl, —CN, —OH, —O($C_1$-$C_4$ alkyl), —$NH_2$, —NH($C_1$-$C_4$ alkyl), and —N($C_1$-$C_4$ alkyl)($C_1$-$C_4$ alkyl).

Yet even more preferably, $R^{51}$ is oxadiazolyl (e.g., [1,3,4]oxadiazol-2-yl) or —O($C_1$-$C_4$ alkyl) (particularly methoxy), wherein said oxadiazolyl is optionally substituted with one group selected from halogen, $C_1$-$C_4$ haloalkyl, —CN, $C_1$-$C_4$ alkyl, —OH, —O($C_1$-$C_4$ alkyl), —$NH_2$, —NH($C_1$-$C_4$ alkyl), and —N($C_1$-$C_4$ alkyl)($C_1$-$C_4$ alkyl).

Still more preferably, $R^{51}$ is oxadiazolyl (e.g., [1,3,4]oxadiazol-2-yl), wherein said oxadiazolyl is optionally substituted with one group selected from halogen, $C_1$-$C_4$ haloalkyl, —CN, $C_1$-$C_4$ alkyl, —OH, —O($C_1$-$C_4$ alkyl), —$NH_2$, —NH($C_1$-$C_4$ alkyl), and —N($C_1$-$C_4$ alkyl)($C_1$-$C_4$ alkyl).

Most preferably, $R^{51}$ is oxadiazolyl (particularly [1,3,4]oxadiazol-2-yl).

In one preferred embodiment, each $R^{51}$ is independently selected from aryl, heteroaryl, cycloalkyl, heterocycloalkyl, cycloalkenyl, heterocycloalkenyl, halogen, $C_1$-$C_4$ haloalkyl, —CN, —$NH_2$, —NH($C_1$-$C_4$ alkyl), —N($C_1$-$C_4$ alkyl)($C_1$-$C_4$ alkyl), —OH, and —O($C_1$-$C_4$ alkyl), wherein said aryl, said heteroaryl, said cycloalkyl, said heterocycloalkyl, said cycloalkenyl and said heterocycloalkenyl are each optionally substituted with one or more groups independently selected from halogen, $C_1$-$C_4$ haloalkyl, —CN, $C_1$-$C_4$ alkyl, —OH, —O($C_1$-$C_4$ alkyl), —($C_1$-$C_4$ alkylene)-OH, —($C_1$-$C_4$ alkylene)-O($C_1$-$C_4$ alkyl), —$NH_2$, —NH($C_1$-$C_4$ alkyl), —N($C_1$-$C_4$ alkyl)($C_1$-$C_4$ alkyl), —CHO, —CO($C_1$-$C_4$ alkyl), —COOH, tetrazolyl, —COO($C_1$-$C_4$ alkyl), —OCO($C_1$-$C_4$ alkyl), —CO—$NH_2$, —CO—NH($C_1$-$C_4$ alkyl), —CO—N($C_1$-$C_4$ alkyl)($C_1$-$C_4$ alkyl), —NH—CO—($C_1$-$C_4$ alkyl), —N($C_1$-$C_4$ alkyl)-CO—($C_1$-$C_4$ alkyl), —$SO_2$—$NH_2$, —$SO_2$—NH($C_1$-$C_4$ alkyl), —$SO_2$—N($C_1$-$C_4$ alkyl)($C_1$-$C_4$ alkyl), —NH—$SO_2$—($C_1$-$C_4$ alkyl), —N($C_1$-$C_4$ alkyl)-$SO_2$—($C_1$-$C_4$ alkyl), cycloalkyl, heterocycloalkyl, aryl, and heteroaryl.

Each $R^{52}$ is independently selected from hydrogen, $C_1$-$C_{10}$ alkyl, $C_2$-$C_{10}$ alkenyl, $C_2$-$C_{10}$ alkynyl, aryl, heteroaryl, cycloalkyl, and heterocycloalkyl, wherein said aryl, said heteroaryl, said cycloalkyl, and said heterocycloalkyl are each optionally substituted with one or more groups (e.g., one, two, or three groups) independently selected from $C_1$-$C_{10}$ alkyl, $C_2$-$C_{10}$ alkenyl, $C_2$-$C_{10}$ alkynyl, halogen, $C_1$-$C_{10}$ haloalkyl, —CN, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), cycloalkyl, and heterocycloalkyl, wherein if $R^{52}$ is $C_1$-$C_{10}$ alkyl, $C_2$-$C_{10}$ alkenyl or $C_2$-$C_{10}$ alkynyl, then said alkyl, said alkenyl or said alkynyl is optionally substituted with one or more groups (e.g., one, two, or three groups) independently selected from halogen, $C_1$-$C_{10}$ haloalkyl, —CN, —OH, —O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), cycloalkyl, and heterocycloalkyl, and further if two groups $R^{52}$ are attached to the same nitrogen atom, then these two groups $R^{52}$ may also together form a $C_2$-$C_8$ alkylene (so that the resulting group is a 3- to 9-membered nitrogen-containing heterocycloalkyl ring which is formed from the two groups $R^{52}$ and the nitrogen atom that they are attached to).

In a preferred embodiment, each $R^{52}$ is independently selected from hydrogen, $C_2$-$C_{10}$ alkenyl, $C_2$-$C_{10}$ alkynyl, aryl, heteroaryl, cycloalkyl, and heterocycloalkyl, wherein said aryl, said heteroaryl, said cycloalkyl, and said heterocycloalkyl are each optionally substituted with one or more groups (e.g., one, two, or three groups) independently selected from $C_1$-$C_{10}$ alkyl, $C_2$-$C_{10}$ alkenyl, $C_2$-$C_{10}$ alkynyl, halogen, $C_1$-$C_{10}$ haloalkyl, —CN, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), cycloalkyl, and heterocycloalkyl, wherein if $R^{52}$ is $C_1$-$C_{10}$ alkyl, $C_2$-$C_{10}$ alkenyl or $C_2$-$C_{10}$ alkynyl, then said alkyl, said alkenyl or said alkynyl is optionally substituted with one or more groups (e.g., one, two, or three groups) independently selected from halogen, $C_1$-$C_{10}$ haloalkyl, —CN, —OH, —O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), cycloalkyl, and heterocycloalkyl, and further if two groups $R^{52}$ are attached to the same nitrogen atom, then these two groups $R^{52}$ may also together form a $C_2$-$C_8$ alkylene.

Preferably, each $R^{52}$ is independently selected from hydrogen, $C_1$-$C_{10}$ alkyl, aryl, heteroaryl, cycloalkyl, and heterocycloalkyl, wherein said aryl, said heteroaryl, said cycloalkyl, and said heterocycloalkyl are each optionally substituted with one or more groups (e.g., one, two, or three groups) independently selected from $C_1$-$C_4$ alkyl, halogen, $C_1$-$C_4$ haloalkyl, —CN, —OH, —O($C_1$-$C_4$ alkyl), —($C_1$-$C_4$ alkylene)-OH, —($C_1$-$C_4$ alkylene)-O($C_1$-$C_4$ alkyl), —$NH_2$, —NH($C_1$-$C_4$ alkyl), —N($C_1$-$C_4$ alkyl)($C_1$-$C_4$ alkyl), cycloalkyl, and heterocycloalkyl, wherein said $C_1$-$C_{10}$ alkyl is optionally substituted with one or more groups (e.g., one, two, or three groups) independently selected from halogen, $C_1$-$C_4$ haloalkyl, —CN, —OH, —O($C_1$-$C_4$ alkyl), —$NH_2$, —NH($C_1$-$C_4$ alkyl), —N($C_1$-$C_4$ alkyl)($C_1$-$C_4$ alkyl), cycloalkyl, and heterocycloalkyl, and further if two groups $R^{52}$ are attached to the same nitrogen atom, then these two groups $R^{52}$ may also together form a $C_2$-$C_8$ alkylene (so that the resulting group is a 3- to 9-membered nitrogen-containing heterocycloalkyl ring which is formed from the two groups $R^{52}$ and the nitrogen atom that they are attached to).

More preferably, each $R^{52}$ is independently selected from hydrogen and $C_1$-$C_{10}$ alkyl, wherein said alkyl is optionally substituted with one or more groups (e.g., one, two, or three groups) independently selected from halogen, $C_1$-$C_4$ haloalkyl, —CN, —OH, —O($C_1$-$C_4$ alkyl), —$NH_2$, —NH($C_1$-$C_4$ alkyl), —N($C_1$-$C_4$ alkyl)($C_1$-$C_4$ alkyl), cycloalkyl, and heterocycloalkyl, and further if two groups $R^{52}$ are attached to the same nitrogen atom, then these two groups $R^{52}$ may also together form a $C_2$-$C_8$ alkylene (so that the resulting group is a 3- to 9-membered nitrogen-containing heterocycloalkyl ring which is formed from the two groups $R^{52}$ and the nitrogen atom that they are attached to).

Even more preferably, each $R^{52}$ is independently selected from hydrogen and $C_1$-$C_4$ alkyl, wherein said alkyl is optionally substituted with one or more groups (e.g., one, two, or three groups) independently selected from halogen, $C_1$-$C_4$ haloalkyl, —CN, —OH, —O($C_1$-$C_4$ alkyl), —$NH_2$, —NH($C_1$-$C_4$ alkyl), and —N($C_1$-$C_4$ alkyl)($C_1$-$C_4$ alkyl), and further if two groups $R^{52}$ are attached to the same nitrogen atom, then these two groups $R^{52}$ may also together form a $C_4$-$C_6$ alkylene.

Yet even more preferably, each $R^{52}$ is independently selected from hydrogen and $C_1$-$C_4$ alkyl, and if two groups $R^{52}$ are attached to the same nitrogen atom, then these two groups $R^{52}$ may also together form a $C_4$-$C_6$ alkylene.

Most preferably, each $R^{52}$ is independently selected from hydrogen and $C_1$-$C_4$ alkyl (e.g., methyl or ethyl).

Each $L^{51}$ is independently selected from a bond, $C_1$-$C_{10}$ alkylene, $C_2$-$C_{10}$ alkenylene, and $C_2$-$C_{10}$ alkynylene, wherein one or more —$CH_2$— units (e.g., one, two or three —$CH_2$— units) comprised in said alkylene, said alkenylene or said alkynylene are each optionally replaced by a group independently selected from —O—, —NH—, —N($C_1$-$C_{10}$ alkyl)-, —CO—, —S—, —SO—, and —$SO_2$—.

Preferably, each $L^{51}$ is independently selected from a bond and $C_1$-$C_{10}$ alkylene, wherein one or more —$CH_2$— units (e.g., one or two —$CH_2$— units) comprised in said alkylene are each optionally replaced by a group independently selected from —O—, —NH—, —N($C_1$-$C_4$ alkyl)-, —CO—, —S—, —SO—, and —$SO_2$—.

Each $R^{53}$ is independently selected from aryl, heteroaryl, cycloalkyl, heterocycloalkyl, cycloalkenyl, heterocycloalkenyl, halogen, $C_1$-$C_{10}$ haloalkyl, —CN, $C_1$-$C_{10}$ alkyl, $C_2$-$C_{10}$ alkenyl, $C_2$-$C_{10}$ alkynyl, —$NH_2$, —NH($C_1$-$C_{10}$ alkyl), —N($C_1$-$C_{10}$ alkyl)($C_1$-$C_{10}$ alkyl), —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —SH, and —S($C_1$-$C_{10}$ alkyl), wherein said aryl, said heteroaryl, said cycloalkyl, said heterocycloalkyl, said cycloalkenyl and said heterocycloalkenyl are each optionally substituted with one or more groups (e.g., one, two or three groups) independently selected from halogen, $C_1$-$C_{10}$ haloalkyl, —CN, $C_1$-$C_{10}$ alkyl, $C_2$-$C_{10}$ alkenyl, $C_2$-$C_{10}$ alkynyl, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), cycloalkyl, and heterocycloalkyl.

Preferably, each $R^{53}$ is independently selected from aryl, heteroaryl, cycloalkyl, heterocycloalkyl, cycloalkenyl, heterocycloalkenyl, halogen, $C_1$-$C_4$ haloalkyl, —CN, $C_1$-$C_4$ alkyl, —$NH_2$, —NH($C_1$-$C_4$ alkyl), —N($C_1$-$C_4$ alkyl)($C_1$-$C_4$ alkyl), —OH, —O($C_1$-$C_4$ alkyl), —($C_1$-$C_4$ alkylene)-OH, —($C_1$-$C_4$ alkylene)-O($C_1$-$C_4$ alkyl), —SH, and —S($C_1$-$C_4$ alkyl), wherein said aryl, said heteroaryl, said cycloalkyl, said heterocycloalkyl, said cycloalkenyl and said heterocycloalkenyl are each optionally substituted with one or more groups (e.g., one, two or three groups) independently selected from halogen, $C_1$-$C_4$ haloalkyl, —CN, $C_1$-$C_4$ alkyl, —OH, —O($C_1$-$C_4$ alkyl), —($C_1$-$C_4$ alkylene)-OH, —($C_1$-$C_4$ alkylene)-O($C_1$-$C_4$ alkyl), —$NH_2$, —NH($C_1$-$C_4$ alkyl), —N($C_1$-$C_4$ alkyl)($C_1$-$C_4$ alkyl), cycloalkyl, and heterocycloalkyl.

In accordance with the above definitions of $L^5$ and $R^{51}$, it is particularly preferred that each $L^5$ is independently a bond or $C_1$-$C_4$ alkylene (particularly methylene), and that each $R^{51}$ is independently selected from: phenyl; heteroaryl having 5 or 6 ring members, wherein 1, 2 or 3 ring members are heteroatoms selected independently from O, S and N, and the remaining ring members are carbon atoms (such as, e.g., pyridinyl (e.g., pyridin-3-yl or pyridin-4-yl), thiazolyl (e.g., thiazol-2-yl), imidazolyl (e.g., 1H-imidazol-2-yl or 3H-imidazol-4-yl), pyrazolyl (e.g., 1H-pyrazol-3-yl or 2H-pyrazol-3-yl), oxazolyl (e.g., oxazol-5-yl), or oxadiazolyl (e.g., [1,3,4]oxadiazol-2-yl)); $C_1$-$C_4$ haloalkyl (e.g., —$CF_3$ or —$CHF_2$); $C_1$-$C_4$ alkyl (e.g., methyl or ethyl); —$NH_2$; —NH($C_1$-$C_4$ alkyl) (e.g., —$NHCH_3$); —N($C_1$-$C_4$ alkyl)($C_1$-$C_4$ alkyl) (e.g., —N($CH_3$)$_2$); —OH; and —O($C_1$-$C_4$ alkyl); wherein said phenyl and said heteroaryl are each optionally substituted with one or more groups (e.g., one or two groups) independently selected from halogen, $C_1$-$C_4$ haloalkyl, —CN, $C_1$-$C_4$ alkyl, —OH, —O($C_1$-$C_4$ alkyl) (e.g., —$OCH_3$), —$NH_2$, —NH($C_1$-$C_4$ alkyl), and —N($C_1$-$C_4$ alkyl)($C_1$-$C_4$ alkyl); and further wherein, if $R^{51}$ is $C_1$-$C_4$ alkyl, then said alkyl is optionally substituted with one or more groups (e.g., one or two groups) independently selected from halogen, $C_1$-$C_4$ haloalkyl, —CN, —OH, —O($C_1$-$C_4$ alkyl), —$NH_2$, —NH($C_1$-$C_4$ alkyl), and —N($C_1$-$C_4$ alkyl)($C_1$-$C_4$ alkyl).

Even more preferably, $L^5$ is a bond and $R^{51}$ is oxadiazolyl (e.g., [1,3,4]oxadiazol-2-yl), wherein said oxadiazolyl is optionally substituted with one group selected from halogen, $C_1$-$C_4$ haloalkyl, —CN, $C_1$-$C_4$ alkyl, —OH, —O($C_1$-$C_4$ alkyl), —$NH_2$, —NH($C_1$-$C_4$ alkyl), and —N($C_1$-$C_4$ alkyl)($C_1$-$C_4$ alkyl), or $L^5$ is $C_1$-$C_4$ alkylene (particularly methylene) and $R^{51}$ is —O($C_1$-$C_4$ alkyl) (particularly —$OCH_3$). Accordingly, it is even more preferred that each $R^5$ (if present) is independently oxadiazolyl (e.g., [1,3,4]oxadiazol-2-yl) or —($C_1$-$C_4$ alkylene)-O—($C_1$-$C_4$ alkyl) (particularly —$CH_2$—O—$CH_3$), wherein said oxadiazolyl is optionally substituted with one group selected from halogen, $C_1$-$C_4$ haloalkyl, —CN, $C_1$-$C_4$ alkyl, —OH, —O($C_1$-$C_4$ alkyl), —$NH_2$, —NH($C_1$-$C_4$ alkyl), and —N($C_1$-$C_4$ alkyl)($C_1$-$C_4$ alkyl). Yet even more preferably, $L^5$ is a bond, and $R^{51}$ is oxadiazolyl (e.g., [1,3,4]oxadiazol-2-yl), wherein said oxadiazolyl is optionally substituted with one group selected from halogen, $C_1$-$C_4$ haloalkyl, —CN, $C_1$-$C_4$ alkyl, —OH, —O($C_1$-$C_4$ alkyl), —$NH_2$, —NH($C_1$-$C_4$ alkyl), and —N($C_1$-$C_4$ alkyl)($C_1$-$C_4$ alkyl).

Most preferably, $L^5$ is a bond, and $R^{51}$ is oxadiazolyl (particularly [1,3,4]oxadiazol-2-yl).

m is an integer of 0 to 3. Preferably, m is 0, 1 or 2. More preferably, m is 0 or 1. Even more preferably, m is 0.

It is to be understood that m indicates the number of substituents $R^5$ that are bound to the 5-membered heterocyclic ring group (containing the ring atoms $X_1$, $X_2$ and $X_3$) which is comprised in the tricyclic ring system of the compound of formula (I). If m is 0, then this 5-membered heterocyclic ring group is not substituted with any group $R^5$, i.e. is substituted with hydrogen instead of $R^5$. It will further be understood that the upper limit of m, i.e. the maximum number of substituents $R^5$, depends on whether the ring atoms $X_1$, $X_2$ and $X_3$ are C or N, and whether the bonds connecting these ring atoms are single bonds or double bonds.

A preferred point of attachment of $R^5$ is the ring atom $X_2$ depicted in formula (I). It is thus preferred that at least one of the group(s) $R^5$, if present, is attached to $X_2$. Accordingly, it is particularly preferred that m is 0 or 1, and that the one group $R^5$, if present (i.e., if m is 1), is attached to $X_2$.

In the first aspect of the invention, the following compounds may be excluded, preferably from formula (I):
5-methyl-4-oxo-5,6-dihydro-4H-1,2,5,10b-tetraaza-benzo[e]azulene-3-carboxylic acid ethyl ester; and
5-methyl-4-oxo-5,6-dihydro-4H-1,2,5,10b-tetraaza-benzo[e]azulene-3-carboxylic acid methyl ester.

In the second aspect of the invention, the following compounds are excluded from formula (I):
5-allyl-3,3a,5,6-tetrahydro-1H-benzo[f]pyrrolo-[1,2-a][1,4]diazepin-4(2H)-one;
5-butyl-3,3a,5,6-tetrahydro-1H-benzo[f]pyrrolo-[1,2-a][1,4]diazepin-4(2H)-one;
5-methyl-5,6-dihydro-benzo[f]pyrrolo[1,2-a][1,4]diazepin-4-one; and
5-methyl-5,6-dihydro-3,5,10b-triaza-benzo[e]azulen-4-one.

In the second aspect of the invention it is preferred that these compounds are additionally excluded from formula I:
5-methyl-4-oxo-5,6-dihydro-4H-1,2,5,10b-tetraaza-benzo[e]azulene-3-carboxylic acid ethyl ester;
5-methyl-5,6-dihydro-1,5,10b-triaza-benzo[e]azulen-4-one;
9-fluoro-5-methyl-5,6-dihydro-1,5,10b-triaza-benzo[e]azulen-4-one;
8-methoxy-5-methyl-5,6-dihydro-1,5,10b-triaza-benzo[e]azulen-4-one;
3-bromo-5-methyl-5,6-dihydro-1,5,10b-triaza-benzo[e]azulen-4-one;
5-(4-chloro-butyl)-5,6-dihydro-benzo[f]pyrrolo[1,2-a][1,4]diazepin-4-one; and
5-(4-chloro-butyl)-benzo[f]pyrrolo[1,2-a][1,4]diazepine-4,6-dione.

Even more preferably, in the second aspect of the invention, as well as the above compounds, 5-methyl-4-oxo-5,6-dihydro-4H-1,2,5,10b-tetraaza-benzo[e]azulene-3-carboxylic acid methyl ester is also excluded from formula I.

It is particularly preferred that the compound of formula (I) according to the first or second aspect of the invention is one of the specific compounds of formula (I) described in the examples section of this specification, including any one of the Examples 1 to 223 described further below, either in non-salt form (e.g., in free base or free acid form) or as a pharmaceutically acceptable salt, solvate or prodrug of the respective compound.

Accordingly, it is particularly preferred that the compound of formula (I) according to the first or the second aspect of the invention is selected from:
9-Bromo-5-methyl-spiro[benzo[f]pyrrolo[1,2-a][1,4]diazepine-6,1'-cyclopropan]-4(5H)-one;
9-Bromo-5-methoxymethyl-spiro[benzo[f]pyrrolo[1,2-a][1,4]diazepine-6,1'-cyclopropan]-4(5H)-one;
9-Bromo-5-(methyl-d$_3$)-spiro[benzo[f]pyrrolo[1,2-a][1,4]diazepine-6,1'-cyclopropan]-4(5H)-one;
2,9-Dibromo-5-methyl-spiro[benzo[f]pyrrolo[1,2-a][1,4]diazepine-6,1'-cyclopropan]-4(5H)-one;
9-Bromo-2-chloro-5-methyl-spiro[benzo[f]pyrrolo[1,2-a][1,4]diazepine-6,1'-cyclopropan]-4(5H)-one;
9-Bromo-3-chloro-5-methyl-spiro[benzo[f]pyrrolo[1,2-a][1,4]diazepine-6,1'-cyclopropan]-4(5H)-one;
9-Bromo-7-fluoro-5-methyl-spiro[benzo[f]pyrrolo[1,2-a][1,4]diazepine-6,1'-cyclopropan]-4(5H)-one;
9-Bromo-10-fluoro-5-methyl-spiro[benzo[f]pyrrolo[1,2-a][1,4]diazepine-6,1'-cyclopropan]-4(5H)-one;
9-Bromo-8-fluoro-5-methyl-spiro[benzo[f]pyrrolo[1,2-a][1,4]diazepine-6,1'-cyclopropan]-4(5H)-one;
9-Bromo-2-phenyl-5-methyl-spiro[benzo[f]pyrrolo[1,2-a][1,4]diazepine-6,1'-cyclopropan]-4(5H)-one;
9-Bromo-5-methyl-2-phenyl-spiro[benzo[f]pyrazolo[1,5-a][1,4]diazepine-6,1'-cyclopropan]-4(5H)-one;
9-Bromo-6,6-spirocyclopropyl-5-methyl-2-phenyl-5,6-dihydro-3,5,10b-triaza-benzo[e]azulen-4-one;
8-Bromo-5-methyl-spiro[benzo[f]pyrrolo[1,2-a][1,4]diazepine-6,1'-cyclopropan]-4(5H)-one;

7-Bromo-5-methyl-spiro[benzo[f]pyrrolo[1,2-a][1,4]diazepine-6,1'-cyclopropan]-4(5H)-one;

10-Bromo-5-methyl-spiro[benzo[f]pyrrolo[1,2-a][1,4]diazepine-6,1'-cyclopropan]-4(5H)-one;

8-Bromo-5-methyl-2-phenyl-spiro[benzo[f]pyrrolo[1,2-a][1,4]diazepine-6,1'-cyclopropan]-4(5H)-one;

2-Bromo-5-methyl-9-(2-methyl-pyridin-3-yl)-spiro[benzo[f]pyrrolo[1,2-a][1,4]diazepine-6,1'-cyclopropan]-4(5H)-one;

2-Bromo-5-methyl-9-(6-methyl-pyridin-3-yl)-spiro[benzo[f]pyrrolo[1,2-a][1,4]diazepine-6,1'-cyclopropan]-4(5H)-one;

2-Bromo-5-methyl-9-(2-ethyl-pyridin-3-yl)-spiro[benzo[f]pyrrolo[1,2-a][1,4]diazepine-6,1'-cyclopropan]-4(5H)-one;

5-Methyl-9-(2-methyl-pyridin-3-yl)-spiro[benzo[f]pyrrolo[1,2-a][1,4]diazepine-6,1'-cyclopropan]-4(5H)-one;

5-Methoxymethyl-9-(2-methyl-pyridin-3-yl)-spiro[benzo[f]pyrrolo[1,2-a][1,4]diazepine-6,1'-cyclopropan]-4(5H)-one;

5-Methyl-9-(pyridin-4-yl)-spiro[benzo[f]pyrrolo[1,2-a][1,4]diazepine-6,1'-cyclopropan]-4(5H)-one;

5-Methyl-9-(pyridin-3-yl)-spiro[benzo[f]pyrrolo[1,2-a][1,4]diazepine-6,1'-cyclopropan]-4(5H)-one;

5-Methyl-9-(2-ethylpyridin-3-yl)-spiro[benzo[f]pyrrolo[1,2-a][1,4]diazepine-6,1'-cyclopropan]-4(5H)-one;

5-Methyl-9-(6-methylpyridin-3-yl)-spiro[benzo[f]pyrrolo[1,2-a][1,4]diazepine-6,1'-cyclopropan]-4(5H)-one;

5-Methyl-9-(2-methylpyridin-4-yl)-spiro[benzo[f]pyrrolo[1,2-a][1,4]diazepine-6,1'-cyclopropan]-4(5H)-one;

5-Methyl-9-(3,5-dimethyl-1H-pyrazol-4-yl)-spiro[benzo[f]pyrrolo[1,2-a][1,4]diazepine-6,1'-cyclopropan]-4(5H)-one;

5-Methyl-9-(3-trifluoromethyl-1H-pyrazol-4-yl)-spiro[benzo[f]pyrrolo[1,2-a][1,4]diazepine-6,1'-cyclopropan]-4(5H)-one;

5-Methyl-9-(1-methyl-pyrazol-4-yl)-spiro[benzo[f]pyrrolo[1,2-a][1,4]diazepine-6,1'-cyclopropan]-4(5H)-one;

5-Methyl-9-(1-methyl-pyrazol-5-yl)-spiro[benzo[f]pyrrolo[1,2-a][1,4]diazepine-6,1'-cyclopropan]-4(5H)-one;

5-Methyl-9-(6-fluoropyridin-3-yl)-spiro[benzo[f]pyrrolo[1,2-a][1,4]diazepine-6,1'-cyclopropan]-4(5H)-one;

5-Methyl-9-(6-fluoro-2-methylpyridin-3-yl)-spiro[benzo[f]pyrrolo[1,2-a][1,4]diazepine-6,1'-cyclopropan]-4(5H)-one;

5-Methyl-9-(2-fluoropyridin-3-yl)-spiro[benzo[f]pyrrolo[1,2-a][1,4]diazepine-6,1'-cyclopropan]-4(5H)-one;

5-Methyl-9-(2-fluoropyridin-4-yl)-spiro[benzo[f]pyrrolo[1,2-a][1,4]diazepine-6,1'-cyclopropan]-4(5H)-one;

5-Methyl-9-(2-trifluoromethylpyridin-4-yl)-spiro[benzo[f]pyrrolo[1,2-a][1,4]diazepine-6,1'-cyclopropan]-4(5H)-one;

5-Methyl-9-(2-trifluoromethylpyridin-3-yl)-spiro[benzo[f]pyrrolo[1,2-a][1,4]diazepine-6,1'-cyclopropan]-4(5H)-one;

5-Methyl-9-(4-trifluoromethylpyridin-3-yl)-spiro[benzo[f]pyrrolo[1,2-a][1,4]diazepine-6,1'-cyclopropan]-4(5H)-one;

5-Methyl-9-(3-methylpyridin-4-yl)-spiro[benzo[f]pyrrolo[1,2-a][1,4]diazepine-6,1'-cyclopropan]-4(5H)-one;

5-Methyl-9-(3,4-dimethoxy-phenyl)-spiro[benzo[f]pyrrolo[1,2-a][1,4]diazepine-6,1'-cyclopropan]-4(5H)-one;

5-Methyl-9-(6-amino-5-trifluoromethyl-pyridin-3-yl)-spiro[benzo[f]pyrrolo[1,2-a][1,4]diazepine-6,1'-cyclopropan]-4(5H)-one;

5-Methyl-9-(imidazo[1,2-a]pyridin-6-yl)-spiro[benzo[f]pyrrolo[1,2-a][1,4]diazepine-6,1'-cyclopropan]-4(5H)-one;

5-Methyl-9-(6-morpholin-4-yl-pyridin-3-yl)-spiro[benzo[f]pyrrolo[1,2-a][1,4]diazepine-6,1'-cyclopropan]-4(5H)-one;

5-Methyl-9-(3,4,5,6-tetrahydro-2H-[1,2']bipyridinyl-5'-yl)-spiro[benzo[f]pyrrolo[1,2-a][1,4]diazepine-6,1'-cyclopropan]-4(5H)-one;

5-Methyl-9-(3-cyanophenyl)-spiro[benzo[f]pyrrolo[1,2-a][1,4]diazepine-6,1'-cyclopropan]-4(5H)-one;

5-Methyl-9-(3-(1H-tetrazol-5-yl)-phenyl)-spiro[benzo[f]pyrrolo[1,2-a][1,4]diazepine-6,1'-cyclopropan]-4(5H)-one;

5-Methyl-9-(1,2,3,6-tetrahydro-pyridin-4-yl)-spiro[benzo[f]pyrrolo[1,2-a][1,4]diazepine-6,1'-cyclopropan]-4(5H)-one;

5-Methyl-9-(1-pyrimidin-4-yl-1,2,3,6-tetrahydro-pyridin-4-yl)-spiro[benzo[f]pyrrolo[1,2-a][1,4]diazepine-6,1'-cyclopropan]-4(5H)-one;

5-Methyl-9-(1-acetyl-1,2,3,6-tetrahydro-pyridin-4-yl)-spiro[benzo[f]pyrrolo[1,2-a][1,4]diazepine-6,1'-cyclopropan]-4(5H)-one;

5-Methyl-9-(4-methyl-oxazol-5-yl)-spiro[benzo[f]pyrrolo[1,2-a][1,4]diazepine-6,1'-cyclopropan]-4(5H)-one;

5-Methyl-9-(4-methylthiazol-5-yl)-spiro[benzo[f]pyrrolo[1,2-a][1,4]diazepine-6,1'-cyclopropan]-4(5H)-one;

5-Methyl-9-acetonitrile-spiro[benzo[f]pyrrolo[1,2-a][1,4]diazepine-6,1'-cyclopropan]-4(5H)-one;

5-Methyl-9-acrylonitrile-spiro[benzo[f]pyrrolo[1,2-a][1,4]diazepine-6,1'-cyclopropan]-4(5H)-one;

5-Methyl-9-propionitrile-spiro[benzo[f]pyrrolo[1,2-a][1,4]diazepine-6,1'-cyclopropan]-4(5H)-one;

5-Methyl-9-(6-chloropyridin-3-yl)-spiro[benzo[f]pyrrolo[1,2-a][1,4]diazepine-6,1'-cyclopropan]-4(5H)-one;

5-(Methyl-$d_3$)-9-(6-fluoropyridin-3-yl)-spiro[benzo[f]pyrrolo[1,2-a][1,4]diazepine-6,1'-cyclopropan]-4(5H)-one;

5-Methyl-9-(2,6-dimethylpyridin-3-yl)-spiro[benzo[f]pyrrolo[1,2-a][1,4]diazepine-6,1'-cyclopropan]-4(5H)-one;

5-Methyl-9-(4-fluoropyridin-2-yl)-spiro[benzo[f]pyrrolo[1,2-a][1,4]diazepine-6,1'-cyclopropan]-4(5H)-one;

5-Methyl-9-(3-methyl-pyrazin-2-yl)-5,6-spiro[benzo[f]pyrrolo[1,2-a][1,4]diazepine-6,1'-cyclopropan]-4(5H)-one;

5-Methyl-9-(4-methyl-pyrimidin-5-yl)-spiro[benzo[f]pyrrolo[1,2-a][1,4]diazepine-6,1'-cyclopropan]-4(5H)-one;

5-Methyl-9-(6-trifluoromethylpyridin-3-yl)-spiro[benzo[f]pyrrolo[1,2-a][1,4]diazepine-6,1'-cyclopropan]-4(5H)-one;

5-Methyl-9-(2-propylpyridin-3-yl)-spiro[benzo[f]pyrrolo[1,2-a][1,4]diazepine-6,1'-cyclopropan]-4(5H)-one;

5-Methyl-9-(2-cyclopropylpyridin-3-yl)-spiro[benzo[f]pyrrolo[1,2-a][1,4]diazepine-6,1'-cyclopropan]-4(5H)-one;

5-Methyl-9-(5-fluoropyridin-2-yl)-spiro[benzo[f]pyrrolo[1,2-a][1,4]diazepine-6,1'-cyclopropan]-4(5H)-one;

5-(Methyl-$d_3$)-9-(5-fluoropyridin-2-yl)-spiro[benzo[f]pyrrolo[1,2-a][1,4]diazepine-6,1'-cyclopropan]-4(5H)-one;

5-Methyl-9-(2,4-dimethylpyridin-3-yl)-spiro[benzo[f]pyrrolo[1,2-a][1,4]diazepine-6,1'-cyclopropan]-4(5H)-one;

5-Methyl-9-(3-fluoropyridin-2-yl)-spiro[benzo[f]pyrrolo[1,2-a][1,4]diazepine-6,1'-cyclopropan]-4(5H)-one;

5-Methyl-9-(6-fluoropyridin-2-yl)-spiro[benzo[f]pyrrolo[1,2-a][1,4]diazepine-6,1'-cyclopropan]-4(5H)-one;

5-Methyl-9-(2-hydroxypyridin-4-yl)-spiro[benzo[f]pyrrolo[1,2-a][1,4]diazepine-6,1'-cyclopropan]-4(5H)-one;

5-Methyl-9-(5-trifluoromethylpyridin-2-yl)-spiro[benzo[f]pyrrolo[1,2-a][1,4]diazepine-6,1'-cyclopropan]-4(5H)-one;

5-Methyl-9-(pyridazin-3-yl)-spiro[benzo[f]pyrrolo[1,2-a][1,4]diazepine-6,1'-cyclopropan]-4(5H)-one;

5-Methyl-9-(2-methoxycarbonylpyridin-3-yl)-spiro[benzo[f]pyrrolo[1,2-a][1,4]diazepine-6,1'-cyclopropan]-4(5H)-one;
5-Methyl-9-(2-(1-hydroxy-1-methyl-ethyl)-pyridin-3-yl)-spiro[benzo[f]pyrrolo[1,2-a][1,4]diazepine-6,1'-cyclopropan]-4(5H)-one;
7-Fluoro-5-methyl-9-(2-methyl-pyridin-3-yl)-spiro[benzo[f]pyrrolo[1,2-a][1,4]diazepine-6,1'-cyclopropan]-4(5H)-one;
7-Fluoro-5-methyl-9-(6-fluoro-pyridin-3-yl)-spiro[benzo[f]pyrrolo[1,2-a][1,4]diazepine-6,1'-cyclopropan]-4(5H)-one;
10-Fluoro-5-methyl-9-(2-methyl-pyridin-3-yl)-spiro[benzo[f]pyrrolo[1,2-a][1,4]diazepine-6,1'-cyclopropan]-4(5H)-one;
10-Fluoro-5-Methyl-9-(6-fluoro-pyridin-3-yl)-spiro[benzo[f]pyrrolo[1,2-a][1,4]diazepine-6,1'-cyclopropan]-4(5H)-one;
8-Fluoro-5-methyl-9-(2-methyl-pyridin-3-yl)-spiro[benzo[f]pyrrolo[1,2-a][1,4]diazepine-6,1'-cyclopropan]-4(5H)-one;
8-Fluoro-5-methyl-9-(6-fluoro-pyridin-3-yl)-spiro[benzo[f]pyrrolo[1,2-a][1,4]diazepine-6,1'-cyclopropan]-4(5H)-one;
9-Bromo-1-fluoro-5-methyl-spiro[benzo[f]pyrrolo[1,2-a][1,4]diazepine-6,1'-cyclopropan]-4(5H)-one;
9-Bromo-2-chloro-1-fluoro-5-methyl-spiro[benzo[f]pyrrolo[1,2-a][1,4]diazepine-6,1'-cyclopropan]-4(5H)-one;
9-(2-Methyl-pyridin-3-yl)-1-fluoro-5-methyl-spiro[benzo[f]pyrrolo[1,2-a][1,4]diazepine-6,1'-cyclopropan]-4(5H)-one;
9-(2-Methyl-pyridin-3-yl)-2-chloro-5-methyl-spiro[benzo[f]pyrrolo[1,2-a][1,4]diazepine-6,1'-cyclopropan]-4(5H)-one;
9-(2-Methyl-pyridin-3-yl)-2-chloro-1-fluoro-5-methyl-spiro[benzo[f]pyrrolo[1,2-a][1,4]diazepine-6,1'-cyclopropan]-4(5H)-one;
9-(2-Methyl-pyridin-3-yl)-3-chloro-5-methyl-spiro[benzo[f]pyrrolo[1,2-a][1,4]diazepine-6,1'-cyclopropan]-4(5H)-one;
1-Bromo-5-methyl-9-(5-fluoropyridin-2-yl)-spiro[benzo[f]pyrrolo[1,2-a][1,4]diazepine-6,1'-cyclopropan]-4(5H)-one;
5-Methyl-1-(2-methyl-2H-pyrazol-3-yl)9-(5-fluoropyridin-2-yl)-spiro[benzo[f]pyrrolo[1,2-a][1,4]diazepine-6,1'-cyclopropan]-4(5H)-one;
5,8-Dimethyl-spiro[benzo[f]pyrrolo[1,2-a][1,4]diazepine-6,1'-cyclopropan]-4(5H)-one;
8-Morpholin-4-yl-5-methyl-spiro[benzo[f]pyrrolo[1,2-a][1,4]diazepine-6,1'-cyclopropan]-4(5H)-one;
5,7-Dimethyl-spiro[benzo[f]pyrrolo[1,2-a][1,4]diazepine-6,1'-cyclopropan]-4(5H)-one;
5,10-Dimethyl-spiro[benzo[f]pyrrolo[1,2-a][1,4]diazepine-6,1'-cyclopropan]-4(5H)-one;
10-Cyano-5-methyl-spiro[benzo[f]pyrrolo[1,2-a][1,4]diazepine-6,1'-cyclopropan]-4(5H)-one;
10-(2-Methyl-pyridin-3-yl)-5-methyl-spiro[benzo[f]pyrrolo[1,2-a][1,4]diazepine-6,1'-cyclopropan]-4(5H)-one;
5-Methyl-2-phenyl-9-pyridin-3-yl-spiro[benzo[f]pyrrolo[1,2-a][1,4]diazepine-6,1'-cyclopropan]-4(5H)-one;
3-(5-methyl-4-oxo-2-phenyl-4,5-dihydrospiro[benzo[f]pyrrolo[1,2-a][1,4]diazepine-6,1'-cyclopropan]-9-yl)benzoic acid;
5-Methyl-2-phenyl-9-(2-methyl-pyridin-3-yl)-spiro[benzo[f]pyrrolo[1,2-a][1,4]diazepine-6,1'-cyclopropan]-4(5H)-one;
5-Methyl-2-phenyl-9-(6-amino-pyridin-3-yl)-spiro[benzo[f]pyrrolo[1,2-a][1,4]diazepine-6,1'-cyclopropan]-4(5H)-one;
5-Methyl-2-phenyl-9-(2,6-dimethyl-pyridin-4-yl)-spiro[benzo[f]pyrrolo[1,2-a][1,4]diazepine-6,1'-cyclopropan]-4(5H)-one;
5-Methyl-2-phenyl-9-(5-methyl-pyridin-3-yl)-spiro[benzo[f]pyrrolo[1,2-a][1,4]diazepine-6,1'-cyclopropan]-4(5H)-one;
5-Methyl-2-phenyl-9-(2-ethyl-pyridin-3-yl)-spiro[benzo[f]pyrrolo[1,2-a][1,4]diazepine-6,1'-cyclopropan]-4(5H)-one;
5-Methyl-2-phenyl-9-(2-trifluoromethyl-pyridin-3-yl)-spiro[benzo[f]pyrrolo[1,2-a][1,4]diazepine-6,1'-cyclopropan]-4(5H)-one;
5-Methyl-2-phenyl-9-(4-methyl-pyridin-3-yl)-spiro[benzo[f]pyrrolo[1,2-a][1,4]diazepine-6,1'-cyclopropan]-4(5H)-one;
5-Methyl-2-phenyl-9-(pyridin-4-yl)-spiro[benzo[f]pyrrolo[1,2-a][1,4]diazepine-6,1'-cyclopropan]-4(5H)-one;
5-Methyl-2-phenyl-9-(6-methyl-pyridin-3-yl)-spiro[benzo[f]pyrrolo[1,2-a][1,4]diazepine-6,1'-cyclopropan]-4(5H)-one;
5-Methyl-2-phenyl-9-(pyrimidin-5-yl)-spiro[benzo[f]pyrrolo[1,2-a][1,4]diazepine-6,1'-cyclopropan]-4(5H)-one;
5-Methyl-2-phenyl-9-(2-methyl-pyridin-4-yl)-spiro[benzo[f]pyrrolo[1,2-a][1,4]diazepine-6,1'-cyclopropan]-4(5H)-one;
5-Methyl-2-phenyl-9-(6-fluoro-pyridin-3-yl)-spiro[benzo[f]pyrrolo[1,2-a][1,4]diazepine-6,1'-cyclopropan]-4(5H)-one;
5-Methyl-2-phenyl-9-(2,6-dimethyl-pyridin-3-yl)-spiro[benzo[f]pyrrolo[1,2-a][1,4]diazepine-6,1'-cyclopropan]-4(5H)-one;
5-Methyl-2-phenyl-9-pyrazin-2-yl-spiro[benzo[f]pyrrolo[1,2-a][1,4]diazepine-6,1'-cyclopropan]-4(5H)-one;
5-Methyl-2-phenyl-9-pyridazin-3-yl-spiro[benzo[f]pyrrolo[1,2-a][1,4]diazepine-6,1'-cyclopropan]-4(5H)-one;
5-Methyl-2-phenyl-9-(5-fluoro-pyridin-2-yl)-spiro[benzo[f]pyrrolo[1,2-a][1,4]diazepine-6,1'-cyclopropan]-4(5H)-one;
5-Methyl-2-phenyl-9-(pyridin-2-yl)-spiro[benzo[f]pyrrolo[1,2-a][1,4]diazepine-6,1'-cyclopropan]-4(5H)-one;
5-methyl-2-phenyl-9-(6-ethylpyridin-3-yl)-spiro[benzo[f]pyrrolo[1,2-a][1,4]diazepine-6,1'-cyclopropan]-4(5H)-one;
5-Methyl-2-phenyl-9-(2-fluoro-pyridin-3-yl)-spiro[benzo[f]pyrrolo[1,2-a][1,4]diazepine-6,1'-cyclopropan]-4(5H)-one;
5-Methyl-2-phenyl-9-(6-dimethylamino-pyridin-3-yl)-spiro[benzo[f]pyrrolo[1,2-a][1,4]diazepine-6,1'-cyclopropan]-4(5H)-one;
9-Dimethylamino-5-methyl-2-phenyl-spiro[benzo[f]pyrrolo[1,2-a][1,4]diazepine-6,1'-cyclopropan]-4(5H)-one;
5-Methyl-2-phenyl-9-(2-methoxy-pyridin-3-yl)-spiro[benzo[f]pyrrolo[1,2-a][1,4]diazepine-6,1'-cyclopropan]-4(5H)-one;
5-Methyl-2-phenyl-9-(6-cyano-pyridin-3-yl)-spiro[benzo[f]pyrrolo[1,2-a][1,4]diazepine-6,1'-cyclopropan]-4(5H)-one;
5-Methyl-2-phenyl-9-(6-methylamino-pyridin-3-yl)-spiro[benzo[f]pyrrolo[1,2-a][1,4]diazepine-6,1'-cyclopropan]-4(5H)-one;
5-Methyl-2-phenyl-9-(2-dimethylamino-pyridin-3-yl)-spiro[benzo[f]pyrrolo[1,2-a][1,4]diazepine-6,1'-cyclopropan]-4(5H)-one;

8-Morpholin-4-yl-5-methyl-2-phenyl-spiro[benzo[f]pyrrolo[1,2-a][1,4]diazepine-6,1'-cyclopropan]-4(5H)-one;

9-(2,6-Dimethyl-pyridin-4-yl)-5-methyl-2-phenyl-spiro[benzo[f]pyrazolo[1,5-a][1,4]diazepine-6,1'-cyclopropan]-4(5H)-one;

9-(2-Methyl-pyridin-4-yl)-5-methyl-2-phenyl-spiro[benzo[f]pyrazolo[1,5-a][1,4]diazepine-6,1'-cyclopropan]-4(5H)-one;

2,9-Diphenyl-5-methyl-2-spiro[benzo[f]pyrazolo[1,5-a][1,4]diazepine-6,1'-cyclopropan]-4(5H)-one;

9-(4-Amino-phenyl)-5-methyl-2-phenyl-spiro[benzo[f]pyrazolo[1,5-a][1,4]diazepine-6,1'-cyclopropan]-4(5H)-one;

9-(2-Methyl-pyridin-3-yl)-5-methyl-2-phenyl-spiro[benzo[f]pyrazolo[1,5-a][1,4]diazepine-6,1'-cyclopropan]-4(5H)-one;

9-(2,6-Dimethyl-pyridin-3-yl)-5-methyl-2-phenyl-spiro[benzo[f]pyrazolo[1,5-a][1,4]diazepine-6,1'-cyclopropan]-4(5H)-one;

9-(6-Amino-pyridin-3-yl)-5-methyl-2-phenyl-spiro[benzo[f]pyrazolo[1,5-a][1,4]diazepine-6,1'-cyclopropan]-4(5H)-one;

9-(4-Methoxy-phenyl)-5-methyl-2-phenyl-spiro[benzo[f]pyrazolo[1,5-a][1,4]diazepine-6,1'-cyclopropan]-4(5H)-one;

9-(3-Cyano-phenyl)-5-methyl-2-phenyl-spiro[benzo[f]pyrazolo[1,5-a][1,4]diazepine-6,1'-cyclopropan]-4(5H)-one;

9-(3-Chloro-phenyl)-5-methyl-2-phenyl-spiro[benzo[f]pyrazolo[1,5-a][1,4]diazepine-6,1'-cyclopropan]-4(5H)-one;

9-(2-Chloro-phenyl)-5-methyl-2-phenyl-spiro[benzo[f]pyrazolo[1,5-a][1,4]diazepine-6,1'-cyclopropan]-4(5H)-one;

9-(Oxazol-5-yl)-5-methyl-2-phenyl-spiro[benzo[f]pyrazolo[1,5-a][1,4]diazepine-6,1'-cyclopropan]-4(5H)-one;

3-(5-methyl-4-oxo-2-phenyl-4,5-dihydrospiro[benzo[f]pyrazolo[1,5-a][1,4]diazepine-6,1'-cyclopropan]-9-yl)benzoic acid;

9-(1H-pyrazol-4-yl)-5-methyl-2-phenyl-spiro[benzo[f]pyrazolo[1,5-a][1,4]diazepine-6,1'-cyclopropan]-4(5H)-one;

9-(4-Chloro-phenyl)-5-methyl-2-phenyl-spiro[benzo[f]pyrazolo[1,5-a][1,4]diazepine-6,1'-cyclopropan]-4(5H)-one;

9-(1H-pyrazol-3-yl)-5-methyl-2-phenyl-spiro[benzo[f]pyrazolo[1,5-a][1,4]diazepine-6,1'-cyclopropan]-4(5H)-one;

9-Cyano-5-methyl-2-phenyl-spiro[benzo[f]pyrazolo[1,5-a][1,4]diazepine-6,1'-cyclopropan]-4(5H)-one;

5-Methyl-2-phenyl-spiro[benzo[f]pyrazolo[1,5-a][1,4]diazepine-6,1'-cyclopropan]-4(5H)-one;

5-Methyl-2-phenyl-9-(pyrrolidin-1-yl)spiro[benzo[f]pyrazolo[1,5-a][1,4]diazepine-6,1'-cyclopropan]-4(5H)-one;

9-(2-Methyl-pyridin-3-yl)-5-methyl-2-phenyl-spiro[benzo[f]imidazo[1,2-a][1,4]diazepine-6,1'-cyclopropan]-4(5H)-one;

N,N-dimethyl-3-(5-methyl-4-oxo-2-phenyl-4,5-dihydrospiro[benzo[f]pyrrolo[1,2-a][1,4]diazepine-6,1'-cyclopropan]-9-yl)benzenesulfonamide;

N,N-dimethyl-3-(5-methyl-4-oxo-2-phenyl-4,5-dihydrospiro[benzo[f]pyrazolo[1,5-a][1,4]diazepine-6,1'-cyclopropan]-9-yl)benzenesulfonamide;

5-Methyl-2-(pyridine-3-yl)-9-(2-methyl-pyridin-3-yl)-spiro[benzo[f]pyrazolo[1,5-a][1,4]diazepine-6,1'-cyclopropan]-4(5H)-one;

2,5-Dimethyl-9-(2-methyl-pyridin-3-yl)-spiro[benzo[f]pyrazolo[1,5-a][1,4]diazepine-6,1'-cyclopropan]-4(5H)-one;

5-Methyl-2-(pyridine-4-yl)-9-(2-methyl-pyridin-3-yl)-spiro[benzo[f]pyrazolo[1,5-a][1,4]diazepine-6,1'-cyclopropan]-4(5H)-one;

5-Methyl-2-(1H-pyrazol-3-yl)-9-(2-methyl-pyridin-3-yl)-spiro[benzo[f]pyrazolo[1,5-a][1,4]diazepine-6,1'-cyclopropan]-4(5H)-one;

5-Methyl-2-(2-chlorophenyl)-9-(2-methyl-pyridin-3-yl)-spiro[benzo[f]pyrazolo[1,5-a][1,4]diazepine-6,1'-cyclopropan]-4(5H)-one;

5-Methyl-2-(3-chlorophenyl)-9-(2-methyl-pyridin-3-yl)-spiro[benzo[f]pyrazolo[1,5-a][1,4]diazepine-6,1'-cyclopropan]-4(5H)-one;

5-Methyl-2-(4-chlorophenyl)-9-(2-methyl-pyridin-3-yl)-spiro[benzo[f]pyrazolo[1,5-a][1,4]diazepine-6,1'-cyclopropan]-4(5H)-one;

5-Methyl-2-(4-fluorophenyl)-9-(2-methyl-pyridin-3-yl)-spiro[benzo[f]pyrazolo[1,5-a][1,4]diazepine-6,1'-cyclopropan]-4(5H)-one;

5-Methyl-2-(2-fluorophenyl)-9-(2-methyl-pyridin-3-yl)-spiro[benzo[f]pyrazolo[1,5-a][1,4]diazepine-6,1'-cyclopropan]-4(5H)-one;

5-Methyl-2-(3-fluorophenyl)-9-(2-methyl-pyridin-3-yl)-spiro[benzo[f]pyrazolo[1,5-a][1,4]diazepine-6,1'-cyclopropan]-4(5H)-one;

5-Methyl-2-cyano-9-(2-methyl-pyridin-3-yl)-spiro[benzo[f]pyrazolo[1,5-a][1,4]diazepine-6,1'-cyclopropan]-4(5H)-one;

5-Methyl-2-dimethylamino-9-(2-methyl-pyridin-3-yl)-spiro[benzo[f]pyrazolo[1,5-a][1,4]diazepine-6,1'-cyclopropan]-4(5H)-one;

5-Methyl-2-cyclopropyl-9-(2-methyl-pyridin-3-yl)-spiro[benzo[f]pyrazolo[1,5-a][1,4]diazepine-6,1'-cyclopropan]-4(5H)-one;

5-Methyl-2-cyclopentyl-9-(2-methyl-pyridin-3-yl)-spiro[benzo[f]pyrazolo[1,5-a][1,4]diazepine-6,1'-cyclopropan]-4(5H)-one;

5-Methyl-2-(thiazol-2-yl)-9-(2-methyl-pyridin-3-yl)-spiro[benzo[f]pyrazolo[1,5-a][1,4]diazepine-6,1'-cyclopropan]-4(5H)-one;

5-Methyl-2-(thiazol-2-yl)-9-(6-methyl-pyridin-3-yl)-spiro[benzo[f]pyrazolo[1,5-a][1,4]diazepine-6,1'-cyclopropan]-4(5H)-one;

5-Methyl-2-(2-methyl-2H-pyrazol-3-yl)-9-(6-methyl-pyridin-3-yl)-spiro[benzo[f]pyrazolo[1,5-a][1,4]diazepine-6,1'-cyclopropan]-4(5H)-one;

5-Methyl-2-(2-methyl-2H-pyrazol-3-yl)-9-(2-methyl-pyridin-3-yl)-spiro[benzo[f]pyrazolo[1,5-a][1,4]diazepine-6,1'-cyclopropan]-4(5H)-one;

5-Methyl-2-dimethylamino-9-(6-methyl-pyridin-3-yl)-spiro[benzo[f]pyrazolo[1,5-a][1,4]diazepine-6,1'-cyclopropan]-4(5H)-one;

5-Methyl-2-(2-fluorophenyl)-9-(2-ethyl-pyridin-3-yl)-spiro[benzo[f]pyrazolo[1,5-a][1,4]diazepine-6,1'-cyclopropan]-4(5H)-one;

5-Methyl-2-(2-methyl-2H-pyrazol-3-yl)-9-(2-ethyl-pyridin-3-yl)-spiro[benzo[f]pyrazolo[1,5-a][1,4]diazepine-6,1'-cyclopropan]-4(5H)-one;

9-Bromo-5-methyl-2-phenyl-5,6-dihydro-benzo[f]pyrrolo[1,2-a][1,4]diazepin-4-one;

9-(6-Amino-pyridin-3-yl)-5-methyl-2-phenyl-5,6-dihydro-benzo[f]pyrrolo[1,2-a][1,4]diazepin-4-one;

5-Methyl-9-(2-methylpyridin-3-yl)-2-phenyl-5,6-dihydro-4H-benzo[f]imidazo[1,2-a][1,4]diazepin-4-one;

5-Ethyl-9-(2-methylpyridin-3-yl)-2-phenyl-5,6-dihydro-4H-benzo[f]imidazo[1,2-a][1,4]diazepin-4-one;

5-Methyl-9-(2-methylpyridin-3-yl)-4-oxo-4,5-dihydrospiro[benzo[f]pyrrolo[1,2-a][1,4]diazepine-6,1'-cyclopropane]-2-carbaldehyde;

5-Methyl-9-(2-ethyl-pyridin-3-yl)-4-oxo-4,5-dihydrospiro[benzo[f]pyrrolo[1,2-a][1,4]diazepine-6,1'-cyclopropane]-2-carbaldehyde;

5-Methyl-9-(6-methyl-pyridin-3-yl)-4-oxo-4,5-dihydrospiro[benzo[f]pyrrolo[1,2-a][1,4]diazepine-6,1'-cyclopropane]-2-carbaldehyde;

5-Methyl-9-(6-fluoro-pyridin-3-yl)-4-oxo-4,5-dihydrospiro[benzo[f]pyrrolo[1,2-a][1,4]diazepine-6,1'-cyclopropane]-2-carbaldehyde;

5-(Methyl-d$_3$)-9-(6-fluoro-pyridin-3-yl)-4-oxo-4,5-dihydrospiro[benzo[f]pyrrolo[1,2-a][1,4]diazepine-6,1'-cyclopropane]-2-carbaldehyde;

5-Methyl-9-bromo-4-oxo-4,5-dihydrospiro[benzo[f]pyrrolo[1,2-a][1,4]diazepine-6,1'-cyclopropane]-2-carbaldehyde;

5-Methyl-9-(3-cyanophenyl)-4-oxo-4,5-dihydrospiro[benzo[f]pyrrolo[1,2-a][1,4]diazepine-6,1'-cyclopropane]-2-carbaldehyde;

5-Methyl-9-(pyridazin-3-yl)-4-oxo-4,5-dihydrospiro[benzo[f]pyrrolo[1,2-a][1,4]diazepine-6,1'-cyclopropane]-2-carbaldehyde;

5-Methyl-9-(2-methylpyridin-3-yl)-4-oxo-4,5-dihydrospiro[benzo[f]pyrrolo[1,2-a][1,4]diazepine-6,1'-cyclopropane]-2-carboxylic acid;

5-Methyl-9-(6-fluoro-pyridin-3-yl)-4-oxo-4,5-dihydrospiro[benzo[f]pyrrolo[1,2-a][1,4]diazepine-6,1'-cyclopropane]-2-carboxylic acid;

5-(Methyl-d$_3$)-9-(6-fluoro-pyridin-3-yl)-4-oxo-4,5-dihydrospiro[benzo[f]pyrrolo[1,2-a][1,4]diazepine-6,1'-cyclopropane]-2-carboxylic acid;

5-Methyl-9-bromo-4-oxo-4,5-dihydrospiro[benzo[f]pyrrolo[1,2-a][1,4]diazepine-6,1'-cyclopropane]-2-carboxylic acid;

5-Methyl-9-(pyridazin-3-yl)-4-oxo-4,5-dihydrospiro[benzo[f]pyrrolo[1,2-a][1,4]diazepine-6,1'-cyclopropane]-2-carboxylic acid;

5-Methyl-9-(3-cyanophenyl)-4-oxo-4,5-dihydrospiro[benzo[f]pyrrolo[1,2-a][1,4]diazepine-6,1'-cyclopropane]-2-carboxylic acid;

5-Methyl-9-(2-methyl-pyridin-3-yl)-2-(oxazol-5-yl)-spiro[benzo[f]pyrazolo[1,5-a][1,4]diazepine-6,1'-cyclopropan]-4(5H)-one;

5-Methyl-9-(2-methyl-pyridin-3-yl)-2-(3H-imidazol-4-yl)-spiro[benzo[f]pyrazolo[1,5-a][1,4]diazepine-6,1'-cyclopropan]-4(5H)-one;

5-Methyl-9-(2-methyl-pyridin-3-yl)-2-(1H-imidazol-2-yl)-spiro[benzo[f]pyrazolo[1,5-a][1,4]diazepine-6,1'-cyclopropan]-4(5H)-one;

5-Methyl-9-(2-methyl-pyridin-3-yl)-2-[1,3,4]oxadiazol-2-yl-spiro[benzo[f]pyrazolo[1,5-a][1,4]diazepine-6,1'-cyclopropan]-4(5H)-one;

5-Methyl-9-(6-fluoro-pyridin-3-yl)-2-(1H-imidazol-2-yl)-spiro[benzo[f]pyrazolo[1,5-a][1,4]diazepine-6,1'-cyclopropan]-4(5H)-one;

5-Methyl-9-(6-fluoro-pyridin-3-yl)-2-[1,3,4]oxadiazol-2-yl-spiro[benzo[f]pyrazolo[1,5-a][1,4]diazepine-6,1'-cyclopropan]-4(5H)-one;

5-(Methyl-d$_3$)-9-(6-fluoro-pyridin-3-yl)-2-[1,3,4]oxadiazol-2-yl-spiro[benzo[f]pyrazolo[1,5-a][1,4]diazepine-6,1'-cyclopropan]-4(5H)-one;

5-Methyl-9-bromo-2-[1,3,4]oxadiazol-2-yl-spiro[benzo[f]pyrazolo[1,5-a][1,4]diazepine-6,1'-cyclopropan]-4(5H)-one;

5-Methyl-9-(6-dimethylamino-pyridin-3-yl)-2-[1,3,4]oxadiazol-2-yl-spiro[benzo[f]pyrazolo[1,5-a][1,4]diazepine-6,1'-cyclopropan]-4(5H)-one;

5-Methyl-9-(6-chloro-pyridin-3-yl)-2-[1,3,4]oxadiazol-2-yl-spiro[benzo[f]pyrazolo[1,5-a][1,4]diazepine-6,1'-cyclopropan]-4(5H)-one;

5-Methyl-9-(3-cyanophenyl)-2-[1,3,4]oxadiazol-2-yl-spiro[benzo[f]pyrazolo[1,5-a][1,4]diazepine-6,1'-cyclopropan]-4(5H)-one;

5-Methyl-9-(pyridazin-3-yl)-2-[1,3,4]oxadiazol-2-yl-spiro[benzo[f]pyrazolo[1,5-a][1,4]diazepine-6,1'-cyclopropan]-4(5H)-one;

5-Methyl-9-(2-methyl-pyridin-3-yl)-2-(cyclopentanecarbonyl)-spiro[benzo[f]pyrazolo[1,5-a][1,4]diazepine-6,1'-cyclopropan]-4(5H)-one;

5-Methyl-9-(2-methyl-pyridin-3-yl)-2-acetyl-spiro[benzo[f]pyrazolo[1,5-a][1,4]diazepine-6,1'-cyclopropan]-4(5H)-one;

5-Methyl-9-(2-methyl-pyridin-3-yl)-2-(cyclopentylmethyl)-spiro[benzo[f]pyrazolo[1,5-a][1,4]diazepine-6,1'-cyclopropan]-4(5H)-one;

5-Methyl-9-(2-methyl-pyridin-3-yl)-2-ethyl-spiro[benzo[f]pyrazolo[1,5-a][1,4]diazepine-6,1'-cyclopropan]-4(5H)-one;

2,5-Dimethyl-9-(6-methyl-pyridin-3-yl)-spiro[benzo[f]pyrazolo[1,5-a][1,4]diazepine-6,1'-cyclopropan]-4(5H)-one;

2,5-Dimethyl-9-(2-ethyl-pyridin-3-yl)-spiro[benzo[f]pyrazolo[1,5-a][1,4]diazepine-6,1'-cyclopropan]-4(5H)-one;

5-Methyl-9-(2-methyl-pyridin-3-yl)-2-(morpholin-4-ylmethyl)-spiro[benzo[f]pyrazolo[1,5-a][1,4]diazepine-6,1'-cyclopropan]-4(5H)-one;

5-Methyl-9-(2-methyl-pyridin-3-yl)-2-difluoromethyl-spiro[benzo[f]pyrazolo[1,5-a][1,4]diazepine-6,1'-cyclopropan]-4(5H)-one;

2-Hydroxymethyl-5-methyl-9-(6-methyl-pyridin-3-yl)-spiro[benzo[f]pyrazolo[1,5-a][1,4]diazepine-6,1'-cyclopropan]-4(5H)-one;

2-Hydroxymethyl-5-methyl-9-(2-ethyl-pyridin-3-yl)-spiro[benzo[f]pyrazolo[1,5-a][1,4]diazepine-6,1'-cyclopropan]-4(5H)-one;

2-Hydroxymethyl-5-methyl-9-(6-fluoro-pyridin-3-yl)-spiro[benzo[f]pyrazolo[1,5-a][1,4]diazepine-6,1'-cyclopropan]-4(5H)-one;

2-Methoxymethyl-5-methyl-9-(6-methyl-pyridin-3-yl)-spiro[benzo[f]pyrazolo[1,5-a][1,4]diazepine-6,1'-cyclopropan]-4(5H)-one;

2-Methoxymethyl-5-methyl-9-(2-ethyl-pyridin-3-yl)-spiro[benzo[f]pyrazolo[1,5-a][1,4]diazepine-6,1'-cyclopropan]-4(5H)-one;

2-Methoxymethyl-5-methyl-9-(6-fluoro-pyridin-3-yl)-spiro[benzo[f]pyrazolo[1,5-a][1,4]diazepine-6,1'-cyclopropan]-4(5H)-one;

9-Bromo-5-methyl-1,2,3,3a-tetrahydro-spiro[benzo[f]pyrrolo[1,2-a][1,4]diazepine-6,1'-cyclopropan]-4(5H)-one;

5-Methyl-9-(2-methylpyridin-3-yl)-1,2,3,3a-tetrahydro-spiro[benzo[f]pyrrolo[1,2-a][1,4]diazepine-6,1'-cyclopropan]-4(5H)-one;

5-Methyl-9-bromo-5,6-dihydro-4H-benzo[f]imidazo[1,5-a][1,4]diazepin-4-one;

5-Methyl-9-bromo-5,6-dihydro-4H-benzo[f]imidazo[1,2-a][1,4]diazepin-4-one;

5-Methyl-9-bromo-5,6-dihydro-4H-benzo[f]pyrazolo[1,5-a][1,4]diazepin-4-one;

9-Bromo-5,6-dimethyl-5,6-dihydro-benzo[f]pyrrolo[1,2-a][1,4]diazepin-4-one;

9-Bromo-5-methyl-6-ethyl-5,6-dihydro-benzo[f]pyrrolo[1,2-a][1,4]diazepin-4-one;

5-Methyl-9-(2-methylpyridin-3-yl)-5,6-dihydro-4H-benzo[f]imidazo[1,5-a][1,4]diazepin-4-one;

5-Methyl-9-(2-methylpyridin-3-yl)-5,6-dihydro-4H-benzo[f]imidazo[1,2-a][1,4]diazepin-4-one;

5-Methyl-9-(2-methylpyridin-3-yl)-5,6-dihydro-4H-benzo[f]pyrazolo[1,5-a][1,4]diazepin-4-one;

5,6-Dimethyl-9-(2-methyl-pyridin-3-yl)-5,6-dihydro-benzo[f]pyrrolo[1,2-a][1,4]diazepin-4-one;

9-(6-Dimethylamino-pyridin-3-yl)-5,6-dimethyl-5,6-dihydro-benzo[f]pyrrolo[1,2-a][1,4]diazepin-4-one;

6-Ethyl-5-methyl-9-(2-methyl-pyridin-3-yl)-5,6-dihydro-benzo[f]pyrrolo[1,2-a][1,4]diazepin-4-one;

5,6,6-Trimethyl-5,6-dihydro-benzo[f]pyrrolo[1,2-a][1,4]diazepin-4-one;

9-Chloro-5,6,6-trimethyl-5,6-dihydro-benzo[f]pyrrolo[1,2-a][1,4]diazepin-4-one;

5,6,6-Trimethyl-9-(2-methyl-pyridin-3-yl)-5,6-dihydro-benzo[f]pyrrolo[1,2-a][1,4]diazepin-4-one;

and pharmaceutically acceptable salts, solvates and prodrugs of any one of the aforementioned compounds.

As described above, it is particularly preferred that m is 0 or 1, and even more preferably m is 0. In one specific embodiment, m is 0 and the further groups/variables comprised in the compound of formula (I) according to the first or second aspect of the invention have the same meanings, including the same preferred meanings, as described and defined herein above. In a further specific embodiment, m is 1, $R^5$ is oxadiazolyl (e.g., [1,3,4]oxadiazol-2-yl), wherein said oxadiazolyl is optionally substituted with one group selected from halogen, $C_1$-$C_4$ haloalkyl, —CN, $C_1$-$C_4$ alkyl, —OH, —O($C_1$-$C_4$ alkyl), —NH$_2$, —NH($C_1$-$C_4$ alkyl), and —N($C_1$-$C_4$ alkyl)($C_1$-$C_4$ alkyl), and the further groups/variables comprised in the compound of formula (I) according to the first or second aspect of the invention have the same meanings, including the same preferred meanings, as described and defined herein above. In a further specific embodiment, m is 1, $R^5$ is —($C_1$-$C_4$ alkylene)-O—($C_1$-$C_4$ alkyl) (preferably —CH$_2$—O—CH$_3$), and the further groups/variables comprised in the compound of formula (I) according to the first or second aspect of the invention have the same meanings, including the same preferred meanings, as described and defined herein above.

For a person skilled in the field of synthetic chemistry, various ways for the preparation of the compounds of general formula (I) will be readily apparent. For example, the compounds of the present invention can be prepared in accordance with or in analogy to the synthetic routes described in detail in the examples section. In particular, compounds of the general formula (I) and their pharmaceutically acceptable salts can be synthesized according to methods described in the following schemes, where X represents a halogen, M a metallic species and R any group at the corresponding position of the general formula (I). While the numbering of the groups R in the following schemes differs from the designation of the groups in the general formula (I), it will be understood that these schemes explain the preparation of compounds of formula (I) and, thus, that these groups R are defined in accordance with the corresponding groups at the same positions of attachment in the general formula (I).

Intermediate C can be obtained by an aromatic nucleophilic substitution between reactants A and B. A subsequent Kulinkovich-Szymoniak cyclopropanation of C which undergoes an in situ intramolecular cyclization allows the formation of the core structure (D). Alkylation of intermediate D gives examples of the present invention (F). Examples can be further modified by methods well known in the art. For example, the $R_1$ group can be introduced by a cross-coupling reaction with a metallic species G. Borylation of intermediate F can also be performed (J) in order to perform a Suzuki-Miyaura reaction providing different compounds K (scheme 1).

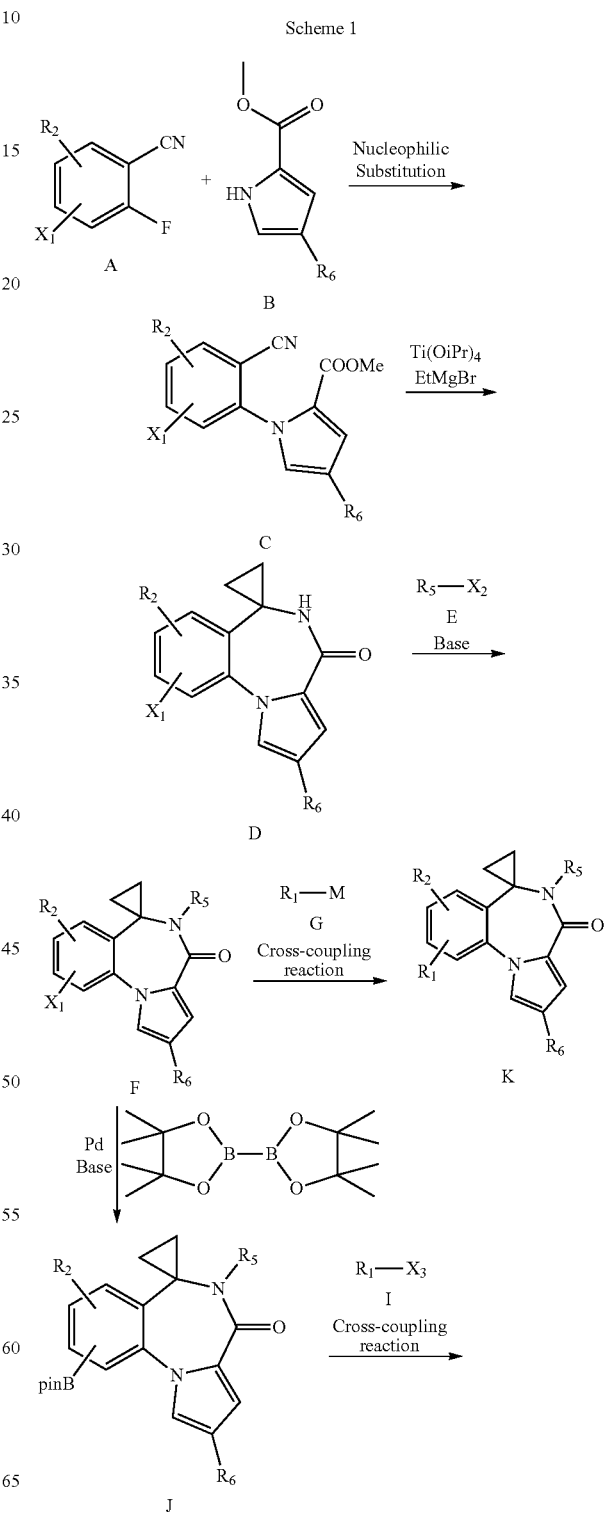

Scheme 1

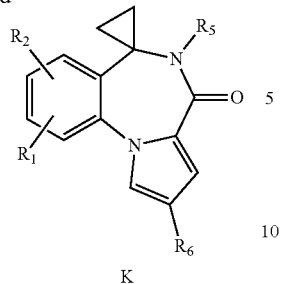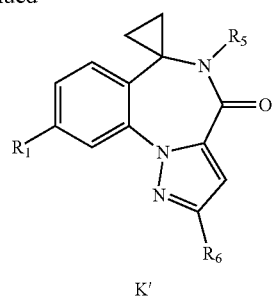
The pyrrole ring of intermediate B can be replaced by a pyrazole (B') or an imidazole (B") analogue in a similar 4-step sequence, as depicted in the following scheme 2:
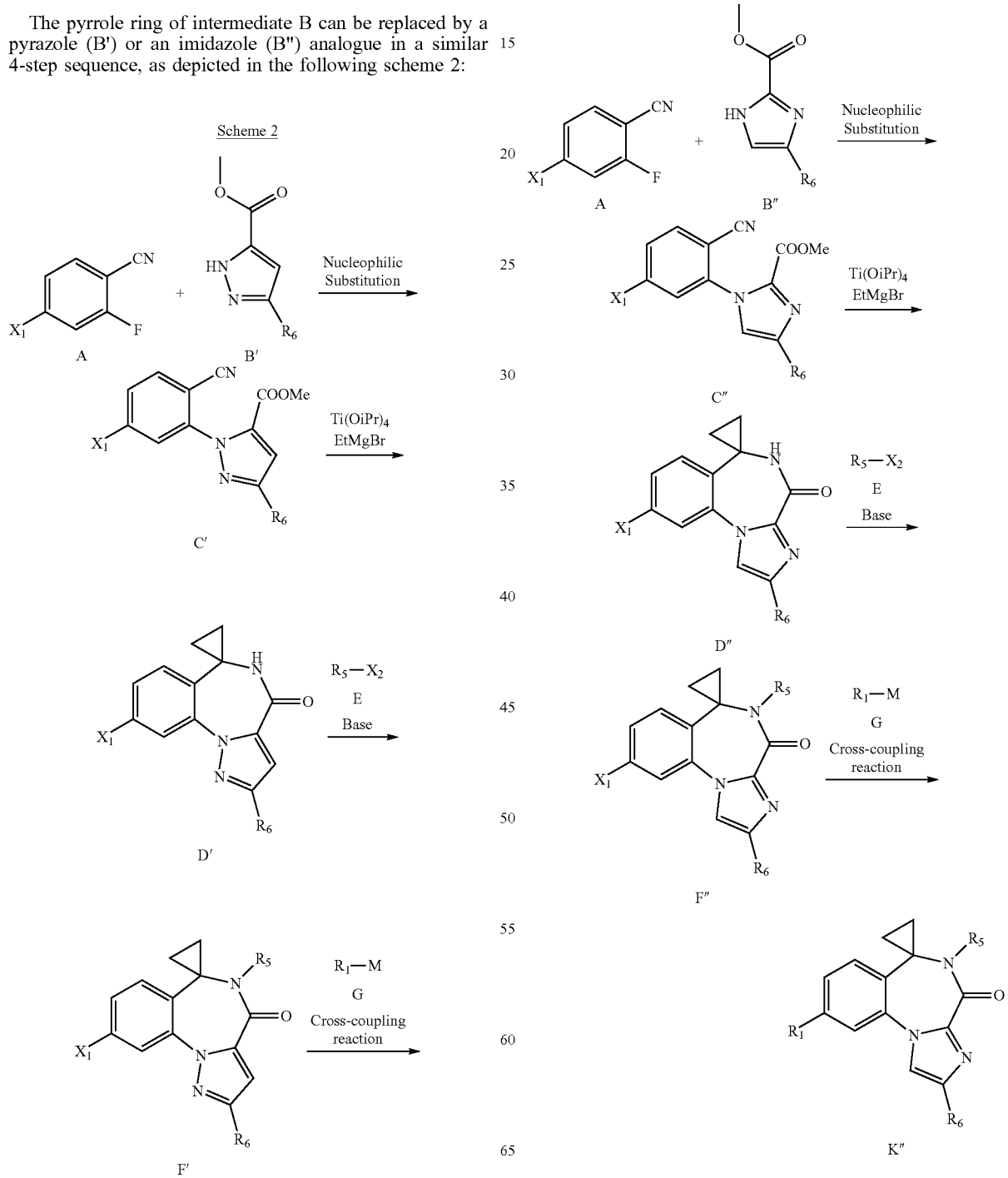

In an alternative method, a reductive cyclization of intermediate C or C" giving intermediate L or L" can be performed with a hydride source (scheme 3).
Scheme 3
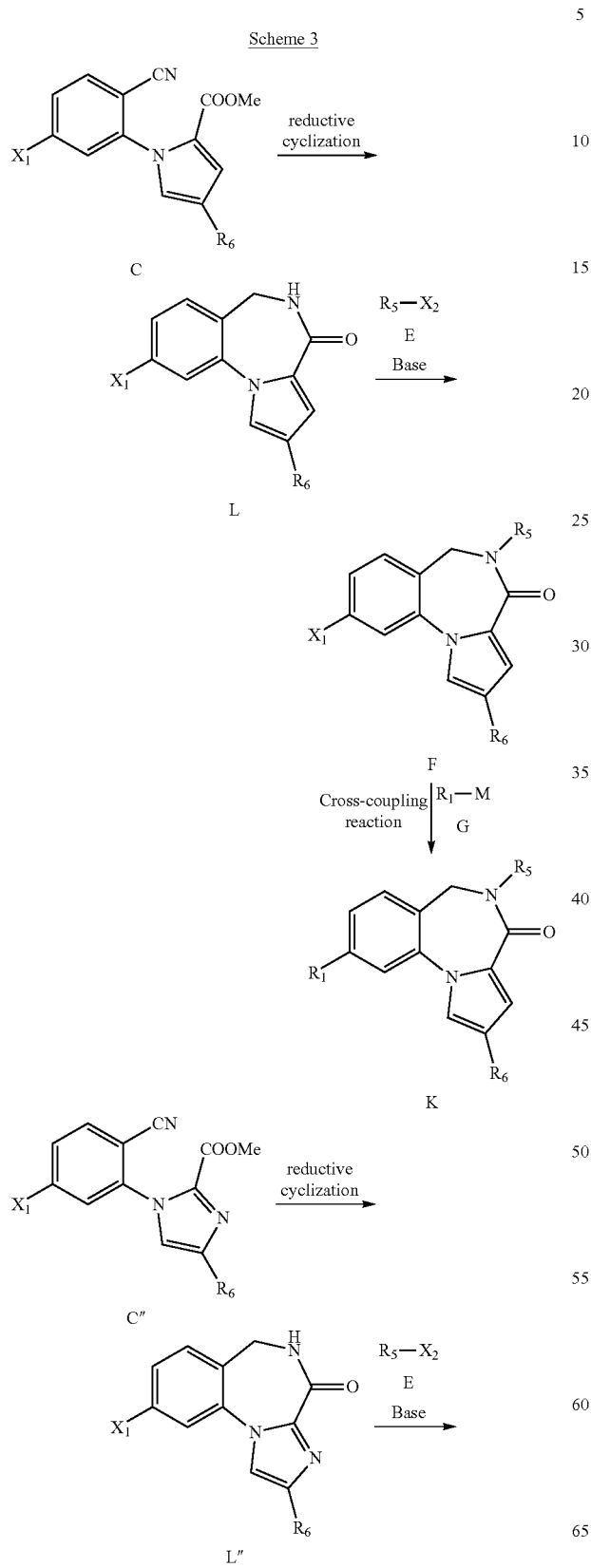
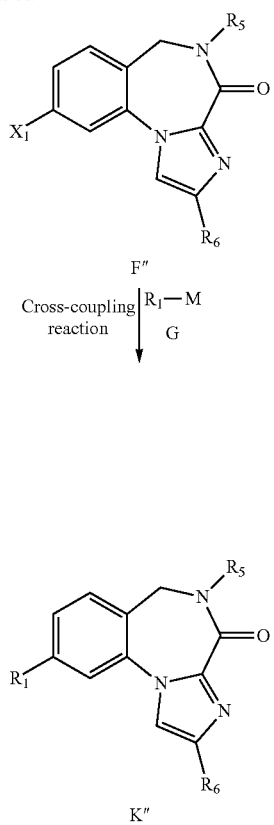
When $X_1=R_6=Br$ in compound C, a regioselective cross-coupling reaction giving intermediate Ci can be performed before the cyclization which forms the benzodiazepinone core structure Di (scheme 4).
Scheme 4
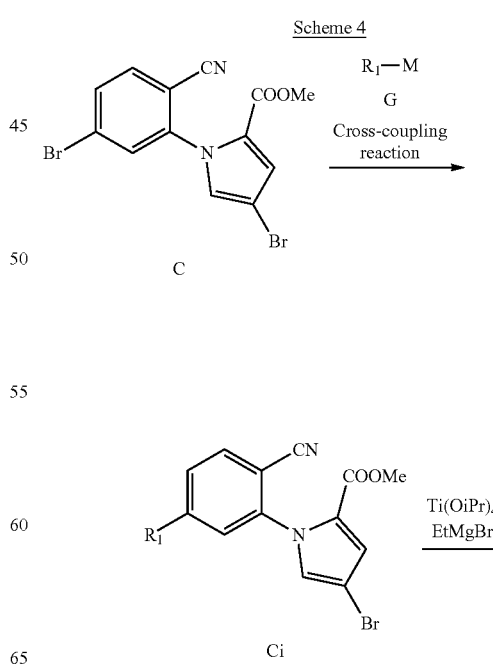

47

-continued

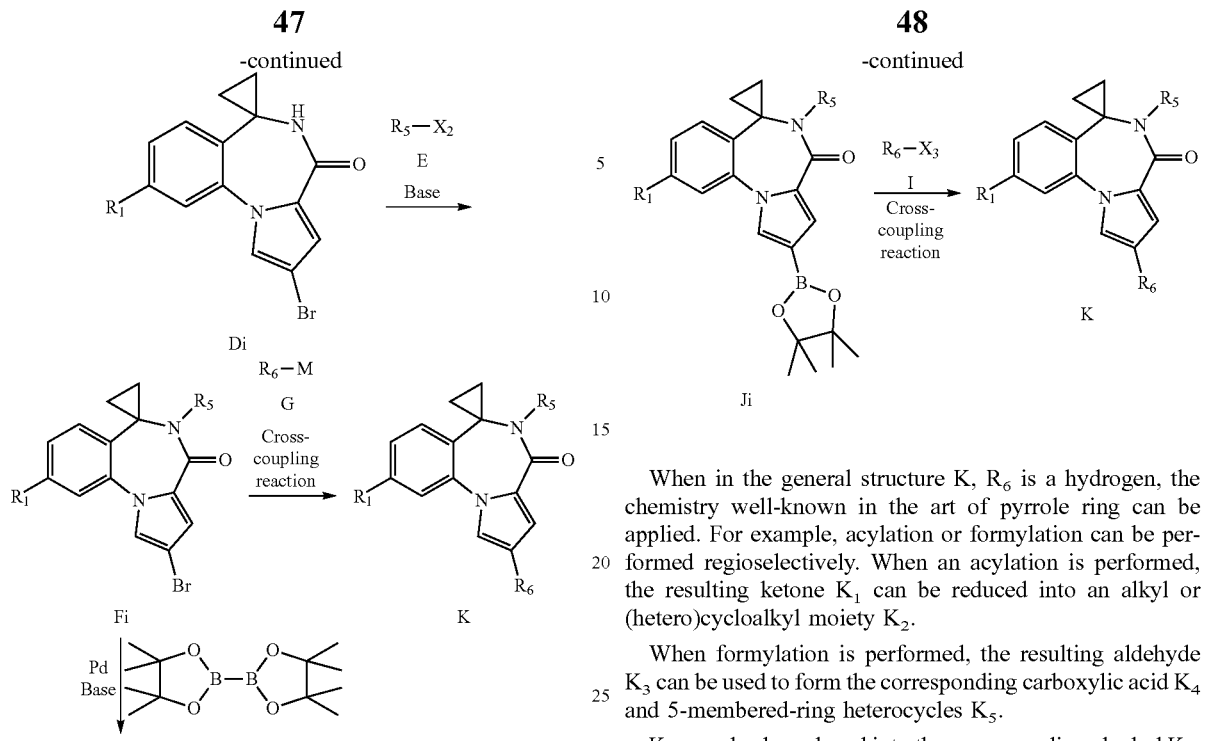

48

-continued

When in the general structure K, $R_6$ is a hydrogen, the chemistry well-known in the art of pyrrole ring can be applied. For example, acylation or formylation can be performed regioselectively. When an acylation is performed, the resulting ketone $K_1$ can be reduced into an alkyl or (hetero)cycloalkyl moiety $K_2$.

When formylation is performed, the resulting aldehyde $K_3$ can be used to form the corresponding carboxylic acid $K_4$ and 5-membered-ring heterocycles $K_5$.

$K_3$ can also be reduced into the corresponding alcohol $K_6$, which can be alkylated giving $K_7$ (scheme 5).

Scheme 5

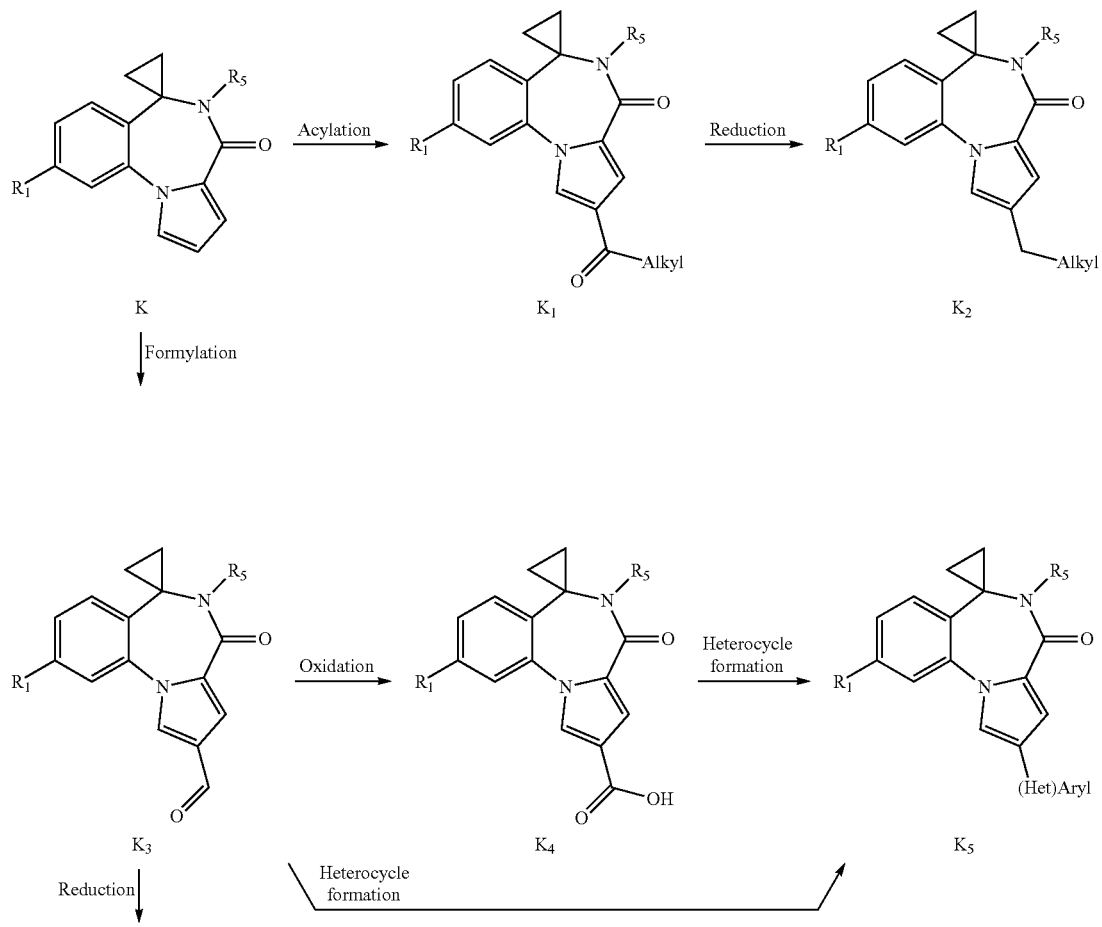

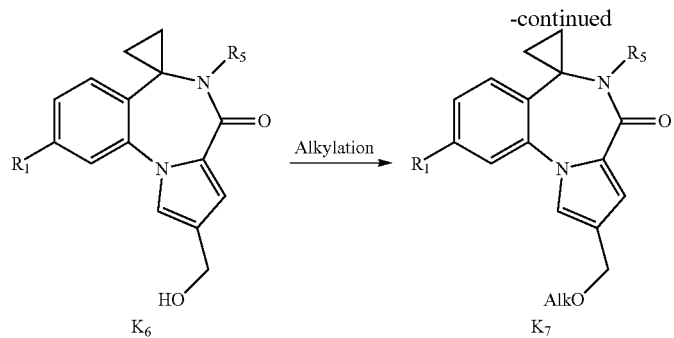
The 7-membered diazepinone ring can also be obtained by forming the amide junction at first, giving intermediate S, S' or S". A subsequent intramolecular aromatic nucleophilic substitution can be used to close the ring, giving access to compounds T, T' and T" (scheme 6).
Scheme 6
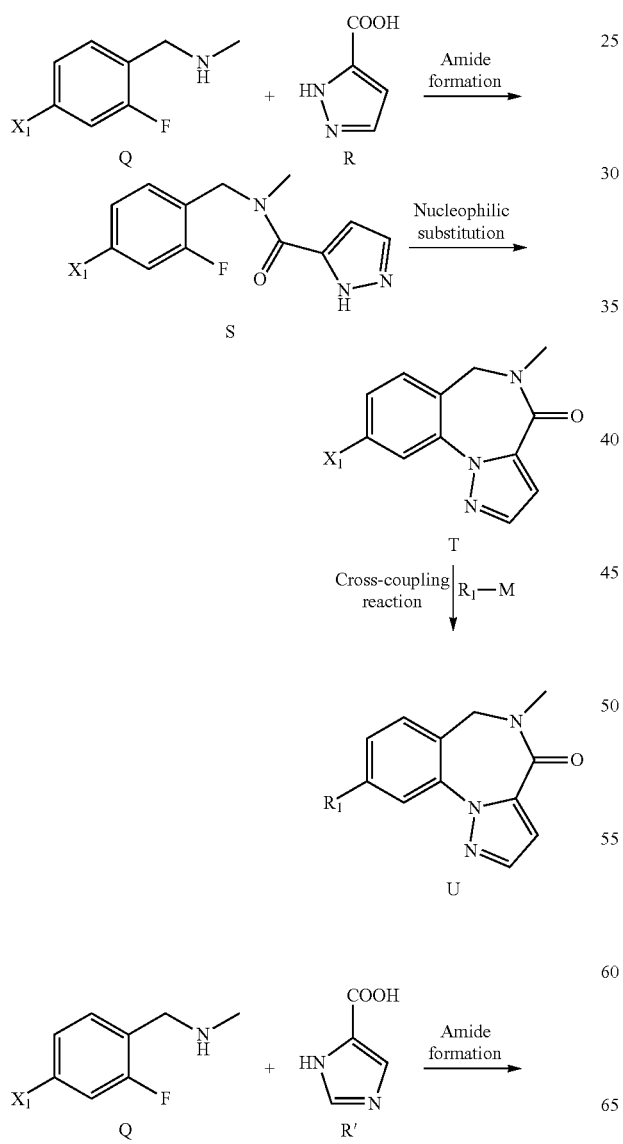
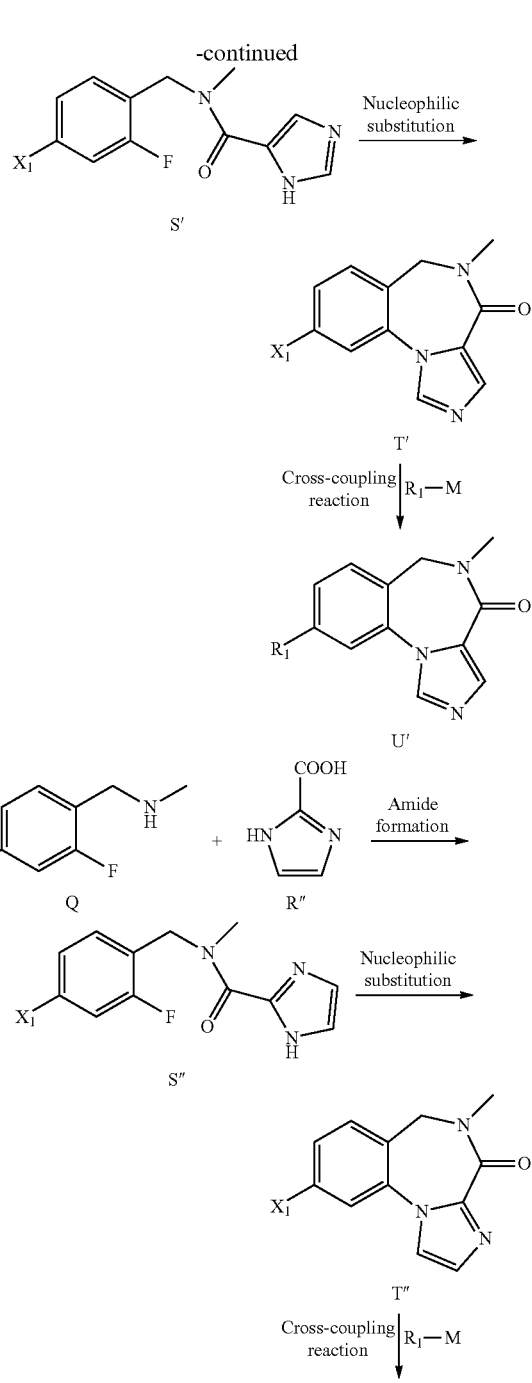

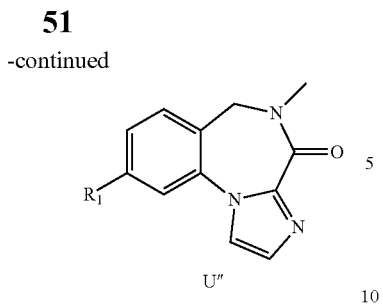
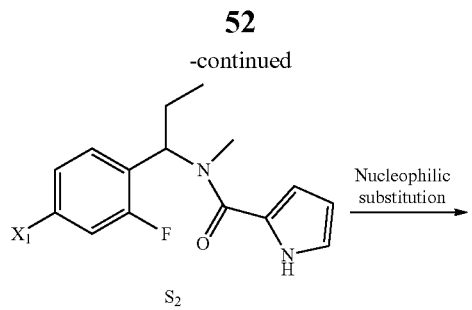

By using the same sequence as depicted in scheme 6, modification in R² and R³ to give other groups than spiro-cyclopropyl can be implemented: for example a mono-methyl group starting from Q₁ or a mono-ethyl group starting from Q₂ (scheme 7).

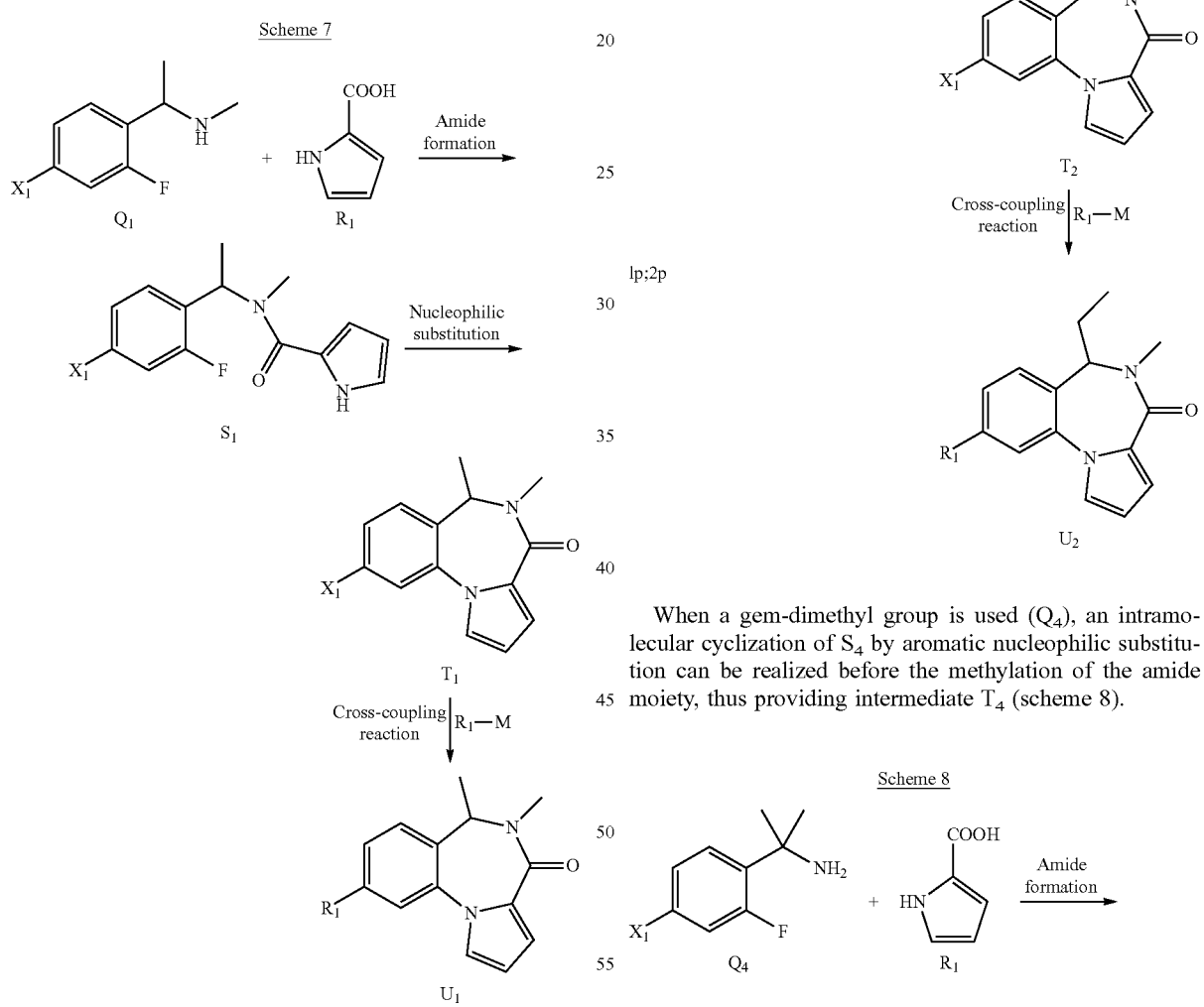

When a gem-dimethyl group is used (Q₄), an intramolecular cyclization of S₄ by aromatic nucleophilic substitution can be realized before the methylation of the amide moiety, thus providing intermediate T₄ (scheme 8).

Scheme 8

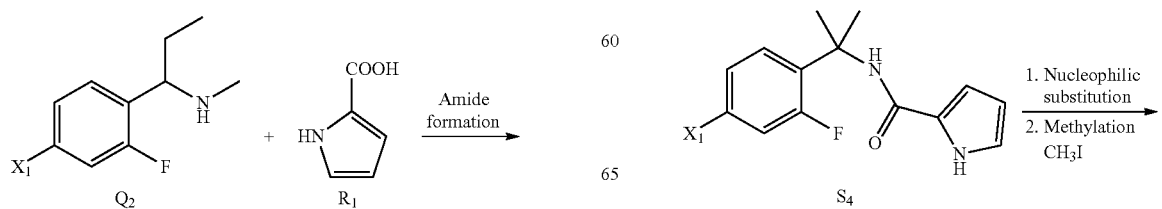

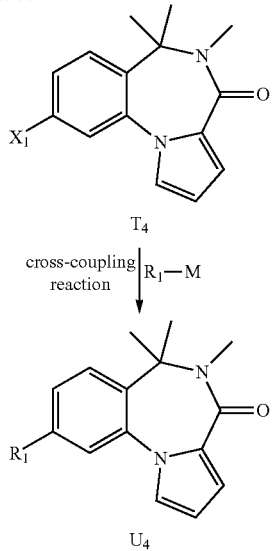

The following definitions apply throughout the present specification, unless specifically indicated otherwise.

As used herein, the term "hydrocarbon group" refers to a group consisting of carbon atoms and hydrogen atoms.

The term "alicyclic" is used in connection with cyclic groups and denotes that the corresponding cyclic group is non-aromatic.

As used herein, the term "alkyl" refers to a monovalent saturated acyclic (i.e., non-cyclic) hydrocarbon group which may be linear or branched. Accordingly, an "alkyl" group does not comprise any carbon-to-carbon double bond or any carbon-to-carbon triple bond. A "$C_1$-$C_{10}$ alkyl" denotes an alkyl group having 1 to 10 carbon atoms. Preferred exemplary alkyl groups are methyl, ethyl, propyl (e.g., n-propyl or isopropyl), or butyl (e.g., n-butyl, isobutyl, sec-butyl, or tert-butyl). Unless defined otherwise, the term "alkyl" preferably refers to $C_1$-$C_6$ alkyl, more preferably to $C_1$-$C_4$ alkyl, even more preferably to methyl or ethyl, and most preferably to methyl.

As used herein, the term "alkenyl" refers to a monovalent unsaturated acyclic hydrocarbon group which may be linear or branched and comprises one or more (e.g., one, two or three) carbon-to-carbon double bonds while it does not comprise any carbon-to-carbon triple bond. The term "$C_2$-$C_{10}$ alkenyl" denotes an alkenyl group having 2 to 10 carbon atoms. Preferred exemplary alkenyl groups are ethenyl, propenyl (e.g., prop-1-en-1-yl, prop-1-en-2-yl, or prop-2-en-1-yl), butenyl, butadienyl (e.g., buta-1,3-dien-1-yl or buta-1,3-dien-2-yl), pentenyl, or pentadienyl (e.g., isoprenyl). Unless defined otherwise, the term "alkenyl" preferably refers to $C_2$-$C_6$ alkenyl, and more preferably to $C_2$-$C_4$ alkenyl.

As used herein, the term "alkynyl" refers to a monovalent unsaturated acyclic hydrocarbon group which may be linear or branched and comprises one or more (e.g., one or two) carbon-to-carbon triple bonds and optionally one or more carbon-to-carbon double bonds. The term "$C_2$-$C_{10}$ alkynyl" denotes an alkynyl group having 2 to 10 carbon atoms. Preferred exemplary alkynyl groups are ethynyl, propynyl (e.g., propargyl), or butynyl. Unless defined otherwise, the term "alkynyl" preferably refers to $C_2$-$C_6$ alkynyl, and more preferably to $C_2$-$C_4$ alkynyl.

As used herein, the term "alkylene" refers to an alkanediyl group, i.e. a divalent saturated acyclic hydrocarbon group which may be linear or branched. A "$C_1$-$C_{10}$ alkylene" denotes an alkylene group having 1 to 10 carbon atoms. Preferred exemplary alkylene groups are methylene (—$CH_2$—), ethylene (e.g., —$CH_2$—$CH_2$— or —CH(—$CH_3$)—), propylene (e.g., —$CH_2$—$CH_2$—$CH_2$—, —CH(—$CH_2$—$CH_3$)—, —$CH_2$—CH(—$CH_3$)—, or —CH(—$CH_3$)—$CH_2$—), or butylene (e.g., —$CH_2$—$CH_2$—$CH_2$—$CH_2$—). Unless defined otherwise, the term "alkylene" preferably refers to $C_1$-$C_6$ alkylene, more preferably to $C_1$-$C_4$ alkylene (including, in particular, linear $C_1$-$C_4$ alkylene), even more preferably to methylene or ethylene, and most preferably to methylene.

As used herein, the term "alkenylene" refers to an alkenediyl group, i.e. a divalent unsaturated acyclic hydrocarbon group which may be linear or branched and comprises one or more (e.g., one or two) carbon-to-carbon double bonds while it does not comprise any carbon-to-carbon triple bond. A "$C_2$-$C_{10}$ alkenylene" denotes an alkenylene group having 2 to 10 carbon atoms. Unless defined otherwise, the term "alkenylene" preferably refers to $C_2$-$C_6$ alkenylene, and more preferably to $C_2$-$C_4$ alkenylene (including, in particular, linear $C_1$-$C_4$ alkenylene).

As used herein, the term "alkynylene" refers to an alkynediyl group, i.e. a divalent unsaturated acyclic hydrocarbon group which may be linear or branched and comprises one or more (e.g., one or two) carbon-to-carbon triple bonds and optionally one or more carbon-to-carbon double bonds. A "$C_2$-$C_{10}$ alkynylene" denotes an alkynylene group having 2 to 10 carbon atoms. Unless defined otherwise, the term "alkynylene" preferably refers to $C_2$-$C_6$ alkynylene, and more preferably to $C_2$-$C_4$ alkynylene (including, in particular, linear $C_1$-$C_4$ alkynylene).

As used herein, the term "aryl" refers to an aromatic hydrocarbon ring group, including monocyclic aromatic rings as well as bridged ring and/or fused ring systems containing at least one aromatic ring (e.g., ring systems composed of two or three fused rings, wherein at least one of these fused rings is aromatic; or bridged ring systems composed of two or three rings, wherein at least one of these bridged rings is aromatic). "Aryl" may, e.g., refer to phenyl, naphthyl, dialinyl (i.e., 1,2-dihydronaphthyl), tetralinyl (i.e., 1,2,3,4-tetrahydronaphthyl), indanyl, indenyl (e.g., 1H-indenyl), anthracenyl, phenanthrenyl, 9H-fluorenyl, or azulenyl. Unless defined otherwise, an "aryl" preferably has 6 to 14 ring atoms, more preferably 6 to 10 ring atoms, even more preferably refers to phenyl or naphthyl, and most preferably refers to phenyl.

As used herein, the term "heteroaryl" refers to an aromatic ring group, including monocyclic aromatic rings as well as bridged ring and/or fused ring systems containing at least one aromatic ring (e.g., ring systems composed of two or three fused rings, wherein at least one of these fused rings is aromatic; or bridged ring systems composed of two or three rings, wherein at least one of these bridged rings is aromatic), wherein said aromatic ring group comprises one or more (such as, e.g., one, two, three, or four) ring heteroatoms independently selected from O, S and N, and the remaining ring atoms are carbon atoms, wherein one or more S ring atoms (if present) and/or one or more N ring atoms (if present) may optionally be oxidized, and further wherein one or more carbon ring atoms may optionally be oxidized (i.e., to form an oxo group). For example, each heteroatom-containing ring comprised in said aromatic ring group may contain one or two O atoms and/or one or two S atoms (which may optionally be oxidized) and/or one, two, three or four N atoms (which may optionally be oxidized), provided that the total number of heteroatoms in the corresponding heteroatom-containing ring is 1 to 4 and that there is at least one carbon ring atom (which may optionally be oxidized) in the corresponding heteroatom-containing ring. "Heteroaryl" may, e.g., refer to thienyl (i.e., thiophenyl), benzo[b]thienyl, naphtho[2,3-b]thienyl, thianthrenyl, furyl (i.e., furanyl), benzofuranyl, isobenzofuranyl, chromanyl, chromenyl (e.g., 2H-1-benzopyranyl or 4H-1-benzopyranyl), isochromenyl (e.g., 1H-2-benzopyranyl), chromonyl, xanthenyl, phenoxathiinyl, pyrrolyl (e.g., 2H-pyrrolyl), imidazolyl, pyrazolyl, pyridyl (i.e., pyridinyl; e.g., 2-pyridyl, 3-pyridyl, or 4-pyridyl), pyrazinyl, pyrimidinyl, pyridazinyl, indolyl (e.g., 3H-indolyl), isoindolyl, indazolyl, indolizinyl, purinyl, quinolyl, isoquinolyl, phthalazinyl, naphthyridinyl, quinoxalinyl, cinnolinyl, pteridinyl, carbazolyl, β-carbolinyl, phenanthridinyl, acridinyl, perimidinyl, phenanthrolinyl (e.g., [1,10]phenanthrolinyl, [1,7]phenanthrolinyl, or [4,7] phenanthrolinyl), phenazinyl, thiazolyl, isothiazolyl, phenothiazinyl, oxazolyl, isoxazolyl, oxadiazolyl (e.g., 1,2,4-oxadiazolyl, 1,2,5-oxadiazolyl (i.e., furazanyl), or 1,3,4-oxadiazolyl), thiadiazolyl (e.g., 1,2,4-thiadiazolyl, 1,2,5-thiadiazolyl, or 1,3,4-thiadiazolyl), phenoxazinyl, pyrazolo[1,5-a]pyrimidinyl (e.g., pyrazolo[1,5-a]pyrimidin-3-yl), 1,2-benzoisoxazol-3-yl, benzothiazolyl, benzothiadiazolyl, benzoxazolyl, benzisoxazolyl, benzimidazolyl, benzo[b] thiophenyl (i.e., benzothienyl), triazolyl (e.g., 1H-1,2,3-triazolyl, 2H-1,2,3-triazolyl, 1H-1,2,4-triazolyl, or 4H-1,2,4-triazolyl), benzotriazolyl, 1H-tetrazolyl, 2H-tetrazolyl, triazinyl (e.g., 1,2,3-triazinyl, 1,2,4-triazinyl, or 1,3,5-triazinyl), furo[2,3-c]pyridinyl, dihydrofuropyridinyl (e.g., 2,3-dihydrofuro[2,3-c]pyridinyl or 1,3-dihydrofuro[3,4-c]pyridinyl), imidazopyridinyl (e.g., imidazo[1,2-a]pyridinyl or imidazo[3,2-a]pyridinyl), quinazolinyl, thienopyridinyl, tetrahydrothienopyridinyl (e.g., 4,5,6,7-tetrahydrothieno[3,2-c]pyridinyl), dibenzofuranyl, 1,3-benzodioxolyl, benzodioxanyl (e.g., 1,3-benzodioxanyl or 1,4-benzodioxanyl), or coumarinyl. Unless defined otherwise, the term "heteroaryl" preferably refers to a 5 to 14 membered (more preferably 5 to 10 membered) monocyclic ring or fused ring system comprising one or more (e.g., one, two, three or four) ring heteroatoms independently selected from O, S and N, wherein one or more S ring atoms (if present) and/or one or more N ring atoms (if present) are optionally oxidized, and wherein one or more carbon ring atoms are optionally oxidized; even more preferably, a "heteroaryl" refers to a 5 or 6 membered monocyclic ring comprising one or more (e.g., one, two or three) ring heteroatoms independently selected from O, S and N, wherein one or more S ring atoms (if present) and/or one or more N ring atoms (if present) are optionally oxidized, and wherein one or more carbon ring atoms are optionally oxidized. Moreover, unless defined otherwise, the term "heteroaryl" particularly preferably refers to pyridinyl (e.g., 2-pyridyl, 3-pyridyl, or 4-pyridyl), imidazolyl, thiazolyl, 1H-tetrazolyl, 2H-tetrazolyl, thienyl (i.e., thiophenyl), or pyrimidinyl.

As used herein, the term "cycloalkyl" refers to a saturated hydrocarbon ring group, including monocyclic rings as well as bridged ring, spiro ring and/or fused ring systems (which may be composed, e.g., of two or three rings; such as, e.g., a fused ring system composed of two or three fused rings). "Cycloalkyl" may, e.g., refer to cyclopropyl, cyclobutyl, cyclopentyl, cyclohexyl, cycloheptyl, decalinyl (i.e., decahydronaphthyl), or adamantyl. Unless defined otherwise, "cycloalkyl" preferably refers to a $C_3$-$C_{11}$ cycloalkyl, and more preferably refers to a $C_3$-$C_7$ cycloalkyl. A particularly preferred "cycloalkyl" is a monocyclic saturated hydrocarbon ring having 3 to 7 ring members (e.g., cyclopropyl or cyclohexyl).

As used herein, the term "heterocycloalkyl" refers to a saturated ring group, including monocyclic rings as well as bridged ring, spiro ring and/or fused ring systems (which may be composed, e.g., of two or three rings; such as, e.g., a fused ring system composed of two or three fused rings), wherein said ring group contains one or more (such as, e.g., one, two, three, or four) ring heteroatoms independently selected from O, S and N, and the remaining ring atoms are carbon atoms, wherein one or more S ring atoms (if present) and/or one or more N ring atoms (if present) may optionally be oxidized, and further wherein one or more carbon ring atoms may optionally be oxidized (i.e., to form an oxo group). For example, each heteroatom-containing ring comprised in said saturated ring group may contain one or two O atoms and/or one or two S atoms (which may optionally be oxidized) and/or one, two, three or four N atoms (which may optionally be oxidized), provided that the total number of heteroatoms in the corresponding heteroatom-containing ring is 1 to 4 and that there is at least one carbon ring atom (which may optionally be oxidized) in the corresponding heteroatom-containing ring. "Heterocycloalkyl" may, e.g., refer to aziridinyl, azetidinyl, pyrrolidinyl, imidazolidinyl, pyrazolidinyl, piperidinyl, piperazinyl, azepanyl, diazepanyl (e.g., 1,4-diazepanyl), oxazolidinyl, isoxazolidinyl, thiazolidinyl, isothiazolidinyl, morpholinyl (e.g., morpholin-4-yl), thiomorpholinyl (e.g., thiomorpholin-4-yl), oxazepanyl, oxiranyl, oxetanyl, tetrahydrofuranyl, 1,3-dioxolanyl, tetrahydropyranyl, 1,4-dioxanyl, oxepanyl, thiiranyl, thietanyl, tetrahydrothiophenyl (i.e., thiolanyl), 1,3-dithiolanyl, thianyl, thiepanyl, decahydroquinolinyl, decahydroisoquinolinyl, or 2-oxa-5-aza-bicyclo[2.2.1]hept-5-yl. Unless defined otherwise, "heterocycloalkyl" preferably refers to a 3 to 11 membered saturated ring group, which is a monocyclic ring or a fused ring system (e.g., a fused ring system composed of two fused rings), wherein said ring group contains one or more (e.g., one, two, three, or four) ring heteroatoms independently selected from O, S and N, wherein one or more S ring atoms (if present) and/or one or more N ring atoms (if present) are optionally oxidized, and wherein one or more carbon ring atoms are optionally oxidized; more preferably, "heterocycloalkyl" refers to a 5 to 7 membered saturated monocyclic ring group containing one or more (e.g., one, two, or three) ring heteroatoms independently selected from O, S and N, wherein one or more S ring atoms (if present) and/or one or more N ring atoms (if present) are optionally oxidized, and wherein one or more carbon ring atoms are optionally oxidized. Moreover, unless defined otherwise, "heterocycloalkyl" even more preferably refers to tetrahydropyranyl, piperidinyl, piperazinyl, morpholinyl, pyrrolidinyl, or tetrahydrofuranyl.

As used herein, the term "cycloalkenyl" refers to an unsaturated alicyclic (non-aromatic) hydrocarbon ring group, including monocyclic rings as well as bridged ring, spiro ring and/or fused ring systems (which may be composed, e.g., of two or three rings; such as, e.g., a fused ring system composed of two or three fused rings), wherein said hydrocarbon ring group comprises one or more (e.g., one or two) carbon-to-carbon double bonds and does not comprise any carbon-to-carbon triple bond. "Cycloalkenyl" may, e.g., refer to cyclopropenyl, cyclobutenyl, cyclopentenyl, cyclohexenyl, cyclohexadienyl, cycloheptenyl, or cycloheptadienyl. Unless defined otherwise, "cycloalkenyl" preferably refers to a $C_3$-$C_{11}$ cycloalkenyl, and more preferably refers to a $C_3$-$C_7$ cycloalkenyl. A particularly preferred "cycloalkenyl" is a monocyclic unsaturated alicyclic hydrocarbon ring having 3 to 7 ring members and containing one or more (e.g., one or two; preferably one) carbon-to-carbon double bonds.

As used herein, the term "heterocycloalkenyl" refers to an unsaturated alicyclic (non-aromatic) ring group, including monocyclic rings as well as bridged ring, spiro ring and/or fused ring systems (which may be composed, e.g., of two or three rings; such as, e.g., a fused ring system composed of two or three fused rings), wherein said ring group contains one or more (such as, e.g., one, two, three, or four) ring heteroatoms independently selected from O, S and N, and the remaining ring atoms are carbon atoms, wherein one or more S ring atoms (if present) and/or one or more N ring atoms (if present) may optionally be oxidized, wherein one or more carbon ring atoms may optionally be oxidized (i.e., to form an oxo group), and further wherein said ring group comprises at least one double bond between adjacent ring atoms and does not comprise any triple bond between adjacent ring atoms. For example, each heteroatom-containing ring comprised in said unsaturated alicyclic ring group may contain one or two O atoms and/or one or two S atoms (which may optionally be oxidized) and/or one, two, three or four N atoms (which may optionally be oxidized), provided that the total number of heteroatoms in the corresponding heteroatom-containing ring is 1 to 4 and that there is at least one carbon ring atom (which may optionally be oxidized) in the corresponding heteroatom-containing ring. "Heterocycloalkenyl" may, e.g., refer to imidazolinyl (e.g., 2-imidazolinyl (i.e., 4,5-dihydro-1H-imidazolyl), 3-imidazolinyl, or 4-imidazolinyl), tetrahydropyridinyl (e.g., 1,2,3,6-tetrahydropyridinyl), pyranyl (e.g., 2H-pyranyl or 4H-pyranyl), thiopyranyl (e.g., 2H-thiopyranyl or 4H-thiopyranyl), octahydroquinolinyl (e.g., 1,2,3,4,4a,5,6,7-octahydroquinolinyl), or octahydroisoquinolinyl (e.g., 1,2,3,4,5,6,7,8-octahydroisoquinolinyl). Unless defined otherwise, "heterocycloalkenyl" preferably refers to a 3 to 11 membered unsaturated alicyclic ring group, which is a monocyclic ring or a fused ring system (e.g., a fused ring system composed of two fused rings), wherein said ring group contains one or more (e.g., one, two, three, or four) ring heteroatoms independently selected from O, S and N, wherein one or more S ring atoms (if present) and/or one or more N ring atoms (if present) are optionally oxidized, wherein one or more carbon ring atoms are optionally oxidized, and wherein said ring group comprises at least one double bond between adjacent ring atoms and does not comprise any triple bond between adjacent ring atoms; more preferably, "heterocycloalkenyl" refers to a 5 to 7 membered monocyclic unsaturated non-aromatic ring group containing one or more (e.g., one, two, or three) ring heteroatoms independently selected from O, S and N, wherein one or more S ring atoms (if present) and/or one or more N ring atoms (if present) are optionally oxidized, wherein one or more carbon ring atoms are optionally oxidized, and wherein said ring group comprises at least one double bond between adjacent ring atoms and does not comprise any triple bond between adjacent ring atoms.

As used herein, the term "halogen" refers to fluoro (—F), chloro (—Cl), bromo (—Br), or iodo (—I).

As used herein, the term "haloalkyl" refers to an alkyl group substituted with one or more (preferably 1 to 6, more preferably 1 to 3) halogen atoms which are selected independently from fluoro, chloro, bromo and iodo, and are preferably all fluoro atoms. It will be understood that the maximum number of halogen atoms is limited by the number of available attachment sites and, thus, depends on the number of carbon atoms comprised in the alkyl moiety of the haloalkyl group. "Haloalkyl" may, e.g., refer to —CF$_3$, —CHF$_2$, —CH$_2$F, —CF$_2$—CH$_3$, —CH$_2$—CF$_3$, —CH$_2$—CHF$_2$, —CH$_2$—CF$_2$—CH$_3$, —CH$_2$—CF$_2$—CF$_3$, or —CH(CF$_3$)$_2$. A particularly preferred "haloalkyl" group is —CF$_3$.

Various groups are referred to as being "optionally substituted" in this specification. Generally, these groups may carry one or more substituents, such as, e.g., one, two, three or four substituents. It will be understood that the maximum number of substituents is limited by the number of attachment sites available on the substituted moiety. Unless defined otherwise, the "optionally substituted" groups referred to in this specification carry preferably not more than two substituents and may, in particular, carry only one substituent. Moreover, unless defined otherwise, it is preferred that the optional substituents are absent, i.e. that the corresponding groups are unsubstituted.

As used herein, the terms "optional", "optionally" and "may" denote that the indicated feature may be present but can also be absent. Whenever the term "optional", "optionally" or "may" is used, the present invention specifically relates to both possibilities, i.e., that the corresponding feature is present or, alternatively, that the corresponding feature is absent. For example, the expression "X is optionally substituted with Y" (or "X may be substituted with Y") means that X is either substituted with Y or is unsubstituted. Likewise, if a component of a composition is indicated to be "optional", the invention specifically relates to both possibilities, i.e., that the corresponding component is present (contained in the composition) or that the corresponding component is absent from the composition.

A skilled person will appreciate that the substituent groups comprised in the compounds of formula (I) may be attached to the remainder of the respective compound via a number of different positions of the corresponding specific substituent group. Unless defined otherwise, the preferred attachment positions for the various specific substituent groups are as illustrated in the examples.

As used herein, the term "about" preferably refers to ±10% of the indicated numerical value, more preferably to ±5% of the indicated numerical value, and in particular to the exact numerical value indicated.

As used herein, the term "comprising" (or "comprise", "comprises", "contain", "contains", or "containing"), unless explicitly indicated otherwise or contradicted by context, has the meaning of "containing, inter alia", i.e., "containing, among further optional elements, . . . ". In addition thereto, this term also includes the narrower meanings of "consisting essentially of" and "consisting of". For example, the term "A comprising B and C" has the meaning of "A containing, inter alia, B and C", wherein A may contain further optional elements (e.g., "A containing B, C and D" would also be encompassed), but this term also includes the meaning of "A consisting essentially of B and C" and the meaning of "A consisting of B and C" (i.e., no other components than B and C are comprised in A).

In the following, where reference is made to the compounds of the general formula (I), this is intended to refer to the compounds of formula (I) according to the first and/or the second aspect of the invention.

Compounds of the general formula (I) may exist in the form of different isomers, in particular stereoisomers (including geometric isomers (or cis-trans isomers), enantiomers and diastereomers) or tautomers. All such isomers of the compounds according to the invention are contemplated as being part of the present invention, either in admixture or in pure or substantially pure form. As for stereoisomers, the invention embraces mixtures (such as racemic forms) and the isolated optical isomers of the compounds according to the invention. The racemic forms can be resolved by physical methods, such as, e.g., fractional crystallization, separation or crystallization of diastereomeric derivatives or separation by chiral column chromatography.

The scope of the invention also embraces compounds of the general formula (I), in which one or more atoms are replaced by a specific isotope of the corresponding atom. For example, the invention encompasses compounds of formula (I), in which one or more hydrogen atoms (or, e.g., all hydrogen atoms) are replaced by deuterium atoms (i.e., $^2$H; also referred to as "D"). Accordingly, the invention also embraces compounds of formula (I) which are enriched in deuterium. Naturally occurring hydrogen is an isotopic mixture comprising about 99.98 mol-% hydrogen-1 ($^1$H) and about 0.0156 mol-% deuterium ($^2$H or D). The content of deuterium in one or more hydrogen positions in the compounds of formula (I) can be increased using deuteration techniques known in the art. For example, a compound of formula (I) or a reactant or precursor to be used in the synthesis of the compound of formula (I) can be subjected to an H/D exchange reaction using, e.g., heavy water ($D_2O$). Further suitable deuteration techniques are described in: Atzrodt J et al., *Bioorg Med Chem*, 20(18), 5658-5667, 2012; William J S et al., *Journal of Labelled Compounds and Radiopharmaceuticals*, 53(11-12), 635-644, 2010; Modvig A et al., *J Org Chem*, 79, 5861-5868, 2014. The content of deuterium can be determined, e.g., using mass spectrometry or NMR spectroscopy. Unless specifically indicated otherwise, it is preferred that the compound of formula (I) is not enriched in deuterium. Accordingly, the presence of naturally occurring hydrogen atoms or $^1$H hydrogen atoms in the compounds of formula (I) is preferred. The present invention also embraces compounds of formula (I), in which one or more atoms are replaced by a positron-emitting isotope of the corresponding atom, such as, e.g., $^{18}$F, $^{11}$C, $^{13}$N, $^{15}$O, $^{76}$Br, $^{77}$Br, $^{120}$I and/or $^{124}$I. Such compounds can be used as tracers or imaging probes in positron emission tomography (PET). The invention thus includes (i) compounds of formula (I), in which one or more fluorine atoms (or, e.g., all fluorine atoms) are replaced by $^{18}$F atoms, (ii) compounds of formula (I), in which one or more carbon atoms (or, e.g., all carbon atoms) are replaced by $^{11}$C atoms, (iii) compounds of formula (I), in which one or more nitrogen atoms (or, e.g., all nitrogen atoms) are replaced by $^{13}$N atoms, (iv) compounds of formula (I), in which one or more oxygen atoms (or, e.g., all oxygen atoms) are replaced by $^{15}$O atoms, (v) compounds of formula (I), in which one or more bromine atoms (or, e.g., all bromine atoms) are replaced by $^{76}$Br atoms, (vi) compounds of formula (I), in which one or more bromine atoms (or, e.g., all bromine atoms) are replaced by $^{77}$Br atoms, (vii) compounds of formula (I), in which one or more iodine atoms (or, e.g., all iodine atoms) are replaced by $^{120}$I atoms, and (viii) compounds of formula (I), in which one or more iodine atoms (or, e.g., all iodine atoms) are replaced by $^{124}$I atoms. In general, it is preferred that none of the atoms in the compounds of formula (I) are replaced by specific isotopes.

The scope of the invention embraces all pharmaceutically acceptable salt forms of the compounds of the general formula (I) which may be formed, e.g., by protonation of an atom carrying an electron lone pair which is susceptible to protonation, such as an amino group, with an inorganic or organic acid, or as a salt of a carboxylic acid group with a physiologically acceptable cation as they are well known in the art. Exemplary base addition salts comprise, for example, alkali metal salts such as sodium or potassium salts; alkaline-earth metal salts such as calcium or magnesium salts; ammonium salts; aliphatic amine salts such as trimethylamine, triethylamine, dicyclohexylamine, ethanolamine, diethanolamine, triethanolamine, procaine salts, meglumine salts, diethanol amine salts or ethylenediamine salts; aralkyl amine salts such as N,N-dibenzylethylenediamine salts, benetamine salts; heterocyclic aromatic amine salts such as pyridine salts, picoline salts, quinoline salts or isoquinoline salts; quaternary ammonium salts such as tetramethylammonium salts, tetraethylammonium salts, benzyltrimethylammonium salts, benzyltriethylammonium salts, benzyltributylammonium salts, methyltrioctylammonium salts or tetrabutylammonium salts; and basic amino acid salts such as arginine salts or lysine salts. Exemplary acid addition salts comprise, for example, mineral acid salts such as hydrochloride, hydrobromide, hydroiodide, sulfate salts, nitrate salts, phosphate salts (such as, e.g., phosphate, hydrogenphosphate, or dihydrogenphosphate salts), carbonate salts, hydrogencarbonate salts or perchlorate salts; organic acid salts such as acetate, propionate, butyrate, pentanoate, hexanoate, heptanoate, octanoate, cyclopentanepropionate, undecanoate, lactate, maleate, oxalate, fumarate, tartrate, malate, citrate, nicotinate, benzoate, salicylate or ascorbate salts; sulfonate salts such as methanesulfonate, ethanesulfonate, 2-hydroxyethanesulfonate, benzenesulfonate, p-toluenesulfonate (tosylate), 2-naphthalenesulfonate, 3-phenylsulfonate, or camphorsulfonate salts; and acidic amino acid salts such as aspartate or glutamate salts.

Moreover, the scope of the invention embraces solid forms of the compounds of the general formula (I) in any solvated form, including e.g. solvates with water, for example hydrates, or with organic solvents such as, e.g., methanol, ethanol or acetonitrile, i.e. as a methanolate, ethanolate or acetonitrilate, respectively; or in the form of any polymorph.

Pharmaceutically acceptable prodrugs of compounds of the general formula (I) are derivatives which have chemically or metabolically cleavable groups and become, by solvolysis or under physiological conditions, the compounds of formula (I) which are pharmaceutically active in vivo. Prodrugs of compounds of formula (I) may be formed in a conventional manner with a functional group of the compounds such as with an amino, hydroxy or carboxy group. The prodrug derivative form often offers advantages of solubility, tissue compatibility or delayed release in a mammalian organism (see, Bundgaard, H., Design of Prodrugs, pp. 7-9, 21-24, Elsevier, Amsterdam 1985). Prodrugs include acid derivatives well known to the person skilled in the art, such as, for example, esters prepared by reaction of the parent acidic compound with a suitable alcohol, or amides prepared by reaction of the parent acid compound with a suitable amine. When a compound of the general formula (I) has a carboxyl group, an ester derivative prepared by reacting the carboxyl group with a suitable alcohol or an amide derivative prepared by reacting the carboxyl group with a suitable amine is exemplified as a prodrug. An especially preferred ester derivative as a prodrug is methylester, ethylester, n-propylester, isopropylester, n-butylester, isobutylester, tert-butylester, morpholinoethylester or N,N-diethylglycolamidoester. When a compound of formula (I) has a hydroxy group, an acyloxy derivative prepared by reacting the hydroxyl group with a suitable acylhalide or a suitable acid anhydride is exemplified as a prodrug. An especially preferred acyloxy derivative as a prodrug is —OC(=O)—CH$_3$, —OC(=O)—C$_2$H$_5$, —OC(=O)—C$_3$H$_7$, —OC(=O)-(tert-butyl), —OC(=O)—C$_{15}$H$_{31}$, —OC(=O)—CH$_2$CH$_2$COONa, —O(C=O)—CH(NH$_2$)CH$_3$ or —OC(=O)—CH$_2$—N(CH$_3$)$_2$. When a compound of formula (I) has an amino group, an amide derivative prepared by reacting the amino group with a suitable acid halide or a suitable mixed anhydride is exemplified as a prodrug. An especially preferred amide derivative as a prodrug is —NHC(=O)—(CH$_2$)$_2$OCH$_3$ or —NHC(=O)—CH(NH$_2$)CH$_3$.

The compounds of general formula (I) or pharmaceutically acceptable salts, solvates or prodrugs thereof, may be administered as compounds per se or may be formulated as medicaments. Within the scope of the present invention are pharmaceutical compositions comprising as an active ingredient one or more compounds of the general formula (I), or pharmaceutically acceptable salts, solvates or prodrugs thereof. The pharmaceutical compositions may optionally comprise one or more pharmaceutically acceptable excipients, such as carriers, diluents, fillers, disintegrants, lubricating agents, binders, colorants, pigments, stabilizers, preservatives, or antioxidants.

The pharmaceutical compositions may also comprise one or more solubility enhancers, such as, e.g., poly(ethylene glycol), including poly(ethylene glycol) having a molecular weight in the range of about 200 to about 5,000 Da, ethylene glycol, propylene glycol, non-ionic surfactants, tyloxapol, polysorbate 80, macrogol-15-hydroxystearate, phospholipids, lecithin, dimyristoyl phosphatidylcholine, dipalmitoyl phosphatidylcholine, distearoyl phosphatidylcholine, cyclodextrins, hydroxyethyl-β-cyclodextrin, hydroxypropyl-β-cyclodextrin, hydroxyethyl-γ-cyclodextrin, hydroxypropyl-γ-cyclodextrin, dihydroxypropyl-β-cyclodextrin, glucosyl-α-cyclodextrin, glucosyl-β-cyclodextrin, diglucosyl-β-cyclodextrin, maltosyl-α-cyclodextrin, maltosyl-β-cyclodextrin, maltosyl-γ-cyclodextrin, maltotriosyl-β-cyclodextrin, maltotriosyl-γ-cyclodextrin, dimaltosyl-β-cyclodextrin, methyl-β-cyclodextrin, carboxyalkyl thioethers, hydroxypropyl methylcellulose, hydroxypropylcellulose, polyvinylpyrrolidone, vinyl acetate copolymers, vinyl pyrrolidone, sodium lauryl sulfate, dioctyl sodium sulfosuccinate, or any combination thereof.

The pharmaceutical compositions can be formulated by techniques known to the person skilled in the art, such as the techniques published in Remington's Pharmaceutical Sciences, 20$^{th}$ Edition. The pharmaceutical compositions can be formulated as dosage forms for oral, parenteral, such as intramuscular, intravenous, subcutaneous, intradermal, intraarterial, rectal, nasal, topical, aerosol or vaginal administration. Dosage forms for oral administration include coated and uncoated tablets, soft gelatin capsules, hard gelatin capsules, lozenges, troches, solutions, emulsions, suspensions, syrups, elixirs, powders and granules for reconstitution, dispersible powders and granules, medicated gums, chewing tablets and effervescent tablets. Dosage forms for parenteral administration include solutions, emulsions, suspensions, dispersions and powders and granules for reconstitution. Emulsions are a preferred dosage form for parenteral administration. Dosage forms for rectal and vaginal administration include suppositories and ovula. Dosage forms for nasal administration can be administered via inhalation and insufflation, for example by a metered inhaler. Dosage forms for topical administration include creams, gels, ointments, salves, patches and transdermal delivery systems.

The compounds of the general formula (I) or pharmaceutically acceptable salts, solvates or prodrugs thereof, or the above described pharmaceutical compositions, may be administered to a subject by any convenient route of administration, whether systemically/peripherally or at the site of desired action, including but not limited to one or more of: oral (e.g. as a tablet, capsule, or as an ingestible solution), topical (e.g., transdermal, intranasal, ocular, buccal, and sublingual), parenteral (e. g., using injection techniques or infusion techniques, and including, for example, by injection, e.g. subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, or intrasternal by, e.g., implant of a depot, for example, subcutaneously or intramuscularly), pulmonary (e.g., by inhalation or insufflation therapy using, e.g., an aerosol, e.g., through mouth or nose), gastrointestinal, intrauterine, intraocular, subcutaneous, ophthalmic (including intravitreal or intracameral), rectal, and vaginal.

If said compounds or pharmaceutical compositions are administered parenterally, then examples of such administration include one or more of: intravenously, intraarterially, intraperitoneally, intrathecally, intraventricularly, intraurethrally, intrasternally, intracranially, intramuscularly or subcutaneously administering the compounds pharmaceutical compositions, and/or by using infusion techniques. For parenteral administration, the compounds are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

Said compounds or pharmaceutical compositions can also be administered orally in the form of tablets, capsules, ovules, elixirs, solutions or suspensions, which may contain flavoring or coloring agents, for immediate-, delayed-, modified-, sustained-, pulsed- or controlled-release applications.

The tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycolate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included. Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the agent may be combined with various sweetening or flavoring agents, coloring matter or dyes, with emulsifying and/or suspending agents and with diluents such as water, ethanol, propylene glycol and glycerin, and combinations thereof.

Said compounds or pharmaceutical compositions may also be administered by sustained release systems. Suitable examples of sustained-release compositions include semipermeable polymer matrices in the form of shaped articles, e.g., films, or microcapsules. Sustained-release matrices include, e.g., polylactides (U.S. Pat. No. 3,773,919), copolymers of L-glutamic acid and gamma-ethyl-L-glutamate (Sidman, U. et al., Biopolymers 22:547-556 (1983)), poly (2-hydroxyethyl methacrylate) (R. Langer et al., J. Biomed. Mater. Res. 15:167-277 (1981), and R. Langer, Chem. Tech.

12:98-105 (1982)), ethylene vinyl acetate (R. Langer et al., Id.) or poly-D-(−)-3-hydroxybutyric acid (EP133988). Sustained-release pharmaceutical compositions also include liposomally entrapped compounds. Liposomes containing a compound of the present invention can be prepared by methods known in the art, such as, e.g., the methods described in any one of: DE3218121; Epstein et al., Proc. Natl. Acad. Sci. (USA) 82:3688-3692 (1985); Hwang et al., Proc. Natl. Acad. Sci. (USA) 77:4030-4034 (1980); EP0052322; EP0036676; EP088046; EP0143949; EP0142641; Japanese Pat. Appl. 83-118008; U.S. Pat. Nos. 4,485,045 and 4,544,545; and EP0102324.

Alternatively, said compounds or pharmaceutical compositions can be administered in the form of a suppository or pessary, or may be applied topically in the form of a gel, hydrogel, lotion, solution, cream, ointment or dusting powder. The compounds of the present invention may also be dermally or transdermally administered, for example, by the use of a skin patch.

Said compounds or pharmaceutical compositions may also be administered by the pulmonary route, rectal routes, or the ocular route. For ophthalmic use, they can be formulated as micronized suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For topical application to the skin, said compounds or pharmaceutical compositions can be formulated as a suitable ointment containing the active compound suspended or dissolved in, for example, a mixture with one or more of the following: mineral oil, liquid petrolatum, white petrolatum, propylene glycol, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, 2-octyldodecanol, benzyl alcohol and water.

Typically, a physician will determine the actual dosage which will be most suitable for an individual subject. The specific dose level and frequency of dosage for any particular individual subject may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual subject undergoing therapy.

A proposed, yet non-limiting dose of the compounds of the general formula (I) for administration to a human (of approximately 70 kg body weight) may be 0.05 to 2000 mg, preferably 0.1 mg to 1000 mg, of the active ingredient per unit dose. The unit dose may be administered, for example, 1 to 4 times per day. The unit dose may also be administered 1 to 7 times per week, e.g., with not more than one administration per day. The dose will depend on the route of administration. It will be appreciated that it may be necessary to make routine variations to the dosage depending on the age and weight of the patient/subject as well as the severity of the condition to be treated. The precise dose and route of administration will ultimately be at the discretion of the attendant physician or veterinarian.

The subject or patient, such as the subject in need of treatment or prophylaxis, may be an animal (e.g., a non-human animal), a vertebrate animal, a mammal (e.g., a non-human mammal), a rodent (e.g., a guinea pig, a hamster, a rat, a mouse), a murine (e.g., a mouse), a canine (e.g., a dog), a feline (e.g., a cat), an equine (e.g., a horse), a primate, a simian (e.g., a monkey or ape), a monkey (e.g., a marmoset, a baboon), an ape (e.g., a gorilla, chimpanzee, orang-utan, gibbon), or a human. In the context of this invention, it is particularly envisaged that animals are to be treated which are economically, agronomically or scientifically important. Scientifically important organisms include, but are not limited to, mice, rats, and rabbits. Lower organisms such as, e.g., fruit flies like *Drosophila melagonaster* and nematodes like *Caenorhabditis elegans* may also be used in scientific approaches. Non-limiting examples of agronomically important animals are sheep, cattle and pigs, while, for example, cats and dogs may be considered as economically important animals. Preferably, the subject/patient is a mammal. More preferably, the subject/patient is a human ora non-human mammal (such as, e.g., a guinea pig, a hamster, a rat, a mouse, a rabbit, a dog, a cat, a horse, a monkey, an ape, a marmoset, a baboon, a gorilla, a chimpanzee, an orang-utan, a gibbon, a sheep, cattle, or a pig). Most preferably, the subject/patient is a human.

The term "treatment" of a condition, disorder or disease as used herein is well known in the art. "Treatment" of a condition, disorder or disease implies that a disorder or disease is suspected or has been diagnosed in a patient/subject. A patient/subject suspected of suffering from a disorder or disease typically shows specific clinical and/or pathological symptoms which a skilled person can easily attribute to a specific pathological condition (i.e. diagnose a disorder or disease).

The treatment of a condition, disorder or disease may, for example, lead to a halt in the progression of the condition, disorder or disease (e.g. no deterioration of symptoms) or a delay in the progression of the disorder or disease (in case the halt in progression is of a transient nature only). Treatment may also lead to a partial response (e.g. amelioration of symptoms) or complete response (e.g. disappearance of symptoms) of the subject/patient suffering from the condition, disorder or disease. Amelioration of a condition, disorder or disease may, for example, lead to a halt in the progression of the disorder or disease or a delay in the progresssion of the disorder or disease. Such a partial or complete response may be followed by a relapse. It is to be understood that a subject/patient may experience a broad range of responses to a treatment (e.g. the exemplary responses as described herein above).

Treatment of a condition, disorder or disease may, inter alia, comprise curative treatment (preferably leading to a complete response and eventually to healing of the disorder or disease) and palliative treatment (including symptomatic relief).

Also the term "prophylaxis" or "prevention" of a condition, disorder or disease as used herein is well known in the art. For example, a patient/subject suspected of being prone to suffer from a condition, disorder or disease as defined herein may, in particular, benefit from a prophylaxis of the disorder or disease. Said subject/patient may have a susceptibility or predisposition for a condition, disorder or disease, including but not limited to hereditary predisposition. Such a predisposition can be determined by standard assays, using, for example, genetic markers or phenotypic indicators. It is to be understood that a condition, disorder or disease to be prevented in accordance with the present invention has not been diagnosed or cannot be diagnosed in said patient/subject (for example, said patient/subject does not show any clinical or pathological symptoms). Thus, the term "prophylaxis" comprises the use of compounds of the present invention before any clinical and/or pathological symptoms are diagnosed or determined or can be diagnosed or determined by the attending physician. The terms "prophylaxis" and "prevention" are used herein interchangeably.

It is to be understood that the present invention specifically relates to each and every combination of features and embodiments described herein, including any combination of general and/or preferred features/embodiments. In particular, the invention specifically relates to each combination of meanings (including general and/or preferred meanings) for the various groups and variables comprised in the general formula (I).

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

The invention is also described by the following illustrative figures. The appended figures show:

FIG. 1: Neuroprotective effects on cortical primary neurons were shown for a compound of formula (I) in an NMDA-induced neurotoxicity assay (see Example 225).

Figure 2:
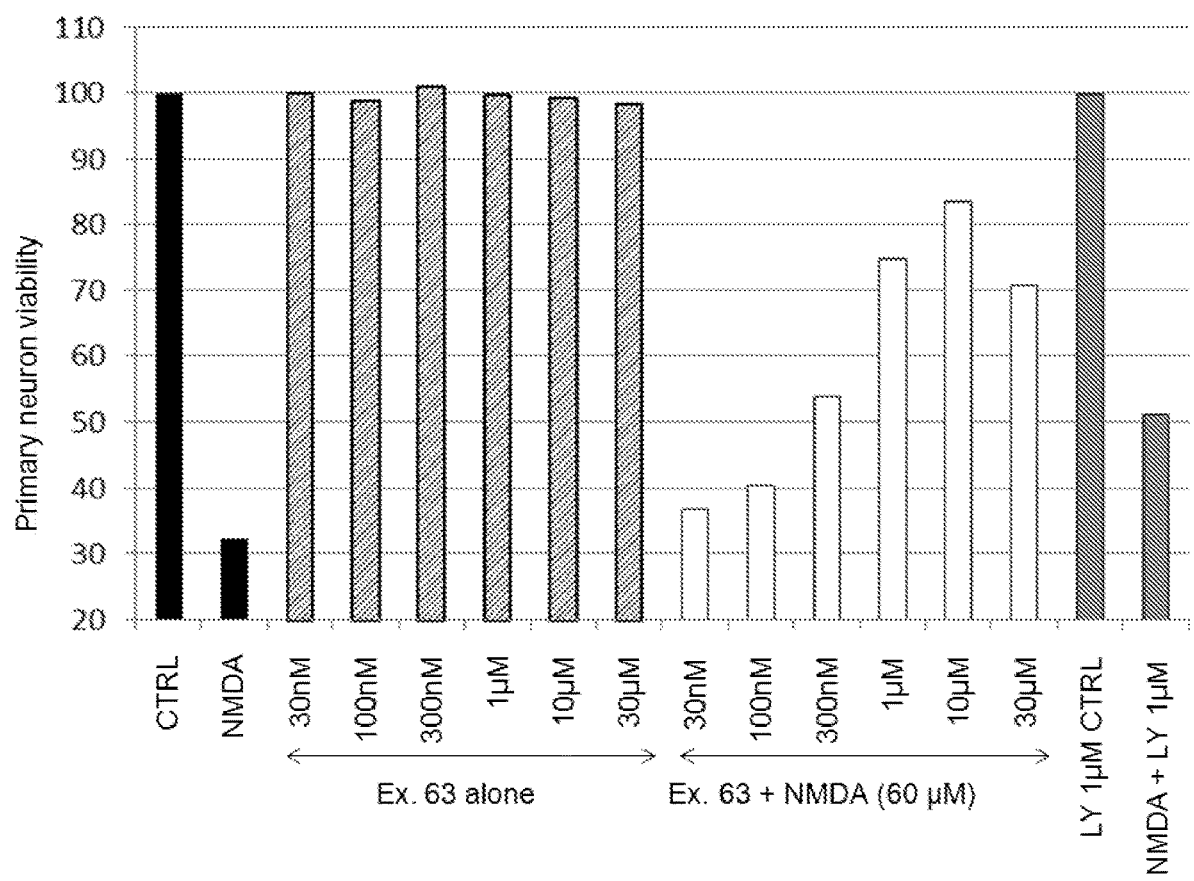

FIG. 2: Neuroprotective effects on striatal primary neurons were shown for a compound of formula (I) in an NMDA-induced neurotoxicity assay (see Example 226).

The present invention relates, in particular, to the following items:

1. A compound of the general formula (I):

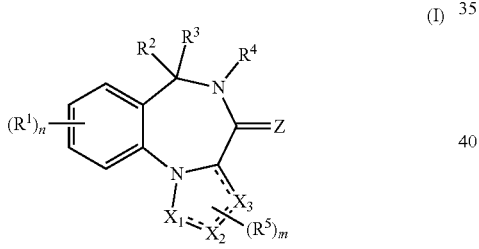

wherein:
X$_1$, X$_2$ and X$_3$ are each independently C or N;
each ==== is independently a single bond or a double bond, wherein at least one of any two adjacent bonds ==== is a single bond;
Z is O, S or N(—R$^Z$);
R$^Z$ is selected from hydrogen, C$_1$-C$_{10}$ alkyl, C$_2$-C$_{10}$ alkenyl, C$_2$-C$_{10}$ alkynyl, aryl, heteroaryl, cycloalkyl, and heterocycloalkyl, wherein said aryl, said heteroaryl, said cycloalkyl, and said heterocycloalkyl are each optionally substituted with one or more groups independently selected from C$_1$-C$_{10}$ alkyl, C$_2$-C$_{10}$ alkenyl, C$_2$-C$_{10}$ alkynyl, halogen, C$_1$-C$_{10}$ haloalkyl, —CN, —OH, —O(C$_1$-C$_{10}$ alkyl), —(C$_1$-C$_{10}$ alkylene)-OH, —(C$_1$-C$_{10}$ alkylene)-O(C$_1$-C$_{10}$ alkyl), —NH$_2$, —NH(C$_1$-C$_{10}$ alkyl), —N(C$_1$-C$_{10}$ alkyl)(C$_1$-C$_{10}$ alkyl), cycloalkyl, and heterocycloalkyl, and further wherein, if R$^Z$ is C$_1$-C$_{10}$ alkyl, C$_2$-C$_{10}$ alkenyl or C$_2$-C$_{10}$ alkynyl, then said alkyl, said alkenyl or said alkynyl is optionally substituted with one or more groups independently selected from halogen, C$_1$-C$_{10}$ haloalkyl, —CN, —OH, —O(C$_1$-C$_{10}$ alkyl), —NH$_2$, —NH(C$_1$-C$_{10}$ alkyl), —N(C$_1$-C$_{10}$ alkyl)(C$_1$-C$_{10}$ alkyl), cycloalkyl, and heterocycloalkyl;
each R$^1$ is independently a group -L$^1$-R$^{11}$;
each L$^1$ is independently selected from a bond, C$_1$-C$_{10}$ alkylene, C$_2$-C$_{10}$ alkenylene, and C$_2$-C$_{10}$ alkynylene, wherein said alkylene, said alkenylene and said alkynylene are each optionally substituted with one or more groups independently selected from halogen, C$_1$-C$_{10}$ haloalkyl, —CN, —OR$^{12}$, —NR$^{12}$R$^{12}$, —COR$^{12}$, —COOR$^{12}$, —OCOR$^{12}$, —CONR$^{12}$R$^{12}$, —NR$^{12}$COR$^{12}$, —SR$^{12}$, —SOR$^{12}$, —SO$_2$R$^{12}$, —SO$_2$NR$^{12}$R$^{12}$, and —NR$^{12}$SO$_2$R$^{12}$, and further wherein one or more —CH$_2$— units comprised in said alkylene, said alkenylene or said alkynylene are each optionally replaced by a group independently selected from —O—, —NR$^{12}$—, —CO—, —S—, —SO—, and —SO$_2$—;
each R$^{11}$ is independently selected from aryl, heteroaryl, cycloalkyl, heterocycloalkyl, cycloalkenyl, heterocycloalkenyl, halogen, C$_1$-C$_{10}$ haloalkyl, —CN, C$_1$-C$_{10}$ alkyl, C$_2$-C$_{10}$ alkenyl, C$_2$-C$_{10}$ alkynyl, —NR$^{12}$R$^{12}$, —OR$^{12}$, —SR$^{12}$, —SOR$^{12}$, —SO$_2$R$^{12}$, —COR$^{12}$, —COOR$^{12}$, —OCOR$^{12}$, —CONR$^{12}$R$^{12}$, —NR$^{12}$COR$^{12}$, —SO$_2$NR$^{12}$R$^{12}$, —NR$^{12}$SO$_2$R$^{12}$, and —SO$_3$R$^{12}$, wherein said aryl, said heteroaryl, said cycloalkyl, said heterocycloalkyl, said cycloalkenyl and said heterocycloalkenyl are each optionally substituted with one or more groups independently selected from halogen, C$_1$-C$_{10}$ haloalkyl, —CN, C$_1$-C$_{10}$ alkyl, C$_2$-C$_{10}$ alkenyl, C$_2$-C$_{10}$ alkynyl, —OH, —O(C$_1$-C$_{10}$ alkyl), —(C$_1$-C$_{10}$ alkylene)-OH, —(C$_1$-C$_{10}$ alkylene)-O(C$_1$-C$_{10}$ alkyl), —NH$_2$, —NH(C$_1$-C$_{10}$ alkyl), —N(C$_1$-C$_{10}$ alkyl)(C$_1$-C$_{10}$ alkyl), —CHO, —CO(C$_1$-C$_{10}$ alkyl), —COOH, tetrazolyl, —COO(C$_1$-C$_{10}$ alkyl), —OCO(C$_1$-C$_{10}$ alkyl), —CO—NH$_2$, —CO—NH(C$_1$-C$_{10}$ alkyl), —CO—N(C$_1$-C$_{10}$ alkyl)(C$_1$-C$_{10}$ alkyl), —NH—CO—(C$_1$-C$_{10}$ alkyl), —N(C$_1$-C$_{10}$ alkyl)-CO—(C$_1$-C$_{10}$ alkyl), —SO$_2$—NH$_2$, —SO$_2$—NH(C$_1$-C$_{10}$ alkyl), —SO$_2$—N(C$_1$-C$_{10}$ alkyl)(C$_1$-C$_{10}$ alkyl), —NH—SO$_2$—(C$_1$-C$_{10}$ alkyl), —N(C$_1$-C$_{10}$ alkyl)-SO$_2$—(C$_1$-C$_{10}$ alkyl), cycloalkyl, heterocycloalkyl, aryl, heteroaryl, and -L$^{11}$-R$^{13}$, and further wherein, if R$^{11}$ is C$_1$-C$_{10}$ alkyl, C$_2$-C$_{10}$ alkenyl or C$_2$-C$_{10}$ alkynyl, then said alkyl, said alkenyl or said alkynyl is optionally substituted with one or more groups independently selected from halogen, C$_1$-C$_{10}$ haloalkyl, —CN, —OH, —O(C$_1$-C$_{10}$ alkyl), —NH$_2$, —NH(C$_1$-C$_{10}$ alkyl), —N(C$_1$-C$_{10}$ alkyl)(C$_1$-C$_{10}$ alkyl), —CHO, —CO (C$_1$-C$_{10}$ alkyl), —COOH, tetrazolyl, —COO(C$_1$-C$_{10}$ alkyl), —OCO(C$_1$-C$_{10}$ alkyl), —CO—NH$_2$, —CO—NH(C$_1$-C$_{10}$ alkyl), —CO—N(C$_1$-C$_{10}$ alkyl)(C$_1$-C$_{10}$ alkyl), —NH—CO—(C$_1$-C$_{10}$ alkyl), —N(C$_1$-C$_{10}$ alkyl)-CO—(C$_1$-C$_{10}$ alkyl), —SO$_2$—NH$_2$, —SO$_2$—NH(C$_1$-C$_{10}$ alkyl), —SO$_2$—N(C$_1$-C$_{10}$ alkyl)(C$_1$-C$_{10}$ alkyl), —NH—SO$_2$—(C$_1$-C$_{10}$ alkyl), —N(C$_1$-C$_{10}$ alkyl)-SO$_2$—(C$_1$-C$_{10}$ alkyl), cycloalkyl, heterocycloalkyl, aryl, heteroaryl, and -L$^{11}$-R$^{13}$;
each R$^{12}$ is independently selected from hydrogen, C$_1$-C$_{10}$ alkyl, C$_2$-C$_{10}$ alkenyl, C$_2$-C$_{10}$ alkynyl, aryl, heteroaryl, cycloalkyl, and heterocycloalkyl, wherein said aryl, said heteroaryl, said cycloalkyl, and said heterocycloalkyl are each optionally substituted with one or more groups independently selected from C$_1$-C$_{10}$ alkyl, C$_2$-C$_{10}$ alkenyl, C$_2$-C$_{10}$ alkynyl, halogen, $C_1$-$C_{10}$ haloalkyl, —CN, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —NH$_2$, —NH($C_1$-$C_{10}$ alkyl), —N($C_1$-$C_{10}$ alkyl)($C_1$-$C_{10}$ alkyl), cycloalkyl, and heterocycloalkyl, wherein if $R^{12}$ is $C_1$-$C_{10}$ alkyl, $C_2$-$C_{10}$ alkenyl or $C_2$-$C_{10}$ alkynyl, then said alkyl, said alkenyl or said alkynyl is optionally substituted with one or more groups independently selected from halogen, $C_1$-$C_{10}$ haloalkyl, —CN, —OH, —O($C_1$-$C_{10}$ alkyl), —NH$_2$, —NH($C_1$-$C_{10}$ alkyl), —N($C_1$-$C_{10}$ alkyl)($C_1$-$C_{10}$ alkyl), cycloalkyl, and heterocycloalkyl, and further if two groups $R^{12}$ are attached to the same nitrogen atom, then these two groups $R^{12}$ may also together form a $C_2$-$C_8$ alkylene;

each $L^{11}$ is independently selected from a bond, $C_1$-$C_{10}$ alkylene, $C_2$-$C_{10}$ alkenylene, and $C_2$-$C_{10}$ alkynylene, wherein one or more —CH$_2$— units comprised in said alkylene, said alkenylene or said alkynylene are each optionally replaced by a group independently selected from —O—, —NH—, —N($C_1$-$C_{10}$ alkyl)-, —CO—, —S—, —SO—, and —SO$_2$—;

each $R^{13}$ is independently selected from aryl, heteroaryl, cycloalkyl, heterocycloalkyl, cycloalkenyl, heterocycloalkenyl, halogen, $C_1$-$C_{10}$ haloalkyl, —CN, $C_1$-$C_{10}$ alkyl, $C_2$-$C_{10}$ alkenyl, $C_2$-$C_{10}$ alkynyl, —NH$_2$, —NH($C_1$-$C_{10}$ alkyl), —N($C_1$-$C_{10}$ alkyl)($C_1$-$C_{10}$ alkyl), —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —SH, and —S($C_1$-$C_{10}$ alkyl), wherein said aryl, said heteroaryl, said cycloalkyl, said heterocycloalkyl, said cycloalkenyl and said heterocycloalkenyl are each optionally substituted with one or more groups independently selected from halogen, $C_1$-$C_{10}$ haloalkyl, —CN, $C_1$-$C_{10}$ alkyl, $C_2$-$C_{10}$ alkenyl, $C_2$-$C_{10}$ alkynyl, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —NH$_2$, —NH($C_1$-$C_{10}$ alkyl), —N($C_1$-$C_{10}$ alkyl)($C_1$-$C_{10}$ alkyl), cycloalkyl, and heterocycloalkyl;

n is an integer of 0 to 4;

$R^2$ and $R^3$ are mutually linked to form, together with the carbon atom that they are attached to, a cycloalkyl or a heterocycloalkyl; or $R^2$ and $R^3$ are each independently selected from hydrogen, halogen, $C_1$-$C_{10}$ haloalkyl, $C_1$-$C_{10}$ alkyl, $C_2$-$C_{10}$ alkenyl, $C_2$-$C_{10}$ alkynyl, —OH, —O($C_1$-$C_{10}$ alkyl), —SH, —S($C_1$-$C_{10}$ alkyl), —SO—($C_1$-$C_{10}$ alkyl), —SO$_2$—($C_1$-$C_{10}$ alkyl), —CN, aryl, heteroaryl, cycloalkyl, and heterocycloalkyl, wherein said aryl, said heteroaryl, said cycloalkyl, and said heterocycloalkyl are each optionally substituted with one or more groups independently selected from $C_1$-$C_{10}$ alkyl, $C_2$-$C_{10}$ alkenyl, $C_2$-$C_{10}$ alkynyl, halogen, $C_1$-$C_{10}$ haloalkyl, —CN, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —NH$_2$, —NH($C_1$-$C_{10}$ alkyl), —N($C_1$-$C_{10}$ alkyl)($C_1$-$C_{10}$ alkyl), cycloalkyl, and heterocycloalkyl, and further wherein, if one or both of $R^2$ and $R^3$ is/are $C_1$-$C_{10}$ alkyl, $C_2$-$C_{10}$ alkenyl or $C_2$-$C_{10}$ alkynyl, then said alkyl, said alkenyl or said alkynyl is optionally substituted with one or more groups independently selected from halogen, $C_1$-$C_{10}$ haloalkyl, —CN, —OH, —O($C_1$-$C_{10}$ alkyl), —NH$_2$, —NH($C_1$-$C_{10}$ alkyl), —N($C_1$-$C_{10}$ alkyl)($C_1$-$C_{10}$ alkyl), cycloalkyl, and heterocycloalkyl; or $R^2$ and $R^3$ together form a divalent group selected from =O, =S, =NH and =N($C_1$-$C_{10}$ alkyl);

$R^4$ is selected from $C_1$-$C_{10}$ alkyl, $C_2$-$C_{10}$ alkenyl, $C_2$-$C_{10}$ alkynyl, cycloalkyl, and heterocycloalkyl, wherein said alkyl, said alkenyl and said alkynyl are each optionally substituted with one or more groups independently selected from halogen, $C_1$-$C_{10}$ haloalkyl, —O—($C_1$-$C_{10}$ haloalkyl), —CN, —OH, —O($C_1$-$C_{10}$ alkyl), and cycloalkyl, and further wherein, if $R^4$ is cycloalkyl or heterocycloalkyl, then said cycloalkyl or said heterocycloalkyl is optionally substituted with one or more groups independently selected from $C_1$-$C_{10}$ alkyl, $C_2$-$C_{10}$ alkenyl, $C_2$-$C_{10}$ alkynyl, halogen, $C_1$-$C_{10}$ haloalkyl, —CN, —OH, —O($C_1$-$C_{10}$ alkyl), and cycloalkyl;

each $R^5$ is independently a group -$L^5$-$R^{51}$;

each $L^5$ is independently selected from a bond, $C_1$-$C_{10}$ alkylene, $C_2$-$C_{10}$ alkenylene, and $C_2$-$C_{10}$ alkynylene, wherein said alkylene, said alkenylene and said alkynylene are each optionally substituted with one or more groups independently selected from halogen, $C_1$-$C_{10}$ haloalkyl, —CN, —OR$^{52}$, —NR$^{52}$R$^{52}$, —COR$^{52}$, —COOR$^{52}$, —OCOR$^{52}$, —CONR$^{52}$R$^{52}$, —NR$^{52}$COR$^{52}$, —SR$^{52}$, —SOR$^{52}$, —SO$_2$R$^{52}$, —SO$_2$NR$^{52}$R$^{52}$, and —NR$^{52}$SO$_2$R$^{52}$, and further wherein one or more —CH$_2$— units comprised in said alkylene, said alkenylene or said alkynylene are each optionally replaced by a group independently selected from —O—, —NR$^{52}$—, —CO—, —S—, —SO—, and —SO$_2$—;

each $R^{51}$ is independently selected from aryl, heteroaryl, cycloalkyl, heterocycloalkyl, cycloalkenyl, heterocycloalkenyl, halogen, $C_1$-$C_{10}$ haloalkyl, —CN, $C_1$-$C_{10}$ alkyl, $C_2$-$C_{10}$ alkenyl, $C_2$-$C_{10}$ alkynyl, —NR$^{52}$R$^{52}$, —OR$^{52}$, —SR$^{52}$, —SOR$^{52}$, —SO$_2$R$^{52}$, —COR$^{52}$, —COOR$^{52}$, —OCOR$^{52}$, —CONR$^{52}$R$^{52}$, —NR$^{52}$COR$^{52}$, —SO$_2$NR$^{52}$R$^{52}$, —NR$^{52}$SO$_2$R$^{52}$, and —SO$_3$R$^{52}$, wherein said aryl, said heteroaryl, said cycloalkyl, said heterocycloalkyl, said cycloalkenyl and said heterocycloalkenyl are each optionally substituted with one or more groups independently selected from halogen, $C_1$-$C_{10}$ haloalkyl, —CN, $C_1$-$C_{10}$ alkyl, $C_2$-$C_{10}$ alkenyl, $C_2$-$C_{10}$ alkynyl, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —NH$_2$, —NH($C_1$-$C_{10}$ alkyl), —N($C_1$-$C_{10}$ alkyl)($C_1$-$C_{10}$ alkyl), —CHO, —CO($C_1$-$C_{10}$ alkyl), —COOH, tetrazolyl, —COO($C_1$-$C_{10}$ alkyl), —OCO($C_1$-$C_{10}$ alkyl), —CO—NH$_2$, —CO—NH($C_1$-$C_{10}$ alkyl), —CO—N($C_1$-$C_{10}$ alkyl)($C_1$-$C_{10}$ alkyl), —NH—CO—($C_1$-$C_{10}$ alkyl), —N($C_1$-$C_{10}$ alkyl)-CO—($C_1$-$C_{10}$ alkyl), —SO$_2$—NH$_2$, —SO$_2$—NH($C_1$-$C_{10}$ alkyl), —SO$_2$—N($C_1$-$C_{10}$ alkyl)($C_1$-$C_{10}$ alkyl), —NH—SO$_2$—($C_1$-$C_{10}$ alkyl), —N($C_1$-$C_{10}$ alkyl)-SO$_2$—($C_1$-$C_{10}$ alkyl), cycloalkyl, heterocycloalkyl, aryl, heteroaryl, and -$L^{51}$-$R^{53}$, and further wherein, if $R^{51}$ is $C_1$-$C_{10}$ alkyl, $C_2$-$C_{10}$ alkenyl or $C_2$-$C_{10}$ alkynyl, then said alkyl, said alkenyl or said alkynyl is optionally substituted with one or more groups independently selected from halogen, $C_1$-$C_{10}$ haloalkyl, —CN, —OH, —O($C_1$-$C_{10}$ alkyl), —NH$_2$, —NH($C_1$-$C_{10}$ alkyl), —N($C_1$-$C_{10}$ alkyl)($C_1$-$C_{10}$ alkyl), —CHO, —CO($C_1$-$C_{10}$ alkyl), —COOH, tetrazolyl, —COO($C_1$-$C_{10}$ alkyl), —OCO($C_1$-$C_{10}$ alkyl), —CO—NH$_2$, —CO—NH($C_1$-$C_{10}$ alkyl), —CO—N($C_1$-$C_{10}$ alkyl)($C_1$-$C_{10}$ alkyl), —NH—CO—($C_1$-$C_{10}$ alkyl), —N($C_1$-$C_{10}$ alkyl)-CO—($C_1$-$C_{10}$ alkyl), —SO$_2$—NH$_2$, —SO$_2$—NH($C_1$-$C_{10}$ alkyl), —SO$_2$—N($C_1$-$C_{10}$ alkyl)($C_1$-$C_{10}$ alkyl), —NH—SO$_2$—($C_1$-$C_{10}$ alkyl), —N(C$_1$-C$_{10}$ alkyl)-SO$_2$—(C$_1$-C$_{10}$ alkyl), cycloalkyl, heterocycloalkyl, aryl, heteroaryl, and -L$^{51}$-R$^{53}$;

each R$^{52}$ is independently selected from hydrogen, C$_1$-C$_{10}$ alkyl, C$_2$-C$_{10}$ alkenyl, C$_2$-C$_{10}$ alkynyl, aryl, heteroaryl, cycloalkyl, and heterocycloalkyl, wherein said aryl, said heteroaryl, said cycloalkyl, and said heterocycloalkyl are each optionally substituted with one or more groups independently selected from C$_1$-C$_{10}$ alkyl, C$_2$-C$_{10}$ alkenyl, C$_2$-C$_{10}$ alkynyl, halogen, C$_1$-C$_{10}$ haloalkyl, —CN, —OH, —O(C$_1$-C$_{10}$ alkyl), —(C$_1$-C$_{10}$ alkylene)-OH, —(C$_1$-C$_{10}$ alkylene)-O(C$_1$-C$_{10}$ alkyl), —NH$_2$, —NH(C$_1$-C$_{10}$ alkyl), —N(C$_1$-C$_{10}$ alkyl)(C$_1$-C$_{10}$ alkyl), cycloalkyl, and heterocycloalkyl, wherein if R$^{52}$ is C$_1$-C$_{10}$ alkyl, C$_2$-C$_{10}$ alkenyl or C$_2$-C$_{10}$ alkynyl, then said alkyl, said alkenyl or said alkynyl is optionally substituted with one or more groups independently selected from halogen, C$_1$-C$_{10}$ haloalkyl, —CN, —OH, —O(C$_1$-C$_{10}$ alkyl), —NH$_2$, —NH(C$_1$-C$_{10}$ alkyl), —N(C$_1$-C$_{10}$ alkyl)(C$_1$-C$_{10}$ alkyl), cycloalkyl, and heterocycloalkyl, and further if two groups R$^{52}$ are attached to the same nitrogen atom, then these two groups R$^{52}$ may also together form a C$_2$-C$_8$ alkylene;

each L$^{51}$ is independently selected from a bond, C$_1$-C$_{10}$ alkylene, C$_2$-C$_{10}$ alkenylene, and C$_2$-C$_{10}$ alkynylene, wherein one or more —CH$_2$— units comprised in said alkylene, said alkenylene or said alkynylene are each optionally replaced by a group independently selected from —O—, —NH—, —N(C$_1$-C$_{10}$ alkyl)-, —CO—, —S—, —SO—, and —SO$_2$—;

each R$^{53}$ is independently selected from aryl, heteroaryl, cycloalkyl, heterocycloalkyl, cycloalkenyl, heterocycloalkenyl, halogen, C$_1$-C$_{10}$ haloalkyl, —CN, C$_1$-C$_{10}$ alkyl, C$_2$-C$_{10}$ alkenyl, C$_2$-C$_{10}$ alkynyl, —NH$_2$, —NH(C$_1$-C$_{10}$ alkyl), —N(C$_1$-C$_{10}$ alkyl)(C$_1$-C$_{10}$ alkyl), —OH, —O(C$_1$-C$_{10}$ alkyl), —(C$_1$-C$_{10}$ alkylene)-OH, —(C$_1$-C$_{10}$ alkylene)-O(C$_1$-C$_{10}$ alkyl), —SH, and —S(C$_1$-C$_{10}$ alkyl), wherein said aryl, said heteroaryl, said cycloalkyl, said heterocycloalkyl, said cycloalkenyl and said heterocycloalkenyl are each optionally substituted with one or more groups independently selected from halogen, C$_1$-C$_{10}$ haloalkyl, —CN, C$_1$-C$_{10}$ alkyl, C$_2$-C$_{10}$ alkenyl, C$_2$-C$_{10}$ alkynyl, —OH, —O(C$_1$-C$_{10}$ alkyl), —(C$_1$-C$_{10}$ alkylene)-OH, —(C$_1$-C$_{10}$ alkylene)-O(C$_1$-C$_{10}$ alkyl), —NH$_2$, —NH(C$_1$-C$_{10}$ alkyl), —N(C$_1$-C$_{10}$ alkyl)(C$_1$-C$_{10}$ alkyl), cycloalkyl, and heterocycloalkyl; and m is an integer of 0 to 3;

or a pharmaceutically acceptable salt, solvate or prodrug thereof, for use as a medicament.

2. A compound of the general formula (I):

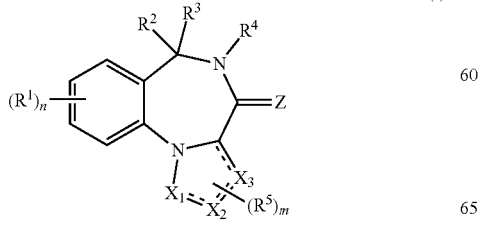

(I)

wherein:

X$_1$, X$_2$ and X$_3$ are each independently C or N;

each ===== is independently a single bond or a double bond, wherein at least one of any two adjacent bonds ===== is a single bond;

Z is O, S or N(—R$^Z$);

R$^Z$ is selected from hydrogen, C$_1$-C$_{10}$ alkyl, C$_2$-C$_{10}$ alkenyl, C$_2$-C$_{10}$ alkynyl, aryl, heteroaryl, cycloalkyl, and heterocycloalkyl, wherein said aryl, said heteroaryl, said cycloalkyl, and said heterocycloalkyl are each optionally substituted with one or more groups independently selected from C$_1$-C$_{10}$ alkyl, C$_2$-C$_{10}$ alkenyl, C$_2$-C$_{10}$ alkynyl, halogen, C$_1$-C$_{10}$ haloalkyl, —CN, —OH, —O(C$_1$-C$_{10}$ alkyl), —(C$_1$-C$_{10}$ alkylene)-OH, —(C$_1$-C$_{10}$ alkylene)-O(C$_1$-C$_{10}$ alkyl), —NH$_2$, —NH(C$_1$-C$_{10}$ alkyl), —N(C$_1$-C$_{10}$ alkyl)(C$_1$-C$_{10}$ alkyl), cycloalkyl, and heterocycloalkyl, and further wherein, if R$^Z$ is C$_1$-C$_{10}$ alkyl, C$_2$-C$_{10}$ alkenyl or C$_2$-C$_{10}$ alkynyl, then said alkyl, said alkenyl or said alkynyl is optionally substituted with one or more groups independently selected from halogen, C$_1$-C$_{10}$ haloalkyl, —CN, —OH, —O(C$_1$-C$_{10}$ alkyl), —NH$_2$, —NH(C$_1$-C$_{10}$ alkyl), —N(C$_1$-C$_{10}$ alkyl)(C$_1$-C$_{10}$ alkyl), cycloalkyl, and heterocycloalkyl;

each R$^1$ is independently a group -L$^1$-R$^{11}$;

each L$^1$ is independently selected from a bond, C$_1$-C$_{10}$ alkylene, C$_2$-C$_{10}$ alkenylene, and C$_2$-C$_{10}$ alkynylene, wherein said alkylene, said alkenylene and said alkynylene are each optionally substituted with one or more groups independently selected from halogen, C$_1$-C$_{10}$ haloalkyl, —CN, —OR$^{12}$, —NR$^{12}$R$^{12}$, —COR$^{12}$, —COOR$^{12}$, —OCOR$^{12}$, —CONR$^{12}$R$^{12}$, —NR$^{12}$COR$^{12}$, —SR$^{12}$, —SOR$^{12}$, —SO$_2$R$^{12}$, —SO$_2$NR$^{12}$R$^{12}$, and —NR$^{12}$SO$_2$R$^{12}$, and further wherein one or more —CH$_2$— units comprised in said alkylene, said alkenylene or said alkynylene are each optionally replaced by a group independently selected from —O—, —NR$^{12}$—, —CO—, —S—, —SO—, and —SO$_2$—;

each R$^{11}$ is independently selected from aryl, heteroaryl, cycloalkyl, heterocycloalkyl, cycloalkenyl, heterocycloalkenyl, halogen, C$_1$-C$_{10}$ haloalkyl, —CN, C$_1$-C$_{10}$ alkyl, C$_2$-C$_{10}$ alkenyl, C$_2$-C$_{10}$ alkynyl, —NR$^{12}$R$^{12}$, —OR$^{12}$, —SR$^{12}$, —SOR$^{12}$, —SO$_2$R$^{12}$, —COR$^{12}$, —COOR$^{12}$, —OCOR$^{12}$, —CONR$^{12}$R$^{12}$, —NR$^{12}$COR$^{12}$, —SO$_2$NR$^{12}$R$^{12}$, —NR$^{12}$SO$_2$R$^{12}$, and —SO$_3$R$^{12}$, wherein said aryl, said heteroaryl, said cycloalkyl, said heterocycloalkyl, said cycloalkenyl and said heterocycloalkenyl are each optionally substituted with one or more groups independently selected from halogen, C$_1$-C$_{10}$ haloalkyl, —CN, C$_1$-C$_{10}$ alkyl, C$_2$-C$_{10}$ alkenyl, C$_2$-C$_{10}$ alkynyl, —OH, —O(C$_1$-C$_{10}$ alkyl), —(C$_1$-C$_{10}$ alkylene)-OH, —(C$_1$-C$_{10}$ alkylene)-O(C$_1$-C$_{10}$ alkyl), —NH$_2$, —NH(C$_1$-C$_{10}$ alkyl), —N(C$_1$-C$_{10}$ alkyl)(C$_1$-C$_{10}$ alkyl), —CHO, —CO(C$_1$-C$_{10}$ alkyl), —COOH, tetrazolyl, —COO(C$_1$-C$_{10}$ alkyl), —OCO(C$_1$-C$_{10}$ alkyl), —CO—NH$_2$, —CO—NH(C$_1$-C$_{10}$ alkyl), —CO—N(C$_1$-C$_{10}$ alkyl)(C$_1$-C$_{10}$ alkyl), —NH—CO—(C$_1$-C$_{10}$ alkyl), —N(C$_1$-C$_{10}$ alkyl)-CO—(C$_1$-C$_{10}$ alkyl), —SO$_2$—NH$_2$, —SO$_2$—NH(C$_1$-C$_{10}$ alkyl), —SO$_2$—N(C$_1$-C$_{10}$ alkyl)(C$_1$-C$_{10}$ alkyl), —NH—SO$_2$—(C$_1$-C$_{10}$ alkyl), —N(C$_1$-C$_{10}$ alkyl)-SO$_2$—(C$_1$-C$_{10}$ alkyl), cycloalkyl, heterocycloalkyl, aryl, heteroaryl, and -L$^{11}$-R$^{13}$, and further wherein, if R$^{11}$ is C$_1$-C$_{10}$ alkyl, C$_2$-C$_{10}$ alkenyl or C$_2$-C$_{10}$ alkynyl, then said alkyl, said alkenyl or said alkynyl is optionally substituted with one or more groups independently selected from halogen, $C_1$-$C_{10}$ haloalkyl, —CN, —OH, —O($C_1$-$C_{10}$ alkyl), —NH$_2$, —NH($C_1$-$C_{10}$ alkyl), —N($C_1$-$C_{10}$ alkyl)($C_1$-$C_{10}$ alkyl), —CHO, —CO($C_1$-$C_{10}$ alkyl), —COOH, tetrazolyl, —COO($C_1$-$C_{10}$ alkyl), —OCO($C_1$-$C_{10}$ alkyl), —CO—NH$_2$, —CO—NH($C_1$-$C_{10}$ alkyl), —CO—N($C_1$-$C_{10}$ alkyl)($C_1$-$C_{10}$ alkyl), —NH—CO—($C_1$-$C_{10}$ alkyl), —N($C_1$-$C_{10}$ alkyl)-CO—($C_1$-$C_{10}$ alkyl), —SO$_2$—NH$_2$, —SO$_2$—NH($C_1$-$C_{10}$ alkyl), —SO$_2$—N($C_1$-$C_{10}$ alkyl)($C_1$-$C_{10}$ alkyl), —NH—SO$_2$—($C_1$-$C_{10}$ alkyl), —N($C_1$-$C_{10}$ alkyl)-SO$_2$—($C_1$-$C_{10}$ alkyl), cycloalkyl, heterocycloalkyl, aryl, heteroaryl, and -L$^{11}$-R$^{13}$;

each R$^{12}$ is independently selected from hydrogen, $C_1$-$C_{10}$ alkyl, $C_2$-$C_{10}$ alkenyl, $C_2$-$C_{10}$ alkynyl, aryl, heteroaryl, cycloalkyl, and heterocycloalkyl, wherein said aryl, said heteroaryl, said cycloalkyl, and said heterocycloalkyl are each optionally substituted with one or more groups independently selected from $C_1$-$C_{10}$ alkyl, $C_2$-$C_{10}$ alkenyl, $C_2$-$C_{10}$ alkynyl, halogen, $C_1$-$C_{10}$ haloalkyl, —CN, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —NH$_2$, —NH($C_1$-$C_{10}$ alkyl), —N($C_1$-$C_{10}$ alkyl)($C_1$-$C_{10}$ alkyl), cycloalkyl, and heterocycloalkyl, wherein if R$^{12}$ is $C_1$-$C_{10}$ alkyl, $C_2$-$C_{10}$ alkenyl or $C_2$-$C_{10}$ alkynyl, then said alkyl, said alkenyl or said alkynyl is optionally substituted with one or more groups independently selected from halogen, $C_1$-$C_{10}$ haloalkyl, —CN, —OH, —O($C_1$-$C_{10}$ alkyl), —NH$_2$, —NH($C_1$-$C_{10}$ alkyl), —N($C_1$-$C_{10}$ alkyl)($C_1$-$C_{10}$ alkyl), cycloalkyl, and heterocycloalkyl, and further if two groups R$^{12}$ are attached to the same nitrogen atom, then these two groups R$^{12}$ may also together form a $C_2$-$C_8$ alkylene;

each L$^{11}$ is independently selected from a bond, $C_1$-$C_{10}$ alkylene, $C_2$-$C_{10}$ alkenylene, and $C_2$-$C_{10}$ alkynylene, wherein one or more —CH$_2$— units comprised in said alkylene, said alkenylene or said alkynylene are each optionally replaced by a group independently selected from —O—, —NH—, —N($C_1$-$C_{10}$ alkyl)-, —CO—, —S—, —SO—, and —SO$_2$—;

each R$^{13}$ is independently selected from aryl, heteroaryl, cycloalkyl, heterocycloalkyl, cycloalkenyl, heterocycloalkenyl, halogen, $C_1$-$C_{10}$ haloalkyl, —CN, $C_1$-$C_{10}$ alkyl, $C_2$-$C_{10}$ alkenyl, $C_2$-$C_{10}$ alkynyl, —NH$_2$, —NH($C_1$-$C_{10}$ alkyl), —N($C_1$-$C_{10}$ alkyl)($C_1$-$C_{10}$ alkyl), —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —SH, and —S($C_1$-$C_{10}$ alkyl), wherein said aryl, said heteroaryl, said cycloalkyl, said heterocycloalkyl, said cycloalkenyl and said heterocycloalkenyl are each optionally substituted with one or more groups independently selected from halogen, $C_1$-$C_{10}$ haloalkyl, —CN, $C_1$-$C_{10}$ alkyl, $C_2$-$C_{10}$ alkenyl, $C_2$-$C_{10}$ alkynyl, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —NH$_2$, —NH($C_1$-$C_{10}$ alkyl), —N($C_1$-$C_{10}$ alkyl)($C_1$-$C_{10}$ alkyl), cycloalkyl, and heterocycloalkyl;

n is an integer of 0 to 4;

R$^2$ and R$^3$ are mutually linked to form, together with the carbon atom that they are attached to, a cycloalkyl or a heterocycloalkyl; or R$^2$ and R$^3$ are each independently selected from hydrogen, halogen, $C_1$-$C_{10}$ haloalkyl, $C_1$-$C_{10}$ alkyl, $C_2$-$C_{10}$ alkenyl, $C_2$-$C_{10}$ alkynyl, —OH, —O($C_1$-$C_{10}$ alkyl), —SH, —S($C_1$-$C_{10}$ alkyl), —SO—($C_1$-$C_{10}$ alkyl), —SO$_2$—($C_1$-$C_{10}$ alkyl), —CN, aryl, heteroaryl, cycloalkyl, and heterocycloalkyl, wherein said aryl, said heteroaryl, said cycloalkyl, and said heterocycloalkyl are each optionally substituted with one or more groups independently selected from $C_1$-$C_{10}$ alkyl, $C_2$-$C_{10}$ alkenyl, $C_2$-$C_{10}$ alkynyl, halogen, $C_1$-$C_{10}$ haloalkyl, —CN, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —NH$_2$, —NH($C_1$-$C_{10}$ alkyl), —N($C_1$-$C_{10}$ alkyl)($C_1$-$C_{10}$ alkyl), cycloalkyl, and heterocycloalkyl, and further wherein, if one or both of R$^2$ and R$^3$ is/are $C_1$-$C_{10}$ alkyl, $C_2$-$C_{10}$ alkenyl or $C_2$-$C_{10}$ alkynyl, then said alkyl, said alkenyl or said alkynyl is optionally substituted with one or more groups independently selected from halogen, $C_1$-$C_{10}$ haloalkyl, —CN, —OH, —O($C_1$-$C_{10}$ alkyl), —NH$_2$, —NH($C_1$-$C_{10}$ alkyl), —N($C_1$-$C_{10}$ alkyl)($C_1$-$C_{10}$ alkyl), cycloalkyl, and heterocycloalkyl; or R$^2$ and R$^3$ together form a divalent group selected from =O, =S, =NH and =N($C_1$-$C_{10}$ alkyl);

R$^4$ is selected from $C_1$-$C_{10}$ alkyl, $C_2$-$C_{10}$ alkenyl, $C_2$-$C_{10}$ alkynyl, cycloalkyl, and heterocycloalkyl, wherein said alkyl, said alkenyl and said alkynyl are each optionally substituted with one or more groups independently selected from halogen, $C_1$-$C_{10}$ haloalkyl, —O—($C_1$-$C_{10}$ haloalkyl), —CN, —OH, —O($C_1$-$C_{10}$ alkyl), and cycloalkyl, and further wherein, if R$^4$ is cycloalkyl or heterocycloalkyl, then said cycloalkyl or said heterocycloalkyl is optionally substituted with one or more groups independently selected from $C_1$-$C_{10}$ alkyl, $C_2$-$C_{10}$ alkenyl, $C_2$-$C_{10}$ alkynyl, halogen, $C_1$-$C_{10}$ haloalkyl, —CN, —OH, —O($C_1$-$C_{10}$ alkyl), and cycloalkyl;

each R$^5$ is independently a group -L$^5$-R$^{51}$;

each L$^5$ is independently selected from a bond, $C_1$-$C_{10}$ alkylene, $C_2$-$C_{10}$ alkenylene, and $C_2$-$C_{10}$ alkynylene, wherein said alkylene, said alkenylene and said alkynylene are each optionally substituted with one or more groups independently selected from halogen, $C_1$-$C_{10}$ haloalkyl, —CN, —OR$^{52}$, —NR$^{52}$R$^{52}$, —COR$^{52}$, —COOR$^{52}$, —OCOR$^{52}$, —CONR$^{52}$R$^{52}$, —NR$^{52}$COR$^{52}$, —SR$^{52}$, —SOR$^{52}$, —SO$_2$R$^{52}$, —SO$_2$NR$^{52}$R$^{52}$, and —NR$^{52}$SO$_2$R$^{52}$, and further wherein one or more —CH$_2$— units comprised in said alkylene, said alkenylene or said alkynylene are each optionally replaced by a group independently selected from —O—, —NR$^{52}$—, —CO—, —S—, —SO—, and —SO$_2$—;

each R$^{51}$ is independently selected from aryl, heteroaryl, cycloalkyl, heterocycloalkyl, cycloalkenyl, heterocycloalkenyl, halogen, $C_1$-$C_{10}$ haloalkyl, —CN, $C_1$-$C_{10}$ alkyl, $C_2$-$C_{10}$ alkenyl, $C_2$-$C_{10}$ alkynyl, —NR$^{52}$R$^{52}$, —OR$^{52}$, —SR$^{52}$, —SOR$^{52}$, —SO$_2$R$^{52}$, —COR$^{52}$, —COOR$^{52}$, —OCOR$^{52}$, —CONR$^{52}$R$^{52}$, —NR$^{52}$COR$^{52}$, —SO$_2$NR$^{52}$R$^{52}$, —NR$^{52}$SO$_2$R$^{52}$, and —SO$_3$R$^{52}$, wherein said aryl, said heteroaryl, said cycloalkyl, said heterocycloalkyl, said cycloalkenyl and said heterocycloalkenyl are each optionally substituted with one or more groups independently selected from halogen, $C_1$-$C_{10}$ haloalkyl, —CN, $C_1$-$C_{10}$ alkyl, $C_2$-$C_{10}$ alkenyl, $C_2$-$C_{10}$ alkynyl, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —NH$_2$, —NH($C_1$-$C_{10}$ alkyl), —N($C_1$-$C_{10}$ alkyl)($C_1$-$C_{10}$ alkyl), —CHO, —CO($C_1$-$C_{10}$ alkyl), —COOH, tetrazolyl, —COO($C_1$-$C_{10}$ alkyl), —OCO($C_1$-$C_{10}$ alkyl), —CO—$NH_2$, —CO—NH($C_1$-$C_{10}$ alkyl), —CO—N($C_1$-$C_{10}$ alkyl)($C_1$-$C_{10}$ alkyl), —NH—CO—($C_1$-$C_{10}$ alkyl), —N($C_1$-$C_{10}$ alkyl)-CO—($C_1$-$C_{10}$ alkyl), —$SO_2$—$NH_2$, —$SO_2$—NH($C_1$-$C_{10}$ alkyl), —$SO_2$—N($C_1$-$C_{10}$ alkyl)($C_1$-$C_{10}$ alkyl), —NH—$SO_2$—($C_1$-$C_{10}$ alkyl), —N($C_1$-$C_{10}$ alkyl)-$SO_2$—($C_1$-$C_{10}$ alkyl), cycloalkyl, heterocycloalkyl, aryl, heteroaryl, and -$L^{51}$-$R^{53}$, and further wherein, if $R^{51}$ is $C_1$-$C_{10}$ alkyl, $C_2$-$C_{10}$ alkenyl or $C_2$-$C_{10}$ alkynyl, then said alkyl, said alkenyl or said alkynyl is optionally substituted with one or more groups independently selected from halogen, $C_1$-$C_{10}$ haloalkyl, —CN, —OH, —O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), —CHO, —CO($C_1$-$C_{10}$ alkyl), —COOH, tetrazolyl, —COO($C_1$-$C_{10}$ alkyl), —OCO($C_1$-$C_{10}$ alkyl), —CO—$NH_2$, —CO—NH($C_1$-$C_{10}$ alkyl), —CO—N($C_1$-$C_{10}$ alkyl)($C_1$-$C_{10}$ alkyl), —NH—CO—($C_1$-$C_{10}$ alkyl), —N($C_1$-$C_{10}$ alkyl)-CO—($C_1$-$C_{10}$ alkyl), —$SO_2$—$NH_2$, —$SO_2$—NH($C_1$-$C_{10}$ alkyl), —$SO_2$—N($C_1$-$C_{10}$ alkyl)($C_1$-$C_{10}$ alkyl), —NH—$SO_2$—($C_1$-$C_{10}$ alkyl), —N($C_1$-$C_{10}$ alkyl)-$SO_2$—($C_1$-$C_{10}$ alkyl), cycloalkyl, heterocycloalkyl, aryl, heteroaryl, and -$L^{51}$-$R^{53}$;

each $R^{52}$ is independently selected from hydrogen, $C_1$-$C_{10}$ alkyl, $C_2$-$C_{10}$ alkenyl, $C_2$-$C_{10}$ alkynyl, aryl, heteroaryl, cycloalkyl, and heterocycloalkyl, wherein said aryl, said heteroaryl, said cycloalkyl, and said heterocycloalkyl are each optionally substituted with one or more groups independently selected from $C_1$-$C_{10}$ alkyl, $C_2$-$C_{10}$ alkenyl, $C_2$-$C_{10}$ alkynyl, halogen, $C_1$-$C_{10}$ haloalkyl, —CN, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), cycloalkyl, and heterocycloalkyl, wherein if $R^{52}$ is $C_1$-$C_{10}$ alkyl, $C_2$-$C_{10}$ alkenyl or $C_2$-$C_{10}$ alkynyl, then said alkyl, said alkenyl or said alkynyl is optionally substituted with one or more groups independently selected from halogen, $C_1$-$C_{10}$ haloalkyl, —CN, —OH, —O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), cycloalkyl, and heterocycloalkyl, and further if two groups $R^{52}$ are attached to the same nitrogen atom, then these two groups $R^{52}$ may also together form a $C_2$-$C_8$ alkylene;

each $L^{51}$ is independently selected from a bond, $C_1$-$C_{10}$ alkylene, $C_2$-$C_{10}$ alkenylene, and $C_2$-$C_{10}$ alkynylene, wherein one or more —$CH_2$— units comprised in said alkylene, said alkenylene or said alkynylene are each optionally replaced by a group independently selected from —O—, —NH—, —N($C_1$-$C_{10}$ alkyl)-, —CO—, —S—, —SO—, and —$SO_2$—;

each $R^{53}$ is independently selected from aryl, heteroaryl, cycloalkyl, heterocycloalkyl, cycloalkenyl, heterocycloalkenyl, halogen, $C_1$-$C_{10}$ haloalkyl, —CN, $C_1$-$C_{10}$ alkyl, $C_2$-$C_{10}$ alkenyl, $C_2$-$C_{10}$ alkynyl, —$NH_2$, —NH($C_1$-$C_{10}$ alkyl), —N($C_1$-$C_{10}$ alkyl)($C_1$-$C_{10}$ alkyl), —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —SH, and —S($C_1$-$C_{10}$ alkyl), wherein said aryl, said heteroaryl, said cycloalkyl, said heterocycloalkyl, said cycloalkenyl and said heterocycloalkenyl are each optionally substituted with one or more groups independently selected from halogen, $C_1$-$C_{10}$ haloalkyl, —CN, $C_1$-$C_{10}$ alkyl, $C_2$-$C_{10}$ alkenyl, $C_2$-$C_{10}$ alkynyl, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), cycloalkyl, and heterocycloalkyl; and m is an integer of 0 to 3;

or a pharmaceutically acceptable salt, solvate or prodrug thereof;

with the proviso that the following compounds are excluded from formula (I):

5-allyl-3,3a,5,6-tetrahydro-1H-benzo[f]pyrrolo-[1,2-a][1,4]diazepin-4(2H)-one;

5-butyl-3,3a,5,6-tetrahydro-1H-benzo[f]pyrrolo-[1,2-a][1,4]diazepin-4(2H)-one;

5-methyl-5,6-dihydro-benzo[f]pyrrolo[1,2-a][1,4]diazepin-4-one;

5-methyl-5,6-dihydro-3,5,10b-triaza-benzo[e]azulen-4-one;

5-methyl-4-oxo-5,6-dihydro-4H-1,2,5,10b-tetraaza-benzo[e]azulene-3-carboxylic acid ethyl ester;

5-methyl-4-oxo-5,6-dihydro-4H-1,2,5,10b-tetraaza-benzo[e]azulene-3-carboxylic acid methyl ester;

5-methyl-5,6-dihydro-1,5,10b-triaza-benzo[e]azulen-4-one;

9-fluoro-5-methyl-5,6-dihydro-1,5,10b-triaza-benzo[e]azulen-4-one;

8-methoxy-5-methyl-5,6-dihydro-1,5,10b-triaza-benzo[e]azulen-4-one;

3-bromo-5-methyl-5,6-dihydro-1,5,10b-triaza-benzo[e]azulen-4-one;

5-(4-chloro-butyl)-5,6-dihydro-benzo[f]pyrrolo[1,2-a][1,4]diazepin-4-one; and 5-(4-chloro-butyl)-benzo[f]pyrrolo[1,2-a][1,4]diazepine-4,6-dione.

3. The compound for use according to item 1 or the compound of item 2, wherein at least two of $X_1$, $X_2$ and $X_3$ are each C, and the other one of $X_1$, $X_2$ and $X_3$ is C or N.

4. The compound for use according to item 1 or 3 or the compound of item 2 or 3, wherein the fused 5-membered ring moiety containing $X_1$, $X_2$ and $X_3$ is selected from:

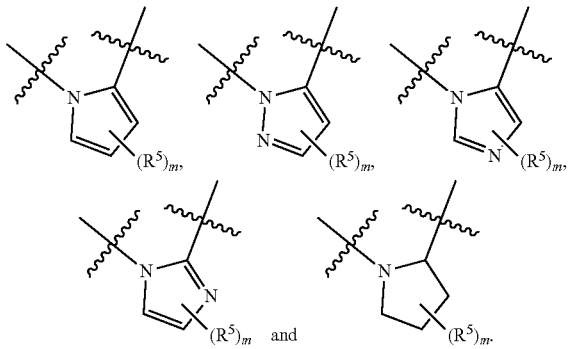

5. The compound for use according to item 1, 3 or 4 or the compound of any one of items 2 to 4, wherein the fused 5-membered ring moiety containing $X_1$, $X_2$ and $X_3$ is:

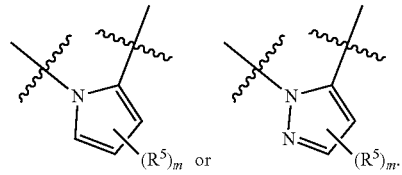

6. The compound for use according to any one of items 1 and 3 to 5 or the compound of any one of items 2 to 5, wherein Z is O.

7. The compound for use according to any one of items 1 and 3 to 6 or the compound of any one of items 2 to 6, wherein each $L^1$ is independently selected from a bond and $C_1$-$C_{10}$ alkylene, wherein said alkylene is optionally substituted with one or more groups independently selected from halogen, $C_1$-$C_4$ haloalkyl, —CN, —OH, —O($C_1$-$C_4$ alkyl), —NH$_2$, —NH($C_1$-$C_4$ alkyl), —N($C_1$-$C_4$ alkyl)($C_1$-$C_4$ alkyl), —SH, and —S($C_1$-$C_4$ alkyl), and further wherein one or two —CH$_2$— units comprised in said alkylene is/are each optionally replaced by a group independently selected from —O—, —NH—, —N($C_1$-$C_4$ alkyl)-, —CO—, and —SO$_2$—.

8. The compound for use according to any one of items 1 and 3 to 7 or the compound of any one of items 2 to 7, wherein each $L^1$ is independently selected from a bond and $C_1$-$C_4$ alkylene.

9. The compound for use according to any one of items 1 and 3 to 8 or the compound of any one of items 2 to 8, wherein each $R^{11}$ is independently selected from aryl, heteroaryl, cycloalkyl, heterocycloalkyl, cycloalkenyl, heterocycloalkenyl, halogen, $C_1$-$C_4$ haloalkyl, —CN, $C_1$-$C_4$ alkyl, —NH$_2$, —NH($C_1$-$C_4$ alkyl), —N($C_1$-$C_4$ alkyl)($C_1$-$C_4$ alkyl), —OH, and —O($C_1$-$C_4$ alkyl), wherein said aryl, said heteroaryl, said cycloalkyl, said heterocycloalkyl, said cycloalkenyl and said heterocycloalkenyl are each optionally substituted with one or more groups independently selected from halogen, $C_1$-$C_4$ haloalkyl, —CN, $C_1$-$C_4$ alkyl, —OH, —O($C_1$-$C_4$ alkyl), —($C_1$-$C_4$ alkylene)-OH, —($C_1$-$C_4$ alkylene)-O($C_1$-$C_4$ alkyl), —NH$_2$, —NH($C_1$-$C_4$ alkyl), —N($C_1$-$C_4$ alkyl)($C_1$-$C_4$ alkyl), —CHO, —CO($C_1$-$C_4$ alkyl), —COOH, tetrazolyl, —COO($C_1$-$C_4$ alkyl), —OCO($C_1$-$C_4$ alkyl), —CO—NH$_2$, —CO—NH($C_1$-$C_4$ alkyl), —CO—N($C_1$-$C_4$ alkyl)($C_1$-$C_4$ alkyl), —NH—CO—($C_1$-$C_4$ alkyl), —N($C_1$-$C_4$ alkyl)-CO—($C_1$-$C_4$ alkyl), —SO$_2$—NH($C_1$-$C_4$ alkyl), —SO$_2$—N($C_1$-$C_4$ alkyl)($C_1$-$C_4$ alkyl), —NH—SO$_2$—($C_1$-$C_4$ alkyl), —N($C_1$-$C_4$ alkyl)-SO$_2$—($C_1$-$C_4$ alkyl), cycloalkyl, heterocycloalkyl, aryl, and heteroaryl, and further wherein, if $R^{11}$ is $C_1$-$C_4$ alkyl, then said alkyl is optionally substituted with one or more groups independently selected from halogen, $C_1$-$C_4$ haloalkyl, —CN, —OH, —O($C_1$-$C_4$ alkyl), —NH$_2$, —NH($C_1$-$C_4$ alkyl), —N($C_1$-$C_4$ alkyl)($C_1$-$C_4$ alkyl), —CHO, —CO($C_1$-$C_4$ alkyl), —COOH, tetrazolyl, —COO($C_1$-$C_4$ alkyl), —OCO($C_1$-$C_4$ alkyl), —CO—NH$_2$, —CO—NH($C_1$-$C_4$ alkyl), —CO—N($C_1$-$C_4$ alkyl)($C_1$-$C_4$ alkyl), —NH—CO—($C_1$-$C_4$ alkyl), —N($C_1$-$C_4$ alkyl)-CO—($C_1$-$C_4$ alkyl), —SO$_2$—NH$_2$, —SO$_2$—NH($C_1$-$C_4$ alkyl), —SO$_2$—N($C_1$-$C_4$ alkyl)($C_1$-$C_4$ alkyl), —NH—SO$_2$—($C_1$-$C_4$ alkyl), —N($C_1$-$C_4$ alkyl)-SO$_2$—($C_1$-$C_4$ alkyl), cycloalkyl, heterocycloalkyl, aryl, and heteroaryl.

10. The compound for use according to any one of items 1 and 3 to 9 or the compound of any one of items 2 to 9, wherein each $R^{11}$ is independently selected from: phenyl; heteroaryl having 5 to 10 ring members, wherein 1, 2 or 3 ring members are heteroatoms selected independently from O, S and N, and the remaining ring members are carbon atoms; $C_3$-$C_7$ cycloalkyl; heterocycloalkyl having 5, 6 or 7 ring members, wherein 1, 2 or 3 ring members are heteroatoms selected independently from O, S and N, and the remaining ring members are carbon atoms; $C_5$-$C_7$ cycloalkenyl; and heterocycloalkenyl having 5, 6 or 7 ring members, wherein 1, 2 or 3 ring members are heteroatoms selected independently from O, S and N, and the remaining ring members are carbon atoms; wherein said phenyl, said heteroaryl, said cycloalkyl, said heterocycloalkyl, said cycloalkenyl and said heterocycloalkenyl are each optionally substituted with one or more groups independently selected from halogen, $C_1$-$C_4$ haloalkyl, —CN, $C_1$-$C_4$ alkyl, —OH, —O($C_1$-$C_4$ alkyl), —($C_1$-$C_4$ alkylene)-OH, —($C_1$-$C_4$ alkylene)-O($C_1$-$C_4$ alkyl), —NH$_2$, —NH($C_1$-$C_4$ alkyl), —N($C_1$-$C_4$ alkyl)($C_1$-$C_4$ alkyl), —CHO, —CO($C_1$-$C_4$ alkyl), —COOH, tetrazolyl, —COO($C_1$-$C_4$ alkyl), —SO$_2$—NH($C_1$-$C_4$ alkyl), —SO$_2$—N($C_1$-$C_4$ alkyl)($C_1$-$C_4$ alkyl), cycloalkyl, heterocycloalkyl, aryl, and heteroaryl.

11. The compound for use according to any one of items 1 and 3 to 10 or the compound of any one of items 2 to 10, wherein each $R^{11}$ is independently selected from phenyl, pyridinyl, and imidazo[1,2-a]pyridinyl, wherein said phenyl, said pyridinyl and said imidazo[1,2-a]pyridinyl are each optionally substituted with one or more groups independently selected from halogen, $C_1$-$C_4$ haloalkyl, —CN, $C_1$-$C_4$ alkyl, —OH, —O($C_1$-$C_4$ alkyl), —NH$_2$, —NH($C_1$-$C_4$ alkyl), —N($C_1$-$C_4$ alkyl)($C_1$-$C_4$ alkyl), and —COOH.

12. The compound for use according to any one of items 1 and 3 to 11 or the compound of any one of items 2 to 11, wherein each $R^{11}$ is independently pyridinyl, wherein said pyridinyl is optionally substituted with one or two groups independently selected from halogen, $C_1$-$C_4$ haloalkyl, —CN, $C_1$-$C_4$ alkyl, —OH, —O($C_1$-$C_4$ alkyl), —NH$_2$, —NH($C_1$-$C_4$ alkyl), —N($C_1$-$C_4$ alkyl)($C_1$-$C_4$ alkyl), and —COOH.

13. The compound for use according to any one of items 1 and 3 to 12 or the compound of any one of items 2 to 12, wherein n is 0, 1 or 2.

14. The compound for use according to any one of items 1 and 3 to 13 or the compound of any one of items 2 to 13, wherein n is 1.

15. The compound for use according to item 14 or the compound of item 14, wherein $R^1$ is attached to the tricyclic moiety comprised in formula (I) at position 8 or 9, preferably at position 9, wherein the numbering is as indicated in the following:

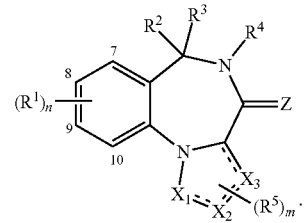

16. The compound for use according to any one of items 1 and 3 to 6 or the compound of any one of items 2 to 6, wherein n is 1, wherein $R^1$ is attached to position 9 of the tricyclic moiety comprised in formula (I), and wherein $R^1$ is selected from: phenyl; heteroaryl having 5 to 10 ring members, wherein 1, 2 or 3 ring members are heteroatoms selected independently from O, S and N, and the remaining ring members are carbon atoms; $C_3$-$C_7$ cycloalkyl; heterocycloalkyl having 5, 6 or 7 ring members, wherein 1, 2 or 3 ring members are heteroatoms selected independently from O, S and N, and the remaining ring members are carbon atoms; $C_5$-$C_7$ cycloalkenyl; and heterocycloalkenyl having 5, 6 or 7 ring members, wherein 1, 2 or 3 ring members are heteroatoms selected independently from O, S and N, and the remaining ring members are carbon atoms; wherein said phenyl, said heteroaryl, said cycloalkyl, said heterocycloalkyl, said cycloalkenyl and said heterocycloalkenyl are each optionally substituted with one or more groups independently selected from halogen, $C_1$-$C_4$ haloalkyl, —CN, $C_1$-$C_4$ alkyl, —OH, —O($C_1$-$C_4$ alkyl), —($C_1$-$C_4$ alkylene)-OH, —($C_1$-$C_4$ alkylene)-O($C_1$-$C_4$ alkyl), —NH$_2$, —NH($C_1$-$C_4$ alkyl), —N($C_1$-$C_4$ alkyl)($C_1$-$C_4$ alkyl), —CHO, —CO($C_1$-$C_4$ alkyl), —COOH, tetrazolyl, —COO($C_1$-$C_4$ alkyl), —SO$_2$—NH($C_1$-$C_4$ alkyl), —SO$_2$—N($C_1$-$C_4$ alkyl)($C_1$-$C_4$ alkyl), cycloalkyl, heterocycloalkyl, aryl, and heteroaryl.

17. The compound for use according to item 16 or the compound of item 16, wherein $R^1$ is selected from phenyl, pyridinyl, and imidazo[1,2-a]pyridinyl, wherein said phenyl, said pyridinyl and said imidazo[1,2-a]pyridinyl are each optionally substituted with one or more groups independently selected from halogen, $C_1$-$C_4$ haloalkyl, —CN, $C_1$-$C_4$ alkyl, —OH, —O($C_1$-$C_4$ alkyl), —NH$_2$, —NH($C_1$-$C_4$ alkyl), —N($C_1$-$C_4$ alkyl)($C_1$-$C_4$ alkyl), and —COOH.

18. The compound for use according to item 16 or 17 or the compound of item 16 or 17, wherein $R^1$ is pyridinyl, and wherein said pyridinyl is optionally substituted with one or two groups independently selected from halogen, $C_1$-$C_4$ haloalkyl, —CN, $C_1$-$C_4$ alkyl, —OH, —O($C_1$-$C_4$ alkyl), —NH$_2$, —NH($C_1$-$C_4$ alkyl), —N($C_1$-$C_4$ alkyl)($C_1$-$C_4$ alkyl), and —COOH.

19. The compound for use according to any one of items 16 to 18 or the compound of any one of items 16 to 18, wherein $R^1$ is pyridinyl which is substituted with one methyl or fluoro group.

20. The compound for use according to any one of items 1 and 3 to 19 or the compound of any one of items 2 to 19, wherein $R^2$ and $R^3$ are mutually linked to form, together with the carbon atom that they are attached to, a $C_3$-$C_5$ cycloalkyl, or $R^2$ and $R^3$ are each independently selected from hydrogen, halogen, $C_1$-$C_4$ alkyl, —OH, and —O($C_1$-$C_4$ alkyl).

21. The compound for use according to any one of items 1 and 3 to 20 or the compound of any one of items 2 to 20, wherein $R^2$ and $R^3$ are mutually linked to form, together with the carbon atom that they are attached to, a $C_3$-$C_5$ cycloalkyl.

22. The compound for use according to any one of items 1 and 3 to 21 or the compound of any one of items 2 to 21, wherein $R^2$ and $R^3$ are mutually linked to form, together with the carbon atom that they are attached to, a cyclopropyl.

23. The compound for use according to any one of items 1 and 3 to 22 or the compound of any one of items 2 to 22, wherein $R^4$ is $C_1$-$C_4$ alkyl, wherein said alkyl is optionally substituted with one or more groups independently selected from halogen, $C_1$-$C_4$ haloalkyl, —O—($C_1$-$C_4$ haloalkyl), —CN, —OH and —O($C_1$-$C_4$ alkyl).

24. The compound for use according to any one of items 1 and 3 to 23 or the compound of any one of items 2 to 23, wherein $R^4$ is methyl.

25. The compound for use according to any one of items 1 and 3 to 24 or the compound of any one of items 2 to 24, wherein each $L^5$ is independently selected from a bond and $C_1$-$C_{10}$ alkylene, wherein said alkylene is optionally substituted with one or more groups independently selected from halogen, $C_1$-$C_4$ haloalkyl, —CN, —OH, —O($C_1$-$C_4$ alkyl), —NH$_2$, —NH($C_1$-$C_4$ alkyl), —N($C_1$-$C_4$ alkyl)($C_1$-$C_4$ alkyl), —SH, and —S($C_1$-$C_4$ alkyl), and further wherein one or two —CH$_2$— units comprised in said alkylene is/are each optionally replaced by a group independently selected from —O—, —NH—, —N($C_1$-$C_4$ alkyl)-, —CO—, and —SO$_2$—.

26. The compound for use according to any one of items 1 and 3 to 25 or the compound of any one of items 2 to 25, wherein each $L^5$ is independently selected from a bond and $C_1$-$C_4$ alkylene.

27. The compound for use according to any one of items 1 and 3 to 26 or the compound of any one of items 2 to 26, wherein each $R^{51}$ is independently selected from aryl, heteroaryl, cycloalkyl, heterocycloalkyl, cycloalkenyl, heterocycloalkenyl, halogen, $C_1$-$C_4$ haloalkyl, —CN, $C_1$-$C_4$ alkyl, —NH$_2$, —NH($C_1$-$C_4$ alkyl), —N($C_1$-$C_4$ alkyl)($C_1$-$C_4$ alkyl), —OH, and —O($C_1$-$C_4$ alkyl), wherein said aryl, said heteroaryl, said cycloalkyl, said heterocycloalkyl, said cycloalkenyl and said heterocycloalkenyl are each optionally substituted with one or more groups independently selected from halogen, $C_1$-$C_4$ haloalkyl, —CN, $C_1$-$C_4$ alkyl, —OH, —O($C_1$-$C_4$ alkyl), —($C_1$-$C_4$ alkylene)-OH, —($C_1$-$C_4$ alkylene)-O($C_1$-$C_4$ alkyl), —NH$_2$, —NH($C_1$-$C_4$ alkyl), —N($C_1$-$C_4$ alkyl)($C_1$-$C_4$ alkyl), —CHO, —CO($C_1$-$C_4$ alkyl), —COOH, tetrazolyl, —COO($C_1$-$C_4$ alkyl), —OCO($C_1$-$C_4$ alkyl), —CO—NH$_2$, —CO—NH($C_1$-$C_4$ alkyl), —CO—N($C_1$-$C_4$ alkyl)($C_1$-$C_4$ alkyl), —NH—CO—($C_1$-$C_4$ alkyl), —N($C_1$-$C_4$ alkyl)-CO—($C_1$-$C_4$ alkyl), —SO$_2$—NH$_2$, —SO$_2$—NH($C_1$-$C_4$ alkyl), —SO$_2$—N($C_1$-$C_4$ alkyl)($C_1$-$C_4$ alkyl), —NH—SO$_2$—($C_1$-$C_4$ alkyl), —N($C_1$-$C_4$ alkyl)-SO$_2$—($C_1$-$C_4$ alkyl), cycloalkyl, heterocycloalkyl, aryl, and heteroaryl, and further wherein, if $R^{51}$ is $C_1$-$C_4$ alkyl, then said alkyl is optionally substituted with one or more groups independently selected from halogen, $C_1$-$C_4$ haloalkyl, —CN, —OH, —O($C_1$-$C_4$ alkyl), —NH$_2$, —NH($C_1$-$C_4$ alkyl), —N($C_1$-$C_4$ alkyl)($C_1$-$C_4$ alkyl), —CHO, —CO($C_1$-$C_4$ alkyl), —COOH, tetrazolyl, —COO($C_1$-$C_4$ alkyl), —OCO($C_1$-$C_4$ alkyl), —CO—NH$_2$, —CO—NH($C_1$-$C_4$ alkyl), —CO—N($C_1$-$C_4$ alkyl)($C_1$-$C_4$ alkyl), —NH—CO—($C_1$-$C_4$ alkyl), —N($C_1$-$C_4$ alkyl)-CO—($C_1$-$C_4$ alkyl), —SO$_2$—NH$_2$, —SO$_2$—NH($C_1$-$C_4$ alkyl), —SO$_2$—N($C_1$-$C_4$ alkyl)($C_1$-$C_4$ alkyl), —NH—SO$_2$—($C_1$-$C_4$ alkyl), —N($C_1$-$C_4$ alkyl)-SO$_2$—($C_1$-$C_4$ alkyl), cycloalkyl, heterocycloalkyl, aryl, and heteroaryl.

28. The compound for use according to any one of items 1 and 3 to 27 or the compound of any one of items 2 to 27, wherein each $R^{51}$ is independently selected from: phenyl; heteroaryl having 5 or 6 ring members, wherein 1, 2 or 3 ring members are heteroatoms selected independently from O, S and N, and the remaining ring members are carbon atoms; $C_1$-$C_4$ haloalkyl; $C_1$-$C_4$ alkyl; —NH$_2$; —NH($C_1$-$C_4$ alkyl); —N($C_1$-$C_4$ alkyl)($C_1$-$C_4$ alkyl); —OH; and —O($C_1$-$C_4$ alkyl); wherein said phenyl and said heteroaryl are each optionally substituted with one or more groups independently selected from halogen, $C_1$-$C_4$ haloalkyl, —CN, $C_1$-$C_4$ alkyl, —OH, —O($C_1$-$C_4$ alkyl), —NH$_2$, —NH($C_1$-$C_4$ alkyl), and —N($C_1$-$C_4$ alkyl)($C_1$-$C_4$ alkyl); and further wherein, if $R^{51}$ is $C_1$-$C_4$ alkyl, then said alkyl is optionally substituted with one or more groups independently selected from halogen, $C_1$-$C_4$ haloalkyl, —CN, —OH, —O($C_1$-$C_4$ alkyl), —NH$_2$, —NH($C_1$-$C_4$ alkyl), and —N($C_1$-$C_4$ alkyl)($C_1$-$C_4$ alkyl).

29. The compound for use according to any one of items 1 and 3 to 28 or the compound of any one of items 2 to 28, wherein $R^{51}$ is oxadiazolyl, wherein said oxadiazolyl is optionally substituted with one group selected from halogen, $C_1$-$C_4$ haloalkyl, —CN, $C_1$-$C_4$ alkyl, —OH, —O($C_1$-$C_4$ alkyl), —NH$_2$, —NH($C_1$-$C_4$ alkyl), and —N($C_1$-$C_4$ alkyl)($C_1$-$C_4$ alkyl).

30. The compound for use according to any one of items 1 and 3 to 24 or the compound of any one of items 2 to 24, wherein each $L^5$ is independently a bond or $C_1$-$C_4$ alkylene, and wherein each $R^{51}$ is independently selected from: phenyl; heteroaryl having 5 or 6 ring members, wherein 1, 2 or 3 ring members are heteroatoms selected independently from O, S and N, and the remaining ring members are carbon atoms; $C_1$-$C_4$ haloalkyl; $C_1$-$C_4$ alkyl; —NH$_2$; —NH($C_1$-$C_4$ alkyl); —N($C_1$-$C_4$ alkyl)($C_1$-$C_4$ alkyl); —OH; and —O($C_1$-$C_4$ alkyl); wherein said phenyl and said heteroaryl are each optionally substituted with one or more groups independently selected from halogen, $C_1$-$C_4$ haloalkyl, —CN, $C_1$-$C_4$ alkyl, —OH, —O($C_1$-$C_4$ alkyl), —NH$_2$, —NH($C_1$-$C_4$ alkyl), and —N($C_1$-$C_4$ alkyl)($C_1$-$C_4$ alkyl); and further wherein, if $R^{51}$ is $C_1$-$C_4$ alkyl, then said alkyl is optionally substituted with one or more groups independently selected from halogen, $C_1$-$C_4$ haloalkyl, —CN, —OH, —O($C_1$-$C_4$ alkyl), —NH$_2$, —NH($C_1$-$C_4$ alkyl), and —N($C_1$-$C_4$ alkyl)($C_1$-$C_4$ alkyl).

31. The compound for use according to any one of items 1, 3 to 24 and 30 or the compound of any one of items 2 to 24 and 30, wherein $L^5$ is a bond, and $R^{51}$ is oxadiazolyl, wherein said oxadiazolyl is optionally substituted with one group selected from halogen, $C_1$-$C_4$ haloalkyl, —CN, $C_1$-$C_4$ alkyl, —OH, —O($C_1$-$C_4$ alkyl), —NH$_2$, —NH($C_1$-$C_4$ alkyl), and —N($C_1$-$C_4$ alkyl)($C_1$-$C_4$ alkyl).

32. The compound for use according to any one of items 1 and 3 to 31 or the compound of any one of items 2 to 31, wherein m is 0 or 1.

33. The compound for use according to item 32 or the compound of item 32, wherein the group $R^5$, if present, is attached to the ring atom $X_2$ depicted in formula (I).

34. The compound for use according to any one of items 1 and 3 to 33 or the compound of any one of items 2 to 33, wherein m is 0.

35. The compound for use according to item 1 or the compound of item 2, wherein said compound is selected from:
9-Bromo-5-methyl-spiro[benzo[f]pyrrolo[1,2-a][1,4]diazepine-6,1'-cyclopropan]-4(5H)-one;
9-Bromo-5-methoxymethyl-spiro[benzo[f]pyrrolo[1,2-a][1,4]diazepine-6,1'-cyclopropan]-4(5H)-one;
9-Bromo-5-(methyl-d$_3$)-spiro[benzo[f]pyrrolo[1,2-a][1,4]diazepine-6,1'-cyclopropan]-4(5H)-one;
2,9-Dibromo-5-methyl-spiro[benzo[f]pyrrolo[1,2-a][1,4]diazepine-6,1'-cyclopropan]-4(5H)-one;
9-Bromo-2-chloro-5-methyl-spiro[benzo[f]pyrrolo[1,2-a][1,4]diazepine-6,1'-cyclopropan]-4(5H)-one;
9-Bromo-3-chloro-5-methyl-spiro[benzo[f]pyrrolo[1,2-a][1,4]diazepine-6,1'-cyclopropan]-4(5H)-one;
9-Bromo-7-fluoro-5-methyl-spiro[benzo[f]pyrrolo[1,2-a][1,4]diazepine-6,1'-cyclopropan]-4(5H)-one;
9-Bromo-10-fluoro-5-methyl-spiro[benzo[f]pyrrolo[1,2-a][1,4]diazepine-6,1'-cyclopropan]-4(5H)-one;
9-Bromo-8-fluoro-5-methyl-spiro[benzo[f]pyrrolo[1,2-a][1,4]diazepine-6,1'-cyclopropan]-4(5H)-one;
9-Bromo-2-phenyl-5-methyl-spiro[benzo[f]pyrrolo[1,2-a][1,4]diazepine-6,1'-cyclopropan]-4(5H)-one;
9-Bromo-5-methyl-2-phenyl-spiro[benzo[f]pyrazolo[1,5-a][1,4]diazepine-6,1'-cyclopropan]-4(5H)-one;
9-Bromo-6,6-spirocyclopropyl-5-methyl-2-phenyl-5,6-dihydro-3,5,10b-triaza-benzo[e]azulen-4-one;
8-Bromo-5-methyl-spiro[benzo[f]pyrrolo[1,2-a][1,4]diazepine-6,1'-cyclopropan]-4(5H)-one;
7-Bromo-5-methyl-spiro[benzo[f]pyrrolo[1,2-a][1,4]diazepine-6,1'-cyclopropan]-4(5H)-one;
10-Bromo-5-methyl-spiro[benzo[f]pyrrolo[1,2-a][1,4]diazepine-6,1'-cyclopropan]-4(5H)-one;
8-Bromo-5-methyl-2-phenyl-spiro[benzo[f]pyrrolo[1,2-a][1,4]diazepine-6,1'-cyclopropan]-4(5H)-one;
2-Bromo-5-methyl-9-(2-methyl-pyridin-3-yl)-spiro[benzo[f]pyrrolo[1,2-a][1,4]diazepine-6,1'-cyclopropan]-4(5H)-one;
2-Bromo-5-methyl-9-(6-methyl-pyridin-3-yl)-spiro[benzo[f]pyrrolo[1,2-a][1,4]diazepine-6,1'-cyclopropan]-4(5H)-one;
2-Bromo-5-methyl-9-(2-ethyl-pyridin-3-yl)-spiro[benzo[f]pyrrolo[1,2-a][1,4]diazepine-6,1'-cyclopropan]-4(5H)-one;
5-Methyl-9-(2-methyl-pyridin-3-yl)-spiro[benzo[f]pyrrolo[1,2-a][1,4]diazepine-6,1'-cyclopropan]-4(5H)-one;
5-Methoxymethyl-9-(2-methyl-pyridin-3-yl)-spiro[benzo[f]pyrrolo[1,2-a][1,4]diazepine-6,1'-cyclopropan]-4(5H)-one;
5-Methyl-9-(pyridin-4-yl)-spiro[benzo[f]pyrrolo[1,2-a][1,4]diazepine-6,1'-cyclopropan]-4(5H)-one;
5-Methyl-9-(pyridin-3-yl)-spiro[benzo[f]pyrrolo[1,2-a][1,4]diazepine-6,1'-cyclopropan]-4(5H)-one;
5-Methyl-9-(2-ethylpyridin-3-yl)-spiro[benzo[f]pyrrolo[1,2-a][1,4]diazepine-6,1'-cyclopropan]-4(5H)-one;
5-Methyl-9-(6-methylpyridin-3-yl)-spiro[benzo[f]pyrrolo[1,2-a][1,4]diazepine-6,1'-cyclopropan]-4(5H)-one;
5-Methyl-9-(2-methylpyridin-4-yl)-spiro[benzo[f]pyrrolo[1,2-a][1,4]diazepine-6,1'-cyclopropan]-4(5H)-one;
5-Methyl-9-(3,5-dimethyl-1H-pyrazol-4-yl)-spiro[benzo[f]pyrrolo[1,2-a][1,4]diazepine-6,1'-cyclopropan]-4(5H)-one;
5-Methyl-9-(3-trifluoromethyl-1H-pyrazol-4-yl)-spiro[benzo[f]pyrrolo[1,2-a][1,4]diazepine-6,1'-cyclopropan]-4(5H)-one;
5-Methyl-9-(1-methyl-pyrazol-4-yl)-spiro[benzo[f]pyrrolo[1,2-a][1,4]diazepine-6,1'-cyclopropan]-4(5H)-one;
5-Methyl-9-(1-methyl-pyrazol-5-yl)-spiro[benzo[f]pyrrolo[1,2-a][1,4]diazepine-6,1'-cyclopropan]-4(5H)-one;
5-Methyl-9-(6-fluoropyridin-3-yl)-spiro[benzo[f]pyrrolo[1,2-a][1,4]diazepine-6,1'-cyclopropan]-4(5H)-one;
5-Methyl-9-(6-fluoro-2-methylpyridin-3-yl)-spiro[benzo[f]pyrrolo[1,2-a][1,4]diazepine-6,1'-cyclopropan]-4(5H)-one;
5-Methyl-9-(2-fluoropyridin-3-yl)-spiro[benzo[f]pyrrolo[1,2-a][1,4]diazepine-6,1'-cyclopropan]-4(5H)-one;
5-Methyl-9-(2-fluoropyridin-4-yl)-spiro[benzo[f]pyrrolo[1,2-a][1,4]diazepine-6,1'-cyclopropan]-4(5H)-one;
5-Methyl-9-(2-trifluoromethylpyridin-4-yl)-spiro[benzo[f]pyrrolo[1,2-a][1,4]diazepine-6,1'-cyclopropan]-4(5H)-one;
5-Methyl-9-(2-trifluoromethylpyridin-3-yl)-spiro[benzo[f]pyrrolo[1,2-a][1,4]diazepine-6,1'-cyclopropan]-4(5H)-one;
5-Methyl-9-(4-trifluoromethylpyridin-3-yl)-spiro[benzo[f]pyrrolo[1,2-a][1,4]diazepine-6,1'-cyclopropan]-4(5H)-one;
5-Methyl-9-(3-methylpyridin-4-yl)-spiro[benzo[f]pyrrolo[1,2-a][1,4]diazepine-6,1'-cyclopropan]-4(5H)-one;
5-Methyl-9-(3,4-dimethoxy-phenyl)-spiro[benzo[f]pyrrolo[1,2-a][1,4]diazepine-6,1'-cyclopropan]-4(5H)-one;
5-Methyl-9-(6-amino-5-trifluoromethyl-pyridin-3-yl)-spiro[benzo[f]pyrrolo[1,2-a][1,4]diazepine-6,1'-cyclopropan]-4(5H)-one;
5-Methyl-9-(imidazo[1,2-a]pyridin-6-yl)-spiro[benzo[f]pyrrolo[1,2-a][1,4]diazepine-6,1'-cyclopropan]-4(5H)-one;

5-Methyl-9-(6-morpholin-4-yl-pyridin-3-yl)-spiro[benzo[f]pyrrolo[1,2-a][1,4]diazepine-6,1'-cyclopropan]-4(5H)-one;
5-Methyl-9-(3,4,5,6-tetrahydro-2H-[1,2']bipyridinyl-5'-yl)-spiro[benzo[f]pyrrolo[1,2-a][1,4]diazepine-6,1'-cyclopropan]-4(5H)-one;
5-Methyl-9-(3-cyanophenyl)-spiro[benzo[f]pyrrolo[1,2-a][1,4]diazepine-6,1'-cyclopropan]-4(5H)-one;
5-Methyl-9-(3-(1H-tetrazol-5-yl)-phenyl)-spiro[benzo[f]pyrrolo[1,2-a][1,4]diazepine-6,1'-cyclopropan]-4(5H)-one;
5-Methyl-9-(1,2,3,6-tetrahydro-pyridin-4-yl)-spiro[benzo[f]pyrrolo[1,2-a][1,4]diazepine-6,1'-cyclopropan]-4(5H)-one;
5-Methyl-9-(1-pyrimidin-4-yl-1,2,3,6-tetrahydro-pyridin-4-yl)-spiro[benzo[f]pyrrolo[1,2-a][1,4]diazepine-6,1'-cyclopropan]-4(5H)-one;
5-Methyl-9-(1-acetyl-1,2,3,6-tetrahydro-pyridin-4-yl)-spiro[benzo[f]pyrrolo[1,2-a][1,4]diazepine-6,1'-cyclopropan]-4(5H)-one;
5-Methyl-9-(4-methyl-oxazol-5-yl)-spiro[benzo[f]pyrrolo[1,2-a][1,4]diazepine-6,1'-cyclopropan]-4(5H)-one;
5-Methyl-9-(4-methylthiazol-5-yl)-spiro[benzo[f]pyrrolo[1,2-a][1,4]diazepine-6,1'-cyclopropan]-4(5H)-one;
5-Methyl-9-acetonitrile-spiro[benzo[f]pyrrolo[1,2-a][1,4]diazepine-6,1'-cyclopropan]-4(5H)-one;
5-Methyl-9-acrylonitrile-spiro[benzo[f]pyrrolo[1,2-a][1,4]diazepine-6,1'-cyclopropan]-4(5H)-one;
5-Methyl-9-propionitrile-spiro[benzo[f]pyrrolo[1,2-a][1,4]diazepine-6,1'-cyclopropan]-4(5H)-one;
5-Methyl-9-(6-chloropyridin-3-yl)-spiro[benzo[f]pyrrolo[1,2-a][1,4]diazepine-6,1'-cyclopropan]-4(5H)-one;
5-(Methyl-d$_3$)-9-(6-fluoropyridin-3-yl)-spiro[benzo[f]pyrrolo[1,2-a][1,4]diazepine-6,1'-cyclopropan]-4(5H)-one;
5-Methyl-9-(2,6-dimethylpyridin-3-yl)-spiro[benzo[f]pyrrolo[1,2-a][1,4]diazepine-6,1'-cyclopropan]-4(5H)-one;
5-Methyl-9-(4-fluoropyridin-2-yl)-spiro[benzo[f]pyrrolo[1,2-a][1,4]diazepine-6,1'-cyclopropan]-4(5H)-one;
5-Methyl-9-(3-methyl-pyrazin-2-yl)-5,6-spiro[benzo[f]pyrrolo[1,2-a][1,4]diazepine-6,1'-cyclopropan]-4(5H)-one;
5-Methyl-9-(4-methyl-pyrimidin-5-yl)-spiro[benzo[f]pyrrolo[1,2-a][1,4]diazepine-6,1'-cyclopropan]-4(5H)-one;
5-Methyl-9-(6-trifluoromethylpyridin-3-yl)-spiro[benzo[f]pyrrolo[1,2-a][1,4]diazepine-6,1'-cyclopropan]-4(5H)-one;
5-Methyl-9-(2-propylpyridin-3-yl)-spiro[benzo[f]pyrrolo[1,2-a][1,4]diazepine-6,1'-cyclopropan]-4(5H)-one;
5-Methyl-9-(2-cyclopropylpyridin-3-yl)-spiro[benzo[f]pyrrolo[1,2-a][1,4]diazepine-6,1'-cyclopropan]-4(5H)-one;
5-Methyl-9-(5-fluoropyridin-2-yl)-spiro[benzo[f]pyrrolo[1,2-a][1,4]diazepine-6,1'-cyclopropan]-4(5H)-one;
5-(Methyl-d$_3$)-9-(5-fluoropyridin-2-yl)-spiro[benzo[f]pyrrolo[1,2-a][1,4]diazepine-6,1'-cyclopropan]-4(5H)-one;
5-Methyl-9-(2,4-dimethylpyridin-3-yl)-spiro[benzo[f]pyrrolo[1,2-a][1,4]diazepine-6,1'-cyclopropan]-4(5H)-one;
5-Methyl-9-(3-fluoropyridin-2-yl)-spiro[benzo[f]pyrrolo[1,2-a][1,4]diazepine-6,1'-cyclopropan]-4(5H)-one;
5-Methyl-9-(6-fluoropyridin-2-yl)-spiro[benzo[f]pyrrolo[1,2-a][1,4]diazepine-6,1'-cyclopropan]-4(5H)-one;
5-Methyl-9-(2-hydroxypyridin-4-yl)-spiro[benzo[f]pyrrolo[1,2-a][1,4]diazepine-6,1'-cyclopropan]-4(5H)-one;
5-Methyl-9-(5-trifluoromethylpyridin-2-yl)-spiro[benzo[f]pyrrolo[1,2-a][1,4]diazepine-6,1'-cyclopropan]-4(5H)-one;
5-Methyl-9-(pyridazin-3-yl)-spiro[benzo[f]pyrrolo[1,2-a][1,4]diazepine-6,1'-cyclopropan]-4(5H)-one;
5-Methyl-9-(2-methoxycarbonylpyridin-3-yl)-spiro[benzo[f]pyrrolo[1,2-a][1,4]diazepine-6,1'-cyclopropan]-4(5H)-one;
5-Methyl-9-(2-(1-hydroxy-1-methyl-ethyl)-pyridin-3-yl)-spiro[benzo[f]pyrrolo[1,2-a][1,4]diazepine-6,1'-cyclopropan]-4(5H)-one;
7-Fluoro-5-methyl-9-(2-methyl-pyridin-3-yl)-spiro[benzo[f]pyrrolo[1,2-a][1,4]diazepine-6,1'-cyclopropan]-4(5H)-one;
7-Fluoro-5-methyl-9-(6-fluoro-pyridin-3-yl)-spiro[benzo[f]pyrrolo[1,2-a][1,4]diazepine-6,1'-cyclopropan]-4(5H)-one;
10-Fluoro-5-methyl-9-(2-methyl-pyridin-3-yl)-spiro[benzo[f]pyrrolo[1,2-a][1,4]diazepine-6,1'-cyclopropan]-4(5H)-one;
10-Fluoro-5-Methyl-9-(6-fluoro-pyridin-3-yl)-spiro[benzo[f]pyrrolo[1,2-a][1,4]diazepine-6,1'-cyclopropan]-4(5H)-one;
8-Fluoro-5-methyl-9-(2-methyl-pyridin-3-yl)-spiro[benzo[f]pyrrolo[1,2-a][1,4]diazepine-6,1'-cyclopropan]-4(5H)-one;
8-Fluoro-5-methyl-9-(6-fluoro-pyridin-3-yl)-spiro[benzo[f]pyrrolo[1,2-a][1,4]diazepine-6,1'-cyclopropan]-4(5H)-one;
9-Bromo-1-fluoro-5-methyl-spiro[benzo[f]pyrrolo[1,2-a][1,4]diazepine-6,1'-cyclopropan]-4(5H)-one;
9-Bromo-2-chloro-1-fluoro-5-methyl-spiro[benzo[f]pyrrolo[1,2-a][1,4]diazepine-6,1'-cyclopropan]-4(5H)-one;
9-(2-Methyl-pyridin-3-yl)-1-fluoro-5-methyl-spiro[benzo[f]pyrrolo[1,2-a][1,4]diazepine-6,1'-cyclopropan]-4(5H)-one;
9-(2-Methyl-pyridin-3-yl)-2-chloro-5-methyl-spiro[benzo[f]pyrrolo[1,2-a][1,4]diazepine-6,1'-cyclopropan]-4(5H)-one;
9-(2-Methyl-pyridin-3-yl)-2-chloro-1-fluoro-5-methyl-spiro[benzo[f]pyrrolo[1,2-a][1,4]diazepine-6,1'-cyclopropan]-4(5H)-one;
9-(2-Methyl-pyridin-3-yl)-3-chloro-5-methyl-spiro[benzo[f]pyrrolo[1,2-a][1,4]diazepine-6,1'-cyclopropan]-4(5H)-one;
1-Bromo-5-methyl-9-(5-fluoropyridin-2-yl)-spiro[benzo[f]pyrrolo[1,2-a][1,4]diazepine-6,1'-cyclopropan]-4(5H)-one;
5-Methyl-1-(2-methyl-2H-pyrazol-3-yl)9-(5-fluoropyridin-2-yl)-spiro[benzo[f]pyrrolo[1,2-a][1,4]diazepine-6,1'-cyclopropan]-4(5H)-one;
5,8-Dimethyl-spiro[benzo[f]pyrrolo[1,2-a][1,4]diazepine-6,1'-cyclopropan]-4(5H)-one;
8-Morpholin-4-yl-5-methyl-spiro[benzo[f]pyrrolo[1,2-a][1,4]diazepine-6,1'-cyclopropan]-4(5H)-one;
5,7-Dimethyl-spiro[benzo[f]pyrrolo[1,2-a][1,4]diazepine-6,1'-cyclopropan]-4(5H)-one;
5,10-Dimethyl-spiro[benzo[f]pyrrolo[1,2-a][1,4]diazepine-6,1'-cyclopropan]-4(5H)-one;
10-Cyano-5-methyl-spiro[benzo[f]pyrrolo[1,2-a][1,4]diazepine-6,1'-cyclopropan]-4(5H)-one;
10-(2-Methyl-pyridin-3-yl)-5-methyl-spiro[benzo[f]pyrrolo[1,2-a][1,4]diazepine-6,1'-cyclopropan]-4(5H)-one;
5-Methyl-2-phenyl-9-pyridin-3-yl-spiro[benzo[f]pyrrolo[1,2-a][1,4]diazepine-6,1'-cyclopropan]-4(5H)-one;
3-(5-methyl-4-oxo-2-phenyl-4,5-dihydrospiro[benzo[f]pyrrolo[1,2-a][1,4]diazepine-6,1'-cyclopropan]-9-yl)benzoic acid;
5-Methyl-2-phenyl-9-(2-methyl-pyridin-3-yl)-spiro[benzo[f]pyrrolo[1,2-a][1,4]diazepine-6,1'-cyclopropan]-4(5H)-one;

5-Methyl-2-phenyl-9-(6-amino-pyridin-3-yl)-spiro[benzo[f]pyrrolo[1,2-a][1,4]diazepine-6,1'-cyclopropan]-4(5H)-one;

5-Methyl-2-phenyl-9-(2,6-dimethyl-pyridin-4-yl)-spiro[benzo[f]pyrrolo[1,2-a][1,4]diazepine-6,1'-cyclopropan]-4(5H)-one;

5-Methyl-2-phenyl-9-(5-methyl-pyridin-3-yl)-spiro[benzo[f]pyrrolo[1,2-a][1,4]diazepine-6,1'-cyclopropan]-4(5H)-one;

5-Methyl-2-phenyl-9-(2-ethyl-pyridin-3-yl)-spiro[benzo[f]pyrrolo[1,2-a][1,4]diazepine-6,1'-cyclopropan]-4(5H)-one;

5-Methyl-2-phenyl-9-(2-trifluoromethyl-pyridin-3-yl)-spiro[benzo[f]pyrrolo[1,2-a][1,4]diazepine-6,1'-cyclopropan]-4(5H)-one;

5-Methyl-2-phenyl-9-(4-methyl-pyridin-3-yl)-spiro[benzo[f]pyrrolo[1,2-a][1,4]diazepine-6,1'-cyclopropan]-4(5H)-one;

5-Methyl-2-phenyl-9-(pyridin-4-yl)-spiro[benzo[f]pyrrolo[1,2-a][1,4]diazepine-6,1'-cyclopropan]-4(5H)-one;

5-Methyl-2-phenyl-9-(6-methyl-pyridin-3-yl)-spiro[benzo[f]pyrrolo[1,2-a][1,4]diazepine-6,1'-cyclopropan]-4(5H)-one;

5-Methyl-2-phenyl-9-(pyrimidin-5-yl)-spiro[benzo[f]pyrrolo[1,2-a][1,4]diazepine-6,1'-cyclopropan]-4(5H)-one;

5-Methyl-2-phenyl-9-(2-methyl-pyridin-4-yl)-spiro[benzo[f]pyrrolo[1,2-a][1,4]diazepine-6,1'-cyclopropan]-4(5H)-one;

5-Methyl-2-phenyl-9-(6-fluoro-pyridin-3-yl)-spiro[benzo[f]pyrrolo[1,2-a][1,4]diazepine-6,1'-cyclopropan]-4(5H)-one;

5-Methyl-2-phenyl-9-(2,6-dimethyl-pyridin-3-yl)-spiro[benzo[f]pyrrolo[1,2-a][1,4]diazepine-6,1'-cyclopropan]-4(5H)-one;

5-Methyl-2-phenyl-9-pyrazin-2-yl-spiro[benzo[f]pyrrolo[1,2-a][1,4]diazepine-6,1'-cyclopropan]-4(5H)-one;

5-Methyl-2-phenyl-9-pyridazin-3-yl-spiro[benzo[f]pyrrolo[1,2-a][1,4]diazepine-6,1'-cyclopropan]-4(5H)-one;

5-Methyl-2-phenyl-9-(5-fluoro-pyridin-2-yl)-spiro[benzo[f]pyrrolo[1,2-a][1,4]diazepine-6,1'-cyclopropan]-4(5H)-one;

5-Methyl-2-phenyl-9-(pyridin-2-yl)-spiro[benzo[f]pyrrolo[1,2-a][1,4]diazepine-6,1'-cyclopropan]-4(5H)-one;

5-methyl-2-phenyl-9-(6-ethylpyridin-3-yl)-spiro[benzo[f]pyrrolo[1,2-a][1,4]diazepine-6,1'-cyclopropan]-4(5H)-one;

5-Methyl-2-phenyl-9-(2-fluoro-pyridin-3-yl)-spiro[benzo[f]pyrrolo[1,2-a][1,4]diazepine-6,1'-cyclopropan]-4(5H)-one;

5-Methyl-2-phenyl-9-(6-dimethylamino-pyridin-3-yl)-spiro[benzo[f]pyrrolo[1,2-a][1,4]diazepine-6,1'-cyclopropan]-4(5H)-one;

9-Dimethylamino-5-methyl-2-phenyl-spiro[benzo[f]pyrrolo[1,2-a][1,4]diazepine-6,1'-cyclopropan]-4(5H)-one;

5-Methyl-2-phenyl-9-(2-methoxy-pyridin-3-yl)-spiro[benzo[f]pyrrolo[1,2-a][1,4]diazepine-6,1'-cyclopropan]-4(5H)-one;

5-Methyl-2-phenyl-9-(6-cyano-pyridin-3-yl)-spiro[benzo[f]pyrrolo[1,2-a][1,4]diazepine-6,1'-cyclopropan]-4(5H)-one;

5-Methyl-2-phenyl-9-(6-methylamino-pyridin-3-yl)-spiro[benzo[f]pyrrolo[1,2-a][1,4]diazepine-6,1'-cyclopropan]-4(5H)-one;

5-Methyl-2-phenyl-9-(2-dimethylamino-pyridin-3-yl)-spiro[benzo[f]pyrrolo[1,2-a][1,4]diazepine-6,1'-cyclopropan]-4(5H)-one;

8-Morpholin-4-yl-5-methyl-2-phenyl-spiro[benzo[f]pyrrolo[1,2-a][1,4]diazepine-6,1'-cyclopropan]-4(5H)-one;

9-(2,6-Dimethyl-pyridin-4-yl)-5-methyl-2-phenyl-spiro[benzo[f]pyrazolo[1,5-a][1,4]diazepine-6,1'-cyclopropan]-4(5H)-one;

9-(2-Methyl-pyridin-4-yl)-5-methyl-2-phenyl-spiro[benzo[f]pyrazolo[1,5-a][1,4]diazepine-6,1'-cyclopropan]-4(5H)-one;

2,9-Diphenyl-5-methyl-2-spiro[benzo[f]pyrazolo[1,5-a][1,4]diazepine-6,1'-cyclopropan]-4(5H)-one;

9-(4-Amino-phenyl)-5-methyl-2-phenyl-spiro[benzo[f]pyrazolo[1,5-a][1,4]diazepine-6,1'-cyclopropan]-4(5H)-one;

9-(2-Methyl-pyridin-3-yl)-5-methyl-2-phenyl-spiro[benzo[f]pyrazolo[1,5-a][1,4]diazepine-6,1'-cyclopropan]-4(5H)-one;

9-(2,6-Dimethyl-pyridin-3-yl)-5-methyl-2-phenyl-spiro[benzo[f]pyrazolo[1,5-a][1,4]diazepine-6,1'-cyclopropan]-4(5H)-one;

9-(6-Amino-pyridin-3-yl)-5-methyl-2-phenyl-spiro[benzo[f]pyrazolo[1,5-a][1,4]diazepine-6,1'-cyclopropan]-4(5H)-one;

9-(4-Methoxy-phenyl)-5-methyl-2-phenyl-spiro[benzo[f]pyrazolo[1,5-a][1,4]diazepine-6,1'-cyclopropan]-4(5H)-one;

9-(3-Cyano-phenyl)-5-methyl-2-phenyl-spiro[benzo[f]pyrazolo[1,5-a][1,4]diazepine-6,1'-cyclopropan]-4(5H)-one;

9-(3-Chloro-phenyl)-5-methyl-2-phenyl-spiro[benzo[f]pyrazolo[1,5-a][1,4]diazepine-6,1'-cyclopropan]-4(5H)-one;

9-(2-Chloro-phenyl)-5-methyl-2-phenyl-spiro[benzo[f]pyrazolo[1,5-a][1,4]diazepine-6,1'-cyclopropan]-4(5H)-one;

9-(Oxazol-5-yl)-5-methyl-2-phenyl-spiro[benzo[f]pyrazolo[1,5-a][1,4]diazepine-6,1'-cyclopropan]-4(5H)-one;

3-(5-methyl-4-oxo-2-phenyl-4,5-dihydrospiro[benzo[f]pyrazolo[1,5-a][1,4]diazepine-6,1'-cyclopropan]-9-yl)benzoic acid;

9-(1H-pyrazol-4-yl)-5-methyl-2-phenyl-spiro[benzo[f]pyrazolo[1,5-a][1,4]diazepine-6,1'-cyclopropan]-4(5H)-one;

9-(4-Chloro-phenyl)-5-methyl-2-phenyl-spiro[benzo[f]pyrazolo[1,5-a][1,4]diazepine-6,1'-cyclopropan]-4(5H)-one;

9-(1H-pyrazol-3-yl)-5-methyl-2-phenyl-spiro[benzo[f]pyrazolo[1,5-a][1,4]diazepine-6,1'-cyclopropan]-4(5H)-one;

9-Cyano-5-methyl-2-phenyl-spiro[benzo[f]pyrazolo[1,5-a][1,4]diazepine-6,1'-cyclopropan]-4(5H)-one;

5-Methyl-2-phenyl-spiro[benzo[f]pyrazolo[1,5-a][1,4]diazepine-6,1'-cyclopropan]-4(5H)-one;

5-Methyl-2-phenyl-9-(pyrrolidin-1-yl)-spiro[benzo[f]pyrazolo[1,5-a][1,4]diazepine-6,1'-cyclopropan]-4(5H)-one;

9-(2-Methyl-pyridin-3-yl)-5-methyl-2-phenyl-spiro[benzo[f]imidazo[1,2-a][1,4]diazepine-6,1'-cyclopropan]-4(5H)-one;

N,N-dimethyl-3-(5-methyl-4-oxo-2-phenyl-4,5-dihydrospiro[benzo[f]pyrrolo[1,2-a][1,4]diazepine-6,1'-cyclopropan]-9-yl)benzenesulfonamide;

N,N-dimethyl-3-(5-methyl-4-oxo-2-phenyl-4,5-dihydrospiro[benzo[f]pyrazolo[1,5-a][1,4]diazepine-6,1'-cyclopropan]-9-yl)benzenesulfonamide;

5-Methyl-2-(pyridine-3-yl)-9-(2-methyl-pyridin-3-yl)-spiro[benzo[f]pyrazolo[1,5-a][1,4]diazepine-6,1'-cyclopropan]-4(5H)-one;

2,5-Dimethyl-9-(2-methyl-pyridin-3-yl)-spiro[benzo[f]pyrazolo[1,5-a][1,4]diazepine-6,1'-cyclopropan]-4(5H)-one;

5-Methyl-2-(pyridine-4-yl)-9-(2-methyl-pyridin-3-yl)-spiro[benzo[f]pyrazolo[1,5-a][1,4]diazepine-6,1'-cyclopropan]-4(5H)-one;

5-Methyl-2-(1H-pyrazol-3-yl)-9-(2-methyl-pyridin-3-yl)-spiro[benzo[f]pyrazolo[1,5-a][1,4]diazepine-6,1'-cyclopropan]-4(5H)-one;

5-Methyl-2-(2-chlorophenyl)-9-(2-methyl-pyridin-3-yl)-spiro[benzo[f]pyrazolo[1,5-a][1,4]diazepine-6,1'-cyclopropan]-4(5H)-one;

5-Methyl-2-(3-chlorophenyl)-9-(2-methyl-pyridin-3-yl)-spiro[benzo[f]pyrazolo[1,5-a][1,4]diazepine-6,1'-cyclopropan]-4(5H)-one;

5-Methyl-2-(4-chlorophenyl)-9-(2-methyl-pyridin-3-yl)-spiro[benzo[f]pyrazolo[1,5-a][1,4]diazepine-6,1'-cyclopropan]-4(5H)-one;

5-Methyl-2-(4-fluorophenyl)-9-(2-methyl-pyridin-3-yl)-spiro[benzo[f]pyrazolo[1,5-a][1,4]diazepine-6,1'-cyclopropan]-4(5H)-one;

5-Methyl-2-(2-fluorophenyl)-9-(2-methyl-pyridin-3-yl)-spiro[benzo[f]pyrazolo[1,5-a][1,4]diazepine-6,1'-cyclopropan]-4(5H)-one;

5-Methyl-2-(3-fluorophenyl)-9-(2-methyl-pyridin-3-yl)-spiro[benzo[f]pyrazolo[1,5-a][1,4]diazepine-6,1'-cyclopropan]-4(5H)-one;

5-Methyl-2-cyano-9-(2-methyl-pyridin-3-yl)-spiro[benzo[f]pyrazolo[1,5-a][1,4]diazepine-6,1'-cyclopropan]-4(5H)-one;

5-Methyl-2-dimethylamino-9-(2-methyl-pyridin-3-yl)-spiro[benzo[f]pyrazolo[1,5-a][1,4]diazepine-6,1'-cyclopropan]-4(5H)-one;

5-Methyl-2-cyclopropyl-9-(2-methyl-pyridin-3-yl)-spiro[benzo[f]pyrazolo[1,5-a][1,4]diazepine-6,1'-cyclopropan]-4(5H)-one;

5-Methyl-2-cyclopentyl-9-(2-methyl-pyridin-3-yl)-spiro[benzo[f]pyrazolo[1,5-a][1,4]diazepine-6,1'-cyclopropan]-4(5H)-one;

5-Methyl-2-(thiazol-2-yl)-9-(2-methyl-pyridin-3-yl)-spiro[benzo[f]pyrazolo[1,5-a][1,4]diazepine-6,1'-cyclopropan]-4(5H)-one;

5-Methyl-2-(thiazol-2-yl)-9-(6-methyl-pyridin-3-yl)-spiro[benzo[f]pyrazolo[1,5-a][1,4]diazepine-6,1'-cyclopropan]-4(5H)-one;

5-Methyl-2-(2-methyl-2H-pyrazol-3-yl)-9-(6-methyl-pyridin-3-yl)-spiro[benzo[f]pyrazolo[1,5-a][1,4]diazepine-6,1'-cyclopropan]-4(5H)-one;

5-Methyl-2-(2-methyl-2H-pyrazol-3-yl)-9-(2-methyl-pyridin-3-yl)-spiro[benzo[f]pyrazolo[1,5-a][1,4]diazepine-6,1'-cyclopropan]-4(5H)-one;

5-Methyl-2-dimethylamino-9-(6-methyl-pyridin-3-yl)-spiro[benzo[f]pyrazolo[1,5-a][1,4]diazepine-6,1'-cyclopropan]-4(5H)-one;

5-Methyl-2-(2-fluorophenyl)-9-(2-ethyl-pyridin-3-yl)-spiro[benzo[f]pyrazolo[1,5-a][1,4]diazepine-6,1'-cyclopropan]-4(5H)-one;

5-Methyl-2-(2-methyl-2H-pyrazol-3-yl)-9-(2-ethyl-pyridin-3-yl)-spiro[benzo[f]pyrazolo[1,5-a][1,4]diazepine-6,1'-cyclopropan]-4(5H)-one;

9-Bromo-5-methyl-2-phenyl-5,6-dihydro-benzo[f]pyrrolo[1,2-a][1,4]diazepin-4-one;

9-(6-Amino-pyridin-3-yl)-5-methyl-2-phenyl-5,6-dihydro-benzo[f]pyrrolo[1,2-a][1,4]diazepin-4-one;

5-Methyl-9-(2-methylpyridin-3-yl)-2-phenyl-5,6-dihydro-4H-benzo[f]imidazo[1,2-a][1,4]diazepin-4-one;

5-Ethyl-9-(2-methylpyridin-3-yl)-2-phenyl-5,6-dihydro-4H-benzo[f]imidazo[1,2-a][1,4]diazepin-4-one;

5-Methyl-9-(2-methylpyridin-3-yl)-4-oxo-4,5-dihydrospiro[benzo[f]pyrrolo[1,2-a][1,4]diazepine-6,1'-cyclopropane]-2-carbaldehyde;

5-Methyl-9-(2-ethyl-pyridin-3-yl)-4-oxo-4,5-dihydrospiro[benzo[f]pyrrolo[1,2-a][1,4]diazepine-6,1'-cyclopropane]-2-carbaldehyde;

5-Methyl-9-(6-methyl-pyridin-3-yl)-4-oxo-4,5-dihydrospiro[benzo[f]pyrrolo[1,2-a][1,4]diazepine-6,1'-cyclopropane]-2-carbaldehyde;

5-Methyl-9-(6-fluoro-pyridin-3-yl)-4-oxo-4,5-dihydrospiro[benzo[f]pyrrolo[1,2-a][1,4]diazepine-6,1'-cyclopropane]-2-carbaldehyde;

5-(Methyl-$d_3$)-9-(6-fluoro-pyridin-3-yl)-4-oxo-4,5-dihydrospiro[benzo[f]pyrrolo[1,2-a][1,4]diazepine-6,1'-cyclopropane]-2-carbaldehyde;

5-Methyl-9-bromo-4-oxo-4,5-dihydrospiro[benzo[f]pyrrolo[1,2-a][1,4]diazepine-6,1'-cyclopropane]-2-carbaldehyde;

5-Methyl-9-(3-cyanophenyl)-4-oxo-4,5-dihydrospiro[benzo[f]pyrrolo[1,2-a][1,4]diazepine-6,1'-cyclopropane]-2-carbaldehyde;

5-Methyl-9-(pyridazin-3-yl)-4-oxo-4,5-dihydrospiro[benzo[f]pyrrolo[1,2-a][1,4]diazepine-6,1'-cyclopropane]-2-carbaldehyde;

5-Methyl-9-(2-methylpyridin-3-yl)-4-oxo-4,5-dihydrospiro[benzo[f]pyrrolo[1,2-a][1,4]diazepine-6,1'-cyclopropane]-2-carboxylic acid;

5-Methyl-9-(6-fluoro-pyridin-3-yl)-4-oxo-4,5-dihydrospiro[benzo[f]pyrrolo[1,2-a][1,4]diazepine-6,1'-cyclopropane]-2-carboxylic acid;

5-(Methyl-$d_3$)-9-(6-fluoro-pyridin-3-yl)-4-oxo-4,5-dihydrospiro[benzo[f]pyrrolo[1,2-a][1,4]diazepine-6,1'-cyclopropane]-2-carboxylic acid;

5-Methyl-9-bromo-4-oxo-4,5-dihydrospiro[benzo[f]pyrrolo[1,2-a][1,4]diazepine-6,1'-cyclopropane]-2-carboxylic acid;

5-Methyl-9-(pyridazin-3-yl)-4-oxo-4,5-dihydrospiro[benzo[f]pyrrolo[1,2-a][1,4]diazepine-6,1'-cyclopropane]-2-carboxylic acid;

5-Methyl-9-(3-cyanophenyl)-4-oxo-4,5-dihydrospiro[benzo[f]pyrrolo[1,2-a][1,4]diazepine-6,1'-cyclopropane]-2-carboxylic acid;

5-Methyl-9-(2-methyl-pyridin-3-yl)-2-(oxazol-5-yl)-spiro[benzo[f]pyrazolo[1,5-a][1,4]diazepine-6,1'-cyclopropan]-4(5H)-one;

5-Methyl-9-(2-methyl-pyridin-3-yl)-2-(3H-imidazol-4-yl)-spiro[benzo[f]pyrazolo[1,5-a][1,4]diazepine-6,1'-cyclopropan]-4(5H)-one;

5-Methyl-9-(2-methyl-pyridin-3-yl)-2-(1H-imidazol-2-yl)-spiro[benzo[f]pyrazolo[1,5-a][1,4]diazepine-6,1'-cyclopropan]-4(5H)-one;

5-Methyl-9-(2-methyl-pyridin-3-yl)-2-[1,3,4]oxadiazol-2-yl-spiro[benzo[f]pyrazolo[1,5-a][1,4]diazepine-6,1'-cyclopropan]-4(5H)-one;

5-Methyl-9-(6-fluoro-pyridin-3-yl)-2-(1H-imidazol-2-yl)-spiro[benzo[f]pyrazolo[1,5-a][1,4]diazepine-6,1'-cyclopropan]-4(5H)-one;

5-Methyl-9-(6-fluoro-pyridin-3-yl)-2-[1,3,4]oxadiazol-2-yl-spiro[benzo[f]pyrazolo[1,5-a][1,4]diazepine-6,1'-cyclopropan]-4(5H)-one;

5-(Methyl-$d_3$)-9-(6-fluoro-pyridin-3-yl)-2-[1,3,4]oxadiazol-2-yl-spiro[benzo[f]pyrazolo[1,5-a][1,4]diazepine-6,1'-cyclopropan]-4(5H)-one;

5-Methyl-9-bromo-2-[1,3,4]oxadiazol-2-yl-spiro[benzo[f]pyrazolo[1,5-a][1,4]diazepine-6,1'-cyclopropan]-4(5H)-one;

5-Methyl-9-(6-dimethylamino-pyridin-3-yl)-2-[1,3,4]oxadiazol-2-yl-spiro[benzo[f]pyrazolo[1,5-a][1,4]diazepine-6,1'-cyclopropan]-4(5H)-one;

5-Methyl-9-(6-chloro-pyridin-3-yl)-2-[1,3,4]oxadiazol-2-yl-spiro[benzo[f]pyrazolo[1,5-a][1,4]diazepine-6,1'-cyclopropan]-4(5H)-one;

5-Methyl-9-(3-cyanophenyl)-2-[1,3,4]oxadiazol-2-yl-spiro[benzo[f]pyrazolo[1,5-a][1,4]diazepine-6,1'-cyclopropan]-4(5H)-one;

5-Methyl-9-(pyridazin-3-yl)-2-[1,3,4]oxadiazol-2-yl-spiro[benzo[f]pyrazolo[1,5-a][1,4]diazepine-6,1'-cyclopropan]-4(5H)-one;

5-Methyl-9-(2-methyl-pyridin-3-yl)-2-(cyclopentanecarbonyl)-spiro[benzo[f]pyrazolo[1,5-a][1,4]diazepine-6,1'-cyclopropan]-4(5H)-one;

5-Methyl-9-(2-methyl-pyridin-3-yl)-2-acetyl-spiro[benzo[f]pyrazolo[1,5-a][1,4]diazepine-6,1'-cyclopropan]-4(5H)-one;

5-Methyl-9-(2-methyl-pyridin-3-yl)-2-(cyclopentylmethyl)-spiro[benzo[f]pyrazolo[1,5-a][1,4]diazepine-6,1'-cyclopropan]-4(5H)-one;

5-Methyl-9-(2-methyl-pyridin-3-yl)-2-ethyl-spiro[benzo[f]pyrazolo[1,5-a][1,4]diazepine-6,1'-cyclopropan]-4(5H)-one;

2,5-Dimethyl-9-(6-methyl-pyridin-3-yl)-spiro[benzo[f]pyrazolo[1,5-a][1,4]diazepine-6,1'-cyclopropan]-4(5H)-one;

2,5-Dimethyl-9-(2-ethyl-pyridin-3-yl)-spiro[benzo[f]pyrazolo[1,5-a][1,4]diazepine-6,1'-cyclopropan]-4(5H)-one;

5-Methyl-9-(2-methyl-pyridin-3-yl)-2-(morpholin-4-ylmethyl)-spiro[benzo[f]pyrazolo[1,5-a][1,4]diazepine-6,1'-cyclopropan]-4(5H)-one;

5-Methyl-9-(2-methyl-pyridin-3-yl)-2-difluoromethyl-spiro[benzo[f]pyrazolo[1,5-a][1,4]diazepine-6,1'-cyclopropan]-4(5H)-one;

2-Hydroxymethyl-5-methyl-9-(6-methyl-pyridin-3-yl)-spiro[benzo[f]pyrazolo[1,5-a][1,4]diazepine-6,1'-cyclopropan]-4(5H)-one;

2-Hydroxymethyl-5-methyl-9-(2-ethyl-pyridin-3-yl)-spiro[benzo[f]pyrazolo[1,5-a][1,4]diazepine-6,1'-cyclopropan]-4(5H)-one;

2-Hydroxymethyl-5-methyl-9-(6-fluoro-pyridin-3-yl)-spiro[benzo[f]pyrazolo[1,5-a][1,4]diazepine-6,1'-cyclopropan]-4(5H)-one;

2-Methoxymethyl-5-methyl-9-(6-methyl-pyridin-3-yl)-spiro[benzo[f]pyrazolo[1,5-a][1,4]diazepine-6,1'-cyclopropan]-4(5H)-one;

2-Methoxymethyl-5-methyl-9-(2-ethyl-pyridin-3-yl)-spiro[benzo[f]pyrazolo[1,5-a][1,4]diazepine-6,1'-cyclopropan]-4(5H)-one;

2-Methoxymethyl-5-methyl-9-(6-fluoro-pyridin-3-yl)-spiro[benzo[f]pyrazolo[1,5-a][1,4]diazepine-6,1'-cyclopropan]-4(5H)-one;

9-Bromo-5-methyl-1,2,3,3a-tetrahydro-spiro[benzo[f]pyrrolo[1,2-a][1,4]diazepine-6,1'-cyclopropan]-4(5H)-one;

5-Methyl-9-(2-methylpyridin-3-yl)-1,2,3,3a-tetrahydro-spiro[benzo[f]pyrrolo[1,2-a][1,4]diazepine-6,1'-cyclopropan]-4(5H)-one;

5-Methyl-9-bromo-5,6-dihydro-4H-benzo[f]imidazo[1,5-a][1,4]diazepin-4-one;

5-Methyl-9-bromo-5,6-dihydro-4H-benzo[f]imidazo[1,2-a][1,4]diazepin-4-one;

5-Methyl-9-bromo-5,6-dihydro-4H-benzo[f]pyrazolo[1,5-a][1,4]diazepin-4-one;

9-Bromo-5,6-dimethyl-5,6-dihydro-benzo[f]pyrrolo[1,2-a][1,4]diazepin-4-one;

9-Bromo-5-methyl-6-ethyl-5,6-dihydro-benzo[f]pyrrolo[1,2-a][1,4]diazepin-4-one;

5-Methyl-9-(2-methylpyridin-3-yl)-5,6-dihydro-4H-benzo[f]imidazo[1,5-a][1,4]diazepin-4-one;

5-Methyl-9-(2-methylpyridin-3-yl)-5,6-dihydro-4H-benzo[f]imidazo[1,2-a][1,4]diazepin-4-one;

5-Methyl-9-(2-methylpyridin-3-yl)-5,6-dihydro-4H-benzo[f]pyrazolo[1,5-a][1,4]diazepin-4-one;

5,6-Dimethyl-9-(2-methyl-pyridin-3-yl)-5,6-dihydro-benzo[f]pyrrolo[1,2-a][1,4]diazepin-4-one;

9-(6-Dimethylamino-pyridin-3-yl)-5,6-dimethyl-5,6-dihydro-benzo[f]pyrrolo[1,2-a][1,4]diazepin-4-one;

6-Ethyl-5-methyl-9-(2-methyl-pyridin-3-yl)-5,6-dihydro-benzo[f]pyrrolo[1,2-a][1,4]diazepin-4-one;

5,6,6-Trimethyl-5,6-dihydro-benzo[f]pyrrolo[1,2-a][1,4]diazepin-4-one;

9-Chloro-5,6,6-trimethyl-5,6-dihydro-benzo[f]pyrrolo[1,2-a][1,4]diazepin-4-one;

5,6,6-Trimethyl-9-(2-methyl-pyridin-3-yl)-5,6-dihydro-benzo[f]pyrrolo[1,2-a][1,4]diazepin-4-one;

and pharmaceutically acceptable salts, solvates and prodrugs thereof.

36. A pharmaceutical composition comprising a compound as defined in any one of items 1 to 35 and optionally a pharmaceutically acceptable excipient.

37. A compound as defined in any one of items 1 to 35 or the pharmaceutical composition of item 36 for use in the treatment and/or prophylaxis of a condition associated with altered glutamatergic signalling and/or functions, and/or a condition which can be affected by alteration of glutamate level or signalling.

38. Use of a compound as defined in any one of items 1 to 35 for the preparation of a medicament for the treatment and/or prophylaxis of a condition associated with altered glutamatergic signalling and/or functions, and/or a condition which can be affected by alteration of glutamate level or signalling.

39. A method of treating and/or preventing a condition associated with altered glutamatergic signalling and/or functions, and/or a condition which can be affected by alteration of glutamate level or signalling, the method comprising the administration of a compound as defined in any one of items 1 to 35 or the pharmaceutical composition of item 36 to a subject in need of such treatment or prevention.

40. The compound for use according to item 37 or the pharmaceutical composition for use according to item 37 or the use of item 38 or the method of item 39, wherein the condition to be treated or prevented is selected from: epilepsy; dementias; parkinsonism and movement disorders; motor neuron disease; amyotrophic lateral sclerosis; neurodegenerative and/or hereditary disorders of the nervous system; disorders of the peripheral nervous system; multiple sclerosis and other demyelinating diseases of the nervous system; infantile cerebral palsy; hemiplegia and hemiparesis, and other paralytic syndromes; cerebrovascular disorders; migraine; headache; myoneural disorders; disorders of the eye and visual pathways; intracranial trauma/injury; trauma/injury to nerves and spinal cord; poisoning; neurological and psychiatric adverse effects of drugs, medicinal and biological substances; disturbance of sphincter control and sexual function; mental retardation, learning disorders, motor skill disorders, communication disorders, pervasive developmental disorders, attention deficit and disruptive behaviour disorders, feeding and eating disorders, TIC disorders, and elimination disorders; delirium and other cognitive disorders; substance related disorders; schizophrenia and other psychotic disorders; mood disorders; anxiety disorders; eating disorders; sleep disorders; medication-induced movement disorders; endocrine and metabolic diseases; acute and chronic pain; nausea and vomiting; irritable bowel syndrome; and cancers.
41. A compound as defined in any one of items 1 to 35 or the pharmaceutical composition of item 36 for use in the treatment and/or prophylaxis of Parkinson's disease.
42. Use of a compound as defined in any one of items 1 to 35 for the preparation of a medicament for the treatment and/or prophylaxis of Parkinson's disease.
43. A method of treating and/or preventing Parkinson's disease in a subject, the method comprising the administration of a compound as defined in any one of items 1 to 35 or the pharmaceutical composition of item 36 to a subject in need thereof.
44. The method of item 39, 40 or 43, wherein said subject is a human.
45. In vitro use of a compound as defined in any one of items 1 to 35 as a positive allosteric modulator of mGluR3.
46. A method for identifying an agent that binds to metabotropic glutamate receptor 3 (mGluR3), comprising the following steps:
    (a) contacting mGluR3 with the compound of any one of items 1 to 35, wherein said compound is radio-labeled or fluorescence-labeled, under conditions that permit binding of the compound to mGluR3, thereby generating bound, labeled compound;
    (b) detecting a signal that corresponds to the amount of bound, labeled compound in the absence of test agent;
    (c) contacting the bound, labeled compound with a test agent;
    (d) detecting a signal that corresponds to the amount of bound labeled compound in the presence of test agent; and
    (e) comparing the signal detected in step (d) to the signal detected in step (b) to determine whether the test agent binds to mGluR3.

The invention will now be described by reference to the following examples which are merely illustrative and are not to be construed as a limitation of the scope of the present invention.

EXAMPLES

In this section, the term "compound" refers to a synthesis intermediate, and the term "example" refers to a compound of the general formula (I) according to the invention.

The compounds/examples described in this section are defined by their chemical formulae and their corresponding chemical names. In case of conflict between any chemical formula and the corresponding chemical name indicated herein, the present invention relates to both the compound/example defined by the chemical formula and the compound/example defined by the chemical name, and particularly relates to the compound/example defined by the chemical formula.

Experimental:
Experimental Section.
All reagents were commercial grade and used without further purification. Commercially available anhydrous solvents were used for reactions conducted under inert atmosphere. Silica gel generally used for column chromatography was SDS silica gel (60AAC 40-63 µM). Thin layer chromatography was carried out using pre-coated silica gel F-254plate. $^1$H NMR spectra were recorded on a Bruker AMX-400 spectrometer. Proton chemical shifts are listed relative to residual $CDCl_3$ (7.27 ppm), DMSO-D6 (2.51 ppm) or $D_2O$ (4.60 ppm). Splitting patterns are designated as s (singlet), d (doublet), dd (double-doublet), t (triplet), tt (triplet-triplet), td (triplet-doublet), q (quartet), quint (quintuplet), sex (sextuplet), sept (septuplet), m (multiplet), b (broad). Electrospray MS spectra were obtained on a Waters micromass platform LCMS spectrometer. All mass spectra were full-scan experiments (mass range 100-800 amu). Mass spectra were obtained using electro spray ionization. The HPLC system was a Waters platform with a 2767 sample manager, a 2525 pump, a photodiode array detector (190-400 nM). The column used was an XBridge $C_{18}$ 3.5 µM (4.6×50 mm) in analytical mode and an XBridge C18 OBD 5 µM (30×100 mm) in preparative mode. The mobile phase in both cases consisted in an appropriate gradient of A and B. A was water with 0.05% of TFA and B was MeOH with 0.05% of TFA. Flow rate was 1 mL per min in analytical mode and 25 mL min in preparative mode. All LCMS were performed at room temperature. At the end of each preparative HPLC, the tubes were collected and TFA was neutralized with potassium carbonate before extraction or filtration of the product. Microwave experiments were performed on a Biotage Initiator. The microwave modulates the power in order to reach the selected temperature as fast as possible. The time of each experiment is the time at the selected temperature.

Melting Points are measure on a Barnstead Electrothermal 9100 and are not corrected.

General Procedure I: Formation of Intermediate C, C' and C" from the Corresponding Fluoro-Benzonitrile A and Methyl Ester B, B' and B" (Scheme 1 and 2).

Method (i): Under Oil Bath Heating:
At 0° C., to a suspension of sodium hydride (60% dispersion in oil, 1.5 equiv.) in DMF (0.80 mol·L$^{-1}$), a solution of methyl ester B, B' or B" (1.0 equiv.) in DMF (0.65 mol·L$^{-1}$) was slowly added, followed after 15 minutes by a solution of fluorobenzonitrile A (1.1 equiv.) in DMF (0.65 mol·L$^{-1}$).

The reaction mixture was stirred at 70° C. (oil bath) for 3 hours, before being poured into an ice cold saturated aqueous solution of $NH_4Cl$ and extracted twice with $CH_2Cl_2$. The organic layers were combined, washed with brine, dried over $MgSO_4$, concentrated under vacuum and purified by flash column chromatography on silica gel (using a gradient of EtOAc in cyclohexane as eluent) to afford the product.

Method (ii): Under Microwave Irradiation:
Under inert atmosphere, a mixture of fluorobenzonitrile A (1.0 equiv.), methyl ester B, B' or B" (1.0 equiv.) and cesium carbonate (2.5 equiv.) in DMF (0.20 mol·L$^{-1}$) was submitted to microwave irradiation at 130° C. for 10 minutes. The reaction mixture was neutralized with aqueous HCl (1N), and then extracted twice with EtOAc. The organic layers were combined, washed with brine, dried over $MgSO_4$, concentrated and purified by flash column chromatography on silica gel (using a gradient of EtOAc in cyclohexane as eluent) to afford the product.

Compound 1: 1-(5-Bromo-2-cyano-phenyl)-1H-pyrrole-2-carboxylic acid methyl ester Compound 1 was obtained according to general procedure I(i), starting from 4-bromo-2-fluorobenzonitrile and methyl-2-pyrrole carboxylate. It was isolated as a white solid in 80% yield. $^1$H-NMR (400 MHz, DMSO-D6): 7.91 (m, 3H, Ar);

7.38 (dd, J 2.8, 1.8 Hz, 1H, Ar); 7.11 (dd, J 3.8, 1.8 Hz, 1H, Ar); 6.43 (dd, J 3.8, 2.8 Hz, 1H, Ar); 3.66 (s, 3H, CH$_3$). M/Z (M[$^{79}$Br]—OCH$_3$+H)$^+$=275.

Compound 2: 4-Bromo-1-(5-bromo-2-cyano-phenyl)-1H-pyrrole-2-carboxylic acid methyl ester Compound 2 was obtained according to general procedure I(ii), starting from 4-bromo-2-fluorobenzonitrile and 4-Bromo-1H-pyrrole-2-carboxylic acid methyl ester. It was isolated as a white solid in 72% yield. $^1$H-NMR (400 MHz, DMSO-D6): 8.02 (d, J 1.6 Hz, 1H, Ar); 7.96 (d, J 8.2 Hz, 1H, Ar); 7.93 (dd, J 8.2, 1.6 Hz, 1H, Ar); 7.65 (d, J 1.9 Hz, 1H, Ar); 7.18 (d, J 1.9 Hz, 1H, Ar); 3.67 (s, 3H, CH$_3$). M/Z (M[$^{79}$Br][$^{80}$Br]+H)$^+$=385.

Compound 3: 4-Chloro-1-(5-bromo-2-cyano-phenyl)-1H-pyrrole-2-carboxylic acid methyl ester Compound 3 was obtained according to general procedure I(ii), starting from 4-bromo-2-fluorobenzonitrile and 4-chloro-1H-pyrrole-2-carboxylic acid methyl ester. It was isolated as a beige solid in 46% yield. $^1$H-NMR (400 MHz, DMSO-D6): 8.03 (d, J 1.6 Hz, 1H, Ar); 7.96 (d, J 8.2 Hz, 1H, Ar); 7.93 (dd, J 8.2, 1.6 Hz, 1H, Ar); 7.64 (d, J 1.9 Hz, 1H, Ar); 7.14 (d, J 1.9 Hz, 1H, Ar); 3.67 (s, 3H, CH$_3$). M/Z (M[$^{79}$Br][$^{35}$Cl]+H)$^+$=339.

Compound 4: 3-Chloro-1-(5-bromo-2-cyano-phenyl)-1H-pyrrole-2-carboxylic acid methyl ester Compound 4 was obtained according to general procedure I(ii), starting from 4-bromo-2-fluorobenzonitrile and 3-chloro-1H-pyrrole-2-carboxylic acid methyl ester. It was isolated as a white solid in 43% yield. $^1$H-NMR (400 MHz, DMSO-D6): 8.00 (d, J 1.6 Hz, 1H, Ar); 7.95 (d, J 8.2 Hz, 1H, Ar); 7.92 (dd, J 8.2, 1.6 Hz, 1H, Ar); 7.45 (d, J 3.1 Hz, 1H, Ar); 6.59 (d, J 3.1 Hz, 1H, Ar); 3.67 (s, 3H, CH$_3$). M/Z (M[$^{79}$Br][$^{35}$Cl]+H)$^+$=339.

Compound 5: 1-(5-Bromo-2-cyano-3-fluorophenyl)-1H-pyrrole-2-carboxylic acid methyl ester Compound 5 was obtained according to general procedure I(i), starting from 4-bromo-2,6-difluorobenzonitrile and methyl-2-pyrrole carboxylate. It was isolated as a white solid in 72% yield. $^1$H-NMR (400 MHz, DMSO-D6): 8.13 (dd, J 8.8, 1.6 Hz, 1H, Ar); 7.87 (m, 1H, Ar); 7.41 (dd, J 2.8, 1.8 Hz, 1H, Ar); 7.13 (dd, J 3.8, 1.8 Hz, 1H, Ar); 6.45 (dd, J 3.8, 2.8 Hz, 1H, Ar); 3.68 (s, 3H, CH$_3$). M/Z (M[$^{79}$Br]+H)$^+$=323.

Compound 6: 1-(5-Bromo-2-cyano-6-fluorophenyl)-1H-pyrrole-2-carboxylic acid methyl ester Compound 6 was obtained according to general procedure I(i), starting from 4-bromo-2,3-difluorobenzonitrile and methyl-2-pyrrole carboxylate. It was isolated as a yellow oil in 24% yield. $^1$H-NMR (400 MHz, DMSO-D6): 8.09 (dd, J 8.5, 6.6 Hz, 1H, Ar); 7.85 (dd, J 8.5, 1.5 Hz, 1H, Ar); 7.47 (dd, J 2.8, 1.8 Hz, 1H, Ar); 7.16 (dd, J 3.8, 1.8 Hz, 1H, Ar); 6.49 (dd, J 3.8, 2.8 Hz, 1H, Ar); 3.68 (s, 3H, CH$_3$). M/Z (M[$^{79}$Br]+H)$^+$=323.

Compound 7: 1-(5-Bromo-2-cyano-4-fluorophenyl)-1H-pyrrole-2-carboxylic acid methyl ester Compound 7 was obtained according to general procedure I(i), starting from 4-bromo-2,5-difluorobenzonitrile and methyl-2-pyrrole carboxylate. It was isolated as a white solid in 47% yield. $^1$H-NMR (400 MHz, DMSO-D6): 8.22 (d, J 8.3 Hz, 1H, Ar); 8.14 (d, J 6.3 Hz, 1H, Ar); 7.37 (dd, J 2.8, 1.8 Hz, 1H, Ar); 7.11 (dd, J 3.8, 1.8 Hz, 1H, Ar); 6.43 (dd, J 3.8, 2.8 Hz, 1H, Ar); 3.67 (s, 3H, CH$_3$). M/Z (M[$^{79}$Br]+H)$^+$=323.

Compound 8: 1-(5-Bromo-2-cyano-phenyl)-4-phenyl-1H-pyrrole-2-carboxylic acid methyl ester Compound 8 was obtained according to general procedure I(ii), starting from 4-bromo-2-fluorobenzonitrile and 4-phenyl-1H-pyrrole-2-carboxylic acid methyl ester. It was isolated as a white solid in 70% yield. $^1$H-NMR (400 MHz, DMSO-D6): 8.06 (d, J 1.7 Hz, 1H, Ar); 7.97 (d, J 8.4 Hz, 1H, Ar); 7.93 (m, 2H, Ar); 7.70 (m, 2H, Ar); 7.55 (d, J 1.9 Hz, 1H, Ar); 7.39 (m, 2H, Ar); 7.24 (m, 1H, Ar); 3.70 (s, 3H, CH$_3$). M/Z (M[$^{79}$Br]—OCH$_3$+H)$^+$=349.

Compound 9: 2-(5-Bromo-2-cyano-phenyl)-5-phenyl-2H-pyrazole-3-carboxylic acid methyl ester a and its undesired isomer b

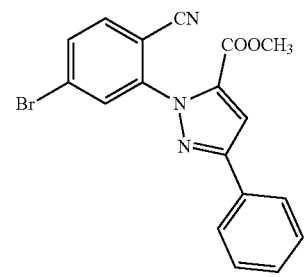

a

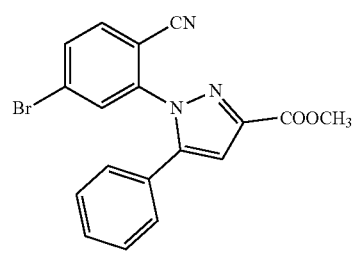

b

Compound 9 was obtained according to general procedure I(ii), starting from 4-bromo-2-fluorobenzonitrile and methyl 3-phenyl-1H-pyrazole-5-carboxylate. It was isolated as a white solid in 29% yield as a 1:1 mixture of isomers a and b. The mixture was taken to the next step without separation. M/Z (M[$^{79}$Br]+H)$^+$=382.0.

Compound 10: 1-(5-Bromo-2-cyano-phenyl)-4-phenyl-1H-imidazole-2-carboxylic acid ethyl ester Compound 10 was obtained according to general procedure I(ii), starting from 4-bromo-2-fluorobenzonitrile and 4-phenyl-1H-imidazole-2-carboxylic acid ethyl ester. It was isolated as a white solid in 81% yield. $^1$H-NMR (400 MHz, DMSO-D6): 8.33 (s, 1H, Ar); 8.23 (d, J 1.7 Hz, 1H, Ar); 8.06 (d, J 8.3 Hz, 1H, Ar); 8.01 (dd, J 8.3, 1.7 Hz, 1H, Ar); 7.89 (m, 2H, Ar); 7.46 (m, 2H, Ar); 7.34 (m, 1H, Ar); 4.24 (q, J 7.0 Hz, 2H, C$\underline{H}_2$—CH$_3$); 1.19 (t, J 7.0 Hz, 3H, CH$_2$—C$\underline{H}_3$). M/Z (M[$^{79}$Br]+H)$^+$=396.0.

Compound 11: 1-(4-Bromo-2-cyano-phenyl)-1H-pyrrole-2-carboxylic acid methyl ester Compound 11 was obtained according to general procedure I(i), starting from 5-bromo-2-fluorobenzonitrile and methyl-2-pyrrole carboxylate. It was isolated as a white solid in 75% yield. $^1$H-NMR (400 MHz, DMSO-D6): 8.33 (d, J 2.2 Hz, 1H, Ar); 8.03 (dd, J 8.4, 2.2 Hz, 1H, Ar); 7.54 (d, J 8.4 Hz, 1H, Ar); 7.36 (dd, J 2.8, 1.8 Hz, 1H, Ar); 7.12 (dd, J 3.9, 1.8 Hz, 1H, Ar); 6.44 (dd, J 3.9, 2.8 Hz, 1H, Ar); 3.66 (s, 3H, CH$_3$). M/Z (M[$^{79}$Br]—OCH$_3$+H)$^+$=275.

Compound 12: 1-(3-Bromo-2-cyano-phenyl)-1H-pyrrole-2-carboxylic acid methyl ester Compound 12 was obtained according to general procedure I(i), starting from 6-bromo-2-fluorobenzonitrile and methyl-2-pyrrole carboxylate. It was isolated as a beige solid in 81% yield. $^1$H-NMR (400 MHz, DMSO-D6): 7.99 (dd, J 8.2, 1.0 Hz, 1H, Ar); 7.75 (t, J 8.2 Hz, 1H, Ar); 7.61 (dd, J 8.2, 1.0 Hz, 1H, Ar); 7.39 (dd, J 2.8, 1.8 Hz, 1H, Ar); 7.12 (dd, J 3.9, 1.8 Hz, 1H, Ar); 6.44 (dd, J 3.9, 2.8 Hz, 1H, Ar); 3.66 (s, 3H, CH$_3$). M/Z (M[$^{79}$Br]+H)$^+$=305.

Compound 13: 1-(6-Bromo-2-cyano-phenyl)-1H-pyrrole-2-carboxylic acid methyl ester Compound 13 was obtained according to general procedure I(i), starting from 3-bromo-2-fluorobenzonitrile and methyl-2-pyrrole carboxylate. It was isolated as a beige solid in 50% yield. $^1$H-NMR (400 MHz, DMSO-D6): 8.13 (dd, J 8.2, 1.3 Hz, 1H, Ar); 7.04 (dd, J 8.2, 1.3 Hz, 1H, Ar); 7.61 (t, J 8.2 Hz, 1H, Ar); 7.32 (dd, J 2.8, 1.8 Hz, 1H, Ar); 7.11 (dd, J 3.9, 1.8 Hz, 1H, Ar); 6.47 (dd, J 3.9, 2.8 Hz, 1H, Ar); 3.64 (s, 3H, CH$_3$). M/Z (M[$^{79}$Br]+H)$^+$=305.

Compound 14: 1-(4-Bromo-2-cyano-phenyl)-4-phenyl-1H-pyrrole-2-carboxylic acid methyl ester Compound 14 was obtained according to general procedure I(ii), starting from 5-bromo-2-fluorobenzonitrile and 4-phenyl-1H-pyrrole-2-carboxylic acid methyl ester. It was isolated as a beige solid in 64% yield. $^1$H-NMR (400 MHz, DMSO-D6): 8.37 (d, J 2.2 Hz, 1H, Ar); 8.08 (d, J 8.5, 2.2 Hz, 1H, Ar); 7.89 (d, J 2.0 Hz, 1H, Ar); 7.70 (m, 2H, Ar); 7.65 (d, J 8.5 Hz, 1H, Ar); 7.56 (d, J 2.0 Hz, 1H, Ar); 7.39 (m, 2H, Ar); 7.25 (m, 1H, Ar); 3.70 (s, 3H, CH$_3$). M/Z (M[$^{79}$Br]+H)$^+$=381.1.

General Procedure II: Formation of Benzodiazepinone D, D', D", Di from Intermediate C, C', C", Ci (Scheme 1, 2 and 4).

Under inert and anhydrous conditions, at room temperature, ethylmagnesium bromide (1M solution in THF, 2.0 equiv.) was added dropwise to a solution of intermediate C, C', C", Ci (1.0 equiv.) and titanium isopropoxide (1.0 equiv.) in CH$_2$Cl$_2$ (0.20 mol·L$^{-1}$). The reaction mixture was stirred at room temperature for 3 hours to give a dark brown solution. When the reaction was not complete, 1.0-2.0 equiv. more of ethylmagnesium bromide (1M solution in THF) was added and the reaction mixture further stirred for 1 hour at room temperature. After cooling at 0° C., the reaction mixture was hydrolysed with HCl (1N in water) and extracted twice with CH$_2$Cl$_2$. The organic layers were combined, washed with brine, dried over MgSO$_4$, concentrated under vacuum and purified by flash column chromatography on silica gel (using a gradient of EtOAc in cyclohexane) to afford the product.

Compound 15: 9-Bromo-spiro[benzo[f]pyrrolo[1,2-a][1,4]diazepine-6,1'-cyclopropan]-4(5H)-one Compound 15 was obtained according to general procedure II, starting from compound 1. The reaction was completed by the addition of more ethylmagnesium bromide (1M solution in THF, 1.0 equiv.). Compound 15 was isolated as a brown solid in 62% yield. $^1$H-NMR (400 MHz, DMSO-D6): 8.62 (s, 1H, NH); 7.76 (d, J 1.9 Hz, 1H, Ar); 7.58 (dd, J 2.8, 1.8 Hz, 1H, Ar); 7.51 (dd, J 8.2, 1.9 Hz, 1H, Ar); 7.38 (d, J 8.2 Hz, 1H, Ar); 6.90 (dd, J 3.8, 1.8 Hz, 1H, Ar); 6.42 (dd, J 3.8, 2.8 Hz, 1H, Ar); 1.50 (m, 1H, cyclopropyl); 1.20 (m, 1H, cyclopropyl); 0.79 (m, 1H, cyclopropyl); 0.47 (m, 1H, cyclopropyl). M/Z (M[$^{79}$Br]+H)$^+$=303.

Compound 16: 2,9-Dibromo-spiro[benzo[f]pyrrolo[1,2-a][1,4]diazepine-6,1'-cyclopropan]-4(5H)-one Compound 16 was obtained according to general procedure II, starting from compound 2. The reaction was completed by the addition of more ethylmagnesium bromide (1M solution in THF, 1.0 equiv.). Compound 16 was isolated as a white solid in 49% yield. $^1$H-NMR (400 MHz, DMSO-D6): 8.79 (s, 1H, NH); 7.82 (d, J 1.9 Hz, 1H, Ar); 7.80 (d, J 1.9 Hz, 1H, Ar); 7.55 (dd, J 8.1, 1.9 Hz, 1H, Ar); 7.39 (d, J 8.1 Hz, 1H, Ar); 6.91 (d, J 1.9 Hz, 1H, Ar); 1.53 (m, 1H, cyclopropyl); 1.22 (m, 1H, cyclopropyl); 0.85 (m, 1H, cyclopropyl); 0.51 (m, 1H, cyclopropyl). M/Z (M[$^{79}$Br][$^{81}$Br]+H)$^+$=383.

Compound 17: 9-Bromo-2-chloro-spiro[benzo[f]pyrrolo[1,2-a][1,4]diazepine-6,1'-cyclopropan]-4(5H)-one Compound 17 was obtained according to general procedure II, starting from compound 3, as a white solid in 57% yield. $^1$H-NMR (400 MHz, DMSO-D6): 8.79 (s, 1H, NH); 7.82 (d, J 1.9 Hz, 1H, Ar); 7.78 (d, J 2.0 Hz, 1H, Ar); 7.54 (dd, J 8.1, 1.9 Hz, 1H, Ar); 7.38 (d, J 8.1 Hz, 1H, Ar); 6.86 (d, J 2.0 Hz, 1H, Ar); 1.52 (m, 1H, cyclopropyl); 1.21 (m, 1H, cyclopropyl); 0.85 (m, 1H, cyclopropyl); 0.51 (m, 1H, cyclopropyl). M/Z (M[$^{79}$Br][$^{35}$Cl]+H)$^+$=337.

Compound 18: 9-Bromo-3-chloro-spiro[benzo[f]pyrrolo[1,2-a][1,4]diazepine-6,1'-cyclopropan]-4(5H)-one Compound 18 was obtained according to general procedure II, starting from compound 4. Ethylmagnesium bromide (1M solution in THF, 2.0 equiv.) was added 2 times more, each time after 1 hour stirring in order to have a complete conversion. Compound 18 was isolated as a beige solid in 62% yield. $^1$H-NMR (400 MHz, DMSO-D6): 8.73 (s, 1H, NH); 7.70 (d, J 2.0 Hz, 1H, Ar); 7.46 (m, 2H, Ar); 7.28 (d, J 8.2 Hz, 1H, Ar); 6.43 (d, J 3.1 Hz, 1H, Ar); 1.43 (m, 1H, cyclopropyl); 1.09 (m, 1H, cyclopropyl); 0.75 (m, 1H, cyclopropyl); 0.42 (m, 1H, cyclopropyl). M/Z (M[$^{79}$Br][$^{35}$Cl]+H)$^+$=337.

Compound 19: 9-Bromo-7-fluoro-spiro[benzo[f]pyrrolo[1,2-a][1,4]diazepine-6,1'-cyclopropan]-4(5H)-one Compound 19 was obtained according to general procedure II, starting from compound 5. The reaction was completed by the addition of more ethylmagnesium bromide (1M solution in THF, 2.0 equiv.). Compound 19 was isolated as a brown solid in 42% yield. $^1$H-NMR (400 MHz, DMSO-D6): 8.78 (s, 1H, NH); 7.64 (m, 1H, Ar); 7.61 (dd, J 2.8, 1.8 Hz, 1H, Ar); 7.55 (dd, J 9.8, 1.9 Hz, 1H, Ar); 7.38 (d, J 8.2 Hz, 1H, Ar); 6.90 (dd, J 3.8, 1.8 Hz, 1H, Ar); 6.43 (dd, J 3.8, 2.8 Hz, 1H, Ar); 1.51 (m, 1H, cyclopropyl); 1.40 (m, 1H, cyclopropyl); 0.71 (m, 1H, cyclopropyl); 0.51 (m, 1H, cyclopropyl). M/Z (M[$^{79}$Br]+H)$^+$=321.

Compound 20: 9-Bromo-10-fluoro-spiro[benzo[f]pyrrolo[1,2-a][1,4]diazepine-6,1'-cyclopropan]-4(5H)-one Compound 20 was obtained according to general procedure II, starting from compound 6. The reaction was completed by the addition of more ethylmagnesium bromide (1M solution in THF, 2.0 equiv.). Compound 20 was isolated as a brown solid in 57% yield. $^1$H-NMR (400 MHz, DMSO-D6): 8.69 (s, 1H, NH); 7.67 (dd, J 8.5, 6.5 Hz, 1H, Ar); 7.44 (m, 1H, Ar); 7.25 (dd, J 8.5, 1.5 Hz, 1H, Ar); 6.86 (dd, J 3.8, 1.8 Hz, 1H, Ar); 6.42 (dd, J 3.8, 2.8 Hz, 1H, Ar); 1.50 (m, 1H, cyclopropyl); 1.21 (m, 1H, cyclopropyl); 0.76 (m, 1H, cyclopropyl); 0.52 (m, 1H, cyclopropyl). M/Z (M[$^{79}$Br]+H)$^+$=321.

Compound 21: 9-Bromo-8-fluoro-spiro[benzo[f]pyrrolo[1,2-a][1,4]diazepine-6,1'-cyclopropan]-4(5H)-one Compound 21 was obtained according to general procedure II, starting from compound 7. The reaction was completed by the addition of more ethylmagnesium bromide (1M solution in THF, 1.5 equiv.). Compound 21 was isolated as a beige solid in 41% yield. $^1$H-NMR (400 MHz, DMSO-D6): 8.63 (s, 1H, NH); 7.90 (d, J 6.3 Hz, 1H, Ar); 7.55 (dd, J 2.8, 1.8 Hz, 1H, Ar); 7.49 (d, J 8.8 Hz, 1H, Ar); 6.88 (dd, J 3.8, 1.8 Hz, 1H, Ar); 6.41 (dd, J 3.8, 2.8 Hz, 1H, Ar); 1.58 (m, 1H, cyclopropyl); 1.21 (m, 1H, cyclopropyl); 0.79 (m, 1H, cyclopropyl); 0.53 (m, 1H, cyclopropyl). M/Z (M[$^{79}$Br]+H)$^+$=321.

Compound 22: 9-Bromo-2-phenyl-spiro[benzo[f]pyrrolo[1,2-a][1,4]diazepine-6,1'-cyclopropan]-4(5H)-one Compound 22 was obtained according to general procedure II, starting from compound 8. The reaction was completed by the addition of more ethylmagnesium bromide (1M solution in THF, 1.0 equiv.). Compound 22 was isolated as a white solid in 64% yield. $^1$H-NMR (400 MHz, DMSO-D6): 8.70 (s, 1H, NH); 8.12 (d, J 2.0 Hz, 1H, Ar); 7.93 (d, J 1.9 Hz, 1H, Ar); 7.78 (m, 2H, Ar); 7.54 (dd, J 8.1, 1.9 Hz, 1H, Ar); 7.40 (m, 3H, Ar); 7.33 (d, J 2.0 Hz, 1H, Ar); 7.24 (m, 1H, Ar); 1.54 (m, 1H, cyclopropyl); 1.24 (m, 1H, cyclopropyl); 0.88 (m, 1H, cyclopropyl); 0.55 (m, 1H, cyclopropyl). M/Z (M[$^{79}$Br]+H)$^+$=379.

Compound 23: 9-bromo-2-phenyl-spiro[benzo[f]pyrazolo[1,5-a][1,4]diazepine-6,1'-cyclopropan]-4(5H)-one Compound 23 was obtained according to general procedure II, starting from compound 9 (mixture of isomers). The reaction mixture was stirred for 16 hours at room temperature before addition of 2.0 more equiv. of ethylmagnesium bromide (1M solution in THF) in order to complete the reaction. Compound 23 was isolated, as a white solid in 53% yield. $^1$H-NMR (400 MHz, DMSO-D6): 9.20 (s, 1H, NH); 8.05 (m, 3H, Ar); 7.61 (dd, J 8.2, 2.0 Hz, 1H, Ar); 7.58 (s, 1H, Ar); 7.52-7.40 (m, 4H, Ar); 1.62 (m, 1H, cyclopropyl); 1.24 (m, 1H, cyclopropyl); 1.03 (m, 1H, cyclopropyl); 0.61 (m, 1H, cyclopropyl). M/Z (M[$^{79}$Br]+H)$^+$=380.0.

Compound 24: 9-bromo-2-phenyl-spiro[benzo[f]imidazo[1,2-a][1,4]diazepine-6,1'-cyclopropan]-4(5H)-one Compound 24 was obtained according to general procedure II, starting from compound 10. The reaction mixture was stirred for 16 hours at room temperature. Compound 24 was isolated as a white solid in 14% yield. M/Z (M[$^{79}$Br]+H)$^+$=380.0.

Compound 25: 8-Bromo-spiro[benzo[f]pyrrolo[1,2-a][1,4]diazepine-6,1'-cyclopropan]-4(5H)-one Compound 25 was obtained according to general procedure II, starting from compound 11. The reaction was completed by the addition of more ethylmagnesium bromide (1M solution in THF, 1.0 equiv.). Compound 25 was isolated as a beige solid in 60% yield. $^1$H-NMR (400 MHz, DMSO-D6): 8.62 (s, 1H, NH); 7.65 (dd, J 8.4, 2.4 Hz, 1H, Ar); 7.60 (d, J 2.4 Hz, 1H, Ar); 7.49 (m, 2H, Ar); 6.90 (dd, J 3.8, 1.8 Hz, 1H, Ar); 6.42 (dd, J 3.8, 2.8 Hz, 1H, Ar); 1.62 (m, 1H, cyclopropyl); 1.22 (m, 1H, cyclopropyl); 0.80 (m, 1H, cyclopropyl); 0.50 (m, 1H, cyclopropyl). M/Z (M[$^{79}$Br]+H)$^+$=303.

Compound 26: 7-Bromo-spiro[benzo[f]pyrrolo[1,2-a][1,4]diazepine-6,1'-cyclopropan]-4(5H)-one Compound 26 was obtained according to general procedure II, starting from compound 12. The reaction was completed by the addition of more ethylmagnesium bromide (1M solution in THF, 1.0 equiv.). Compound 26 was isolated as a brown solid in 25% yield. M/Z (M[$^{79}$Br]+H)$^+$=303.

Compound 27: 10-Bromo-spiro[benzo[f]pyrrolo[1,2-a][1,4]diazepine-6,1'-cyclopropan]-4(5H)-one Compound 27 was obtained according to general procedure II, starting from compound 13. The reaction was completed by the addition of more ethylmagnesium bromide (1M solution in THF, 1.0 equiv.). Compound 27 was isolated as a yellow solid in 61% yield. $^1$H-NMR (400 MHz, DMSO-D6): 8.65 (s, 1H, NH); 7.78 (dd, J 8.2, 1.3 Hz, 1H, Ar); 7.45 (dd, J 8.2, 1.3 Hz, 1H, Ar); 7.42 (dd, J 2.8, 1.8 Hz, 1H, Ar); 729 (t, J 8.2 Hz, 1H, Ar); 6.77 (dd, J 3.8, 1.8 Hz, 1H, Ar); 6.36 (dd, J 3.8, 2.8 Hz, 1H, Ar); 1.48 (m, 1H, cyclopropyl); 1.17 (m, 1H, cyclopropyl); 0.66 (m, 1H, cyclopropyl); 0.45 (m, 1H, cyclopropyl). M/Z (M[$^{79}$Br]+H)$^+$=303.

Compound 28: 8-Bromo-2-phenyl-spiro[benzo[f]pyrrolo[1,2-a][1,4]diazepine-6,1'-cyclopropan]-4(5H)-one Compound 28 was obtained according to general procedure II, starting from compound 14. The reaction was completed by the addition of more ethylmagnesium bromide (1M solution in THF, 1.5 equiv.). Compound 28 was isolated as a brown solid in 60% yield. $^1$H-NMR (400 MHz, DMSO-D6): 8.71 (s, 1H, NH); 8.02 (d, J 2.0 Hz, 1H, Ar); 7.76 (m, 2H, Ar); 7.70 (dd, J 8.4, 2.2 Hz, 1H, Ar); 7.63 (m, 2H, Ar); 7.40 (m, 2H, Ar); 7.33 (d, J 2.0 Hz, 1H, Ar); 7.24 (m, 1H, Ar); 1.64 (m, 1H, cyclopropyl); 1.23 (m, 1H, cyclopropyl); 0.88 (m, 1H, cyclopropyl); 0.58 (m, 1H, cyclopropyl). M/Z (M[$^{79}$Br]+H)$^{+}$=379.

General Procedure III: Formation of N-Substituted Benzodiazepinone F, F', F" and Fi from Benzodiazepinone D, D', D" and Di with Electrophile E (Scheme 1, 2, 3 and 4).

Under anhydrous conditions, to a solution of benzodiazepinone D, D', D" or Di (1.0 equiv.) in DMF (c=0.1 mol·L$^{-1}$) cooled by an ice bath, NaH (60% dispersion in mineral oil, 1.7 equiv.) was added in 3 portions. The mixture was stirred for 15 minutes, then the electrophile E (2.0 equiv.) was added. The ice bath was removed, and the reaction mixture was stirred at room temperature. When the reaction is completed, the mixture was hydrolysed with an aqueous HCl solution (1N) and the product was collected by filtration or extracted with EtOAc. When the product was extracted, the organic layers were combined, washed with brine, dried over MgSO$_4$, concentrated under vacuum and purified by flash column chromatography on silica gel.

Example 1

9-Bromo-5-methyl-spiro[benzo[f]pyrrolo[1,2-a][1,4] diazepine-6,1'-cyclopropan]-4(5H)-one

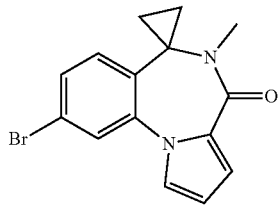 [SMILES: CN1C(=O)c2cccn2-c2cc(Br)ccc2C12CC2]

Example 1 was obtained according to general procedure III, starting from compound 15 in presence of iodomethane. The reaction mixture was stirred at room temperature for 2 hours. Purification by flash column chromatography on silica gel (MeOH in dichloromethane, 0% to 5%) afforded the product as a beige solid in 80% yield. $^1$H-NMR (400 MHz, DMSO-D6): 7.78 (d, J 1.9 Hz 1H, Ar); 7.53 (m, 2H, Ar); 7.45 (d, J 8.2 Hz, 1H, Ar); 6.85 (dd, J 3.7, 1.8 Hz, 1H, Ar); 6.40 (t, J 3.0 Hz, 1H, Ar); 2.89 (s, 3H, CH$_3$); 1.43 (m, 2H, cyclopropyl); 0.88 (m, 1H, cyclopropyl); 0.52 (m, 1H, cyclopropyl). M/Z (M[$^{79}$Br]+H)$^{+}$=317.

Example 2

9-Bromo-5-methoxymethyl-spiro[benzo[f]pyrrolo[1, 2-a][1,4]diazepine-6,1'-cyclopropan]-4(5H)-one

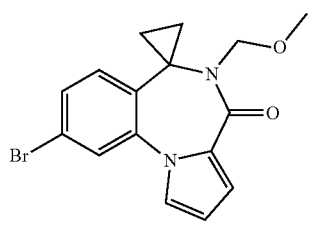 [SMILES: COCN1C(=O)c2cccn2-c2cc(Br)ccc2C12CC2]

Example 2 was obtained according to general procedure III, starting from compound 15 in presence of chloromethyl methyl ether. The reaction mixture was stirred at room temperature for 1 hour. Purification by filtration after hydrolysis afforded the product as a beige solid in 70% yield. $^1$H-NMR (400 MHz, DMSO-D6): 7.79 (d, J 1.8 Hz 1H, Ar); 7.60 (dd, J 2.9, 1.8 Hz, 1H, Ar); 7.52 (dd, J 8.0, 1.8 Hz, 1H, Ar); 7.44 (d, J 8.0 Hz, 1H, Ar); 6.96 (dd, J 3.7, 1.8 Hz, 1H, Ar); 6.45 (dd, J 3.7, 2.9 Hz, 1H, Ar); 4.98 (d, J 10.1 Hz, 1H, CH); 4.66 (d, J 10.1 Hz, 1H, CH); 2.93 (s, 3H, CH$_3$); 1.66 (m, 1H, cyclopropyl); 1.48 (m, 1H, cyclopropyl); 0.86 (m, 1H, cyclopropyl); 0.52 (m, 1H, cyclopropyl). M/Z (M[$^{79}$Br]+H)$^{+}$=347.

Example 3

9-Bromo-5-(methyl-d$_3$)-spiro[benzo[f]pyrrolo[1,2-a] [1,4]diazepine-6,1'-cyclopropan]-4(5H)-one

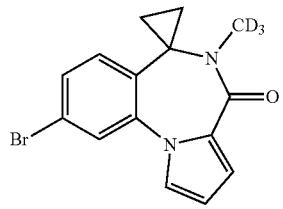 [SMILES: [2H]C([2H])([2H])N1C(=O)c2cccn2-c2cc(Br)ccc2C12CC2]

Example 3 was obtained according to general procedure III, starting from compound 15 in presence of iodomethane-d$_3$. The reaction mixture was stirred at room temperature for 2 hours. Purification by flash column chromatography on silica gel (EtOAc in cyclohexane, 50% to 100%) afforded the product as a beige solid in 99% yield. M/Z (M[$^{79}$Br]+H)$^{+}$=320.

Example 4

2,9-Dibromo-5-methyl-spiro[benzo[f]pyrrolo[1,2-a] [1,4]diazepine-6,1'-cyclopropan]-4(5H)-one

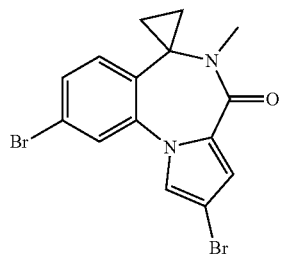

Example 4 was obtained according to general procedure III, starting from compound 16 in presence of iodomethane. The reaction mixture was stirred at room temperature for 2 hours. Purification by flash column chromatography on silica gel (EtOAc in cyclohexane, 50% to 100%) afforded the product as a yellow solid in 70% yield. $^1$H-NMR (400 MHz, DMSO-D6): 7.84 (d, J 1.9 Hz, 1H, Ar); 7.76 (d, J 1.9 Hz, 1H, Ar); 7.56 (dd, J 8.2, 1.9 Hz, 1H, Ar); 7.47 (d, J 8.2 Hz, 1H, Ar); 6.88 (d, J 1.9 Hz, 1H, Ar); 2.89 (s, 3H, CH$_3$); 1.44 (m, 2H, cyclopropyl); 0.96 (m, 1H, cyclopropyl); 0.59 (m, 1H, cyclopropyl). M/Z (M[$^{79}$Br][$^{81}$Br]+H)$^{+}$=397.

Example 5

9-Bromo-2-chloro-5-methyl-spiro[benzo[f]pyrrolo[1,2-a][1,4]diazepine-6,1'-cyclopropan]-4(5H)-one

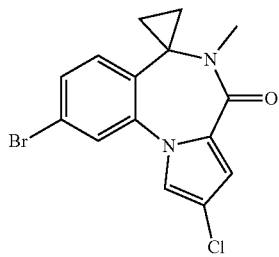 [SMILES: CN1C(=O)c2cc(Br)cn2-c2cc(Br)ccc2C12CC2]

Example 5 was obtained according to general procedure III, starting from compound 17 in presence of iodomethane. The reaction mixture was stirred at room temperature for 2 hours. Purification by flash column chromatography on silica gel (EtOAc in cyclohexane, 50% to 100%) afforded the product as a beige solid in 93% yield. $^1$H-NMR (400 MHz, DMSO-D6): 7.83 (d, J 1.9 Hz, 1H, Ar); 7.74 (d, J 2.0 Hz, 1H, Ar); 7.56 (dd, J 8.1, 1.9 Hz, 1H, Ar); 7.47 (d, J 8.1 Hz, 1H, Ar); 6.84 (d, J 2.0 Hz, 1H, Ar); 2.89 (s, 3H, CH$_3$); 1.45 (m, 2H, cyclopropyl); 0.96 (m, 1H, cyclopropyl); 0.58 (m, 1H, cyclopropyl). M/Z (M[$^{79}$Br][$^{35}$Cl]+H)$^+$=351.

Example 6

9-Bromo-3-chloro-5-methyl-spiro[benzo[f]pyrrolo[1,2-a][1,4]diazepine-6,1'-cyclopropan]-4(5H)-one

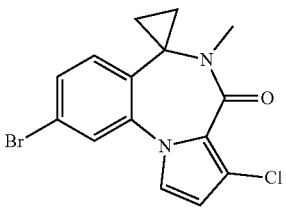 [SMILES: CN1C(=O)c2c(Cl)ccn2-c2cc(Br)ccc2C12CC2]

Example 6 was obtained according to general procedure III, starting from compound 18 in presence of iodomethane. The reaction mixture was stirred at room temperature for 2 hours. Purification by filtration after hydrolysis afforded the product as a beige solid in 92% yield. $^1$H-NMR (400 MHz, DMSO-D6): 7.82 (d, J 1.9 Hz, 1H, Ar); 7.56 (dd, J 8.1, 1.9 Hz 1H, Ar); 7.52 (d, J 8.1 Hz, 1H, Ar); 7.46 (d, J 8.1 Hz, 1H, Ar); 6.51 (d, J 3.1 Hz, 1H, Ar); 2.88 (s, 3H, CH$_3$); 1.44 (m, 2H, cyclopropyl); 0.93 (m, 1H, cyclopropyl); 0.57 (m, 1H, cyclopropyl). M/Z (M[$^{79}$Br][$^{35}$Cl]+H)$^+$=351.

Example 7

9-Bromo-7-fluoro-5-methyl-spiro[benzo[f]pyrrolo[1,2-a][1,4]diazepine-6,1'-cyclopropan]-4(5H)-one

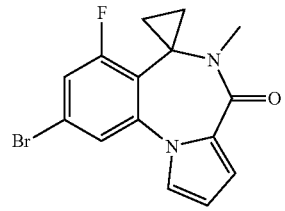 [SMILES: CN1C(=O)c2cccn2-c2cc(Br)cc(F)c2C12CC2]

Example 7 was obtained according to general procedure III, starting from compound 19 in presence of iodomethane. The reaction mixture was stirred at room temperature for 30 minutes. Purification by flash column chromatography on silica gel (EtOAc in cyclohexane, 0% to 60%) afforded the product as a beige solid in 76% yield. $^1$H-NMR (400 MHz, DMSO-D6): 7.68 (m, 1H, Ar); 7.58 (m, 2H, Ar); 6.87 (dd, J 3.7, 1.8 Hz, 1H, Ar); 6.42 (dd, J 3.8, 2.8 Hz, 1H, Ar); 2.93 (s, 3H, CH$_3$); 1.62 (m, 1H, cyclopropyl); 1.45 (m, 1H, cyclopropyl); 0.86 (m, 1H, cyclopropyl); 0.59 (m, 1H, cyclopropyl). M/Z (M[$^{79}$Br]+H)$^+$=335.

Example 8

9-Bromo-10-fluoro-5-methyl-spiro[benzo[f]pyrrolo[1,2-a][1,4]diazepine-6,1'-cyclopropan]-4(5H)-one

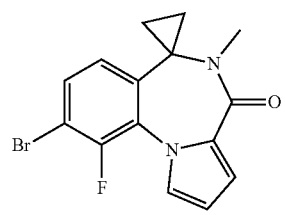 [SMILES: CN1C(=O)c2cccn2-c2c(ccc(Br)c2F)C12CC2]

Example 8 was obtained according to general procedure III, starting from compound 20 in presence of iodomethane. The reaction mixture was stirred at room temperature for 1 hour. Purification by flash column chromatography on silica gel (EtOAc in cyclohexane, 0% to 50%) afforded the product as a beige solid in 72% yield. $^1$H-NMR (400 MHz, DMSO-D6): 7.69 (dd, J 8.4, 6.6 Hz, 1H, Ar); 7.42 (m, 1H, Ar); 7.34 (dd, J 8.4, 1.4 Hz, 1H, Ar); 6.83 (dd, J 3.7, 1.8 Hz, 1H, Ar); 6.42 (dd, J 3.8, 2.8 Hz, 1H, Ar); 2.88 (s, 3H, CH$_3$); 1.44 (m, 2H, cyclopropyl); 0.86 (m, 1H, cyclopropyl); 0.57 (m, 1H, cyclopropyl). M/Z (M[$^{79}$Br]+H)$^+$=335.

Example 9

9-Bromo-8-fluoro-5-methyl-spiro[benzo[f]pyrrolo[1,2-a][1,4]diazepine-6,1'-cyclopropan]-4(5H)-one

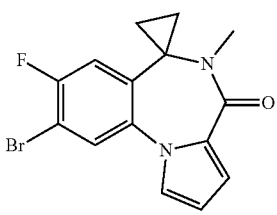 [SMILES: CN1C(=O)c2cccn2-c2cc(Br)c(F)cc2C12CC2]

Example 9 was obtained according to general procedure III, starting from compound 21 in presence of iodomethane. The reaction mixture was stirred at room temperature for 1 hour. Purification by filtration after hydrolysis afforded the product as a beige solid in 89% yield. $^1$H-NMR (400 MHz, DMSO-D6): 7.93 (d, J 5.6 Hz, 1H, Ar); 7.61 (d, J 8.5 Hz, 1H, Ar); 7.51 (s, 1H, Ar); 6.84 (s, 1H, Ar); 6.40 (s, 1H, Ar); 2.90 (s, 3H, CH$_3$); 1.46 (m, 2H, cyclopropyl); 0.89 (m, 1H, cyclopropyl); 0.57 (m, 1H, cyclopropyl). M/Z (M[$^{79}$Br]+H)$^+$=335.

Example 10

9-Bromo-2-phenyl-5-methyl-spiro[benzo[f]pyrrolo[1,2-a][1,4]diazepine-6,1'-cyclopropan]-4(5H)-one

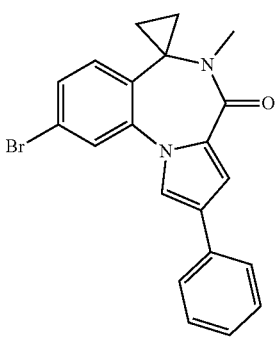 [SMILES: CN1C(=O)c2cc(-c3ccccc3)cn2-c2cc(Br)ccc2C12CC2]

Example 10 was obtained according to general procedure III, starting from compound 22 in presence of iodomethane. The reaction mixture was stirred at room temperature for 3 hours. Purification by filtration after hydrolysis afforded the product as a beige solid in 91% yield. $^1$H-NMR (400 MHz, DMSO-D6): 8.10 (d, J 2.0 Hz, 1H, Ar); 7.90 (d, J 1.9 Hz, 1H, Ar); 7.79 (m, 2H, Ar); 7.52 (dd, J 8.1, 1.9 Hz, 1H, Ar); 7.40 (m, 3H, Ar); 7.31 (d, J 2.0 Hz, 1H, Ar); 7.22 (m, 1H, Ar); 2.90 (s, 3H, CH$_3$); 1.40 (m, 2H, cyclopropyl); 0.93 (m, 1H, cyclopropyl); 0.55 (m, 1H, cyclopropyl). M/Z (M[$^{79}$Br]+H)$^+$=393.

Example 11

9-Bromo-5-methyl-2-phenyl-spiro[benzo[f]pyrazolo[1,5-a][1,4]diazepine-6,1'-cyclopropan]-4(5H)-one

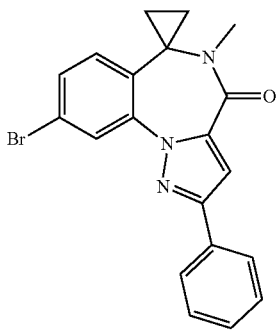 [SMILES: CN1C(=O)c2cc(-c3ccccc3)nn2-c2cc(Br)ccc2C12CC2]

Example 11 was obtained according to general procedure III, starting from compound 23 in presence of iodomethane. The reaction mixture was stirred at room temperature for 2 hours. Purification by filtration after hydrolysis afforded the product as a beige solid in quantitative yield. $^1$H-NMR (400 MHz, DMSO-D6): 8.04 (m, 3H, Ar); 7.63 (dd, J 8.0, 1.8 Hz, 1H, Ar); 7.56 (s, 1H, Ar); 7.53 (d, J 8.0 Hz, 1H, Ar); 7.49 (m, 2H, Ar); 7.41 (m, 1H, Ar); 2.98 (s, 3H, CH$_3$); 1.55 (m, 2H, cyclopropyl); 1.07 (m, 1H, cyclopropyl); 0.62 (m, 1H, cyclopropyl). M/Z (M[$^{79}$Br]+H)$^+$=394.0.

Example 12

9-Bromo-6,6-spirocyclopropyl-5-methyl-2-phenyl-5,6-dihydro-3,5,10b-triaza-benzo[e]azulen-4-one

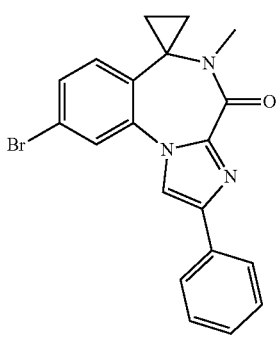 [SMILES: CN1C(=O)c2nc(-c3ccccc3)cn2-c2cc(Br)ccc2C12CC2]

Example 12 was obtained according to general procedure III, starting from compound 24 in presence of iodomethane. The reaction mixture was stirred at room temperature for 2 hours. Purification by filtration after hydrolysis afforded the product as a yellow solid in 91% yield. M/Z (M[$^{79}$Br]+H)$^+$=394.0.

Example 13

8-Bromo-5-methyl-spiro[benzo[f]pyrrolo[1,2-a][1,4]diazepine-6,1'-cyclopropan]-4(5H)-one

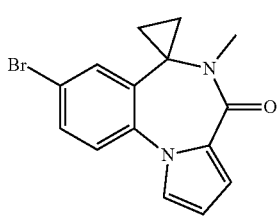 [SMILES: CN1C(=O)c2cccn2-c2ccc(Br)cc2C12CC2]

Example 13 was obtained according to general procedure III, starting from compound 25 in presence of iodomethane. The reaction mixture was stirred at room temperature for 16 hours. Purification by flash column chromatography on silica gel (EtOAc in cyclohexane, 0% to 20%) afforded the product as as a beige solid in 68% yield. $^1$H-NMR (400 MHz, DMSO-D6): 7.74 (d, J 2.3 Hz, 1H, Ar); 7.68 (dd, J 8.4, 2.3 Hz, 1H, Ar); 7.52 (d, J 8.4 Hz, 1H, Ar); 7.46 (dd, J 2.8, 1.8 Hz, 1H, Ar); 6.86 (dd, J 3.8, 1.8 Hz, 1H, Ar); 6.41 (dd, J 3.8, 2.8 Hz, 1H, Ar); 2.92 (s, 3H, CH$_3$); 1.53 (m, 1H, cyclopropyl); 1.42 (m, 1H, cyclopropyl); 0.90 (m, 1H, cyclopropyl); 0.54 (m, 1H, cyclopropyl). M/Z (M[$^{79}$Br]+H)$^+$=317.

Example 14

7-Bromo-5-methyl-spiro[benzo[f]pyrrolo[1,2-a][1,4]diazepine-6,1'-cyclopropan]-4(5H)-one

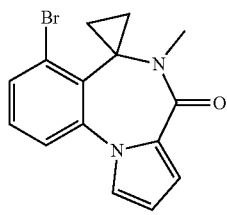 [SMILES: CN1C(=O)c2cccn2-c2cccc(Br)c2C12CC2]

Example 14 was obtained according to general procedure III, starting from compound 26 in presence of iodomethane. The reaction mixture was stirred at room temperature for 16 hours. Purification by flash column chromatography on silica gel (EtOAc in cyclohexane, 0% to 50%) afforded the product as a brown solid in 74% yield. M/Z (M[$^{79}$Br]+H)$^+$=317.

Example 15

10-Bromo-5-methyl-spiro[benzo[f]pyrrolo[1,2-a][1,4]diazepine-6,1'-cyclopropan]-4(5H)-one

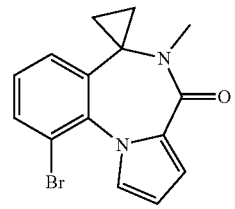 [SMILES: CN1C(=O)c2cccn2-c2c(Br)cccc2C12CC2]

Example 15 was obtained according to general procedure III, starting from compound 27 in presence of iodomethane. The reaction mixture was stirred at room temperature for 2 hours. Purification by flash column chromatography on silica gel (EtOAc in cyclohexane, 0% to 50%) afforded the product as a beige solid in 73% yield. $^1$H-NMR (400 MHz, DMSO-D6): 7.80 (dd, J 8.2, 1.3 Hz, 1H, Ar); 7.54 (dd, J 8.2, 1.3 Hz, 1H, Ar); 7.42 (dd, J 2.8, 1.8 Hz, 1H, Ar); 7.31 (t, J 8.2 Hz, 1H, Ar); 6.74 (dd, J 3.8, 1.8 Hz, 1H, Ar); 6.36 (dd, J 3.8, 2.8 Hz, 1H, Ar); 2.85 (s, 3H, CH$_3$); 1.42 (m, 2H, cyclopropyl); 0.77 (m, 1H, cyclopropyl); 0.50 (m, 1H, cyclopropyl). M/Z (M[$^{79}$Br]+H)$^+$=317.

Example 16

8-Bromo-5-methyl-2-phenyl-spiro[benzo[f]pyrrolo[1,2-a][1,4]diazepine-6,1'-cyclopropan]-4(5H)-one

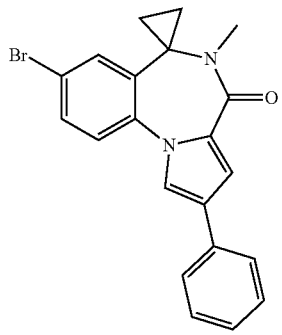 [SMILES: CN1C(=O)c2cc(-c3ccccc3)cn2-c2ccc(Br)cc2C12CC2]

Example 16 was obtained according to general procedure III, starting from compound 28 in presence of iodomethane. The reaction mixture was stirred at room temperature for 16 hours. Purification by flash column chromatography on silica gel (MeOH in dichloromethane, 0% to 1%) afforded the product as as a brown solid in 83% yield. $^1$H-NMR (400 MHz, DMSO-D6): 7.98 (d, J 2.0 Hz, 1H, Ar); 7.75 (m, 3H, Ar); 7.72 (dd, J 8.5, 2.2 Hz, 1H, Ar); 7.64 (d, J 8.5 Hz, 1H, Ar); 7.38 (m, 2H, Ar); 7.29 (d, J 2.0 Hz, 1H, Ar); 7.23 (m, 1H, Ar); 2.93 (s, 3H, CH$_3$); 1.56 (m, 1H, cyclopropyl); 1.44 (m, 1H, cyclopropyl); 0.97 (m, 1H, cyclopropyl); 0.62 (m, 1H, cyclopropyl). M/Z (M[$^{79}$Br]+H)$^+$=393.

General Procedure IV: Formation of Benzodiazepinone Boronic Ester J, Ji from Benzodiazepinone F, Fi (Scheme 1 and 4)

Under inert atmosphere, a mixture of halide F, Fi (1.0 equiv.), bis(pinacolato)diboran (2.0 equiv.), sodium acetate (2.5 equiv.) and PdCl$_2$(dppf)$_2$ (0.2 equiv.) in DMF (0.10 mol·L$^{-1}$) was heated at 80° C. for 3 days. After cooling, the reaction mixture was hydrolysed and extracted twice with EtOAc. The organic layers were combined, washed with brine, dried over MgSO$_4$ and concentrated to afford the product.

Compound 29: 9-(4,4,5,5-tetramethyl-[1,3,2]dioxaborolan-2-yl)-5-methyl-2-phenyl-spiro[benzo[f]pyrrolo[1,2-a][1,4]diazepine-6,1'-cyclopropan]-4(5H)-one Compound 29 was obtained according to general procedure IV, starting from example 10. Compound 29 was obtained as a brown solid in 91% yield and contained one third of boronic acid analogue according to LC/MS analysis. It was taken crude to the next step without purification. M/Z (M+H)$^+$=441.4 (boronic ester). M/Z (M+H)$^+$=359.3 (boronic acid).

Compound 30: 9-(4,4,5,5-tetramethyl-[1,3,2]dioxaborolan-2-yl)-5-methyl-2-phenyl-spiro[benzo[f]imidazo[1,2-a][1,4]diazepine-6,1'-cyclopropan]-4(5H)-one Compound 30 was obtained according to general procedure IV, starting from example 11. Compound 30 was obtained as a brown solid in quantitative yield and contained one third of boronic acid analogue according to LC/MS analysis. It was taken crude to the next step without purification. M/Z (M+H)$^+$=442.1 (boronic ester). M/Z (M+H)$^+$=360.1 (boronic acid).

Compound 31: 5-Methyl-9-(4,4,5,5-tetramethyl-[1,3,2]dioxaborolan-2-yl)-spiro[benzo[f]pyrrolo[1,2-a][1,4]diazepine-6,1'-cyclopropan]-4(5H)-one Compound 31 was obtained according to general procedure IV starting from example 1. Trituration in Et$_2$O afforded the crude product as a beige solid in 80% yield. It was taken crude to the next step without purification. M/Z (M+H)$^+$=365.3.

Compound 32: 5-(Methyl-d$_3$)-9-(4,4,5,5-tetramethyl-[1,3,2]dioxaborolan-2-yl)-spiro[benzo[f]pyrrolo[1,2-a][1,4]diazepine-6,1'-cyclopropan]-4(5H)-one Compound 32 was obtained according to general procedure IV starting from example 3. Trituration in Et$_2$O afforded the crude product as a brown solid in quantitative yield. It was taken crude to the next step without purification. M/Z (M+H)$^+$=368.4.

General Procedure V: Formation of R1-Substituted Intermediate Ci from Dibromo-Substituted Intermediate C (Scheme 4)

Under inert atmosphere, a mixture of dibromo-intermediate C (1.0 equiv.), boronic acid or ester G (1.1 equiv.), cesium fluoride (3.0 equiv.) and tetrakis(triphenylphosphine)palladium (0.10 equiv.) in THF (0.15 mol·L$^{-1}$) was heated at 70° C. for 24 hours. After cooling, the reaction mixture was hydrolysed and extracted twice with EtOAc. The organic layers were combined, washed with brine, dried over MgSO$_4$, concentrated and purified by flash column chromatography (using a gradient of EtOAc in cyclohexane as eluent) to afford the product.

Compound 33: 1-[2-Cyano-5-(2-methyl-pyridin-3-yl)-phenyl]-4-bromo-1H-pyrrole-2-carboxylic acid methyl ester Compound 33 was obtained according to general procedure V, starting from compound 2 and 2-methylpyridine-3-boronic acid pinacol ester. It was isolated as a beige solid in 78% yield. $^1$H-NMR (400 MHz, DMSO-D6): 8.53 (dd, J 4.8, 1.7 Hz, 1H, Ar); 8.09 (d, J 7.9 Hz, 1H, Ar); 7.75 (m, 2H, Ar); 7.72 (dd, J 7.9, 1.7 Hz, 1H, Ar); 7.69 (d, J 1.9 Hz, 1H, Ar); 7.36 (dd, J 7.9, 4.8 Hz, 1H, Ar); 7.17 (d, J 1.9 Hz, 1H, Ar); 3.67 (s, 3H, CH$_3$); 2.47 (s, 3H, CH$_3$). M/Z (M[$^{79}$Br]+H)$^+$=396.

Compound 34: 2-Bromo-9-(2-methyl-pyridin-3-yl)-spiro[benzo[f]pyrrolo[1,2-a][1,4]diazepine-6,1'-cyclopropan]-4(5H)-one Compound 34 was obtained according to general procedure II, starting from compound 33. The reaction was completed by the addition of more ethylmagnesium bromide (1M solution in THF, 1.0 equiv.). Compound 34 was isolated as a white solid in 55% yield. M/Z (M[$^{79}$Br]+H)$^+$=394.

Example 17

2-Bromo-5-methyl-9-(2-methyl-pyridin-3-yl)-spiro[benzo[f]pyrrolo[1,2-a][1,4]diazepine-6,1'-cyclopropan]-4(5H)-one

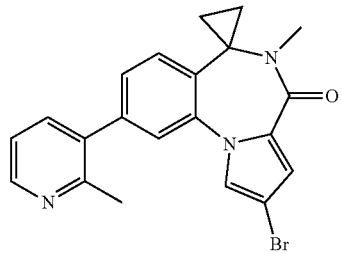 [SMILES: Cc1ncccc1-c1ccc2c(c1)-n1cc(Br)cc1C(=O)N(C)C21CC1]

Example 17 was obtained according to general procedure III, starting from compound 34 in presence of iodomethane. The reaction mixture was stirred at room temperature for 3 hours. Purification by filtration after hydrolysis afforded the product as a yellow solid in 88% yield. M/Z (M[$^{79}$Br]+H)$^+$=408.0.

Compound 35: 1-[2-Cyano-5-(6-methyl-pyridin-3-yl)-phenyl]-4-bromo-1H-pyrrole-2-carboxylic acid methyl ester Compound 35 was obtained according to general procedure V, starting from compound 2 and 2-methylpyridine-5-boronic acid. It was isolated as a white solid in 54% yield. $^1$H-NMR (400 MHz, DMSO-D6): 8.94 (d, J 2.4 Hz, 1H, Ar); 8.17 (dd, J 8.1, 2.4 Hz, 1H, Ar); 8.08 (m, 3H, Ar); 7.71 (d, J 1.9 Hz, 1H, Ar); 7.41 (d, J 8.1 Hz, 1H, Ar); 7.20 (d, J 1.9 Hz, 1H, Ar); 3.67 (s, 3H, CH$_3$); 2.54 (s, 3H, CH$_3$). M/Z (M[$^{79}$Br]+H)$^+$=396.

Compound 36: 2-Bromo-9-(6-methyl-pyridin-3-yl)-6,6-spirocyclopropyl-5,6-dihydro-benzo[f]pyrrolo[1,2-a][1,4]diazepin-4-one Compound 36 was obtained according to general procedure II, starting from compound 35. The reaction was completed by the addition of more ethylmagnesium bromide (1M solution in THF, 1.0 equiv.). Compound 36 was isolated as a grey solid in 65% yield. M/Z (M[$^{79}$Br]+H)$^+$=394.

Example 18

2-Bromo-5-methyl-9-(6-methyl-pyridin-3-yl)-spiro[benzo[f]pyrrolo[1,2-a][1,4]diazepine-6,1'-cyclopropan]-4(5H)-one

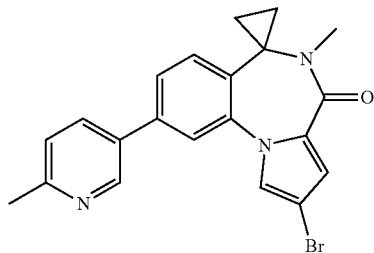 [SMILES: Cc1ccc(-c2ccc3c(c2)-n2cc(Br)cc2C(=O)N(C)C32CC2)cn1]

Example 18 was obtained according to general procedure III, starting from compound 36 in presence of iodomethane. The reaction mixture was stirred at room temperature for 1 hour. Purification by filtration after hydrolysis afforded the product as a yellow solid in 97% yield. $^1$H-NMR (400 MHz, DMSO-D6): 8.88 (d, J 2.4 Hz, 1H, Ar); 8.11 (dd, J 8.1, 2.4 Hz, 1H, Ar); 7.93 (d, J 2.0 Hz, 1H, Ar); 7.88 (d, J 1.7 Hz, 1H, Ar); 7.69 (dd, J 7.8, 1.7 Hz, 1H, Ar); 7.61 (d, J 7.8 Hz, 1H, Ar); 7.37 (d, J 8.1 Hz, 1H, Ar); 6.89 (d, J 2.0 Hz, 1H, Ar); 2.92 (s, 3H, CH$_3$); 2.52 (s, 3H, CH$_3$); 1.49 (m, 2H, cyclopropyl); 0.99 (m, 1H, cyclopropyl); 0.62 (m, 1H, cyclopropyl). M/Z (M[$^{79}$Br]+H)$^+$=408.0.

Compound 37: 1-[2-Cyano-5-(2-ethyl-pyridin-3-yl)-phenyl]-4-bromo-1H-pyrrole-2-carboxylic acid methyl ester Compound 37 was obtained according to general procedure V, starting from compound 2 and 2-ethylpyridine-3-boronic acid. It was isolated as a white solid in 70% yield. $^1$H-NMR (400 MHz, DMSO-D6): 8.59 (d, J 4.9 Hz, 1H, Ar); 8.09 (d, J 8.3 Hz, 1H, Ar); 7.69 (m, 3H, Ar); 7.67 (dd, J 7.8, 1.8 Hz, 1H, Ar); 7.35 (dd, J 8.3, 4.9 Hz, 1H, Ar); 7.18 (d, J 1.9 Hz, 1H, Ar); 3.67 (s, 3H, CH$_3$); 2.74 (q, J 7.7 Hz, 2H, CH$_2$—CH$_3$); 1.14 (t, J 7.7 Hz, 3H, CH$_2$—CH$_3$). M/Z (M[$^{79}$Br]+H)$^+$=410.

Compound 38: 2-Bromo-9-(2-ethyl-pyridin-3-yl)-spiro[benzo[f]pyrrolo[1,2-a][1,4]diazepine-6,1'-cyclopropan]-4(5H)-one Compound 38 was obtained according to general procedure II, starting from compound 37, as a brown solid in 50% yield. $^1$H-NMR (400 MHz, DMSO-D6): 8.82 (s, 1H, NH); 8.55 (dd, J 4.8, 1.6 Hz, 1H, Ar); 7.80 (d, J 2.0 Hz 1H, Ar); 7.69 (dd, J 7.8, 1.7 Hz, 1H, Ar); 7.56 (d, J 1.7 Hz, 1H, Ar); 7.51 (d, J 7.8 Hz, 1H, Ar); 7.34 (dd, J 7.8, 1.6 Hz, 1H, Ar); 7.31 (dd, J 7.8, 4.8 Hz, 1H, Ar); 6.91 (d, J 2.0 Hz, 1H, Ar); 2.74 (q, J 7.5 Hz, 2H, CH$_2$—CH$_3$); 1.59 (m, 1H, cyclopropyl); 1.23 (m, 1H, cyclopropyl); 1.14 (t, J 7.5 Hz, 3H, CH$_2$—CH$_3$); 0.88 (m, 1H, cyclopropyl); 0.59 (m, 1H, cyclopropyl). M/Z (M[$^{79}$Br]+H)$^+$=408.

Example 19

2-Bromo-5-methyl-9-(2-ethyl-pyridin-3-yl)-spiro[benzo[f]pyrrolo[1,2-a][1,4]diazepine-6,1'-cyclopropan]-4(5H)-one

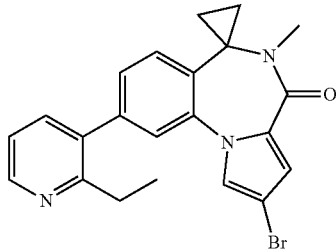 [SMILES: CCc1ncccc1-c1ccc2c(c1)-n1cc(Br)cc1C(=O)N(C)C21CC1]

Example 19 was obtained according to general procedure III, starting from compound 38 in presence of iodomethane. The reaction mixture was stirred at room temperature for 4 hours. Purification by filtration after hydrolysis afforded the product as a beige solid in 97% yield. $^1$H-NMR (400 MHz, DMSO-D6): 8.55 (dd, J 4.8, 1.3 Hz, 1H, Ar); 7.78 (d, J 2.0 Hz, 1H, Ar); 7.70 (dd, J 7.8, 1.5 Hz, 1H, Ar); 7.59 (m, 2H, Ar); 7.37 (dd, J 7.7, 1.3 Hz, 1H, Ar); 7.31 (dd, J 7.7, 4.8 Hz, 1H, Ar); 6.89 (d, J 2.0 Hz, 1H, Ar); 2.94 (s, 3H, CH$_3$); 2.74 (q, J 7.6 Hz, 2H, CH$_2$—CH$_3$); 1.50 (m, 2H, cyclopropyl); 1.16 (t, J 7.6 Hz, 3H, CH$_2$—CH$_3$); 1.00 (m, 1H, cyclopropyl); 0.65 (m, 1H, cyclopropyl). M/Z (M[$^{79}$Br]+H)$^+$=422.0.

General Procedure VI: Formation of Benzodiazepinone K, K' and K'' from Benzodiazepinone F, F', F''', Fi and Boronic Acid Derivatives G or from Benzodiazepinone J, Ji and Halide Derivative I (Scheme 1, 2, 3 and 4). Formation of R$_1$-Substituted Benzodiazepinone U, U', U''', U$_1$, U$_2$, U$_3$ and U$_4$ from Intermediate T, T', T''', T$_1$, T$_2$, T$_3$ and T$_4$ (Scheme 6, 7 and 8).

Method (i): Under Microwave Irradiation:

Under inert atmosphere, a mixture of halide F, F', F''', Fi, I, T, T', T''', T$_1$, T$_2$, T$_3$ or T$_4$ (1.0 equiv.), boronic acid derivative G or J, Ji (1.5 equiv.) and PdCl$_2$(dppf)$_2$ (0.10 equiv.) in a mixture of DMF or DMA (0.10 mol·L$^{-1}$) and aqueous Na$_2$CO$_3$ (1.2 mol·L$^{-1}$) was submitted to microwave irradiation at 150° C. for 15 minutes. The reaction mixture was hydrolysed and extracted twice with EtOAc. The organic layers were combined, washed with brine, dried over MgSO$_4$, concentrated and purified to afford the product.

Method (ii): Under Oil Bath Heating:

Under inert atmosphere, a mixture of halide F, F', F''', Fi, I, or T, T', T''', T$_1$, T$_2$, T$_3$, T$_4$ (1.0 equiv.), boronic acid derivative G or J, Ji (1.5 equiv.) and PdCl$_2$(dppf)$_2$ (0.10 equiv.) in a mixture of DMF or DMA (0.10 mol·L$^{-1}$) and aqueous Na$_2$CO$_3$ (1.2 mol·L$^{-1}$) was heated at 110° C. for 16 hours. After cooling, the reaction mixture was hydrolysed and extracted twice with EtOAc. The organic layers were combined, washed with brine, dried over MgSO$_4$, concentrated and purified to afford the product.

General Procedure VII: Formation of HCl Salt

Method (i): in DCM:

To a solution of the free base in dichloromethane, HCl (2N solution in Et2O, 5 equiv.) was added. The resulting precipitate was collected, washed with Et$_2$O and dried at 50° C. under reduced pressure with P$_2$O$_5$.

Method (ii): Concentration from MeOH:

To a solution or suspension of the free base in methanol, HCl (1.25N solution in MeOH, 5 equiv.) was added. The mixture was vigorously stirred, then concentrated. The residue was taken in Et₂O. The resulting solid was collected, washed with Et₂O and dried at 50° C. under reduced pressure with P₂O₅.

Method (iii): Filtration from MeOH:

The free base was suspended in MeOH and HCl in methanol (1.25N solution in MeOH, 5 equiv.) was added. The suspension was vigorously stirred, and then the solid was collected, washed with Et₂O and dried at 50° C. under reduced pressure with P₂O₅.

Example 20

5-Methyl-9-(2-methyl-pyridin-3-yl)-spiro[benzo[f]pyrrolo[1,2-a][1,4]diazepine-6,1'-cyclopropan]-4(5H)-one

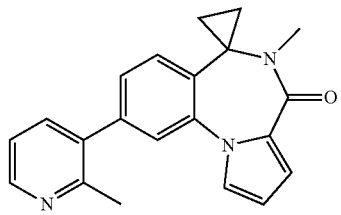 [SMILES: Cc1ncccc1-c1ccc2c(c1)-n1cccc1C(=O)N(C)C21CC1]

Example 20 was obtained according to general procedure VI(ii) starting from example 1 in presence of 2-methylpyridine-3-boronic pinacol ester. Purification by flash column chromatography on silica gel (MeOH in CH₂Cl₂, 1% to 5%) afforded the product as a grey solid in 62% yield. ¹H-NMR (400 MHz, DMSO-D6): 8.50 (dd, J 4.8, 1.6 Hz, 1H, Ar); 7.73 (dd, J 7.6, 1.6 Hz, 1H, Ar); 7.60 (d, J 7.6 Hz, 1H, Ar); 7.58 (d, J 1.6 Hz, 1H, Ar); 7.56 (dd, J 2.8, 1.8 Hz, 1H, Ar); 7.38 (dd, J 7.7, 1.6 Hz, 1H, Ar); 7.33 (dd, J 7.7, 4.8 Hz, 1H, Ar); 6.87 (dd, J 3.7, 1.8 Hz, 1H, Ar); 6.40 (dd, J 3.7, 2.8 Hz, 1H, Ar); 2.95 (s, 3H, CH₃); 2.69 (s, 3H, CH₃); 1.50 (m, 2H, cyclopropyl); 0.94 (m, 1H, cyclopropyl); 0.59 (m, 1H, cyclopropyl). M/Z (M+H)⁺=330.0. MP: 200-210° C.

Example 21

5-Methoxymethyl-9-(2-methyl-pyridin-3-yl)-spiro[benzo[f]pyrrolo[1,2-a][1,4]diazepine-6,1'-cyclopropan]-4(5H)-one

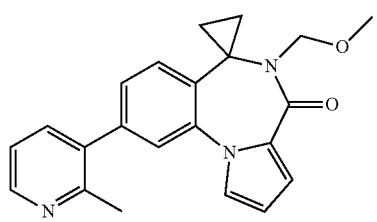 [SMILES: COCN1C(=O)c2cccn2-c2cc(-c3cccnc3C)ccc2C12CC2]

Example 21 was obtained according to general procedure VI(ii) starting from example 2 in presence of 2-methylpyridine-3-boronic pinacol ester. Purification by flash column chromatography on silica gel (100% EtOAc) afforded the product as a white solid in 20% yield. ¹H-NMR (400 MHz, DMSO-D6): 8.42 (dd, J 4.8, 1.6 Hz, 1H, Ar); 7.65 (dd, J 7.7, 1.6 Hz, 1H, Ar); 7.54 (dd, J 2.8, 1.8 Hz, 1H, Ar); 7.51 (d, J 7.8 Hz, 1H, Ar); 7.50 (d, J 1.7 Hz, 1H, Ar); 7.30 (dd, J 7.8, 1.7 Hz, 1H, Ar); 7.25 (dd, J 7.7, 4.8 Hz, 1H, Ar); 6.90 (dd, J 3.7, 1.8 Hz, 1H, Ar); 6.37 (dd, J 3.7, 2.8 Hz, 1H, Ar); 4.92 (d, J 10.3 Hz, 1H, CH); 4.65 (d, J 10.3 Hz, 1H, CH); 2.91 (s, 3H, CH₃); 2.38 (s, 3H, CH₃); 1.64 (m, 1H, cyclopropyl); 1.48 (m, 1H, cyclopropyl); 0.84 (m, 1H, cyclopropyl); 0.52 (m, 1H, cyclopropyl). M/Z (M+H)⁺=360.0. MP: 138-142° C.

Example 22

5-Methyl-9-(pyridin-4-yl)-spiro[benzo[f]pyrrolo[1,2-a][1,4]diazepine-6,1'-cyclopropan]-4(5H)-one, hydrochloride

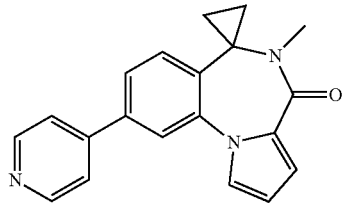 [SMILES: CN1C(=O)c2cccn2-c2cc(-c3ccncc3)ccc2C12CC2]

Example 22 was obtained according to general procedure VI(i) starting from example 1 in presence of 4-pyridineboronic acid. Purification by preparative HPLC afforded the product as a grey solid in 43% yield. Salt formation was performed by method VII(i). ¹H-NMR (400 MHz, DMSO-D6): 8.97 (bs, 2H, Ar); 8.43 (d, J 5.8 Hz, 2H, Ar); 8.11 (d, J 1.7 Hz, 1H, Ar); 7.95 (dd, J 7.9, 1.7 Hz, 1H, Ar); 7.76 (m, 1H, Ar); 7.74 (d, J 7.9 Hz, 1H, Ar); 6.90 (dd, J 3.7, 1.8 Hz, 1H, Ar); 6.47 (dd, J 3.7, 2.8 Hz, 1H, Ar); 2.94 (s, 3H, CH₃); 1.53 (m, 2H, cyclopropyl); 0.96 (m, 1H, cyclopropyl); 0.58 (m, 1H, cyclopropyl). Proton for HCl salt not observed. M/Z (M+H)⁺=316.3. MP>250° C.

Example 23

5-Methyl-9-(pyridin-3-yl)-spiro[benzo[f]pyrrolo[1,2-a][1,4]diazepine-6,1'-cyclopropan]-4(5H)-one, hydrochloride

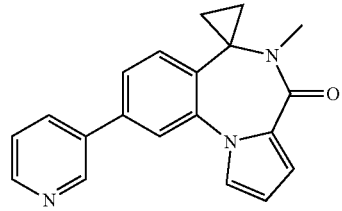

Example 23 was obtained according to general procedure VI(i) starting from example 1 in presence of 3-pyridineboronic acid. Purification by preparative HPLC afforded the product as a grey solid in 50% yield. Salt formation was performed by method VII(ii). ¹H-NMR (400 MHz, DMSO-D6): 9.28 (s, 1H, Ar); 8.83 (d, J 5.2 Hz, 1H, Ar); 8.74 (d, J 8.0 Hz, 1H, Ar); 8.00 (d, J 1.7 Hz, 1H, Ar); 7.96 (dd, J 8.0, 5.2 Hz, 1H, Ar); 7.80 (dd, J 7.9, 1.7 Hz, 1H, Ar); 7.73 (dd, J 2.8, 1.8 Hz, 1H, Ar); 7.69 (d, J 7.9 Hz, 1H, Ar); 6.89 (dd, J 3.7, 1.8 Hz, 1H, Ar); 6.46 (dd, J 3.7, 2.8 Hz, 1H, Ar); 2.94 (s, 3H, CH$_3$); 1.52 (m, 2H, cyclopropyl); 0.96 (m, 1H, cyclopropyl); 0.56 (m, 1H, cyclopropyl). Proton for HCl salt not observed. M/Z (M+H)$^+$=316.3. MP>250° C.

Example 24

5-Methyl-9-(2-ethylpyridin-3-yl)-spiro[benzo[f]pyrrolo[1,2-a][1,4]diazepine-6,1'-cyclopropan]-4(5H)-one, hydrochloride

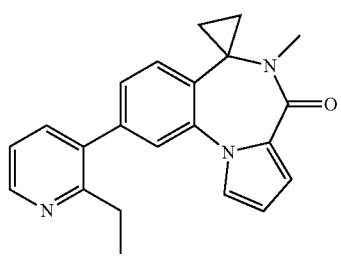 [SMILES: CCc1ncccc1-c1ccc2c(c1)-n1cccc1C(=O)N(C)C21CC1]

Example 24 was obtained according to general procedure VI(i) starting from example 1 in presence of 2-ethylpyridine-3-boronic acid. Purification by preparative HPLC afforded the product as a grey solid in 23% yield. Salt formation was performed by method VII(ii). $^1$H-NMR (400 MHz, DMSO-D6): 8.76 (d, J 5.1 Hz, 1H, Ar); 8.26 (bs, 1H, Ar); 7.78 (bs, 1H, Ar); 7.66 (m, 2H, Ar); 7.53 (dd, J 2.8, 1.8 Hz, 1H, Ar); 7.42 (dd, J 7.8, 1.6 Hz, 1H, Ar); 6.88 (dd, J 3.7, 1.8 Hz, 1H, Ar); 6.42 (dd, J 3.7, 2.8 Hz, 1H, Ar); 2.94 (s, 3H, CH$_3$); 2.94 (q, J 7.4 Hz, 2H, C$\underline{H_2}$—CH$_3$); 1.51 (m, 2H, cyclopropyl); 1.19 (t, J 7.4 Hz, 3H, CH$_2$—C$\underline{H_3}$); 0.95 (m, 1H, cyclopropyl); 0.59 (m, 1H, cyclopropyl). Proton for HCl salt not observed. M/Z (M+H)$^+$=344.4. MP: 136-143° C.

Example 25

5-Methyl-9-(6-methylpyridin-3-yl)-spiro[benzo[f]pyrrolo[1,2-a][1,4]diazepine-6,1'-cyclopropan]-4(5H)-one, hydrochloride

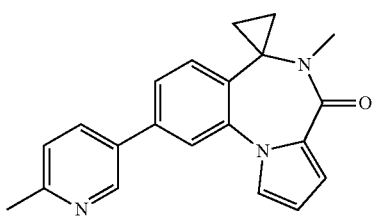 [SMILES: Cc1ccc(-c2ccc3c(c2)-n2cccc2C(=O)N(C)C32CC2)cn1]

Example 25 was obtained according to general procedure VI(i) starting from example 1 in presence of 2-methylpyridine-5-boronic acid. Purification preparative HPLC afforded the product as a white solid in 69% yield. Salt formation was performed by method VII(ii). $^1$H-NMR (400 MHz, DMSO-D6): 8.99 (d, J 1.3 Hz, 1H, Ar); 8.57 (dd, J 8.5, 1.3 Hz, 1H, Ar); 7.78 (d, J 1.7 Hz, 1H, Ar); 7.72 (d, J 8.5 Hz, 1H, Ar); 7.59 (dd, J 7.8, 1.7 Hz, 1H, Ar); 7.51 (dd, J 2.8, 1.8 Hz, Ar); 7.46 (d, J 7.8 Hz, 1H, Ar); 6.66 (dd, J 3.7, 1.8 Hz, 1H, Ar); 6.23 (dd, J 3.7, 2.8 Hz, 1H, Ar); 2.71 (s, 3H, CH$_3$); 2.55 (s, 3H, CH$_3$); 1.29 (m, 2H, cyclopropyl); 0.74 (m, 1H, cyclopropyl); 0.34 (m, 1H, cyclopropyl). Proton for HCl salt not observed. M/Z (M+H)$^+$=330.4. MP: 205-215° C.

Example 26

5-Methyl-9-(2-methylpyridin-4-yl)-spiro[benzo[f]pyrrolo[1,2-a][1,4]diazepine-6,1'-cyclopropan]-4(5H)-one, hydrochloride

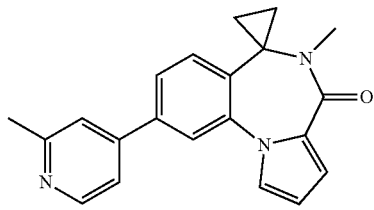 [SMILES: Cc1cc(-c2ccc3c(c2)-n2cccc2C(=O)N(C)C32CC2)ccn1]

Example 26 was obtained according to general procedure VI(i) starting from example 1 in presence of 2-methylpyridine-4-boronic acid. Purification by preparative HPLC afforded the product as a grey solid in 34% yield. Salt formation was performed by method VII(ii). $^1$H-NMR (400 MHz, DMSO-D6): 8.82 (d, J 6.1 Hz, 1H, Ar); 8.35 (bs, 1H, Ar); 8.25 (d, J 6.1 Hz, 1H, Ar); 8.09 (d, J 1.6 Hz, 1H, Ar); 7.93 (dd, J 8.0, 1.6 Hz, 1H, Ar); 7.73 (m, 2H, Ar); 6.90 (dd, J 3.7, 1.8 Hz, 1H, Ar); 6.47 (dd, J 3.7, 2.8 Hz, 1H, Ar); 2.93 (s, 3H, CH$_3$); 2.76 (s, 3H, CH$_3$); 1.52 (m, 2H, cyclopropyl); 0.97 (m, 1H, cyclopropyl); 0.59 (m, 1H, cyclopropyl). Proton for HCl salt not observed. M/Z (M+H)$^+$=330.4. MP: 183-193° C.

Example 27

5-Methyl-9-(3,5-dimethyl-1H-pyrazol-4-yl)-spiro[benzo[f]pyrrolo[1,2-a][1,4]diazepine-6,1'-cyclopropan]-4(5H)-one

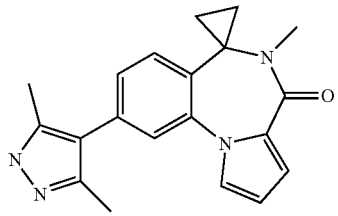 [SMILES: Cc1n[nH]c(C)c1-c1ccc2c(c1)-n1cccc1C(=O)N(C)C21CC1]

Example 27 was obtained according to general procedure VI(i) starting from example 1 in presence of 3,5-dimethylpyrazole-4-boronic pinacol ester. Purification by preparative HPLC afforded the product as a grey solid in 44% yield. $^1$H-NMR (400 MHz, DMSO-D6): 7.52 (d, J 7.8 Hz, 1H, Ar); 7.47 (dd, J 2.8, 1.8 Hz, 1H, Ar); 7.42 (d, J 1.6 Hz, 1H, Ar); 7.26 (dd, J 7.8, 1.6 Hz, 1H, Ar); 6.84 (dd, J 3.7, 1.8 Hz, 1H, Ar); 6.39 (dd, J 3.7, 2.8 Hz, 1H, Ar); 2.92 (s, 3H, CH$_3$); 2.25 (s, 6H, 2CH$_3$); 1.47 (m, 2H, cyclopropyl); 0.90 (m, 1H, cyclopropyl); 0.56 (m, 1H, cyclopropyl). M/Z (M+H)$^+$=333.4. MP: 115-125° C.

Example 28

5-Methyl-9-(3-trifluoromethyl-1H-pyrazol-4-yl)-spiro[benzo[f]pyrrolo[1,2-a][1,4]diazepine-6,1'-cyclopropan]-4(5H)-one

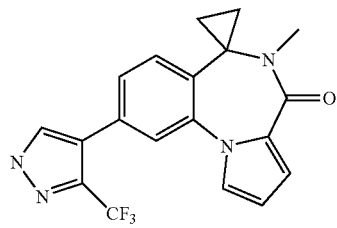 [SMILES: CN1C(=O)c2cccn2-c2cc(-c3c[nH]nc3C(F)(F)F)ccc2C12CC2]

Example 28 was obtained according to general procedure VI(i) starting from example 1 in presence of 3-trifluoromethyl-1H-pyrazole-4-boronic pinacol ester. Purification by preparative HPLC afforded the product as a yellow solid in 54% yield. $^1$H-NMR (400 MHz, DMSO-D6): 13.83 (bs, 1H, NH); 8.34 (s, 1H, Ar); 7.56 (m, 2H, Ar); 7.51 (dd, J 2.8, 1.8 Hz, 1H, Ar); 7.37 (d, J 7.8 Hz, 1H, Ar); 6.86 (dd, J 3.7, 1.8 Hz, 1H, Ar); 6.42 (dd, J 3.7, 2.8 Hz, 1H, Ar); 2.92 (s, 3H, CH$_3$); 1.47 (m, 2H, cyclopropyl); 0.92 (m, 1H, cyclopropyl); 0.57 (m, 1H, cyclopropyl). M/Z (M+H)$^+$=373.4. MP>250° C.

Example 29

5-Methyl-9-(1-methyl-pyrazol-4-yl)-spiro[benzo[f]pyrrolo[1,2-a][1,4]diazepine-6,1'-cyclopropan]-4(5H)-one

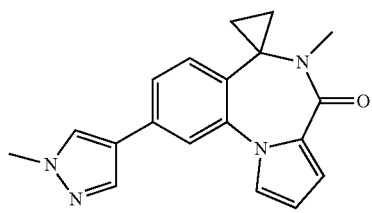 [SMILES: CN1C(=O)c2cccn2-c2cc(-c3cnn(C)c3)ccc2C12CC2]

Example 29 was obtained according to general procedure VI(i) starting from example 1 in presence of 1-methylpyrazole-4-boronic pinacol ester. Purification by preparative HPLC afforded the product as a yellow solid in 58% yield. $^1$H-NMR (400 MHz, DMSO-D6): 8.24 (s, 1H, Ar); 7.96 (s, 1H, Ar); 7.70 (d, J 1.6 Hz, 1H, Ar); 7.56 (dd, J 2.8, 1.8 Hz, 1H, Ar); 7.50 (dd, J 7.8, 1.6 Hz, 1H, Ar); 7.45 (d, J 7.8 Hz, 1H, Ar); 6.84 (dd, J 3.7, 1.8 Hz, 1H, Ar); 6.41 (dd, J 3.7, 2.8 Hz, 1H, Ar); 3.87 (s, 3H, CH$_3$); 2.90 (s, 3H, CH$_3$); 1.43 (m, 2H, cyclopropyl); 0.88 (m, 1H, cyclopropyl); 0.52 (m, 1H, cyclopropyl). M/Z (M+H)$^+$=319.3. MP: 75-83° C.

Example 30

5-Methyl-9-(1-methyl-pyrazol-5-yl)-spiro[benzo[f]pyrrolo[1,2-a][1,4]diazepine-6,1'-cyclopropan]-4(5H)-one

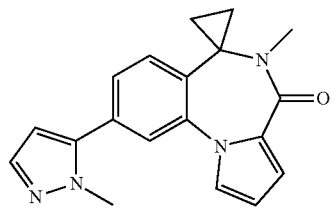 [SMILES: CN1C(=O)c2cccn2-c2cc(-c3ccnn3C)ccc2C12CC2]

Example 30 was obtained according to general procedure VI(i) starting from example 1 in presence of 1-methylpyrazole-5-boronic pinacol ester. Purification by preparative HPLC afforded the product as a grey solid in 52% yield. $^1$H-NMR (400 MHz, DMSO-D6): 7.67 (s, 1H, Ar); 7.60 (m, 2H, Ar); 7.49 (m, 2H, Ar); 6.86 (dd, J 3.7, 1.8 Hz, 1H, Ar); 6.53 (d, J 1.8 Hz, 1H, Ar); 6.41 (dd, J 3.7, 2.8 Hz, 1H, Ar); 3.90 (s, 3H, CH$_3$); 2.93 (s, 3H, CH$_3$); 1.49 (m, 2H, cyclopropyl); 0.94 (m, 1H, cyclopropyl); 0.57 (m, 1H, cyclopropyl). M/Z (M+H)$^+$=319.4. MP: 214-220° C.

Example 31

5-Methyl-9-(6-fluoropyridin-3-yl)-spiro[benzo[f]pyrrolo[1,2-a][1,4]diazepine-6,1'-cyclopropan]-4(5H)-one

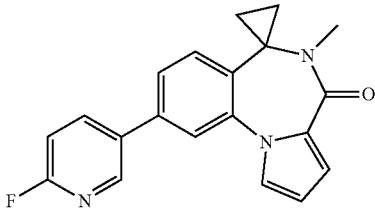

Example 31 was obtained according to general procedure VI(i) starting from example 1 in presence of 2-fluoro-5-pyridinylboronic acid. Purification by flash column chromatography on silica gel (EtOAc in cylohexane, 0% to 50%) afforded the product as a white solid in 43% yield. $^1$H-NMR (400 MHz, DMSO-D6): 8.73 (d, J 2.4 Hz, 1H, Ar); 8.46 (dt, J 8.3, 2.6 Hz, 1H, Ar); 7.91 (d, J 1.6 Hz, 1H, Ar); 7.74 (dd, J 2.8, 1.8 Hz, 1H, Ar); 7.73 (dd, J 7.8, 1.6 Hz, 1H, Ar); 7.67 (d, J 7.8 Hz, 1H, Ar); 7.37 (dd, J 8.3, 2.6 Hz, 1H, Ar); 6.92 (dd, J 3.7, 1.8 Hz, 1H, Ar); 6.48 (dd, J 3.7, 2.8 Hz, 1H, Ar); 2.98 (s, 3H, CH$_3$); 1.54 (m, 2H, cyclopropyl); 0.99 (m, 1H, cyclopropyl); 0.60 (m, 1H, cyclopropyl). M/Z (M+H)$^+$=334.3. MP: 171-176° C.

Example 32

5-Methyl-9-(6-fluoro-2-methylpyridin-3-yl)-spiro[benzo[f]pyrrolo[1,2-a][1,4]diazepine-6,1'-cyclopropan]-4(5H)-one

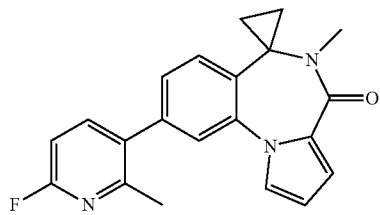 [SMILES: Cc1nc(F)ccc1-c1ccc2c(c1)-n1cccc1C(=O)N(C)C21CC1]

Example 32 was obtained according to general procedure VI(i) starting from example 1 in presence of 2-fluoro-6-picoline-5-boronic acid. Purification by flash column chromatography on silica gel (EtOAc in cylohexane, 0% to 50%) afforded the product as a beige solid in 64% yield. $^1$H-NMR (400 MHz, DMSO-D6): 7.95 (t, J 8.2 Hz, 1H, Ar); 7.60 (d, J 7.8 Hz, 1H, Ar); 7.59 (d, J 1.6 Hz, 1H, Ar); 7.56 (dd, J 2.8, 1.8 Hz, 1H, Ar); 7.38 (dd, J 7.8, 1.6 Hz, 1H, Ar); 7.11 (dd, J 8.2, 3.0 Hz, 1H, Ar); 6.87 (dd, J 3.7, 1.8 Hz, 1H, Ar); 6.41 (dd, J 3.7, 2.8 Hz, 1H, Ar); 2.94 (s, 3H, CH$_3$); 2.43 (s, 3H, CH$_3$); 1.50 (m, 2H, cyclopropyl); 0.93 (m, 1H, cyclopropyl); 0.58 (m, 1H, cyclopropyl). M/Z (M+H)$^+$=348.3. MP: 198-202° C.

Example 33

5-Methyl-9-(2-fluoropyridin-3-yl)-spiro[benzo[f]pyrrolo[1,2-a][1,4]diazepine-6,1'-cyclopropan]-4(5H)-one

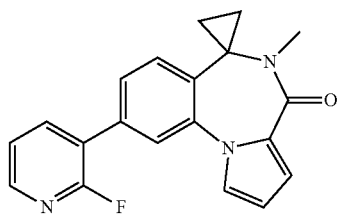

Example 33 was obtained according to general procedure VI(i), starting from example 1 in presence of 2-fluoro-3-pyridineboronic acid. Purification by flash column chromatography on silica gel (EtOAc in cylohexane, 0% to 60%) afforded the product as a white solid in 70% yield. $^1$H-NMR (400 MHz, DMSO-D6): 8.28 (m, 2H, Ar); 7.77 (s, 1H, Ar); 7.64 (d, J 7.8 Hz, 1H, Ar); 7.59 (m, 2H, Ar); 7.51 (m, 1H, Ar); 6.88 (dd, J 3.7, 1.8 Hz, 1H, Ar); 6.43 (dd, J 3.7, 2.8 Hz, 1H, Ar); 2.94 (s, 3H, CH$_3$); 1.51 (m, 2H, cyclopropyl); 0.96 (m, 1H, cyclopropyl); 0.58 (m, 1H, cyclopropyl). M/Z (M+H)$^+$=334.3. MP: 158-162° C.

Example 34

5-Methyl-9-(2-fluoropyridin-4-yl)-spiro[benzo[f]pyrrolo[1,2-a][1,4]diazepine-6,1'-cyclopropan]-4(5H)-one

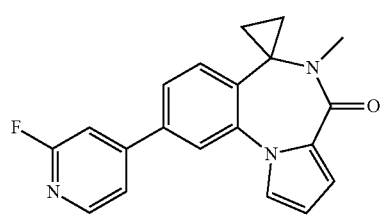

Example 34 was obtained according to general procedure VI(i), starting from example 1 in presence of 2-fluoro-4-pyridineboronic acid. Purification by flash column chromatography on silica gel (EtOAc in cylohexane, 0% to 60%) afforded the product as a beige solid in 76% yield. $^1$H-NMR (400 MHz, DMSO-D6): 8.33 (d, J 5.3 Hz, 1H, Ar); 7.97 (d, J 1.8 Hz, 1H, Ar); 7.81 (m, 2H, Ar); 7.72 (dd, J 2.8, 1.8 Hz, 1H, Ar); 7.69 (m, 1H, Ar); 7.65 (d, J 8.0 Hz, 1H, Ar); 6.88 (dd, J 3.7, 1.8 Hz, 1H, Ar); 6.44 (dd, J 3.7, 2.8 Hz, 1H, Ar); 2.93 (s, 3H, CH$_3$); 1.50 (m, 2H, cyclopropyl); 0.93 (m, 1H, cyclopropyl); 0.56 (m, 1H, cyclopropyl). M/Z (M+H)$^+$=334.3. MP: 197-201° C.

Example 35

5-Methyl-9-(2-trifluoromethylpyridin-4-yl)-spiro[benzo[f]pyrrolo[1,2-a][1,4]diazepine-6,1'-cyclopropan]-4(5H)-one

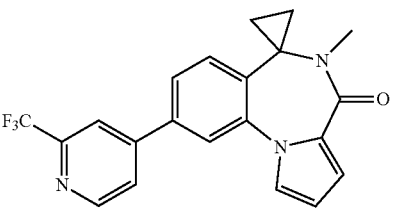 [SMILES: CN1C(=O)c2cccn2-c2cc(-c3ccnc(C(F)(F)F)c3)ccc2C12CC2]

Example 35 was obtained according to general procedure VI(i), starting from example 1 in presence of 2-trifluoromethylpyridine-4-boronic acid. Purification by flash column chromatography on silica gel (EtOAc in cylohexane, 20% to 80%) afforded the product as a white solid in 89% yield. $^1$H-NMR (400 MHz, DMSO-D6): 8.86 (d, J 5.1 Hz, 1H, Ar); 8.35 (d, J 1.3 Hz, 1H, Ar); 8.17 (dd, J 5.1, 1.3 Hz, 1H, Ar); 8.05 (d, J 1.6 Hz, 1H, Ar); 7.87 (dd, J 7.9, 1.6 Hz, 1H, Ar); 7.75 (dd, J 2.8, 1.8 Hz, 1H, Ar); 7.68 (d, J 7.9 Hz, 1H, Ar); 6.89 (dd, J 3.7, 1.8 Hz, 1H, Ar); 6.45 (dd, J 3.7, 2.8 Hz, 1H, Ar); 2.94 (s, 3H, CH$_3$); 1.51 (m, 2H, cyclopropyl); 0.96 (m, 1H, cyclopropyl); 0.57 (m, 1H, cyclopropyl). M/Z (M+H)$^+$=384.3. MP: 169-174° C.

Example 36

5-Methyl-9-(2-trifluoromethylpyridin-3-yl)-spiro[benzo[f]pyrrolo[1,2-a][1,4]diazepine-6,1'-cyclopropan]-4(5H)-one

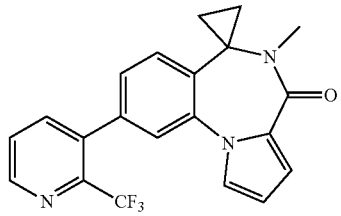 [SMILES: CN1C(=O)c2cccn2-c2cc(-c3cccnc3C(F)(F)F)ccc2C12CC2]

Example 36 was obtained according to general procedure VI(i), starting from example 1 in presence of 2-trifluoromethylpyridine-3-boronic acid. Purification by flash column chromatography on silica gel (EtOAc in cylohexane, 0% to 60%) afforded the product as a white solid in 41% yield. $^1$H-NMR (400 MHz, DMSO-D6): 8.80 (dd, J 4.7, 1.0 Hz, 1H, Ar); 8.06 (dd, J 7.9, 1.0 Hz, 1H, Ar); 7.81 (dd, J 7.9, 4.7 Hz, 1H, Ar); 7.61 (d, J 7.8 Hz, 1H, Ar); 7.60 (d, J 1.6 Hz, 1H, Ar); 7.48 (dd, J 2.8, 1.8 Hz, 1H, Ar); 7.33 (dd, J 7.8, 1.6 Hz, 1H, Ar); 6.87 (dd, J 3.7, 1.8 Hz, 1H, Ar); 6.40 (dd, J 3.7, 2.8 Hz, 1H, Ar); 2.94 (s, 3H, CH$_3$); 1.50 (m, 2H, cyclopropyl); 0.94 (m, 1H, cyclopropyl); 0.58 (m, 1H, cyclopropyl). M/Z (M+H)$^+$=384.3. MP: 160-165° C.

Example 37

5-Methyl-9-(4-trifluoromethylpyridin-3-yl)-spiro[benzo[f]pyrrolo[1,2-a][1,4]diazepine-6,1'-cyclopropan]-4(5H)-one

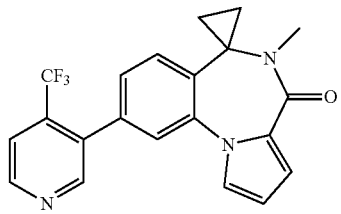 [SMILES: CN1C(=O)c2cccn2-c2cc(-c3cnccc3C(F)(F)F)ccc2C12CC2]

Example 37 was obtained according to general procedure VI(i), starting from example 1 in presence of 4-trifluoromethylpyridine-3-boronic pinacol ester. Purification by flash column chromatography on silica gel (EtOAc in cylohexane, 0% to 60%) afforded the product as a beige solid in 53% yield. $^1$H-NMR (400 MHz, DMSO-D6): 8.92 (d, J 5.2 Hz, 1H, Ar); 8.82 (s, 1H, Ar); 7.89 (d, J 5.2 Hz, 1H, Ar); 7.64 (m, 2H, Ar); 7.51 (dd, J 2.8, 1.8 Hz, 1H, Ar); 7.37 (d, J 7.8 Hz, 1H, Ar); 6.88 (dd, J 3.7, 1.8 Hz, 1H, Ar); 6.42 (dd, J 3.7, 2.8 Hz, 1H, Ar); 2.95 (s, 3H, CH$_3$); 1.52 (m, 2H, cyclopropyl); 0.96 (m, 1H, cyclopropyl); 0.60 (m, 1H, cyclopropyl). M/Z (M+H)$^+$=384.3. MP: 67-78° C.

Example 38

5-Methyl-9-(3-methylpyridin-4-yl)-spiro[benzo[f]pyrrolo[1,2-a][1,4]diazepine-6,1'-cyclopropan]-4(5H)-one, hydrochloride

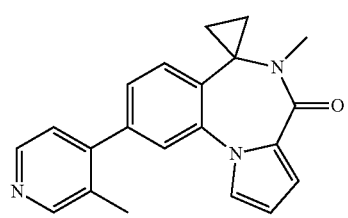 [SMILES: Cc1cnccc1-c1ccc2c(c1)-n1cccc1C(=O)N(C)C21CC1]

Example 38 was obtained according to general procedure VI(i), starting from example 1 in presence of 3-methylpyridine-4-boronic acid. Purification by flash column chromatography on silica gel (EtOAc in cylohexane, 0% to 50%) afforded the product as a brown solid in 36% yield. Salt formation was performed by method (i). $^1$H-NMR (400 MHz, DMSO-D6): 8.90 (s, 1H, Ar); 8.82 (d, J 5.8 Hz, 1H, Ar); 7.97 (d, J 5.8 Hz, 1H, Ar); 7.71 (d, J 1.7 Hz, 1H, Ar); 7.69 (d, J 7.9 Hz, 1H, Ar); 7.57 (dd, J 2.8, 1.8 Hz, 1H, Ar); 7.51 (dd, J 7.9, 1.7 Hz, 1H, Ar); 6.88 (dd, J 3.7, 1.8 Hz, 1H, Ar); 6.43 (dd, J 3.7, 2.8 Hz, 1H, Ar); 2.94 (s, 3H, CH$_3$); 2.44 (s, 3H, CH$_3$); 1.52 (m, 2H, cyclopropyl); 0.96 (m, 1H, cyclopropyl); 0.58 (m, 1H, cyclopropyl). Proton for HCl salt not observed. M/Z (M+H)$^+$=330.4. MP>250° C.

Example 39

5-Methyl-9-(3,4-dimethoxy-phenyl)-spiro[benzo[f]pyrrolo[1,2-a][1,4]diazepine-6,1'-cyclopropan]-4(5H)-one

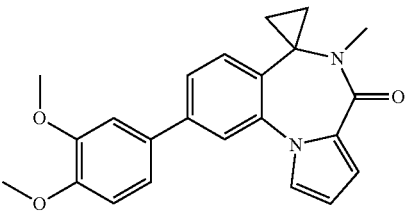 [SMILES: COc1ccc(-c2ccc3c(c2)-n2cccc2C(=O)N(C)C32CC2)cc1OC]

Example 39 was obtained according to general procedure VI(i), starting from example 1 in presence of 3,4-dimethoxyphenylboronic acid. Purification by flash column chromatography on silica gel (EtOAc in cylohexane, 0% to 50%) afforded the product as a beige solid in 72% yield. $^1$H-NMR (400 MHz, DMSO-D6): 7.72 (d, J 1.6 Hz, 1H, Ar); 7.66 (dd, J 2.8, 1.8 Hz, 1H, Ar); 7.58 (dd, J 7.9, 1.6 Hz, 1H, Ar); 7.53 (d, J 7.9 Hz, 1H, Ar); 7.29 (m, 2H, Ar); 7.05 (d, J 8.2 Hz, 1H, Ar); 6.85 (dd, J 3.7, 1.8 Hz, 1H, Ar); 6.41 (dd, J 3.7, 2.8 Hz, 1H, Ar); 3.85 (s, 3H, OCH$_3$); 3.80 (s, 3H, OCH$_3$); 2.92 (s, 3H, CH$_3$); 1.47 (m, 2H, cyclopropyl); 0.91 (m, 1H, cyclopropyl); 0.53 (m, 1H, cyclopropyl). M/Z (M+H)$^+$=375.2. MP: 150-154° C.

Example 40

5-Methyl-9-(6-amino-5-trifluoromethyl-pyridin-3-yl)-spiro[benzo[f]pyrrolo[1,2-a][1,4]diazepine-6,1'-cyclopropan]-4(5H)-one, hydrochloride

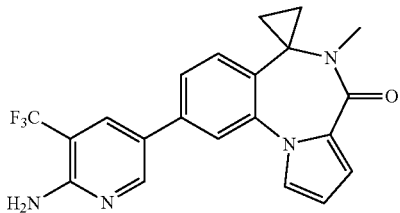

Example 40 was obtained according to general procedure VI(i), starting from example 1 in presence of 2-amino-3-trifluoromethylpyridine-5-boronic pinacol ester. Purification by flash column chromatography on silica gel (EtOAc in cylohexane, 30% to 80%) afforded the product as a beige solid in 64% yield. Salt formation was performed by method VII(ii). $^1$H-NMR (400 MHz, DMSO-D6): 8.67 (s, 1H, Ar); 8.27 (s, 1H, Ar); 7.80 (d, J 1.5 Hz, 1H, Ar); 7.68 (dd, J 2.8, 1.8 Hz, 1H, Ar); 7.62 (dd, J 7.8, 1.5 Hz, 1H, Ar); 7.55 (d, J 7.8 Hz, 1H, Ar); 7.15 (bs, 2H, NH$_2$); 6.85 (dd, J 3.7, 1.8 Hz, 1H, Ar); 6.41 (dd, J 3.7, 2.8 Hz, 1H, Ar); 2.91 (s, 3H, CH$_3$); 1.47 (m, 2H, cyclopropyl); 0.91 (m, 1H, cyclopropyl); 0.52 (m, 1H, cyclopropyl). Proton for HCl salt not observed. M/Z (M+H)$^+$=399.3. MP>250° C.

Example 41

5-Methyl-9-(imidazo[1,2-a]pyridin-6-yl)-spiro[benzo[f]pyrrolo[1,2-a][1,4]diazepine-6,1'-cyclopropan]-4(5H)-one, hydrochloride

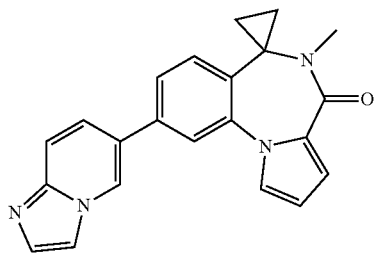 [SMILES: CN1C(=O)c2cccn2-c2cc(-c3ccc4nccn4c3)ccc2C12CC2]

Example 41 was obtained according to general procedure VI(i), starting from example 1 in presence of imidazo[1,2-a]pyridine-6-boronic acid. Purification by flash column chromatography on silica gel (MeOH in CH$_2$Cl$_2$, 0% to 5%) afforded the product as a yellow solid in 59% yield. Salt formation was performed by method VII(ii). $^1$H-NMR (400 MHz, DMSO-D6): 9.45 (s, 1H, Ar); 8.42 (dd, J 9.4, 1.3 Hz, 1H, Ar); 8.32 (s, 1H, Ar); 8.25 (d, J 1.7 Hz, 1H, Ar); 8.08 (d, J 9.4 Hz, 1H, Ar); 7.96 (d, J 1.3 Hz, 1H, Ar); 7.76 (dd, J 7.8, 1.7 Hz, 1H, Ar); 7.71 (d, J 7.8 Hz, 1H, Ar); 7.69 (dd, J 2.8, 1.8 Hz, 1H, Ar); 6.90 (dd, J 3.7, 1.8 Hz, 1H, Ar); 6.47 (dd, J 3.7, 2.8 Hz, 1H, Ar); 2.95 (s, 3H, CH$_3$); 1.52 (m, 2H, cyclopropyl); 0.97 (m, 1H, cyclopropyl); 0.58 (m, 1H, cyclopropyl). Proton for HCl salt not observed. M/Z (M+H)$^+$=355.2. MP>250° C.

Example 42

5-Methyl-9-(6-morpholin-4-yl-pyridin-3-yl)-spiro[benzo[f]pyrrolo[1,2-a][1,4]diazepine-6,1'-cyclopropan]-4(5H)-one, hydrochloride

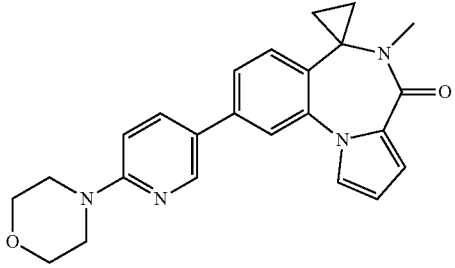 [SMILES: CN1C(=O)c2cccn2-c2cc(-c3ccc(N4CCOCC4)nc3)ccc2C12CC2]

Example 42 was obtained according to general procedure VI(i), starting from example 1 in presence of 6-(morpholin-4-yl)pyridine-3-boronic acid. Purification by flash column chromatography on silica gel (EtOAc in cyclohexane, 30% to 80%) afforded the product as a yellow solid in 57% yield. Salt formation was performed by method VII(ii). $^1$H-NMR (400 MHz, DMSO-D6): 8.50 (s, 1H, Ar); 8.27 (d, J 8.7 Hz, 1H, Ar); 7.80 (d, J 1.3 Hz, 1H, Ar); 7.69 (dd, J 2.8, 1.8 Hz, 1H, Ar); 7.63 (dd, J 7.8, 1.3 Hz, 1H, Ar); 7.58 (d, J 7.8 Hz, 1H, Ar); 7.25 (d, J 8.7 Hz, 1H, Ar); 6.87 (dd, J 3.7, 1.8 Hz, 1H, Ar); 6.43 (dd, J 3.7, 2.8 Hz, 1H, Ar); 3.76 (m, 4H, 2CH$_2$); 3.65 (m, 4H, 2CH$_2$); 2.93 (s, 3H, CH$_3$); 1.48 (m, 2H, cyclopropyl); 0.93 (m, 1H, cyclopropyl); 0.54 (m, 1H, cyclopropyl). Proton for HCl salt not observed. M/Z (M+H)$^+$=401.3. MP: 191-199° C.

Example 43

5-Methyl-9-(3,4,5,6-tetrahydro-2H-[1,2']bipyridinyl-5'-yl)-spiro[benzo[f]pyrrolo[1,2-a][1,4]diazepine-6,1'-cyclopropan]-4(5H)-one, hydrochloride

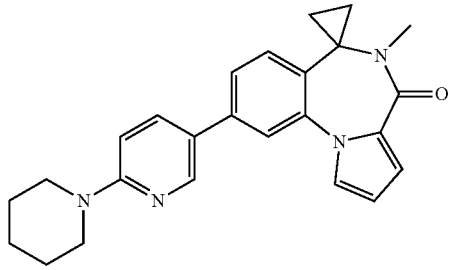 [SMILES: CN1C(=O)c2cccn2-c2cc(-c3ccc(N4CCCCC4)nc3)ccc2C12CC2]

Example 43 was obtained according to general procedure VI(i), starting from example 1 in presence of 6-(piperidin-1-yl)pyridine-3-boronic pinacol ester. Purification by preparative HPLC afforded the product as a beige solid in 42% yield. Salt formation was performed by method VII(ii). $^1$H-NMR (400 MHz, DMSO-D6): 8.37 (s, 1H, Ar); 8.31 (d, J 8.7 Hz, 1H, Ar); 7.80 (d, J 1.4 Hz, 1H, Ar); 7.69 (dd, J 2.8, 1.8 Hz, 1H, Ar); 7.62 (dd, J 7.9, 1.4 Hz, 1H, Ar); 7.58 (d, J 7.9 Hz, 1H, Ar); 7.37 (d, J 8.7 Hz, 1H, Ar); 6.86 (dd, J 3.7, 1.8 Hz, 1H, Ar); 6.43 (dd, J 3.7, 2.8 Hz, 1H, Ar); 3.73 (m, 4H, 2CH$_2$); 2.92 (m, 3H, CH$_3$); 1.64 (m, 6H, 3CH$_2$); 1.48 (m, 2H, cyclopropyl); 0.93 (m, 1H, cyclopropyl); 0.53 (m,

Example 44

5-Methyl-9-(3-cyanophenyl)-spiro[benzo[f]pyrrolo[1,2-a][1,4]diazepine-6,1'-cyclopropan]-4(5H)-one

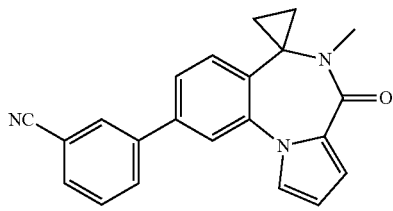 [SMILES: CN1C(=O)c2cccn2-c2cc(-c3cccc(C#N)c3)ccc2C12CC2]

Example 44 was obtained according to general procedure VI(i), starting from example 1 in presence of 3-cyanophenylboronic acid. Purification by flash column chromatography on silica gel (EtOAc in cyclohexane, 0% to 70%) afforded the product as a yellow solid in 90% yield. $^1$H-NMR (400 MHz, DMSO-D6): 8.35 (s, 1H, Ar); 8.14 (d, J 7.9 Hz, 1H, Ar); 7.87 (m, 2H, Ar); 7.73 (dd, J 2.8, 1.8 Hz, 1H, Ar); 7.69 (m, 2H, Ar); 7.61 (d, J 7.9 Hz, 1H, Ar); 6.87 (dd, J 3.7, 1.8 Hz, 1H, Ar); 6.43 (dd, J 3.7, 2.8 Hz, 1H, Ar); 2.93 (m, 3H, CH$_3$); 1.48 (m, 2H, cyclopropyl); 0.92 (m, 1H, cyclopropyl); 0.56 (m, 1H, cyclopropyl). M/Z (M+H)$^+$=340.3. MP: 189-194° C.

Example 45

5-Methyl-9-(3-(1H-tetrazol-5-yl)-phenyl)-spiro[benzo[f]pyrrolo[1,2-a][1,4]diazepine-6,1'-cyclopropan]-4(5H)-one

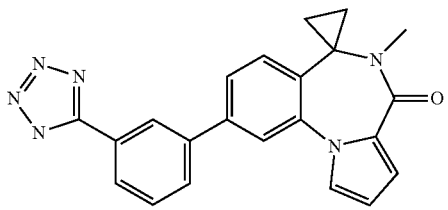 [SMILES: CN1C(=O)c2cccn2-c2cc(-c3cccc(-c4nnn[nH]4)c3)ccc2C12CC2]

Under inert and anhydrous conditions, to a solution of example 44 (1.0 equiv.) in DMF (0.05 mol·L$^{-1}$), sodium azide (5.0 equiv.) and ammonium chloride (5.0 equiv.) were added portionwise. The reaction mixture was heated at 80° C. for 3 days to give a yellow suspension. The solvent was removed under vacuum and the crude product was purified by preparative HPLC to afford example 45 as a white solid in 27% yield. $^1$H-NMR (400 MHz, DMSO-D6): 8.40 (s, 1H, Ar); 8.08 (d, J 7.8 Hz, 1H, Ar); 8.01 (d, J 7.8 Hz, 1H, Ar); 7.88 (d, J 1.6 Hz, 1H, Ar); 7.71 (m, 3H, Ar); 7.65 (d, J 7.8 Hz, 1H, Ar); 6.88 (dd, J 3.7, 1.8 Hz, 1H, Ar); 6.44 (dd, J 3.7, 2.8 Hz, 1H, Ar); 2.94 (m, 3H, CH$_3$); 1.49 (m, 2H, cyclopropyl); 0.94 (m, 1H, cyclopropyl); 0.58 (m, 1H, cyclopropyl). Proton for NH not observed. M/Z (M+H)$^+$=383.3. MP>250° C.

Example 46

5-Methyl-9-(1,2,3,6-tetrahydro-pyridin-4-yl)-spiro[benzo[f]pyrrolo[1,2-a][1,4]diazepine-6,1'-cyclopropan]-4(5H)-one, hydrochloride

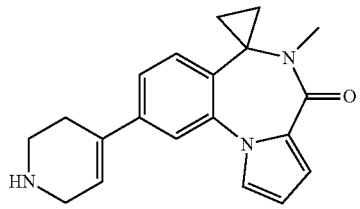 [SMILES: CN1C(=O)c2cccn2-c2cc(C3=CCNCC3)ccc2C12CC2]

Example 46 was obtained according to general procedure VI(i), starting from example 1 in presence of N-boc-1,2,3,6-tetrahydropyridine-4-boronic acid. Purification by flash column chromatography on silica gel (EtOAc in cyclohexane, 0% to 80%) afforded a yellow oil which was taken in a 1:1 mixture (0.10 mol·L$^{-1}$) of CH$_2$Cl$_2$ and HCl (2N in Et$_2$O) for 4 hours at room temperature. The yellow precipitate was collected by filtration and dried under vacuum to afford example 46 as a beige solid in 89% yield. $^1$H-NMR (400 MHz, DMSO-D6): 9.26 (bs, 2H, NH+HCl); 7.58 (d, J 1.6 Hz, 1H, Ar); 7.57 (dd, J 2.8, 1.8 Hz, 1H, Ar); 7.51 (d, J 7.9 Hz, 1H, Ar); 7.43 (dd, J 7.9, 1.6 Hz, 1H, Ar); 6.85 (dd, J 3.7, 1.8 Hz, 1H, Ar); 6.42 (dd, J 3.7, 2.8 Hz, 1H, Ar); 6.36 (m, 1H, =CH); 3.77 (m, 2H, CH$_2$); 3.31 (m, 2H, CH$_2$); 2.91 (m, 3H, CH$_3$); 2.75 (m, 2H, CH$_2$); 1.45 (m, 2H, cyclopropyl); 0.91 (m, 1H, cyclopropyl); 0.51 (m, 1H, cyclopropyl). M/Z (M+H)$^+$=320.4. MP: 208-215° C.

Example 47

5-Methyl-9-(1-pyrimidin-4-yl-1,2,3,6-tetrahydro-pyridin-4-yl)-spiro[benzo[f]pyrrolo[1,2-a][1,4]diazepine-6,1'-cyclopropan]-4(5H)-one, hydrochloride

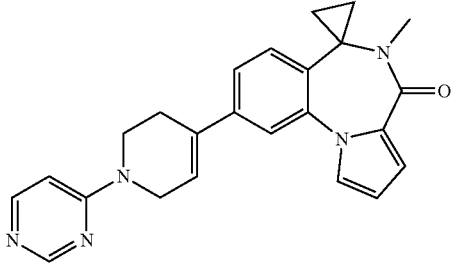 [SMILES: CN1C(=O)c2cccn2-c2cc(C3=CCN(c4ccncn4)CC3)ccc2C12CC2]

A suspension of example 46 (1.0 equiv.), 4-bromopyrimidine hydrochloride (2.0 equiv.) and diisopropylethylamine (4.0 equiv.) in EtOH (0.15 mol·L$^{-1}$) was stirred at room temperature for 16 hours to give a yellow solution. EtOH was removed under vacuum and the crude orange oil was purified by preparative HPLC to afford example 47 as a yellow solid in 25% yield. Salt formation was performed by method VII(ii). $^1$H-NMR (400 MHz, DMSO-D6): 8.85 (s, 1H, Ar); 8.37 (m, 1H, Ar); 7.58 (d, J 1.4 Hz, 1H, Ar); 7.56 (dd, J 2.8, 1.8 Hz, 1H, Ar); 7.49 (d, J 7.9 Hz, 1H, Ar); 7.43 (dd, J 7.9, 1.4 Hz, 1H, Ar); 7.26 (m, 1H, Ar); 6.84 (dd, J 3.7, 1.8 Hz, 1H, Ar); 6.41 (m, 2H, =CH+Ar); 4.48 (m, 2H, CH$_2$); 4.10 (m, 2H, CH$_2$); 2.90 (m, 3H, CH$_3$); 2.73 (m, 2H, CH$_2$); 1.44 (m, 2H, cyclopropyl); 0.89 (m, 1H, cyclopropyl); 0.50 (m, 1H, cyclopropyl). Proton for HCl salt not observed. M/Z (M+H)$^+$=398.4. MP: 210-220° C.

Example 48

5-Methyl-9-(1-acetyl-1,2,3,6-tetrahydro-pyridin-4-yl)-spiro[benzo[f]pyrrolo[1,2-a][1,4]diazepine-6,1'-cyclopropan]-4(5H)-one

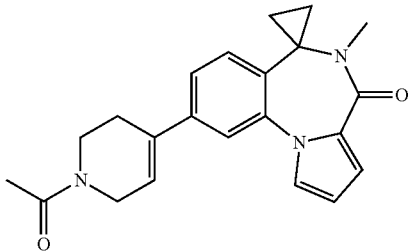 [SMILES: CC(=O)N1CC=C(c2ccc3c(c2)-n2cccc2C(=O)N(C)C32CC2)CC1]

A suspension of example 46 (1.0 equiv.), acetyl chloride (1.2 equiv.) and triethylamine (2.2 equiv.) in CH$_2$Cl$_2$ (0.20 mol·L$^{-1}$) was stirred at room temperature for 16 hours. CH$_2$Cl$_2$ was removed under vacuum and the crude orange oil was purified by preparative HPLC to afford example 48 as a grey solid in 29% yield. $^1$H-NMR (400 MHz, DMSO-D6): 7.54 (m, 2H, Ar); 7.46 (d, J 7.8 Hz, 1H, Ar); 7.39 (m, 1H, Ar); 6.83 (dd, J 3.7, 1.8 Hz, 1H, Ar); 6.39 (dd, J 3.7, 2.8 Hz, 1H, Ar); 6.30 (m, 1H, =CH); 4.13 (m, 2H, CH$_2$); 3.64 (m, 2H, CH$_2$); 2.89 (m, 3H, CH$_3$); 2.60 (m, 2H, CH$_2$); 2.05 (s, 3H, CH$_3$); 1.43 (m, 2H, cyclopropyl); 0.89 (m, 1H, cyclopropyl); 0.50 (m, 1H, cyclopropyl). M/Z (M+H)$^+$=362.3. MP: 101-110° C.

Example 49

5-Methyl-9-(4-methyl-oxazol-5-yl)-spiro[benzo[f]pyrrolo[1,2-a][1,4]diazepine-6,1'-cyclopropan]-4(5H)-one

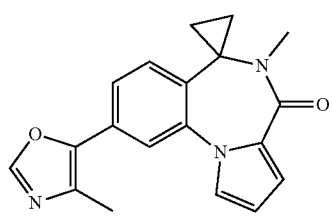 [SMILES: Cc1ncoc1-c1ccc2c(c1)-n1cccc1C(=O)N(C)C21CC1]

Under inert atmosphere, a mixture of example 1 (1.0 equiv.), 4-methyloxazole-5-carboxylic acid (2.0 equiv.), cesium carbonate (1.5 equiv.) and bis(triphenylphosphine)palladium(II) dichloride (0.05 equiv.) in DMA (0.05 mol·L$^{-1}$) was subjected to microwave irradiation for 10 minutes at 170° C. The mixture was hydrolysed and extracted twice with EtOAc. The combined organic extracts were washed with brine, dried over MgSO$_4$ and concentrated under vacuum. The crude yellow oil was purified by preparative HPLC to afford example 49 as a white solid in 24% yield. $^1$H-NMR (400 MHz, DMSO-D6): 8.39 (s, 1H, Ar); 7.67 (d, J 1.6 Hz, 1H, Ar); 7.62 (d, J 7.9 Hz, 1H, Ar); 7.59 (dd, J 2.8, 1.8 Hz, 1H, Ar); 7.56 (dd, J 7.9, 1.6 Hz, 1H, Ar); 6.86 (dd, J 3.7, 1.8 Hz, 1H, Ar); 6.43 (dd, J 3.7, 2.8 Hz, 1H, Ar); 2.92 (m, 3H, CH$_3$); 2.40 (m, 3H, CH$_3$); 1.48 (m, 2H, cyclopropyl); 0.92 (m, 1H, cyclopropyl); 0.55 (m, 1H, cyclopropyl). M/Z (M+H)$^+$=320.3. MP: 120-128° C.

Example 50

5-Methyl-9-(4-methylthiazol-5-yl)-spiro[benzo[f]pyrrolo[1,2-a][1,4]diazepine-6,1'-cyclopropan]-4(5H)-one

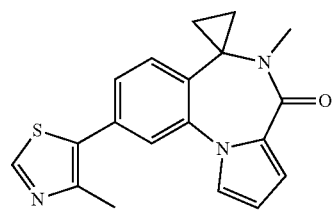 [SMILES: Cc1ncsc1-c1ccc2c(c1)-n1cccc1C(=O)N(C)C21CC1]

Under inert atmosphere, a mixture of example 1 (1.0 equiv.), 4-methylthiazole-5-carboxylic acid (2.0 equiv.), cesium carbonate (1.5 equiv.) and bis(triphenylphosphine)palladium(II) dichloride (0.05 equiv.) in DMA (0.05 mol·L$^{-1}$) was subjected to microwave irradiation for 10 minutes at 170° C. The mixture was hydrolysed and extracted twice with EtOAc. The combined organic extracts were washed with brine, dried over MgSO$_4$ and concentrated under vacuum. The crude yellow oil was purified by preparative HPLC to afford example 50 as a white solid in 55% yield. $^1$H-NMR (400 MHz, DMSO-D6): 9.04 (s, 1H, Ar); 7.61 (d, J 1.6 Hz, 1H, Ar); 7.59 (d, J 7.9 Hz, 1H, Ar); 7.55 (dd, J 2.8, 1.8 Hz, 1H, Ar); 7.45 (dd, J 7.9, 1.6 Hz, 1H, Ar); 6.88 (dd, J 3.7, 1.8 Hz, 1H, Ar); 6.42 (dd, J 3.7, 2.8 Hz, 1H, Ar); 2.93 (m, 3H, CH$_3$); 2.49 (m, 3H, CH$_3$); 1.49 (m, 2H, cyclopropyl); 0.91 (m, 1H, cyclopropyl); 0.56 (m, 1H, cyclopropyl). M/Z (M+H)$^+$=336.4. MP: 205-212° C.

Example 51

5-Methyl-9-acetonitrile-spiro[benzo[f]pyrrolo[1,2-a][1,4]diazepine-6,1'-cyclopropan]-4(5H)-one

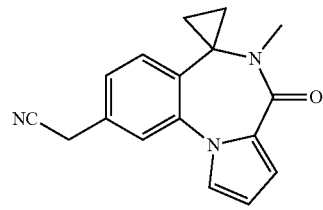 [SMILES: CN1C(=O)c2cccn2-c2cc(CC#N)ccc2C12CC2]

Under inert atmosphere, in a sealed reactor, a mixture of example 1 (1.0 equiv.), cyanoacetic acid (5.0 equiv.), sodium tertbutoxide (5.0 equiv.), RuPhos ligand (0.20 equiv.) and allylpalladium (II) chloride dimer (0.10 equiv.) in xylene (0.10 mol·L$^{-1}$) was heated at 120° C. for 2 days. The mixture was hydrolysed and extracted twice with EtOAc. The combined organic extracts were washed with brine, dried over MgSO$_4$ and concentrated under vacuum. The crude yellow oil was purified by preparative HPLC to afford example 51 as a white solid in 15% yield. ¹H-NMR (400 MHz, DMSO-D6): 7.53 (m, 2H, Ar); 7.43 (dd, J 2.8, 1.8 Hz, 1H, Ar); 7.33 (dd, J 7.9, 1.7 Hz, 1H, Ar); 6.85 (dd, J 3.7, 1.8 Hz, 1H, Ar); 6.42 (dd, J 3.7, 2.8 Hz, 1H, Ar); 4.09 (s, 2H, CH$_2$); 2.89 (m, 3H, CH$_3$); 1.44 (m, 2H, cyclopropyl); 0.90 (m, 1H, cyclopropyl); 0.51 (m, 1H, cyclopropyl). M/Z (M+H)$^+$=278.3. MP: 60-69° C.

Example 52

5-Methyl-9-actylonitrile-spiro[benzo[f]pyrrolo[1,2-a][1,4]diazepine-6,1'-cyclopropan]-4(5H)-one

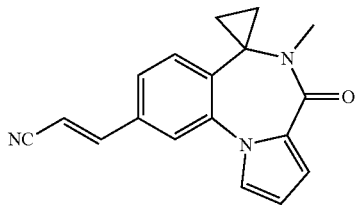 [SMILES: CN1C(=O)c2cccn2-c2cc(/C=C/C#N)ccc2C12CC2]

Under inert atmosphere, in a sealed reactor, a mixture of example 1 (1.0 equiv.), acrylonitrile (1.5 equiv.), potassium carbonate (2.0 equiv.), triphenylphosphine (0.20 equiv.) and palladium acetate (0.10 equiv.) in DMF (0.10 mol·L$^{-1}$) was heated at 110° C. for 16 hours. The mixture was hydrolysed with a saturated aqueous solution of K$_2$CO$_3$ and extracted twice with EtOAc. The combined organic extracts were washed with brine, dried over MgSO$_4$ and concentrated under vacuum. The crude yellow oil was purified by preparative HPLC to afford example 52 as a white solid in 55% yield. A mixture of Z and E diastereoisomers was obtained in a 3:7 ratio. ¹H-NMR (400 MHz, DMSO-D6) of the E isomer: 7.88 (d, J 1.4 Hz, 1H, Ar); 7.71 (d, J 16.7 Hz, 1H, =CH); 7.61 (dd, J 7.9, 1.4 Hz, 1H, Ar); 7.57 (d, J 7.9 Hz, 1H, Ar); 7.52 (dd, J 2.8, 1.8 Hz, 1H, Ar); 6.87 (dd, J 3.7, 1.8 Hz, 1H, Ar); 6.65 (d, J 16.7 Hz, 1H, =CH); 6.44 (dd, J 3.7, 2.8 Hz, 1H, Ar); 2.91 (m, 3H, CH$_3$); 1.47 (m, 2H, cyclopropyl); 0.93 (m, 1H, cyclopropyl); 0.53 (m, 1H, cyclopropyl). M/Z (M+H)$^+$=290.2. MP: 130-138° C.

Example 53

5-Methyl-9-propionitrile-spiro[benzo[f]pyrrolo[1,2-a][1,4]diazepine-6,1'-cyclopropan]-4(5H)-one

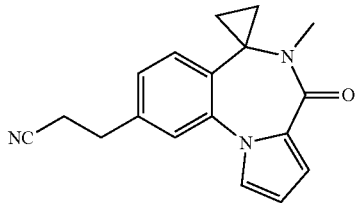 [SMILES: CN1C(=O)c2cccn2-c2cc(CCC#N)ccc2C12CC2]

A mixture of example 52 (1.0 equiv.) and palladium on activated charcoal (10%, 0.20 equiv.) in MeOH (0.10 mol·L$^{-1}$) was placed under hydrogen atmosphere (1 bar) for 3 days at room temperature. The mixture was filtered through celite with ethanol and the filtrate was concentrated under vacuum. The crude yellow oil was purified by preparative HPLC to afford example 53 as a white solid in 60% yield. ¹H-NMR (400 MHz, DMSO-D6): 7.51 (d, J 1.6 Hz, 1H, Ar); 7.45 (m, 2H, Ar); 7.26 (dd, J 7.8, 1.6 Hz, 1H, Ar); 6.85 (dd, J 3.7, 1.8 Hz, 1H, Ar); 6.42 (dd, J 3.7, 2.8 Hz, 1H, Ar); 2.94 (m, 2H, CH$_2$); 2.90 (m, 3H, CH$_3$); 2.88 (m, 2H, CH$_2$); 1.44 (m, 2H, cyclopropyl); 0.89 (m, 1H, cyclopropyl); 0.50 (m, 1H, cyclopropyl). M/Z (M+H)$^+$=292.3. MP: 59-64° C.

Example 54

5-Methyl-9-(6-chloropyridin-3-yl)-spiro[benzo[f]pyrrolo[1,2-a][1,4]diazepine-6,1'-cyclopropan]-4(5H)-one

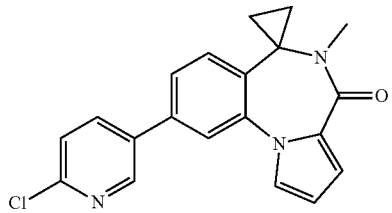 [SMILES: CN1C(=O)c2cccn2-c2cc(-c3ccc(Cl)nc3)ccc2C12CC2]

Example 54 was obtained according to general procedure VI(i), starting from example 1 in presence of 6-chloro-3-pyridinyl boronic acid. Purification by flash column chromatography on silica gel (EtOAc in cylohexane, 0% to 50%) afforded the product as a beige solid in 15% yield. ¹H-NMR (400 MHz, DMSO-D6): 8.85 (d, J 2.5 Hz, 1H, Ar); 8.29 (dd, J 8.3, 2.5 Hz, 1H, Ar); 7.87 (d, J 1.7 Hz, 1H, Ar); 7.69 (m, 2H, Ar); 7.64 (d, J 8.3 Hz, 1H, Ar); 7.62 (d, J 7.9 Hz, 1H, Ar); 6.87 (dd, J 3.7, 1.8 Hz, 1H, Ar); 6.43 (dd, J 3.7, 2.8 Hz, 1H, Ar); 2.92 (s, 3H, CH$_3$); 1.49 (m, 2H, cyclopropyl); 0.93 (m, 1H, cyclopropyl); 0.55 (m, 1H, cyclopropyl). M/Z (M[$^{35}$Cl]+H)$^+$=350.2. MP: 192-198° C.

Example 55

5-(Methyl-d$_3$)-9-(6-fluoropyridin-3-yl)-spiro[benzo[f]pyrrolo[1,2-a][1,4]diazepine-6,1'-cyclopropan]-4(5H)-one

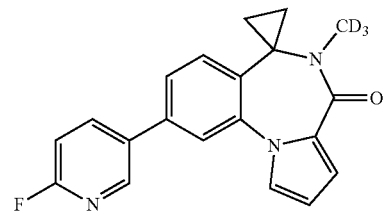 [SMILES: [2H]C([2H])([2H])N1C(=O)c2cccn2-c2cc(-c3ccc(F)nc3)ccc2C12CC2]

Example 55 was obtained according to general procedure VI(i), starting from example 3 in presence of 2-fluoro-5-pyridinylboronic acid. Purification by flash column chromatography on silica gel (EtOAc in cylohexane, 0% to 50%) afforded the product as a beige solid in 82% yield. ¹H-NMR (400 MHz, DMSO-D6): 8.67 (d, J 2.6 Hz, 1H, Ar); 8.41 (dt, J 8.2, 2.6 Hz, 1H, Ar); 7.85 (d, J 1.7 Hz, 1H, Ar); 7.69 (dd, J 3.8, 2.8 Hz, 1H, Ar); 7.67 (dd, J 7.9, 1.7 Hz, 1H, Ar); 7.61 (d, J 7.9 Hz, 1H, Ar); 7.32 (dd, J 8.5, 2.6 Hz, 1H, Ar); 6.86 (dd, J 3.7, 1.8 Hz, 1H, Ar); 6.42 (dd, J 3.7, 2.8 Hz, 1H, Ar);

1.48 (m, 2H, cyclopropyl); 0.93 (m, 1H, cyclopropyl); 0.55 (m, 1H, cyclopropyl). M/Z (M+H)$^+$=337.2. MP: 166-178° C.

Example 56

5-Methyl-9-(2,6-dimethylpyridin-3-yl)-spiro[benzo[f]pyrrolo[1,2-a][1,4]diazepine-6,1'-cyclopropan]-4(5H)-one, hydrochloride

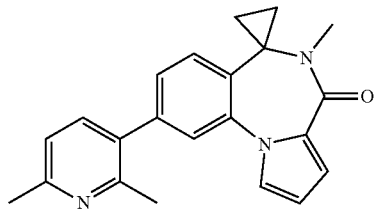 [SMILES: Cc1ccc(-c2ccc3c(c2)-n2cccc2C(=O)N(C)C32CC2)c(C)n1]

Example 56 was obtained according to general procedure VI(i) starting from compound 31 in presence of 3-bromo-2,6-dimethylpyridine. Purification by preparative HPLC afforded the product as a beige solid in 47% yield. Salt formation was performed by method (ii). $^1$H-NMR (400 MHz, DMSO-D6): 8.34 (bs, 1H, Ar); 7.76 (bs, 1H, Ar); 7.65 (m, 2H, Ar); 7.54 (m, 1H, Ar); 7.46 (d, J 7.8 Hz, 1H, Ar); 6.87 (dd, J 3.7, 1.8 Hz, 1H, Ar); 6.42 (dd, J 3.1, 2.8 Hz, 1H, Ar); 2.94 (s, 3H, CH$_3$); 2.77 (s, 3H, CH$_3$); 2.70 (s, 3H, CH$_3$); 1.51 (m, 2H, cyclopropyl); 0.95 (m, 1H, cyclopropyl); 0.58 (m, 1H, cyclopropyl). Proton for HCl salt not observed. M/Z (M+H)$^+$=344.3. MP>250° C.

Example 57

5-Methyl-9-(4-fluoropyridin-2-yl)-spiro[benzo[f]pyrrolo[1,2-a][1,4]diazepine-6,1'-cyclopropan]-4(5H)-one

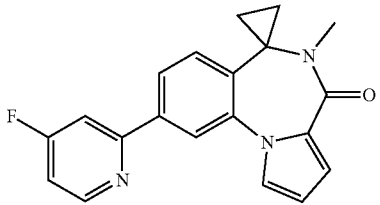

Example 57 was obtained according to general procedure VI(i), starting from compound 31 in presence of 2-bromo-4-fluoropyridine. Purification by flash column chromatography on silica gel (EtOAc in cylohexane, 0% to 50%) afforded the product as a beige solid in 27% yield. $^1$H-NMR (400 MHz, DMSO-D6): 8.74 (dd, J 8.9, 5.6 Hz, 1H, Ar); 8.20 (d, J 1.7 Hz, 1H, Ar); 8.15 (dd, J 11.0, 2.4 Hz, 1H, Ar); 8.09 (dd, J 7.9, 1.7 Hz, 1H, Ar); 7.66 (dd, J 2.8, 1.8 Hz, 1H, Ar); 7.64 (d, J 7.9 Hz, 1H, Ar); 7.37 (ddd, J 11.0, 5.6, 2.4 Hz, 1H, Ar); 6.88 (dd, J 3.7, 1.8 Hz, 1H, Ar); 6.44 (dd, J 3.7, 2.8 Hz, 1H, Ar); 2.93 (s, 3H, CH$_3$); 1.50 (m, 2H, cyclopropyl); 0.94 (m, 1H, cyclopropyl); 0.56 (m, 1H, cyclopropyl). M/Z (M+H)$^+$=344.4. MP: 198-202° C.

Example 58

5-Methyl-9-(3-methyl-pyrazin-2-yl)-5,6-spiro[benzo[f]pyrrolo[1,2-a][1,4]diazepine-6,1'-cyclopropan]-4(5H)-one, hydrochloride

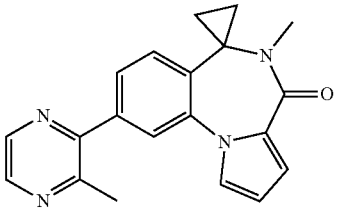 [SMILES: Cc1nccnc1-c1ccc2c(c1)-n1cccc1C(=O)N(C)C21CC1]

Example 58 was obtained according to general procedure VI(i), starting from compound 31 in presence of 2-bromo-3-methylpyrazine. Purification by flash column chromatography on silica gel (EtOAc in cylohexane, 0% to 50%) afforded the product as a yellow solid in 24% yield. Salt formation was performed by method VII(i). $^1$H-NMR (400 MHz, DMSO-D6): 8.56 (d, J 8.5 Hz, 2H, Ar); 7.78 (s, 1H, Ar); 7.60 (m, 2H, Ar); 7.49 (s, 1H, Ar); 6.87 (s, 1H, Ar); 6.40 (s, 1H, Ar); 2.93 (s, 3H, CH$_3$); 2.60 (s, 3H, CH$_3$); 1.49 (m, 2H, cyclopropyl); 0.93 (m, 1H, cyclopropyl); 0.58 (m, 1H, cyclopropyl). Proton for HCl salt not observed. M/Z (M+H)$^+$=331.4. MP: 123-129° C.

Example 59

5-Methyl-9-(4-methyl-pyrimidin-5-yl)-spiro[benzo[f]pyrrolo[1,2-a][1,4]diazepine-6,1'-cyclopropan]-4(5H)-one, hydrochloride

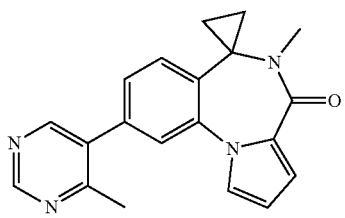 [SMILES: Cc1ncncc1-c1ccc2c(c1)-n1cccc1C(=O)N(C)C21CC1]

Example 59 was obtained according to general procedure VI(i), starting from compound 31 in presence of 5-bromo-4-methylpyrimidine. Purification by flash column chromatography on silica gel (EtOAc in cylohexane, 0% to 50%) afforded the product as a yellow solid in 24% yield. Salt formation was performed by method VII(i). $^1$H-NMR (400 MHz, DMSO-D6): 9.07 (s, 1H, Ar); 8.72 (s, 1H, Ar); 7.67 (d, J 1.6 Hz, 1H, Ar); 7.63 (d, J 7.8 Hz, 1H, Ar); 7.56 (dd, J 2.8, 1.8 Hz, 1H, Ar); 7.45 (dd, J 7.8, 1.6 Hz, 1H, Ar); 6.86 (dd, J 3.7, 1.8 Hz, 1H, Ar); 6.41 (dd, J 3.7, 2.8 Hz, 1H, Ar); 2.93 (s, 3H, CH$_3$); 1.50 (m, 2H, cyclopropyl); 0.94 (m, 1H, cyclopropyl); 0.57 (m, 1H, cyclopropyl). Proton for HCl salt not observed. M/Z (M+H)$^+$=331.4. MP: 140-147° C.

Example 60

5-Methyl-9-(6-trifluoromethylpyridin-3-yl)-spiro[benzo[f]pyrrolo[1,2-a][1,4]diazepine-6,1'-cyclopropan]-4(5H)-one

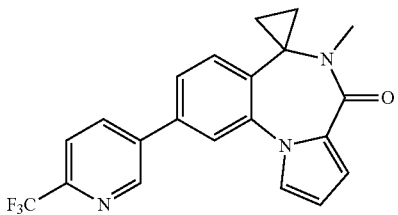 [SMILES: CN1C(=O)c2cccn2-c2cc(-c3ccc(C(F)(F)F)nc3)ccc2C12CC2]

Example 60 was obtained according to general procedure VI(i), starting from compound 31 in presence of 5-bromo-2-trifluoromethylpyridine. Purification by preparative HPLC afforded the product as a beige solid in 33% yield. $^1$H-NMR (400 MHz, DMSO-D6): 9.20 (d, J 1.9 Hz, 1H, Ar); 8.50 (dd, J 8.1, 1.9 Hz, 1H, Ar); 8.02 (d, J 8.1 Hz, 1H, Ar); 7.96 (d, J 1.6 Hz, 1H, Ar); 7.77 (dd, J 7.9, 1.6 Hz, 1H, Ar); 7.71 (dd, J 2.8, 1.8 Hz, 1H, Ar); 7.67 (d, J 7.9 Hz, 1H, Ar); 6.88 (dd, J 3.7, 1.8 Hz, 1H, Ar); 6.44 (dd, J 3.7, 2.8 Hz, 1H, Ar); 2.93 (s, 3H, CH$_3$); 1.50 (m, 2H, cyclopropyl); 0.94 (m, 1H, cyclopropyl); 0.57 (m, 1H, cyclopropyl). M/Z (M+H)$^+$=384.4. MP: 88-97° C.

Compound 39: 3-bromo-2-propylpyridine

Under inert atmosphere, to a solution of 2,3-dibromopyridine (1.0 equiv.) and tetrakistriphenylphosphine palladium (0.05 equiv.) in THF (0.10 mol·L$^{-1}$), a solution of propylzinc bromide (0.5M in THF, 1.5 equiv.) was added dropwise. The reaction mixture was heated at 65° C. for 1 hour, before being neutralized by addition of a saturated aqueous solution of K$_2$CO$_3$ and extracted twice with Et$_2$O. The combined organic extracts were washed with brine, dried over MgSO$_4$ and concentrated under vacuum. The crude yellow oil was purified by flash column chromatography on silica gel (EtOAc in cyclohexane, 0 to 10%) to afford compound 39 as a colorless oil in 77% yield. M/Z (M[$^{79}$Br]+H)$^+$=200.0.

Example 61

5-Methyl-9-(2-propylpyridin-3-yl)-spiro[benzo[f]pyrrolo[1,2-a][1,4]diazepine-6,1'-cyclopropan]-4(5H)-one, hydrochloride

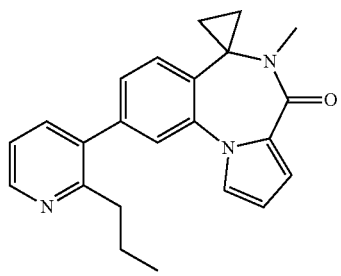 [SMILES: CCCc1ncccc1-c1ccc2c(c1)-n1cccc1C(=O)N(C)C21CC1]

Example 61 was obtained according to general procedure VI(i), starting from compound 31 in presence of compound 39. Purification by flash column chromatography on silica gel (EtOAc in cylohexane, 30% to 80%) afforded the product as a yellow solid in 18% yield. Salt formation was performed by method VII(i). $^1$H-NMR (400 MHz, DMSO-D6): 8.77 (d, J 4.9 Hz, 1H, Ar); 8.30 (m, 1H, Ar); 7.81 (m, 1H, Ar); 7.66 (m, 2H, Ar); 7.51 (m, 1H, Ar); 7.42 (d, J 7.9 Hz, 1H, Ar); 6.88 (m, 1H, Ar); 6.42 (m, 1H, Ar); 2.94 (s, 3H, CH$_3$); 2.92 (m, 2H, CH$_2$); 1.63 (m, 2H, CH$_2$); 1.51 (m, 2H, cyclopropyl); 0.95 (m, 1H, cyclopropyl); 0.78 (t, J 7.1 Hz, 3H, CH$_3$); 0.58 (m, 1H, cyclopropyl). Proton for HCl salt not observed. M/Z (M+H)$^+$=358.3. MP: 150-157° C.

Compound 40: 3-Bromo-2-cyclopropylpyridine

Under inert atmosphere, to a solution of 2,3-dibromopyridine (1.0 equiv.) and tetrakistriphenylphosphine palladium (0.05 equiv.) in THF (0.10 mol·L$^{-1}$), a solution of cyclopropylzinc bromide (0.5M in THF, 1.5 equiv.) was added dropwise. The reaction mixture was heated at 65° C. for 1 hour, before being neutralized by addition of a saturated aqueous solution of K$_2$CO$_3$ and extracted twice with Et$_2$O. The combined organic extracts were washed with brine, dried over MgSO$_4$ and concentrated under vacuum. Compound 40 was obtained as a crude yellow oil and taken to the next step without purification. M/Z (M[$^{79}$Br]+H)$^+$=198.0.

Example 62

5-Methyl-9-(2-cyclopropylpyridin-3-yl)-spiro[benzo[f]pyrrolo[1,2-a][1,4]diazepine-6,1'-cyclopropan]-4(5H)-one, hydrochloride

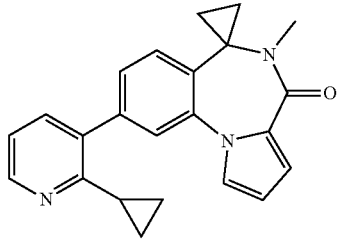 [SMILES: CN1C(=O)c2cccn2-c2cc(-c3cccnc3C3CC3)ccc2C12CC2]

Example 62 was obtained according to general procedure VI(i), starting from compound 31 in presence of compound 40. Purification by flash column chromatography on silica gel (EtOAc in cylohexane, 0% to 50%) afforded the product as a yellow solid in 9% yield. Salt formation was performed by method VII(i). $^1$H-NMR (400 MHz, DMSO-D6): 8.52 (d, J 4.7 Hz, 1H, Ar); 7.98 (m, 1H, Ar); 7.67 (d, J 1.4 Hz, 1H, Ar); 7.64 (d, J 7.8 Hz, 1H, Ar); 7.56 (m, 1H, Ar); 7.46 (m, 2H, Ar); 6.87 (m, 1H, Ar); 6.41 (m, 1H, Ar); 2.94 (s, 3H, CH$_3$); 2.16 (m, 1H, cyclopropyl); 1.50 (m, 2H, cyclopropyl); 1.15 (m, 2H, cyclopropyl); 1.00 (m, 2H, cyclopropyl); 0.94 (m, 1H, cyclopropyl); 0.57 (m, 1H, cyclopropyl). Proton for HCl salt not observed. M/Z (M+H)$^+$=356.3. MP: 160-180° C.

Example 63

5-Methyl-9-(5-fluoropyridin-2-yl)-spiro[benzo[f]pyrrolo[1,2-a][1,4]diazepine-6,1'-cyclopropan]-4(5H)-one

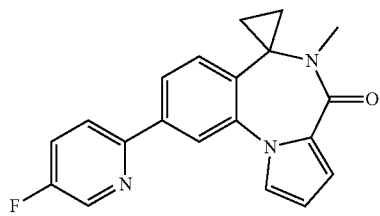 [SMILES: CN1C(=O)c2cccn2-c2cc(-c3ccc(F)cn3)ccc2C12CC2]

Example 63 was obtained according to general procedure VI(i), starting from compound 31 in presence of 2-bromo-5-fluoropyridine. Purification by flash column chromatography on silica gel (EtOAc in cylohexane, 0% to 50%) afforded the product as a beige solid in 60% yield. $^1$H-NMR (400 MHz, DMSO-D6): 8.69 (d, J 2.9 Hz, 1H, Ar); 8.20 (dd, J 8.9, 4.2 Hz, 1H, Ar); 8.13 (d, J 1.6 Hz, 1H, Ar); 8.01 (dd, J 8.0, 1.6 Hz, 1H, Ar); 7.87 (dt, J 8.9, 2.9 Hz, 1H, Ar); 7.62 (m, 2H, Ar); 6.87 (dd, J 3.7, 1.8 Hz, 1H, Ar); 6.43 (dd, J 3.7, 2.8 Hz, 1H, Ar); 2.93 (s, 3H, CH$_3$); 1.48 (m, 2H, cyclopropyl); 0.93 (m, 1H, cyclopropyl); 0.56 (m, 1H, cyclopropyl). M/Z (M+H)$^+$=334.3. MP: 148-156° C.

Example 64

5-(Methyl-d$_3$)-9-(5-fluoropyridin-2-yl)-spiro[benzo[f]pyrrolo[1,2-a][1,4]diazepine-6,1'-cyclopropan]-4(5H)-one

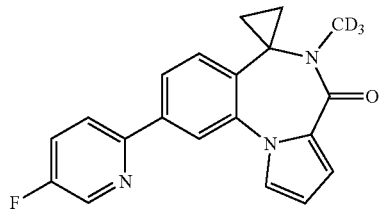 [SMILES: [2H]C([2H])([2H])N1C(=O)c2cccn2-c2cc(-c3ccc(F)cn3)ccc2C12CC2]

Example 64 was obtained according to general procedure VI(i), starting from compound 32 in presence of 2-bromo-5-fluoropyridine. Purification by flash column chromatography on silica gel (EtOAc in cylohexane, 0% to 50%) afforded the product as a beige solid in 62% yield. $^1$H-NMR (400 MHz, DMSO-D6): 8.69 (d, J 2.9 Hz, 1H, Ar); 8.20 (dd, J 8.9, 4.5 Hz, 1H, Ar); 8.13 (d, J 1.7 Hz, 1H, Ar); 8.01 (dd, J 7.9, 1.7 Hz, 1H, Ar); 7.87 (dt, J 8.9, 2.9 Hz, 1H, Ar); 7.62 (m, 2H, Ar); 6.87 (dd, J 3.7, 1.8 Hz, 1H, Ar); 6.43 (dd, J 3.7, 2.8 Hz, 1H, Ar); 1.48 (m, 2H, cyclopropyl); 0.93 (m, 1H, cyclopropyl); 0.56 (m, 1H, cyclopropyl). M/Z (M+H)$^+$=337.2. MP: 138-142° C.

Example 65

5-Methyl-9-(2,4-dimethylpyridin-3-yl)-spiro[benzo[f]pyrrolo[1,2-a][1,4]diazepine-6,1'-cyclopropan]-4(5H)-one, hydrochloride

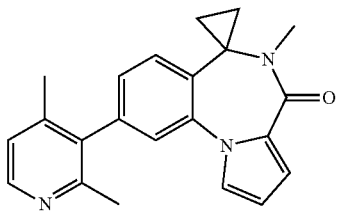 [SMILES: Cc1ccnc(C)c1-c1ccc2c(c1)-n1cccc1C(=O)N(C)C21CC1]

Example 65 was obtained according to general procedure VI(i), starting from compound 31 in presence of 3-bromo-2,4-dimethylpyridine. Purification by preparative HPLC, afforded the product as a white solid in 11% yield. Salt formation was performed by method VII(i). $^1$H-NMR (400 MHz, DMSO-D6): 8.70 (m, 1H, Ar); 7.91 (m, 1H, Ar); 7.69 (d, J 7.9 Hz, 1H, Ar); 7.56 (m, 1H, Ar); 7.50 (m, 1H, Ar); 7.30 (m, 1H, Ar); 6.88 (dd, J 3.7, 1.8 Hz, 1H, Ar); 6.41 (m, 1H, Ar); 2.95 (s, 3H, CH$_3$); 2.32 (s, 3H, CH$_3$); 2.27 (s, 3H, CH$_3$); 1.52 (m, 2H, cyclopropyl); 0.96 (m, 1H, cyclopropyl); 0.59 (m, 1H, cyclopropyl). Proton for HCl salt not observed. M/Z (M+H)$^+$=344.3. MP: 200-208° C.

Example 66

5-Methyl-9-(3-fluoropyridin-2-yl)-spiro[benzo[f]pyrrolo[1,2-a][1,4]diazepine-6,1'-cyclopropan]-4(5H)-one

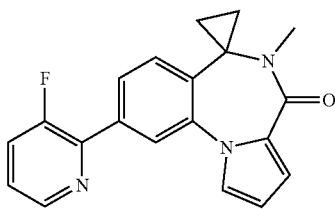 [SMILES: CN1C(=O)c2cccn2-c2cc(-c3ncccc3F)ccc2C12CC2]

Example 66 was obtained according to general procedure VI(i), starting from compound 31 in presence of 2-chloro-3-fluoropyridine. Purification by flash column chromatography on silica gel (EtOAc in cylohexane, 0% to 50%) afforded the product as a beige solid in 44% yield. $^1$H-NMR (400 MHz, DMSO-D6): 8.58 (m, 1H, Ar); 8.01 (m, 1H, Ar); 7.87 (m, 2H, Ar); 7.65 (d, J 7.9 Hz, 1H, Ar); 7.53 (m, 2H, Ar); 6.88 (dd, J 3.7, 1.8 Hz, 1H, Ar); 6.43 (dd, J 3.7, 2.8 Hz, 1H, Ar); 2.94 (s, 3H, CH$_3$); 1.50 (m, 2H, cyclopropyl); 0.94 (m, 1H, cyclopropyl); 0.59 (m, 1H, cyclopropyl). M/Z (M+H)$^+$=334.3. MP: 102-118° C.

Example 67

5-Methyl-9-(6-fluoropyridin-2-yl)-spiro[benzo[f]pyrrolo[1,2-a][1,4]diazepine-6,1'-cyclopropan]-4(5H)-one

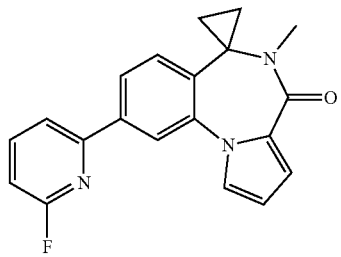 [SMILES: CN1C(=O)c2cccn2-c2cc(-c3cccc(F)n3)ccc2C12CC2]

Example 67 was obtained according to general procedure VI(i), starting from compound 31 in presence of 2-bromo-6-fluoropyridine. Purification by preparative HPLC afforded the product as a beige solid in 35% yield. $^1$H-NMR (400 MHz, DMSO-D6): 8.15-8.08 (m, 3H, Ar); 8.02 (dd, J 7.9, 1.7 Hz, 1H, Ar); 7.64 (m, 2H, Ar); 7.19 (m, 1H, Ar); 6.88 (dd, J 3.7, 1.8 Hz, 1H, Ar); 6.44 (dd, J 3.7, 2.8 Hz, 1H, Ar); 2.93 (s, 3H, CH$_3$); 1.49 (m, 2H, cyclopropyl); 0.93 (m, 1H, cyclopropyl); 0.57 (m, 1H, cyclopropyl). M/Z (M+H)$^+$=334.3. MP: 106-117° C.

Example 68

5-Methyl-9-(2-hydroxypyridin-4-yl)-spiro[benzo[f]pyrrolo[1,2-a][1,4]diazepine-6,1'-cyclopropan]-4(5H)-one

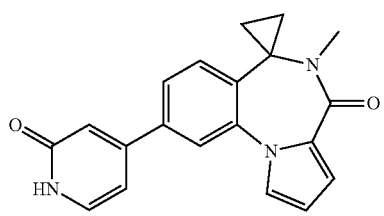 [SMILES: CN1C(=O)c2cccn2-c2cc(-c3cc[nH]c(=O)c3)ccc2C12CC2]

Example 68 was obtained according to general procedure VI(i), starting from compound 31 in presence of 4-bromo-2-hydroxypyridine. Purification by flash column chromatography on silica gel (MeOH in CH$_2$Cl$_2$, 0% to 5%) afforded the product as a brown solid in 38% yield. $^1$H-NMR (400 MHz, DMSO-D6): 11.63 (bs, 1H, NH); 7.79 (d, J 1.7 Hz, 1H, Ar); 7.72 (dd, J 2.8, 1.8 Hz, 1H, Ar); 7.64 (dd, J 7.9, 1.7 Hz, 1H, Ar); 7.60 (d, J 7.9 Hz, 1H, Ar); 7.47 (d, J 6.8 Hz, 1H, Ar); 6.87 (dd, J 3.7, 1.8 Hz, 1H, Ar); 6.75 (d, J 1.7 Hz, 1H, Ar); 6.61 (dd, J 6.8, 1.7 Hz, 1H, Ar); 6.42 (dd, J 3.7, 2.8 Hz, 1H, Ar); 2.92 (s, 3H, CH$_3$); 1.48 (m, 2H, cyclopropyl); 0.93 (m, 1H, cyclopropyl); 0.55 (m, 1H, cyclopropyl). M/Z (M+H)$^+$=332.3. MP: 183-197° C.

Example 69

5-Methyl-9-(5-trifluoromethylpyridin-2-yl)-spiro[benzo[f]pyrrolo[1,2-a][1,4]diazepine-6,1'-cyclopropan]-4(5H)-one

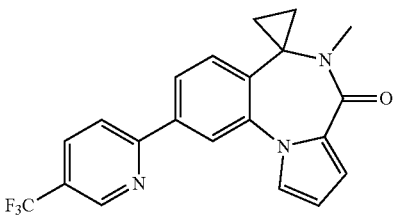

Example 69 was obtained according to general procedure VI(i), starting from compound 31 in presence of 2-bromo-5-trifluoromethylpyridine. Purification by preparative HPLC, afforded the product as a beige solid in 18% yield. $^1$H-NMR (400 MHz, DMSO-D6): 9.08 (m, 1H, Ar); 8.37 (d, J 8.4 Hz, 1H, Ar); 8.34 (m, 1H, Ar); 8.24 (d, J 1.6 Hz, 1H, Ar); 8.13 (dd, J 7.8, 1.6 Hz, 1H, Ar); 7.67 (d, J 7.8 Hz, 1H, Ar); 7.65 (dd, J 2.8, 1.8 Hz, 1H, Ar); 6.88 (dd, J 3.7, 1.8 Hz, 1H, Ar); 6.45 (d, J 3.7, 2.8 Hz, 1H, Ar); 2.93 (s, 3H, CH$_3$); 1.51 (m, 2H, cyclopropyl); 0.95 (m, 1H, cyclopropyl); 0.58 (m, 1H, cyclopropyl). M/Z (M+H)$^+$=384.3. MP: 78-89° C.

Example 70

5-Methyl-9-(pyridazin-3-yl)-spiro[benzo[f]pyrrolo[1,2-a][1,4]diazepine-6,1'-cyclopropan]-4(5H)-one

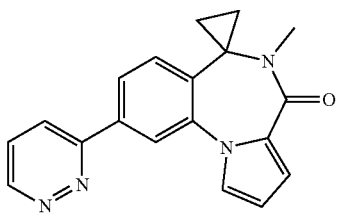 [SMILES: CN1C(=O)c2cccn2-c2cc(-c3cccnn3)ccc2C12CC2]

Example 70 was obtained according to general procedure VI(i), starting from compound 31 in presence of 3-chloropyridazine. Purification by flash column chromatography on silica gel (EtOAc in cylohexane, 50% to 90%), afforded the product as a beige solid in 67% yield. M/Z (M+H)$^+$=317.1.

Example 71

5-Methyl-9-(2-methoxycarbonylpyridin-3-yl)-spiro[benzo[f]pyrrolo[1,2-a][1,4]diazepine-6,1'-cyclopropan]-4(5H)-one

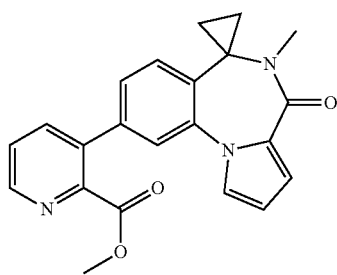 [SMILES: COC(=O)c1ncccc1-c1ccc2c(c1)-n1cccc1C(=O)N(C)C21CC1]

Example 71 was obtained according to general procedure VI(i), starting from compound 31 in presence of methyl 3-bromopicolinate. Purification by flash column chromatography on silica gel (EtOAc in cylohexane, 0% to 50%) afforded the product as a white solid in 63% yield. $^1$H-NMR (400 MHz, DMSO-D6): 8.67 (dd, J 4.6, 1.5 Hz, 1H, Ar); 8.10 (dd, J 7.8, 1.5 Hz, 1H, Ar); 7.69 (dd, J 7.8, 4.6 Hz, 1H, Ar); 7.60 (m, 2H, Ar); 7.53 (dd, J 2.8, 1.8 Hz, 1H, Ar); 7.30 (dd, J 7.9, 1.6 Hz, 1H, Ar); 6.88 (dd, J 3.7, 1.8 Hz, 1H, Ar); 6.43 (dd, J 3.7, 2.8 Hz, 1H, Ar); 3.71 (s, 3H, CH$_3$); 2.94 (s, 3H, CH$_3$); 1.50 (m, 2H, cyclopropyl); 0.95 (m, 1H, cyclopropyl); 0.58 (m, 1H, cyclopropyl). M/Z (M+H)$^+$=374.3. MP: 198-203° C.

Example 72

5-Methyl-9-(2-(1-hydroxy-1-methyl-ethyl)-pyridin-3-yl)-spiro[benzo[f]pyrrolo[1,2-a][1,4]diazepine-6,1'-cyclopropan]-4(5H)-one

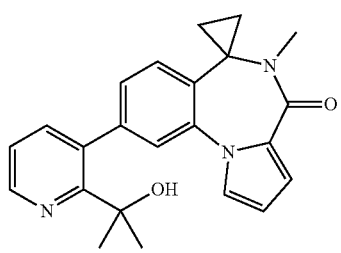 [SMILES: CN1C(=O)c2cccn2-c2cc(-c3cccnc3C(C)(C)O)ccc2C12CC2]

Under inert atmosphere, to a solution of example 71 (1.0 equiv.) in THF (0.10 mol·L$^{-1}$) cooled at −10° C., a solution of methylmagnesium bromide (3.0M in Et$_2$O, 2.2 equiv.) was added dropwise. The reaction mixture was stirred at −10° C. for 1 hour before being hydrolysed by saturated aqueous ammonium chloride and extracted twice with EtOAc. The combined organic extracts were washed with brine, dried over MgSO$_4$ and concentrated under vacuum. Purification by flash column chromatography on silica gel (EtOAc in cylohexane, 40% to 100%) afforded example 72 as a white solid in 46% yield. $^1$H-NMR (400 MHz, DMSO-D6): 8.54 (m, 1H, Ar); 7.55 (m, 1H, Ar); 7.48 (m, 2H, Ar); 7.43 (m, 1H, Ar); 7.34 (dd, J 7.5, 4.8 Hz, 1H, Ar); 7.23 (d, J 7.5 Hz, 1H, Ar); 6.86 (dd, J 3.7, 1.8 Hz, 1H, Ar); 6.39 (dd, J 3.7, 2.8 Hz, 1H, Ar); 2.95 (s, 3H, CH$_3$); 1.49 (m, 2H, cyclopropyl); 1.39 (s, 3H, CH$_3$); 1.35 (s, 3H, CH$_3$); 0.93 (m, 1H, cyclopropyl); 0.54 (m, 1H, cyclopropyl). Proton for OH not observed. M/Z (M+H)$^+$=374.3. MP: 220-228° C.

Example 73

7-Fluoro-5-methyl-9-(2-methyl-pyridin-3-yl)-spiro[benzo[f]pyrrolo[1,2-a][1,4]diazepine-6,1'-cyclopropan]-4(5H)-one, hydrochloride

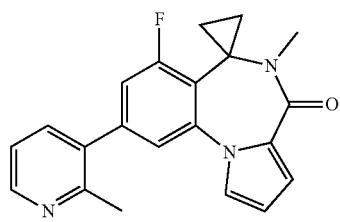 [SMILES: Cc1ncccc1-c1cc(F)c2c(c1)-n1cccc1C(=O)N(C)C21CC1]

Example 73 was obtained according to general procedure VI(ii) starting from example 7 in presence of 2-methylpyridine-3-boronic pinacol ester. Purification by flash column chromatography on silica gel (10 to 70% EtOAc in cyclohexane) afforded the product as a beige solid in 59% yield. Salt formation was performed by method VII(i). $^1$H-NMR (400 MHz, DMSO-D6): 8.77 (d, J 5.8 Hz, 1H, Ar); 8.36 (d, J 7.6 Hz, 1H, Ar); 7.85 (dd, J 7.6, 5.8 Hz, 1H, Ar); 7.57 (m, 2H, Ar); 7.46 (dd, J 10.5, 1.5 Hz, 1H, Ar); 6.89 (dd, J 3.7, 1.8 Hz, 1H, Ar); 6.42 (dd, J 3.7, 2.8 Hz, 1H, Ar); 2.89 (s, 3H, CH$_3$); 2.69 (s, 3H, CH$_3$); 1.68 (m, 1H, cyclopropyl); 1.53 (m, 1H, cyclopropyl); 0.93 (m, 1H, cyclopropyl); 0.65 (m, 1H, cyclopropyl). Proton for HCl salt not observed. M/Z (M+H)$^+$=348.0. MP: 174-188° C.

Example 74

7-Fluoro-5-methyl-9-(6-fluoro-pyridin-3-yl)-spiro[benzo[f]pyrrolo[1,2-a][1,4]diazepine-6,1'-cyclopropan]-4(5H)-one

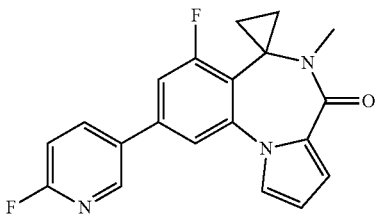 [SMILES: CN1C(=O)c2cccn2-c2cc(-c3ccc(F)nc3)cc(F)c2C12CC2]

Example 74 was obtained according to general procedure VI(ii) starting from example 7 in presence of 6-fluoro-3-pyridinyl boronic acid. Purification by flash column chromatography on silica gel (10 to 100% EtOAc in cyclohexane) afforded the product as a white solid in 41% yield. $^1$H-NMR (400 MHz, DMSO-D6): 8.72 (d, J 2.6 Hz, 1H, Ar); 8.45 (ddd, J 8.4, 7.9, 2.6 Hz, 1H, Ar); 7.74 (m, 2H, Ar); 7.66 (dd, J 11.0, 1.6 Hz, 1H, Ar); 7.33 (dd, J 8.4, 2.8 Hz, 1H, Ar); 6.88 (dd, J 3.7, 1.8 Hz, 1H, Ar); 6.44 (dd, J 3.7, 2.8 Hz, 1H, Ar); 2.97 (s, 3H, CH$_3$); 1.67 (m, 1H, cyclopropyl); 1.51 (m, 1H, cyclopropyl); 0.91 (m, 1H, cyclopropyl); 0.62 (m, 1H, cyclopropyl). M/Z (M+H)$^+$=352.0. MP: 220-225° C.

Example 75

10-Fluoro-5-methyl-9-(2-methyl-pyridin-3-yl)-spiro[benzo[f]pyrrolo[1,2-a][1,4]diazepine-6,1'-cyclopropan]-4(5H)-one, hydrochloride

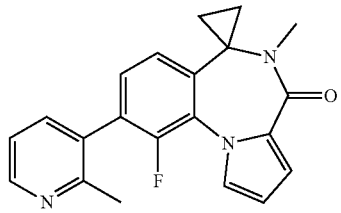 [SMILES: Cc1ncccc1-c1ccc2c(c1F)-n1cccc1C(=O)N(C)C21CC1]

Example 75 was obtained according to general procedure VI(ii) starting from example 8 in presence of 2-methylpyridine-3-boronic pinacol ester. Purification by flash column chromatography on silica gel (10 to 70% EtOAc in cyclohexane) afforded the product as a brown solid in 29% yield. Salt formation was performed by method VII(i). $^1$H-NMR (400 MHz, DMSO-D6): 8.79 (d, J 5.6 Hz, 1H, Ar); 8.35 (d, J 7.5 Hz, 1H, Ar); 7.84 (dd, J 7.5, 5.6 Hz, 1H, Ar); 7.54 (d, J 7.8 Hz, 1H, Ar); 7.45 (m, 2H, Ar); 6.85 (dd, J 3.7, 1.8 Hz, 1H, Ar); 6.42 (dd, J 3.7, 2.8 Hz, 1H, Ar); 2.93 (s, 3H, CH$_3$); 2.59 (s, 3H, CH$_3$); 1.52 (m, 2H, cyclopropyl); 0.91 (m, 1H, cyclopropyl); 0.64 (m, 1H, cyclopropyl). Proton for HCl salt not observed. M/Z (M+H)$^+$=348.0. MP: 166-184° C.

Example 76

10-Fluoro-5-Methyl-9-(6-fluoro-pyridin-3-yl)-spiro[benzo[f]pyrrolo[1,2-a][1,4]diazepine-6,1'-cyclopropan]-4(5H)-one

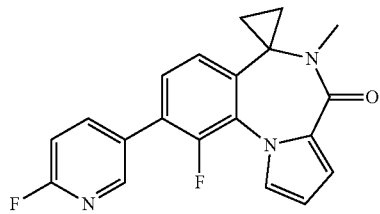 [SMILES: CN1C(=O)c2cccn2-c2c(ccc(-c3ccc(F)nc3)c2F)C12CC2]

Example 76 was obtained according to general procedure VI(ii) starting from example 8 in presence of 6-fluoro-3-pyridinyl boronic acid. Purification by preparative HPLC afforded the product as a white solid in 14% yield. $^1$H-NMR (400 MHz, DMSO-D6): 8.42 (s, 1H, Ar); 8.18 (m, 1H, Ar); 7.51-7.44 (m, 3H, Ar); 7.20 (dd, J 8.5, 2.6 Hz, 1H, Ar); 6.98 (dd, J 3.7, 1.8 Hz, 1H, Ar); 6.45 (dd, J 3.7, 2.8 Hz, 1H, Ar); 3.04 (s, 3H, CH$_3$); 1.53 (m, 2H, cyclopropyl); 0.99 (m, 1H, cyclopropyl); 0.69 (m, 1H, cyclopropyl). M/Z (M+H)$^+$=352.0. MP: 153-157° C.

Example 77

8-Fluoro-5-methyl-9-(2-methyl-pyridin-3-yl)-spiro[benzo[f]pyrrolo[1,2-a][1,4]diazepine-6,1'-cyclopropan]-4(5H)-one, hydrochloride

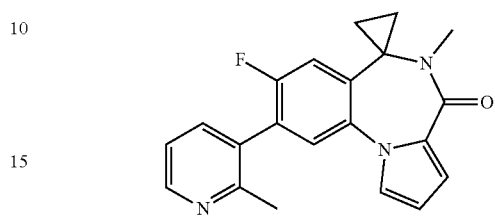

Example 77 was obtained according to general procedure VI(ii) starting from example 9 in presence of 2-methylpyridine-3-boronic pinacol ester. Purification by flash column chromatography on silica gel (100% EtOAc) afforded the product as a beige solid in 56% yield. Salt formation was performed by method VII(i). $^1$H-NMR (400 MHz, DMSO-D6): 8.79 (d, J 5.6 Hz, 1H, Ar); 8.36 (d, J 7.5 Hz, 1H, Ar); 7.84 (dd, J 7.5, 5.6 Hz, 1H, Ar); 7.71 (d, J 6.6 Hz, 1H, Ar); 7.65 (d, J 9.5 Hz, 1H, Ar); 7.50 (dd, J 2.8, 1.8 Hz, 1H, Ar); 6.87 (dd, J 3.7, 1.8 Hz, 1H, Ar); 6.41 (dd, J 3.7, 2.8 Hz, 1H, Ar); 2.93 (s, 3H, CH$_3$); 2.58 (s, 3H, CH$_3$); 1.55 (m, 2H, cyclopropyl); 0.96 (m, 1H, cyclopropyl); 0.63 (m, 1H, cyclopropyl). Proton for HCl salt not observed. M/Z (M+H)$^+$=348.0. MP: 200-210° C.

Example 78

8-Fluoro-5-methyl-9-(6-fluoro-pyridin-3-yl)-spiro[benzo[f]pyrrolo[1,2-a][1,4]diazepine-6,1'-cyclopropan]-4(5H)-one

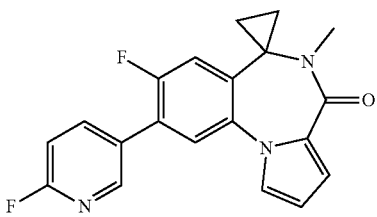 [SMILES: CN1C(=O)c2cccn2-c2cc(-c3ccc(F)nc3)c(F)cc2C12CC2]

Example 78 was obtained according to general procedure VI(ii) starting from example 9 in presence of 6-fluoro-3-pyridinyl boronic acid. Purification by flash column chromatography on silica gel (100% EtOAc) afforded the product as a white solid in 48% yield. $^1$H-NMR (400 MHz, DMSO-D6): 8.55 (s, 1H, Ar); 8.30 (m, 1H, Ar); 7.77 (d, J 6.9 Hz, 1H, Ar); 7.64 (dd, J 2.8, 1.8 Hz, 1H, Ar); 7.60 (d, J 10.3 Hz, 1H, Ar); 7.36 (d, J 8.5, 2.8 Hz, 1H, Ar); 6.86 (dd, J 3.7, 1.8 Hz, 1H, Ar); 6.41 (dd, J 3.7, 2.8 Hz, 1H, Ar); 2.94 (s, 3H, CH$_3$); 1.53 (m, 2H, cyclopropyl); 0.94 (m, 1H, cyclopropyl); 0.60 (m, 1H, cyclopropyl). M/Z (M+H)$^+$=352.0. MP: 185-192° C.

Example 79

9-Bromo-1-fluoro-5-methyl-spiro[benzo[f]pyrrolo[1,2-a][1,4]diazepine-6,1'-cyclopropan]-4(5H)-one

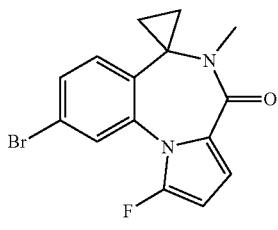 [SMILES: CN1C(=O)c2ccc(F)n2-c2cc(Br)ccc2C12CC2]

A mixture of example 1 (1.0 equiv.) and SelectFluor™ (1.0 equiv.) in acetonitrile (0.10 mol·L$^{-1}$) was subjected to microwave irradiation at 100° C. for 10 minutes. The reaction mixture was neutralized with an aqueous solution of ammonium chloride and extracted twice with dichloromethane. The organic layers were combined, washed with brine, dried over MgSO$_4$ and concentrated under vacuum to afford a 3:1 mixture of product and starting material according to LC/MS analysis. The mixture was obtained as a brown solid in quantitative yield and taken crude to the next step without purification. M/Z (M[$^{79}$Br]+H)$^+$=335.2.

Example 80

9-Bromo-2-chloro-1-fluoro-5-methyl-spiro[benzo[f]pyrrolo[1,2-a][1,4]diazepine-6,1'-cyclopropan]-4(5H)-one

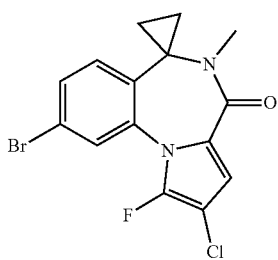 [SMILES: CN1C(=O)c2cc(Cl)c(F)n2-c2cc(Br)ccc2C12CC2]

Example 80 was prepared according to procedure of example 79, starting from example 5. A 3:1 mixture of product and starting material was obtained according to LC/MS analysis. The mixture was obtained as a brown solid in quantitative yield and taken crude to the next step without purification. M/Z (M[$^{79}$Br][$^{35}$Cl]+H)$^+$=369.

Example 81

9-(2-Methyl-pyridin-3-yl)-1-fluoro-5-methyl-spiro[benzo[f]pyrrolo[1,2-a][1,4]diazepine-6,1'-cyclopropan]-4(5H)-one, hydrochloride

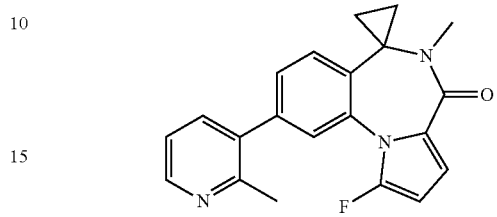

Example 81 was obtained according to general procedure VI(i), starting from example 79 and 2-methylpyridine-3-boronic acid pinacol ester. Purification by preparative HPLC afforded the product as a white solid in 25% yield. Salt formation was performed by method VII(i). $^1$H-NMR (400 MHz, DMSO-D6): 8.78 (d, J 5.5 Hz, 1H, Ar); 8.37 (d, J 7.5 Hz, 1H, Ar); 7.89 (dd, J 7.5, 5.5 Hz, 1H, Ar); 7.75 (m, 2H, Ar); 7.55 (dd, J 7.8, 1.4 Hz, 1H, Ar); 6.76 (dd, J 6.1, 4.2 Hz, 1H, Ar); 6.08 (t, J 6.1 Hz, 1H, Ar); 2.93 (s, 3H, CH$_3$); 2.69 (s, 3H, CH$_3$); 1.53 (m, 2H, cyclopropyl); 0.99 (m, 1H, cyclopropyl); 0.76 (m, 1H, cyclopropyl). Proton for HCl salt not observed. M/Z (M+H)$^+$=348.3. MP=150-158° C.

Example 82

9-(2-Methyl-pyridin-3-yl)-2-chloro-5-methyl-spiro[benzo[f]pyrrolo[1,2-a][1,4]diazepine-6,1'-cyclopropan]-4(5H)-one, hydrochloride

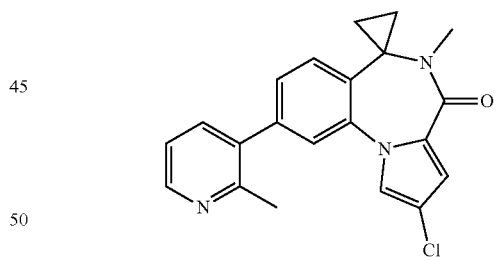

Example 82 was obtained according to general procedure VI(i), starting from example 5 and 2-methylpyridine-3-boronic acid pinacol ester. Purification by flash column chromatography on silica gel (50% to 100% EtOAc in cyclohexane) afforded the product as a white solid in 46% yield. Salt formation was performed by method VII(i). $^1$H-NMR (400 MHz, DMSO-D6): 8.77 (d, J 5.5 Hz, 1H, Ar); 8.39 (d, J 7.5 Hz, 1H, Ar); 7.87 (dd, J 7.5, 5.5 Hz, 1H, Ar); 7.75 (d, J 2.0 Hz, 1H, Ar); 7.74 (d, J 1.6 Hz, 1H, Ar); 7.68 (d, J 7.8 Hz, 1H, Ar); 7.51 (dd, J 7.8, 1.6 Hz, 1H, Ar); 6.87 (d, J 2.0 Hz, 1H, Ar); 2.94 (s, 3H, CH$_3$); 2.68 (s, 3H, CH$_3$); 1.53 (m, 2H, cyclopropyl); 1.03 (m, 1H, cyclopropyl); 0.66 (m, 1H, cyclopropyl). Proton for HCl salt not observed. M/Z (M[$^{35}$Cl]+H)$^+$=364.3. MP=210-219° C.

Example 83

9-(2-Methyl-pyridin-3-yl)-2-chloro-1-fluoro-5-methyl-spiro[benzo[f]pyrrolo[1,2-a][1,4]diazepine-6,1'-cyclopropan]-4(5H)-one, hydrochloride

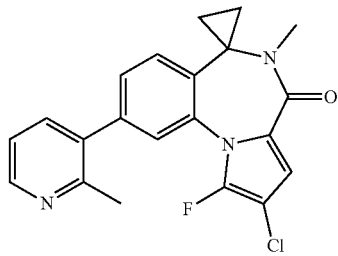 [SMILES: Cc1ncccc1-c1ccc2c(c1)-n1c(cc(Cl)c1F)C(=O)N(C)C21CC1]

Example 83 was obtained according to general procedure VI(i), starting from example 80 and 2-methylpyridine-3-boronic acid pinacol ester. Purification by preparative HPLC afforded the product as a white solid in 12% yield. Salt formation was performed by method VII(i). $^1$H-NMR (400 MHz, DMSO-D6): 8.78 (d, J 5.5 Hz, 1H, Ar); 8.33 (d, J 7.5 Hz, 1H, Ar); 7.87 (dd, J 7.5, 5.5 Hz, 1H, Ar); 7.84 (dd, J 5.6, 1.6 Hz, 1H, Ar); 7.77 (d, J 7.9 Hz, 1H, Ar); 7.58 (dd, J 7.9, 1.6 Hz, 1H, Ar); 6.89 (d, J 5.6 Hz, 1H, Ar); 2.93 (s, 3H, CH$_3$); 2.68 (s, 3H, CH$_3$); 1.55 (m, 2H, cyclopropyl); 1.03 (m, 1H, cyclopropyl); 0.83 (m, 1H, cyclopropyl). Proton for HCl salt not observed. M/Z (M[$^{35}$Cl]+H)$^+$=382.2. MP>250° C.

Example 84

9-(2-Methyl-pyridin-3-yl)-3-chloro-5-methyl-spiro[benzo[f]pyrrolo[1,2-a][1,4]diazepine-6,1'-cyclopropan]-4(5H)-one, hydrochloride

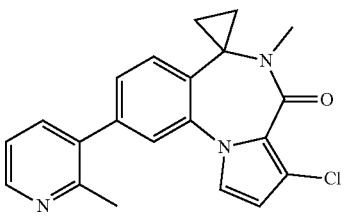 [SMILES: Cc1ncccc1-c1ccc2c(c1)-n1ccc(Cl)c1C(=O)N(C)C21CC1]

Example 84 was obtained according to general procedure VI(i), starting from example 6 and 2-methylpyridine-3-boronic acid pinacol ester. Purification by preparative HPLC afforded the product as a beige solid in 29% yield. Salt formation was performed by method VII(ii). $^1$H-NMR (400 MHz, DMSO-D6): 8.77 (d, J 5.5 Hz, 1H, Ar); 8.39 (d, J 7.5 Hz, 1H, Ar); 7.87 (dd, J 7.5, 5.5 Hz, 1H, Ar); 7.72 (d, J 1.6 Hz, 1H, Ar); 7.67 (d, J 7.9 Hz, 1H, Ar); 7.52 (m, 2H, Ar); 6.54 (d, J 3.1 Hz, 1H, Ar); 2.93 (s, 3H, CH$_3$); 2.68 (s, 3H, CH$_3$); 1.51 (m, 2H, cyclopropyl); 0.99 (m, 1H, cyclopropyl); 0.63 (m, 1H, cyclopropyl). Proton for HCl salt not observed. M/Z (M[$^{35}$Cl]+H)$^+$=364.3. MP=191-208° C.

Example 85

1-Bromo-5-methyl-9-(5-fluoropyridin-2-yl)-spiro[benzo[f]pyrrolo[1,2-a][1,4]diazepine-6,1'-cyclopropan]-4(5H)-one

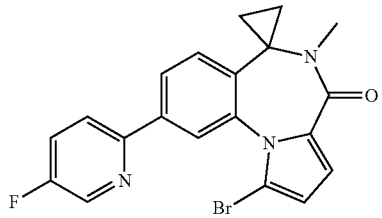 [SMILES: CN1C(=O)c2ccc(Br)n2-c2cc(-c3ccc(F)cn3)ccc2C12CC2]

At 0° C., a solution of N-bromosuccinimide (1.0 equiv.) in DMF (0.2 mol·L$^{-1}$) was added dropwise to a solution of example 65 (1.0 equiv.) in DMF (0.2 mol·L$^{-1}$). The reaction mixture was stirred for 1 hour at 0° C. before being hydrolysed and extracted twice with EtOAc. The organic layers were combined, washed with brine, dried over MgSO$_4$ and concentrated under vacuum to afford a 6:1 mixture of product and di-brominated byproduct according to LC/MS analysis. The mixture was obtained as a white solid in 83% yield and taken crude to the next step without purification. $^1$H-NMR (400 MHz, DMSO-D6): 8.69 (d, J 2.9 Hz, 1H, Ar); 8.31 (d, J 1.7 Hz, 1H, Ar); 8.12 (m, 2H, Ar); 7.86 (dt, J 8.9, 2.9 Hz, 1H, Ar); 7.68 (d, J 8.0 Hz, 1H, Ar); 6.84 (d, J 4.0 Hz, 1H, Ar); 6.62 (d, J 4.0 Hz, 1H, Ar); 2.90 (s, 3H, CH$_3$); 1.49 (m, 2H, cyclopropyl); 0.93 (m, 1H, cyclopropyl); 0.58 (m, 1H, cyclopropyl). M/Z (M[$^{79}$Br]+H)$^+$=412.0.

Example 86

5-Methyl-1-(2-methyl-2H-pyrazol-3-yl)9-(5-fluoropyridin-2-yl)-spiro[benzo[f]pyrrolo[1,2-a][1,4]diazepine-6,1'-cyclopropan]-4(5H)-one

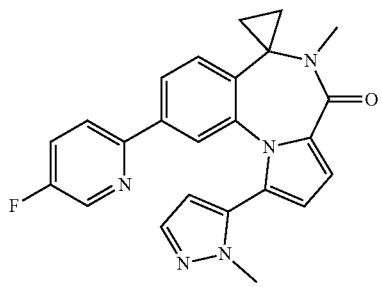 [SMILES: CN1C(=O)c2ccc(-c3ccnn3C)n2-c2cc(-c3ccc(F)cn3)ccc2C12CC2]

Example 86 was obtained according to general procedure VI(i) starting from example 85 in presence of 1-methyl-1H-pyrazole-5-boronic acid pinacol ester. Purification by preparative HPLC afforded the product as a beige solid in 12% yield. $^1$H-NMR (400 MHz, DMSO-D6): 8.58 (d, J 2.9 Hz, 1H, Ar); 7.97 (dd, J 8.0, 1.7 Hz, 1H, Ar); 7.77 (dt, J 8.7, 2.9 Hz, 1H, Ar); 7.66 (d, J 8.0 Hz, 1H, Ar); 7.53 (dd, J 8.7, 4.2 Hz, 1H, Ar); 7.39 (d, J 1.9 Hz, 1H, Ar); 7.33 (dd, J 1.7 Hz, 1H, Ar); 6.97 (d, J 3.8 Hz, 1H, Ar); 6.69 (d, J 3.8 Hz, 1H, Ar); 6.20 (d, J 1.9 Hz, 1H, Ar); 3.55 (s, 3H, CH$_3$); 2.93 (s,

Example 87

5,8-Dimethyl-spiro[benzo[f]pyrrolo[1,2-a][1,4]diazepine-6,1'-cyclopropan]-4(5H)-one

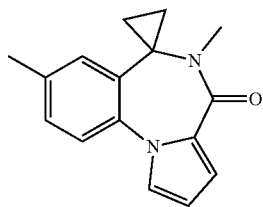 [SMILES: Cc1ccc2c(c1)C1(CC1)N(C)C(=O)c1cccn1-2]

Under inert atmosphere, a mixture of example 13 (1.0 equiv.), dimethyl zinc (2M solution in toluene, 4.0 equiv.) and 1,1'-bis(1,2-diphenylphosphino)ferrocene palladium (II) chloride, complex with dichloromethane (0.2 equiv.) in dioxane (0.15 mol·L$^{-1}$) was heated at 90° C. for 16 hours. The reaction mixture was neutralized with aqueous potassium carbonate and extracted twice with EtOAc. The organic layers were combined, washed with brine, dried over MgSO$_4$, concentrated and purified by flash column chromatography on silica gel (20% to 100% EtOAc in cyclohexane) to afford example 87 as a grey solid in 98% yield. $^1$H-NMR (400 MHz, DMSO-D6): 7.42 (d, J 8.1 Hz, 1H, Ar); 7.41 (dd, J 2.8, 1.8 Hz, 1H, Ar); 7.32 (d, J 1.7 Hz, 1H, Ar); 7.28 (dd, J 8.1, 1.7 Hz, 1H, Ar); 6.82 (dd, J 3.8, 1.8 Hz, 1H, Ar); 6.37 (dd, J 3.8, 2.8 Hz, 1H, Ar); 2.90 (s, 3H, CH$_3$); 2.36 (s, 3H, CH$_3$); 1.44 (m, 2H, cyclopropyl); 0.87 (m, 1H, cyclopropyl); 0.49 (m, 1H, cyclopropyl). M/Z (M+H)$^+$=253.2. MP=143-150° C.

Example 88

8-Morpholin-4-yl-5-methyl-spiro[benzo[f]pyrrolo[1,2-a][1,4]diazepine-6,1'-cyclopropan]-4(5H)-one

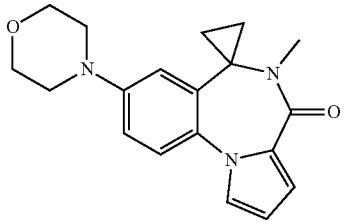 [SMILES: CN1C(=O)c2cccn2-c2ccc(N3CCOCC3)cc2C12CC2]

Under inert atmosphere, a mixture of example 13 (1.0 equiv.), morpholine (1.2 equiv.), sodium tert-butoxide (1.2 equiv.) and bis(tri-tert-butylphosphine)palladium (0.3 equiv.) in toluene (0.2 mol·L$^{-1}$) was heated at 100° C. for 3 hours. The reaction mixture was hydrolyzed and extracted twice with EtOAc. The organic layers were combined, washed with brine, dried over MgSO$_4$, concentrated and purified by preparative HPLC to afford example 88 as a white solid in 41% yield. $^1$H-NMR (400 MHz, DMSO-D6): 7.38 (d, J 8.6 Hz, 1H, Ar); 7.35 (dd, J 2.8, 1.8 Hz, 1H, Ar); 7.04 (d, J 2.6 Hz, 1H, Ar); 7.00 (dd, J 8.6, 2.6 Hz, 1H, Ar); 6.78 (dd, J 3.8, 1.8 Hz, 1H, Ar); 6.33 (dd, J 3.8, 2.8 Hz, 1H, Ar); 3.76 (m, 4H, 2CH$_2$); 3.19 (m, 4H, 2CH$_2$); 2.91 (s, 3H, CH$_3$); 1.52 (m, 1H, cyclopropyl); 1.37 (m, 1H, cyclopropyl); 0.86 (m, 1H, cyclopropyl); 0.49 (m, 1H, cyclopropyl). M/Z (M+H)$^+$=324.2. MP=140-146° C.

Example 89

5,7-Dimethyl-spiro[benzo[f]pyrrolo[1,2-a][1,4]diazepine-6,1'-cyclopropan]-4(5H)-one

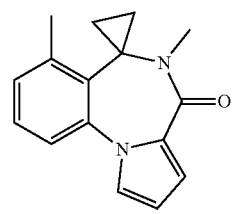 [SMILES: Cc1cccc2c1C1(CC1)N(C)C(=O)c1cccn1-2]

Example 89 was obtained according to the procedure of example 87, starting from example 14 (1.0 equiv.). Purification by preparative HPLC afforded example 89 as a white solid in 37% yield. $^1$H-NMR (400 MHz, DMSO-D6): 7.44 (dd, J 2.8, 1.8 Hz, 1H, Ar); 7.33 (m, 2H, Ar); 7.19 (m, 1H, Ar); 6.79 (dd, J 3.8, 1.8 Hz, 1H, Ar); 6.37 (dd, J 3.8, 2.8 Hz, 1H, Ar); 2.98 (s, 3H, CH$_3$); 2.56 (s, 3H, CH$_3$); 1.65 (m, 1H, cyclopropyl); 1.44 (m, 1H, cyclopropyl); 0.77 (m, 1H, cyclopropyl); 0.47 (m, 1H, cyclopropyl). M/Z (M+H)$^+$=253.2. MP=126-134° C.

Example 90

5,10-Dimethyl-spiro[benzo[f]pyrrolo[1,2-a][1,4]diazepine-6,1'-cyclopropan]-4(5H)-one

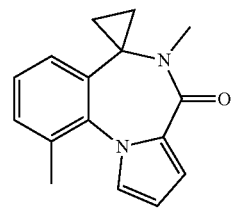 [SMILES: Cc1cccc2c1-n1cccc1C(=O)N(C)C21CC1]

Example 90 was obtained according to the procedure of example 87, starting from example 15 (1.0 equiv.). Purification by flash column chromatography on silica gel (0% to 50% EtOAc in cyclohexane) afforded example 90 as a white solid in 47% yield. $^1$H-NMR (400 MHz, DMSO-D6): 7.38-7.26 (m, 4H, Ar); 6.70 (dd, J 3.8, 1.8 Hz, 1H, Ar); 6.34 (dd, J 3.8, 2.8 Hz, 1H, Ar); 2.83 (s, 3H, CH$_3$); 2.32 (s, 3H, CH$_3$); 1.36 (m, 2H, cyclopropyl); 0.75 (m, 1H, cyclopropyl); 0.45 (m, 1H, cyclopropyl). M/Z (M+H)$^+$=253.2. MP=200-207° C.

Example 91

10-Cyano-5-methyl-spiro[benzo[f]pyrrolo[1,2-a][1,4]diazepine-6,1'-cyclopropan]-4(5H)-one

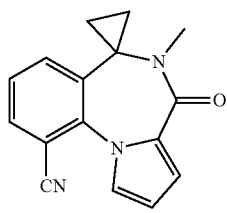 [SMILES: CN1C(=O)c2cccn2-c2c(C#N)cccc2C12CC2]

Under inert atmosphere, a mixture of example 15 (1.0 equiv.), zinc cyanide (1.6 equiv.), and tetrakis(triphenylphosphine)palladium (0.1 equiv.) in DMF (0.10 mol·L$^{-1}$) was subjected to microwave irradiation at 130° C. for 10 minutes. The reaction mixture was poured into water and the grey precipitate was collected by filtration. Purification by flash column chromatography on silica gel (0% to 70% EtOAc in cyclohexane) afforded example 91 as a beige solid in 50% yield. $^1$H-NMR (400 MHz, DMSO-D6): 7.99 (dd, J 7.8, 1.5 Hz, 1H, Ar); 7.87 (dd, J 7.8, 1.5 Hz, 1H, Ar); 7.59 (dd, J 2.8, 1.8 Hz, 1H, Ar); 7.54 (t, J 7.8 Hz, 1H, Ar); 6.87 (dd, J 3.8, 1.8 Hz, 1H, Ar); 6.48 (dd, J 3.8, 2.8 Hz, 1H, Ar); 2.88 (s, 3H, CH$_3$); 1.48 (m, 2H, cyclopropyl); 0.86 (m, 1H, cyclopropyl); 0.52 (m, 1H, cyclopropyl). M/Z (M+H)$^+$=264.2. MP=250° C.

Example 92

10-(2-Methyl-pyridin-3-yl)-5-methyl-spiro[benzo[f]pyrrolo[1,2-a][1,4]diazepine-6,1'-cyclopropan]-4(5H)-one, hydrochloride

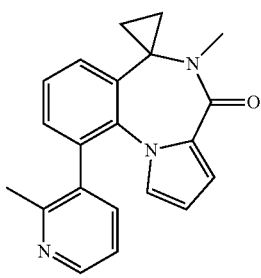 [SMILES: Cc1ncccc1-c1cccc2c1-n1cccc1C(=O)N(C)C21CC1]

Example 92 was obtained according to general procedure VI(i), starting from example 15 and 2-methylpyridine-3-boronic acid pinacol ester. Purification by flash column chromatography on silica gel (0% to 100% EtOAc in cyclohexane) afforded the product as a beige solid in 37% yield. Salt formation was performed by method VII(ii). $^1$H-NMR (400 MHz, DMSO-D6): 8.69 (d, J 5.6 Hz, 1H, Ar); 8.43 (d, J 7.7 Hz, 1H, Ar); 7.87 (dd, J 7.7, 5.6 Hz, 1H, Ar); 7.72 (dd, J 7.5, 1.5 Hz, 1H, Ar); 7.56 (t, J 7.5 Hz, 1H, Ar); 7.48 (dd, J 7.5, 1.5 Hz, 1H, Ar); 6.70 (dd, J 3.8, 1.8 Hz, 1H, Ar); 6.25 (dd, J 2.8, 1.8 Hz, 1H, Ar); 6.09 (dd, J 3.8, 2.8 Hz, 1H, Ar); 2.94 (s, 3H, CH$_3$); 1.67 (s, 3H, CH$_3$); 1.48 (m, 2H, cyclopropyl); 0.85 (m, 1H, cyclopropyl); 0.53 (m, 1H, cyclopropyl). Proton for HCl not observed. M/Z (M+H)$^+$=330.2. MP=250° C.

Example 93

5-Methyl-2-phenyl-9-pyridin-3-yl-spiro[benzo[f]pyrrolo[1,2-a][1,4]diazepine-6,1'-cyclopropan]-4(5H)-one, hydrochloride

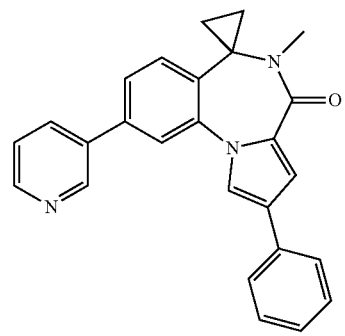 [SMILES: CN1C(=O)c2cc(-c3ccccc3)cn2-c2cc(-c3cccnc3)ccc2C12CC2]

Example 93 was obtained according to general procedure VI(i) starting from example 10 in presence of 3-pyridineboronic acid. Purification by flash column chromatography on silica gel (MeOH in CH$_2$Cl$_2$, 0% to 5%) afforded the product as a grey solid in 50% yield. Salt formation was performed by method VII(i). $^1$H-NMR (400 MHz, DMSO-D6): 9.33 (d, J 1.7 Hz, 1H, Ar); 8.86 (d, J 5.4 Hz, 1H, Ar); 8.80 (d, J 7.9 Hz, 1H, Ar); 8.23 (d, J 1.9 Hz, 1H, Ar); 8.14 (d, J 1.7 Hz, 1H, Ar); 7.99 (dd, J 7.9, 5.4 Hz, 1H, Ar); 7.88 (dd, J 7.8, 1.7 Hz, 1H, Ar); 7.78 (m, 2H, Ar); 7.72 (d, J 7.8 Hz, 1H, Ar); 7.42 (m, 2H, Ar); 7.33 (d, J 1.9 Hz, 1H, Ar); 7.25 (m, 1H, Ar); 2.97 (s, 3H, CH$_3$); 1.54 (m, 2H, cyclopropyl); 1.04 (m, 1H, cyclopropyl); 0.66 (m, 1H, cyclopropyl). Proton for HCl not observed. M/Z (M+H)$^+$=392.2. MP: 218-222° C.

Example 94

3-(5-methyl-4-oxo-2-phenyl-4,5-dihydrospiro[benzo[f]pyrrolo[1,2-a][1,4]diazepine-6,1'-cyclopropan]-9-yl)benzoic acid

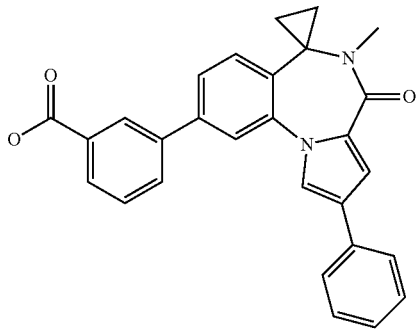 [SMILES: CN1C(=O)c2cc(-c3ccccc3)cn2-c2cc(-c3cccc(C(=O)O)c3)ccc2C12CC2]

Example 94 was obtained according to general procedure VI(i) starting from example 10 in presence of 3-carboxyphenylboronic acid. Purification by flash column chromatography on silica gel (MeOH in CH$_2$Cl$_2$, 0% to 5%) afforded the product as a beige solid in 41% yield. $^1$H-NMR (400 MHz, DMSO-D6): 13.1 (s, 1H, COOH), 8.29 (s, 1H, Ar); 8.22 (d, J 1.9 Hz, 1H, Ar); 8.08 (d, J 7.7 Hz, 1H, Ar);

7.98 (m, 2H, Ar); 7.78 (m, 2H, Ar); 7.65 (m, 3H, Ar); 7.39 (m, 2H, Ar); 7.30 (d, J 1.8 Hz, 1H, Ar); 7.23 (m, 1H, Ar); 2.96 (s, 3H, CH$_3$); 1.51 (m, 2H, cyclopropyl); 1.01 (m, 1H, cyclopropyl); 0.65 (m, 1H, cyclopropyl). M/Z (M+H)$^+$=435.1. MP>250° C.

Example 95

5-Methyl-2-phenyl-9-(2-methyl-pyridin-3-yl)-spiro[benzo[f]pyrrolo[1,2-a][1,4]diazepine-6,1'-cyclopropan]-4(5H)-one, hydrochloride

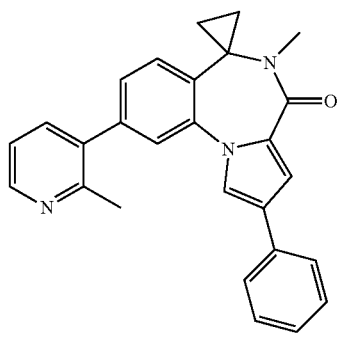 [SMILES: Cc1ncccc1-c1ccc2c(c1)-n1cc(-c3ccccc3)cc1C(=O)N(C)C21CC1]

Example 95 was obtained according to general procedure VI(i) starting from example 10 in presence of 2-methylpyridine-3-boronic acid pinacol ester. Purification by flash column chromatography on silica gel (100% EtOAc) afforded the product as a white solid in 58% yield. Salt formation was performed by method VII(i). $^1$H-NMR (400 MHz, DMSO-D6): 8.78 (dd, J 5.5, 1.3 Hz, 1H, Ar); 8.40 (d, J 7.5 Hz, 1H, Ar); 8.06 (d, J 2.0 Hz, 1H, Ar); 7.87 (m, 1H, Ar); 7.83 (d, J 1.7 Hz, 1H, Ar); 7.75 (m, 2H, Ar); 7.69 (d, J 7.9 Hz, 1H, Ar); 7.50 (dd, J 7.9, 1.7 Hz, 1H, Ar); 7.38 (m, 2H, Ar); 7.32 (d, J 2.0 Hz, 1H, Ar); 7.23 (m, 1H, Ar); 2.97 (s, 3H, CH$_3$); 2.70 (s, 3H, CH$_3$); 1.55 (m, 2H, cyclopropyl); 1.04 (m, 1H, cyclopropyl); 0.67 (m, 1H, cyclopropyl). Proton for HCl salt not observed. M/Z (M+H)$^+$=406.1. MP=174-180° C.

Example 96

5-Methyl-2-phenyl-9-(6-amino-pyridin-3-yl)-spiro[benzo[f]pyrrolo[1,2-a][1,4]diazepine-6,1'-cyclopropan]-4(5H)-one, hydrochloride

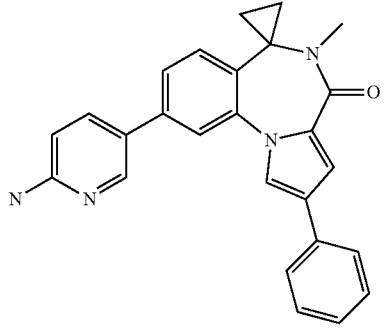

Example 96 was obtained according to general procedure VI(i) starting from example 10 in presence of 2-aminopyridine-5-boronic acid pinacol ester. Purification by flash column chromatography on silica gel (100% EtOAc) afforded the product as a yellow solid in 36% yield. Salt formation was performed by method VII(i). $^1$H-NMR (400 MHz, DMSO-D6): 14.2 (bs, 1H, HCl salt); 8.45 (m, 2H, Ar); 8.16 (d, J 1.9 Hz, 1H, Ar); 8.16 (bs, 2H, NH$_2$); 7.94 (d, J 1.2 Hz, 1H, Ar); 7.77 (m, 2H, Ar); 7.65 (dd, J 8.0, 1.5 Hz, 1H, Ar); 7.62 (d, J 8.0 Hz, 1H, Ar); 7.40 (m, 2H, Ar); 7.30 (d, J 1.9 Hz, 1H, Ar); 7.24 (m, 1H, Ar); 7.13 (d, J 9.0 Hz, 1H, Ar); 2.94 (s, 3H, CH$_3$); 1.49 (m, 2H, cyclopropyl); 1.01 (m, 1H, cyclopropyl); 0.62 (m, 1H, cyclopropyl). M/Z (M+H)$^+$=407.2. MP>250° C.

Example 97

5-Methyl-2-phenyl-9-(2,6-dimethyl-pyridin-4-yl)-spiro[benzo[f]pyrrolo[1,2-a][1,4]diazepine-6,1'-cyclopropan]-4(5H)-one, hydrochloride

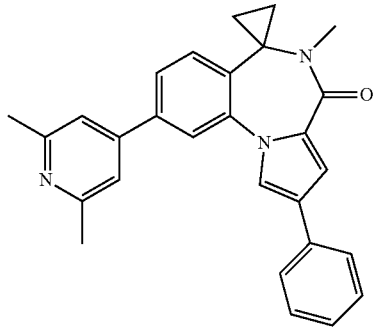 [SMILES: Cc1cc(-c2ccc3c(c2)-n2cc(-c4ccccc4)cc2C(=O)N(C)C32CC2)cc(C)n1]

Example 97 was obtained according to general procedure VI(i) starting from example 10 in presence of 2,6-dimethylpyridine-4-boronic acid pinacol ester. Purification by flash column chromatography on silica gel (100% EtOAc) afforded the product as a beige solid in 59% yield. Salt formation was performed by method VII(i). $^1$H-NMR (400 MHz, DMSO-D6): 15.8 (bs, 1H, HCl salt); 8.22 (m, 3H, Ar); 8.20 (d, J 2.0 Hz, 1H, Ar); 7.96 (dd, J 7.8, 1.6 Hz, 1H, Ar); 7.78 (m, 3H, Ar); 7.42 (m, 2H, Ar); 7.34 (d, J 2.0 Hz, 1H, Ar); 7.25 (m, 1H, Ar); 2.96 (s, 3H, CH$_3$); 2.77 (s, 6H, 2CH$_3$); 1.56 (m, 2H, cyclopropyl); 1.05 (m, 1H, cyclopropyl); 0.67 (m, 1H, cyclopropyl). M/Z (M+H)$^+$=420.2. MP=227-234° C.

Example 98

5-Methyl-2-phenyl-9-(5-methyl-pyridin-3-yl)-spiro[benzo[f]pyrrolo[1,2-a][1,4]diazepine-6,1'-cyclopropan]-4(5H)-one, hydrochloride

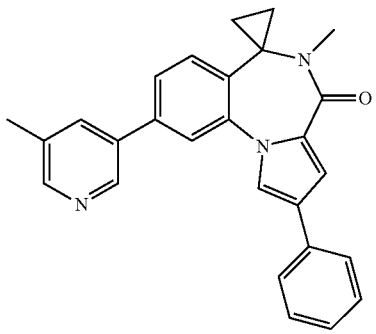 [SMILES: Cc1cncc(-c2ccc3c(c2)-n2cc(-c4ccccc4)cc2C(=O)N(C)C32CC2)c1]

Example 98 was obtained according to general procedure VI(i) starting from example 10 in presence of 5-methylpyridine-3-boronic acid. Purification by flash column chromatography on silica gel (100% EtOAc) afforded the product as a beige solid in 55% yield. Salt formation was performed by method VII(i). $^1$H-NMR (400 MHz, DMSO-D6): 9.18 (s, 1H, Ar); 8.74 (m, 2H, Ar); 8.20 (d, J 1.9 Hz, 1H, Ar); 8.13 (d, J 1.6 Hz, 1H, Ar); 7.84 (d, J 7.9, 1.6 Hz, 1H, Ar); 7.78 (m, 2H, Ar); 7.71 (d, J 7.9 Hz, 1H, Ar); 7.41 (m, 2H, Ar); 7.32 (d, J 1.9 Hz, 1H, Ar); 7.25 (m, 1H, Ar); 2.96 (s, 3H, CH$_3$); 2.54 (s, 3H, CH$_3$); 1.53 (m, 2H, cyclopropyl); 1.03 (m, 1H, cyclopropyl); 0.64 (m, 1H, cyclopropyl). Proton for HCl salt not observed. M/Z (M+H)$^+$=406.2. MP=212-220° C.

Example 99

5-Methyl-2-phenyl-9-(2-ethyl-pyridin-3-yl)-spiro[benzo[f]pyrrolo[1,2-a][1,4]diazepine-6,1'-cyclopropan]-4(5H)-one, hydrochloride

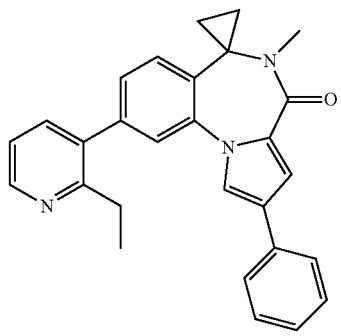 [SMILES: CCc1ncccc1-c1ccc2c(c1)-n1cc(-c3ccccc3)cc1C(=O)N(C)C21CC1]

Example 99 was obtained according to general procedure VI(i) starting from example 10 in presence of 2-ethylpyridine-3-boronic acid. Purification by flash column chromatography on silica gel (80% EtOAc in cyclohexane to 100% EtOAc) afforded the product as a beige solid in 56% yield. Salt formation was performed by method VII(ii). $^1$H-NMR (400 MHz, DMSO-D6): 8.79 (d, J 5.5 Hz, 1H, Ar); 8.31 (s, 1H, Ar); 8.06 (d, J 2.0 Hz, 1H, Ar); 7.85 (m, 2H, Ar); 7.74 (m, 2H, Ar); 7.68 (d, J 7.9 Hz, 1H, Ar); 7.45 (dd, J 7.7, 1.5 Hz, 1H, Ar); 7.38 (m, 2H, Ar); 7.32 (d, J 2.0 Hz, 1H, Ar); 7.22 (m, 1H, Ar); 2.97 (s, 3H, CH$_3$); 2.97 (q, J 8.0 Hz, 2H, C$\underline{H}_2$CH$_3$); 1.53 (m, 2H, cyclopropyl); 1.21 (t, J 8.0 Hz, 3H, CH$_2$C$\underline{H}_3$); 1.05 (m, 1H, cyclopropyl); 0.67 (m, 1H, cyclopropyl). Proton for HCl salt not observed. M/Z (M+H)$^+$=420.2. MP=179-183° C.

Example 100

5-Methyl-2-phenyl-9-(2-trifluoromethyl-pyridin-3-yl)-spiro[benzo[f]pyrrolo[1,2-a][1,4]diazepine-6,1'-cyclopropan]-4(5H)-one

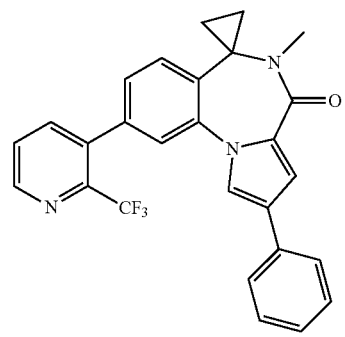 [SMILES: CN1C(=O)c2cc(-c3ccccc3)cn2-c2cc(-c3cccnc3C(F)(F)F)ccc2C12CC2]

Example 100 was obtained according to general procedure VI(i) starting from example 10 in presence of 2-(trifluoromethyl)pyridine-3-boronic acid. Purification by flash column chromatography on silica gel (0% to 60% EtOAc in cyclohexane) afforded the product as a white solid in 29% yield. $^1$H-NMR (400 MHz, DMSO-D6): 8.82 (d, J 5.4 Hz, 1H, Ar); 8.08 (d, J 7.8 Hz, 1H, Ar); 8.05 (d, J 2.0 Hz, 1H, Ar); 7.83 (dd, J 7.8, 5.4 Hz, 1H, Ar); 7.74 (m, 3H, Ar); 7.63 (d, J 7.8 Hz, 1H, Ar); 7.36 (m, 3H, Ar); 7.31 (d, J 2.0 Hz, 1H, Ar); 7.21 (m, 1H, Ar); 2.97 (s, 3H, CH$_3$); 1.53 (m, 2H, cyclopropyl); 1.03 (m, 1H, cyclopropyl); 0.66 (m, 1H, cyclopropyl). M/Z (M+H)$^+$=460.3. MP=199-204° C.

Example 101

5-Methyl-2-phenyl-9-(4-methyl-pyridin-3-yl)-spiro[benzo[f]pyrrolo[1,2-a][1,4]diazepine-6,1'-cyclopropan]-4(5H)-one, hydrochloride

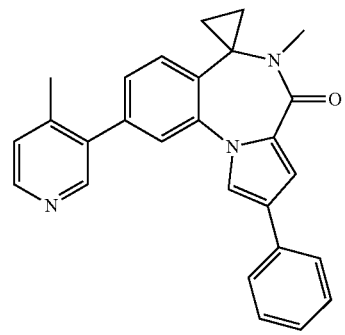 [SMILES: Cc1ccncc1-c1ccc2c(c1)-n1cc(-c3ccccc3)cc1C(=O)N(C)C21CC1]

Example 101 was obtained according to general procedure VI(i) starting from example 10 in presence of 4-methylpyridine-3-boronic acid. Purification by flash column chromatography on silica gel (100% EtOAc) afforded the product as a beige solid in 48% yield. Salt formation was performed by method VII(ii). ¹H-NMR (400 MHz, DMSO-D6): 8.86 (s, 1H, Ar); 8.78 (d, J 5.7 Hz, 1H, Ar); 8.09 (d, J 2.0 Hz, 1H, Ar); 7.96 (d, J 5.7 Hz, 1H, Ar); 7.85 (d, J 1.6 Hz, 1H, Ar); 7.75 (m, 2H, Ar); 7.70 (d, J 7.8 Hz, 1H, Ar); 7.52 (dd, J 7.8, 1.6 Hz, 1H, Ar); 7.39 (m, 2H, Ar); 7.33 (d, J 2.0 Hz, 1H, Ar); 7.24 (m, 1H, Ar); 2.98 (s, 3H, CH$_3$); 2.55 (s, 3H, CH$_3$); 1.56 (m, 2H, cyclopropyl); 1.06 (m, 1H, cyclopropyl); 0.67 (m, 1H, cyclopropyl). Proton for HCl salt not observed. M/Z (M+H)$^+$=406.3. MP=205-217° C.

Example 102

5-Methyl-2-phenyl-9-(pyridin-4-yl)-spiro[benzo[f]pyrrolo[1,2-a][1,4]diazepine-6,1'-cyclopropan]-4(5H)-one, hydrochloride

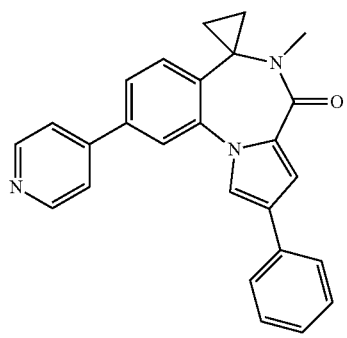 [SMILES: CN1C(=O)c2cc(-c3ccccc3)cn2-c2cc(-c3ccncc3)ccc2C12CC2]

Example 102 was obtained according to general procedure VI(i) starting from example 10 in presence of 4-pyridineboronic acid. Purification by flash column chromatography on silica gel (50% to 100% EtOAc in cycloheaxane) afforded the product as a white solid in 70% yield. Salt formation was performed by method VII(i). ¹H-NMR (400 MHz, DMSO-D6): 8.99 (d, J 6.2 Hz, 2H, Ar); 8.46 (d, J 6.2 Hz, 2H, Ar); 8.26 (d, J 2.0 Hz, 1H, Ar); 8.24 (d, J 1.7 Hz, 1H, Ar); 7.98 (dd, J 7.9, 1.7 Hz, 1H, Ar); 7.78 (m, 3H, Ar); 7.42 (m, 2H, Ar); 7.34 (d, J 2.0 Hz, 1H, Ar); 7.26 (m, 1H, Ar); 2.97 (s, 3H, CH$_3$); 1.56 (m, 2H, cyclopropyl); 1.06 (m, 1H, cyclopropyl); 0.67 (m, 1H, cyclopropyl). Proton for HCl salt not observed. M/Z (M+H)$^+$=392.4. MP=220-230° C.

Example 103

5-Methyl-2-phenyl-9-(6-methyl-pyridin-3-yl)-spiro[benzo[f]pyrrolo[1,2-a][1,4]diazepine-6,1'-cyclopropan]-4(5H)-one, hydrochloride

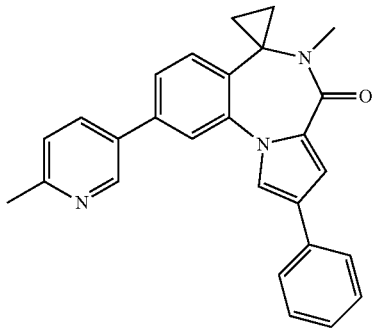 [SMILES: Cc1ccc(-c2ccc3c(c2)-n2cc(-c4ccccc4)cc2C(=O)N(C)C32CC2)cn1]

Example 103 was obtained according to general procedure VI(i) starting from example 10 in presence of 2-methylpyridine-5-boronic acid. Purification by flash column chromatography on silica gel (100% EtOAc) afforded the product as a white solid in 71% yield. Salt formation was performed by method VII(i). ¹H-NMR (400 MHz, DMSO-D6): 9.23 (d, J 1.5 Hz, 1H, Ar); 8.81 (dd, J 8.1, 1.5 Hz, 1H, Ar); 8.23 (d, J 2.0 Hz, 1H, Ar); 8.13 (d, J 1.7 Hz, 1H, Ar); 7.95 (d, J 8.1 Hz, 1H, Ar); 7.84 (dd, J 7.8, 1.7 Hz, 1H, Ar); 7.78 (m, 2H, Ar); 7.71 (d, J 7.8 Hz, 1H, Ar); 7.42 (m, 2H, Ar); 7.33 (d, J 2.0 Hz, 1H, Ar); 7.26 (m, 1H, Ar); 2.97 (s, 3H, CH$_3$); 2.77 (s, 3H, CH$_3$); 1.54 (m, 2H, cyclopropyl); 1.05 (m, 1H, cyclopropyl); 0.65 (m, 1H, cyclopropyl). Proton for HCl salt not observed. M/Z (M+H)$^+$=406.3. MP=200-215° C.

Example 104

5-Methyl-2-phenyl-9-(pyrimidin-5-yl)-spiro[benzo[f]pyrrolo[1,2-a][1,4]diazepine-6,1'-cyclopropan]-4(5H)-one, hydrochloride

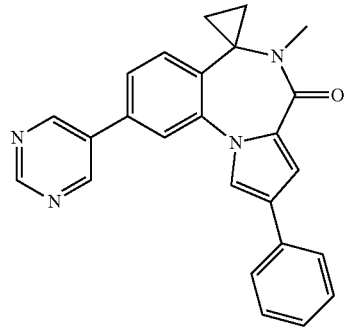 [SMILES: CN1C(=O)c2cc(-c3ccccc3)cn2-c2cc(-c3cncnc3)ccc2C12CC2]

Example 104 was obtained according to general procedure VI(i) starting from example 10 in presence of 5-pyrimidine boronic acid pinacol ester. Purification by flash column chromatography on silica gel (100% EtOAc) afforded the product as a white solid in 60% yield. Salt formation was performed by method VII(i). ¹H-NMR (400 MHz, DMSO-D6): 9.31 (s, 2H, Ar); 9.25 (s, 1H, Ar); 8.23

(d, J 2.0 Hz, 1H, Ar); 8.11 (d, J 1.7 Hz, 1H, Ar); 7.81 (dd, J 7.8, 1.7 Hz, 1H, Ar); 7.79 (m, 2H, Ar); 7.69 (d, J 7.8 Hz, 1H, Ar); 7.41 (m, 2H, Ar); 7.32 (d, J 2.0 Hz, 1H, Ar); 7.25 (m, 1H, Ar); 2.97 (s, 3H, CH$_3$); 1.53 (m, 2H, cyclopropyl); 1.03 (m, 1H, cyclopropyl); 0.66 (m, 1H, cyclopropyl). Proton for HCl salt not observed. M/Z (M+H)$^+$=393.1. MP=168-173° C.

Example 105

5-Methyl-2-phenyl-9-(2-methyl-pyridin-4-yl)-spiro[benzo[f]pyrrolo[1,2-a][1,4]diazepine-6,1'-cyclopropan]-4(5H)-one, hydrochloride

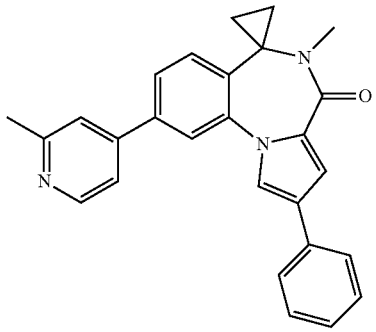 [SMILES: Cc1cc(-c2ccc3c(c2)-n2cc(-c4ccccc4)cc2C(=O)N(C)C32CC2)ccn1]

Example 105 was obtained according to general procedure VI(i) starting from example 10 in presence of 2-methylpyridine-4-boronic acid. Purification by flash column chromatography on silica gel (50% to 100% EtOAc in cyclohexane) afforded the product as a white solid in 57% yield. Salt formation was performed by method VII(i). $^1$H-NMR (400 MHz, DMSO-D6): 8.85 (d, J 6.0 Hz, 1H, Ar); 8.39 (s, 1H, Ar); 8.30 (d, J 6.0 Hz, 1H, Ar); 8.22 (m, 2H, Ar); 7.97 (dd, J 7.9, 1.4 Hz, 1H, Ar); 7.79 (m, 3H, Ar); 7.42 (m, 2H, Ar); 7.34 (d, J 2.0 Hz, 1H, Ar); 7.27 (m, 1H, Ar); 2.97 (s, 3H, CH$_3$); 2.78 (s, 3H, CH$_3$); 1.56 (m, 2H, cyclopropyl); 1.07 (m, 1H, cyclopropyl); 0.68 (m, 1H, cyclopropyl). Proton for HCl salt not observed. M/Z (M+H)$^+$=406.2. MP=225-235° C.

Example 106

5-Methyl-2-phenyl-9-(6-fluoro-pyridin-3-yl)-spiro[benzo[f]pyrrolo[1,2-a][1,4]diazepine-6,1'-cyclopropan]-4(5H)-one

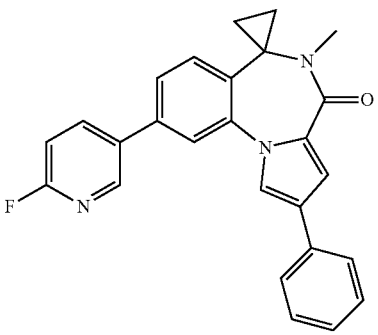 [SMILES: CN1C(=O)c2cc(-c3ccccc3)cn2-c2cc(-c3ccc(F)nc3)ccc2C12CC2]

Example 106 was obtained according to general procedure VI(i) starting from example 10 in presence of 6-fluoropyridine-3-boronic acid. Purification by flash column chromatography on silica gel (50% EtOAc in cyclohexane to 100% EtOAc) afforded the product as a beige solid in 22% yield. $^1$H-NMR (400 MHz, DMSO-D6): 8.72 (d, J 2.4 Hz, 1H, Ar); 8.44 (dt, J 8.4, 2.6 Hz, 1H, Ar); 8.19 (d, J 2.0 Hz, 1H, Ar); 7.99 (d, J 1.6 Hz, 1H, Ar); 7.77 (m, 2H, Ar); 7.69 (dd, J 7.8, 1.6 Hz, 1H, Ar); 7.63 (d, J 7.8 Hz, 1H, Ar); 7.40 (m, 2H, Ar); 7.32 (dd, J 8.4, 2.6 Hz, 1H, Ar); 7.30 (d, J 2.0 Hz, 1H, Ar); 7.24 (m, 1H, Ar); 2.96 (s, 3H, CH$_3$); 1.50 (m, 2H, cyclopropyl); 1.02 (m, 1H, cyclopropyl); 0.65 (m, 1H, cyclopropyl). M/Z (M+H)$^+$=410.3. MP=177-184° C.

Example 107

5-Methyl-2-phenyl-9-(2,6-dimethyl-pyridin-3-yl)-spiro[benzo[f]pyrrolo[1,2-a][1,4]diazepine-6,1'-cyclopropan]-4(5H)-one, hydrochloride

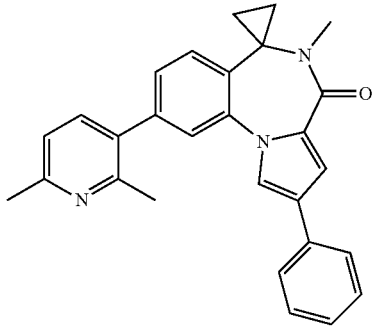 [SMILES: Cc1ccc(-c2ccc3c(c2)-n2cc(-c4ccccc4)cc2C(=O)N(C)C32CC2)c(C)n1]

Example 107 was obtained according to general procedure VI(i) starting from compound 29 in presence of 3-bromo-2,6-dimethylpyridine. Purification by flash column chromatography on silica gel (50% EtOAc in cyclohexane to 100% EtOAc) afforded the product as a yellow solid in 60% yield. Salt formation was performed by method VII(ii). $^1$H-NMR (400 MHz, DMSO-D6): 8.42 (d, J 7.9 Hz, 1H, Ar); 8.05 (d, J 2.0 Hz, 1H, Ar); 7.82 (m, 2H, Ar); 7.74 (m, 2H, Ar); 7.69 (d, J 7.8 Hz, 1H, Ar); 7.49 (dd, J 7.8, 1.7 Hz, 1H, Ar); 7.39 (m, 2H, Ar); 7.32 (d, J 2.0 Hz, 1H, Ar); 7.23 (m, 1H, Ar); 2.96 (s, 3H, CH$_3$); 2.80 (s, 3H, CH$_3$); 2.75 (s, 3H, CH$_3$); 1.53 (m, 2H, cyclopropyl); 1.03 (m, 1H, cyclopropyl); 0.66 (m, 1H, cyclopropyl). Proton for HCl salt not observed. M/Z (M+H)$^+$=420.3. MP=206-214° C.

Example 108

5-Methyl-2-phenyl-9-pyrazin-2-yl-spiro[benzo[f]pyrrolo[1,2-a][1,4]diazepine-6,1'-cyclopropan]-4(5H)-one

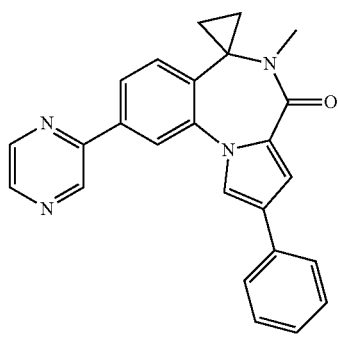 [SMILES: CN1C(=O)c2cc(-c3ccccc3)cn2-c2cc(-c3cnccn3)ccc2C12CC2]

Example 108 was obtained according to general procedure VI(i) starting from compound 29 in presence of chloropyrazine. Purification by flash column chromatography on silica gel (50% EtOAc in cyclohexane to 100% EtOAc) afforded the product as a beige solid in 39% yield. $^1$H-NMR (400 MHz, DMSO-D6): 9.46 (d, J 1.4 Hz, 1H, Ar); 8.78 (dd, 2.3, 1.4, 1H, Ar); 8.69 (d, J 2.3 Hz, 1H, Ar); 8.37 (d, J 1.5 Hz, 1H, Ar); 8.21 (d, J 2.0 Hz, 1H, Ar); 8.13 (dd, J 7.9, 1.5 Hz, 1H, Ar); 7.80 (m, 2H, Ar); 7.70 (d, J 7.9 Hz, 1H, Ar); 7.41 (m, 2H, Ar); 7.33 (d, J 2.0 Hz, 1H, Ar); 7.25 (m, 1H, Ar); 2.97 (s, 3H, CH$_3$); 1.53 (m, 2H, cyclopropyl); 1.03 (m, 1H, cyclopropyl); 0.67 (m, 1H, cyclopropyl). M/Z (M+H)$^+$=393.3. MP=130-141° C.

Example 109

5-Methyl-2-phenyl-9-pyridazin-3-yl-spiro[benzo[f]pyrrolo[1,2-a][1,4]diazepine-6,1'-cyclopropan]-4(5H)-one

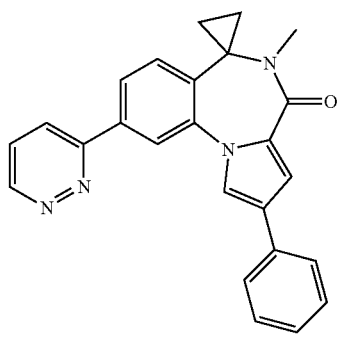 [SMILES: CN1C(=O)c2cc(-c3ccccc3)cn2-c2cc(-c3cccnn3)ccc2C12CC2]

Example 109 was obtained according to general procedure VI(i) starting from compound 29 in presence of 3-chloropyridazine. Purification by flash column chromatography on silica gel (50% EtOAc in cyclohexane to 100% EtOAc) afforded the product as a brown solid in 40% yield. $^1$H-NMR (400 MHz, DMSO-D6): 9.27 (dd, J 4.8, 1.3 Hz, 1H, Ar); 8.42 (dd, J 8.5, 1.3 Hz, 1H, Ar); 8.35 (d, J 1.4 Hz, 1H, Ar); 8.20 (d, J 1.9 Hz, 1H, Ar); 8.17 (dd, J 7.8, 1.4 Hz, 1H, Ar); 7.85 (dd, J 8.5, 4.8 Hz, 1H, Ar); 7.80 (m, 2H, Ar); 7.72 (d, J 7.8 Hz, 1H, Ar); 7.40 (m, 2H, Ar); 7.32 (d, J 1.9 Hz, 1H, Ar); 7.24 (m, 1H, Ar); 2.97 (s, 3H, CH$_3$); 1.54 (m, 2H, cyclopropyl); 1.03 (m, 1H, cyclopropyl); 0.67 (m, 1H, cyclopropyl). M/Z (M+H)$^+$=393.3.

Example 110

5-Methyl-2-phenyl-9-(5-fluoro-pyridin-2-yl)-spiro[benzo[f]pyrrolo[1,2-a][1,4]diazepine-6,1'-cyclopropan]-4(5H)-one

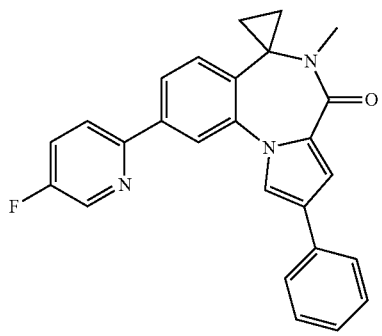 [SMILES: CN1C(=O)c2cc(-c3ccccc3)cn2-c2cc(-c3ccc(F)cn3)ccc2C12CC2]

Example 110 was obtained according to general procedure VI(i) starting from compound 29 in presence of 2-bromo-5-fluoropyridine. Purification by flash column chromatography on silica gel (0% to 50% EtOAc in cyclohexane) afforded the product as a yellow solid in 57% yield. $^1$H-NMR (400 MHz, DMSO-D6): 8.70 (d, J 2.8 Hz, 1H, Ar); 8.24 (m, 2H, Ar); 8.17 (d, J 2.0 Hz, 1H, Ar); 8.04 (dd, J 7.9, 1.7 Hz, 1H, Ar); 7.89 (dt, J 8.7, 2.8 Hz, 1H, Ar); 7.79 (m, 2H, Ar); 7.64 (d, J 7.9 Hz, 1H, Ar); 7.40 (m, 2H, Ar); 7.30 (d, J 2.0 Hz, 1H, Ar); 7.24 (m, 1H, Ar); 2.95 (s, 3H, CH$_3$); 1.50 (m, 2H, cyclopropyl); 1.01 (m, 1H, cyclopropyl); 0.65 (m, 1H, cyclopropyl). M/Z (M+H)$^+$=410.2. MP=140-151° C.

Example 111

5-Methyl-2-phenyl-9-(pyridin-2-yl)-spiro[benzo[f]pyrrolo[1,2-a][1,4]diazepine-6,1'-cyclopropan]-4(5H)-one, hydrochloride

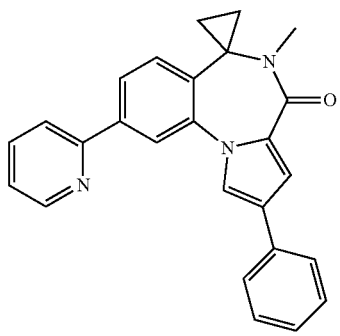 [SMILES: CN1C(=O)c2cc(-c3ccccc3)cn2-c2cc(-c3ccccn3)ccc2C12CC2]

Example 111 was obtained according to general procedure VI(i) starting from compound 29 in presence of 2-bromopyridine. Purification by flash column chromatography on silica gel (0% to 80% EtOAc in cyclohexane) afforded the product as a yellow solid in 57% yield. Salt formation was performed by method VII(ii). ¹H-NMR (400 MHz, DMSO-D6): 8.79 (m, 1H, Ar); 8.34 (d, J 1.7 Hz, 1H, Ar); 8.30 (d, J 8.1 Hz, 1H, Ar); 8.26 (d, J 2.0 Hz, 1H, Ar); 8.18 (m, 1H, Ar); 8.07 (dd, J 7.9, 1.7 Hz, 1H, Ar); 7.80 (m, 2H, Ar); 7.70 (d, J 7.9 Hz, 1H, Ar); 7.62 (m, 1H, Ar); 7.41 (m, 2H, Ar); 7.31 (d, J 2.0 Hz, 1H, Ar); 7.25 (m, 1H, Ar); 2.97 (s, 3H, CH₃); 1.53 (m, 2H, cyclopropyl); 1.04 (m, 1H, cyclopropyl); 0.67 (m, 1H, cyclopropyl). Proton for HCl salt not observed. M/Z (M+H)⁺=392.3. MP=185-198° C.

Example 112

5-methyl-2-phenyl-9-(6-ethylpyridin-3-yl)-spiro[benzo[f]pyrrolo[1,2-a][1,4]diazepine-6,1'-cyclopropan]-4(5H)-one, hydrochloride

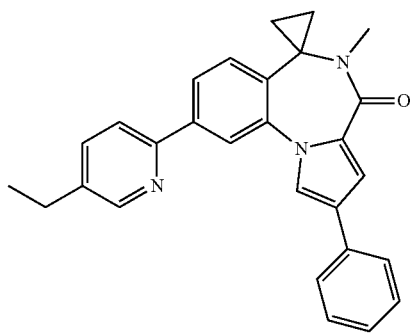 [SMILES: CCc1ccc(-c2ccc3c(c2)-n2cc(-c4ccccc4)cc2C(=O)N(C)C32CC2)nc1]

Example 112 was obtained according to general procedure VI(i) starting from compound 29 in presence of 5-bromo-2-ethylpyridine. Purification by flash column chromatography on silica gel (40% to 100% EtOAc in cyclohexane) afforded the product as a yellow solid in 46% yield. Salt formation was performed by method VII(ii). ¹H-NMR (400 MHz, DMSO-D6): 9.18 (s, 1H, Ar); 8.73 (d, J 7.8 Hz, 1H, Ar); 8.22 (d, J 2.0 Hz, 1H, Ar); 8.11 (d, J 1.4 Hz, 1H, Ar); 7.90 (d, J 7.8 Hz, 1H, Ar); 7.82-7.77 (m, 3H, Ar); 7.70 (d, J 7.9 Hz, 1H, Ar); 7.42 (m, 2H, Ar); 7.33 (d, J 2.0 Hz, 1H, Ar); 7.25 (m, 1H, Ar); 3.03 (q, J 7.7 Hz, 2H, CH₂—CH₃); 2.97 (s, 3H, CH₃); 1.53 (m, 2H, cyclopropyl); 1.35 (t, J 7.7 Hz, 3H, CH₂—CH₃); 1.04 (m, 1H, cyclopropyl); 0.65 (m, 1H, cyclopropyl). Proton for HCl salt not observed. M/Z (M+H)⁺=420.4. MP=209-212° C.

Example 113

5-Methyl-2-phenyl-9-(2-fluoro-pyridin-3-yl)-spiro[benzo[f]pyrrolo[1,2-a][1,4]diazepine-6,1'-cyclopropan]-4(5H)-one

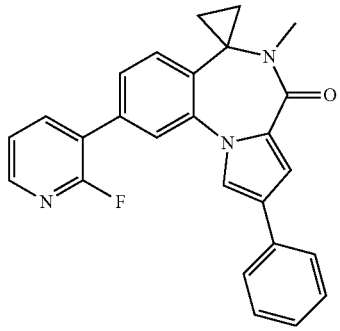 [SMILES: CN1C(=O)c2cc(-c3ccccc3)cn2-c2cc(-c3cccnc3F)ccc2C12CC2]

Example 113 was obtained according to general procedure VI(i) starting from example 10 in presence of 2-fluoro-3-pyridineboronic acid. Purification by flash column chromatography on silica gel (0% to 70% EtOAc in cyclohexane) afforded the product as a beige solid in 59% yield. ¹H-NMR (400 MHz, DMSO-D6): 8.29 (m, 2H, Ar); 8.12 (d, J 1.9 Hz, 1H, Ar); 7.91 (s, 1H, Ar); 7.76 (m, 2H, Ar); 7.65 (d, J 7.8 Hz, 1H, Ar); 7.60 (m, 1H, Ar); 7.52 (m, 1H, Ar); 7.38 (m, 2H, Ar); 7.31 (d, J 1.9 Hz, 1H, Ar); 7.23 (m, 1H, Ar); 2.96 (s, 3H, CH₃); 1.53 (m, 2H, cyclopropyl); 1.02 (m, 1H, cyclopropyl); 0.66 (m, 1H, cyclopropyl). M/Z (M+H)⁺=410.2. MP=143-149° C.

Example 114

5-Methyl-2-phenyl-9-(6-dimethylamino-pyridin-3-yl)-spiro[benzo[f]pyrrolo[1,2-a][1,4]diazepine-6,1'-cyclopropan]-4(5H)-one, hydrochloride

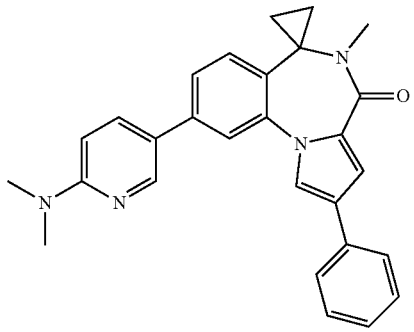 [SMILES: CN(C)c1ccc(-c2ccc3c(c2)-n2cc(-c4ccccc4)cc2C(=O)N(C)C32CC2)cn1]

Example 114 was obtained according to general procedure VI(i) starting from example 10 in presence of 6-fluoropyridine-3-boronic acid and dimethylamine (2M in THF, 2 equiv.). Purification by flash column chromatography on silica gel (0% to 60% EtOAc in cyclohexane) afforded the product as a yellow solid in 53% yield. Salt formation was performed by method (ii). ¹H-NMR (400 MHz, DMSO-D6): 8.39 (s, 2H, Ar); 8.19 (d, J 2.0 Hz, 1H, Ar); 7.95 (d, J 1.5 Hz, 1H, Ar); 7.77 (m, 2H, Ar); 7.66 (dd, J 7.9, 1.5 Hz, 1H, Ar); 7.61 (d, J 7.9 Hz, 1H, Ar); 7.40 (m, 2H, Ar); 7.30 (d, J 2.0

Hz, 1H, Ar); 7.24 (m, 2H, Ar); 3.26 (s, 6H, 2CH₃); 2.95 (s, 3H, CH₃); 1.50 (m, 2H, cyclopropyl); 1.01 (m, 1H, cyclopropyl); 0.62 (m, 1H, cyclopropyl). Proton for HCl salt not observed. M/Z (M+H)⁺=435.3. MP=200-208° C.

Example 115

9-Dimethylamino-5-methyl-2-phenyl-spiro[benzo[f]pyrrolo[1,2-a][1,4]diazepine-6,1'-cyclopropan]-4(5H)-one, hydrochloride

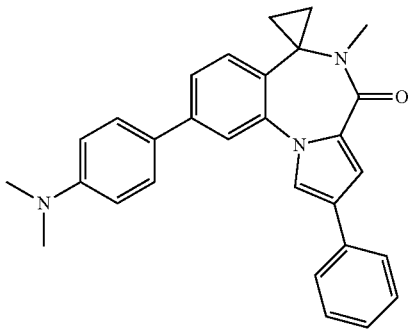 [SMILES: CN(C)c1ccc(-c2ccc3c(c2)-n2cc(-c4ccccc4)cc2C(=O)N(C)C32CC2)cc1]

Under inert atmosphere, a mixture of example 10 (1.0 equiv.), dimethylamine (2M solution in THF, 1.2 equiv.), sodium tertbutoxide (1.2 equiv.) and bis(tri-tert-butylphosphine)palladium (0.1 equiv.) in toluene (0.2 mol·L⁻¹) was heated at 100° C. for 16 hours. The reaction mixture was neutralized with aqueous potassium carbonate and extracted twice with EtOAc. The organic layers were combined, washed with brine, dried over MgSO₄, concentrated and purified by flash column chromatography on silica gel (0% to 50% EtOAc in cyclohexane) to afford example 115 as a beige solid in 53% yield. Salt formation was performed by method VII(i). ¹H-NMR (400 MHz, DMSO-D6): 8.01 (d, J 2.0 Hz, 1H, Ar); 7.75 (m, 2H, Ar); 7.38 (m, 2H, Ar); 7.33 (d, J 8.4 Hz, 1H, Ar); 7.22 (m, 2H, Ar); 7.02 (s, 1H, Ar); 6.78 (m, 1H, Ar); 3.00 (s, 6H, 2CH₃); 2.90 (s, 3H, CH₃); 1.39 (m, 2H, cyclopropyl); 0.91 (m, 1H, cyclopropyl); 0.52 (m, 1H, cyclopropyl). Proton for HCl salt not observed. M/Z (M+H)⁺=358.3. MP=160-170° C.

Example 116

5-Methyl-2-phenyl-9-(2-methoxy-pyridin-3-yl)-spiro[benzo[f]pyrrolo[1,2-a][1,4]diazepine-6,1'-cyclopropan]-4(5H)-one

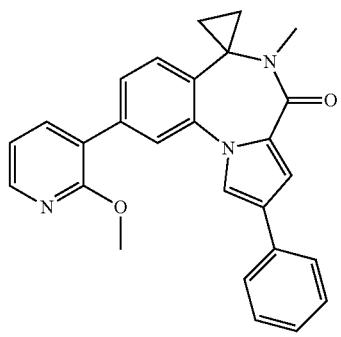 [SMILES: COc1ncccc1-c1ccc2c(c1)-n1cc(-c3ccccc3)cc1C(=O)N(C)C21CC1]

Example 116 was obtained according to general procedure VI(i) starting from example 10 in presence of 2-methoxy-3-pyridineboronic acid. Purification by flash column chromatography on silica gel (0% to 40% EtOAc in cyclohexane) afforded the product as a white solid in 59% yield. ¹H-NMR (400 MHz, DMSO-D6): 8.23 (dd, J 5.0, 1.8 Hz, 1H, Ar); 8.09 (d, J 1.9 Hz, 1H, Ar); 7.91 (dd, J 7.9, 1.7 Hz, 1H, Ar); 7.81 (s, 1H, Ar); 7.76 (m, 2H, Ar); 7.57 (m, 2H, Ar); 7.38 (m, 2H, Ar); 7.29 (d, J 1.9 Hz, 1H, Ar); 7.22 (m, 1H, Ar); 7.14 (dd, J 7.2, 5.0 Hz, 1H, Ar); 3.97 (s, 3H, OCH₃); 2.96 (s, 3H, CH₃); 1.50 (m, 2H, cyclopropyl); 1.00 (m, 1H, cyclopropyl); 0.64 (m, 1H, cyclopropyl). M/Z (M+H)⁺=422.2. MP=183-186° C.

Example 117

5-Methyl-2-phenyl-9-(6-cyano-pyridin-3-yl)-spiro[benzo[f]pyrrolo[1,2-a][1,4]diazepine-6,1'-cyclopropan]-4(5H)-one

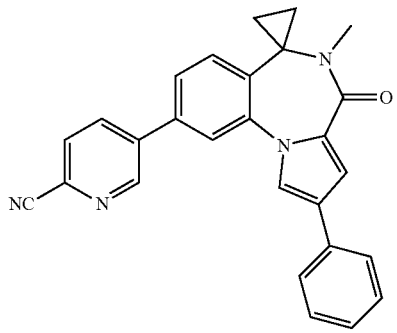 [SMILES: CN1C(=O)c2cc(-c3ccccc3)cn2-c2cc(-c3ccc(C#N)nc3)ccc2C12CC2]

A solution of example 106 (1.0 equiv.) and tetraethylammonium cyanide (8.0 equiv.) in DMA (0.10 mol·L⁻¹) was subjected to microwave irradiation for 40 minutes at 120° C. The reaction mixture was neutralized with aqueous potassium carbonate and extracted twice with EtOAc. The organic layers were combined, washed with brine, dried over MgSO₄, concentrated and purified by flash column chromatography on silica gel (0% to 50% EtOAc in cyclohexane) to afford example 117 as a white solid in 50% yield. ¹H-NMR (400 MHz, DMSO-D6): 9.28 (d, J 2.3 Hz, 1H, Ar); 8.53 (dd, J 8.2, 2.3 Hz, 1H, Ar); 8.24 (d, J 2.0 Hz, 1H, Ar); 8.20 (d, J 8.2 Hz, 1H, Ar); 8.11 (d, J 1.7 Hz, 1H, Ar); 7.83 (dd, J 7.9, 1.7 Hz, 1H, Ar); 7.78 (m, 2H, Ar); 7.70 (d, J 7.9 Hz, 1H, Ar); 7.41 (m, 2H, Ar); 7.32 (d, J 2.0 Hz, 1H, Ar); 7.25 (m, 1H, Ar); 2.97 (s, 3H, CH₃); 1.54 (m, 2H, cyclopropyl); 1.04 (m, 1H, cyclopropyl); 0.66 (m, 1H, cyclopropyl). M/Z (M+H)⁺=417.3. MP=200-204° C.

Example 118

5-Methyl-2-phenyl-9-(6-methylamino-pyridin-3-yl)-spiro[benzo[f]pyrrolo[1,2-a][1,4]diazepine-6,1'-cyclopropan]-4(5H)-one, hydrochloride

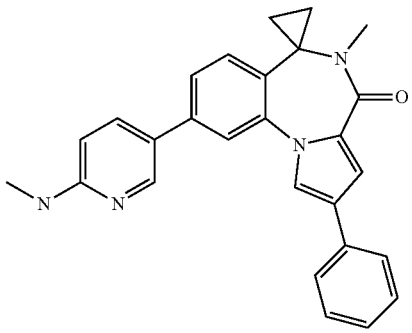 [SMILES: CNc1ccc(-c2ccc3c(c2)-n2cc(-c4ccccc4)cc2C(=O)N(C)C32CC2)cn1]

Example 118 was obtained according to general procedure VI(i) starting from example 10 in presence of 6-(methylamino)-3-pyridinylboronic acid pinacol ester. Purification by flash column chromatography on silica gel (50% to 100% EtOAc in cyclohexane) afforded the product as a yellow solid in 33% yield. Salt formation was performed by method VII(ii). $^{1}$H-NMR (400 MHz, DMSO-D6): 8.75 (bs, 1H, NH); 8.35 (m, 2H, Ar); 8.18 (d, J 1.9 Hz, 1H, Ar); 7.94 (s, 1H, Ar); 7.76 (m, 2H, Ar); 7.65 (dd, J 7.9, 1.5 Hz, 1H, Ar); 7.61 (d, J 7.9 Hz, 1H, Ar); 7.40 (m, 2H, Ar); 7.30 (d, J 1.9 Hz, 1H, Ar); 7.24 (m, 1H, Ar); 7.15 (d, J 9.2 Hz, 1H, Ar); 3.01 (s, 3H, CH$_3$); 2.94 (s, 3H, CH$_3$); 1.50 (m, 2H, cyclopropyl); 1.01 (m, 1H, cyclopropyl); 0.62 (m, 1H, cyclopropyl). HCl proton not observed. M/Z (M+H)$^{+}$=421.3. MP>250° C.

Example 119

5-Methyl-2-phenyl-9-(2-dimethylamino-pyridin-3-yl)-spiro[benzo[f]pyrrolo[1,2-a][1,4]diazepine-6,1'-cyclopropan]-4(5H)-one, hydrochloride

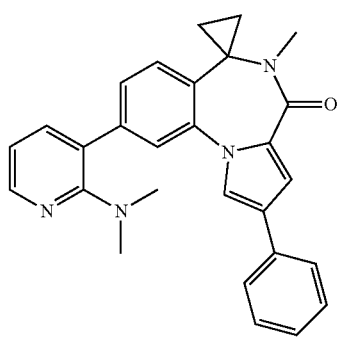 [SMILES: CN(C)c1ncccc1-c1ccc2c(c1)-n1cc(-c3ccccc3)cc1C(=O)N(C)C21CC1]

Example 119 was obtained according to general procedure VI(i) starting from example 10 in presence of 2-fluoro-3-pyridine boronic acid and dimethylamine (2M in THF, 6 equiv.). The reaction mixture was subjected to microwave irradiation for 3 hours at 150° C. Purification by flash column chromatography on silica gel (0% to 50% EtOAc in cyclohexane) afforded the product as a yellow solid in 28% yield. Salt formation was performed by method VII(i). $^{1}$H-NMR (400 MHz, DMSO-D6): 8.16 (dd, J 5.6, 1.7 Hz, 1H, Ar); 8.08 (d, J 1.8 Hz, 1H, Ar); 7.95 (m, 1H, Ar); 7.79 (s, 1H, Ar); 7.75 (m, 2H, Ar); 7.61 (d, J 7.8 Hz, 1H, Ar); 7.44 (dd, J 7.8, 1.4 Hz, 1H, Ar); 7.38 (m, 2H, Ar); 7.31 (d, J 1.8 Hz, 1H, Ar); 7.23 (m, 1H, Ar); 7.09 (m, 1H, Ar); 2.96 (s, 3H, CH$_3$); 2.82 (s, 6H, 2CH$_3$); 1.51 (m, 2H, cyclopropyl); 1.02 (m, 1H, cyclopropyl); 0.63 (m, 1H, cyclopropyl). Proton for HCl salt not observed. M/Z (M+H)$^{+}$=435.3. MP=209-213° C.

Example 120

8-Morpholin-4-yl-5-methyl-2-phenyl-spiro[benzo[f]pyrrolo[1,2-a][1,4]diazepine-6,1'-cyclopropan]-4(5H)-one

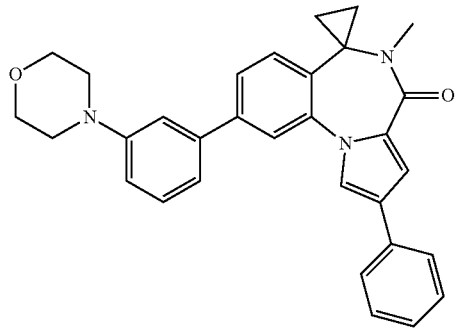 [SMILES: CN1C(=O)c2cc(-c3ccccc3)cn2-c2cc(-c3cccc(N4CCOCC4)c3)ccc2C12CC2]

Under inert atmosphere, a mixture of example 16 (1.0 equiv.), morpholine (1.2 equiv.), sodium tert-butoxide (1.2 equiv.) and bis(tri-tert-butylphosphine)palladium (0.3 equiv.) in toluene (0.25 mol·L$^{-1}$) was heated at 100° C. for 3 hours. The reaction mixture was hydrolyzed and extracted twice with EtOAc. The organic layers were combined, washed with brine, dried over MgSO$_4$, concentrated and purified by preparative HPLC to afford example 120 as a white solid in 23% yield. $^{1}$H-NMR (400 MHz, DMSO-D6): 7.86 (d, J 2.0 Hz, 1H, Ar); 7.72 (m, 2H, Ar); 7.50 (dd, J 8.3, 1.6 Hz, 1H, Ar); 7.37 (m, 2H, Ar); 7.20 (m, 2H, Ar); 7.04 (m, 2H, Ar); 3.76 (m, 4H, 2CH$_2$); 3.20 (m, 4H, 2CH$_2$); 2.92 (s, 3H, CH$_3$); 1.53 (m, 1H, cyclopropyl); 1.39 (m, 1H, cyclopropyl); 0.93 (m, 1H, cyclopropyl); 0.56 (m, 1H, cyclopropyl). M/Z (M+H)$^{+}$=400.4. MP=117-123° C.

Example 121

9-(2,6-Dimethyl-pyridin-4-yl)-5-methyl-2-phenyl-spiro[benzo[f]pyrazolo[1,5-a][1,4]diazepine-6,1'-cyclopropan]-4(5H)-one, hydrochloride

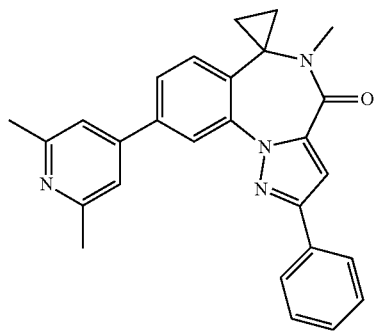 [SMILES: Cc1cc(-c2ccc3c(c2)-n2nc(-c4ccccc4)cc2C(=O)N(C)C32CC2)cc(C)n1]

Example 121 was obtained according to general procedure VI(i) starting from example 11 in presence of 2,6-dimethylpyridine-4-boronic acid pinacol ester. Purification by flash column chromatography on silica gel (50% to 80% EtOAc in cyclohexane) afforded the product as a white solid in 48% yield. Salt formation was performed by method VII(iii). $^1$H-NMR (400 MHz, DMSO-D6): 8.37 (s, 1H, Ar); 8.13-8.00 (m, 4H, Ar); 7.98 (d, J 8.0 Hz, 1H, Ar); 7.81 (d, J 8.0 Hz, 1H, Ar); 7.60 (s, 1H, Ar); 7.51 (m, 2H, Ar); 7.43 (m, 1H, Ar); 3.03 (s, 3H, CH$_3$); 2.72 (s, 6H, 2CH$_3$); 1.64 (m, 2H, cyclopropyl); 1.14 (m, 1H, cyclopropyl); 0.66 (m, 1H, cyclopropyl). Proton for HCl salt not observed. M/Z (M+H)$^+$=421.1. MP>250° C.

Example 122

9-(2-Methyl-pyridin-4-yl)-5-methyl-2-phenyl-spiro[benzo[f]pyrazolo[1,5-a][1,4]diazepine-6,1'-cyclopropan]-4(5H)-one, hydrochloride

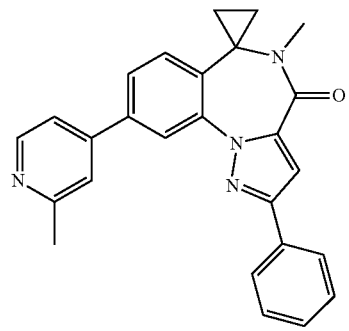 [SMILES: Cc1cc(-c2ccc3c(c2)-n2nc(-c4ccccc4)cc2C(=O)N(C)C32CC2)ccn1]

Example 122 was obtained according to general procedure VI(i) starting from example 11 in presence of 2-methylpyridine-4-boronic acid. Purification by flash column chromatography on silica gel (50% to 100% EtOAc in cyclohexane) afforded the product as a white solid in 65% yield. Salt formation was performed by method VII(iii). $^1$H-NMR (400 MHz, DMSO-D6): 8.83 (d, J 6.2 Hz, 1H, Ar); 8.41 (d, J 1.8 Hz, 1H, Ar); 8.34 (s, 1H, Ar); 8.24 (d, J 6.2 Hz, 1H, Ar); 8.08 (m, 2H, Ar); 8.03 (dd, J 8.0, 1.8 Hz, 1H, Ar); 7.83 (d, J 8.0 Hz, 1H, Ar); 7.61 (s, 1H, Ar); 7.51 (m, 2H, Ar); 7.43 (m, 1H, Ar); 3.04 (s, 3H, CH$_3$); 2.79 (s, 3H, CH$_3$); 1.64 (m, 2H, cyclopropyl); 1.15 (m, 1H, cyclopropyl); 0.67 (m, 1H, cyclopropyl). Proton for HCl salt not observed. M/Z (M+H)$^+$=407.2. MP>250° C.

Example 123

2,9-Diphenyl-5-methyl-2-spiro[benzo[f]pyrazolo[1,5-a][1,4]diazepine-6,1'-cyclopropan]-4(5H)-one

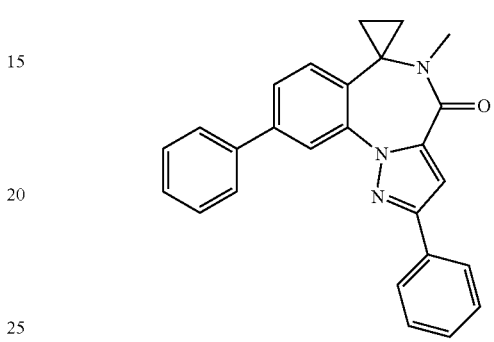

Example 123 was obtained according to general procedure VI(i) starting from example 11 in presence of phenyl boronic acid. Purification by flash column chromatography on silica gel (40% to 80% EtOAc in cyclohexane) afforded the product as a white solid in 50% yield. $^1$H-NMR (400 MHz, DMSO-D6): 8.12 (d, J 1.7 Hz, 1H, Ar); 8.05 (m, 2H, Ar); 7.76 (m, 2H, Ar); 7.72 (dd, J 7.8, 1.7 Hz, 1H, Ar); 7.66 (d, J 7.8 Hz, 1H, Ar); 7.56 (s, 1H, Ar); 7.54-7.42 (m, 6H, Ar); 3.03 (s, 3H, CH$_3$); 1.59 (m, 2H, cyclopropyl); 1.10 (m, 1H, cyclopropyl); 0.66 (m, 1H, cyclopropyl). M/Z (M+H)$^+$=392.1. MP=133-140° C.

Example 124

9-(4-Amino-phenyl)-5-methyl-2-phenyl-spiro[benzo[f]pyrazolo[1,5-a][1,4]diazepine-6,1'-cyclopropan]-4(5H)-one

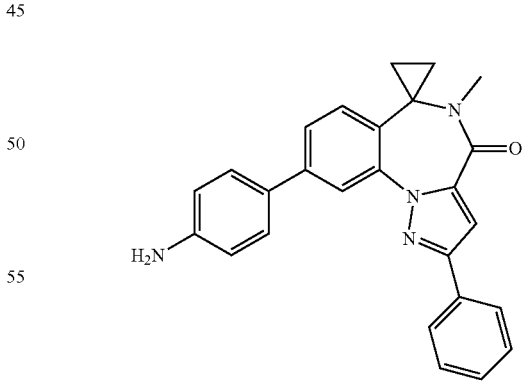

Example 124 was obtained according to general procedure VI(i) starting from example 11 in presence of 4-aminophenyl boronic acid pinacol ester. Purification by flash column chromatography on silica gel (40% to 80% EtOAc in cyclohexane) afforded the product as a white solid in 45% yield. $^1$H-NMR (400 MHz, DMSO-D6): 8.07 (m, 3H, Ar); 7.72 (m, 2H, Ar); 7.68 (dd, J 7.8, 1.7 Hz, 1H, Ar); 7.63 (d, J 7.8 Hz, 1H, Ar); 7.55 (s, 1H, Ar); 7.49 (m, 2H, Ar); 7.42 (m, 1H, Ar); 7.19 (d, J 8.0 Hz, 2H, Ar); 3.02 (s, 3H, CH$_3$); 1.59 (m, 2H, cyclopropyl); 1.10 (m, 1H, cyclopropyl); 0.63 (m, 1H, cyclopropyl). Protons for NH$_2$ not observed. M/Z (M+H)$^+$=407.2. MP=195-209° C.

Example 125

9-(2-Methyl-pyridin-3-yl)-5-methyl-2-phenyl-spiro[benzo[f]pyrazolo[1,5-a][1,4]diazepine-6,1'-cyclopropan]-4(5H)-one, hydrochloride

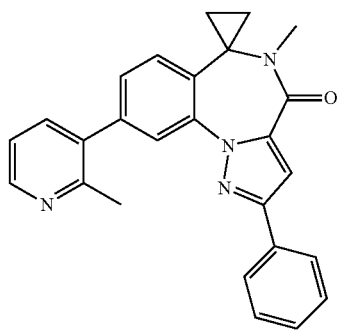 [SMILES: Cc1ncccc1-c1ccc2c(c1)-n1nc(-c3ccccc3)cc1C(=O)N(C)C21CC1]

Example 125 was obtained according to general procedure VI(i) starting from example 11 in presence of 2-methylpyridine-3-boronic acid pinacol ester. Purification by flash column chromatography on silica gel (40% to 100% EtOAc in cyclohexane) afforded the product as a beige solid in 65% yield. Salt formation was performed by method VII(iii). $^1$H-NMR (400 MHz, DMSO-D6): 8.78 (d, J 5.6 Hz, 1H, Ar); 8.36 (d, J 6.8 Hz, 1H, Ar); 8.03 (m, 2H, Ar); 8.00 (d, J 1.7 Hz, 1H, Ar); 7.86 (dd, J 6.8, 5.6 Hz, 1H, Ar); 7.75 (d, J 7.9 Hz, 1H, Ar); 7.59 (s, 1H, Ar); 7.57 (dd, J 7.9, 1.7 Hz, 1H, Ar); 7.48 (m, 2H, Ar); 7.40 (m, 1H, Ar); 3.43 (s, 3H, CH$_3$); 2.67 (s, 3H, CH$_3$); 1.63 (m, 2H, cyclopropyl); 1.14 (m, 1H, cyclopropyl); 0.68 (m, 1H, cyclopropyl). Proton for HCl salt not observed. M/Z (M+H)$^+$=407.1. MP=185-206° C.

Example 126

9-(2,6-Dimethyl-pyridin-3-yl)-5-methyl-2-phenyl-spiro[benzo[f]pyrazolo[1,5-a][1,4]diazepine-6,1'-cyclopropan]-4(5H)-one, hydrochloride

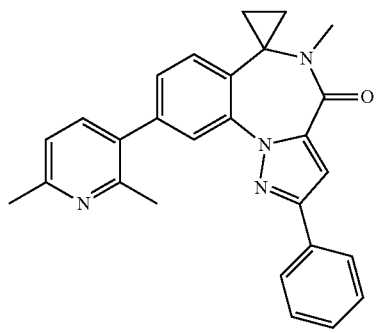 [SMILES: Cc1ccc(-c2ccc3c(c2)-n2nc(-c4ccccc4)cc2C(=O)N(C)C32CC2)c(C)n1]

Example 126 was obtained according to general procedure VI(i) starting from compound 30 in presence of 3-bromo-2,6-dimethylpyridine. Purification by flash column chromatography on silica gel (60% to 100% EtOAc in cyclohexane) afforded the product as a beige solid in 27% yield. Salt formation was performed by method VII(ii). $^1$H-NMR (400 MHz, DMSO-D6): 8.37 (bs, 1H, Ar); 8.02 (m, 2H, Ar); 7.98 (d, J 1.7 Hz, 1H, Ar); 7.77 (bs, 1H, Ar); 7.74 (d, J 7.9 Hz, 1H, Ar); 7.59 (s, 1H, Ar); 7.55 (dd, J 7.9, 1.7 Hz, 1H, Ar); 7.48 (m, 2H, Ar); 7.41 (m, 1H, Ar); 3.04 (s, 3H, CH$_3$); 2.77 (s, 3H, CH$_3$); 2.68 (s, 3H, CH$_3$); 1.63 (m, 2H, cyclopropyl); 1.13 (m, 1H, cyclopropyl); 0.68 (m, 1H, cyclopropyl). Proton for HCl salt not observed. M/Z (M+H)$^+$=421.1. MP>250° C.

Example 127

9-(6-Amino-pyridin-3-yl)-5-methyl-2-phenyl-spiro[benzo[f]pyrazolo[1,5-a][1,4]diazepine-6,1'-cyclopropan]-4(5H)-one, hydrochloride

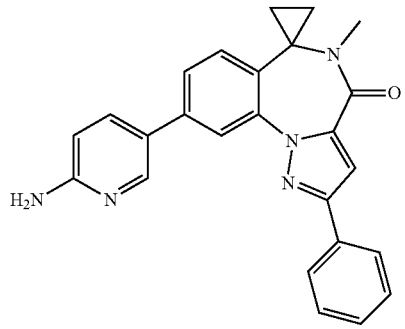 [SMILES: CN1C(=O)c2cc(-c3ccccc3)nn2-c2cc(-c3ccc(N)nc3)ccc2C12CC2]

Example 127 was obtained according to general procedure VI(i) starting from example 11 in presence of 2-aminopyridine-5-boronic acid pinacol ester. Purification by flash column chromatography on silica gel (100% EtOAc) afforded the product as a beige solid in 54% yield. Salt formation was performed by method VII(ii). $^1$H-NMR (400 MHz, DMSO-D6): 8.41 (d, J 2.0 Hz, 1H, Ar); 8.34 (dd, J 9.2, 2.0 Hz, 1H, Ar); 8.11 (d, J 1.5 Hz, 1H, Ar); 8.05 (m, 4H, Ar+NH$_2$); 7.71 (dd, J 7.9, 1.5 Hz, 1H, Ar); 7.67 (d, J 7.9 Hz, 1H, Ar); 7.57 (s, 1H, Ar); 7.48 (m, 2H, Ar); 7.41 (m, 1H, Ar); 7.09 (d, J 9.2 Hz, 1H, Ar); 3.00 (s, 3H, CH$_3$); 1.59 (m, 2H, cyclopropyl); 1.10 (m, 1H, cyclopropyl); 0.60 (m, 1H, cyclopropyl). Proton for HCl salt not observed. M/Z (M+H)$^+$=408.1. MP>250° C.

Example 128

9-(4-Methoxy-phenyl)-5-methyl-2-phenyl-spiro[benzo[f]pyrazolo[1,5-a][1,4]diazepine-6,1'-cyclopropan]-4(5H)-one

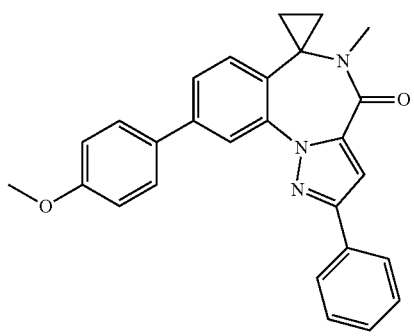 [SMILES: COc1ccc(-c2ccc3c(c2)-n2nc(-c4ccccc4)cc2C(=O)N(C)C32CC2)cc1]

Example 128 was obtained according to general procedure VI(i) starting from example 11 in presence of 4-methoxyphenyl boronic acid. Purification by flash column chromatography on silica gel (40% to 80% EtOAc in cyclohexane) afforded the product as a white solid in 47% yield. $^1$H-NMR (400 MHz, DMSO-D6): 8.06 (m, 3H, Ar); 7.70 (m, 2H, Ar); 7.67 (dd, J 7.8, 1.7 Hz, 1H, Ar); 7.62 (d, J 7.8 Hz, 1H, Ar); 7.55 (s, 1H, Ar); 7.49 (m, 2H, Ar); 7.42 (m, 1H, Ar); 7.08 (d, J 8.8 Hz, 2H, Ar); 3.82 (s, 3H, O—CH$_3$); 3.02 (s, 3H, CH$_3$); 1.58 (m, 2H, cyclopropyl); 1.10 (m, 1H, cyclopropyl); 0.63 (m, 1H, cyclopropyl). M/Z (M+H)$^+$=422.1. MP>250° C.

Example 129

9-(3-Cyano-phenyl)-5-methyl-2-phenyl-spiro[benzo[f]pyrazolo[1,5-a][1,4]diazepine-6,1'-cyclopropan]-4(5H)-one

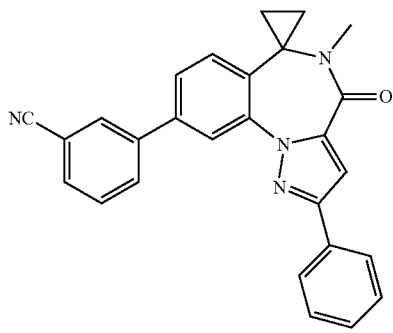

Example 129 was obtained according to general procedure VI(i) starting from example 11 in presence of 3-cyanophenyl boronic acid. Purification by flash column chromatography on silica gel (40% to 80% EtOAc in cyclohexane) afforded the product as a white solid in 64% yield. $^1$H-NMR (400 MHz, DMSO-D6): 8.28 (s, 1H, Ar); 8.21 (d, J 1.8 Hz, 1H, Ar); 8.13 (d, J 7.9 Hz, 1H, Ar); 8.07 (m, 2H, Ar); 7.90 (d, J 7.9 Hz, 1H, Ar); 7.81 (dd, J 8.0, 1.8 Hz, 1H, Ar); 7.73 (t, J 7.9 Hz, 1H, Ar); 7.70 (d, J 8.0 Hz, 1H, Ar); 7.57 (s, 1H, Ar); 7.49 (m, 2H, Ar); 7.42 (m, 1H, Ar); 3.02 (s, 3H, CH$_3$); 1.61 (m, 2H, cyclopropyl); 1.12 (m, 1H, cyclopropyl); 0.66 (m, 1H, cyclopropyl). M/Z (M+H)$^+$=417.1. MP=185-190° C.

Example 130

9-(3-Chloro-phenyl)-5-methyl-2-phenyl-spiro[benzo[f]pyrazolo[1,5-a][1,4]diazepine-6,1'-cyclopropan]-4(5H)-one

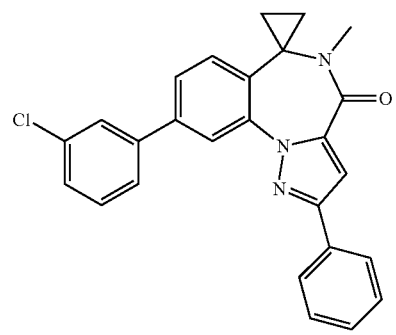 [SMILES: CN1C(=O)c2cc(-c3ccccc3)nn2-c2cc(-c3cccc(Cl)c3)ccc2C12CC2]

Example 130 was obtained according to general procedure VI(i) starting from example 11 in presence of 3-chlorophenyl boronic acid. Purification by flash column chromatography on silica gel (40% to 80% EtOAc in cyclohexane) afforded the product as a white solid in 59% yield. $^1$H-NMR (400 MHz, DMSO-D6): 8.14 (d, J 1.7 Hz, 1H, Ar); 8.06 (m, 2H, Ar); 7.83 (m, 1H, Ar); 7.75 (m, 2H, Ar); 7.67 (d, J 7.9 Hz, 1H, Ar); 7.57 (s, 1H, Ar); 7.55-7.47 (m, 4H, Ar); 7.42 (m, 1H, Ar); 3.02 (s, 3H, CH$_3$); 1.59 (m, 2H, cyclopropyl); 1.09 (m, 1H, cyclopropyl); 0.65 (m, 1H, cyclopropyl). M/Z (M[$^{35}$Cl]+H)$^+$=426.1. MP=177-182° C.

Example 131

9-(2-Chloro-phenyl)-5-methyl-2-phenyl-spiro[benzo[f]pyrazolo[1,5-a][1,4]diazepine-6,1'-cyclopropan]-4(5H)-one

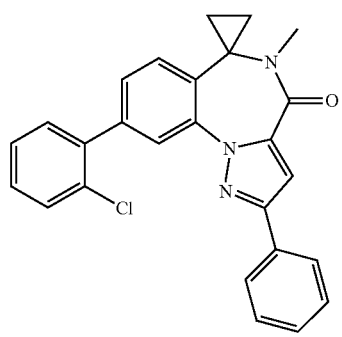 [SMILES: CN1C(=O)c2cc(-c3ccccc3)nn2-c2cc(-c3ccccc3Cl)ccc2C12CC2]

Example 131 was obtained according to general procedure VI(i) starting from example 11 in presence of 2-chlorophenyl boronic acid. Purification by flash column chromatography on silica gel (40% to 80% EtOAc in cyclohexane) afforded the product as a white solid in 37% yield. $^1$H-NMR (400 MHz, DMSO-D6): 8.02 (m, 2H, Ar); 7.93 (d, J 1.7 Hz, 1H, Ar); 7.68 (d, J 8.0 Hz, 1H, Ar); 7.62 (m, 1H, Ar); 7.57 (s, 1H, Ar); 7.55-7.45 (m, 6H, Ar); 7.40

(m, 1H, Ar); 3.04 (s, 3H, CH₃); 1.61 (m, 2H, cyclopropyl); 1.11 (m, 1H, cyclopropyl); 0.69 (m, 1H, cyclopropyl). M/Z (M[³⁵Cl]+H)⁺=426.1. MP=163-170° C.

Example 132

9-(Oxazol-5-yl)-5-methyl-2-phenyl-spiro[benzo[f]pyrazolo[1,5-a][1,4]diazepine-6,1'-cyclopropan]-4(5H)-one

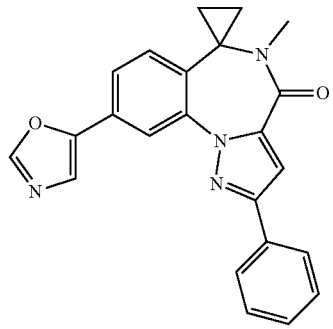 [SMILES: CN1C(=O)c2cc(-c3ccccc3)nn2-c2cc(-c3cnco3)ccc2C12CC2]

Under inert atmosphere, a mixture of example 11 (1.0 equiv.), oxazole (2.0 equiv.), potassium carbonate (3.0 equiv.), pivalic acid (0.4 equiv.), palladium acetate (0.05 equiv.) and di(1-adamantyl)-n-butylphosphine hydriodide (0.1 equiv.) in dimethylacetamide (0.15 mol·L⁻¹) was heated at 110° C. for 4 hours. The reaction mixture was neutralized with aqueous HCl (1 N) and extracted twice with EtOAc. The organic layers were combined, washed with brine, dried over MgSO₄, concentrated and purified by flash column chromatography on silica gel (40% to 100% EtOAc in cyclohexane) to afford example 132 as a white solid in 32% yield. ¹H-NMR (400 MHz, DMSO-D6): 8.52 (s, 1H, Ar); 8.19 (d, J 1.7 Hz, 1H, Ar); 8.06 (m, 2H, Ar); 7.91 (s, 1H, Ar); 7.80 (dd, J 7.9, 1.7 Hz, 1H, Ar); 7.69 (d, J 7.9 Hz, 1H, Ar); 7.57 (s, 1H, Ar); 7.51 (m, 2H, Ar); 7.43 (m, 1H, Ar); 3.02 (s, 3H, CH₃); 1.60 (m, 2H, cyclopropyl); 1.10 (m, 1H, cyclopropyl); 0.65 (m, 1H, cyclopropyl). M/Z (M+H)⁺=383.1. MP=214-220° C.

Example 133

3-(5-methyl-4-oxo-2-phenyl-4,5-dihydrospiro[benzo[f]pyrazolo[1,5-a][1,4]diazepine-6,1'-cyclopropan]-9-yl)benzoic acid

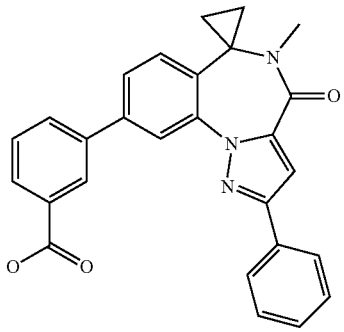 [SMILES: CN1C(=O)c2cc(-c3ccccc3)nn2-c2cc(-c3cccc(C(=O)O)c3)ccc2C12CC2]

Example 133 was obtained according to general procedure VI(i) starting from example 11 in presence of 3-carboxyphenyl boronic acid. Purification by precipitation from water and colletion by filtration afforded the product as a beige solid in 74% yield. ¹H-NMR (400 MHz, DMSO-D6): 13.12 (bs, 1H, COOH); 8.24 (s, 1H, Ar); 8.13 (d, J 1.7 Hz, 1H, Ar); 8.06-7.99 (m, 3H, Ar); 7.96 (s, 1H, Ar); 7.76 (dd, J 7.9, 1.7 Hz, 1H, Ar); 7.68 (d, J 7.9 Hz, 1H, Ar); 7.64 (t, J 7.8 Hz, 1H, Ar); 7.56 (s, 1H, Ar); 7.49 (m, 2H, Ar); 7.41 (m, 1H, Ar); 3.02 (s, 3H, CH₃); 1.61 (m, 2H, cyclopropyl); 1.11 (m, 1H, cyclopropyl); 0.67 (m, 1H, cyclopropyl). M/Z (M+H)⁺=436.1. MP=211-217° C.

Example 134

9-(1H-pyrazol-4-yl)-5-methyl-2-phenyl-spiro[benzo[f]pyrazolo[1,5-a][1,4]diazepine-6,1'-cyclopropan]-4(5H)-one

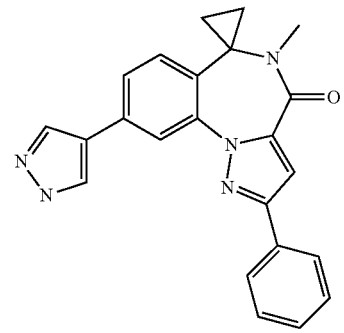 [SMILES: CN1C(=O)c2cc(-c3ccccc3)nn2-c2cc(-c3cn[nH]c3)ccc2C12CC2]

Example 134 was obtained according to general procedure VI(i) starting from example 11 in presence of 1H-pyrazole-4-boronic acid. Purification by flash column chromatography on silica gel (40% to 100% EtOAc in cyclohexane) afforded the product as a white solid in 45% yield. ¹H-NMR (400 MHz, DMSO-D6): 13.06 (bs, 1H, NH); 8.36 (s, 1H, Ar); 8.07 (m, 3H, Ar); 8.04 (s, 1H, Ar); 7.66 (dd, J 7.9, 1.7 Hz, 1H, Ar); 7.54 (d, J 7.9 Hz, 1H, Ar); 7.53 (s, 1H, Ar); 7.50 (m, 2H, Ar); 7.42 (m, 1H, Ar); 3.00 (s, 3H, CH₃); 1.55 (m, 2H, cyclopropyl); 1.06 (m, 1H, cyclopropyl); 0.60 (m, 1H, cyclopropyl). M/Z (M+H)⁺=382.0. MP=199-208° C.

Example 135

9-(4-Chloro-phenyl)-5-methyl-2-phenyl-spiro[benzo[f]pyrazolo[1,5-a][1,4]diazepine-6,1'-cyclopropan]-4(5H)-one

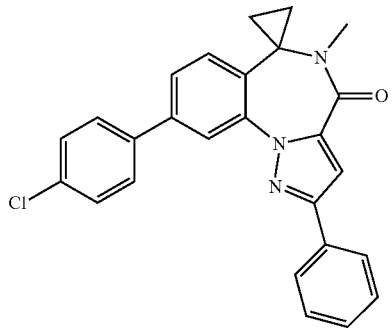 [SMILES: CN1C(=O)c2cc(-c3ccccc3)nn2-c2cc(-c3ccc(Cl)cc3)ccc2C12CC2]

Example 135 was obtained according to general procedure VI(i) starting from example 11 in presence of potassium 4-chlorophenyltrifluoroborate. Purification by flash column chromatography on silica gel (0% to 60% EtOAc in cyclohexane) afforded the product as a white solid in 53% yield. $^1$H-NMR (400 MHz, DMSO-D6): 8.12 (d, J 1.7 Hz, 1H, Ar); 8.06 (m, 2H, Ar); 7.80 (m, 2H, Ar); 7.73 (dd, J 7.9, 1.7 Hz, 1H, Ar); 7.66 (d, J 7.9 Hz, 1H, Ar); 7.57 (m, 3H, Ar); 7.50 (m, 2H, Ar); 7.42 (m, 1H, Ar); 3.02 (s, 3H, CH$_3$); 1.59 (m, 2H, cyclopropyl); 1.10 (m, 1H, cyclopropyl); 0.65 (m, 1H, cyclopropyl). M/Z (M[$^{35}$Cl]+H)$^+$=426.1. MP=248-255° C.

Example 136

9-(1H-pyrazol-3-yl)-5-methyl-2-phenyl-spiro[benzo[f]pyrazolo[1,5-a][1,4]diazepine-6,1'-cyclopropan]-4(5H)-one

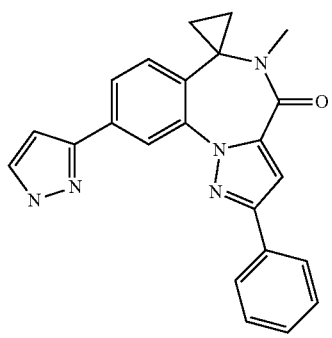 [SMILES: CN1C(=O)c2cc(-c3ccccc3)nn2-c2cc(-c3cc[nH]n3)ccc2C12CC2]

Example 136 was obtained according to general procedure VI(i) starting from example 11 in presence of potassium 1H-pyrazole-3-trifluoroborate. Purification by flash column chromatography on silica gel (0% to 5% MeOH in dichloromethane) afforded the product as a beige solid in 45% yield. $^1$H-NMR (400 MHz, DMSO-D6): 13.02 (bs, 1H, NH); 8.31 (s, 1H, Ar); 8.06 (m, 2H, Ar); 7.85 (m, 2H, Ar); 7.59 (d, J 8.0 Hz, 1H, Ar); 7.55 (s, 1H, Ar); 7.50 (m, 2H, Ar); 7.42 (m, 1H, Ar); 6.85 (s, 1H, Ar); 3.02 (s, 3H, CH$_3$); 1.58 (m, 2H, cyclopropyl); 1.09 (m, 1H, cyclopropyl); 0.63 (m, 1H, cyclopropyl). M/Z (M+H)$^+$=382.0. MP=218-224° C.

Example 137

9-Cyano-5-methyl-2-phenyl-spiro[benzo[f]pyrazolo[1,5-a][1,4]diazepine-6,1'-cyclopropan]-4(5H)-one

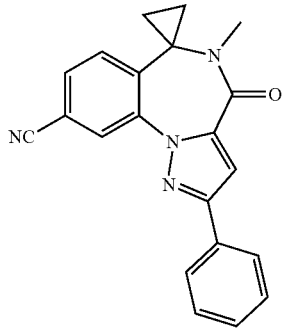 [SMILES: CN1C(=O)c2cc(-c3ccccc3)nn2-c2cc(C#N)ccc2C12CC2]

Under inert atmosphere, a mixture of example 11 (1.0 equiv.), zinc cyanide (1.6 equiv.), and tetrakis(triphenylphosphine)palladium (0.1 equiv.) in DMF (0.1 mol·L$^{-1}$) was subjected to microwave irradiation at 120° C. for 10 minutes. The reaction mixture was poured into water and the grey precipitate was collected by filtration. Purification by flash column chromatography on silica gel (50% to 100% EtOAc in cyclohexane) afforded example 137 as a white solid in 51% yield. $^1$H-NMR (400 MHz, DMSO-D6): 8.33 (d, J 1.6 Hz, 1H, Ar); 8.06 (m, 2H, Ar); 7.91 (dd, J 7.9, 1.6 Hz, 1H, Ar); 7.79 (d, J 7.9 Hz, 1H, Ar); 7.60 (s, 1H, Ar); 7.50 (m, 2H, Ar); 7.42 (m, 1H, Ar); 3.00 (s, 3H, CH$_3$); 1.61 (m, 2H, cyclopropyl); 1.11 (m, 1H, cyclopropyl); 0.67 (m, 1H, cyclopropyl). M/Z (M+H)$^+$=341.1. MP=196-200° C.

Example 138

5-Methyl-2-phenyl-spiro[benzo[f]pyrazolo[1,5-a][1,4]diazepine-6,1'-cyclopropan]-4(5H)-one

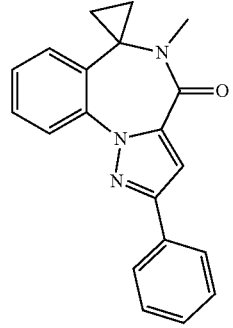 [SMILES: CN1C(=O)c2cc(-c3ccccc3)nn2-c2ccccc2C12CC2]

Under hydrogen atmosphere (1 bar), a mixture of example 11 (1.0 equiv.), and palladium 10% on charcoal (0.2 equiv.) in a 1:1 mixture of MeOH and DMF (0.1 mol·L$^{-1}$) was stirred at room temperature for 24 hours. The reaction mixture was filtered through celite and the filtrate was concentrated to give a colorless oil. Trituration in water afforded example 138 as a white solid in 45% yield. $^1$H-NMR (400 MHz, DMSO-D6): 8.02 (d, J 7.2 Hz, 2H, Ar); 7.89 (d, J 8.0 Hz, 1H, Ar); 7.58-7.40 (m, 7H, Ar); 2.99 (s, 3H, CH$_3$); 1.55 (m, 2H, cyclopropyl); 1.06 (m, 1H, cyclopropyl); 0.59 (m, 1H, cyclopropyl). M/Z (M+H)$^+$=316.1. MP=212-218° C.

Example 139

5-Methyl-2-phenyl-9-(pyrrolidin-1-yl)-spiro[benzo[f]pyrazolo[1,5-a][1,4]diazepine-6,1'-cyclopropan]-4(5H)-one

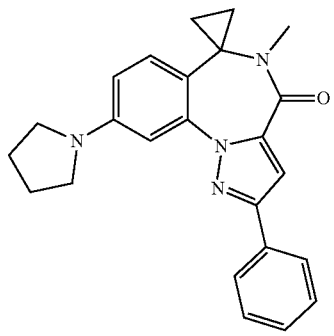 [SMILES: CN1C(=O)c2cc(-c3ccccc3)nn2-c2cc(N3CCCC3)ccc2C12CC2]

Under inert atmosphere, a mixture of example 11 (1.0 equiv.), pyrrolidine (1.5 equiv.), sodium tert-butoxide (3.0 equiv.), BINAP (0.2 equiv.) and palladium acetate (0.1 equiv.) in toluene (0.06 mol·L$^{-1}$) was heated at 120° C. for 2 hours. The reaction mixture was neutralized with aqueous HCl (1 N) and extracted twice with dichloromethane. The organic layers were combined, washed with brine, dried over MgSO$_4$, concentrated and purified by flash column chromatography on silica gel (0% to 30% EtOAc in cyclohexane) to afford example 139 as a white solid in 27% yield. $^1$H-NMR (400 MHz, DMSO-D6): 7.94 (m, 2H, Ar); 7.46 (m, 2H, Ar); 7.37 (m, 2H, Ar); 7.27 (m, 1H, Ar); 6.90 (s, 1H, Ar); 6.52 (m, 1H, Ar); 3.23 (m, 4H, 2 N—CH$_2$); 2.92 (s, 3H, CH$_3$); 1.93 (m, 4H, 2 CH$_2$); 1.42 (m, 2H, cyclopropyl); 0.94 (m, 1H, cyclopropyl); 0.42 (m, 1H, cyclopropyl). M/Z (M+H)$^+$=385.1. MP=226-230° C.

Example 140

9-(2-Methyl-pyridin-3-yl)-5-methyl-2-phenyl-spiro[benzo[f]imidazo[1,2-a][1,4]diazepine-6,1'-cyclopropan]-4(5H)-one, hydrochloride

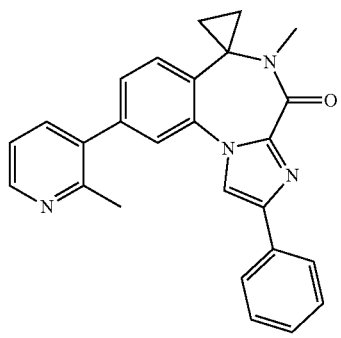 [SMILES: Cc1ncccc1-c1ccc2c(c1)-n1cc(-c3ccccc3)nc1C(=O)N(C)C21CC1]

Example 140 was obtained according to general procedure VI(i) starting from example 12 in presence of 2-methylpyridine-3-boronic acid pinacol ester. Purification by flash column chromatography on silica gel (0% to 5% MeOH in dichloromethane) afforded the product as a yellow solid in 57% yield. Salt formation was performed by method VII(ii). $^1$H-NMR (400 MHz, DMSO-D6): 8.84 (d, J 5.6 Hz, 1H, Ar); 8.51 (d, J 7.8 Hz, 1H, Ar); 8.48 (s, 1H, Ar); 8.00-7.93 (m, 4H, Ar); 7.78 (d, J 7.8 Hz, 1H, Ar); 7.63 (dd, J 7.8, 1.5 Hz, 1H, Ar); 7.46 (m, 2H, Ar); 7.32 (m, 1H, Ar); 3.02 (s, 3H, CH$_3$); 2.77 (s, 3H, CH$_3$); 1.59 (m, 2H, cyclopropyl); 1.10 (m, 1H, cyclopropyl); 0.68 (m, 1H, cyclopropyl). Proton for HCl salt not observed. M/Z (M+H)$^+$=407.1. MP=235-240° C.

Compound 41: N,N-dimethyl-3-(4-oxo-2-phenyl-4,5-dihydrospiro[benzo[f]pyrrolo[1,2-a][1,4]diazepine-6,1'-cyclopropan]-9-yl)benzenesulfonamide Compound 41 was obtained according to general procedure VI(i) starting from compound 22 in presence of N,N-dimethyl-3-boronobenzene sulfonamide. Purification by flash column chromatography on silica gel (50% to 70% EtOAc in cyclohexane) afforded the product as an orange solid in 96% yield. $^1$H-NMR (400 MHz, DMSO-D6): 8.71 (s, 1H, NH); 8.25 (d, J 1.9 Hz, 1H, Ar); 8.18 (m, 1H, Ar); 8.03 (s, 1H, Ar); 7.96 (d, J 1.6 Hz, 1H, Ar); 7.88 (m, 4H, Ar); 7.68 (dd, J 7.8, 1.6 Hz, 1H, Ar); 7.56 (d, J 7.8 Hz, 1H, Ar); 7.40 (m, 2H, Ar); 7.33 (d, J 1.9 Hz, 1H, Ar); 7.23 (m, 1H, Ar); 2.66 (s, 6H, 2CH$_3$); 1.60 (m, 1H, cyclopropyl); 1.27 (m, 1H, cyclopropyl); 0.91 (m, 1H, cyclopropyl); 0.59 (m, 1H, cyclopropyl). M/Z (M+H)$^+$=484.0. MP>250° C.

Example 141

N,N-dimethyl-3-(5-methyl-4-oxo-2-phenyl-4,5-dihydrospiro[benzo[f]pyrrolo[1,2-a][1,4]diazepine-6,1'-cyclopropan]-9-yl)benzenesulfonamide

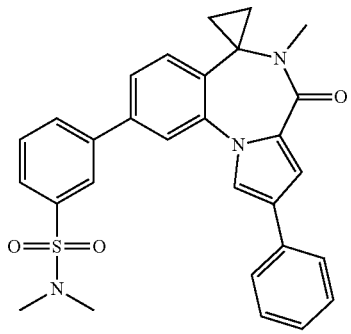 [SMILES: CN1C(=O)c2cc(-c3ccccc3)cn2-c2cc(-c3cccc(S(=O)(=O)N(C)C)c3)ccc2C12CC2]

Example 141 was obtained according to general procedure III, starting from compound 41 in presence of iodomethane. The reaction mixture was stirred at room temperature for 2 hours. Purification by preparative HPLC afforded the product as a white solid in 35% yield. $^1$H-NMR (400 MHz, DMSO-D6): 8.22 (d, J 1.9 Hz, 1H, Ar); 8.17 (m, 1H, Ar); 8.03 (s, 1H, Ar); 7.97 (d, J 1.4 Hz, 1H, Ar); 7.79 (m, 4H, Ar); 7.70 (dd, J 7.8, 1.4 Hz, 1H, Ar); 7.65 (d, J 7.8 Hz, 1H, Ar); 7.40 (m, 2H, Ar); 7.30 (d, J 1.9 Hz, 1H, Ar); 7.23 (m, 1H, Ar); 2.96 (s, 3H, CH$_3$); 2.66 (s, 6H, 2CH$_3$); 1.52 (m, 2H, cyclopropyl); 1.02 (m, 1H, cyclopropyl); 0.64 (m, 1H, cyclopropyl). M/Z (M+H)$^+$=498.2. MP=198-205° C.

Compound 42: N,N-dimethyl-3-(4-oxo-2-phenyl-4,5-dihydrospiro[benzo[f]pyrazolo[1,5-a][1,4]diazepine-6,1'-cyclopropan]-9-yl)benzenesulfonamide Compound 42 was obtained according to general procedure VI(i) starting from compound 23 in presence of N,N- dimethyl-3-boronobenzene sulfonamide. Purification by flash column chromatography on silica gel (50% to 70% EtOAc in cyclohexane) afforded the product as an orange solid in 98% yield. ¹H-NMR (400 MHz, DMSO-D6): 9.23 (s, 1H, NH); 8.16 (s, 1H, Ar); 8.12 (m, 1H, Ar); 8.03 (m, 2H, Ar); 7.99 (s, 1H, Ar); 7.81 (m, 2H, Ar); 7.76 (d, J 7.8 Hz, 1H, Ar); 7.62 (d, J 7.8 Hz, 1H, Ar); 7.58 (s, 1H, Ar); 7.49 (m, 2H, Ar); 7.42 (m, 1H, Ar); 2.67 (s, 6H, 2CH₃); 1.60 (m, 1H, cyclopropyl); 1.27 (m, 1H, cyclopropyl); 0.91 (m, 1H, cyclopropyl); 0.59 (m, 1H, cyclopropyl). M/Z (M+H)⁺=485.0. MP=234-240° C.

Example 142

N,N-dimethyl-3-(5-methyl-4-oxo-2-phenyl-4,5-dihydrospiro[benzo[f]pyrazolo[1,5-a][1,4]diazepine-6,1'-cyclopropan]-9-yl)benzenesulfonamide

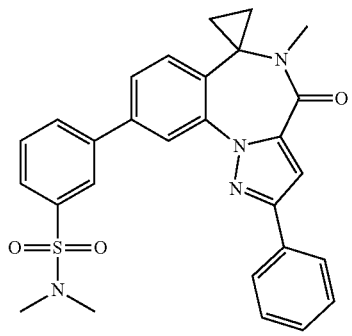 [SMILES: CN1C(=O)c2cc(-c3ccccc3)nn2-c2cc(-c3cccc(S(=O)(=O)N(C)C)c3)ccc2C12CC2]

Example 142 was obtained according to general procedure III, starting from compound 42 in presence of iodomethane. The reaction mixture was stirred at room temperature for 2 hours. Purification by preparative HPLC afforded the product as a white solid in 23% yield. ¹H-NMR (400 MHz, DMSO-D6): 8.15 (d, J 1.8 Hz, 1H, Ar); 8.11 (m, 1H, Ar); 8.04 (m, 2H, Ar); 7.99 (s, 1H, Ar); 7.78 (m, 3H, Ar); 7.70 (d, J 7.9 Hz, 1H, Ar); 7.57 (s, 1H, Ar); 7.48 (m, 2H, Ar); 7.40 (m, 1H, Ar); 3.02 (s, 3H, CH₃); 2.66 (s, 6H, 2CH₃); 1.60 (m, 2H, cyclopropyl); 1.11 (m, 1H, cyclopropyl); 0.65 (m, 1H, cyclopropyl). M/Z (M+H)⁺=499.1. MP=182-189° C.

Example 143

5-Methyl-2-(pyridine-3-yl)-9-(2-methyl-pyridin-3-yl)-spiro[benzo[f]pyrazolo[1,5-a][1,4]diazepine-6,1'-cyclopropan]-4(5H)-one, hydrochloride

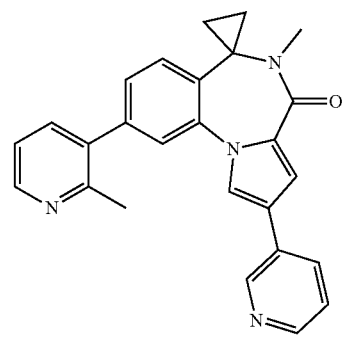 [SMILES: Cc1ncccc1-c1ccc2c(c1)-n1cc(-c3cccnc3)cc1C(=O)N(C)C21CC1]

Example 143 was obtained according to general procedure VI(i) starting from example 17 in presence of 3-pyridine-boronic acid. Purification by preparative HPLC afforded the product as a yellow solid in 16% yield. Salt formation was performed by method VII(ii). ¹H-NMR (400 MHz, DMSO-D6): 9.34 (m, 1H, Ar); 8.81 (m, 2H, Ar); 8.72 (m, 1H, Ar); 8.49 (d, J 1.9 Hz, 1H, Ar); 8.45 (m, 1H, Ar); 7.98 (m, 1H, Ar); 7.91 (m, 1H, Ar); 7.86 (d, J 1.4 Hz, 1H, Ar); 7.73 (d, J 7.8 Hz, 1H, Ar); 7.62 (d, J 1.9 Hz, 1H, Ar); 7.56 (dd, J 7.8, 1.4 Hz, 1H, Ar); 2.98 (s, 3H, CH₃); 2.75 (s, 3H, CH₃); 1.56 (m, 2H, cyclopropyl); 1.04 (m, 1H, cyclopropyl); 0.68 (m, 1H, cyclopropyl). Proton for HCl salt not observed. M/Z (M+H)⁺=407.2. MP>250° C.

Example 144

2,5-Dimethyl-9-(2-methyl-pyridin-3-yl)-spiro[benzo[f]pyrazolo[1,5-a][1,4]diazepine-6,1'-cyclopropan]-4(5H)-one, hydrochloride

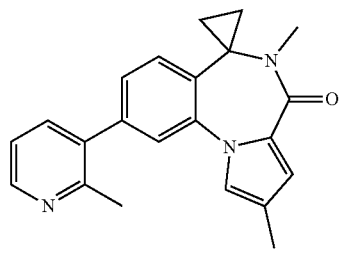

Under inert atmosphere, a mixture of example 17 (1.0 equiv.), dimethyl zinc (2M solution in toluene, 4.0 equiv.) and 1,1'-bis(1,2-diphenylphosphino)ferrocene palladium (II) chloride, complex with dichloromethane (0.2 equiv.) in dioxane (0.15 mol·L⁻¹) was heated at 90° C. for 16 hours. The reaction mixture was neutralized with aqueous potassium carbonate and extracted twice with EtOAc. The organic layers were combined, washed with brine, dried over MgSO₄, concentrated and purified by flash column chromatography on silica gel (0% to 5% MeOH in dichloromethane) to afford example 144 as a white solid in 78% yield. Salt formation was performed by method VII(i). ¹H-NMR (400 MHz, DMSO-D6): 8.82 (d, J 5.7 Hz, 1H, Ar); 8.43 (d, J 7.5 Hz, 1H, Ar); 7.91 (dd, J 7.5, 5.7 Hz, 1H, Ar); 7.69 (m, 2H, Ar); 7.49 (dd, J 7.8, 1.4 Hz, 1H, Ar); 7.39 (d, J 1.4 Hz, 1H, Ar); 6.79 (d, J 1.7 Hz, 1H, Ar); 2.99 (s, 3H, CH₃); 2.73 (s, 3H, CH₃); 2.19 (s, 3H, CH₃); 1.56 (m, 2H, cyclopropyl); 1.03 (m, 1H, cyclopropyl); 0.66 (m, 1H, cyclopropyl). Proton for HCl salt not observed. M/Z (M+H)⁺=344.2. MP=162-175° C.

Example 145

5-Methyl-2-(pyridine-4-yl)-9-(2-methyl-pyridin-3-yl)-spiro[benzo[f]pyrazolo[1,5-a][1,4]diazepine-6,1'-cyclopropan]-4(5H)-one, hydrochloride

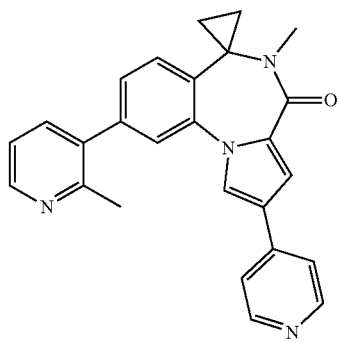 [SMILES: Cc1ncccc1-c1ccc2c(c1)-n1cc(-c3ccncc3)cc1C(=O)N(C)C21CC1]

Example 145 was obtained according to general procedure VI(i) starting from example 17 in presence of 4-pyridine-boronic acid. Purification by flash column chromatography on silica gel (0% to 5% MeOH in dichloromethane) afforded the product as a beige solid in 27% yield. Salt formation was performed by method VII(i). $^1$H-NMR (400 MHz, DMSO-D6): 8.84 (d, J 6.7 Hz, 2H, Ar); 8.79 (d, J 5.3 Hz, 1H, Ar); 8.75 (d, J 1.8 Hz, 1H, Ar); 8.39 (m, 3H, Ar); 7.89 (m, 2H, Ar); 7.75 (m, 2H, Ar); 7.60 (dd, J 7.8, 1.4 Hz, 1H, Ar); 3.00 (s, 3H, CH$_3$); 2.74 (s, 3H, CH$_3$); 1.58 (m, 2H, cyclopropyl); 1.05 (m, 1H, cyclopropyl); 0.71 (m, 1H, cyclopropyl). Proton for HCl salt not observed. M/Z (M+H)$^+$=407.2. MP>250° C.

Example 146

5-Methyl-2-(1H-pyrazol-3-yl)-9-(2-methyl-pyridin-3-yl)-spiro[benzo[f]pyrazolo[1,5-a][1,4]diazepine-6,1'-cyclopropan]-4(5H)-one, hydrochloride

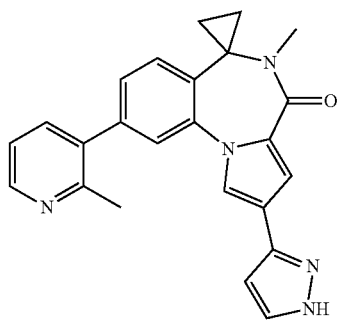 [SMILES: Cc1ncccc1-c1ccc2c(c1)-n1cc(-c3cc[nH]n3)cc1C(=O)N(C)C21CC1]

Example 146 was obtained according to general procedure VI(i) starting from example 17 in presence of potassium 1H-pyrazole-3-trifluoroborate. Purification by flash column chromatography on silica gel (0% to 5% MeOH in dichloromethane) afforded the product as a beige solid in 24% yield. Salt formation was performed by method VII(ii). $^1$H-NMR (400 MHz, DMSO-D6): 8.82 (dd, J 5.8, 1.4 Hz, 1H, Ar); 8.54 (dd, J 7.9, 1.4 Hz, 1H, Ar); 7.99 (m, 2H, Ar); 7.79 (d, J 1.6 Hz, 1H, Ar); 7.73 (d, J 2.1 Hz, 1H, Ar); 7.71 (d, J 7.8 Hz, 1H, Ar); 7.52 (dd, J 7.8, 1.6 Hz, 1H, Ar); 7.28 (d, J 1.9 Hz, 1H, Ar); 6.62 (d, J 2.1 Hz, 1H, Ar); 2.97 (s, 3H, CH$_3$); 2.76 (s, 3H, CH$_3$); 1.54 (m, 2H, cyclopropyl); 1.03 (m, 1H, cyclopropyl); 0.66 (m, 1H, cyclopropyl). Proton for HCl salt not observed. M/Z (M+H)$^+$=396.3. MP=240-250° C.

Example 147

5-Methyl-2-(2-chlorophenyl)-9-(2-methyl-pyridin-3-yl)-spiro[benzo[f]pyrazolo[1,5-a][1,4]diazepine-6,1'-cyclopropan]-4(5H)-one, hydrochloride

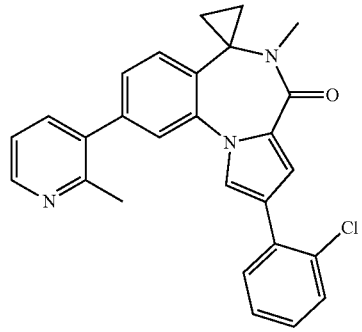 [SMILES: Cc1ncccc1-c1ccc2c(c1)-n1cc(-c3ccccc3Cl)cc1C(=O)N(C)C21CC1]

Example 147 was obtained according to general procedure VI(i) starting from example 17 in presence of 2-chlorophenyl boronic acid. Purification by preparative HPLC afforded the product as a yellow solid in 23% yield. Salt formation was performed by method VII(ii). $^1$H-NMR (400 MHz, DMSO-D6): 8.74 (d, J 5.1 Hz, 1H, Ar); 8.34 (d, J 7.5 Hz, 1H, Ar); 7.96 (d, J 2.0 Hz, 1H, Ar); 7.81 (m, 2H, Ar); 7.74 (dd, J 7.9, 1.7 Hz, 1H, Ar); 7.69 (d, J 7.9 Hz, 1H, Ar); 7.51 (m, 2H, Ar); 7.38 (m, 1H, Ar); 7.30 (m, 2H, Ar); 2.98 (s, 3H, CH$_3$); 2.68 (s, 3H, CH$_3$); 1.55 (m, 2H, cyclopropyl); 1.05 (m, 1H, cyclopropyl); 0.68 (m, 1H, cyclopropyl). Proton for HCl salt not observed. M/Z (M[$^{35}$Cl]+H)$^+$=440.3. MP=192-200° C.

Example 148

5-Methyl-2-(3-chlorophenyl)-9-(2-methyl-pyridin-3-yl)-spiro[benzo[f]pyrazolo[1,5-a][1,4]diazepine-6,1'-cyclopropan]-4(5H)-one, hydrochloride

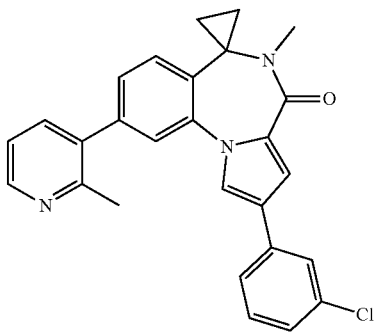 [SMILES: Cc1ncccc1-c1ccc2c(c1)-n1cc(-c3cccc(Cl)c3)cc1C(=O)N(C)C21CC1]

Example 148 was obtained according to general procedure VI(i) starting from example 17 in presence of 3-chlorophenyl boronic acid. Purification by preparative HPLC afforded the product as a yellow solid in 25% yield. Salt formation was performed by method VII(ii). ¹H-NMR (400 MHz, DMSO-D6): 8.76 (d, J 5.1 Hz, 1H, Ar); 8.37 (d, J 7.5 Hz, 1H, Ar); 8.14 (d, J 1.9 Hz, 1H, Ar); 7.83 (m, 3H, Ar); 7.70 (m, 2H, Ar); 7.50 (dd, J 7.8, 1.5 Hz, 1H, Ar); 7.40 (t, J 8.0 Hz, 1H, Ar); 7.36 (d, J 1.9 Hz, 1H, Ar); 7.27 (d, J 8.0 Hz, 1H, Ar); 2.97 (s, 3H, CH₃); 2.70 (s, 3H, CH₃); 1.54 (m, 2H, cyclopropyl); 1.03 (m, 1H, cyclopropyl); 0.66 (m, 1H, cyclopropyl). Proton for HCl salt not observed. M/Z (M[$^{35}$Cl]+H)$^+$=440.3. MP=211-220° C.

Example 149

5-Methyl-2-(4-chlorophenyl)-9-(2-methyl-pyridin-3-yl)-spiro[benzo[f]pyrazolo[1,5-a][1,4]diazepine-6,1'-cyclopropan]-4(5H)-one, hydrochloride

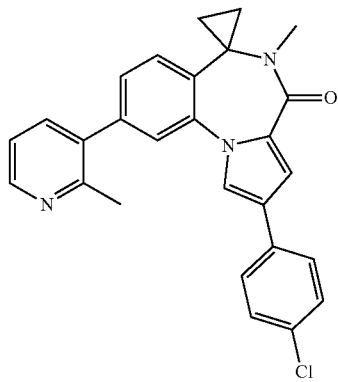 [SMILES: Cc1ncccc1-c1ccc2c(c1)-n1cc(-c3ccc(Cl)cc3)cc1C(=O)N(C)C21CC1]

Example 149 was obtained according to general procedure VI(i) starting from example 17 in presence of potassium 4-chlorophenyltrifluoroborate. Purification by preparative HPLC afforded the product as a yellow solid in 23% yield. Salt formation was performed by method VII(ii). ¹H-NMR (400 MHz, DMSO-D6): 8.77 (d, J 5.1 Hz, 1H, Ar); 8.38 (d, J 7.5 Hz, 1H, Ar); 8.09 (d, J 1.9 Hz, 1H, Ar); 7.87 (dd, J 7.5, 5.1 Hz, 1H, Ar); 7.82 (d, J 1.3 Hz, 1H, Ar); 7.78 (d, J 8.4 Hz, 2H, Ar); 7.69 (d, J 7.8 Hz, 1H, Ar); 7.50 (dd, J 7.8, 1.3 Hz, 1H, Ar); 7.43 (d, J 8.4 Hz, 2H, Ar); 7.33 (d, J 1.9 Hz, 1H, Ar); 2.98 (s, 3H, CH₃); 2.71 (s, 3H, CH₃); 1.55 (m, 2H, cyclopropyl); 1.05 (m, 1H, cyclopropyl); 0.67 (m, 1H, cyclopropyl). Proton for HCl salt not observed. M/Z (M[$^{35}$Cl]+H)$^+$=440.3. MP=214-231° C.

Example 150

5-Methyl-2-(4-fluorophenyl)-9-(2-methyl-pyridin-3-yl)-spiro[benzo[f]pyrazolo[1,5-a][1,4]diazepine-6,1'-cyclopropan]-4(5H)-one, hydrochloride

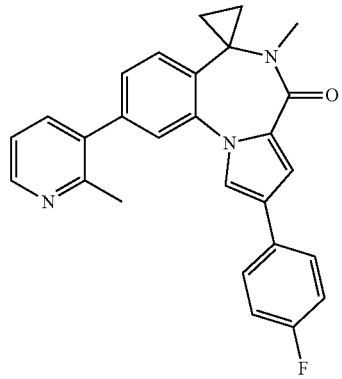 [SMILES: Cc1ncccc1-c1ccc2c(c1)-n1cc(-c3ccc(F)cc3)cc1C(=O)N(C)C21CC1]

Example 150 was obtained according to general procedure VI(i) starting from example 17 in presence of potassium 4-fluorophenylboronic acid. Purification by preparative HPLC afforded the product as a beige solid in 29% yield. Salt formation was performed by method VII(ii). ¹H-NMR (400 MHz, DMSO-D6): 8.76 (d, J 5.1 Hz, 1H, Ar); 8.37 (d, J 7.5 Hz, 1H, Ar); 8.04 (d, J 2.0 Hz, 1H, Ar); 7.85 (dd, J 7.5, 5.1 Hz, 1H, Ar); 7.79 (m, 3H, Ar); 7.68 (d, J 7.8 Hz, 1H, Ar); 7.49 (dd, J 7.8, 1.5 Hz, 1H, Ar); 7.31 (d, J 2.0 Hz, 1H, Ar); 7.21 (t, J 8.9 Hz, 2H, Ar); 2.97 (s, 3H, CH₃); 2.70 (s, 3H, CH₃); 1.53 (m, 2H, cyclopropyl); 1.04 (m, 1H, cyclopropyl); 0.65 (m, 1H, cyclopropyl). Proton for HCl salt not observed. M/Z (M+H)$^+$=424.2. MP=226-230° C.

Example 151

5-Methyl-2-(2-fluorophenyl)-9-(2-methyl-pyridin-3-yl)-spiro[benzo[f]pyrazolo[1,5-a][1,4]diazepine-6,1'-cyclopropan]-4(5H)-one, hydrochloride

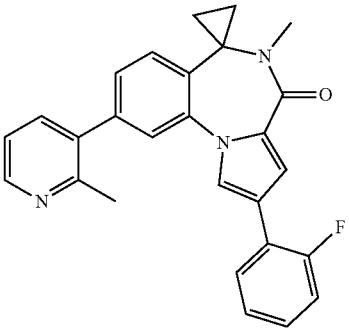 [SMILES: Cc1ncccc1-c1ccc2c(c1)-n1cc(-c3ccccc3F)cc1C(=O)N(C)C21CC1]

Example 151 was obtained according to general procedure VI(i) starting from example 17 in presence of 2-fluorophenyl boronic acid. Purification by preparative HPLC afforded the product as a yellow solid in 20% yield. Salt formation was performed by method VII(ii). ¹H-NMR (400 MHz, DMSO-D6): 8.76 (d, J 5.1 Hz, 1H, Ar); 8.40 (d, J 7.5 Hz, 1H, Ar); 7.99 (s, 1H, Ar); 7.86 (m, 3H, Ar); 7.70 (d, J 7.9, 1H, Ar); 7.51 (d, J 7.9 Hz, 1H, Ar); 7.33 (s, 1H, Ar); 7.26 (m, 3H, Ar); 2.97 (s, 3H, CH₃); 2.70 (s, 3H, CH₃); 1.54 (m, 2H, cyclopropyl); 1.04 (m, 1H, cyclopropyl); 0.67 (m, 1H, cyclopropyl). Proton for HCl salt not observed. M/Z (M+H)⁺=424.3. MP=185-190° C.

Example 152

5-Methyl-2-(3-fluorophenyl)-9-(2-methyl-pyridin-3-yl)-spiro[benzo[f]pyrazolo[1,5-a][1,4]diazepine-6,1'-cyclopropan]-4(5H)-one, hydrochloride

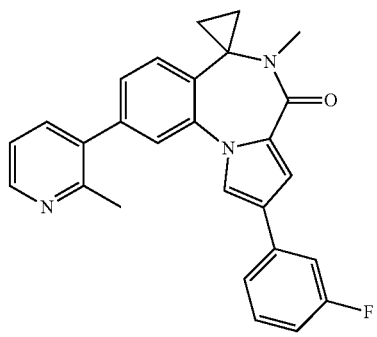 [SMILES: Cc1ncccc1-c1ccc2c(c1)-n1cc(-c3cccc(F)c3)cc1C(=O)N(C)C21CC1]

Example 152 was obtained according to general procedure VI(i) starting from example 17 in presence of 3-fluorophenyl boronic acid. Purification by flash column chromatography on silica gel (EtOAc in cylohexane, 50% to 100%) afforded the product as a yellow solid in 35% yield. Salt formation was performed by method VII(ii). ¹H-NMR (400 MHz, DMSO-D6): 8.77 (d, J 5.4 Hz, 1H, Ar); 8.39 (d, J 7.5 Hz, 1H, Ar); 8.13 (d, J 2.0 Hz, 1H, Ar); 7.87 (dd, J 7.5, 5.4 Hz, 1H, Ar); 7.83 (d, J 1.5 Hz, 1H, Ar); 7.70 (d, J 7.8 Hz, 1H, Ar); 7.60 (m, 2H, Ar); 7.51 (dd, J 7.8, 1.5 Hz, 1H, Ar); 7.42 (m, 1H, Ar); 7.37 (d, J 2.0 Hz, 1H, Ar); 7.04 (m, 1H, Ar); 2.98 (s, 3H, CH₃); 2.72 (s, 3H, CH₃); 1.54 (m, 2H, cyclopropyl); 1.05 (m, 1H, cyclopropyl); 0.68 (m, 1H, cyclopropyl). Proton for HCl salt not observed. M/Z (M+H)⁺=424.3. MP=183-190° C.

Example 153

5-Methyl-2-cyano-9-(2-methyl-pyridin-3-yl)-spiro[benzo[f]pyrazolo[1,5-a][1,4]diazepine-6,1'-cyclopropan]-4(5H)-one

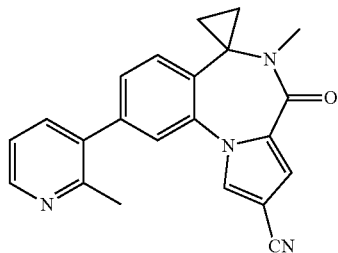 [SMILES: Cc1ncccc1-c1ccc2c(c1)-n1cc(C#N)cc1C(=O)N(C)C21CC1]

Under inert atmosphere, a mixture of example 17 (1.0 equiv.), zinc cyanide (3.2 equiv.), and tetrakis(triphenylphosphine)palladium (0.2 equiv.) in DMF (0.1 mol·L⁻¹) was subjected to microwave irradiation at 130° C. for 30 minutes. The reaction mixture was poured into water and the grey precipitate was collected by filtration. Purification by flash column chromatography on silica gel (80% to 100% EtOAc in cyclohexane) afforded example 153 as a white solid in 35% yield. ¹H-NMR (400 MHz, DMSO-D6): 8.50 (dd, J 4.9, 1.7 Hz, 1H, Ar); 8.41 (d, J 1.9 Hz, 1H, Ar); 7.73 (dd, J 7.8, 1.7 Hz, 1H, Ar); 7.71 (d, J 1.7 Hz, 1H, Ar); 7.64 (d, J 7.8 Hz, 1H, Ar); 7.49 (dd, J 7.8, 1.7 Hz, 1H, Ar); 7.33 (dd, J 7.8, 4.9 Hz, 1H, Ar); 7.25 (d, J 1.9 Hz, 1H, Ar); 2.95 (s, 3H, CH₃); 2.48 (s, 3H, CH₃); 1.52 (m, 2H, cyclopropyl); 0.98 (m, 1H, cyclopropyl); 0.67 (m, 1H, cyclopropyl). M/Z (M+H)⁺=355.3. MP>250° C.

Example 154

5-Methyl-2-dimethylamino-9-(2-methyl-pyridin-3-yl)-spiro[benzo[f]pyrazolo[1,5-a][1,4]diazepine-6,1'-cyclopropan]-4(5H)-one, hydrochloride

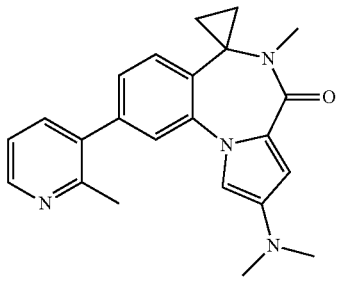 [SMILES: Cc1ncccc1-c1ccc2c(c1)-n1cc(N(C)C)cc1C(=O)N(C)C21CC1]

Under inert atmosphere, a mixture of example 17 (1.0 equiv.), dimethylamine (2M solution in THF, 2.4 equiv.), sodium tertbutoxide (1.2 equiv.) and bis(tri-tert-butylphosphine)palladium (0.2 equiv.) in toluene (0.2 mol·L⁻¹) was heated at 90° C. for 2 days. The reaction mixture was neutralized with aqueous potassium carbonate and extracted twice with EtOAc. The organic layers were combined, washed with brine, dried over MgSO₄, concentrated and purified by flash column chromatography on silica gel (0% to 5% MeOH in dichloromethane) to afford example 154 as a yellow solid in 11% yield. Salt formation was performed by method VII(i). ¹H-NMR (400 MHz, DMSO-D6): 8.79 (d, J 5.1 Hz, 1H, Ar); 8.43 (d, J 7.5 Hz, 1H, Ar); 7.91 (dd, J 7.5, 5.1 Hz, 1H, Ar); 7.72 (d, J 1.2 Hz, 1H, Ar); 7.68 (d, J 7.8 Hz, 1H, Ar); 7.58 (s, 1H, Ar); 7.50 (dd, J 7.8, 1.2 Hz, 1H, Ar); 7.00 (s, 1H, Ar); 3.01 (s, 6H, 2CH₃); 2.95 (s, 3H, CH₃); 2.69 (s, 3H, CH₃); 1.55 (m, 2H, cyclopropyl); 1.00 (m, 1H, cyclopropyl); 0.63 (m, 1H, cyclopropyl). Proton for HCl salt not observed. M/Z (M+H)⁺=373.3. MP=120-134° C.

Example 155

5-Methyl-2-cyclopropyl-9-(2-methyl-pyridin-3-yl)-spiro[benzo[f]pyrazolo[1,5-a][1,4]diazepine-6,1'-cyclopropan]-4(5H)-one, hydrochloride

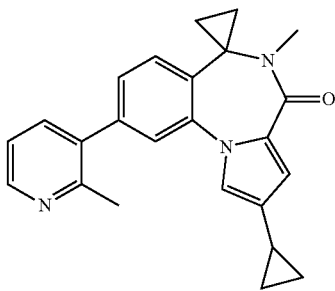 [SMILES: Cc1ncccc1-c1ccc2c(c1)-n1cc(C3CC3)cc1C(=O)N(C)C21CC1]

Under inert atmosphere, a mixture of example 17 (1.0 equiv.), cyclopropylzinc bromide (0.5M solution in THF, 0.1 mol·L$^{-1}$), copper iodide (0.2 equiv.) and bis(tri-tert-butylphosphine)palladium (0.2 equiv.) was heated at 80° C. for 1 hour. The reaction mixture was neutralized with aqueous potassium carbonate and extracted twice with EtOAc. The organic layers were combined, washed with brine, dried over MgSO$_4$, concentrated and purified by preparative HPLC to afford example 155 as a beige solid in 15% yield. Salt formation was performed by method VII(i). $^1$H-NMR (400 MHz, DMSO-D6): 8.78 (d, J 5.1 Hz, 1H, Ar); 8.41 (d, J 7.5 Hz, 1H, Ar); 7.90 (dd, J 7.5, 5.1 Hz, 1H, Ar); 7.64 (m, 2H, Ar); 7.44 (dd, J 7.8, 1.7 Hz, 1H, Ar); 7.34 (d, J 2.0 Hz, 1H, Ar); 6.65 (d, J 2.0 Hz, 1H, Ar); 2.93 (s, 3H, CH$_3$); 2.70 (s, 3H, CH$_3$); 1.80 (m, 1H, cyclopropyl); 1.51 (m, 2H, cyclopropyl); 0.98 (m, 1H, cyclopropyl); 0.86 (m, 2H, cyclopropyl); 0.60 (m, 3H, cyclopropyl). Proton for HCl salt not observed. M/Z (M+H)$^+$=370.3. MP=190-198° C.

Example 156

5-Methyl-2-cyclopentyl-9-(2-methyl-pyridin-3-yl)-spiro[benzo[f]pyrazolo[1,5-a][1,4]diazepine-6,1'-cyclopropan]-4(5H)-one, hydrochloride

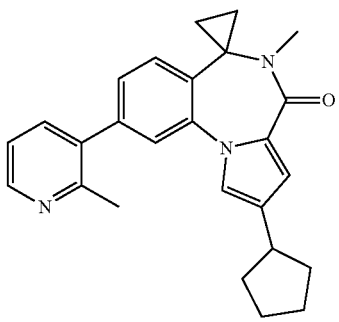 [SMILES: Cc1ncccc1-c1ccc2c(c1)-n1cc(C3CCCC3)cc1C(=O)N(C)C21CC1]

Under inert atmosphere, a mixture of example 17 (1 equiv.), cyclopentylzinc bromide (0.5M solution in THF, 2.2 equiv.) and bis(tri-tert-butylphosphine)palladium (0.2 equiv.) in dioxane (0.2 mol·L$^{-1}$) was heated at 100° C. for 1 hour. The reaction mixture was neutralized with aqueous potassium carbonate and extracted twice with EtOAc. The organic layers were combined, washed with brine, dried over MgSO$_4$, concentrated and purified by flash column chromatography on silica gel (0% to 5% MeOH in dichloromethane) to afford example 156 as a yellow solid in 43% yield. Salt formation was performed by method VII(i). $^1$H-NMR (400 MHz, DMSO-D6): 8.78 (d, J 5.5 Hz, 1H, Ar); 8.40 (d, J 7.4 Hz, 1H, Ar); 7.88 (dd, J 7.4, 5.5 Hz, 1H, Ar); 7.67 (d, J 1.6 Hz, 1H, Ar); 7.65 (d, J 7.8 Hz, 1H, Ar); 7.43 (dd, J 7.8, 1.6 Hz, 1H, Ar); 7.35 (d, J 1.9 Hz, 1H, Ar); 6.78 (d, J 1.9 Hz, 1H, Ar); 2.95 (m, 1H, CH); 2.93 (s, 3H, CH$_3$); 2.68 (s, 3H, CH$_3$); 2.02 (m, 2H, 2CH); 1.74 (m, 2H, 2CH); 1.56 (m, 6H, 2cyclopropyl+4CH); 0.97 (m, 1H, cyclopropyl); 0.60 (m, 1H, cyclopropyl). Proton for HCl salt not observed. M/Z (M+H)$^+$=398.4. MP=230-235° C.

Example 157

5-Methyl-2-(thiazol-2-yl)-9-(2-methyl-pyridin-3-yl)-spiro[benzo[f]pyrazolo[1,5-a][1,4]diazepine-6,1'-cyclopropan]-4(5H)-one, hydrochloride

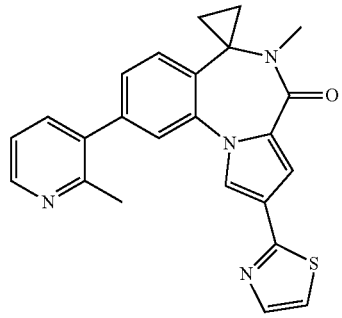 [SMILES: Cc1ncccc1-c1ccc2c(c1)-n1cc(-c3nccs3)cc1C(=O)N(C)C21CC1]

Under inert atmosphere, a mixture of example 17 (1.0 equiv.), 2-thiazolzinc bromide (0.5M solution in THF, 0.1 mol·L$^{-1}$) copper iodide (0.4 equiv.) and bis(tri-tert-butylphosphine)palladium (0.2 equiv.) was heated at 80° C. for 8 hours. The reaction mixture was neutralized with aqueous potassium carbonate and extracted twice with EtOAc. The organic layers were combined, washed with brine, dried over MgSO$_4$, concentrated and purified by preparative HPLC to afford example 157 as a beige solid in 15% yield. Salt formation was performed by method VII(i). $^1$H-NMR (400 MHz, DMSO-D6): 8.68 (d, J 5.5 Hz, 1H, Ar); 8.37 (d, J 7.5 Hz, 1H, Ar); 8.06 (d, J 1.9 Hz, 1H, Ar); 7.81 (dd, J 7.5, 5.5 Hz, 1H, Ar); 7.76 (d, J 1.5 Hz, 1H, Ar); 7.70 (d, J 3.3 Hz, 1H, Ar); 7.59 (d, J 7.8 Hz, 1H, Ar); 7.53 (d, J 3.3 Hz, 1H, Ar); 7.42 (dd, J 7.8, 1.5 Hz, 1H, Ar); 7.13 (d, J 1.9 Hz, 1H, Ar); 2.85 (s, 3H, CH$_3$); 2.59 (s, 3H, CH$_3$); 1.42 (m, 2H, cyclopropyl); 0.93 (m, 1H, cyclopropyl); 0.57 (m, 1H, cyclopropyl). Proton for HCl salt not observed. M/Z (M+H)$^+$=413.3. MP=240-245° C.

Example 158

5-Methyl-2-(thiazol-2-yl)-9-(6-methyl-pyridin-3-yl)-spiro[benzo[f]pyrazolo[1,5-a][1,4]diazepine-6,1'-cyclopropan]-4(5H)-one, hydrochloride

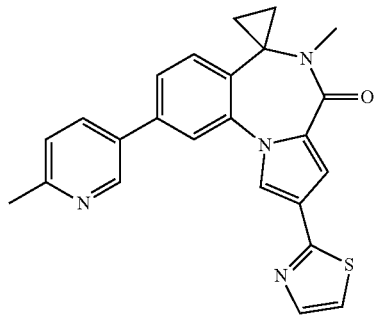 [SMILES: Cc1ccc(-c2ccc3c(c2)-n2cc(-c4nccs4)cc2C(=O)N(C)C32CC2)cn1]

Example 158 was prepared according to the procedure of example 157, starting from example 18. Purification by flash column chromatography on silica gel (50% to 100% EtOAc in cyclohexane) afforded example 158 as a brown solid in 18% yield. Salt formation was performed by method VII(i). $^1$H-NMR (400 MHz, DMSO-D6): 9.29 (s, 1H, Ar); 8.93 (d, J 8.5 Hz, 1H, Ar); 8.39 (d, J 1.9 Hz, 1H, Ar); 8.19 (d, J 1.7 Hz, 1H, Ar); 8.02 (d, J 8.5 Hz, 1H, Ar); 7.89 (dd, J 7.8, 1.7 Hz, 1H, Ar); 7.85 (d, J 3.3 Hz, 1H, Ar); 7.73 (d, J 7.8 Hz, 1H, Ar); 7.68 (d, J 3.3 Hz, 1H, Ar); 7.27 (d, J 1.9 Hz, 1H, Ar); 2.96 (s, 3H, CH$_3$); 2.80 (s, 3H, CH$_3$); 1.54 (m, 2H, cyclopropyl); 1.05 (m, 1H, cyclopropyl); 0.67 (m, 1H, cyclopropyl). Proton for HCl salt not observed. M/Z (M+H)$^+$=413.2. MP=228-239° C.

Example 159

5-Methyl-2-(2-methyl-2H-pyrazol-3-yl)-9-(6-methyl-pyridin-3-yl)-spiro[benzo[f]pyrazolo[1,5-a][1,4]diazepine-6,1'-cyclopropan]-4(5H)-one, hydrochloride

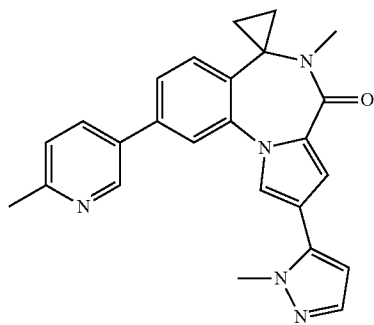 [SMILES: Cc1ccc(-c2ccc3c(c2)-n2cc(-c4ccnn4C)cc2C(=O)N(C)C32CC2)cn1]

Example 159 was obtained according to general procedure VI(i) starting from example 18 in presence of 1-methyl-1H-pyrazole-5-boronic acid pinacol ester. Purification by flash column chromatography on silica gel (0% to 5% MeOH in dichloromethane) afforded the product as a greenish solid in 33% yield. Salt formation was performed by method VII(ii). $^1$H-NMR (400 MHz, DMSO-D6): 9.26 (d, J 1.6 Hz, 1H, Ar); 8.85 (dd, J 8.3, 1.6 Hz, 1H, Ar); 8.16 (d, J 1.5 Hz, 1H, Ar); 8.06 (d, J 2.0 Hz, 1H, Ar); 7.99 (d, J 8.3 Hz, 1H, Ar); 7.87 (dd, J 7.9, 1.5 Hz, 1H, Ar); 7.73 (d, J 7.9 Hz, 1H, Ar); 7.45 (d, J 1.8 Hz, 1H, Ar); 7.19 (d, J 2.0 Hz, 1H, Ar); 6.55 (d, J 1.8 Hz, 1H, Ar); 4.03 (s, 3H, CH$_3$); 2.97 (s, 3H, CH$_3$); 2.79 (s, 3H, CH$_3$); 1.55 (m, 2H, cyclopropyl); 1.05 (m, 1H, cyclopropyl); 0.66 (m, 1H, cyclopropyl). Proton for HCl salt not observed. M/Z (M+H)$^+$=410.4. MP=187-194° C.

Example 160

5-Methyl-2-(2-methyl-2H-pyrazol-3-yl)-9-(2-methyl-pyridin-3-yl)-spiro[benzo[f]pyrazolo[1,5-a][1,4]diazepine-6,1'-cyclopropan]-4(5H)-one, hydrochloride

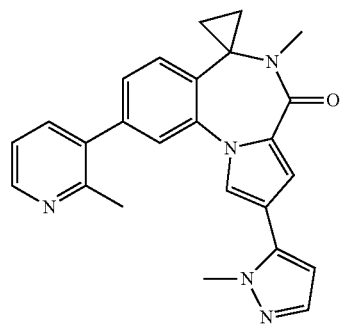 [SMILES: Cc1ncccc1-c1ccc2c(c1)-n1cc(-c3ccnn3C)cc1C(=O)N(C)C21CC1]

Example 160 was obtained according to general procedure VI(i) starting from example 17 in presence of 1-methyl-1H-pyrazole-5-boronic acid pinacol ester. Purification by flash column chromatography on silica gel (0% to 5% MeOH in dichloromethane) afforded the product as a yellow solid in 31% yield. Salt formation was performed by method VII(ii). $^1$H-NMR (400 MHz, DMSO-D6): 8.81 (d, J 5.5 Hz, 1H, Ar); 8.49 (d, J 7.5 Hz, 1H, Ar); 7.95 (dd, J 7.5, 5.5 Hz, 1H, Ar); 7.86 (m, 2H, Ar); 7.72 (d, J 7.8 Hz, 1H, Ar); 7.54 (dd, J 7.8, 1.3 Hz, 1H, Ar); 7.41 (d, J 1.8 Hz, 1H, Ar); 7.18 (d, J 2.0 Hz, 1H, Ar); 6.52 (d, J 1.8 Hz, 1H, Ar); 3.99 (s, 3H, CH$_3$); 2.97 (s, 3H, CH$_3$); 2.74 (s, 3H, CH$_3$); 1.55 (m, 2H, cyclopropyl); 1.04 (m, 1H, cyclopropyl); 0.66 (m, 1H, cyclopropyl). Proton for HCl salt not observed. M/Z (M+H)$^+$=410.3. MP=229-237° C.

Example 161

5-Methyl-2-dimethylamino-9-(6-methyl-pyridin-3-yl)-spiro[benzo[f]pyrazolo[1,5-a][1,4]diazepine-6,1'-cyclopropan]-4(5H)-one, hydrochloride

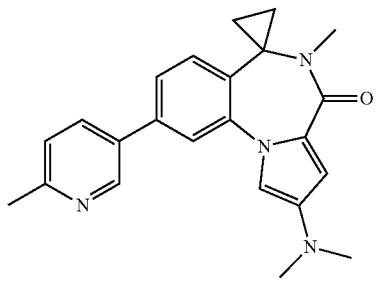 [SMILES: Cc1ccc(-c2ccc3c(c2)-n2cc(N(C)C)cc2C(=O)N(C)C32CC2)cn1]

Under inert atmosphere, a mixture of example 18 (1.0 equiv.), dimethylamine (2M solution in THF, 2.4 equiv.), sodium tertbutoxide (1.2 equiv.) and bis(tri-tert-butylphosphine)palladium (0.2 equiv.) in toluene (0.2 mol·L$^{-1}$) was heated at 90° C. for 16 hours. The reaction mixture was neutralized with aqueous potassium carbonate and extracted twice with EtOAc. The organic layers were combined, washed with brine, dried over MgSO$_4$, concentrated and purified by preparative HPLC to afford example 161 as a yellow solid in 20% yield. Salt formation was performed by method VII(ii). $^1$H-NMR (400 MHz, DMSO-D6): 9.19 (s, 1H, Ar); 8.73 (d, J 8.2 Hz, 1H, Ar); 8.00 (s, 1H, Ar); 7.90 (d, J 8.2 Hz, 1H, Ar); 7.80 (d, J 8.0 Hz, 1H, Ar); 7.76 (s, 1H, Ar); 7.68 (d, J 8.0 Hz, 1H, Ar); 6.97 (s, 1H, Ar); 3.03 (s, 6H, 2CH$_3$); 2.93 (s, 3H, CH$_3$); 2.74 (s, 3H, CH$_3$); 1.53 (m, 2H, cyclopropyl); 0.99 (m, 1H, cyclopropyl); 0.60 (m, 1H, cyclopropyl). Proton for HCl salt not observed. M/Z (M+H)$^+$=373.3. MP=183-190° C.

Example 162

5-Methyl-2-(2-fluorophenyl)-9-(2-ethyl-pyridin-3-yl)-spiro[benzo[f]pyrazolo[1,5-a][1,4]diazepine-6,1'-cyclopropan]-4(5H)-one, hydrochloride

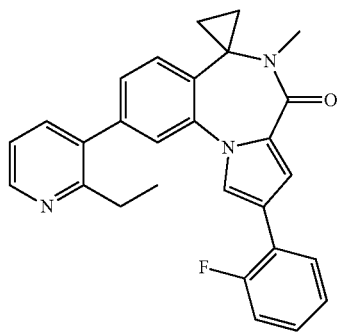 [SMILES: CCc1ncccc1-c1ccc2c(c1)-n1cc(-c3ccccc3F)cc1C(=O)N(C)C21CC1]

Example 162 was obtained according to general procedure VI(i) starting from example 19 in presence of 2-fluoroboronic acid. Purification by preparative HPLC afforded the product as a white solid in 17% yield. Salt formation was performed by method VII(i). $^1$H-NMR (400 MHz, DMSO-D6): 8.79 (m, 1H, Ar); 8.36 (m, 1H, Ar); 7.97 (s, 1H, Ar); 7.86 (m, 2H, Ar); 7.80 (s, 1H, Ar); 7.69 (m, 1H, Ar); 7.46 (m, 1H, Ar); 7.33 (s, 1H, Ar); 7.26 (m, 3H, Ar); 2.97 (m, 5H, CH$_3$+C$\underline{H}_2$—CH$_3$); 1.54 (m, 2H, cyclopropyl); 1.21 (t, J 6.6 Hz, 3H, CH$_2$—C$\underline{H}_3$); 1.02 (m, 1H, cyclopropyl); 0.67 (m, 1H, cyclopropyl). Proton for HCl salt not observed. M/Z (M+H)$^+$=438.3. MP=189-195° C.

Example 163

5-Methyl-2-(2-methyl-2H-pyrazol-3-yl)-9-(2-ethyl-pyridin-3-yl)-spiro[benzo[f]pyrazolo[1,5-a][1,4]diazepine-6,1'-cyclopropan]-4(5H)-one, hydrochloride

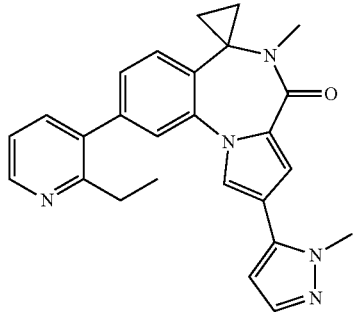 [SMILES: CCc1ncccc1-c1ccc2c(c1)-n1cc(-c3ccnn3C)cc1C(=O)N(C)C21CC1]

Example 163 was obtained according to general procedure VI(i) starting from example 19 in presence of 1-methyl-1H-pyrazole-5-boronic acid pinacol ester. Purification by preparative HPLC afforded the product as a white solid in 13% yield. Salt formation was performed by method VII(ii). $^1$H-NMR (400 MHz, DMSO-D6): 8.82 (d, J 4.8 Hz, 1H, Ar); 8.41 (d, J 7.2 Hz, 1H, Ar); 7.90 (dd, J 7.2, 4.8 Hz, 1H, Ar); 7.86 (d, J 1.9 Hz, 1H, Ar); 7.84 (d, J 1.5 Hz, 1H, Ar); 7.71 (d, J 7.8 Hz, 1H, Ar); 7.49 (dd, J 7.8, 1.5 Hz, 1H, Ar); 7.41 (d, J 1.8 Hz, 1H, Ar); 7.18 (d, J 1.9 Hz, 1H, Ar); 6.52 (d, J 1.8 Hz, 1H, Ar); 3.98 (s, 3H, CH$_3$); 2.97 (m, 5H, CH$_3$+C$\underline{H}_2$—CH$_3$); 1.54 (m, 2H, cyclopropyl); 1.22 (t, J 7.6 Hz, 3H, CH$_2$—C$\underline{H}_3$); 1.04 (m, 1H, cyclopropyl); 0.67 (m, 1H, cyclopropyl). Proton for HCl salt not observed. M/Z (M+H)$^+$=424.4. MP=187-192° C.

General Procedure VIII: Reductive Cyclization of Intermediate C, C" into Benzodiazepinone L, L" (Scheme 3).

At 0° C., sodium borohydrate (10 equiv.) was slowly added to a mixture of intermediate C, C" (1.0 equiv.) and cobalt chloride hexahydrate (2.0 equiv.) in methanol (0.15 mol·L$^{-1}$). The reaction mixture was heated for 24 hours at 85° C. The reaction mixture was neutralized with an aqueous solution of ammonium chloride and extracted twice with dichloromethane. The organic layers were combined, washed with brine, dried over MgSO$_4$, concentrated and purified by flash column chromatography on silica gel (unsing a gradient of EtOAc in cyclohexane as eluent) to afford the product.

Compound 43: 9-Bromo-2-phenyl-5,6-dihydro-benzo[f]pyrrolo[1,2-a][1,4]diazepin-4-one Compound 43 was prepared according to procedure VIII starting from compound 8. It was obtained as a white solid in 38% yield. $^1$H-NMR (400 MHz, DMSO-D6): 8.40 (m, 1H, NH); 8.10 (d, J 2.0 Hz, 1H, Ar); 7.91 (d, J 1.9 Hz, 1H, Ar); 7.75 (m, 2H, Ar); 7.55 (dd, J 8.0, 1.9 Hz, 1H, Ar); 7.45 (d, J 8.0 Hz, 1H, Ar); 7.39 (m, 2H, Ar); 7.32 (d, J 2.0 Hz, 1H, Ar); 7.24 (m, 1H, Ar); 4.13 (s, 2H, CH$_2$). M/Z (M[$^{79}$Br]+H)$^+$=353.0.

Example 164

9-Bromo-5-methyl-2-phenyl-5,6-dihydro-benzo[f]pyrrolo[1,2-a][1,4]diazepin-4-one

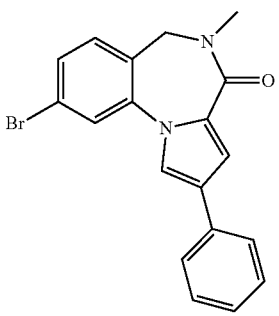 [SMILES: CN1Cc2ccc(Br)cc2-n2cc(-c3ccccc3)cc2C1=O]

Example 164 was prepared according to general procedure III, starting from compound 43 in presence of iodomethane. The reaction mixture was stirred at room temperature for 2 hours. Purification by filtration after hydrolysis afforded the product as a white solid in 97% yield. $^1$H-NMR (400 MHz, DMSO-D6): 8.10 (s, 1H, Ar); 7.94 (s, 1H, Ar); 7.75 (m, 2H, Ar); 7.60 (m, 2H, Ar); 7.39 (m, 2H, Ar); 7.32-7.24 (m, 2H, Ar); 4.39 (s, 2H, CH$_2$); 3.08 (s, 3H, CH$_3$). M/Z (M[$^{79}$Br]+H)$^+$=367.0. MP=76-84° C.

Example 165

9-(6-Amino-pyridin-3-yl)-5-methyl-2-phenyl-5,6-dihydro-benzo[f]pyrrolo[1,2-a][1,4]diazepin-4-one, hydrochloride

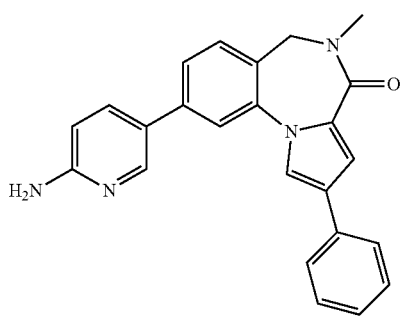 [SMILES: CN1Cc2ccc(-c3ccc(N)nc3)cc2-n2cc(-c3ccccc3)cc2C1=O]

Example 165 was obtained according to general procedure VI(i) starting from example 164 in presence of 2-aminopyridine-5-boronic acid pinacol ester. Purification by flash column chromatography on silica gel (100% EtOAc) afforded the product as a white solid in 44% yield. Salt formation was performed by method VII(i). $^1$H-NMR (400 MHz, DMSO-D6): 14.30 (bs, 1H, HCl salt); 8.50 (d, J 1.9 Hz, 1H, Ar); 8.45 (dd, J 9.3, 2.0 Hz, 1H, Ar); 8.17 (d, J 2.0 Hz, 1H, Ar); 8.11 (bs, 2H, NH$_2$); 7.94 (d, J 1.6 Hz, 1H, Ar); 7.74 (m, 3H, Ar); 7.68 (dd, J 7.8, 1.6 Hz, 1H, Ar); 7.41 (m, 2H, Ar); 7.32 (d, J 1.9 Hz, 1H, Ar); 7.25 (m, 1H, Ar); 7.12 (d, J 9.3 Hz, 1H, Ar); 4.44 (s, 2H, CH$_2$); 3.10 (s, 3H, CH$_3$). M/Z (M+H)$^+$=381.1. MP>250° C.

Compound 44: 1-[2-Cyano-5-(2-methyl-pyridin-3-yl)-phenyl]-4-phenyl-1H-imidazole-2-carboxylic acid ethyl ester Compound 44 was obtained according to general procedure V, starting from compound 10 and 2-methylpyridine-3-boronic acid pinacol ester. It was isolated as a yellow oil in 98% yield. $^1$H-NMR (400 MHz, DMSO-D6): 8.55 (dd, J 4.8, 1.7 Hz, 1H, Ar); 8.37 (s, 1H, Ar); 8.20 (d, J 7.9 Hz, 1H, Ar); 7.96 (d, J 1.6 Hz, 1H, Ar); 7.90 (m, 2H, Ar); 7.82 (dd, J 8.0, 1.7 Hz, 1H, Ar); 7.75 (dd, J 7.9, 1.6 Hz, 1H, Ar); 7.46 (m, 2H, Ar); 7.39 (dd, J 8.0, 4.8 Hz, 1H, Ar); 7.34 (m, 1H, Ar); 4.23 (q, J 7.0 Hz, 2H, C$\underline{H_2}$—CH$_3$); 2.51 (s, 3H, CH$_3$); 1.18 (t, J 7.0 Hz, 3H, CH$_2$—C$\underline{H_3}$). M/Z (M+H)$^+$=409.1.

Compound 45: 9-(2-Methylpyridin-3-yl)-2-phenyl-5,6-dihydro-4H-benzo[f]imidazo[1,2-a][1,4]diazepin-4-one Compound 45 was obtained according to general procedure VIII starting from compound 44. It was obtained as a white solid in quantitative yield. $^1$H-NMR (400 MHz, DMSO-D6): 8.98 (m, 1H, NH); 8.86 (d, J 5.5 Hz, 1H, Ar); 8.56 (d, J 7.9 Hz, 1H, Ar); 8.51 (s, 1H, Ar); 8.02 (dd, J 7.9, 5.5 Hz, 1H, Ar); 7.93 (m, 3H, Ar); 7.76 (d, J 7.8 Hz, 1H, Ar); 7.63 (dd, J 7.8, 1.6 Hz, 1H, Ar); 7.46 (m, 2H, Ar); 7.33 (m, 1H, Ar); 4.32 (s, 2H, CH$_2$); 2.78 (s, 3H, CH$_3$). M/Z (M+H)$^+$=367.1. MP=240-250° C.

Example 166

5-Methyl-9-(2-methylpyridin-3-yl)-2-phenyl-5,6-dihydro-4H-benzo[f]imidazo[1,2-a][1,4]diazepin-4-one, hydrochloride

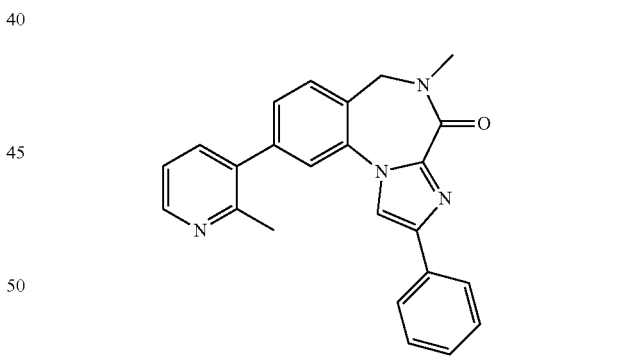

Example 166 was prepared according to general procedure III, starting from compound 45 in presence of iodomethane. The reaction mixture was stirred at room temperature for 3 hours. Purification by filtration after hydrolysis afforded the product as a white solid in 95% yield. Salt formation was performed by method VII(ii). $^1$H-NMR (400 MHz, DMSO-D6): 8.76 (d, J 5.5 Hz, 1H, Ar); 8.45 (d, J 7.5 Hz, 1H, Ar); 8.40 (s, 1H, Ar); 7.91 (dd, J 7.5, 5.5 Hz, 1H, Ar); 7.84 (m, 3H, Ar); 7.80 (d, J 7.8 Hz, 1H, Ar); 7.56 (dd, J 7.8, 1.6 Hz, 1H, Ar); 7.37 (m, 2H, Ar); 7.24 (m, 1H, Ar); 4.50 (s, 2H, CH$_2$); 3.07 (s, 3H, CH$_3$); 2.69 (s, 3H, CH$_3$). Proton for HCl salt not observed. M/Z (M+H)$^+$=381.1. MP=240-245° C.

Example 167

5-Ethyl-9-(2-methylpyridin-3-yl)-2-phenyl-5,6-dihydro-4H-benzo[f]imidazo[1,2-a][1,4]diazepin-4-one, hydrochloride

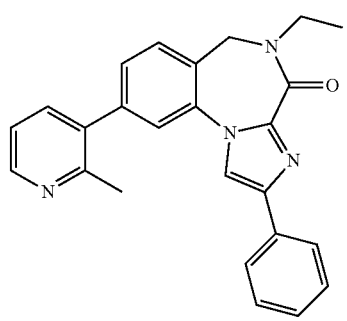 [SMILES: CCN1Cc2ccc(-c3cccnc3C)cc2-n2cc(-c3ccccc3)nc2C1=O]

Example 167 was prepared according to general procedure III, starting from compound 45 in presence of iodoethane. The reaction mixture was stirred at room temperature for 3 hours. Purification by filtration after hydrolysis afforded the product as a white solid in 61% yield. Salt formation was performed by method VII(ii). $^1$H-NMR (400 MHz, DMSO-D6): 8.85 (d, J 5.5 Hz, 1H, Ar); 8.56 (d, J 7.5 Hz, 1H, Ar); 8.50 (s, 1H, Ar); 8.01 (dd, J 7.5, 5.5 Hz, 1H, Ar); 7.93 (m, 3H, Ar); 7.91 (d, J 7.8 Hz, 1H, Ar); 7.65 (dd, J 7.8, 1.4 Hz, 1H, Ar); 7.46 (m, 2H, Ar); 7.33 (m, 1H, Ar); 4.60 (s, 2H, CH$_2$); 3.62 (q, J 6.8 Hz, 2H, C$\underline{H}_2$—CH$_3$); 2.78 (s, 3H, CH$_3$); 1.18 (t, J 6.8 Hz, 3H, CH$_2$—C$\underline{H}_3$). Proton for HCl salt not observed. M/Z (M+H)$^+$=395.1. MP=200-220° C.

General Procedure IX: Formylation of Benzodiazepinone K into Carboxaldehyde K$_3$ (Scheme 5).

At 0° C., to a solution of benzodiazepinone K (1.0 equiv.) and dichloromethylmethyl ether (2.2 equiv.) in a mixture of 1,2-dichloroethane (0.30 mol·L$^{-1}$) and nitromethane (0.30 mol·L$^{-1}$), aluminium chloride (2.2 equiv.) was slowly added. The reaction mixture was stirred for 1 hour and allowed to reach room temperature. Aluminium chloride (2.2 equiv.) was added again and the reaction mixture was stirred for one more hour at room temperature. The reaction mixture was neutralized with aqueous potassium carbonate and extracted twice with EtOAc. The organic layers were combined, washed with brine, dried over MgSO$_4$ and concentrated to dryness to afford the product. No purification, otherwise specified.

Example 168

5-Methyl-9-(2-methylpyridin-3-yl)-4-oxo-4,5-dihydrospiro[benzo[f]pyrrolo[1,2-a][1,4]diazepine-6,1'-cyclopropane]-2-carbaldehyde

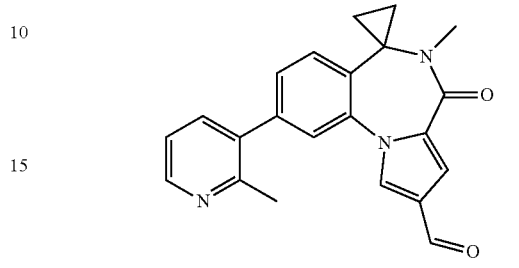

Example 168 was obtained according to general procedure IX, starting from the free base of example 20. It was isolated as a brown oil in quantitative yield. $^1$H-NMR (400 MHz, DMSO-D6): 9.87 (s, 1H, COH); 8.51 (dd, J 4.8, 1.6 Hz, 1H, Ar); 8.43 (d, J 1.9 Hz, 1H, Ar); 7.75 (m, 2H, Ar); 7.65 (d, J 7.9 Hz, 1H, Ar); 7.49 (dd, J 7.9, 1.6 Hz, 1H, Ar); 7.34 (dd, J 7.9, 4.8 Hz, 1H, Ar); 7.19 (d, J 1.9 Hz, 1H, Ar); 3.32 (s, 3H, CH$_3$); 2.97 (s, 3H, CH$_3$); 1.54 (m, 2H, cyclopropyl); 1.01 (m, 1H, cyclopropyl); 0.68 (m, 1H, cyclopropyl). M/Z (M+H)$^+$=358.3.

Example 169

5-Methyl-9-(2-ethyl-pyridin-3-yl)-4-oxo-4,5-dihydrospiro[benzo[f]pyrrolo[1,2-a][1,4]diazepine-6,1'-cyclopropane]-2-carbaldehyde

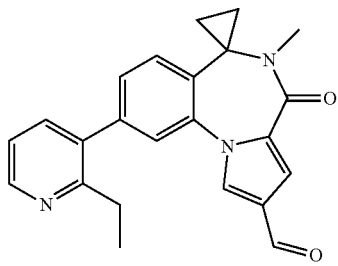 [SMILES: CCc1ncccc1-c1ccc2c(c1)-n1cc(C=O)cc1C(=O)N(C)C21CC1]

Example 169 was obtained according to general procedure IX starting from the free base of example 24. Purification by flash column chromatography (40% to 100% EtOAc in cyclohexane) afforded example 169 as a white solid in 56% yield. M/Z (M+H)$^+$=372.2.

Example 170

5-Methyl-9-(6-methyl-pyridin-3-yl)-4-oxo-4,5-dihydrospiro[benzo[f]pyrrolo[1,2-a][1,4]diazepine-6,1'-cyclopropane]-2-carbaldehyde

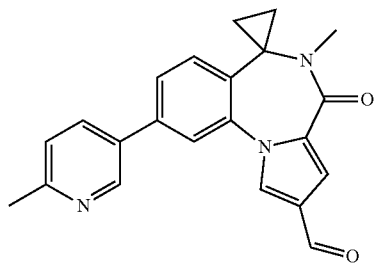 [SMILES: Cc1ccc(-c2ccc3c(c2)-n2cc(C=O)cc2C(=O)N(C)C32CC2)cn1]

Example 170 was obtained according to general procedure IX, starting from the free base of example 25. It was isolated as a brown oil in quantitative yield. M/Z (M+H)$^+$=358.2.

Example 171

5-Methyl-9-(6-fluoro-pyridin-3-yl)-4-oxo-4,5-dihydrospiro[benzo[f]pyrrolo[1,2-a][1,4]diazepine-6,1'-cyclopropane]-2-carbaldehyde

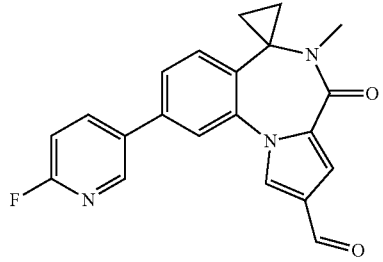 [SMILES: CN1C(=O)c2cc(C=O)cn2-c2cc(-c3ccc(F)nc3)ccc2C12CC2]

Example 171 was obtained according to general procedure IX, starting from example 31. It was isolated as a brown oil in quantitative yield. M/Z (M+H)$^+$=362.3.

Example 172

5-(Methyl-d$_3$)-9-(6-fluoro-pyridin-3-yl)-4-oxo-4,5-dihydrospiro[benzo[f]pyrrolo[1,2-a][1,4]diazepine-6,1'-cyclopropane]-2-carbaldehyde

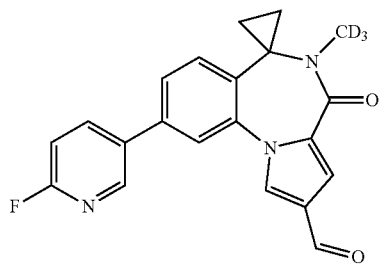 [SMILES: [2H]C([2H])([2H])N1C(=O)c2cc(C=O)cn2-c2cc(-c3ccc(F)nc3)ccc2C12CC2]

Example 172 was obtained according to general procedure IX starting from example 55. It was isolated as a brown oil in 82% yield. $^1$H-NMR (400 MHz, DMSO-D6): 9.89 (s, 1H, COH); 8.72 (d, J 2.6 Hz, 1H, Ar); 8.54 (d, J 1.9 Hz, 1H, Ar); 8.45 (dt, J 8.4, 2.6 Hz, 1H, Ar); 8.04 (d, J 1.6 Hz, 1H, Ar); 7.78 (dd, J 7.8, 1.6 Hz, 1H, Ar); 7.67 (d, J 7.8 Hz, 1H, Ar); 7.34 (dd, J 8.4, 2.6 Hz, 1H, Ar); 7.20 (d, J 1.9 Hz, 1H, Ar); 1.50 (m, 2H, cyclopropyl); 0.99 (m, 1H, cyclopropyl); 0.64 (m, 1H, cyclopropyl). M/Z (M+H)$^+$=365.2.

Example 173

5-Methyl-9-bromo-4-oxo-4,5-dihydrospiro[benzo[f]pyrrolo[1,2-a][1,4]diazepine-6,1'-cyclopropane]-2-carbaldehyde

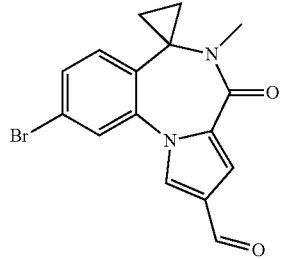 [SMILES: CN1C(=O)c2cc(C=O)cn2-c2cc(Br)ccc2C12CC2]

Example 173 was prepared according to general procedure IX starting from example 1. It was obtained as a yellow solid in quantitative yield. M/Z (M[$^{79}$Br]+H)$^+$=345.0.

Example 174

5-Methyl-9-(3-cyanophenyl)-4-oxo-4,5-dihydrospiro[benzo[f]pyrrolo[1,2-a][1,4]diazepine-6,1'-cyclopropane]-2-carbaldehyde

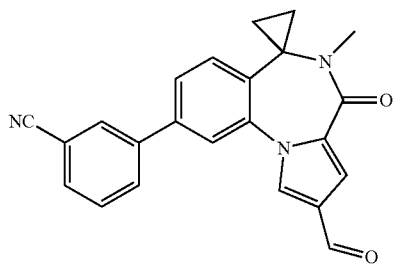 [SMILES: CN1C(=O)c2cc(C=O)cn2-c2cc(-c3cccc(C#N)c3)ccc2C12CC2]

Example 174 was prepared according to general procedure IX starting from example 44. It was obtained as a yellow solid in quantitative yield. M/Z (M+H)$^+$=368.2.

Example 175

5-Methyl-9-(pyridazin-3-yl)-4-oxo-4,5-dihydrospiro[benzo[f]pyrrolo[1,2-a][1,4]diazepine-6,1'-cyclopropane]-2-carbaldehyde

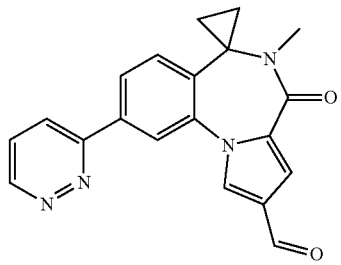 [SMILES: CN1C(=O)c2cc(C=O)cn2-c2cc(-c3cccnn3)ccc2C12CC2]

Example 175 was prepared according to general procedure IX starting from example 70. It was obtained as a brown solid in 93% yield. M/Z (M+H)$^+$=345.2.

General Procedure X: Oxydation of Carboxaldehyde K$_3$ into Carboxylic Acid K$_4$ (Scheme 5).

To a solution of carboxaldehyde K$_3$ (1.0 equiv.) and 2-methyl-2-butene (0.13 mol·L$^{-1}$) in a mixture of THF (0.10 mol·L$^{-1}$) and tert-butanol (0.10 mol·L$^{-1}$), a solution of sodium chlorite (3.0 equiv.) and sodium phosphate monobasic (4.5 equiv.) in water (0.10 mol·L$^{-1}$) was slowly added. The reaction mixture was stirred for 2 days at room temperature. The reaction mixture was acidified with aqueous hydrogene chloride (0.1N) and extracted twice with EtOAc. The organic layers were combined, washed with brine, dried over MgSO$_4$ and concentrated to dryness to afford the product. No purification, otherwise specified.

Example 176

5-Methyl-9-(2-methylpyridin-3-yl)-4-oxo-4,5-dihydrospiro[benzo[f]pyrrolo[1,2-a][1,4]diazepine-6,1'-cyclopropane]-2-carboxylic acid

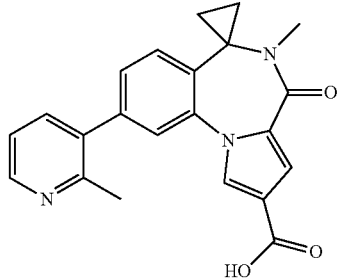 [SMILES: Cc1ncccc1-c1ccc2c(c1)-n1cc(C(=O)O)cc1C(=O)N(C)C21CC1]

Example 176 was prepared according to general procedure X starting from example 168. It was obtained as a yellow solid in 95% yield. $^1$H-NMR (400 MHz, DMSO-D6): 12.10 (bs, 1H, COOH); 8.52 (dd, J 4.8, 1.6 Hz, 1H, Ar); 8.12 (d, J 1.9 Hz, 1H, Ar); 7.83 (dd, J 7.9, 1.6 Hz, 1H, Ar); 7.73 (d, J 1.5 Hz, 1H, Ar); 7.63 (d, J 7.8 Hz, 1H, Ar); 7.46 (dd, J 7.8, 1.5 Hz, 1H, Ar); 7.38 (dd, J 7.9, 4.8 Hz, 1H, Ar); 7.09 (d, J 1.9 Hz, 1H, Ar); 3.35 (s, 3H, CH$_3$); 2.95 (s, 3H, CH$_3$); 1.53 (m, 2H, cyclopropyl); 0.99 (m, 1H, cyclopropyl); 0.66 (m, 1H, cyclopropyl). M/Z (M+H)$^+$=374.3. MP>250° C.

Example 177

5-Methyl-9-(6-fluoro-pyridin-3-yl)-4-oxo-4,5-dihydrospiro[benzo[f]pyrrolo[1,2-a][1,4]diazepine-6,1'-cyclopropane]-2-carboxylic acid

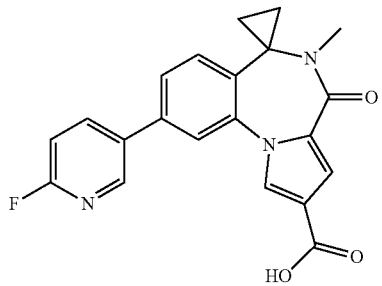 [SMILES: CN1C(=O)c2cc(C(=O)O)cn2-c2cc(-c3ccc(F)nc3)ccc2C12CC2]

Example 177 was prepared according to general procedure X starting from example 171. It was obtained as an orange solid in quantitative yield. $^1$H-NMR (400 MHz, DMSO-D6): 12.38 (bs, 1H, COOH); 8.79 (d, J 2.5 Hz, 1H, Ar); 8.53 (dt, J 8.4, 2.5 Hz, 1H, Ar); 8.36 (d, J 1.9 Hz, 1H, Ar); 8.07 (d, J 1.6 Hz, 1H, Ar); 7.80 (dd, J 7.8, 1.6 Hz, 1H, Ar); 7.71 (d, J 7.8 Hz, 1H, Ar); 7.38 (dd, J 8.4, 2.5 Hz, 1H, Ar); 7.15 (d, J 1.9 Hz, 1H, Ar); 2.99 (s, 3H, CH$_3$); 1.55 (m, 2H, cyclopropyl); 1.05 (m, 1H, cyclopropyl); 0.69 (m, 1H, cyclopropyl). M/Z (M+H)$^+$=378.2. MP>250° C.

Example 178

5-(Methyl-d$_3$)-9-(6-fluoro-pyridin-3-yl)-4-oxo-4,5-dihydrospiro[benzo[f]pyrrolo[1,2-a][1,4]diazepine-6,1'-cyclopropane]-2-carboxylic acid

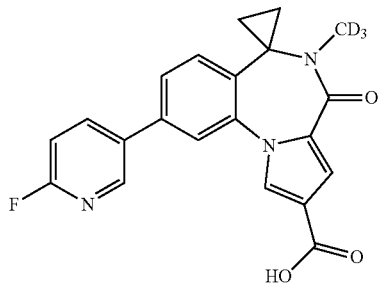 [SMILES: [2H]C([2H])([2H])N1C(=O)c2cc(C(=O)O)cn2-c2cc(-c3ccc(F)nc3)ccc2C12CC2]

Example 178 was prepared according to general procedure X starting from example 172. It was obtained as an orange solid in quantitative yield. $^1$H-NMR (400 MHz, DMSO-D6): 12.23 (bs, 1H, COOH); 8.78 (d, J 2.5 Hz, 1H, Ar); 8.53 (dt, J 8.4, 2.5 Hz, 1H, Ar); 8.35 (d, J 1.9 Hz, 1H, Ar); 8.06 (d, J 1.7 Hz, 1H, Ar); 7.80 (dd, J 7.8, 1.7 Hz, 1H, Ar); 7.70 (d, J 7.8 Hz, 1H, Ar); 7.38 (dd, J 8.4, 2.5 Hz, 1H, Ar); 7.15 (d, J 1.9 Hz, 1H, Ar); 1.55 (m, 2H, cyclopropyl); 1.04 (m, 1H, cyclopropyl); 0.68 (m, 1H, cyclopropyl). M/Z (M+H)$^+$=381.2. MP>250° C.

Example 179

5-Methyl-9-bromo-4-oxo-4,5-dihydrospiro[benzo[f]pyrrolo[1,2-a][1,4]diazepine-6,1'-cyclopropane]-2-carboxylic acid

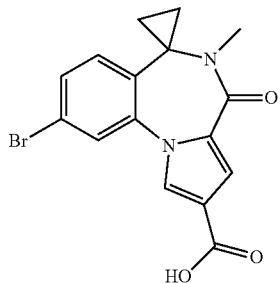 [SMILES: CN1C(=O)c2cc(C(=O)O)cn2-c2cc(Br)ccc2C12CC2]

Example 179 was prepared according to general procedure X starting from example 173. It was obtained as an orange solid in quantitative yield. M/Z (M[$^{79}$Br]+H)$^+$=361.0.

Example 180

5-Methyl-9-(pyridazin-3-yl)-4-oxo-4,5-dihydrospiro[benzo[f]pyrrolo[1,2-a][1,4]diazepine-6,1'-cyclopropane]-2-carboxylic acid

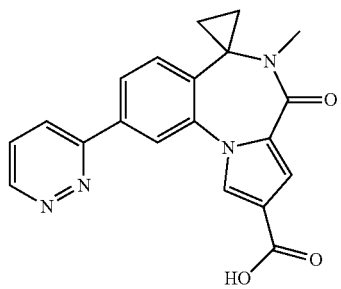 [SMILES: CN1C(=O)c2cc(C(=O)O)cn2-c2cc(-c3cccnn3)ccc2C12CC2]

Example 180 was prepared according to general procedure X starting from example 175. It was obtained as a yellow solid in quantitative yield. M/Z (M+H)$^+$=361.1.

Example 181

5-Methyl-9-(3-cyanophenyl)-4-oxo-4,5-dihydrospiro[benzo[f]pyrrolo[1,2-a][1,4]diazepine-6,1'-cyclopropane]-2-carboxylic acid

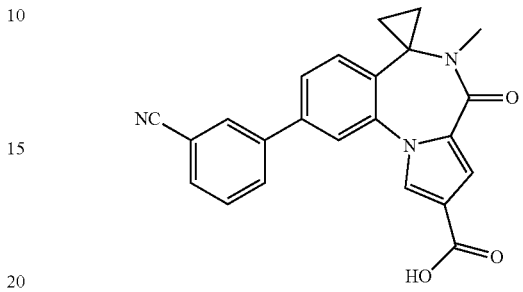

Example 181 was prepared according to general procedure X starting from example 174. It was obtained as a yellow solid in quantitative yield. M/Z (M+H)$^+$=384.1.

Example 182

5-Methyl-9-(2-methyl-pyridin-3-yl)-2-(oxazol-5-yl)-spiro[benzo[f]pyrazolo[1,5-a][1,4]diazepine-6,1'-cyclopropan]-4(5H)-one, hydrochloride A suspension of example 168 (1.0 equiv.), tosylmethylisocyanide (1.2 equiv.) and sodium methoxide (4.2 equiv.) in methanol (0.05 mol·L$^{-1}$) was refluxed for 16 hours. Methanol was removed under reduced pressure and the crude mixture was purified by preparative HPLC to afford example 182 as a yellow solid in 66% yield. Salt formation was performed by method VII(i). $^1$H-NMR (400 MHz, DMSO-D6): 8.89 (d, J 5.0 Hz, 1H, Ar); 8.56 (d, J 7.6 Hz, 1H, Ar); 8.45 (s, 1H, Ar); 8.05 (d, J 1.9 Hz, 1H, Ar); 8.01 (dd, J 7.6, 5.0 Hz, 1H, Ar); 7.91 (d, J 1.6 Hz, 1H, Ar); 7.79 (d, J 7.9 Hz, 1H, Ar); 7.62 (dd, J 7.9, 1.6 Hz, 1H, Ar); 7.53 (s, 1H, Ar); 7.29 (d, J 1.9 Hz, 1H, Ar); 3.05 (s, 3H, CH$_3$); 2.80 (s, 3H, CH$_3$); 1.62 (m, 2H, cyclopropyl); 1.11 (m, 1H, cyclopropyl); 0.75 (m, 1H, cyclopropyl). Proton for HCl salt not observed. M/Z (M+H)$^+$=397.3. MP=158-168° C.

Example 183

5-Methyl-9-(2-methyl-pyridin-3-yl)-2-(3H-imidazol-4-yl)-spiro[benzo[f]pyrazolo[1,5-a][1,4]diazepine-6,1'-cyclopropan]-4(5H)-one, hydrochloride

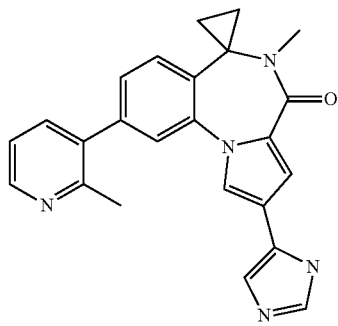 [SMILES: Cc1ncccc1-c1ccc2c(c1)-n1cc(-c3cnc[nH]3)cc1C(=O)N(C)C21CC1]

In a sealed vial, a suspension of example 168 (1.0 equiv.), tosylmethylisocyanide (1.2 equiv.), cyanide potassium (0.1 equiv.) and ammonia (7M solution in methanol, 0.05 mol·L$^{-1}$) was heated at 110° C. for 16 hours. Methanol was removed under vacuum and the crude mixture was purified by flash column chromatography on silica gel (0% to 5% MeOH in dichloromethane) to afford example 183 as a dark solid in 15% yield. Salt formation was performed by method VII(ii). $^1$H-NMR (400 MHz, DMSO-D6): 9.17 (d, J 1.3 Hz, 1H, Ar); 8.76 (d, J 5.0 Hz, 1H, Ar); 8.39 (d, J 2.0 Hz, 1H, Ar); 8.35 (d, J 7.5 Hz, 1H, Ar); 7.97 (d, J 1.3 Hz, 1H, Ar); 7.85 (dd, J 7.5, 5.0 Hz, 1H, Ar); 7.73 (m, 2H, Ar); 7.54 (dd, J 7.8, 1.6 Hz, 1H, Ar); 7.43 (d, J 2.0 Hz, 1H, Ar); 2.98 (s, 3H, CH$_3$); 2.74 (s, 3H, CH$_3$); 1.56 (m, 2H, cyclopropyl); 1.04 (m, 1H, cyclopropyl); 0.69 (m, 1H, cyclopropyl). Proton for HCl salt not observed. Proton for NH not observed. M/Z (M+H)$^+$=396.3. MP>250° C.

Example 184

5-Methyl-9-(2-methyl-pyridin-3-yl)-2-(1H-imidazol-2-yl)-spiro[benzo[f]pyrazolo[1,5-a][1,4]diazepine-6,1'-cyclopropan]-4(5H)-one, hydrochloride

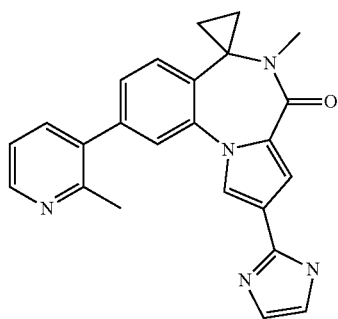 [SMILES: Cc1ncccc1-c1ccc2c(c1)-n1cc(-c3ncc[nH]3)cc1C(=O)N(C)C21CC1]

In a sealed vial, a suspension of example 168 (1.0 equiv.), glyoxal (40% aqueous solution, 0.3 mol·L$^{-1}$), ammonium hydroxide (28% aqueous solution, 0.6 mol·L$^{-1}$) in ethanol (0.05 mol·L$^{-1}$) was heated at 80° C. for 5 days. After cooling, the reaction mixture was hydrolysed and extracted twice with EtOAc. The organic layers were combined, washed with brine, dried over MgSO$_4$, concentrated and purified by preparative HPLC to afford example 184 as a yellow solid in 6% yield. Salt formation was performed by method VII(i). $^1$H-NMR (400 MHz, DMSO-D6): 14.80 (bs, 1H, NH); 8.71 (m, 2H, Ar); 8.19 (d, J 7.0 Hz, 1H, Ar); 7.76-7.71 (m, 5H, Ar); 7.64 (d, J 2.0 Hz, 1H, Ar); 7.57 (dd, J 7.8, 1.6 Hz, 1H, Ar); 2.99 (s, 3H, CH$_3$); 2.69 (s, 3H, CH$_3$); 1.58 (m, 2H, cyclopropyl); 1.05 (m, 1H, cyclopropyl); 0.72 (m, 1H, cyclopropyl). Proton for HCl salt not observed. M/Z (M+H)$^+$=396.2. MP>250° C.

Example 185

5-Methyl-9-(2-methyl-pyridin-3-yl)-2-[1,3,4]oxadiazol-2-yl-spiro[benzo[f]pyrazolo[1,5-a][1,4]diazepine-6,1'-cyclopropan]-4(5H)-one

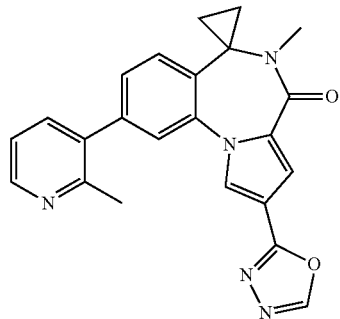 [SMILES: Cc1ncccc1-c1ccc2c(c1)-n1cc(-c3nnco3)cc1C(=O)N(C)C21CC1]

A solution of example 176 (1.0 equiv.) and isocyanoiminotriphenylphosphorane (2.0 equiv.) in DMF (0.05 mol·L$^{-1}$) was heated at 80° C. for 2 days. After cooling, the reaction mixture was hydrolysed and extracted twice with EtOAc. The organic layers were combined, washed with brine, dried over MgSO$_4$, concentrated and purified by flash column chromatography on silica gel (0% to 5% MeOH in dichloromethane) to afford example 185 as a yellow solid in 36% yield. $^1$H-NMR (400 MHz, DMSO-D6): 9.27 (s, 1H, Ar); 8.51 (dd, J 4.8, 1.6 Hz, 1H, Ar); 8.39 (d, J 1.9 Hz, 1H, Ar); 7.81 (d, J 1.5 Hz, 1H, Ar); 7.79 (dd, J 7.8, 1.5 Hz, 1H, Ar); 7.65 (d, J 7.8 Hz, 1H, Ar); 7.49 (dd, J 7.8, 1.6 Hz, 1H, Ar); 7.34 (dd, J 7.8, 4.8 Hz, 1H, Ar); 7.29 (d, J 1.9 Hz, 1H, Ar); 2.99 (s, 3H, CH$_3$); 2.52 (s, 3H, CH$_3$); 1.54 (m, 2H, cyclopropyl); 1.03 (m, 1H, cyclopropyl); 0.69 (m, 1H, cyclopropyl). M/Z (M+H)$^+$=398.3. MP>250° C.

Example 186

5-Methyl-9-(6-fluoro-pyridin-3-yl)-2-(1H-imidazol-2-yl)-spiro[benzo[f]pyrazolo[1,5-a][1,4]diazepine-6,1'-cyclopropan]-4(5H)-one

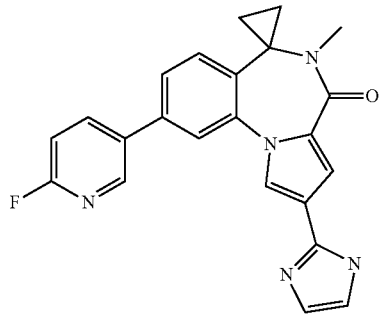

Example 186 was obtained according to the procedure of example 184, starting from example 171. Purification by preparative HPLC afforded a beige solid in 16% yield. $^1$H-NMR (400 MHz, DMSO-D6): 13.60 (bs, 1H, NH); 8.69 (s, 1H, Ar); 8.43 (t, J 8.2 Hz, 1H, Ar); 8.31 (m, 1H, Ar); 7.96 (s, 1H, Ar); 7.75 (d, J 7.8 Hz, 1H, Ar); 7.67 (d, J 7.8 Hz, 1H, Ar); 7.43-7.32 (m, 4H, Ar); 2.96 (s, 3H, $CH_3$); 1.52 (m, 2H, cyclopropyl); 1.02 (m, 1H, cyclopropyl); 0.66 (m, 1H, cyclopropyl). M/Z $(M+H)^+$=400.3. MP>250° C.

Example 187

5-Methyl-9-(6-fluoro-pyridin-3-yl)-2-[1,3,4]oxadiazol-2-yl-spiro[benzo[f]pyrazolo[1,5-a][1,4]diazepine-6,1'-cyclopropan]-4(5H)-one

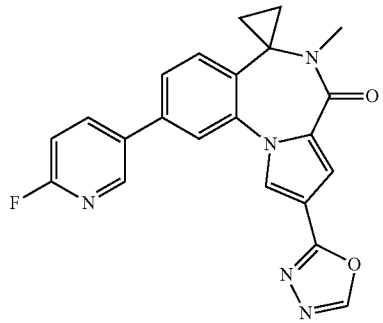 [SMILES: CN1C(=O)c2cc(-c3nnco3)cn2-c2cc(-c3ccc(F)nc3)ccc2C12CC2]

Example 187 was prepared according to the procedure of example 185, starting from example 177. Purification by preparative HPLC afforded a beige solid in 41% yield. $^1$H-NMR (400 MHz, DMSO-D6): 9.28 (s, 1H, Ar); 8.75 (d, J 2.6 Hz, 1H, Ar); 8.55 (d, J 1.9 Hz, 1H, Ar); 8.48 (dt, J 8.4, 2.6 Hz, 1H, Ar); 8.08 (d, J 1.6 Hz, 1H, Ar); 7.78 (dd, J 7.8, 1.6 Hz, 1H, Ar); 7.68 (d, J 7.8 Hz, 1H, Ar); 7.34 (dd, J 8.4, 2.6 Hz, 1H, Ar); 7.29 (d, J 1.9 Hz, 1H, Ar); 2.97 (s, 3H, $CH_3$); 1.54 (m, 2H, cyclopropyl); 1.03 (m, 1H, cyclopropyl); 0.67 (m, 1H, cyclopropyl). M/Z $(M+H)^+$=402.3. MP=160-175° C.

Example 188

5-(Methyl-d$_3$)-9-(6-fluoro-pyridin-3-yl)-2-[1,3,4]oxadiazol-2-yl-spiro[benzo[f]pyrazolo[1,5-a][1,4]diazepine-6,1'-cyclopropan]-4(5H)-one

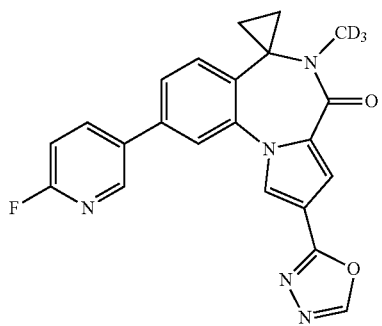 [SMILES: [2H]C([2H])([2H])N1C(=O)c2cc(-c3nnco3)cn2-c2cc(-c3ccc(F)nc3)ccc2C12CC2]

Example 188 was prepared according to the procedure of example 185, starting from example 178. Purification by preparative HPLC afforded a white solid in 25% yield. $^1$H-NMR (400 MHz, DMSO-D6): 9.28 (s, 1H, Ar); 8.75 (d, J 2.6 Hz, 1H, Ar); 8.55 (d, J 1.9 Hz, 1H, Ar); 8.48 (dt, J 8.4, 2.6 Hz, 1H, Ar); 8.08 (d, J 1.6 Hz, 1H, Ar); 7.77 (dd, J 7.8, 1.6 Hz, 1H, Ar); 7.68 (d, J 7.8 Hz, 1H, Ar); 7.34 (dd, J 8.4, 2.6 Hz, 1H, Ar); 7.29 (d, J 1.9 Hz, 1H, Ar); 1.53 (m, 2H, cyclopropyl); 1.03 (m, 1H, cyclopropyl); 0.67 (m, 1H, cyclopropyl). M/Z $(M+H)^+$=405.3. MP>250° C.

Example 189

5-Methyl-9-bromo-2-[1,3,4]oxadiazol-2-yl-spiro[benzo[f]pyrazolo[1,5-a][1,4]diazepine-6,1'-cyclopropan]-4(5H)-one

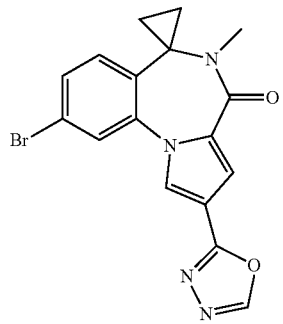 [SMILES: CN1C(=O)c2cc(-c3nnco3)cn2-c2cc(Br)ccc2C12CC2]

Example 189 was prepared according to the procedure of example 185, starting from example 179. Purification by preparative HPLC afforded a white solid in 36% yield. $^1$H-NMR (400 MHz, DMSO-D6): 9.26 (s, 1H, Ar); 8.34 (d, J 1.7 Hz, 1H, Ar); 8.02 (d, J 1.6 Hz, 1H, Ar); 7.62 (dd, J 7.9, 1.6 Hz, 1H, Ar); 7.51 (d, J 7.9 Hz, 1H, Ar); 7.26 (d, J 1.7 Hz, 1H, Ar); 2.93 (s, 3H, $CH_3$); 1.48 (m, 2H, cyclopropyl); 0.99 (m, 1H, cyclopropyl); 0.61 (m, 1H, cyclopropyl). M/Z $(M[^{79}Br]+H)^+$=385.0. MP=246-252° C.

Example 190

5-Methyl-9-(6-dimethylamino-pyridin-3-yl)-2-[1,3,4]oxadiazol-2-yl-spiro[benzo[f]pyrazolo[1,5-a][1,4]diazepine-6,1'-cyclopropan]-4(5H)-one

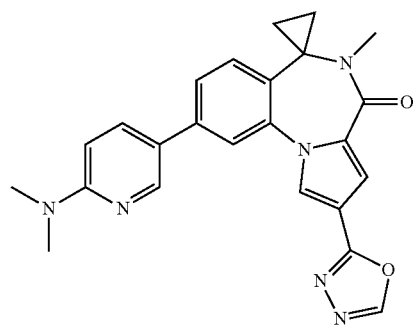 [SMILES: CN(C)c1ccc(-c2ccc3c(c2)-n2cc(-c4nnco4)cc2C(=O)N(C)C32CC2)cn1]

Example 190 was prepared according to general procedure VI(i) starting from example 189 in presence of 6-fluoropyridine-3-boronic acid and dimethylamine (2M in THF, 2 equiv.). Purification by preparative HPLC afforded the product as a beige solid in 10% yield. $^1$H-NMR (400 MHz, DMSO-D6): 9.26 (s, 1H, Ar); 8.59 (s, 1H, Ar); 8.49 (s, 1H, Ar); 8.00 (d, J 8.5 Hz, 1H, Ar); 7.92 (s, 1H, Ar); 7.64 (d, J 7.8 Hz, 1H, Ar); 7.57 (d, J 7.8 Hz, 1H, Ar); 7.26 (s, 1H, Ar); 6.73 (d, J 8.5 Hz, 1H, Ar); 3.08 (s, 6H, 2CH$_3$); 2.95 (s, 3H, CH$_3$); 1.49 (m, 2H, cyclopropyl); 1.00 (m, 1H, cyclopropyl); 0.63 (m, 1H, cyclopropyl). M/Z (M+H)$^+$=427.3. MP>250° C.

Example 191

5-Methyl-9-(6-chloro-pyridin-3-yl)-2-[1,3,4]oxadiazol-2-yl-spiro[benzo[f]pyrazolo[1,5-a][1,4]diazepine-6,1'-cyclopropan]-4(5H)-one

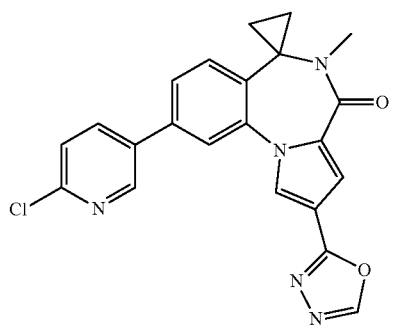 [SMILES: CN1C(=O)c2cc(-c3nnco3)cn2-c2cc(-c3ccc(Cl)nc3)ccc2C12CC2]

Example 191 was prepared according to general procedure VI(i) starting from example 189 in presence of 6-chloropyridine-3-boronic acid. Purification by preparative HPLC afforded the product as a white solid in 10% yield. $^1$H-NMR (400 MHz, DMSO-D6): 9.27 (s, 1H, Ar); 8.92 (d, J 2.5 Hz, 1H, Ar); 8.55 (d, J 1.9 Hz, 1H, Ar); 8.35 (dd, J 8.3, 2.5 Hz, 1H, Ar); 8.09 (d, J 1.7 Hz, 1H, Ar); 7.79 (dd, J 7.8, 1.7 Hz, 1H, Ar); 7.68 (d, J 7.8 Hz, 1H, Ar); 7.66 (d, J 8.3 Hz, 1H, Ar); 7.28 (d, J 1.9 Hz, 1H, Ar); 2.96 (s, 3H, CH$_3$); 1.53 (m, 2H, cyclopropyl); 1.03 (m, 1H, cyclopropyl); 0.66 (m, 1H, cyclopropyl). M/Z (M[$^{35}$Cl]+H)$^+$=418.1. MP>250° C.

Example 192

5-Methyl-9-(3-cyanophenyl)-2-[1,3,4]oxadiazol-2-yl-spiro[benzo[f]pyrazolo[1,5-a][1,4]diazepine-6,1'-cyclopropan]-4(5H)-one

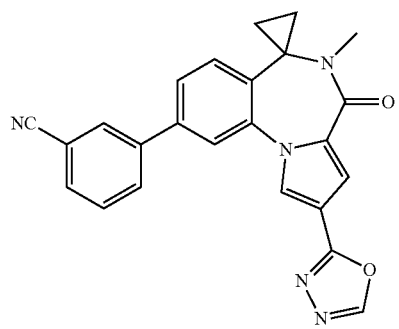 [SMILES: CN1C(=O)c2cc(-c3nnco3)cn2-c2cc(-c3cccc(C#N)c3)ccc2C12CC2]

Example 192 was prepared according to the procedure of example 185, starting from example 181. Purification by flash column chromatography on silica gel (EtOAc in cyclohexane, 0% to 50%) afforded the product as a white solid in 19% yield. $^1$H-NMR (400 MHz, DMSO-D6): 9.27 (s, 1H, Ar); 8.55 (d, J 1.9 Hz, 1H, Ar); 8.40 (m, 1H, Ar); 8.19 (m, 1H, Ar); 8.08 (d, J 1.7 Hz, 1H, Ar); 7.87 (m, 1H, Ar); 7.80 (dd, J 7.8, 1.7 Hz, 1H, Ar); 7.69 (m, 2H, Ar); 7.28 (d, J 1.9 Hz, 1H, Ar); 2.96 (s, 3H, CH$_3$); 1.53 (m, 2H, cyclopropyl); 1.03 (m, 1H, cyclopropyl); 0.66 (m, 1H, cyclopropyl). M/Z (M+H)$^+$=408.2. MP>250° C.

Example 193

5-Methyl-9-(pyridazin-3-yl)-2-[1,3,4]oxadiazol-2-yl-spiro[benzo[f]pyrazolo[1,5-a][1,4]diazepine-6,1'-cyclopropan]-4(5H)-one

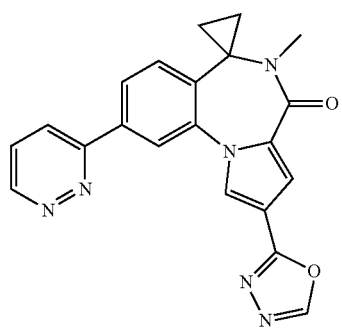 [SMILES: CN1C(=O)c2cc(-c3nnco3)cn2-c2cc(-c3cccnn3)ccc2C12CC2]

Example 193 was prepared according to the procedure of example 185, starting from example 180. Purification by preparative HPLC afforded the product as a brown solid in 22% yield. $^1$H-NMR (400 MHz, DMSO-D6): 9.27 (m, 2H, Ar); 8.50 (d, J 1.9 Hz, 1H, Ar); 8.46 (dd, J 8.6, 1.5 Hz, 1H, Ar); 8.40 (d, J 1.7 Hz, 1H, Ar); 8.25 (dd, J 8.0, 1.7 Hz, 1H, Ar); 7.85 (dd, J 8.6, 4.8 Hz, 1H, Ar); 7.75 (d, J 8.0 Hz, 1H, Ar); 7.30 (d, J 1.9 Hz, 1H, Ar); 2.98 (s, 3H, CH$_3$); 1.55 (m, 2H, cyclopropyl); 1.05 (m, 1H, cyclopropyl); 0.69 (m, 1H, cyclopropyl). M/Z (M+H)$^+$=385.2. MP>250° C.

General Procedure XI: Acylation of Benzodiazepinone K from Alcyl Chloride Derivatives (Scheme 5).

At 0° C., to a solution of benzodiazepinone K (1.0 equiv.) in a mixture of 1,2-dichloroethane (0.30 mol·L$^{-1}$) and nitromethane (0.30 mol·L$^{-1}$), aluminium chloride (2.5 equiv.) was slowly added. After 10 minutes of vigorous stirring, acyl chloride (2.5 equiv.) was added dropwise and the reaction mixture was stirred for 1 hour and allowed to reach room temperature. At 0° C., Aluminium chloride (2.2 equiv.) and acyl chloride (2.5 equiv.) were added again and the reaction mixture was stirred for one more hour at room temperature. The reaction mixture was neutralized with aqueous potassium carbonate and extracted twice with EtOAc. The organic layers were combined, washed with brine, dried over MgSO$_4$, concentrated, and purified to afford the product.

Example 194

5-Methyl-9-(2-methyl-pyridin-3-yl)-2-(cyclopentanecarbonyl)-spiro[benzo[f]pyrazolo[1,5-a][1,4]diazepine-6,1'-cyclopropan]-4(5H)-one, hydrochloride

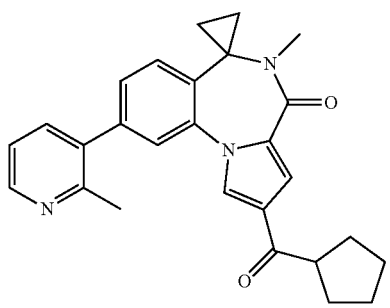 [SMILES: Cc1ncccc1-c1ccc2c(c1)-n1cc(C(=O)C3CCCC3)cc1C(=O)N(C)C21CC1]

Example 194 was prepared according to procedure XI starting from the free base of example 20 in presence of cyclopentane carbonyl chloride. Purification by flash column chromatography on silica gel (MeOH in dichloromethane, 0% to 5%) afforded the product as a white solid in 92% yield. Salt formation was performed by method VII(i). $^1$H-NMR (400 MHz, DMSO-D6): 8.78 (d, J 5.5 Hz, 1H, Ar); 8.40 (d, J 7.9 Hz, 1H, Ar); 8.29 (d, J 1.9 Hz, 1H, Ar); 7.87 (m, 2H, Ar); 7.71 (d, J 7.9 Hz, 1H, Ar); 7.56 (dd, J 7.9, 1.6 Hz, 1H, Ar); 7.20 (d, J 1.9 Hz, 1H, Ar); 3.63 (quint, J 7.4 Hz, 1H, CH); 2.97 (s, 3H, CH$_3$); 2.69 (s, 3H, CH$_3$); 1.90 (m, 2H, 2CH); 1.81-1.50 (m, 8H, 6CH+2cyclopropyl); 1.02 (m, 1H, cyclopropyl); 0.66 (m, 1H, cyclopropyl). Proton for HCl salt not observed. M/Z (M+H)$^+$=426.2. MP=177-190° C.

Example 195

5-Methyl-9-(2-methyl-pyridin-3-yl)-2-acetyl-spiro[benzo[f]pyrazolo[1,5-a][1,4]diazepine-6,1'-cyclopropan]-4(5H)-one, hydrochloride

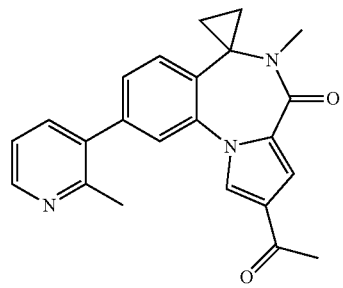 [SMILES: CC(=O)c1cc2n(c1)-c1cc(-c3cccnc3C)ccc1C1(CC1)N(C)C2=O]

Example 195 was prepared according to procedure XI starting from the free base of example 20 in presence of acetyl chloride. Purification by flash column chromatography on silica gel (MeOH in dichloromethane, 0% to 5%) afforded the product as a white solid in 92% yield. Salt formation was performed by method VII(i). $^1$H-NMR (400 MHz, DMSO-D6): 8.84 (d, J 5.5 Hz, 1H, Ar); 8.47 (d, J 7.5 Hz, 1H, Ar); 8.35 (d, J 1.9 Hz, 1H, Ar); 7.93 (m, 2H, Ar); 7.77 (d, J 7.9 Hz, 1H, Ar); 7.62 (dd, J 7.9, 1.6 Hz, 1H, Ar); 7.24 (d, J 1.9 Hz, 1H, Ar); 3.02 (s, 3H, CH$_3$); 2.75 (s, 3H, CH$_3$); 2.52 (s, 3H, CH$_3$); 1.60 (m, 2H, cyclopropyl); 1.07 (m, 1H, cyclopropyl); 0.71 (m, 1H, cyclopropyl). Proton for HCl salt not observed. M/Z (M+H)$^+$=372.3. MP=200-220° C.

General Procedure XII: Reduction of Benzodiazepinone K$_1$ or K$_3$ into Benzodiazepinone K$_2$ (Scheme 5).

A solution of benzodiazepinone K$_1$ or K$_3$ (1.0 equiv.) and triethylsilane (4.0 equiv.) in trifluoroacetic acid (0.15 mol·L$^{-1}$) was stirred for 16 hours at room temperature. The reaction mixture was neutralized with aqueous sodium hydroxide (1N) and extracted twice with EtOAc. The organic layers were combined, washed with brine, dried over MgSO$_4$, concentrated, and purified to afford the product.

Example 196

5-Methyl-9-(2-methyl-pyridin-3-yl)-2-(cyclopentylmethyl)-spiro[benzo[f]pyrazolo[1,5-a][1,4]diazepine-6,1'-cyclopropan]-4(5H)-one, hydrochloride

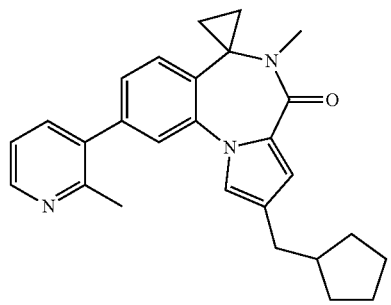 [SMILES: Cc1ncccc1-c1ccc2c(c1)-n1cc(CC3CCCC3)cc1C(=O)N(C)C21CC1]

Example 196 was obtained according to procedure XII starting from example 194. Purification by flash column chromatography on silica gel (100% EtOAc) afforded the product as as a white solid in 25% yield. Salt formation was performed by method VII(i). $^1$H-NMR (400 MHz, DMSO-D6): 8.77 (d, J 5.4 Hz, 1H, Ar); 8.38 (d, J 7.5 Hz, 1H, Ar); 7.87 (dd, J 7.5, 5.4 Hz, 1H, Ar); 7.64 (m, 2H, Ar); 7.43 (dd, J 7.8, 1.7 Hz, 1H, Ar); 7.33 (d, J 1.7 Hz, 1H, Ar); 6.74 (d, J 1.9 Hz, 1H, Ar); 2.93 (s, 3H, CH$_3$); 2.67 (s, 3H, CH$_3$); 2.48 (m, 2H, CH$_2$); 2.12 (m, 1H, CH); 1.75 (m, 2H, 2CH); 1.60 (m, 2H, 2CH); 1.51 (m, 4H, 2CH+2cyclopropyl); 1.23 (m, 2H, 2CH); 0.97 (m, 1H, cyclopropyl); 0.58 (m, 1H, cyclopropyl). Proton for HCl salt not observed. M/Z (M+H)$^+$=412.3. MP=165-176° C.

Example 197

5-Methyl-9-(2-methyl-pyridin-3-yl)-2-ethyl-spiro[benzo[f]pyrazolo[1,5-a][1,4]diazepine-6,1'-cyclopropan]-4(5H)-one, hydrochloride

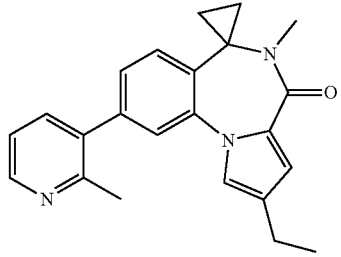 [SMILES: CCc1cc2n(c1)-c1cc(-c3cccnc3C)ccc1C1(CC1)N(C)C2=O]

Example 197 was obtained according to procedure XII starting from example 195. Purification by flash column chromatography on silica gel (100% EtOAc) afforded the product as a white solid in 81% yield. Salt formation was performed by method VII(i). $^1$H-NMR (400 MHz, DMSO-D6): 8.79 (d, J 5.4 Hz, 1H, Ar); 8.42 (d, J 7.5 Hz, 1H, Ar); 7.89 (dd, J 7.5, 5.4 Hz, 1H, Ar); 7.65 (m, 2H, Ar); 7.44 (dd, J 7.8, 1.7 Hz, 1H, Ar); 7.35 (d, J 1.7 Hz, 1H, Ar); 6.78 (d, J 1.8 Hz, 1H, Ar); 2.94 (s, 3H, CH$_3$); 2.70 (s, 3H, CH$_3$); 2.55 (q, J 7.5 Hz, 2H, C$\underline{H_2}$—CH$_3$); 1.51 (m, 2H, cyclopropyl); 1.23 (t, J 7.5 Hz, 3H, CH$_2$—C$\underline{H_3}$); 0.98 (m, 1H, cyclopropyl); 0.60 (m, 1H, cyclopropyl). Proton for HCl salt not observed. M/Z (M+H)$^+$=358.3. MP=165-175° C.

Example 198

2,5-Dimethyl-9-(6-methyl-pyridin-3-yl)-spiro[benzo[f]pyrazolo[1,5-a][1,4]diazepine-6,1'-cyclopropan]-4(5H)-one, hydrochloride

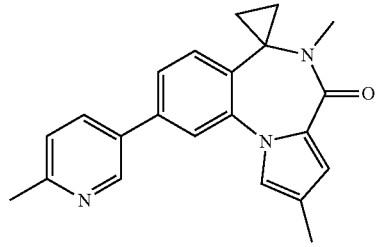 [SMILES: Cc1cc2n(c1)-c1cc(-c3ccc(C)nc3)ccc1C1(CC1)N(C)C2=O]

Example 198 was obtained according to procedure XII starting from example 170. Purification by flash column chromatography on silica gel (100% EtOAc) afforded the product as a white solid in 31% yield. Salt formation was performed by method VII(i). $^1$H-NMR (400 MHz, DMSO-D6): 9.18 (s, 1H, Ar); 8.76 (d, J 8.2 Hz, 1H, Ar); 7.95 (d, J 1.7 Hz, 1H, Ar); 7.91 (d, J 8.2 Hz, 1H, Ar); 7.77 (dd, J 7.9, 1.7 Hz, 1H, Ar); 7.66 (d, J 7.9 Hz, 1H, Ar); 7.51 (m, 1H, Ar); 6.74 (d, J 1.8 Hz, 1H, Ar); 2.92 (s, 3H, CH$_3$); 2.76 (s, 3H, CH$_3$); 2.18 (s, 3H, CH$_3$); 1.51 (m, 2H, cyclopropyl); 0.97 (m, 1H, cyclopropyl); 0.58 (m, 1H, cyclopropyl). Proton for HCl salt not observed. M/Z (M+H)$^+$=344.3.

Example 199

2,5-Dimethyl-9-(2-ethyl-pyridin-3-yl)-spiro[benzo[f]pyrazolo[1,5-a][1,4]diazepine-6,1'-cyclopropan]-4(5H)-one, hydrochloride

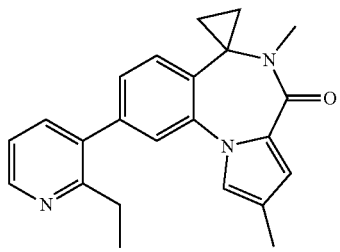 [SMILES: CCc1ncccc1-c1ccc2c(c1)-n1cc(C)cc1C(=O)N(C)C21CC1]

Example 199 was obtained according to procedure XII starting from example 169. Purification by flash column chromatography on silica gel (100% EtOAc) afforded the product as a yellow solid in 22% yield. Salt formation was performed by method VII(i). $^1$H-NMR (400 MHz, DMSO-D6): 8.78 (s, 1H, Ar); 8.33 (m, 1H, Ar); 7.84 (m, 1H, Ar); 7.61 (m, 2H, Ar); 7.39 (d, J 6.9 Hz, 1H, Ar); 7.31 (s, 1H, Ar); 6.72 (s, 1H, Ar); 2.95 (q, J 7.2 Hz, 2H, C$\underline{H_2}$—CH$_3$); 2.92 (s, 3H, CH$_3$); 2.12 (s, 3H, CH$_3$); 1.50 (m, 2H, cyclopropyl); 1.19 (t, J 7.2 Hz, 3H, CH$_2$—C$\underline{H_3}$); 0.96 (m, 1H, cyclopropyl); 0.59 (m, 1H, cyclopropyl). Proton for HCl salt not observed. M/Z (M+H)$^+$=358.2. MP=179-184° C.

Example 200

5-Methyl-9-(2-methyl-pyridin-3-yl)-2-(morpholin-4-ylmethyl)-spiro[benzo[f]pyrazolo[1,5-a][1,4]diazepine-6,1'-cyclopropan]-4(5H)-one, hydrochloride

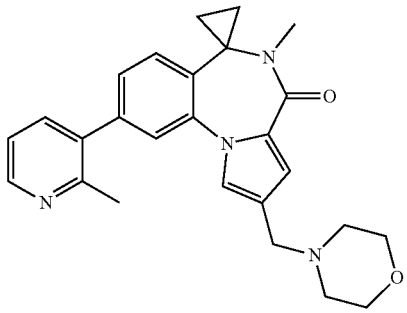 [SMILES: Cc1ncccc1-c1ccc2c(c1)-n1cc(CN3CCOCC3)cc1C(=O)N(C)C21CC1]

At 0° C., sodium triacetoxyborohydride (2.2 equiv.) was added in one portion to a solution of example 168 (1.0 equiv.) and morpholine (2.0 equiv.) in THF (0.1 mol·L$^{-1}$).

The reaction mixture was stirred for 6 hours at room temperature before being hydrolyzed and extracted twice with EtOAc. The organic layers were combined, washed with brine, dried over MgSO₄, concentrated, and purified by flash column chromatography on silica gel (0% to 5% MeOH in dichloromethane) to afford example 200 as a yellow solid in 65% yield. Salt formation was performed by method (i). $^1$H-NMR (400 MHz, DMSO-D6): 11.39 (bs, 1H, HCl salt); 8.79 (d, J 5.4 Hz, 1H, Ar); 8.39 (d, J 7.5 Hz, 1H, Ar); 7.89 (dd, J 7.5, 5.4 Hz, 1H, Ar); 7.79 (d, J 1.9 Hz, 1H, Ar); 7.75 (d, J 1.6 Hz, 1H, Ar); 7.71 (d, J 7.8 Hz, 1H, Ar); 7.53 (dd, J 7.8, 1.6 Hz, 1H, Ar); 7.10 (d, J 1.9 Hz, 1H, Ar); 4.26 (m, 2H, CH₂); 3.96 (m, 2H, 2CH); 3.83 (m, 2H, 2CH); 3.31 (m, 2H, 2CH); 3.06 (m, 2H, 2CH); 2.96 (s, 3H, CH₃); 2.73 (s, 3H, CH₃); 1.53 (m, 2H, cyclopropyl); 0.99 (m, 1H, cyclopropyl); 0.64 (m, 1H, cyclopropyl). M/Z (M+H)⁺=342.2. MP=242-250° C.

Example 201

5-Methyl-9-(2-methyl-pyridin-3-yl)-2-difluoromethyl-spiro[benzo[f]pyrazolo[1,5-a][1,4]diazepine-6,1'-cyclopropan]-4(5H)-one, hydrochloride

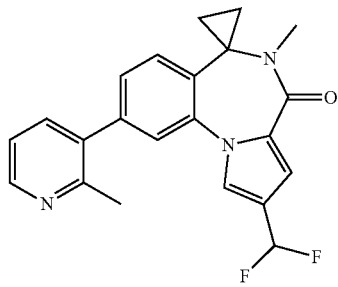 [SMILES: Cc1ncccc1-c1ccc2c(c1)-n1cc(C(F)F)cc1C(=O)N(C)C21CC1]

A solution of example 168 (1.0 equiv.) and Deoxofluor™ (50% solution in toluene, 0.25 mol·L⁻¹) in dichloromethane (0.10 mol·L⁻¹) was stirred for 36 hours at room temperature before being hydrolyzed and extracted twice with EtOAc. The organic layers were combined, washed with brine, dried over MgSO₄, concentrated, and purified by flash column chromatography on silica gel (0% to 10% MeOH in dichloromethane) to afford example 201 as a white solid in 16% yield. Salt formation was performed by method VII(i). $^1$H-NMR (400 MHz, DMSO-D6): 8.69 (d, J 5.4 Hz, 1H, Ar); 8.31 (d, J 7.5 Hz, 1H, Ar); 7.82 (d, J 1.9 Hz, 1H, Ar); 7.78 (dd, J 7.5, 5.4 Hz, 1H, Ar); 7.68 (d, J 1.6 Hz, 1H, Ar); 7.61 (d, J 7.8 Hz, 1H, Ar); 7.44 (dd, J 7.8, 1.6 Hz, 1H, Ar); 6.97 (t, J 56.0 Hz, 1H, CF₂H); 6.92 (d, J 1.9 Hz, 1H, Ar); 2.87 (s, 3H, CH₃); 2.60 (s, 3H, CH₃); 1.45 (m, 2H, cyclopropyl); 0.91 (m, 1H, cyclopropyl); 0.55 (m, 1H, cyclopropyl). Proton for HCl salt not observed. M/Z (M+H)⁺=380.3. MP=240-250° C.

General Procedure XIII: Reduction of Carboxaldehyde K₃ into the Corresponding Alcohol K₆ (Scheme 5).

At 0° C., sodium borohydride (1.1 equiv.) was added in one portion to a solution of carboxaldehyde K₃ (1.0 equiv.) in THF (0.10 mol·L⁻¹). The reaction mixture was stirred for 16 hours at room temperature before being neutralized with aqueous ammonium chloride and extracted twice with EtOAc. The organic layers were combined, washed with brine, dried over MgSO₄, concentrated and purified to afford the product.

Example 202

2-Hydroxymethyl-5-methyl-9-(6-methyl-pyridin-3-yl)-spiro[benzo[f]pyrazolo[1,5-a][1,4]diazepine-6,1'-cyclopropan]-4(5H)-one

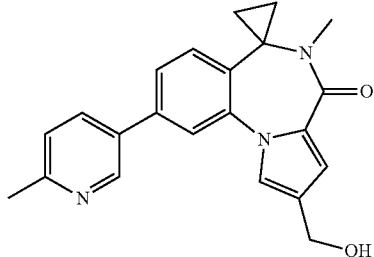 [SMILES: Cc1ccc(-c2ccc3c(c2)-n2cc(CO)cc2C(=O)N(C)C32CC2)cn1]

Example 202 was obtained according to procedure XIII starting from example 170. Purification by preparative HPLC to afford the product as a white solid in 42% yield. $^1$H-NMR (400 MHz, DMSO-D6): 8.93 (d, J 1.9 Hz, 1H, Ar); 8.76 (dd, J 8.2, 2.4 Hz, 1H, Ar); 7.84 (d, J 1.6 Hz, 1H, Ar); 7.69 (dd, J 7.9, 1.6 Hz, 1H, Ar); 7.65 (m, 2H, Ar); 7.45 (d, J 8.2 Hz, 1H, Ar); 6.89 (d, J 1.9 Hz, 1H, Ar); 4.99 (bs, 1H, OH); 4.52 (s, 2H, CH₂); 2.98 (s, 3H, CH₃); 2.59 (s, 3H, CH₃); 1.52 (m, 2H, cyclopropyl); 1.01 (m, 1H, cyclopropyl); 0.63 (m, 1H, cyclopropyl). M/Z (M+H)⁺=360.3. MP=144-154° C.

Example 203

2-Hydroxymethyl-5-methyl-9-(2-ethyl-pyridin-3-yl)-spiro[benzo[f]pyrazolo[1,5-a][1,4]diazepine-6,1'-cyclopropan]-4(5H)-one, hydrochloride

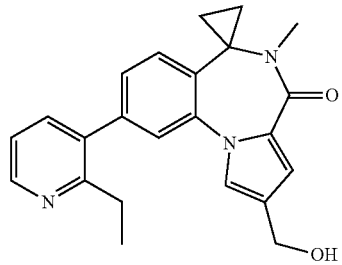 [SMILES: CCc1ncccc1-c1ccc2c(c1)-n1cc(CO)cc1C(=O)N(C)C21CC1]

Example 203 was obtained according to procedure XIII starting from example 169. Purification by flash column chromatography on silica gel (80% to 100% EtOAc in cyclohexane) afforded the product as a white solid in 29% yield. Salt formation was performed by method VII(i). $^1$H-NMR (400 MHz, DMSO-D6): 8.75 (s, 1H, Ar); 8.24 (m, 1H, Ar); 7.76 (m, 1H, Ar); 7.65 (m, 3H, Ar); 7.42 (d, J 7.8 Hz, 1H, Ar); 6.91 (s, 1H, Ar); 4.75 (s, 2H, CH₂); 2.94 (s, 3H, CH₃); 2.91 (q, J 7.3 Hz, 2H, C$\underline{H}_2$—CH₃); 1.51 (m, 2H, cyclopropyl); 1.18 (t, J 7.3 Hz, 3H, CH₂—C$\underline{H}_3$); 0.98 (m, 1H, cyclopropyl); 0.61 (m, 1H, cyclopropyl). Protons for HCl salt and OH were not observed. M/Z (M+H)⁺=374.3. MP>250° C.

Example 204

2-Hydroxymethyl-5-methyl-9-(6-fluoro-pyridin-3-yl)-spiro[benzo[f]pyrazolo[1,5-a][1,4]diazepine-6,1'-cyclopropan]-4(5H)-one

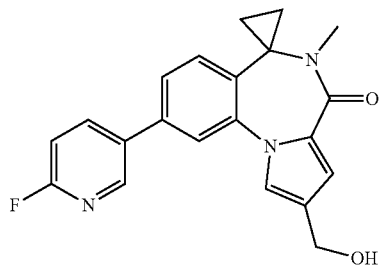 [SMILES: CN1C(=O)c2cc(CO)cn2-c2cc(-c3ccc(F)nc3)ccc2C12CC2]

Example 204 was obtained according to procedure XIII starting from example 171. It was obtained as a yellow solid in 71% yield and was taken crude to the next step. M/Z (M+H)$^+$=364.3.

General Procedure XIV: Alkylation of Alcohol K$_6$ into the Corresponding Alkyloxy K$_7$ (Scheme 5).

At 0° C., sodium hydride (60% dispersion in oil, 2.0 equiv.) was added in one portion to a solution of alcohol K$_6$ (1.0 equiv.) in THF (0.10 mol·L$^{-1}$). After 10 minutes, iodomethane (3.0 equiv.) was added dropwise and the reaction mixture was stirred for 2 hours at room temperature. The reaction mixture was neutralized with aqueous ammonium chloride and extracted twice with EtOAc. The organic layers were combined, washed with brine, dried over MgSO$_4$, concentrated and purified to afford the product.

Example 205

2-Methoxymethyl-5-methyl-9-(6-methyl-pyridin-3-yl)-spiro[benzo[f]pyrazolo[1,5-a][1,4]diazepine-6,1'-cyclopropan]-4(5H)-one, hydrochloride

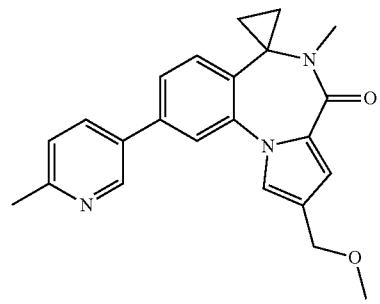 [SMILES: COCc1cc2n(c1)-c1cc(-c3ccc(C)nc3)ccc1C1(CC1)N(C)C2=O]

Example 205 was obtained according to procedure XIV starting from example 202. Purification by flash column chromatography on silica gel (100% EtOAc) afforded the product as a white solid in 27% yield. Salt formation was performed by method VII(i). $^1$H-NMR (400 MHz, DMSO-D6): 9.22 (s, 1H, Ar); 8.78 (d, J 8.2 Hz, 1H, Ar); 8.03 (d, J 1.6 Hz, 1H, Ar); 7.93 (d, J 8.2 Hz, 1H, Ar); 7.84 (dd, J 7.9, 1.6 Hz, 1H, Ar); 7.74 (m, 2H, Ar); 6.90 (d, J 1.8 Hz, 1H, Ar); 4.45 (s, 2H, CH$_2$); 3.38 (s, 3H, OCH$_3$); 2.98 (s, 3H, CH$_3$); 2.79 (s, 3H, CH$_3$); 1.55 (m, 2H, cyclopropyl); 1.03 (m, 1H, cyclopropyl); 0.63 (m, 1H, cyclopropyl). M/Z (M+H)$^+$=374.3. MP=113-123° C.

Example 206

2-Methoxymethyl-5-methyl-9-(2-ethyl-pyridin-3-yl)-spiro[benzo[f]pyrazolo[1,5-a][1,4]diazepine-6,1'-cyclopropan]-4(5H)-one

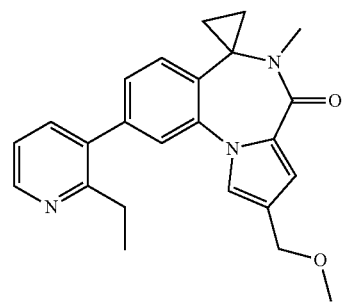 [SMILES: CCc1ncccc1-c1ccc2c(c1)-n1cc(COC)cc1C(=O)N(C)C21CC1]

Example 206 was prepared according to procedure XIV starting from the free base of example 203. Purification by flash column chromatography on silica gel (50% to 100% EtOAc in cyclohexane) afforded the product as a white solid in 39% yield. $^1$H-NMR (400 MHz, DMSO-D6): 8.76 (d, J 5.5 Hz, 1H, Ar); 8.26 (d, J 6.4 Hz, 1H, Ar); 7.77 (dd, J 6.4, 5.5 Hz, 1H, Ar); 7.64 (m, 2H, Ar); 7.53 (d, J 1.6 Hz, 1H, Ar); 7.41 (dd, J 7.8, 1.6 Hz, 1H, Ar); 6.83 (d, J 1.8 Hz, 1H, Ar); 4.34 (s, 2H, CH$_2$); 3.28 (s, 3H, OCH$_3$); 2.94 (s, 3H, CH$_3$); 2.92 (q, J 7.7 Hz, 2H, C$\underline{H_2}$—CH$_3$); 1.51 (m, 2H, cyclopropyl); 1.18 (t, J 7.7 Hz, 3H, CH$_2$—C$\underline{H_3}$); 0.98 (m, 1H, cyclopropyl); 0.60 (m, 1H, cyclopropyl). M/Z (M+H)$^+$=388.3. MP=206-121° C.

Example 207

2-Methoxymethyl-5-methyl-9-(6-fluoro-pyridin-3-yl)-spiro[benzo[f]pyrazolo[1,5-a][1,4]diazepine-6,1'-cyclopropan]-4(5H)-one

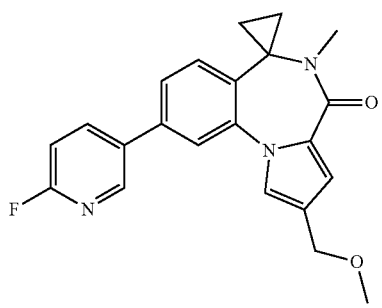

Example 207 was prepared according to procedure XIV starting from example 204. Purification by flash column chromatography on silica gel (50% to 100% EtOAc in cyclohexane) afforded the product as a beige solid in 44% yield. $^1$H-NMR (400 MHz, DMSO-D6): 8.59 (s, 1H, Ar); 8.33 (m, 1H, Ar); 7.77 (s, 1H, Ar); 7.61 (m, 3H, Ar); 7.26 (d, J 8.5 Hz, 1H, Ar); 6.83 (s, 1H, Ar); 4.35 (s, 2H, CH$_2$); 3.27 (s, 3H, CH$_3$); 2.90 (s, 3H, CH$_3$); 1.47 (m, 2H, cyclopropyl;

0.92 (m, 1H, cyclopropyl); 0.54 (m, 1H, cyclopropyl). M/Z (M+H)$^+$=378.3. MP=71-80° C.

Compound 46: 1-(5-Bromo-2-cyano-phenyl)-pyrrolidine-2-carboxylic acid

A mixture of 4-bromo-2-fluorobenzonitrile (1.0 equiv.), I-proline methyl ester hydrochloride (2.0 equiv.), potassium carbonate (2.0 equiv.) in anhydrous DMSO (0.5 mol·L$^{-1}$) was heated at 100° C. for 20 hours. The mixture was poured into an aqueous solution of potassium hydroxide (6 N) and washed twice with Et$_2$O. The aqueous phase was acidified to pH=1-2 with aqueous HCl (6N). The resulting white precipitate was collected by filtration and dried under reduced pressure to afford the product as a white solid in 68% yield. $^1$H-NMR (400 MHz, DMSO-D6): 12.88 (bs, 1H, COOH); 7.45 (d, J 8.3 Hz, 1H, Ar); 6.91 (dd, J 8.3, 1.8 Hz, 1H, Ar); 6.86 (d, J 1.8 Hz, 1H, Ar); 4.75 (m, 1H, CH); 3.69 (m, 1H, CH); 3.63 (m, 1H, CH); 2.30 (m, 1H, CH); 2.07 (m, 1H, CH); 1.96 (m, 2H, 2CH). M/Z (M[$^{79}$Br]+H)$^+$=295.2.

Compound 47: 1-(5-Bromo-2-cyano-phenyl)-pyrrolidine-2-carboxylic acid methyl ester At 0° C., thionyl chloride (2.0 equiv.) was added dropwise to a solution of compound 46 (1.0 equiv.) in anhydrous methanol (0.15 mol·L$^{-1}$). The reaction mixture was stirred at room temperature for 16 hours. MeOH and excess of thionyl chloride were removed under vacuum. The crude mixture was hydrolyzed and extracted twice with CH$_2$Cl$_2$. The combined organic layers were washed with brine, dried over MgSO$_4$ and concentrated under vacuum to afford the product as a thick yellow oil in 93% yield. $^1$H-NMR (400 MHz, DMSO-D6): 7.45 (d, J 8.3 Hz, 1H, Ar); 6.93 (dd, J 8.3, 1.8 Hz, 1H, Ar); 6.91 (d, J 1.8 Hz, 1H, Ar); 4.90 (m, 1H, CH); 3.67 (m, 4H, CH+CH$_3$); 3.59 (m, 1H, CH); 2.32 (m, 1H, CH); 2.10 (m, 1H, CH); 1.99 (m, 1H, CH); 1.90 (m, 1H, CH). M/Z (M[$^{79}$Br]+H)$^+$=309.2.

Compound 48: 9-Bromol-1,2,3,3a-tetrahydro-spiro[benzo[f]pyrrolo[1,2-a][1,4]diazepine-6,1'-cyclopropan]-4(5H)-one Compound 48 was obtained according to general procedure II, starting from compound 47, as a white solid in 42% yield. $^1$H-NMR (400 MHz, DMSO-D6): 8.37 (s, 1H, NH); 6.86 (d, J 8.3 Hz 1H, Ar); 6.62 (dd, J 8.3, 1.8 Hz, 1H, Ar); 6.59 (d, J 1.8 Hz, 1H, Ar); 5.21 (m, 1H, CH); 3.28 (m, 2H, 2CH); 2.37 (m, 1H, CH); 1.90 (m, 3H, 3CH); 1.74 (m, 1H, CH); 1.12 (m, 1H, CH); 1.02 (m, 1H, CH); 0.97 (m, 1H, CH). M/Z (M[$^{79}$Br]+H)$^+$=307.2.

Example 208

9-Bromo-5-methyl-1,2,3,3a-tetrahydro-spiro[benzo[f]pyrrolo[1,2-a][1,4]diazepine-6,1'-cyclopropan]-4(5H)-one

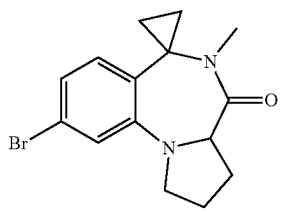 [SMILES: CN1C(=O)C2CCCN2c2cc(Br)ccc2C12CC2]

Example 208 was obtained according to general procedure III, starting from compound 48 in presence of iodomethane. The reaction mixture was stirred at room temperature for 2 hours. Purification by flash column chromatography on silica gel (EtOAc in cyclohexane, 10% to 60%) afforded the product as as a yellow solid in 81% yield. $^1$H-NMR (400 MHz, DMSO-D6): 6.94 (d, J 8.3 Hz 1H, Ar); 6.63 (dd, J 8.3, 1.8 Hz, 1H, Ar); 6.57 (d, J 1.8 Hz, 1H, Ar); 5.44 (m, 1H, CH); 3.26 (m, 2H, 2CH); 2.77 (s, 3H, CH$_3$); 2.38 (m, 1H, CH); 1.92 (m, 3H, 3CH); 1.68 (m, 1H, CH); 1.33 (m, 1H, CH); 1.27 (m, 1H, CH); 1.19 (m, 1H, CH). M/Z (M[$^{79}$Br]+H)$^+$=321.2.

Example 209

5-Methyl-9-(2-methylpyridin-3-yl)-1,2,3,3a-tetrahydro-spiro[benzo[f]pyrrolo[1,2-a][1,4]diazepine-6,1'-cyclopropan]-4(5H)-one

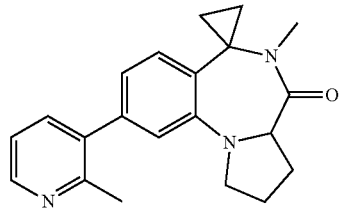 [SMILES: Cc1ncccc1-c1ccc2c(c1)N1CCCC1C(=O)N(C)C21CC1]

Example 209 was obtained according to general procedure VI(ii) starting from example 208 in presence of 2-methylpyridine-3-boronic pinacol ester. Purification by preparative HPLC afforded the product as a green solid in 22% yield. $^1$H-NMR (400 MHz, DMSO-D6): 8.63 (d, J 5.1 Hz, 1H, Ar); 8.07 (d, J 7.2 Hz, 1H, Ar); 7.65 (dd, J 7.2, 5.1 Hz, 1H, Ar); 7.14 (d, J 7.8 Hz, 1H, Ar); 6.56 (dd, J 7.8, 1.6 Hz, 1H, Ar); 6.48 (d, J 1.6 Hz, 1H, Ar); 5.50 (m, 1H, CH); 3.34 (m, 2H, 2CH); 2.82 (s, 3H, CH$_3$); 2.58 (s, 3H, CH$_3$); 2.41 (m, 1H, CH); 1.95 (m, 3H, 3CH); 1.78 (m, 1H, CH); 1.39 (m, 1H, CH); 1.27 (m, 1H, CH); 1.24 (m, 1H, CH). M/Z (M+H)$^+$=334.3.

Compound 49: (4-Bromo-2-fluoro-benzyl)-methyl-amine

A mixture of 4-bromo-2-fluorobenzoic acid (1.0 equiv.), methylamine hydrochloride (1.1 equiv.), benzotriazol-1-yloxytris(dimethylamino)phosphonium hexafluorophosphate (1.1 equiv.) and diisopropylethylamine (3.3 equiv.) in dichloromethane (0.20 mol·L$^{-1}$) was stirred for 2 hours at room temperature. The reaction mixture was hydrolyzed and extracted twice with dichloromethane. The organic layers were combined, washed with brine, dried over MgSO$_4$, concentrated, and purified by flash column chromatography on silica gel (10% to 50% EtOAc in cyclohexane) to afford the intermediate methylamide as a white solid in quantitative yield. The white solid was dissolved in a solution of borane-THF complex (1M, 0.15 mol·L$^{-1}$) and heated at 60° C. for 16 hours. The reaction mixture was neutralized with methanol (gas evolution!) and the solvent was removed under vacuum. The crude mixture was taken in HCl (1N, 0.05 mol·L$^{-1}$) and heated at 100° C. for 1 hour, cooled to 0° C. and basified with NaOH (6N) to pH=12. The milky mixture was extracted twice with EtOAc. The organic layers were combined, washed with brine, dried over MgSO$_4$ and concentrated to afford the product as a pale yellow oil in 46% yield. $^1$H-NMR (400 MHz, DMSO-D6): 7.48 (m, 1H, Ar); 7.40 (m, 2H, Ar); 3.63 (s, 2H, CH$_2$); 2.25 (s, 3H, CH$_3$); Proton for NH not observed. M/Z (M[$^{79}$Br]+H)$^+$=319.2.

Compound 50: [1-(4-Bromo-2-fluoro-phenyl)-ethyl]-methyl-amine

A solution of 4-bromo-2-fluoroacetophenone (1.0 equiv.), methylamine (2M solution in THF, 1.2 equiv.) and titanium isopropoxide (0.6 equiv.) was stirred for 16 hours at room temperature. Sodium borohydride (4.3 equiv.) was slowly added and the reaction mixture was stirred for 2 hours at room temperature. The mixture was treated with ammonia (28% aqueous) and stirred for 1 hour at room temperature before being filtered through celite with ethyl acetate. The filtrate was extracted twice with EtOAc, dried with brine and MgSO$_4$, filtered and concentrated to dryness to afford compound 50 as a yellow oil in 94% yield. $^1$H-NMR (400 MHz, DMSO-D6): 7.48-7.38 (m, 4H, NH+4Ar); 3.83 (q, J 6.2 Hz, 1H, C$\underline{H}$—CH$_3$); 2.11 (s, 3H, N—CH$_3$); 1.21 (d, J 6.2 Hz, 3H, CH—C$\underline{H_3}$). M/Z (M[$^{79}$Br]+H)$^+$=232.

Compound 51: 1-(4-Bromo-2-fluoro-phenyl)-propan-1-one

A solution of 4-bromo-2-fluorobenzoic acid (1.0 equiv.), N,O-dimethylhydroxylamine (1.2 equiv.), HOBt (1.2 equiv.), EDAC (1.2 equiv.) and diisopropylethylamine (4 equiv.) in DMA (0.40 mol·L$^{-1}$) was stirred at room temperature for 16 hours. The reaction mixture was hydrolyzed with aqueous sodium carbonate and extracted twice with EtOAc. The organic layers were combined, washed with brine, dried over MgSO$_4$ and concentrated to dryness to give the Weinreb amide as a thick colorless oil. The amide was dissolved in dichloromethane (0.5 mol·L$^{-1}$) and cooled to 0° C. Ethylmagnesium bromide (1M solution in THF, 1.3 equiv.) was added dropwise and the reaction mixture was stirred at room temperature for 2 hours. The reaction mixture was neutralized with citric acid (0.5 M) and extracted twice with diethyl ether. The organic layers were combined, washed with brine, dried over MgSO$_4$ and concentrated. Purification by flash column chromatography on silica gel (0% to 20% EtOAc in cyclohexane) afforded the product as a colorless oil in 44% yield. $^1$H-NMR (400 MHz, DMSO-D6): 7.77 (t, J 8.3 Hz, 1H, Ar); 7.73 (dd, J 10.7, 1.7 Hz, 1H, Ar); 7.56 (dd, J 8.3, 1.7 Hz, 1H, Ar); 2.96 (q, J 7.2 Hz, 2H, C$\underline{H_2}$—CH$_3$); 1.07 (t, J 7.2 Hz, 3H, CH$_2$—C$\underline{H_3}$). M/Z (M[$^{79}$Br]+H)$^+$=231.

Compound 52: [1-(4-Bromo-2-fluoro-phenyl)-propyl]-methyl-amine

Compound 52 was prepared according to the procedure of compound 50, starting from compound 51. It was isolated as a colorless oil in quantitative yield. $^1$H-NMR (400 MHz, DMSO-D6): 7.45-7.40 (m, 4H, NH+4Ar); 3.66 (t, J 6.7 Hz, 1H, C$\underline{H}$—CH$_2$); 2.09 (s, 3H, N—CH$_3$); 1.60 (m, 2H, CH—C$\underline{H_2}$—CH$_3$); 0.76 (m, 3H, CH$_2$—C$\underline{H_3}$); M/Z (M[$^{79}$Br]+H)$^+$=246.

Compound 53: 1-(4-Chloro-2-fluoro-phenyl)-1-methyl-ethylamine, hydrochloride

Under inert and anhydrous conditions, a mixture of 4-chloro-2-fluorobenzonitrile (1.0 equiv.) and methylmagnesium bromide (3M solution in Et$_2$O, 3.5 equiv.) in THF (0.20 mol·L$^{-1}$) was subjected to microwave irradiation at 100° C. for 10 minutes. Titanium isopropoxide (3.5 equiv.) was added dropwise and the reaction mixture was again subjected to microwave irradiation at 50° C. for 1 hour, then stirred at room temperature overnight. The mixture was treated with brine and extracted twice with dichloromethane. The combined organic extracts were dried over sodium sulfate and filtered through celite with dichloromethane. The filtrate was acidified by addition of HCl (2M solution in Et$_2$O, 2.5 equiv.) and concentrated to dryness. Trituration in Et$_2$O afforded the product as a greenish solid in 60% yield. $^1$H-NMR (400 MHz, DMSO-D6): 8.81 (bs, 3H, NH$_2$+HCl); 7.55 (dd, J 12.4, 2.2 Hz, 1H, Ar); 7.47 (t, J 8.6 Hz, 1H, Ar); 7.40 (dd, J 8.6, 2.2 Hz, 1H, Ar); 1.67 (s, 6H, 2CH$_3$).
M/Z (M[$^{35}$Cl]+H)$^+$=188.

General Procedure XV: Preparation of Intermediate S, S', S", S$_1$, S$_2$, S$_4$ from Benzylamine Q, Q$_1$, Q$_2$, Q$_4$ and Carboxylic Acid R, R', R", R$_1$ (Scheme 6, 7 and 8).

A mixture of benzylamine Q, Q$_1$, Q$_2$ or Q$_4$ (1.0 equiv.), carboxylic acid R, R', R" or R$_1$ (1.0 equiv.), benzotriazol-1-yloxytris(dimethylamino)phosphonium hexafluorophosphate (1.5 equiv.) and diisopropylethylamine (3.0 equiv.) in DMF (0.20 mol·L$^{-1}$) was stirred for 16 hours at room temperature. The reaction mixture was hydrolyzed and extracted twice with EtOAc. The organic layers were combined, washed with brine, dried over MgSO$_4$, concentrated, and purified by flash column chromatography on silica gel (using a gradient of MeOH in dichloromethane as eluent) to afford the product.

Compound 54: 3H-Imidazole-4-carboxylic acid (4-bromo-2-fluoro-benzyl)-methyl-amide Compound 54 was prepared according to procedure XV starting from compound 49 and 4-imidazolecarboxylic acid. It was obtained as a white solid in 51% yield. M/Z (M[$^{79}$Br]+H)$^+$=312.2.

Compound 55: 1H-Imidazole-2-carboxylic acid (4-bromo-2-fluoro-benzyl)-methyl-amide Compound 55 was prepared according to procedure XV starting from compound 49 and 2-imidazolecarboxylic acid. It was obtained as a white solid in 54% yield. M/Z (M[$^{79}$Br]+H)$^+$=312.1.

Compound 56: 2H-Pyrazole-3-carboxylic acid (4-bromo-2-fluoro-benzyl)-methyl-amide Compound 56 was prepared according to procedure XV starting from compound 49 and 3-pyrazolecarboxylic acid. It was obtained as a brown solid in 87% yield. M/Z (M[$^{79}$Br]+H)$^+$=312.1.

Compound 57: 1H-Pyrrole-2-carboxylic acid [1-(4-bromo-2-fluoro-phenyl)-ethyl]-methyl-amide Compound 57 was prepared according to procedure XV starting from compound 50 and pyrrole-2-carboxylic acid. It was obtained as a yellow oil in 50% yield. $^1$H-NMR (400 MHz, DMSO-D6): 11.44 (bs, 1H, NH); 7.51 (m, 1H, Ar); 7.43 (m, 2H, Ar); 6.89 (m, 1H, Ar); 6.51 (m, 1H, Ar); 6.11 (m, 1H, Ar); 5.92 (q, J 7.0 Hz, 1H, C$\underline{H}$—CH$_3$); 2.89 (s, 3H, N—CH$_3$); 1.52 (d, J 7.0 Hz, 3H, CH—C$\underline{H_3}$). M/Z (M[$^{79}$Br]+H)$^+$=325.

Compound 58: 1H-Pyrrole-2-carboxylic acid [1-(4-bromo-2-fluoro-phenyl)-propyl]-methyl-amide Compound 58 was prepared according to procedure XV starting from compound 52 and pyrrole-2-carboxylic acid. It was obtained as a beige solid in 29% yield. $^1$H-NMR (400 MHz, DMSO-D6): 11.44 (bs, 1H, NH); 7.53-7.42 (m, 3H, Ar); 6.89 (m, 1H, Ar); 6.52 (m, 1H, Ar); 6.11 (m, 1H, Ar); 5.77 (t, J 7.7 Hz, 1H, C$\underline{H}$—CH$_2$); 2.94 (s, 3H, N—CH$_3$); 1.99 (m, 2H, CH—C$\underline{H_2}$—CH$_3$); 0.89 (t, J 7.2 Hz, 3H, CH$_2$—C$\underline{H_3}$). M/Z (M[$^{79}$Br]+H)$^+$=339.

Compound 59: 1H-Pyrrole-2-carboxylic acid [1-(2-fluoro-phenyl)-1-methyl-ethyl]-amide Compound 59 was prepared according to procedure XV starting from 2-(2-fluorophenyl)propan-2-amine and pyrrole-2-carboxylic acid. It was obtained as a white solid in 62% yield. $^1$H-NMR (400 MHz, DMSO-D6): 11.26 (bs, 1H, NH); 7.90 (s, 1H, NH); 7.35 (m, 1H, Ar); 7.23 (m, 1H, Ar); 7.08 (m, 2H, Ar); 6.88 (m, 1H, Ar); 6.83 (m, 1H, Ar); 6.07 (m, 1H, Ar); 1.72 (s, 6H, 2CH$_3$). M/Z (M+H)$^+$=247.3.

Compound 60: 1H-Pyrrole-2-carboxylic acid [1-(4-chloro-2-fluoro-phenyl)-1-methyl-ethyl]-amide Compound 60 was prepared according to procedure XV starting from compound 53 and pyrrole-2-carboxylic acid. It was obtained as a yellow solid in 32% yield. $^1$H-NMR (400 MHz, DMSO-D6): 11.26 (bs, 1H, NH); 7.97 (s, 1H, NH); 7.37 (t, J 8.5 Hz, 1H, Ar); 7.27 (dd, J 12.2, 2.2 Hz, 1H, Ar); 7.20 (dd, J 8.5, 2.2 Hz, 1H, Ar); 6.88 (m, 1H, Ar); 6.83 (m, 1H, Ar); 6.07 (m, 1H, Ar); 1.69 (s, 6H, 2CH$_3$). M/Z (M[$^{35}$Cl]+H)$^+$=281.

General Procedure XVI: Preparation of Benzodiazepinone T, T', T'', T$_1$, T$_2$, T$_3$ and T$_4$ from Intermediate S, S', S'', S$_1$, S$_2$, S$_3$ and S$_4$ (Scheme 6, 7 and 8).

Method (i):

A mixture of intermediate S, S' or S'' (1.0 equiv.) and potassium carbonate (3.0 equiv.) in DMA (0.20 mol·L$^{-1}$) was heated at 170° C. for 16 hours. The reaction mixture was hydrolyzed and extracted twice with EtOAc. The organic layers were combined, washed with brine, dried over MgSO$_4$ and concentrated to afford the product. No purification, otherwise specified.

Method (ii):

At room temperature, sodium hydride (1.2 equiv.) was added to a solution of compound S$_1$, S$_2$ or S$_3$ in dry DMA (0.15 mol·L$^{-1}$). After 10 minutes stirring, the reaction mixture was heated at 100° C. for 2 hours before being hydrolyzed and extracted twice with EtOAc. The organic layers were combined, washed with brine, dried over MgSO$_4$, concentrated, and purified to afford the product.

Example 210

5-Methyl-9-bromo-5,6-dihydro-4H-benzo[f]imidazo[1,5-a][1,4]diazepin-4-one

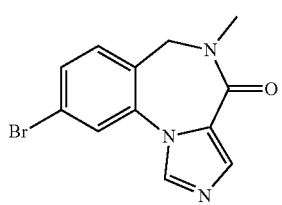 [SMILES: CN1Cc2ccc(Br)cc2-n2cncc2C1=O]

Example 210 was prepared according to procedure XVI(i) starting from compound 54. It was obtained as a white solid in 71% yield and taken to the next step without purification. $^1$H-NMR (400 MHz, DMSO-D6): 8.45 (s, 1H, Ar); 8.00 (d, J 1.7 Hz, 1H, Ar); 7.67 (dd, J 7.9, 1.7 Hz, 1H, Ar); 7.62 (m, 2H, Ar); 4.37 (s, 2H, CH$_2$); 3.06 (s, 3H, CH$_3$). M/Z (M[$^{79}$Br]+H)$^+$=292.2.

Example 211

5-Methyl-9-bromo-5,6-dihydro-4H-benzo[f]imidazo[1,2-a][1,4]diazepin-4-one

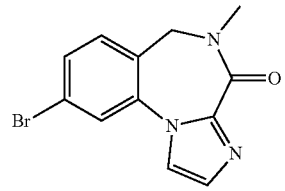 [SMILES: CN1Cc2ccc(Br)cc2-n2ccnc2C1=O]

Example 211 was prepared according to procedure XVI(i) starting from compound 55. It was obtained as a yellow solid in 55% yield and taken to the next step without purification. $^1$H-NMR (400 MHz, DMSO-D6): 7.83 (d, J 1.3 Hz, 1H, Ar); 7.80 (d, J 1.6 Hz, 1H, Ar); 7.55 (dd, J 7.9, 1.6 Hz, 1H, Ar); 7.51 (d, J 7.9 Hz, 1H, Ar); 7.18 (d, J 1.3 Hz, 1H, Ar); 4.26 (s, 2H, CH$_2$); 2.95 (s, 3H, CH$_3$). M/Z (M[$^{79}$Br]+H)$^+$=292.2.

Example 212

5-Methyl-9-bromo-5,6-dihydro-4H-benzo[f]pyrazolo[1,5-a][1,4]diazepin-4-one

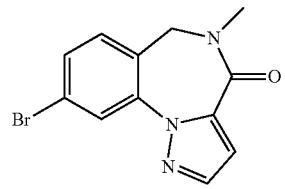 [SMILES: CN1Cc2ccc(Br)cc2-n2nccc2C1=O]

Example 212 was prepared according to procedure XVI(i) starting from compound 56. Purification by flash column chromatography on silica gel (MeOH in dichloromethane, 0% to 4%) afforded the product as a white solid in 73% yield. $^1$H-NMR (400 MHz, DMSO-D6): 7.96 (m, 2H, Ar); 7.71 (dd, J 7.8, 1.7 Hz, 1H, Ar); 7.67 (d, J 7.8 Hz, 1H, Ar); 7.09 (d, J 1.9 Hz, 1H, Ar); 4.48 (s, 2H, CH$_2$); 3.16 (s, 3H, CH$_3$). M/Z (M[$^{79}$Br]+H)$^+$=292.2.

Example 213

9-Bromo-5,6-dimethyl-5,6-dihydro-benzo[f]pyrrolo[1,2-a][1,4]diazepin-4-one

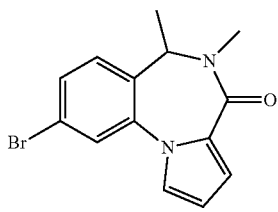 [SMILES: CC1c2ccc(Br)cc2-n2cccc2C(=O)N1C]

Example 213 was prepared according to procedure XVI (ii) starting from compound 57. Purification by flash column chromatography on silica gel (0% to 50% EtOAc in cyclohexane) afforded the product as a beige solid in 85% yield. $^1$H-NMR (400 MHz, DMSO-D6): 7.76 (d, J 1.7 Hz, 1H, Ar); 7.53 (m, 2H, Ar); 7.47 (d, J 8.0 Hz, 1H, Ar); 6.85 (dd, J 3.8, 1.8 Hz, 1H, Ar); 6.39 (dd, J 3.8, 2.8 Hz, 1H, Ar); 4.69 (q, J 7.2 Hz, 1H, C$\underline{H}$—CH$_3$); 3.10 (s, 3H, N—CH$_3$); 1.05 (d, J 7.2 Hz, 3H, CH—C$\underline{H_3}$). M/Z (M[$^{79}$Br]+H)$^+$=305.

Example 214

9-Bromo-5-methyl-6-ethyl-5,6-dihydro-benzo[f]pyrrolo[1,2-a][1,4]diazepin-4-one

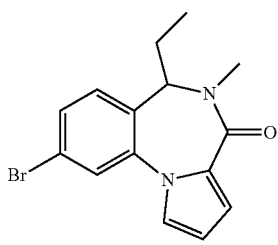 [SMILES: CCC1c2ccc(Br)cc2-n2cccc2C(=O)N1C]

Example 214 was prepared according to procedure XVI (ii) starting from compound 58. Purification by flash column chromatography on silica gel (0% to 50% EtOAc in cyclohexane) afforded the product as a colorless oil in 63% yield. $^1$H-NMR (400 MHz, DMSO-D6): 7.75 (d, J 1.8 Hz, 1H, Ar); 7.53 (m, 2H, Ar); 7.46 (d, J 8.0 Hz, 1H, Ar); 6.84 (dd, J 3.8, 1.8 Hz, 1H, Ar); 6.37 (dd, J 3.8, 2.8 Hz, 1H, Ar); 4.43 (t, J 8.0 Hz, 1H, C$\underline{H}$—CH$_2$); 3.12 (s, 3H, N—CH$_3$); 1.30 (m, 2H, CH—C$\underline{H_2}$—CH$_3$); 0.70 (t, J 7.4 Hz, 3H, CH$_2$—C$\underline{H_3}$). M/Z (M[$^{79}$Br]+H)$^+$=319.

Example 215

5-Methyl-9-(2-methylpyridin-3-yl)-5,6-dihydro-4H-benzo[f]imidazo[1,5-a][1,4]diazepin-4-one, hydrochloride

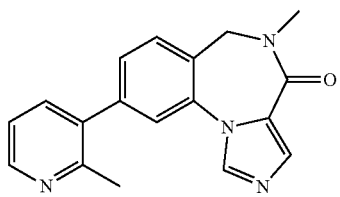 [SMILES: Cc1ncccc1-c1ccc2c(c1)-n1cncc1C(=O)N(C)C2]

Example 215 was prepared according to general procedure VI(i) starting from example 210 in presence of 2-methylpyridine-3-boronic acid pinacol ester. Purification by flash column chromatography on silica gel (MeOH in dichloromethane, 0% to 10%) afforded the product as a brown solid in 69% yield. Salt formation was performed by method VII(ii). $^1$H-NMR (400 MHz, DMSO-D6): 8.88 (s, 1H, Ar); 8.82 (d, J 5.4 Hz, 1H, Ar); 8.45 (d, J 7.6 Hz, 1H, Ar); 7.92 (m, 3H, Ar); 7.87 (d, J 7.8 Hz, 1H, Ar); 7.66 (dd, J 7.8, 1.6 Hz, 1H, Ar); 4.53 (s, 2H, CH$_2$); 3.12 (s, 3H, CH$_3$); 2.73 (s, 3H, CH$_3$). Proton for HCl salt not observed. M/Z (M+H)$^+$=305.2. MP=158-170° C.

Example 216

5-Methyl-9-(2-methylpyridin-3-yl)-5,6-dihydro-4H-benzo[f]imidazo[1,2-a][1,4]diazepin-4-one, hydrochloride

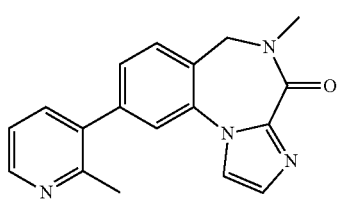 [SMILES: Cc1ncccc1-c1ccc2c(c1)-n1ccnc1C(=O)N(C)C2]

Example 216 was prepared according to general procedure VI(i) starting from example 211 in presence of 2-methylpyridine-3-boronic acid pinacol ester. Purification by flash column chromatography on silica gel (MeOH in dichloromethane, 0% to 4%) afforded the product as a brown solid in 43% yield. Salt formation was performed by method VII(ii). $^1$H-NMR (400 MHz, DMSO-D6): 8.84 (d, J 5.4 Hz, 1H, Ar); 8.51 (d, J 7.5 Hz, 1H, Ar); 8.26 (s, 1H, Ar); 7.99 (dd, J 7.5, 5.4 Hz, 1H, Ar); 7.95 (d, J 1.4 Hz, 1H, Ar); 7.92 (d, J 7.8 Hz, 1H, Ar); 7.77 (s, 1H, Ar); 7.72 (d, J 7.8, 1.4 Hz, 1H, Ar); 4.66 (s, 2H, CH$_2$); 3.18 (s, 3H, CH$_3$); 2.75 (s, 3H, CH$_3$). Proton for HCl salt not observed. M/Z (M+H)$^+$=305.3. MP=210-230° C.

Example 217

5-Methyl-9-(2-methylpyridin-3-yl)-5,6-dihydro-4H-benzo[f]pyrazolo[1,5-a][1,4]diazepin-4-one, hydrochloride

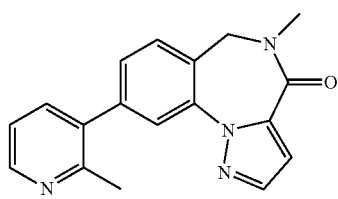 [SMILES: Cc1ncccc1-c1ccc2c(c1)-n1nccc1C(=O)N(C)C2]

Example 217 was prepared according to general procedure VI(i) starting from example 212 in presence of 2-methylpyridine-3-boronic acid pinacol ester. It was purified by preparative HPLC to afford the product as a yellow solid in 32% yield. Salt formation was performed by method VII(i). $^1$H-NMR (400 MHz, DMSO-D6): 8.77 (d, J 4.2 Hz, 1H, Ar); 8.35 (d, J 6.8 Hz, 1H, Ar); 7.90-7.81 (m, 4H, Ar); 7.57 (d, J 7.4 Hz, 1H, Ar); 7.05 (s, 1H, Ar); 4.53 (s, 2H, CH$_2$); 3.15 (s, 3H, CH$_3$); 2.66 (s, 3H, CH$_3$). Proton for HCl salt not observed. M/Z (M+H)$^+$=305.3. MP=120-140° C.

Example 218

5,6-Dimethyl-9-(2-methyl-pyridin-3-yl)-5,6-dihydro-benzo[f]pyrrolo[1,2-a][1,4]diazepin-4-one, hydrochloride

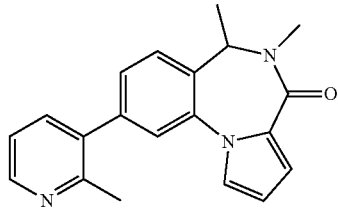 [SMILES: Cc1ncccc1-c1ccc2c(c1)-n1cccc1C(=O)N(C)C2C]

Example 218 was prepared according to general procedure VI(i) starting from example 213 in presence of 2-methylpyridine-3-boronic acid pinacol ester. Purification by flash column chromatography on silica gel (0% to 4% MeOH in dichloromethane) afforded example 218 as a white solid in 84% yield. Salt formation was performed by method VII(i). $^1$H-NMR (400 MHz, DMSO-D6): 8.79 (d, J 5.6 Hz, 1H, Ar); 8.47 (d, J 7.8 Hz, 1H, Ar); 7.93 (dd, J 7.8, 5.6 Hz, 1H, Ar); 7.68 (m, 2H, Ar); 7.55 (dd, J 2.8, 1.8 Hz, 1H, Ar); 7.48 (dd, J 7.9, 1.3 Hz, 1H, Ar); 6.87 (dd, J 3.8, 1.8 Hz, 1H, Ar); 6.42 (dd, J 3.8, 2.8 Hz, 1H, Ar); 4.79 (q, J 7.2 Hz, 1H, C$\underline{H}$—CH$_3$); 2.72 (s, 3H, N—CH$_3$); 1.12 (d, J 7.2 Hz, 3H, CH—C$\underline{H}_3$); Proton for HCl salt not observed. M/Z (M+H)$^+$=318.3. MP=140-156° C.

Example 219

9-(6-Dimethylamino-pyridin-3-yl)-5,6-dimethyl-5,6-dihydro-benzo[f]pyrrolo[1,2-a][1,4]diazepin-4-one, hydrochloride

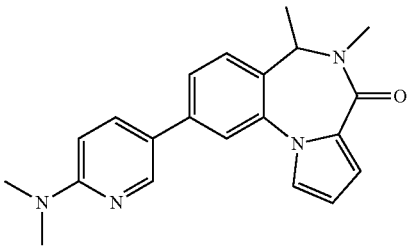 [SMILES: CC1c2ccc(-c3ccc(N(C)C)nc3)cc2-n2cccc2C(=O)N1C]

Example 219 was prepared according to general procedure VI(i) starting from example 213 in presence of 6-fluoropyridine-3-boronic acid and DMF as solvent. Purification by flash column chromatography on silica gel (0% to 10% MeOH in dichloromethane) afforded example 219 as a white solid in 62% yield. Salt formation was performed by method VII(i). $^1$H-NMR (400 MHz, DMSO-D6): 8.39 (m, 2H, Ar); 7.80 (dd, J 5.6, 1.4 Hz, 1H, Ar); 7.71 (dd, J 2.8, 1.8 Hz, 1H, Ar); 7.65 (dd, J 7.8, 1.6 Hz, 1H, Ar); 7.61 (d, J 7.8 Hz, 1H, Ar); 7.28 (d, J 9.1 Hz, 1H, Ar); 6.86 (dd, J 3.8, 1.8 Hz, 1H, Ar); 6.43 (dd, J 3.8, 2.8 Hz, 1H, Ar); 4.73 (q, J 7.3 Hz, 1H, C$\underline{H}$—CH$_3$); 3.26 (s, 6H, N—(CH$_3$)$_2$); 3.13 (s, 3H, N—CH$_3$); 1.09 (d, J 7.3 Hz, 3H, CH—C$\underline{H}_3$); Proton for HCl salt not observed. M/Z (M+H)$^+$=347.3. MP=145-162° C.

Example 220

6-Ethyl-5-methyl-9-(2-methyl-pyridin-3-yl)-5,6-dihydro-benzo[f]pyrrolo[1,2-a][1,4]diazepin-4-one, hydrochloride

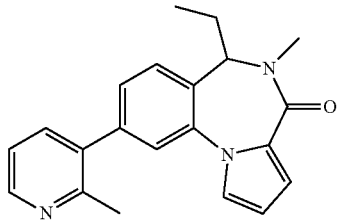 [SMILES: CCC1c2ccc(-c3cccnc3C)cc2-n2cccc2C(=O)N1C]

Example 220 was prepared according to general procedure VI(i) starting from example 214 in presence of 2-methylpyridine-3-boronic acid pinacol ester. Purification by flash column chromatography on silica gel (30% to 100% EtOAc in cyclohexane) afforded example 220 as a beige solid in 35% yield. Salt formation was performed by method VII(i). $^1$H-NMR (400 MHz, DMSO-D6): 8.78 (d, J 5.6 Hz, 1H, Ar); 8.44 (d, J 7.8 Hz, 1H, Ar); 7.90 (dd, J 7.8, 5.6 Hz, 1H, Ar); 7.67 (m, 2H, Ar); 7.53 (dd, J 2.8, 1.8 Hz, 1H, Ar); 7.48 (dd, J 7.8, 1.4 Hz, 1H, Ar); 6.86 (dd, J 3.8, 1.8 Hz, 1H, Ar); 6.40 (dd, J 3.8, 2.8 Hz, 1H, Ar); 4.53 (t, J 8.0 Hz, 1H, C$\underline{H}$—CH$_2$); 3.17 (s, 3H, N—CH$_3$); 2.70 (s, 3H, CH$_3$); 1.40 (m, 2H, CH—C$\underline{H}_2$—CH$_3$); 0.77 (t, J 7.4 Hz, 3H, CH$_2$—C$\underline{H}_3$); Proton for HCl salt not observed. M/Z (M+H)$^+$=332.3. MP=160-170° C.

Compound 61: 6,6-dimethyl-5,6-dihydro-benzo[f] pyrrolo[1,2-a][1,4]diazepin-4-one A suspension of compound 59 (1.0 equiv.) and potassium carbonate (3.0 equiv.) in DMA (0.20 mol·L$^{-1}$) was heated at 180° C. for 36 hours. As the reaction was not complete, the mixture was subjected to microwave irradiation at 220° C. for 1 hour, before being hydrolyzed and extracted twice with EtOAc. The organic layers were combined, washed with brine, dried over MgSO$_4$, concentrated, and purified by flash column chromatography on silica gel (50% to 90% EtOAc in cyclohexane) to afford the product as a brown solid in 58% yield. $^1$H-NMR (400 MHz, DMSO-D6): 8.10 (s, 1H, NH); 7.52-7.43 (m, 4H, Ar); 7.36 (m, 1H, Ar); 6.85 (dd, J 3.8, 1.9 Hz, 1H, Ar); 6.40 (dd, J 3.8, 2.8 Hz, 1H, Ar); 1.39 (bs, 6H, 2CH$_3$). M/Z (M[$^{35}$Cl]+H)$^+$=227.3.

Compound 62: 9-Chloro-6,6-dimethyl-5,6-dihydro-benzo[f]pyrrolo[1,2-a][1,4]diazepin-4-one A suspension of compound 60 (1.0 equiv.) and potassium carbonate (3.0 equiv.) in DMA (0.20 mol·L$^{-1}$) was subjected to microwave irradiation at 220° C. for 1 hour. The mixture was hydrolyzed and extracted twice with EtOAc. The organic layers were combined, washed with brine, dried over MgSO$_4$, concentrated, and purified by flash column chromatography on silica gel (0% to 90% EtOAc in cyclohexane) to afford the product as a brown solid in 49% yield. $^1$H-NMR (400 MHz, DMSO-D6): 8.16 (s, 1H, NH); 7.59 (d, J 2.2 Hz, 1H, Ar); 7.56 (dd, J 2.8, 1.8 Hz, 1H, Ar); 7.52 (d, J 8.6 Hz, 1H, Ar); 7.42 (dd, J 8.6, 2.2 Hz, 1H, Ar); 6.87 (dd, J 3.8, 1.8 Hz, 1H, Ar); 6.42 (dd, J 3.8, 2.8 Hz, 1H, Ar); 1.37 (bs, 6H, 2CH$_3$). M/Z (M[$^{35}$Cl]+H)$^+$=261.

Example 221

5,6,6-Trimethyl-5,6-dihydro-benzo[f]pyrrolo[1,2-a][1,4]diazepin-4-one

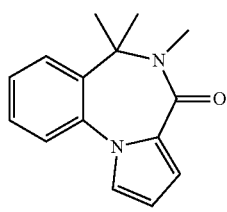 [SMILES: CN1C(=O)c2cccn2-c2ccccc2C1(C)C]

Example 221 was obtained according to general procedure III, starting from compound 61 in presence of iodomethane. The reaction mixture was stirred at room temperature for 2 hours. Purification by flash column chromatography on silica gel (0% to 100% EtOAc in cyclohexane) afforded the product as a yellow solid in 86% yield. $^1$H-NMR (400 MHz, DMSO-D6): 7.60 (dd, J 7.9, 1.3 Hz, 1H, Ar); 7.50 (m, 2H, Ar); 7.43 (dd, J 2.8, 1.8 Hz, 1H, Ar); 7.38 (m, 1H, Ar); 6.80 (dd, J 3.8, 1.8 Hz, 1H, Ar); 6.40 (dd, J 3.8, 2.8 Hz, 1H, Ar); 3.02 (s, 3H, CH$_3$); 1.92 (s, 3H, CH$_3$); 1.09 (s, 3H, CH$_3$). M/Z (M+H)$^+$=241.1. MP=127-130° C.

Example 222

9-Chloro-5,6,6-trimethyl-5,6-dihydro-benzo[f]pyrrolo[1,2-a][1,4]diazepin-4-one

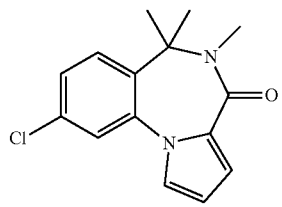 [SMILES: CN1C(=O)c2cccn2-c2cc(Cl)ccc2C1(C)C]

Example 222 was obtained according to general procedure III, starting from compound 62 in presence of iodomethane. The reaction mixture was stirred at room temperature for 2 hours. Purification by flash column chromatography on silica gel (0% to 100% EtOAc in cyclohexane) afforded the product as a yellow solid in 72% yield. $^1$H-NMR (400 MHz, DMSO-D6): 7.63 (d, J 2.2 Hz, 1H, Ar); 7.60 (d, J 8.5 Hz, 1H, Ar); 7.53 (dd, J 2.8, 1.8 Hz, 1H, Ar); 7.44 (dd, J 8.5, 2.2 Hz, 1H, Ar); 6.82 (dd, J 3.8, 1.8 Hz, 1H, Ar); 6.42 (dd, J 3.8, 2.8 Hz, 1H, Ar); 3.01 (s, 3H, CH$_3$); 1.90 (s, 3H, CH$_3$); 1.08 (s, 3H, CH$_3$). M/Z (M[$^{35}$Cl]+H)$^+$=275.

Example 223

5,6,6-Trimethyl-9-(2-methyl-pyridin-3-yl)-5,6-dihydro-benzo[f]pyrrolo[1,2-a][1,4]diazepin-4-one, hydrochloride

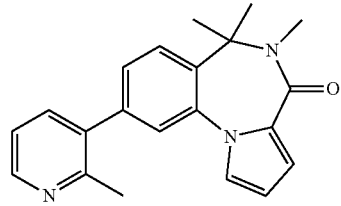 [SMILES: Cc1ncccc1-c1ccc2c(c1)-n1cccc1C(=O)N(C)C2(C)C]

Under inert atmosphere, XPhos precatalyst (0.05 equiv.) was added to a mixture of example 222 (1.0 equiv.), 2-methylpyridine-3-boronic acid pinacol ester (2.0 equiv.) and tripotassium phosphate (2.0 equiv.) in dioxane (0.17 mol·L$^{-1}$) and water (1.0 mol·L$^{-1}$). The reaction mixture was heated at 80° C. for 2 hours. After cooling, the reaction mixture was hydrolysed and the resulting precipitate was collected by filtration, washed with water and dried by succion. Purification by preparative HPLC afforded the product as a white solid in 45% yield. Salt formation was performed according to method VII(i). $^1$H-NMR (400 MHz, DMSO-D6): 8.82 (d, J 5.6 Hz, 1H, Ar); 8.43 (d, J 7.5 Hz, 1H, Ar); 7.90 (dd, J 7.5, 5.6 Hz, 1H, Ar); 7.80 (d, J 8.2 Hz, 1H, Ar); 7.71 (d, J 1.6 Hz, 1H, Ar); 7.58 (m, 2H, Ar); 6.90 (dd, J 3.8, 1.8 Hz, 1H, Ar); 6.49 (dd, J 3.8, 2.8 Hz, 1H, Ar); 3.12 (s, 3H, CH$_3$); 2.74 (s, 3H, CH$_3$); 2.04 (s, 3H, CH$_3$); 1.20 (s, 3H, CH$_3$). M/Z (M+H)$^+$=332.1. MP=230-250° C.

Example 224

Human mGluR3 Positive Allosteric Modulator Evaluation Using Ca++ Functional Assay Compounds of the present invention were tested successively for their agonist and positive allosteric modulator activities on human mGluR3 (hmGluR3) transiently overexpressed in HEK-293 cells. Compounds exert agonist activity if they are able to activate hmGluR3 by themselves, i.e., in absence of the endogenous agonist glutamate; and they exert positive allosteric modulator activity if they increase the action of the endogenous agonist glutamate.

Cell Culture and Transfection:

HEK-293 cells were maintained in Modified Eagle's Medium supplemented with 10% Foetal Calf Serum, 1% Penicillin/Streptomycin and 1% non-essential amino acids at 37° C./5% $CO_2$.

Cells were co-transfected by electroporation with four DNA plasmids encoding hmGluR3, a chimeric G protein allowing redirection of the activation signal toward intracellular calcium pathway, and two glutamate transporters so as to decrease extracellular glutamate levels and avoid receptor desensitization (Brabet I et al., Neuropharmacology 37(8), 1043-51, 1998). After transfection, cells were seeded in 75 cm² culture flasks, and cultured for 24 h.

Calcium Assay EC50 Determination:

Receptor activity was detected by changes in intracellular calcium measured using the fluorescent $Ca^{2+}$ sensitive dye, Fluo4AM (Molecular Probes).

The day of the assay, medium was aspirated and replaced during 3 hrs by freshly prepared buffer B (HBSS 1×, Hepes 20 mM, $MgSO_4$-$7H_2O$ 1 mM, $Na_2CO_3$ 3.3 mM, $CaCl_2$-$2H_2O$ 1.3 mM, 0.5% BSA, Probenecid 2.5 mM). Then, cells were loaded at 37° C./5% $CO_2$ for 1.5 hrs with buffer B containing 1 µM Fluo4AM, 0.1 mg/mL Pluronic Acid, 7 µg/mL Glutamate Pyruvate Transaminase and 2 mM sodium pyruvate. Afterwards cells were washed with buffer B. Cells were then detached from the 75 cm² culture flasks with Accutase® (5 min incubation at 37° C.), centrifuged (5 min at 840 rpm), resuspended in buffer B and finally seeded at a density of 30,000 cells/well in black-walled clear-bottom 384-well plates. Addition of compounds on cells and intracellular $Ca^{2+}$ measurements (excitation 485 nm, emission 525 nm) were performed by the fluorescence microplate reader FLIPR Tetra (Molecular Devices).

Agonist and positive allosteric modulator activities of compounds were consecutively evaluated on the same cells plate. Agonist activity was first tested during 10 min with the addition of compound alone on the cells. Then, the cells were stimulated by an EC50 glutamate concentration and fluorescence was recorded for additional 3 min. EC50 glutamate concentration is the concentration giving 50% of the maximal glutamate response. Agonist and/or positive allosteric modulator activity(ies) were evaluated in comparison to basal signal or signal evoked by EC50 glutamate concentration alone, respectively.

For potency determination, a dose-response test was performed using 20 concentrations of each compound of the invention. Dose-response curves were fitted using the sigmoïdal dose-response (variable slope) analysis in XLfit Scientific Curve Fitting for Excel (IDBS). EC50 of agonist/EC50 of positive allosteric modulator activity(ies) were calculated. Dose-response experiments were all performed in duplicate, two times independently.

The compounds of the present invention were found to have no agonist activity on hmGluR3. The EC50 of the hmGluR3 positive allosteric modulator compounds of the present invention are preferably 1 µM or less, more preferably 0.1 µM or less.

The following list represents selected examples of the compounds of the present invention showing mGluR3 positive allosteric modulator activity with an EC50>1.0 µM:

Examples: 5, 6, 7, 9, 11, 13, 16, 21, 27, 28, 37, 40, 43, 46, 49, 51, 53, 58, 59, 65, 66, 68, 71, 72, 86, 87, 88, 89, 90, 91, 92, 100, 115, 119, 120, 123, 124, 131, 135, 137, 138, 139, 167, 189, 200, 209, 214, 215, 216, 217, 221 and 222.

The following list represents selected examples of the compounds of the present invention showing mGluR3 positive allosteric modulator activity with 0.1 µM<EC50<1.0 µM:

Examples: 1, 17, 19, 20, 22, 23, 24, 26, 29, 30, 33, 34, 35, 36, 38, 39, 42, 45, 47, 48, 50, 52, 57, 60, 62, 67, 69, 75, 77, 78, 84, 96, 97, 98, 99, 101, 104, 105, 108, 109, 113, 116, 117, 121, 122, 128, 129, 130, 132, 134, 136, 141, 142, 147, 148, 149, 150, 153, 154, 156, 165, 166, 176, 193, 194, 195, 196, 203, 218, 220 and 223.

The following list represents selected examples of the compounds of the present invention showing mGluR3 positive allosteric modulator activity with an EC50<0.1 µM:

Examples: 18, 25, 31, 32, 41, 44, 54, 55, 56, 61, 63, 64, 73, 74, 76, 81, 82, 83, 93, 94, 95, 102, 103, 106, 107, 110, 111, 112, 114, 118, 125, 126, 127, 133, 140, 143, 144, 145, 146, 151, 152, 155, 157, 158, 159, 160, 161, 162, 163, 182, 183, 184, 185, 186, 187, 188, 190, 191, 192, 197, 198, 199, 201, 202, 205, 206, 207 and 219.

Example 225

Neuroprotection of Example 207 on Cortical Primary Neurons

Primary mouse neurons were incubated with vehicle or NMDA (60 µM)+vehicle or example 207 or LY379268 (mixed mGluR2/3 agonist used as positive control) for 24 hours. Tests were performed in triplicate. Neuron viability was measured using a MTT test.

Results:

In FIG. 1, it can be observed that NMDA treatment induced a close to 50% reduction of the neuron viability (black histograms). Example 207 alone, in absence of NMDA challenge, has no toxicity on cortical primary neuron viability at concentrations ranging from 30 nM to 30 µM (hashed histograms). Example 207 reduces in a dose-dependent manner the toxicity induced by NMDA up to 1 µM, this effect tending to disappear at higher concentrations (white histograms). Reference LY379268 (mGluR2/3 agonist) has no toxicity alone and decreases NMDA-induced toxicity at 1 µM (grey histograms).

Example 226

Neuroprotection of Example 63 on Striatal Primary Neurons

Primary mouse neurons were incubated with vehicle or NMDA (60 µM)+vehicle or example 63 or LY379268 (mixed mGluR2/3 agonist used as positive control) for 24 hours. Tests were performed in triplicate. Neuron viability was measured using a MTT test.

Results:

In FIG. 2, it can be observed that NMDA treatment induced a close to 70% reduction of the neuron viability (black histograms). Example 63 alone, in absence of NMDA challenge, has no toxicity on striatal primary neuron viability at concentrations ranging from 30 nM to 30 µM (hashed histograms). Example 63 reduces in a dose-dependent manner the toxicity induced by NMDA up to 10 µM, this effect tending to disappear at 30 µM (white histograms). Reference LY379268 (mGluR2/3 agonist) has no toxicity alone and decreases NMDA-induced toxicity at 1 µM (grey histograms).

The invention claimed is:
1. A compound of the general formula (I):

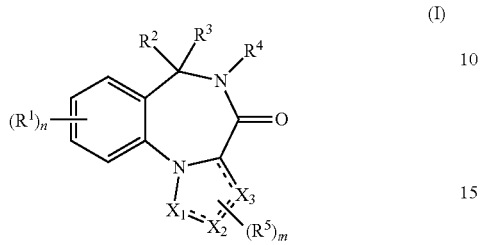

wherein:
- $X_1$, $X_2$ and $X_3$ are each independently C or N;
- each ===== is independently a single bond or a double bond, wherein at least one of any two adjacent bonds ===== is a single bond;
- each $R^1$ is independently a group $-L^1-R^{11}$;
- each $L^1$ is a bond;
- each $R^{11}$ is independently selected from the group consisting of: phenyl, imidazo[1,2-a]pyridinyl, and heteroaryl having 5 to 6 ring members, wherein 1, 2 or 3 ring members are heteroatoms selected independently from O, S and N, and the remaining ring members are carbon atoms; wherein said phenyl, said imidazo[1,2-a]pyridinyl and said heteroaryl are each optionally substituted with one or more groups independently selected from the group consisting of halogen, $C_1$-$C_{10}$ haloalkyl, —CN, $C_1$-$C_{10}$ alkyl, $C_2$-$C_{10}$ alkenyl, $C_2$-$C_{10}$ alkynyl, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), —CHO, —CO($C_1$-$C_{10}$ alkyl), —COOH, tetrazolyl, —COO($C_1$-$C_{10}$ alkyl), —OCO($C_1$-$C_{10}$ alkyl), —CO—$NH_2$, —CO—NH($C_1$-$C_{10}$ alkyl), —CO—N($C_1$-$C_{10}$ alkyl)($C_1$-$C_{10}$ alkyl), —NH—CO—($C_1$-$C_{10}$ alkyl), —N($C_1$-$C_{10}$ alkyl)-CO—($C_1$-$C_{10}$ alkyl), —$SO_2$—$NH_2$, —$SO_2$—NH($C_1$-$C_{10}$ alkyl), —$SO_2$—N($C_1$-$C_{10}$ alkyl)($C_1$-$C_{10}$ alkyl), —NH—$SO_2$—($C_1$-$C_{10}$ alkyl), —N($C_1$-$C_{10}$ alkyl)-$SO_2$—($C_1$-$C_{10}$ alkyl), cycloalkyl, heterocycloalkyl, aryl, heteroaryl having 5 to 6 ring members, wherein 1, 2 or 3 ring members are heteroatoms selected independently from O, S and N, and the remaining ring members are carbon atoms, and $-L^{11}-R^{13}$;
- each $L^{11}$ is independently selected from the group consisting of a bond, $C_1$-$C_{10}$ alkylene, $C_2$-$C_{10}$ alkenylene, and $C_2$-$C_{10}$ alkynylene, wherein one or more —$CH_2$— units comprised in said alkylene, said alkenylene or said alkynylene are each optionally replaced by a group independently selected from the group consisting of —O—, —NH—, —N($C_1$-$C_{10}$ alkyl)-, —CO—, —S—, —SO—, and —$SO_2$—;
- each $R^{13}$ is independently selected from the group consisting of aryl, heteroaryl having 5 to 6 ring members, wherein 1, 2 or 3 ring members are heteroatoms selected independently from O, S and N, and the remaining ring members are carbon atoms, cycloalkyl, heterocycloalkyl, cycloalkenyl, heterocycloalkenyl, halogen, $C_1$-$C_{10}$ haloalkyl, —CN, $C_1$-$C_{10}$ alkyl, $C_2$-$C_{10}$ alkenyl, $C_2$-$C_{10}$ alkynyl, —$NH_2$, —NH($C_1$-$C_{10}$ alkyl), —N($C_1$-$C_{10}$ alkyl)($C_1$-$C_{10}$ alkyl), —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —SH, and —S($C_1$-$C_{10}$ alkyl), wherein said aryl, said heteroaryl, said cycloalkyl, said heterocycloalkyl, said cycloalkenyl and said heterocycloalkenyl are each optionally substituted with one or more groups independently selected from the group consisting of halogen, $C_1$-$C_{10}$ haloalkyl, —CN, $C_1$-$C_{10}$ alkyl, $C_2$-$C_{10}$ alkenyl, $C_2$-$C_{10}$ alkynyl, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), cycloalkyl, and heterocycloalkyl;
- n is an integer of 1 to 4;
- $R^2$ and $R^3$ are mutually linked to form, together with the carbon atom that they are attached to, a $C_3$-$C_5$ cycloalkyl; or $R^2$ and $R^3$ are each independently selected from the group consisting of hydrogen and $C_1$-$C_4$ alkyl;
- $R^4$ is $C_1$-$C_4$ alkyl, wherein said alkyl is optionally substituted with one or more groups independently selected from the group consisting of —OH and —O($C_1$-$C_4$ alkyl);
- each $R^5$ is independently a group $-L^5-R^{51}$;
- each $L^5$ is independently selected from the group consisting of a bond and methylene;
- each $R^{51}$ is independently selected from the group consisting of: phenyl; heteroaryl having 5 or 6 ring members, wherein 1, 2 or 3 ring members are heteroatoms selected independently from O, S and N, and the remaining ring members are carbon atoms; $C_3$-$C_7$ cycloalkyl; heterocycloalkyl having 5, 6 or 7 ring members, wherein 1, 2 or 3 ring members are heteroatoms selected independently from O, S and N, and the remaining ring members are carbon atoms; —CN; $C_1$-$C_4$ alkyl; —$NR^{52}R^{52}$; —$COOR^{52}$; and —$CONR^{52}R^{52}$; wherein said phenyl, said heteroaryl, said cycloalkyl, and said heterocycloalkyl are each optionally substituted with one or more groups independently selected from the group consisting of halogen, $C_1$-$C_{10}$ haloalkyl, —CN, $C_1$-$C_{10}$ alkyl, $C_2$-$C_{10}$ alkenyl, $C_2$-$C_{10}$ alkynyl, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), —CHO, —CO($C_1$-$C_{10}$ alkyl), —COOH, tetrazolyl, —COO($C_1$-$C_{10}$ alkyl), —OCO($C_1$-$C_{10}$ alkyl), —CO—$NH_2$, —CO—NH($C_1$-$C_{10}$ alkyl), —CO—N($C_1$-$C_{10}$ alkyl)($C_1$-$C_{10}$ alkyl), —NH—CO—($C_1$-$C_{10}$ alkyl), —N($C_1$-$C_{10}$ alkyl)-CO—($C_1$-$C_{10}$ alkyl), —$SO_2$—$NH_2$, —$SO_2$—NH($C_1$-$C_{10}$ alkyl), —$SO_2$—N($C_1$-$C_{10}$ alkyl)($C_1$-$C_{10}$ alkyl), —NH—$SO_2$—($C_1$-$C_{10}$ alkyl), —N($C_1$-$C_{10}$ alkyl)-$SO_2$—($C_1$-$C_{10}$ alkyl), cycloalkyl, heterocycloalkyl, aryl, heteroaryl having 5 to 6 ring members, wherein 1, 2 or 3 ring members are heteroatoms selected independently from O, S and N, and the remaining ring members are carbon atoms, and $-L^{51}-R^{53}$;
- each $R^{52}$ is independently selected from the group consisting of hydrogen and $C_1$-$C_4$ alkyl;
- each $L^{51}$ is independently selected from the group consisting of a bond, $C_1$-$C_{10}$ alkylene, $C_2$-$C_{10}$ alkenylene, and $C_2$-$C_{10}$ alkynylene, wherein one or more —$CH_2$— units comprised in said alkylene, said alkenylene or said alkynylene are each optionally replaced by a group independently selected from the group consisting of —O—, —NH—, —N($C_1$-$C_{10}$ alkyl)-, —CO—, —S—, —SO—, and —$SO_2$—;

each $R^{53}$ is independently selected from the group consisting of aryl, heteroaryl having 5 to 6 ring members, wherein 1, 2 or 3 ring members are heteroatoms selected independently from O, S and N, and the remaining ring members are carbon atoms, cycloalkyl, heterocycloalkyl, cycloalkenyl, heterocycloalkenyl, halogen, $C_1$-$C_{10}$ haloalkyl, —CN, $C_1$-$C_{10}$ alkyl, $C_2$-$C_{10}$ alkenyl, $C_2$-$C_{10}$ alkynyl, —$NH_2$, —NH($C_1$-$C_{10}$ alkyl), —N($C_1$-$C_{10}$ alkyl)($C_1$-$C_{10}$ alkyl), —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —SH, and —S($C_1$-$C_{10}$ alkyl), wherein said aryl, said heteroaryl, said cycloalkyl, said heterocycloalkyl, said cycloalkenyl and said heterocycloalkenyl are each optionally substituted with one or more groups independently selected from the group consisting of halogen, $C_1$-$C_{10}$ haloalkyl, —CN, $C_1$-$C_{10}$ alkyl, $C_2$-$C_{10}$ alkenyl, $C_2$-$C_{10}$ alkynyl, —OH, —O($C_1$-$C_{10}$ alkyl), —($C_1$-$C_{10}$ alkylene)-OH, —($C_1$-$C_{10}$ alkylene)-O($C_1$-$C_{10}$ alkyl), —$NH_2$, —NH($C_1$-$C_{10}$ alkyl), —N($C_1$-$C_{10}$ alkyl)($C_1$-$C_{10}$ alkyl), cycloalkyl, and heterocycloalkyl; and m is an integer of 0 to 3;

or a pharmaceutically acceptable salt, solvate or prodrug thereof.

2. The compound of claim 1, wherein at least two of $X_1$, $X_2$ and $X_3$ are each C, and the other one of $X_1$, $X_2$ and $X_3$ is C or N.

3. The compound of claim 1, wherein $X_1$, $X_2$ and $X_3$ are each C.

4. The compound of claim 1, wherein:

n is 1;

each $L^1$ is a bond; and each $R^{11}$ is independently selected from the group consisting of phenyl, pyridinyl, pyrazolyl, oxazolyl, thiazolyl, pyrimidinyl, pyridazinyl, pyrazinyl, and imidazo[1,2-a]pyridinyl, wherein said phenyl, said pyridinyl, said pyrazolyl, said oxazolyl, said thiazolyl, said pyrimidinyl, said pyridazinyl, said pyrazinyl and said imidazo[1,2-a]pyridinyl are each optionally substituted with one or more groups independently selected from the group consisting of halogen, $C_1$-$C_4$ haloalkyl, —CN, $C_1$-$C_4$ alkyl, —OH, —O($C_1$-$C_4$ alkyl), —($C_1$-$C_4$ alkylene)-OH, —($C_1$-$C_4$ alkylene)-O($C_1$-$C_4$ alkyl), —$NH_2$, —NH($C_1$-$C_4$ alkyl), —N($C_1$-$C_4$ alkyl)($C_1$-$C_4$ alkyl), —CHO, —CO($C_1$-$C_4$ alkyl), —COOH, tetrazolyl, —COO($C_1$-$C_4$ alkyl), —OCO($C_1$-$C_4$ alkyl), —CO—$NH_2$, —CO—NH($C_1$-$C_4$ alkyl), —CO—N($C_1$-$C_4$ alkyl)($C_1$-$C_4$ alkyl), —NH—CO—($C_1$-$C_4$ alkyl), —N($C_1$-$C_4$ alkyl)-CO—($C_1$-$C_4$ alkyl), —$SO_2$—NH($C_1$-$C_4$ alkyl), —$SO_2$—N($C_1$-$C_4$ alkyl)($C_1$-$C_4$ alkyl), —NH—$SO_2$—($C_1$-$C_4$ alkyl), —N($C_1$-$C_4$ alkyl)-$SO_2$—($C_1$-$C_4$ alkyl), cycloalkyl, heterocycloalkyl, aryl, and heteroaryl having 5 to 6 ring members, wherein 1, 2 or 3 ring members are heteroatoms selected independently from O, S and N, and the remaining ring members are carbon atoms.

5. The compound of claim 1, wherein n is 1, wherein $R^1$ is attached to position 9 of the tricyclic moiety comprised in formula (I), as indicated in the following:

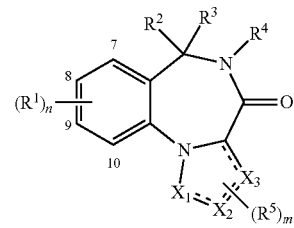

and wherein said $R^1$ is selected from the group consisting of phenyl, pyridinyl, and imidazo[1,2-a]pyridinyl, wherein said phenyl, said pyridinyl and said imidazo[1,2-a]pyridinyl are each optionally substituted with one or more groups independently selected from the group consisting of halogen, $C_1$-$C_4$ haloalkyl, —CN, $C_1$-$C_4$ alkyl, —OH, —O($C_1$-$C_4$ alkyl), —$NH_2$, —NH($C_1$-$C_4$ alkyl), —N($C_1$-$C_4$ alkyl)($C_1$-$C_4$ alkyl), and —COOH.

6. The compound of claim 1, wherein $R^2$ and $R^3$ are each independently selected from the group consisting of hydrogen and $C_1$-$C_4$ alkyl; or wherein $R^2$ and $R^3$ are mutually linked to form, together with the carbon atom that they are attached to, a cyclopropyl.

7. The compound of claim 1, wherein $R^2$ and $R^3$ are not both hydrogen.

8. The compound of claim 1, wherein $R^4$ is selected from the group consisting of methyl and methoxymethyl.

9. The compound of claim 1, wherein each $R^{51}$ is independently selected from the group consisting of: phenyl; heteroaryl having 5 or 6 ring members, wherein 1, 2 or 3 ring members are heteroatoms selected independently from O, S and N, and the remaining ring members are carbon atoms; $C_3$-$C_7$ cycloalkyl; heterocycloalkyl having 5, 6 or 7 ring members, wherein 1, 2 or 3 ring members are heteroatoms selected independently from O, S and N, and the remaining ring members are carbon atoms; —CN; $C_1$-$C_4$ alkyl; —$NH_2$; —NH($C_1$-$C_4$ alkyl); and —N($C_1$-$C_4$ alkyl)($C_1$-$C_4$ alkyl); wherein said phenyl, said heteroaryl, said cycloalkyl and said heterocycloalkyl are each optionally substituted with one or more groups independently selected from the group consisting of halogen, $C_1$-$C_4$ haloalkyl, —CN, $C_1$-$C_4$ alkyl, —OH, —O($C_1$-$C_4$ alkyl), —($C_1$-$C_4$ alkylene)-OH, —($C_1$-$C_4$ alkylene)-O($C_1$-$C_4$ alkyl), —$NH_2$, —NH($C_1$-$C_4$ alkyl), —N($C_1$-$C_4$ alkyl)($C_1$-$C_4$ alkyl), —CHO, —CO($C_1$-$C_4$ alkyl), —COOH, tetrazolyl, —COO($C_1$-$C_4$ alkyl), —OCO($C_1$-$C_4$ alkyl), —CO—$NH_2$, —CO—NH($C_1$-$C_4$ alkyl), —CO—N($C_1$-$C_4$ alkyl)($C_1$-$C_4$ alkyl), —NH—CO—($C_1$-$C_4$ alkyl), —N($C_1$-$C_4$ alkyl)-CO—($C_1$-$C_4$ alkyl), —$SO_2$—$NH_2$, —$SO_2$—NH($C_1$-$C_4$ alkyl), —$SO_2$—N($C_1$-$C_4$ alkyl)($C_1$-$C_4$ alkyl), —NH—$SO_2$—($C_1$-$C_4$ alkyl), —N($C_1$-$C_4$ alkyl)-$SO_2$—($C_1$-$C_4$ alkyl), cycloalkyl, heterocycloalkyl, aryl, and heteroaryl having 5 to 6 ring members, wherein 1, 2 or 3 ring members are heteroatoms selected independently from O, S and N, and the remaining ring members are carbon atoms.

10. The compound of claim 1, wherein:

$R^2$ and $R^3$ are each independently selected from the group consisting of hydrogen and $C_1$-$C_4$ alkyl, wherein $R^2$ and $R^3$ are not both hydrogen, or $R^2$ and $R^3$ are mutually linked to form, together with the carbon atom that they are attached to, a C3-$C_5$ cycloalkyl; and R[4] is C$_1$-C$_4$ alkyl, wherein said alkyl is optionally substituted with one group selected from the group consisting of —OH and —O(C$_1$-C$_4$ alkyl).

11. The compound of claim 1, wherein:
R[2] and R[3] are each independently selected from the group consisting of hydrogen, methyl, and ethyl, wherein R[2] and R[3] are not both hydrogen, or R[2] and R[3] are mutually linked to form, together with the carbon atom that they are attached to, a cyclopropyl; and
R[4] is methyl which is optionally substituted with —OCH$_3$.

12. A compound selected from the group consisting of:
9-Bromo-5-methyl-spiro[benzo[f]pyrrolo[1,2-a][1,4]diazepine-6,1'-cyclopropan]-4(5H)-one;
9-Bromo-5-methoxymethyl-spiro[benzo[f]pyrrolo[1,2-a][1,4]diazepine-6,1'-cyclopropan]-4(5H)-one;
9-Bromo-5-(methyl-d$_3$)-spiro[benzo[f]pyrrolo[1,2-a][1,4]diazepine-6,1'-cyclopropan]-4(5H)-one;
2,9-Dibromo-5-methyl-spiro[benzo[f]pyrrolo[1,2-a][1,4]diazepine-6,1'-cyclopropan]-4(5H)-one;
9-Bromo-2-chloro-5-methyl-spiro[benzo[f]pyrrolo[1,2-a][1,4]diazepine-6,1'-cyclopropan]-4(5H)-one;
9-Bromo-3-chloro-5-methyl-spiro[benzo[f]pyrrolo[1,2-a][1,4]diazepine-6,1'-cyclopropan]-4(5H)-one;
9-Bromo-7-fluoro-5-methyl-spiro[benzo[f]pyrrolo[1,2-a][1,4]diazepine-6,1'-cyclopropan]-4(5H)-one;
9-Bromo-10-fluoro-5-methyl-spiro[benzo[f]pyrrolo[1,2-a][1,4]diazepine-6,1'-cyclopropan]-4(5H)-one;
9-Bromo-8-fluoro-5-methyl-spiro[benzo[f]pyrrolo[1,2-a][1,4]diazepine-6,1'-cyclopropan]-4(5H)-one;
9-Bromo-2-phenyl-5-methyl-spiro[benzo[f]pyrrolo[1,2-a][1,4]diazepine-6,1'-cyclopropan]-4(5H)-one;
9-Bromo-5-methyl-2-phenyl-spiro[benzo[f]pyrazolo[1,5-a][1,4]diazepine-6,1'-cyclopropan]-4(5H)-one;
9-Bromo-6,6-spirocyclopropyl-5-methyl-2-phenyl-5,6-dihydro-3,5,10b-triaza-benzo[e]azulen-4-one;
8-Bromo-5-methyl-spiro[benzo[f]pyrrolo[1,2-a][1,4]diazepine-6,1'-cyclopropan]-4(5H)-one;
7-Bromo-5-methyl-spiro[benzo[f]pyrrolo[1,2-a][1,4]diazepine-6,1'-cyclopropan]-4(5H)-one;
10-Bromo-5-methyl-spiro[benzo[f]pyrrolo[1,2-a][1,4]diazepine-6,1'-cyclopropan]-4(5H)-one;
8-Bromo-5-methyl-2-phenyl-spiro[benzo[f]pyrrolo[1,2-a][1,4]diazepine-6,1'-cyclopropan]-4(5H)-one;
2-Bromo-5-methyl-9-(2-methyl-pyridin-3-yl)-spiro[benzo[f]pyrrolo[1,2-a][1,4]diazepine-6,1'-cyclopropan]-4(5H)-one;
2-Bromo-5-methyl-9-(6-methyl-pyridin-3-yl)-spiro[benzo[f]pyrrolo[1,2-a][1,4]diazepine-6,1'-cyclopropan]-4(5H)-one;
2-Bromo-5-methyl-9-(2-ethyl-pyridin-3-yl)-spiro[benzo[f]pyrrolo[1,2-a][1,4]diazepine-6,1'-cyclopropan]-4(5H)-one;
5-Methyl-9-(2-methyl-pyridin-3-yl)-spiro[benzo[f]pyrrolo[1,2-a][1,4]diazepine-6,1'-cyclopropan]-4(5H)-one;
5-Methoxymethyl-9-(2-methyl-pyridin-3-yl)-spiro[benzo[f]pyrrolo[1,2-a][1,4]diazepine-6,1'-cyclopropan]-4(5H)-one;
5-Methyl-9-(pyridin-4-yl)-spiro[benzo[f]pyrrolo[1,2-a][1,4]diazepine-6,1'-cyclopropan]-4(5H)-one;
5-Methyl-9-(pyridin-3-yl)-spiro[benzo[f]pyrrolo[1,2-a][1,4]diazepine-6,1'-cyclopropan]-4(5H)-one;
5-Methyl-9-(2-ethylpyridin-3-yl)-spiro[benzo[f]pyrrolo[1,2-a][1,4]diazepine-6,1'-cyclopropan]-4(5H)-one;
5-Methyl-9-(6-methylpyridin-3-yl)-spiro[benzo[f]pyrrolo[1,2-a][1,4]diazepine-6,1'-cyclopropan]-4(5H)-one;
5-Methyl-9-(2-methylpyridin-4-yl)-spiro[benzo[f]pyrrolo[1,2-a][1,4]diazepine-6,1'-cyclopropan]-4(5H)-one;
5-Methyl-9-(3,5-dimethyl-1H-pyrazol-4-yl)-spiro[benzo[f]pyrrolo[1,2-a][1,4]diazepine-6,1'-cyclopropan]-4(5H)-one;
5-Methyl-9-(3-trifluoromethyl-1H-pyrazol-4-yl)-spiro[benzo[f]pyrrolo[1,2-a][1,4]diazepine-6,1'-cyclopropan]-4(5H)-one;
5-Methyl-9-(1-methyl-pyrazol-4-yl)-spiro[benzo[f]pyrrolo[1,2-a][1,4]diazepine-6,1'-cyclopropan]-4(5H)-one;
5-Methyl-9-(1-methyl-pyrazol-5-yl)-spiro[benzo[f]pyrrolo[1,2-a][1,4]diazepine-6,1'-cyclopropan]-4(5H)-one;
5-Methyl-9-(6-fluoropyridin-3-yl)-spiro[benzo[f]pyrrolo[1,2-a][1,4]diazepine-6,1'-cyclopropan]-4(5H)-one;
5-Methyl-9-(6-fluoro-2-methylpyridin-3-yl)-spiro[benzo[f]pyrrolo[1,2-a][1,4]diazepine-6,1'-cyclopropan]-4(5H)-one;
5-Methyl-9-(2-fluoropyridin-3-yl)-spiro[benzo[f]pyrrolo[1,2-a][1,4]diazepine-6,1'-cyclopropan]-4(5H)-one;
5-Methyl-9-(2-fluoropyridin-4-yl)-spiro[benzo[f]pyrrolo[1,2-a][1,4]diazepine-6,1'-cyclopropan]-4(5H)-one;
5-Methyl-9-(2-trifluoromethylpyridin-4-yl)-spiro[benzo[f]pyrrolo[1,2-a][1,4]diazepine-6,1'-cyclopropan]-4(5H)-one;
5-Methyl-9-(2-trifluoromethylpyridin-3-yl)-spiro[benzo[f]pyrrolo[1,2-a][1,4]diazepine-6,1'-cyclopropan]-4(5H)-one;
5-Methyl-9-(4-trifluoromethylpyridin-3-yl)-spiro[benzo[f]pyrrolo[1,2-a][1,4]diazepine-6,1'-cyclopropan]-4(5H)-one;
5-Methyl-9-(3-methylpyridin-4-yl)-spiro[benzo[f]pyrrolo[1,2-a][1,4]diazepine-6,1'-cyclopropan]-4(5H)-one;
5-Methyl-9-(3,4-dimethoxy-phenyl)-spiro[benzo[f]pyrrolo[1,2-a][1,4]diazepine-6,1'-cyclopropan]-4(5H)-one;
5-Methyl-9-(6-amino-5-trifluoromethyl-pyridin-3-yl)-spiro[benzo[f]pyrrolo[1,2-a][1,4]diazepine-6,1'-cyclopropan]-4(5H)-one;
5-Methyl-9-(imidazo[1,2-a]pyridin-6-yl)-spiro[benzo[f]pyrrolo[1,2-a][1,4]diazepine-6,1'-cyclopropan]-4(5H)-one;
5-Methyl-9-(6-morpholin-4-yl-pyridin-3-yl)-spiro[benzo[f]pyrrolo[1,2-a][1,4]diazepine-6,1'-cyclopropan]-4(5H)-one;
5-Methyl-9-(3,4,5,6-tetrahydro-2H-[1,2']bipyridinyl-5'-yl)-spiro[benzo[f]pyrrolo[1,2-a][1,4]diazepine-6,1'-cyclopropan]-4(5H)-one;
5-Methyl-9-(3-cyanophenyl)-spiro[benzo[f]pyrrolo[1,2-a][1,4]diazepine-6,1'-cyclopropan]-4(5H)-one;
5-Methyl-9-(3-(1H-tetrazol-5-yl)-phenyl)-spiro[benzo[f]pyrrolo[1,2-a][1,4]diazepine-6,1'-cyclopropan]-4(5H)-one;
5-Methyl-9-(1,2,3,6-tetrahydro-pyridin-4-yl)-spiro[benzo[f]pyrrolo[1,2-a][1,4]diazepine-6,1'-cyclopropan]-4(5H)-one;
5-Methyl-9-(1-pyrimidin-4-yl-1,2,3,6-tetrahydro-pyridin-4-yl)-spiro[benzo[f]pyrrolo[1,2-a][1,4]diazepine-6,1'-cyclopropan]-4(5H)-one;
5-Methyl-9-(1-acetyl-1,2,3,6-tetrahydro-pyridin-4-yl)-spiro[benzo[f]pyrrolo[1,2-a][1,4]diazepine-6,1'-cyclopropan]-4(5H)-one;
5-Methyl-9-(4-methyl-oxazol-5-yl)-spiro[benzo[f]pyrrolo[1,2-a][1,4]diazepine-6,1'-cyclopropan]-4(5H)-one;

5-Methyl-9-(4-methylthiazol-5-yl)-spiro[benzo[f]pyrrolo[1,2-a][1,4]diazepine-6,1'-cyclopropan]-4(5H)-one;
5-Methyl-9-acetonitrile-spiro[benzo[f]pyrrolo[1,2-a][1,4]diazepan-6,1'-cyclopropan]-4(5H)-one;
5-Methyl-9-acrylonitrile-spiro[benzo[f]pyrrolo[1,2-a][1,4]diazepine-6,1'-cyclopropan]-4(5H)-one;
5-Methyl-9-propionitrile-spiro[benzo[f]pyrrolo[1,2-a][1,4]diazepine-6,1'-cyclopropan]-4(5H)-one;
5-Methyl-9-(6-chloropyridin-3-yl)-spiro[benzo[f]pyrrolo[1,2-a][1,4]diazepine-6,1'-cyclopropan]-4(5H)-one;
5-(Methyl-d3)-9-(6-fluoropyridin-3-yl)-spiro[benzo[f]pyrrolo[1,2-a][1,4]diazepine-6,1'-cyclopropan]-4(5H)-one;
5-Methyl-9-(2,6-dimethylpyridin-3-yl)-spiro[benzo[f]pyrrolo[1,2-a][1,4]diazepine-6,1'-cyclopropan]-4(5H)-one;
5-Methyl-9-(4-fluoropyridin-2-yl)-spiro[benzo[f]pyrrolo[1,2-a][1,4]diazepine-6,1'-cyclopropan]-4(5H)-one;
5-Methyl-9-(3-methyl-pyrazin-2-yl)-5,6-spiro[benzo[f]pyrrolo[1,2-a][1,4]diazepine-6,1'-cyclopropan]-4(5H)-one;
5-Methyl-9-(4-methyl-pyrimidin-5-yl)-spiro[benzo[f]pyrrolo[1,2-a][1,4]diazepine-6,1'-cyclopropan]-4(5H)-one;
5-Methyl-9-(6-trifluoromethylpyridin-3-yl)-spiro[benzo[f]pyrrolo[1,2-a][1,4]diazepine-6,1'-cyclopropan]-4(5H)-one;
5-Methyl-9-(2-propylpyridin-3-yl)-spiro[benzo[f]pyrrolo[1,2-a][1,4]diazepine-6,1'-cyclopropan]-4(5H)-one;
5-Methyl-9-(2-cyclopropylpyridin-3-yl)-spiro[benzo[f]pyrrolo[1,2-a][1,4]diazepine-6,1'-cyclopropan]-4(5H)-one;
5-Methyl-9-(5-fluoropyridin-2-yl)-spiro[benzo[f]pyrrolo[1,2-a][1,4]diazepine-6,1'-cyclopropan]-4(5H)-one;
5-(Methyl-d3)-9-(5-fluoropyridin-2-yl)-spiro[benzo[f]pyrrolo[1,2-a][1,4]diazepine-6,1'-cyclopropan]-4(5H)-one;
5-Methyl-9-(2,4-dimethylpyridin-3-yl)-spiro[benzo[f]pyrrolo[1,2-a][1,4]diazepine-6,1'-cyclopropan]-4(5H)-one;
5-Methyl-9-(3-fluoropyridin-2-yl)-spiro[benzo[f]pyrrolo[1,2-a][1,4]diazepine-6,1'-cyclopropan]-4(5H)-one;
5-Methyl-9-(6-fluoropyridin-2-yl)-spiro[benzo[f]pyrrolo[1,2-a][1,4]diazepine-6,1'-cyclopropan]-4(5H)-one;
5-Methyl-9-(2-hydroxypyridin-4-yl)-spiro[benzo[f]pyrrolo[1,2-a][1,4]diazepine-6,1'-cyclopropan]-4(5H)-one;
5-Methyl-9-(5-trifluoromethylpyridin-2-yl)-spiro[benzo[f]pyrrolo[1,2-a][1,4]diazepine-6,1'-cyclopropan]-4(5H)-one;
5-Methyl-9-(pyridazin-3-yl)-spiro[benzo[f]pyrrolo[1,2-a][1,4]diazepine-6,1'-cyclopropan]-4(5H)-one;
5-Methyl-9-(2-methoxycarbonylpyridin-3-yl)-spiro[benzo[f]pyrrolo[1,2-a][1,4]diazepine-6,1'-cyclopropan]-4(5H)-one;
5-Methyl-9-(2-(1-hydroxy-1-methyl-ethyl)-pyridin-3-yl)-spiro[benzo[f]pyrrolo[1,2-a][1,4]diazepine-6,1'-cyclopropan]-4(5H)-one;
7-Fluoro-5-methyl-9-(2-methyl-pyridin-3-yl)-spiro[benzo[f]pyrrolo[1,2-a][1,4]diazepine-6,1'-cyclopropan]-4(5H)-one;
7-Fluoro-5-methyl-9-(6-fluoro-pyridin-3-yl)-spiro[benzo[f]pyrrolo[1,2-a][1,4]diazepine-6,1'-cyclopropan]-4(5H)-one;
10-Fluoro-5-methyl-9-(2-methyl-pyridin-3-yl)-spiro[benzo[f]pyrrolo[1,2-a][1,4]diazepine-6,1'-cyclopropan]-4(5H)-one;
10-Fluoro-5-Methyl-9-(6-fluoro-pyridin-3-yl)-spiro[benzo[f]pyrrolo[1,2-a][1,4]diazepine-6,1'-cyclopropan]-4(5H)-one;
8-Fluoro-5-methyl-9-(2-methyl-pyridin-3-yl)-spiro[benzo[f]pyrrolo[1,2-a][1,4]diazepine-6,1'-cyclopropan]-4(5H)-one;
8-Fluoro-5-methyl-9-(6-fluoro-pyridin-3-yl)-spiro[benzo[f]pyrrolo[1,2-a][1,4]diazepine-6,1'-cyclopropan]-4(5H)-one;
9-Bromo-1-fluoro-5-methyl-spiro[benzo[f]pyrrolo[1,2-a][1,4]diazepine-6,1'-cyclopropan]-4(5H)-one;
9-Bromo-2-chloro-1-fluoro-5-methyl-spiro[benzo[f]pyrrolo[1,2-a][1,4]diazepine-6,1'-cyclopropan]-4(5H)-one;
9-(2-Methyl-pyridin-3-yl)-1-fluoro-5-methyl-spiro[benzo[f]pyrrolo[1,2-a][1,4]diazepine-6,1'-cyclopropan]-4(5H)-one;
9-(2-Methyl-pyridin-3-yl)-2-chloro-5-methyl-spiro[benzo[f]pyrrolo[1,2-a][1,4]diazepine-6,1'-cyclopropan]-4(5H)-one;
9-(2-Methyl-pyridin-3-yl)-2-chloro-1-fluoro-5-methyl-spiro[benzo[f]pyrrolo[1,2-a][1,4]diazepine-6,1'-cyclopropan]-4(5H)-one;
9-(2-Methyl-pyridin-3-yl)-3-chloro-5-methyl-spiro[benzo[f]pyrrolo[1,2-a][1,4]diazepine-6,1'-cyclopropan]-4(5H)-one;
1-Bromo-5-methyl-9-(5-fluoropyridin-2-yl)-spiro[benzo[f]pyrrolo[1,2-a][1,4]diazepine-6,1'-cyclopropan]-4(5H)-one;
5-Methyl-1-(2-methyl-2H-pyrazol-3-yl)9-(5-fluoropyridin-2-yl)-spiro[benzo[f]pyrrolo[1,2-a][1,4]diazepine-6,1'-cyclopropan]-4(5H)-one;
5,8-Dimethyl-spiro[benzo[f]pyrrolo[1,2-a][1,4]diazepine-6,1'-cyclopropan]-4(5H)-one;
8-Morpholin-4-yl-5-methyl-spiro[benzo[f]pyrrolo[1,2-a][1,4]diazepine-6,1'-cyclopropan]-4(5H)-one;
5,7-Dimethyl-spiro[benzo[f]pyrrolo[1,2-a][1,4]diazepine-6,1'-cyclopropan]-4(5H)-one;
5,10-Dimethyl-spiro[benzo[f]pyrrolo[1,2-a][1,4]diazepine-6,1'-cyclopropan]-4(5H)-one;
10-Cyano-5-methyl-spiro[benzo[f]pyrrolo[1,2-a][1,4]diazepine-6,1'-cyclopropan]-4(5H)-one;
10-(2-Methyl-pyridin-3-yl)-5-methyl-spiro[benzo[f]pyrrolo[1,2-a][1,4]diazepine-6,1'-cyclopropan]-4(5H)-one;
5-Methyl-2-phenyl-9-pyridin-3-yl-spiro[benzo[f]pyrrolo[1,2-a][1,4]diazepine-6,1'-cyclopropan]-4(5H)-one;
3-(5-methyl-4-oxo-2-phenyl-4,5-dihydrospiro[benzo[f]pyrrolo[1,2-a][1,4]diazepine-6,1'-cyclopropan]-9-yl)benzoic acid;
5-Methyl-2-phenyl-9-(2-methyl-pyridin-3-yl)-spiro[benzo[f]pyrrolo[1,2-a][1,4]diazepine-6,1'-cyclopropan]-4(5H)-one;
5-Methyl-2-phenyl-9-(6-amino-pyridin-3-yl)-spiro[benzo[f]pyrrolo[1,2-a][1,4]diazepine-6,1'-cyclopropan]-4(5H)-one;
5-Methyl-2-phenyl-9-(2,6-dimethyl-pyridin-4-yl)-spiro[benzo[f]pyrrolo[1,2-a][1,4]diazepine-6,1'-cyclopropan]-4(5H)-one;
5-Methyl-2-phenyl-9-(5-methyl-pyridin-3-yl)-spiro[benzo[f]pyrrolo[1,2-a][1,4]diazepine-6,1'-cyclopropan]-4(5H)-one;
5-Methyl-2-phenyl-9-(2-ethyl-pyridin-3-yl)-spiro[benzo[f]pyrrolo[1,2-a][1,4]diazepine-6,1'-cyclopropan]-4(5H)-one;

5-Methyl-2-phenyl-9-(2-trifluoromethyl-pyridin-3-yl)-spiro[benzo[f]pyrrolo[1,2-a][1,4]diazepine-6,1'-cyclopropan]-4(5H)-one;

5-Methyl-2-phenyl-9-(4-methyl-pyridin-3-yl)-spiro[benzo[f]pyrrolo[1,2-a][1,4]diazepine-6,1'-cyclopropan]-4(5H)-one;

5-Methyl-2-phenyl-9-(pyridin-4-yl)-spiro[benzo[f]pyrrolo[1,2-a][1,4]diazepine-6,1'-cyclopropan]-4(5H)-one;

5-Methyl-2-phenyl-9-(6-methyl-pyridin-3-yl)-spiro[benzo[f]pyrrolo[1,2-a][1,4]diazepine-6,1'-cyclopropan]-4(5H)-one;

5-Methyl-2-phenyl-9-(pyrimidin-5-yl)-spiro[benzo[f]pyrrolo[1,2-a][1,4]diazepine-6,1'-cyclopropan]-4(5H)-one;

5-Methyl-2-phenyl-9-(2-methyl-pyridin-4-yl)-spiro[benzo[f]pyrrolo[1,2-a][1,4]diazepine-6,1'-cyclopropan]-4(5H)-one;

5-Methyl-2-phenyl-9-(6-fluoro-pyridin-3-yl)-spiro[benzo[f]pyrrolo[1,2-a][1,4]diazepine-6,1'-cyclopropan]-4(5H)-one;

5-Methyl-2-phenyl-9-(2,6-dimethyl-pyridin-3-yl)-spiro[benzo[f]pyrrolo[1,2-a][1,4]diazepine-6,1'-cyclopropan]-4(5H)-one;

5-Methyl-2-phenyl-9-pyrazin-2-yl-spiro[benzo[f]pyrrolo[1,2-a][1,4]diazepine-6,1'-cyclopropan]-4(5H)-one;

5-Methyl-2-phenyl-9-pyridazin-3-yl-spiro[benzo[f]pyrrolo[1,2-a][1,4]diazepine-6,1'-cyclopropan]-4(5H)-one;

5-Methyl-2-phenyl-9-(5-fluoro-pyridin-2-yl)-spiro[benzo[f]pyrrolo[1,2-a][1,4]diazepine-6,1'-cyclopropan]-4(5H)-one;

5-Methyl-2-phenyl-9-(pyridin-2-yl)-spiro[benzo[f]pyrrolo[1,2-a][1,4]diazepine-6,1'-cyclopropan]-4(5H)-one;

5-methyl-2-phenyl-9-(6-ethylpyridin-3-yl)-spiro[benzo[f]pyrrolo[1,2-a][1,4]diazepine-6,1'-cyclopropan]-4(5H)-one;

5-Methyl-2-phenyl-9-(2-fluoro-pyridin-3-yl)-spiro[benzo[f]pyrrolo[1,2-a][1,4]diazepine-6,1'-cyclopropan]-4(5H)-one;

5-Methyl-2-phenyl-9-(6-dimethylamino-pyridin-3-yl)-spiro[benzo[f]pyrrolo[1,2-a][1,4]diazepine-6,1'-cyclopropan]-4(5H)-one;

9-Dimethylamino-5-methyl-2-phenyl-spiro[benzo[f]pyrrolo[1,2-a][1,4]diazepine-6,1'-cyclopropan]-4(5H)-one;

5-Methyl-2-phenyl-9-(2-methoxy-pyridin-3-yl)-spiro[benzo[f]pyrrolo[1,2-a][1,4]diazepine-6,1'-cyclopropan]-4(5H)-one;

5-Methyl-2-phenyl-9-(6-cyano-pyridin-3-yl)-spiro[benzo[f]pyrrolo[1,2-a][1,4]diazepine-6,1'-cyclopropan]-4(5H)-one;

5-Methyl-2-phenyl-9-(6-methylamino-pyridin-3-yl)-spiro[benzo[f]pyrrolo[1,2-a][1,4]diazepine-6,1'-cyclopropan]-4(5H)-one;

5-Methyl-2-phenyl-9-(2-dimethylamino-pyridin-3-yl)-spiro[benzo[f]pyrrolo[1,2-a][1,4]diazepine-6,1'-cyclopropan]-4(5H)-one;

8-Morpholin-4-yl-5-methyl-2-phenyl-spiro[benzo[f]pyrrolo[1,2-a][1,4]diazepine-6,1'-cyclopropan]-4(5H)-one;

9-(2,6-Dimethyl-pyridin-4-yl)-5-methyl-2-phenyl-spiro[benzo[f]pyrazolo[1,5-a][1,4]diazepine-6,1'-cyclopropan]-4(5H)-one;

9-(2-Methyl-pyridin-4-yl)-5-methyl-2-phenyl-spiro[benzo[f]pyrazolo[1,5-a][1,4]diazepine-6,1'-cyclopropan]-4(5H)-one;

2,9-Diphenyl-5-methyl-2-spiro[benzo[f]pyrazolo[1,5-a][1,4]diazepine-6,1'-cyclopropan]-4(5H)-one;

9-(4-Amino-phenyl)-5-methyl-2-phenyl-spiro[benzo[f]pyrazolo[1,5-a][1,4]diazepine-6,1'-cyclopropan]-4(5H)-one;

9-(2-Methyl-pyridin-3-yl)-5-methyl-2-phenyl-spiro[benzo[f]pyrazolo[1,5-a][1,4]diazepine-6,1'-cyclopropan]-4(5H)-one;

9-(2,6-Dimethyl-pyridin-3-yl)-5-methyl-2-phenyl-spiro[benzo[f]pyrazolo[1,5-a][1,4]diazepine-6,1'-cyclopropan]-4(5H)-one;

9-(6-Amino-pyridin-3-yl)-5-methyl-2-phenyl-spiro[benzo[f]pyrazolo[1,5-a][1,4]diazepine-6,1'-cyclopropan]-4(5H)-one;

9-(4-Methoxy-phenyl)-5-methyl-2-phenyl-spiro[benzo[f]pyrazolo[1,5-a][1,4]diazepine-6,1'-cyclopropan]-4(5H)-one;

9-(3-Cyano-phenyl)-5-methyl-2-phenyl-spiro[benzo[f]pyrazolo[1,5-a][1,4]diazepine-6,1'-cyclopropan]-4(5H)-one;

9-(3-Chloro-phenyl)-5-methyl-2-phenyl-spiro[benzo[f]pyrazolo[1,5-a][1,4]diazepine-6,1'-cyclopropan]-4(5H)-one;

9-(2-Chloro-phenyl)-5-methyl-2-phenyl-spiro[benzo[f]pyrazolo[1,5-a][1,4]diazepine-6,1'-cyclopropan]-4(5H)-one;

9-(Oxazol-5-yl)-5-methyl-2-phenyl-spiro[benzo[f]pyrazolo[1,5-a][1,4]diazepine-6,1'-cyclopropan]-4(5H)-one;

3-(5-methyl-4-oxo-2-phenyl-4,5-dihydrospiro[benzo[f]pyrazolo[1,5-a][1,4]diazepine-6,1'-cyclopropan]-9-yl)benzoic acid;

9-(1H-pyrazol-4-yl)-5-methyl-2-phenyl-spiro[benzo[f]pyrazolo[1,5-a][1,4]diazepine-6,1'-cyclopropan]-4(5H)-one;

9-(4-Chloro-phenyl)-5-methyl-2-phenyl-spiro[benzo[f]pyrazolo[1,5-a][1,4]diazepine-6,1'-cyclopropan]-4(5H)-one;

9-(1H-pyrazol-3-yl)-5-methyl-2-phenyl-spiro[benzo[f]pyrazolo[1,5-a][1,4]diazepine-6,1'-cyclopropan]-4(5H)-one;

9-Cyano-5-methyl-2-phenyl-spiro[benzo[f]pyrazolo[1,5-a][1,4]diazepine-6,1'-cyclopropan]-4(5H)-one;

5-Methyl-2-phenyl-spiro[benzo[f]pyrazolo[1,5-a][1,4]diazepine-6,1'-cyclopropan]-4(5H)-one;

5-Methyl-2-phenyl-9-(pyrrolidin-1-yl)-spiro[benzo[f]pyrazolo[1,5-a][1,4]diazepine-6,1'-cyclopropan]-4(5H)-one;

9-(2-Methyl-pyridin-3-yl)-5-methyl-2-phenyl-spiro[benzo[f]imidazo[1,2-a][1,4]diazepine-6,1'-cyclopropan]-4(5H)-one;

N,N-dimethyl-3-(5-methyl-4-oxo-2-phenyl-4,5-dihydrospiro[benzo[f]pyrrolo[1,2-a][1,4]diazepine-6,1'-cyclopropan]-9-yl)benzenesulfonamide;

N,N-dimethyl-3-(5-methyl-4-oxo-2-phenyl-4,5-dihydrospiro[benzo[f]pyrazolo[1,5-a][1,4]diazepine-6,1'-cyclopropan]-9-yl)benzenesulfonamide;

5-Methyl-2-(pyridine-3-yl)-9-(2-methyl-pyridin-3-yl)-spiro[benzo[f]pyrazolo[1,5-a][1,4]diazepine-6,1'-cyclopropan]-4(5H)-one;

2,5-Dimethyl-9-(2-methyl-pyridin-3-yl)-spiro[benzo[f]pyrazolo[1,5-a][1,4]diazepine-6,1'-cyclopropan]-4(5H)-one;

5-Methyl-2-(pyridine-4-yl)-9-(2-methyl-pyridin-3-yl)-spiro[benzo[f]pyrazolo[1,5-a][1,4]diazepine-6,1'-cyclopropan]-4(5H)-one;

5-Methyl-2-(1H-pyrazol-3-yl)-9-(2-methyl-pyridin-3-yl)-spiro[benzo[f]pyrazolo[1,5-a][1,4]diazepine-6,1'-cyclopropan]-4(5H)-one;

5-Methyl-2-(2-chlorophenyl)-9-(2-methyl-pyridin-3-yl)-spiro[benzo[f]pyrazolo[1,5-a][1,4]diazepine-6,1'-cyclopropan]-4(5H)-one;

5-Methyl-2-(3-chlorophenyl)-9-(2-methyl-pyridin-3-yl)-spiro[benzo[f]pyrazolo[1,5-a][1,4]diazepine-6,1'-cyclopropan]-4(5H)-one;

5-Methyl-2-(4-chlorophenyl)-9-(2-methyl-pyridin-3-yl)-spiro[benzo[f]pyrazolo[1,5-a][1,4]diazepine-6,1'-cyclopropan]-4(5H)-one;

5-Methyl-2-(4-fluorophenyl)-9-(2-methyl-pyridin-3-yl)-spiro[benzo[f]pyrazolo[1,5-a][1,4]diazepine-6,1'-cyclopropan]-4(5H)-one;

5-Methyl-2-(2-fluorophenyl)-9-(2-methyl-pyridin-3-yl)-spiro[benzo[f]pyrazolo[1,5-a][1,4]diazepine-6,1'-cyclopropan]-4(5H)-one;

5-Methyl-2-(3-fluorophenyl)-9-(2-methyl-pyridin-3-yl)-spiro[benzo[f]pyrazolo[1,5-a][1,4]diazepine-6,1'-cyclopropan]-4(5H)-one;

5-Methyl-2-cyano-9-(2-methyl-pyridin-3-yl)-spiro[benzo[f]pyrazolo[1,5-a][1,4]diazepine-6,1'-cyclopropan]-4(5H)-one;

5-Methyl-2-dimethylamino-9-(2-methyl-pyridin-3-yl)-spiro[benzo[f]pyrazolo[1,5-a][1,4]diazepine-6,1'-cyclopropan]-4(5H)-one;

5-Methyl-2-cyclopropyl-9-(2-methyl-pyridin-3-yl)-spiro[benzo[f]pyrazolo[1,5-a][1,4]diazepine-6,1'-cyclopropan]-4(5H)-one;

5-Methyl-2-cyclopentyl-9-(2-methyl-pyridin-3-yl)-spiro[benzo[f]pyrazolo[1,5-a][1,4]diazepine-6,1'-cyclopropan]-4(5H)-one;

5-Methyl-2-(thiazol-2-yl)-9-(2-methyl-pyridin-3-yl)-spiro[benzo[f]pyrazolo[1,5-a][1,4]diazepine-6,1'-cyclopropan]-4(5H)-one;

5-Methyl-2-(thiazol-2-yl)-9-(6-methyl-pyridin-3-yl)-spiro[benzo[f]pyrazolo[1,5-a][1,4]diazepine-6,1'-cyclopropan]-4(5H)-one;

5-Methyl-2-(2-methyl-2H-pyrazol-3-yl)-9-(6-methyl-pyridin-3-yl)-spiro[benzo[f]pyrazolo[1,5-a][1,4]diazepine-6,1'-cyclopropan]-4(5H)-one;

5-Methyl-2-(2-methyl-2H-pyrazol-3-yl)-9-(2-methyl-pyridin-3-yl)-spiro[benzo[f]pyrazolo[1,5-a][1,4]diazepine-6,1'-cyclopropan]-4(5H)-one;

5-Methyl-2-dimethylamino-9-(6-methyl-pyridin-3-yl)-spiro[benzo[f]pyrazolo[1,5-a][1,4]diazepine-6,1'-cyclopropan]-4(5H)-one;

5-Methyl-2-(2-fluorophenyl)-9-(2-ethyl-pyridin-3-yl)-spiro[benzo[f]pyrazolo[1,5-a][1,4]diazepine-6,1'-cyclopropan]-4(5H)-one;

5-Methyl-2-(2-methyl-2H-pyrazol-3-yl)-9-(2-ethyl-pyridin-3-yl)-spiro[benzo[f]pyrazolo[1,5-a][1,4]diazepine-6,1'-cyclopropan]-4(5H)-one;

9-Bromo-5-methyl-2-phenyl-5,6-dihydro-benzo[f]pyrrolo[1,2-a][1,4]diazepin-4-one;

9-(6-Amino-pyridin-3-yl)-5-methyl-2-phenyl-5,6-dihydro-benzo[f]pyrrolo[1,2-a][1,4]diazepin-4-one;

5-Methyl-9-(2-methylpyridin-3-yl)-2-phenyl-5,6-dihydro-4H-benzo[f]imidazo[1,2-a][1,4]diazepin-4-one;

5-Ethyl-9-(2-methylpyridin-3-yl)-2-phenyl-5,6-dihydro-4H-benzo[f]imidazo[1,2-a][1,4]diazepin-4-one;

5-Methyl-9-(2-methylpyridin-3-yl)-4-oxo-4,5-dihydrospiro[benzo[f]pyrrolo[1,2-a][1,4]diazepine-6,1'-cyclopropane]-2-carbaldehyde;

5-Methyl-9-(2-ethyl-pyridin-3-yl)-4-oxo-4,5-dihydrospiro[benzo[f]pyrrolo[1,2-a][1,4]diazepine-6,1'-cyclopropane]-2-carbaldehyde;

5-Methyl-9-(6-methyl-pyridin-3-yl)-4-oxo-4,5-dihydrospiro[benzo[f]pyrrolo[1,2-a][1,4]diazepine-6,1'-cyclopropane]-2-carbaldehyde;

5-Methyl-9-(6-fluoro-pyridin-3-yl)-4-oxo-4,5-dihydrospiro[benzo[f]pyrrolo[1,2-a][1,4]diazepine-6,1'-cyclopropane]-2-carbaldehyde;

5-(Methyl-d3)-9-(6-fluoro-pyridin-3-yl)-4-oxo-4,5-dihydrospiro[benzo[f]pyrrolo[1,2-a][1,4]diazepine-6,1'-cyclopropane]-2-carbaldehyde;

5-Methyl-9-bromo-4-oxo-4,5-dihydrospiro[benzo[f]pyrrolo[1,2-a][1,4]diazepine-6,1'-cyclopropane]-2-carbaldehyde;

5-Methyl-9-(3-cyanophenyl)-4-oxo-4,5-dihydrospiro[benzo[f]pyrrolo[1,2-a][1,4]diazepine-6,1'-cyclopropane]-2-carbaldehyde;

5-Methyl-9-(pyridazin-3-yl)-4-oxo-4,5-dihydrospiro[benzo[f]pyrrolo[1,2-a][1,4]diazepine-6,1'-cyclopropane]-2-carbaldehyde;

5-Methyl-9-(2-methylpyridin-3-yl)-4-oxo-4,5-dihydrospiro[benzo[f]pyrrolo[1,2-a][1,4]diazepine-6,1'-cyclopropane]-2-carboxylic acid;

5-Methyl-9-(6-fluoro-pyridin-3-yl)-4-oxo-4,5-dihydrospiro[benzo[f]pyrrolo[1,2-a][1,4]diazepine-6,1'-cyclopropane]-2-carboxylic acid;

5-(Methyl-d3)-9-(6-fluoro-pyridin-3-yl)-4-oxo-4,5-dihydrospiro[benzo[f]pyrrolo[1,2-a][1,4]diazepine-6,1'-cyclopropane]-2-carboxylic acid;

5-Methyl-9-bromo-4-oxo-4,5-dihydrospiro[benzo[f]pyrrolo[1,2-a][1,4]diazepine-6,1'-cyclopropane]-2-carboxylic acid;

5-Methyl-9-(pyridazin-3-yl)-4-oxo-4,5-dihydrospiro[benzo[f]pyrrolo[1,2-a][1,4]diazepine-6,1'-cyclopropane]-2-carboxylic acid;

5-Methyl-9-(3-cyanophenyl)-4-oxo-4,5-dihydrospiro[benzo[f]pyrrolo[1,2-a][1,4]diazepine-6,1'-cyclopropane]-2-carboxylic acid;

5-Methyl-9-(2-methyl-pyridin-3-yl)-2-(oxazol-5-yl)-spiro[benzo[f]pyrazolo[1,5-a][1,4]diazepine-6,1'-cyclopropan]-4(5H)-one;

5-Methyl-9-(2-methyl-pyridin-3-yl)-2-(3H-imidazol-4-yl)-spiro[benzo[f]pyrazolo[1,5-a][1,4]diazepine-6,1'-cyclopropan]-4(5H)-one;

5-Methyl-9-(2-methyl-pyridin-3-yl)-2-(1H-imidazol-2-yl)-spiro[benzo[f]pyrazolo[1,5-a][1,4]diazepine-6,1'-cyclopropan]-4(5H)-one;

5-Methyl-9-(2-methyl-pyridin-3-yl)-2-[1,3,4]oxadiazol-2-yl-spiro[benzo[f]pyrazolo[1,5-a][1,4]diazepine-6,1'-cyclopropan]-4(5H)-one;

5-Methyl-9-(6-fluoro-pyridin-3-yl)-2-(1H-imidazol-2-yl)-spiro[benzo[f]pyrazolo[1,5-a][1,4]diazepine-6,1'-cyclopropan]-4(5H)-one;

5-Methyl-9-(6-fluoro-pyridin-3-yl)-2-[1,3,4]oxadiazol-2-yl-spiro[benzo[f]pyrazolo[1,5-a][1,4]diazepine-6,1'-cyclopropan]-4(5H)-one;

5-(Methyl-d3)-9-(6-fluoro-pyridin-3-yl)-2-[1,3,4]oxadiazol-2-yl-spiro[benzo[f]pyrazolo[1,5-a][1,4]diazepine-6,1'-cyclopropan]-4(5H)-one;

5-Methyl-9-bromo-2-[1,3,4]oxadiazol-2-yl-spiro[benzo[f]pyrazolo[1,5-a][1,4]diazepine-6,1'-cyclopropan]-4(5H)-one;

5-Methyl-9-(6-dimethylamino-pyridin-3-yl)-2-[1,3,4] oxadiazol-2-yl-spiro[benzo[f]pyrazolo[1,5-a][1,4]diazepine-6,1'-cyclopropan]-4(5H)-one;

5-Methyl-9-(6-chloro-pyridin-3-yl)-2-[1,3,4]oxadiazol-2-yl-spiro[benzo[f]pyrazolo[1,5-a][1,4]diazepine-6,1'-cyclopropan]-4(5H)-one;

5-Methyl-9-(3-cyanophenyl)-2-[1,3,4]oxadiazol-2-yl-spiro[benzo[f]pyrazolo[1,5-a][1,4]diazepine-6,1'-cyclopropan]-4(5H)-one;

5-Methyl-9-(pyridazin-3-yl)-2-[1,3,4]oxadiazol-2-yl-spiro[benzo[f]pyrazolo[1,5-a][1,4]diazepine-6,1'-cyclopropan]-4(5H)-one;

5-Methyl-9-(2-methyl-pyridin-3-yl)-2-(cyclopentanecarbonyl)-spiro[benzo[f]pyrazolo[1,5-a][1,4]diazepine-6,1'-cyclopropan]-4(5H)-one;

5-Methyl-9-(2-methyl-pyridin-3-yl)-2-acetyl-spiro[benzo[f]pyrazolo[1,5-a][1,4]diazepine-6,1'-cyclopropan]-4(5H)-one;

5-Methyl-9-(2-methyl-pyridin-3-yl)-2-(cyclopentylmethyl)-spiro[benzo[f]pyrazolo[1,5-a][1,4]diazepine-6,1'-cyclopropan]-4(5H)-one;

5-Methyl-9-(2-methyl-pyridin-3-yl)-2-ethyl-spiro[benzo[f]pyrazolo[1,5-a][1,4]diazepine-6,1'-cyclopropan]-4(5H)-one;

2,5-Dimethyl-9-(6-methyl-pyridin-3-yl)-spiro[benzo[f]pyrazolo[1,5-a][1,4]diazepine-6,1'-cyclopropan]-4(5H)-one;

2,5-Dimethyl-9-(2-ethyl-pyridin-3-yl)-spiro[benzo[f]pyrazolo[1,5-a][1,4]diazepine-6,1'-cyclopropan]-4(5H)-one;

5-Methyl-9-(2-methyl-pyridin-3-yl)-2-(morpholin-4-ylmethyl)-spiro[benzo[f]pyrazolo[1,5-a][1,4]diazepine-6,1'-cyclopropan]-4(5H)-one;

5-Methyl-9-(2-methyl-pyridin-3-yl)-2-difluoromethyl-spiro[benzo[f]pyrazolo[1,5-a][1,4]diazepine-6,1'-cyclopropan]-4(5H)-one;

2-Hydroxymethyl-5-methyl-9-(6-methyl-pyridin-3-yl)-spiro[benzo[f]pyrazolo[1,5-a][1,4]diazepine-6,1'-cyclopropan]-4(5H)-one;

2-Hydroxymethyl-5-methyl-9-(2-ethyl-pyridin-3-yl)-spiro[benzo[f]pyrazolo[1,5-a][1,4]diazepine-6,1'-cyclopropan]-4(5H)-one;

2-Hydroxymethyl-5-methyl-9-(6-fluoro-pyridin-3-yl)-spiro[benzo[f]pyrazolo[1,5-a][1,4]diazepine-6,1'-cyclopropan]-4(5H)-one;

2-Methoxymethyl-5-methyl-9-(6-methyl-pyridin-3-yl)-spiro[benzo[f]pyrazolo[1,5-a][1,4]diazepine-6,1'-cyclopropan]-4(5H)-one;

2-Methoxymethyl-5-methyl-9-(2-ethyl-pyridin-3-yl)-spiro[benzo[f]pyrazolo[1,5-a][1,4]diazepine-6,1'-cyclopropan]-4(5H)-one;

2-Methoxymethyl-5-methyl-9-(6-fluoro-pyridin-3-yl)-spiro[benzo[f]pyrazolo[1,5-a][1,4]diazepine-6,1'-cyclopropan]-4(5H)-one;

9-Bromo-5-methyl-1,2,3,3a-tetrahydro-spiro[benzo[f]pyrrolo[1,2-a][1,4]diazepine-6,1'-cyclopropan]-4(5H)-one;

5-Methyl-9-(2-methylpyridin-3-yl)-1,2,3,3a-tetrahydro-spiro[benzo[f]pyrrolo[1,2-a][1,4]diazepine-6,1'-cyclopropan]-4(5H)-one;

5-Methyl-9-bromo-5,6-dihydro-4H-benzo[f]imidazo[1,5-a][1,4]diazepin-4-one;

5-Methyl-9-bromo-5,6-dihydro-4H-benzo[f]imidazo[1,2-a][1,4]diazepin-4-one;

5-Methyl-9-bromo-5,6-dihydro-4H-benzo[f]pyrazolo[1,5-a][1,4]diazepin-4-one;

9-Bromo-5,6-dimethyl-5,6-dihydro-benzo[f]pyrrolo[1,2-a][1,4]diazepin-4-one;

9-Bromo-5-methyl-6-ethyl-5,6-dihydro-benzo[f]pyrrolo[1,2-a][1,4]diazepin-4-one;

5-Methyl-9-(2-methylpyridin-3-yl)-5,6-dihydro-4H-benzo[f]imidazo[1,5-a][1,4]diazepin-4-one;

5-Methyl-9-(2-methylpyridin-3-yl)-5,6-dihydro-4H-benzo[f]imidazo[1,2-a][1,4]diazepin-4-one;

5-Methyl-9-(2-methylpyridin-3-yl)-5,6-dihydro-4H-benzo[f]pyrazolo[1,5-a][1,4]diazepin-4-one;

5,6-Dimethyl-9-(2-methyl-pyridin-3-yl)-5,6-dihydro-benzo[f]pyrrolo[1,2-a][1,4]diazepin-4-one;

9-(6-Dimethylamino-pyridin-3-yl)-5,6-dimethyl-5,6-dihydro-benzo[f]pyrrolo[1,2-a][1,4]diazepin-4-one;

6-Ethyl-5-methyl-9-(2-methyl-pyridin-3-yl)-5,6-dihydro-benzo[f]pyrrolo[1,2-a][1,4]diazepin-4-one;

5,6,6-Trimethyl-5,6-dihydro-benzo[f]pyrrolo[1,2-a][1,4]diazepin-4-one;

9-Chloro-5,6,6-trimethyl-5,6-dihydro-benzo[f]pyrrolo[1,2-a][1,4]diazepin-4-one;

5,6,6-Trimethyl-9-(2-methyl-pyridin-3-yl)-5,6-dihydro-benzo[f]pyrrolo[1,2-a][1,4]diazepin-4-one;

and pharmaceutically acceptable salts, solvates and prodrugs thereof.

13. A pharmaceutical composition comprising the compound as defined in claim 1, or a pharmaceutically acceptable salt, solvate or prodrug thereof, and one or more pharmaceutically acceptable excipients.

* * * * *

UNITED STATES PATENT AND TRADEMARK OFFICE
CERTIFICATE OF CORRECTION

PATENT NO. : 11,008,323 B2  
APPLICATION NO. : 15/775725  
DATED : May 18, 2021  
INVENTOR(S) : Schann et al.

It is certified that error appears in the above-identified patent and that said Letters Patent is hereby corrected as shown below:

In the Claims

In Claim 10, Column 230, Line 67, delete "C3-C$_5$" and insert --C$_3$-C$_5$-- therefor.

In Claim 12, Column 233, Line 11, delete "d3" and insert --d$_3$-- therefor.

In Claim 12, Column 233, Line 35, delete "d3" and insert --d$_3$-- therefor.

In Claim 12, Column 237, Line 9, delete "SH" and insert --5H-- therefor.

In Claim 12, Column 238, Line 14, delete "d3" and insert --d$_3$-- therefor.

In Claim 12, Column 238, Line 32, delete "d3" and insert --d$_3$-- therefor.

In Claim 12, Column 238, Line 62, delete "d3" and insert --d$_3$-- therefor.

Signed and Sealed this  
Seventh Day of December, 2021

Drew Hirshfeld  
*Performing the Functions and Duties of the*  
*Under Secretary of Commerce for Intellectual Property and*  
*Director of the United States Patent and Trademark Office*